United States Patent
Fürstner et al.

(10) Patent No.: US 9,949,978 B2
(45) Date of Patent: *Apr. 24, 2018

(54) BICYCLICALLY SUBSTITUTED URACILS AND THE USE THEREOF

(71) Applicant: Bayer Pharma Aktiengesellschaft, Berlin (DE)

(72) Inventors: Chantal Fürstner, Mülheim/Ruhr (DE); Jens Ackerstaff, Düsseldorf (DE); Alexander Straub, Wuppertal (DE); Heinrich Meier, Wuppertal (DE); Hanna Tinel, Wuppertal (DE); Katja Zimmermann, Düsseldorf (DE); Adrian Tersteegen, Wuppertal (DE); Dmitry Zubov, Remscheid (DE); Raimund Kast, Wuppertal (DE); Jens Schamberger, Velbert-Langenberg (DE); Martina Schäfer, Berlin (DE); Kirsten Börngen, Köln (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,982

(22) Filed: Oct. 7, 2016

(65) Prior Publication Data

US 2017/0020875 A1 Jan. 26, 2017

Related U.S. Application Data

(63) Continuation of application No. 14/399,945, filed as application No. PCT/EP2013/059286 on May 3, 2013, now Pat. No. 9,481,672.

(30) Foreign Application Priority Data

May 9, 2012 (EP) .................................. 12167231

(51) Int. Cl.
| | |
|---|---|
| *A61K 31/506* | (2006.01) |
| *A61K 31/513* | (2006.01) |
| *C07D 413/14* | (2006.01) |
| *C07D 401/04* | (2006.01) |
| *C07D 403/04* | (2006.01) |
| *C07D 409/14* | (2006.01) |
| *C07D 413/04* | (2006.01) |
| *C07D 417/04* | (2006.01) |
| *C07D 471/04* | (2006.01) |
| *A61K 45/06* | (2006.01) |
| *C07D 405/14* | (2006.01) |
| *C07D 417/14* | (2006.01) |
| *A61K 31/538* | (2006.01) |
| *A61K 31/536* | (2006.01) |

(52) U.S. Cl.
CPC .......... *A61K 31/513* (2013.01); *A61K 31/506* (2013.01); *A61K 31/536* (2013.01); *A61K 31/538* (2013.01); *A61K 45/06* (2013.01); *C07D 401/04* (2013.01); *C07D 403/04* (2013.01); *C07D 405/14* (2013.01); *C07D 409/14* (2013.01); *C07D 413/04* (2013.01); *C07D 413/14* (2013.01); *C07D 417/04* (2013.01); *C07D 417/14* (2013.01); *C07D 471/04* (2013.01)

(58) Field of Classification Search
CPC .. C07D 417/14; C07D 413/14; C07D 401/04; C07D 403/04; C07D 409/14; C07D 413/04; C07D 417/04; C07D 471/04; C07D 405/14
See application file for complete search history.

(56) References Cited

U.S. PATENT DOCUMENTS

| | | | | |
|---|---|---|---|---|
| 6,403,599 | B1* | 6/2002 | Chen | A61K 31/435 514/269 |
| 9,481,672 | B2* | 11/2016 | Furstner et al. | C07D 413/14 |
| 2004/0102384 | A1 | 5/2004 | Deguchi et al. | |
| 2006/0258689 | A1 | 11/2006 | Kelly et al. | |
| 2008/0090856 | A1 | 4/2008 | Flylnn et al. | |
| 2010/0305102 | A1 | 12/2010 | Pouzet et al. | |
| 2011/0053974 | A1 | 3/2011 | Toda et al. | |
| 2017/0020876 | A1* | 1/2017 | Furstner | C07D 413/14 |

FOREIGN PATENT DOCUMENTS

| | | |
|---|---|---|
| WO | 2000/006568 | 2/2000 |
| WO | 2000/006569 | 2/2000 |
| WO | 2001/019355 | 3/2001 |
| WO | 2001/019776 | 3/2001 |
| WO | 2001/019780 | 3/2001 |
| WO | 2001/019778 | 3/2002 |
| WO | 2002/042301 | 5/2002 |
| WO | 2002/070462 | 9/2002 |
| WO | 2002/070510 | 9/2002 |
| WO | 2003/072553 | 9/2003 |
| WO | 2003/095451 | 11/2003 |
| WO | 2004/052858 | 6/2004 |
| WO | 2005/072741 | 8/2005 |
| WO | 2005/092899 | 10/2005 |
| WO | 2006/012374 | 2/2006 |
| WO | 2006/071940 | 7/2006 |
| WO | 2007/093904 | 8/2007 |
| WO | 2007/120339 | 10/2007 |
| WO | 2007/150011 | 12/2007 |
| WO | 2008/056257 | 5/2008 |
| WO | 2008/103277 | 8/2008 |
| WO | 2008/128009 | 10/2008 |
| WO | 2009/049112 | 4/2009 |
| WO | 2009/156182 | 12/2009 |

OTHER PUBLICATIONS

Renal Failure and Replacement Therapies, 26-32 (S. Blakeley ed., 2008).*

(Continued)

*Primary Examiner* — Alexander R Pagano
(74) *Attorney, Agent, or Firm* — Morrison & Foerster LLP

(57) ABSTRACT

The present application relates to novel bicyclically substituted uracil derivatives, to processes for preparation thereof, to the use thereof alone or in combinations for treatment and/or prophylaxis of diseases, and to the use thereof for production of medicaments for treatment and/or prophylaxis of diseases.

42 Claims, No Drawings

(56) References Cited

OTHER PUBLICATIONS

H. Vankayala et al., II Renal Cell Carcinoma: Clinical Presentation, Staging, and Prognostic Factors in, Kidney Cancer Principles and Practice, 69-88, 75 (P.N. Lara et al., eds., 2012).*
S.K. Pal et al., IV E merging Agents in Renal Cell Carcinoma in, Kidney Cancer Principles and Practice, 285-301, 286 (P.N. Lara et al., eds., 2012).*
L-J Zhu et al., 2010 Journal of Biomedicine and Biotechnology, 1-8 (2010).*
A. Lateef et al., 14 Arthritis Research & Therapy, 1-9 (2012).*
Z. Wang et al., 19 Drug Discovery Today, 145-150 (2014).*
U.K. Marelli et al., 3 Frontiers in Oncology, 1-12 (2013).*
C. Bacani et al., 14 Cardiology in Review, 187-193 (2006).*
H. Kanemitsu et al., 29 Hypertension Research 57-64 (2006).*
X.R. Huang et al., 14 Journal of the American Society of Nephrology, 1738-1747 (2003).*
N. Shiota et al., 145 British Journal of Pharmacology, 424-431 (2005).*
M.N. Greco et al., 50 Journal of Medicinal Chemistry, 1727-1730 (2007).*
S Takai et al., 118 Journal of Pharmaceutical Science, 311-316 (2012).*
Bacani, et al., "Chymase: A New Pharmacologic Target in Cardiovascular Disease", Cardiology in Review, 14(4), Jul./Aug. 2006, pp. 187-193.
Bastos, et al., "Synthesis of new 3-(Trifluoromethyl)-1 H-indoles by Reduction of Trifluoromethyloxoindoles", Journal of Heterocyclic Chemistry, 45, Jul.-Aug. 2008, pp. 969-973.
Chezal, et al., "Aminoimidazo[1,2-a]pyridines: regioselective synthesis of substituted imidazonaphthyridines, azacarbolines and cyclazines", Tetrahedron, 58, 2002, pp. 295-307.
Danishefsky, et al., "Total Synthesis of Octosyl Acid A. Intramolecular Williamson Reaction via a Cyclic Stannylene Derivative", Journal American Chemical Society, 110(22), 1998, pp. 7434-7440.
Doggrell, "Therapeutic potential of non-peptide chymase inhibitors", Expert Opinion Ther. Patents, 18(5), 2008, pp. 485-499.
Fleming, "Signaling by the Angiotensin-Converting Enzyme", Circulation Research, Apr. 14, 2006, pp. 887-896.
Greco, et al., "Discovery of Potent, Selective, Orally Active, Nonpeptide Inhibitors of Human Mast Cell Chymase", Journal of Medicinal Chemistry, 50, 2007, pp. 1727-1730.
Huang, et al., "Chymase Is Upregulated in Diabetic Nephropathy: Implications for an Alternative Pathway of Angiotensin II-Mediated Diabetic Renal and Vascular Disease", Journal of the American Society of Nephrology, 14, 2003, pp. 1738-1747.
Hughes, "Progress in the Mitsunobu Reaction. A Review", Organic Preparations and Procedures International: The New Journal for Organic Synthesis, 28(2), 1996, pp. 127-164.
Hughes, "The Mitsunobu Reaction", Chapter 2, Organic Reactions, 42, 1992, pp. 335-656.
Jin, et al., "An Antiarrhythmic Effect of a Chymase Inhibitor after Myocardial Infarction", The Journal of Pharmacology and Experimental Therapeutics, 309(2), 2004, pp. 490-497.
Jin, et al., "Beneficial effects of cardiac chymase inhibition during the acute phase of myocardial infarction", Life Sciences, 71, 2002, pp. 437-446.
Kakizoe, et al., "Isoform-Selective Upregulation of Mast Cell Chymase in the Development of Skin Fibrosis in Scleroderma Model Mice", The Journal of Investigative Dermatology, 16, 2001, pp. 118-123.
Kanazawa, et al., "Asymmetric Conjugate Reduction of a,b-Unsaturated Ketones and Esters with Chiral Rhodium(2,6-bisoxazolinylphenyl) Catalysts", Chemistry A European Journal, 12, 2006, pp. 63-71.
Kanemitsu, et al., "Chymase Inhibition Prevents Cardiac Fibrosis and Dysfunction after Myocardial Infarction in Rats", Hypertension Research, 29, 2006, pp. 57-64.
Kovanen, et al., "Infiltrates of Activated Mast Cells at the Site of Coronary Atheromatous Erosion or Rupture in Myocardial Infarction", Circulation, 92(5), Sep. 1, 1995, pp. 1084-1088.
Larsen, et al., "Synthesis of N-1-Alkylated 6-Benzyluracil-5-carboxylic Esters as Potential Non-Nucleoside Reverse Transcriptase Inhibitors", Synthesis, 2004, pp. 1874-1878.
Libby, et al., "Mast Cells as Mediators and Modulators of Atherogenesis", Circulation, May 15, 2007, pp. 2471-2473.
Lukmanov, et al., "Fluorination of Aromatic Carboxylic Acids with Sulfur Tetrafluoride Viil. Synthesis of Vicinal Polytrifluoromethylbenzenes", Translated from Zhurnal Organicheskoi Khimii, 9(5), May 22, 1972, pp. 1019-1024.
Matsumoto, et al., "Chymase Inhibition Prevents Cardiac Fibrosis and Improves Diastolic Dysfunction in the Progression of Heart Failure", Circulation, May 27, 2003, pp. 2555-2558.
McPherson, et al., "Chymase-like Angiotensin II-Generating Activity in End-Stage Human Autosomal Dominant Polycystic Kidney Disease", Journal of the American Society of Nephrology, 15, 2004, pp. 493-500.
Miyazaki, et al., "Pathological roles of angiotensin II produced by mast cell chymase and the effects of chymase inhibition in animal models", Pharmacology & Therapeutics, 112, 2006, pp. 668-676.
Mulvany, et al., "Contractile Properties of Small Arterial Resistance Vessels in Spontaneously Hypertensive and Normotensive Rats", Circulation Research, 41(1), Jul. 1977, pp. 19-26.
Nasr, et al., "7-Aminoquinolines. A Novel Class of Agents Active against Herpesviruses", Journal of Medicinal Chemistry, 31(7), 1988, pp. 1347-1351.
Palladini, et al., "Cardiac mast cells in the transition to heart failure: innocent bystanders or key actors?", Journal of Hypertension, 21, 2003, pp. 1823-1825.
Senda, et al., "Pyrimidine Derivatives and Related Compounds. XVI.1) Synthesis of 1,3-Disubstituted5-Cyanouracil Derivatives and Related Compounds", Chem. Pharm. Bull., vol. 20(7), 1972, pp. 1380-1388.
Shiota, et al., "Effect of mast cell chymase inhibitor on the development of scleroderma in tight-skin mice", British Journal of Pharmacology, 145, 2005, pp. 424-431.
Takai, et al., "An Orally Active Chymase Inhibitor, BCEAB, Suppresses Heart Chymase Activity in the Hamster", Japanese Journal of Pharmacology, 86, 2001, pp. 124-126.
Thurmond, et al., "A Potent and Selective Histamine H4 Receptor Antagonist with Anti-Inflammatory Properties", The Journal of Pharmacology and Experimental Therapeutics, 309, 2004, pp. 404-413.
USPTO, Notice of Allowance for U.S. Appl. No. 14/399,945, dated Jul. 15, 2016, 5 pages.
USPTO, Notice of Allowance for U.S. Appl. No. 14/399,945, dated Mar. 11, 2016, 5 pages.
Van Henegouwen, et al., "First Total Synthesis of ent-Gelsedine via a Novel Iodide-Promoted Allene N-Acyliminium Ion Cyclization", Journal of Organic Chemistry, 65(24), 2000, pp. 8317-8325.
Von der Saal, et al., "Nonsteroidal Cardiotonics. 2. The Inotropic Activity of Linear, Tricyclic 5-6-5 Fused Heterocycles", Journal of Medicinal Chemistry, 32(7), 1989, pp. 1481-1491.
Zanini, et al., "Chymase-positive mast cells play a role in the vascular component of airway remodeling in asthma", Journal of Allergy Clinical Immunology, 120(2), Aug. 2007, pp. 329-333.

* cited by examiner

BICYCLICALLY SUBSTITUTED URACILS AND THE USE THEREOF

CROSS-REFERENCE TO RELATED APPLICATIONS

The present application is a continuation of U.S. patent application Ser. No. 14/399,945, filed Nov. 7, 2014 and titled BICYCLICALLY SUBSTITUTED URACILS AND THE USE THEREOF, which is a U.S. national phase application of International Patent Application No. PCT/EP2013/059286, filed May 3, 2013 and titled BICYCLICALLY SUBSTITUTED URACILS AND THE USE THEREOF, which claims priority to European Patent Application No. 12167231.5, filed May 9, 2012 and titled BICYCLICALLY SUBSTITUTED URACILS AND THE USE THEREOF, the contents of all of which are incorporated herein by reference in their entirety.

The present application relates to novel bicyclically substituted uracil derivatives, to processes for preparation thereof, to the use thereof alone or in combinations for treatment and/or prophylaxis of diseases, and to the use thereof for production of medicaments for treatment and/or prophylaxis of diseases.

Chymase is a chymotrypsin-like serine protease which is stored as a macromolecular complex with heparin proteoglycans in secretory vesicles of mast cells. After activation of the mast cells, chymase is released into the extracellular matrix and activated.

Activated mast cells play an important role in healing wounds and in inflammation processes, for example fibrosis of wounds, angiogenesis and cardiac remodelling (Miyazaki et al., *Pharmacol. Ther.* 112 (2006), 668-676; Shiota et al., *J. Hypertens.* 21 (2003), 1823-1825). An increase in the number of mast cells has been observed in the event of heart failure, myocardial infarction and ischaemia, in human atherosclerotic plaques and in abdominal aortic aneurysms (Kovanen et al., *Circulation* 92 (1995), 1084-1088; Libby and Shi, *Circulation* 115 (2007), 2555-2558; Bacani and Frishman, *Cardiol. Rev.* 14 (4) (2006), 187-193). Chymase-positive mast cells can also play an important role in the vascular remodelling of the respiratory pathways in the event of asthma and chronic obstructive pulmonary disease. An increased number of mast cells has been found in endo-bronchial biopsies of asthma patients (Zanini et al., *J. Allergy Clin. Immunol.* 120 (2007), 329-333). Moreover, chymase is suspected of being partly responsible for the genesis of many renal disorders, such as diabetic nephropathy and polycystic kidney disease (Huang et al., *J. Am. Soc. Nephrol.* 14 (7) (2003), 1738-1747; McPherson et al., *J. Am. Soc. Nephrol.* 15 (2) (2004), 493-500).

Chymase is predominantly involved in the production of angiotensin II in the heart, in the artery wall and in the lung, whereas the angiotensin-converting enzyme is responsible for the formation of the peptide in the circulation system (Fleming I., *Circ. Res.* 98 (2006), 887-896). In addition, chymase cleaves a number of other substrates of pathological significance. Chymase leads to degradation of extracellular matrix proteins, such as fibronectin, procollagen and vitronectin, and to the breakoff of focal adhesions. It brings about activation and release of TGFβ from its latent form, which plays an important role in the genesis of cardiac hypertrophy and cardiac fibrosis. The enzyme has atherogenic action, by degrading apolipoproteins and preventing the absorption of cholesterol by HDL. The action of chymase leads to release and activation of the cytokine interleukin 1 with its pro-inflammatory properties. Furthermore, it contributes to production of endothelin 1 (Bacani and Frishman, *Cordial. Rev.* 14 (4) (2006), 187-193). An accumulation of chymase-positive mast cells has been found in biopsies of patients having atopic dermatitis, Crohn's disease, chronic hepatitis and hepatic cirrhosis, and also idiopathic interstitial pneumonia (Dogrell S. A., *Expert Opin. Ther. Patents* 18 (2008), 485-499).

The possibility of using chymase inhibitors for the treatment of different diseases has been demonstrated in numerous studies involving animal experimentation. Inhibition of chymase can be useful for the treatment of myocardial infarction. Jin et al. (*Pharmacol. Exp. Ther.* 309 (2004), 409-417) showed that a ligature of the coronary artery in dogs led to ventricular arrhythmias and elevated production of angiotensin II and chymase activity in the heart. Intravenous administration of the chymase inhibitor TY-501076 reduced chymase activity and the angiotensin II concentration in the plasma, and suppressed the occurrence of arrhythmias. A positive effect of chymase inhibition was shown in an in vivo model for myocardial infarction in hamsters. Treatment of the animals with the chymase inhibitor BCEAB reduced chymase activity, improved haemodynamics and reduced mortality (Jin et al., *Life Sci.* 71 (2002), 437-446). In the cardiomyopathic Syrian hamster, where the number of mast cells in the heart is elevated, oral treatment of the animals with the chymase inhibitor reduced cardiac fibrosis by 50% (Takai et al., *Jpn. J. Pharmacol.* 86 (2001), 124-126). In a tachycardia-induced heart failure model in dogs, chymase inhibition with SUN-C82257 led to reduction in the number of mast cells and in fibrosis in the heart. In addition, the diastolic function of the heart was improved after the treatment (Matsumoto et al., *Circulation* 107 (2003), 2555-2558).

Inhibition of chymase thus constitutes an effective principle in the treatment of cardiovascular disorders, inflammation and allergic disorders, and various fibrotic disorders.

WO 2007/150011 and WO 2009/049112 disclose a process for preparing pyrimidinetriones with glycine substituents. WO 2008/056257 describes triazinediones as GABA-B receptor modulators for treatment of CNS disorders. WO 2008/103277 discloses various nitrogen heterocycles for treatment of cancer. WO 2009/156182 describes uracil derivatives for suppression or reduction of resistance development in the course of cytostatic treatment.

It was an object of the present invention to provide novel substances which act as inhibitors of chymase and are suitable as such for treatment and/or prophylaxis of disorders, especially cardiovascular disorders.

The present invention relates to compounds of the general formula (I)

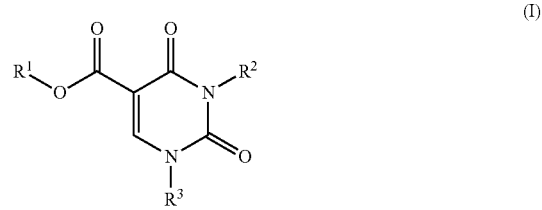

in which
R¹ is hydrogen or $(C_1-C_4)$-alkyl,
R² is a group of the formula

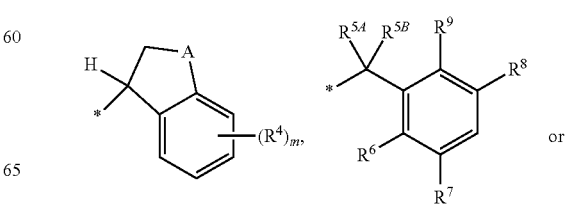

or

-continued

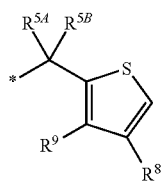

where
* is the attachment site to the uracil nitrogen atom,
A is —CH$_2$— or oxygen,
m is a number 0, 1 or 2,
R$^4$ is halogen, difluoromethyl, trifluoromethyl, (C$_1$-C$_4$)-alkyl, difluoromethoxy, trifluoromethoxy or (C$_1$-C$_4$)-alkoxy,
R$^{5A}$ is hydrogen or deuterium,
R$^{5B}$ is hydrogen, deuterium or (C$_1$-C$_4$)-alkyl,
R$^6$ is hydrogen or fluorine,
R$^7$ is hydrogen or fluorine,
R$^8$ is halogen, difluoromethyl, trifluoromethyl, (C$_1$-C$_4$)-alkyl or nitro,
R$^9$ is hydrogen, halogen, difluoromethyl, trifluoromethyl, (C$_1$-C$_4$)-alkyl, nitro or (C$_1$-C$_4$)-alkylthio,
R$^3$ is a group of the formula

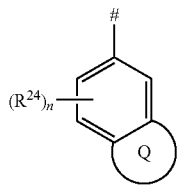

where
# is the attachment site to the uracil nitrogen atom,
the ring Q is 5- to 7-membered heterocyclyl or 5- or 6-membered heteroaryl,
in which 5- to 7-membered heterocyclyl and 5- or 6-membered heteroaryl may be substituted by 1 to 4 substituents independently selected from the group of halogen, difluoromethyl, trifluoromethyl, trideuteromethyl, (C$_1$-C$_6$)-alkyl, (C$_3$-C$_7$)-cycloalkyl, oxo, hydroxyl, (C$_1$-C$_4$)-alkylcarbonyl, (C$_1$-C$_4$)-alkoxycarbonyl, aminocarbonyl and (C$_1$-C$_4$)-alkylsulphonyl,
in which (C$_1$-C$_6$)-alkyl and (C$_3$-C$_7$)-cycloalkyl may in turn be substituted by 1 to 3 substituents independently selected from the group of halogen, cyano, trifluoromethyl, (C$_3$-C$_7$)-cycloalkyl, hydroxyl, (C$_1$-C$_4$)-alkoxy and 4- to 7-membered heterocyclyl,
and
in which two (C$_1$-C$_6$)-alkyl radicals bonded to a carbon atom of 5- to 7-membered heterocyclyl and 5- or 6-membered heteroaryl, together with the carbon atom to which they are bonded, may form a 3- to 6-membered carbocycle,
R$^{24}$ is halogen, (C$_1$-C$_4$)-alkyl or (C$_1$-C$_4$)-alkoxy,
n is a number 0, 1, 2 or 3,
and the salts, solvates and solvates of the salts thereof.

The present invention relates to compounds of the general formula (I)

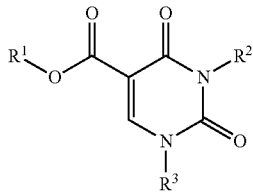

in which
R$^1$ is hydrogen or (C$_1$-C$_4$)-alkyl,
R$^2$ is a group of the formula

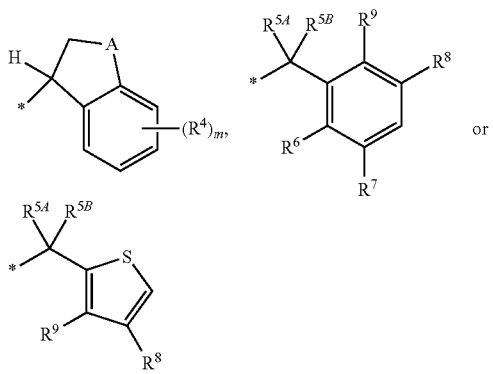

where
* is the attachment site to the uracil nitrogen atom,
A is CH$_2$—, —CH$_2$—CH$_2$—, —O—CH$_2$-## or oxygen,
in which
## is the attachment site to the phenyl ring,
m is a number 0, 1 or 2,
R$^4$ is halogen, difluoromethyl, trifluoromethyl, (C$_1$-C$_4$)-alkyl, difluoromethoxy, trifluoromethoxy or (C$_1$-C$_4$)-alkoxy,
R$^{5A}$ is hydrogen or deuterium,
R$^{5B}$ is hydrogen, deuterium or (C$_1$-C$_4$)-alkyl,
R$^6$ is hydrogen or fluorine,
R$^7$ is hydrogen or fluorine,
R$^8$ is halogen, difluoromethyl, trifluoromethyl, (C$_1$-C$_4$)-alkyl or nitro,
R$^9$ is hydrogen, halogen, difluoromethyl, trifluoromethyl, (C$_1$-C$_4$)-alkyl, nitro or (C$_1$-C$_4$)-alkylthio,
R$^3$ is a group of the formula

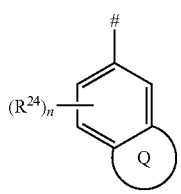

where
# is the attachment site to the uracil nitrogen atom,
the ring Q is 5- to 7-membered heterocyclyl or 5- or 6-membered heteroaryl,
in which 5- to 7-membered heterocyclyl and 5- or 6-membered heteroaryl may be substituted by 1 to 4 substituents independently selected from the group of halogen, difluoromethyl, trifluoromethyl, trideuteromethyl, $(C_1-C_6)$-alkyl, $(C_3-C_7)$-cycloalkyl, oxo, hydroxyl, $(C_1-C_4)$-alkylcarbonyl, $(C_1-C_4)$-alkoxycarbonyl, amino carbonyl and $(C_1-C_4)$-alkylsulphonyl, in which $(C_1-C_6)$-alkyl and $(C_3-C_7)$-cycloalkyl may in turn be substituted by 1 to 3 substituents independently selected from the group of halogen, cyano, trifluoromethyl, $(C_3-C_7)$-cycloalkyl, hydroxyl, $(C_1-C_4)$-alkoxy and 4- to 7-membered heterocyclyl, and in which two $(C_1-C_6)$-alkyl radicals bonded to a carbon atom of 5- to 7-membered heterocyclyl and 5- or 6-membered heteroaryl, together with the carbon atom to which they are bonded, may form a 3- to 6-membered carbocycle, $R^{24}$ is halogen, $(C_1-C_4)$-alkyl or $(C_1-C_4)$-alkoxy, n is a number 0, 1, 2 or 3, and the salts, solvates and solvates of the salts thereof.

Inventive compounds are the compounds of the formula (I) and the salts, solvates and solvates of the salts thereof, the compounds encompassed by formula (I) of the formulae specified hereinafter and the salts, solvates and solvates of the salts thereof, and the compounds encompassed by formula (I) and specified hereinafter as working examples and the salts, solvates and solvates of the salts thereof, to the extent that the compounds encompassed by formula (I) and specified hereinafter are not already salts, solvates and solvates of the salts.

In the context of the present invention, preferred salts are physiologically acceptable salts of the inventive compounds. Also encompassed are salts which are not themselves suitable for pharmaceutical applications but can be used, for example, for the isolation, purification or storage of the inventive compounds.

Physiologically acceptable salts of the inventive compounds include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, N,N-ethyldiisopropylamine, monoethanolamine, diethanolamine, triethanolamine, dimethylaminoethanol, diethylaminoethanol, procaine, dicyclohexylamine, dibenzylamine, N-methylpiperidine, N-methylmorpholine, arginine, lysine, choline and 1,2-ethylenediamine.

In the context of the invention, solvates refer to those forms of the inventive compounds which, in solid or liquid state, form a complex by coordination with solvent molecules. Hydrates are a specific form of the solvates in which the coordination is with water. Preferred solvates in the context of the present invention are hydrates.

Depending on their structure, the inventive compounds may exist in different stereoisomeric forms, i.e. in the form of configurational isomers or if appropriate also as conformational isomers (enantiomers and/or diastereomers, including those in the case of atropisomers). The present invention therefore encompasses the enantiomers or diastereomers and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

Where the inventive compounds can occur in tautomeric forms, the present invention encompasses all the tautomeric forms.

The present invention also encompasses all suitable isotopic variants of the inventive compounds. An isotopic variant of an inventive compound is understood here to mean a compound in which at least one atom within the inventive compound has been exchanged for another atom of the same atomic number, but with a different atomic mass than the atomic mass which usually or predominantly occurs in nature. Examples of isotopes which can be incorporated into an inventive compound are those of hydrogen, carbon, nitrogen, oxygen, phosphorus, sulphur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of an inventive compound, especially those in which one or more radioactive isotopes have been incorporated, may be beneficial, for example, for the examination of the mechanism of action or of the active ingredient distribution in the body; due to comparatively easy preparability and detectability, especially compounds labelled with $^{3}H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the inventive compounds may therefore in some cases also constitute a preferred embodiment of the present invention. Isotopic variants of the inventive compounds can be prepared by processes known to those skilled in the art, for example by the methods described below and the instructions reproduced in the working examples, by using corresponding isotopic modifications of the particular reagents and/or starting compounds therein.

Moreover, the present invention also encompasses prodrugs of the inventive compounds. The term "prodrugs" refers here to compounds which may themselves be biologically active or inactive, but are converted while present in the body, for example by a metabolic or hydrolytic route, to inventive compounds.

In the context of the present invention, unless specified otherwise, the substituents are each defined as follows:

Alkyl in the context of the invention is a linear or branched alkyl radical having the number of carbon atoms specified in each case. Preferred examples include: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl, 1,4-dimethylpentyl, 4,4-dimethylpentyl and 1,4,4-trimethylpentyl.

Cycloalkyl in the context of the invention is a monocyclic saturated alkyl radical having 3 to 7 carbon atoms. Preferred examples include: cyclopropyl, cyclobutyl, cyclopentyl, cyclohexyl and cycloheptyl.

Alkylcarbonyl in the context of the invention is a linear or branched alkyl radical having 1 to 4 carbon atoms and a carbonyl group attached in the 1 position. Preferred examples include: methylcarbonyl, ethylcarbonyl, n-propylcarbonyl, isopropylcarbonyl, n-butylcarbonyl, isobutylcarbonyl and tert-butylcarbonyl.

Alkoxy in the context of the invention is a linear or branched alkoxy radical having 1 to 4 carbon atoms. Preferred examples include: methoxy, ethoxy, n-propoxy, isopropoxy, n-butoxy and tert-butoxy.

Alkoxycarbonyl in the context of the invention is a linear or branched alkoxy radical having 1 to 4 carbon atoms and a carbonyl group attached to the oxygen. Preferred examples include: methoxycarbonyl, ethoxycarbonyl, n-propoxycarbonyl, isopropoxycarbonyl and tert-butoxycarbonyl.

Alkylthio in the context of the invention is a linear or branched alkyl radical which has 1 to 4 carbon atoms and is bonded via a sulphur atom. Preferred examples include: methylthio, ethylthio, n-propylthio, isopropylthio, 1-methylpropylthio, n-butylthio, iso-butylthio and tert-butylthio.

Alkylsulphonyl in the context of the invention is a linear or branched alkyl radical which has 1 to 4 carbon atoms and is bonded via a sulphonyl group. Preferred examples include: methylsulphonyl, ethylsulphonyl, n-propylsulphonyl, isopropylsulphonyl, n-butylsulphonyl and tert-butylsulphonyl.

4- to 7-membered heterocyclyl in the context of the invention is a monocyclic saturated heterocycle which has a total of 4 to 7 ring atoms, contains one or two ring heteroatoms from the group of N, O, S, SO and/or $SO_2$ and is attached via a ring carbon atom or, where appropriate, a ring nitrogen atom. Examples include: azetidinyl, oxetanyl, pyrrolidinyl, pyrazolidinyl, tetrahydrofuranyl, piperidinyl, piperazinyl, tetrahydropyranyl, morpholinyl, thiomorpholinyl. Preference is given to: azetidinyl, oxetanyl, pyrrolidinyl, tetrahydrofuranyl, piperidinyl, piperazinyl, tetrahydropyranyl and morpholinyl.

5- to 7 membered heterocyclyl in the context of the invention is a partly unsaturated heterocycle which has a total of 5 to 7 ring atoms, contains 1 to 3 ring heteroatoms from the group of N, O, S and/or $SO_2$ and is fused to the phenyl ring in $R^3$. Examples include: dihydropyrrolyl, dihydroimidazolyl, dihydrothiazole dioxide, dihydrooxazolyl, dihydropyridyl, tetrahydropyrazinyl and dihydrooxazinyl.

Heteroaryl in the context of the invention is a monocyclic aromatic heterocycle (heteroaromatic) which has a total of 5 or 6 ring atoms, contains up to three identical or different ring heteroatoms from the group of N, O and/or S and is fused to the phenyl ring in $R^3$. Examples include: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl. Preference is given to pyrazolyl, imidazolyl, thiazolyl and triazolyl.

Halogen in the context of the invention includes fluorine, chlorine, bromine and iodine. Preference is given to chlorine or fluorine.

An oxo group in the context of the invention is an oxygen atom bonded via a double bond to a carbon or sulphur atom.

In the formulae of the group that $R^2$ and $R^3$ may represent, the end point of the line marked by a symbol * or # or ## does not represent a carbon atom or a $CH_2$ group but is part of the bond to the respective atom to which $R^2$ and $R^3$ are bonded.

If radicals in the compounds according to the invention are substituted, the radicals may be mono- or polysubstituted, unless specified otherwise. In the context of the present invention, all radicals which occur more than once are defined independently of one another. Substitution by one or two identical or different substituents is preferred. Very particular preference is given to substitution by one substituent.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progress of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

Preference is given in the context of the present invention to compounds of the formula (I) in which
$R^1$ is hydrogen, methyl or ethyl,
$R^2$ is a group of the formula

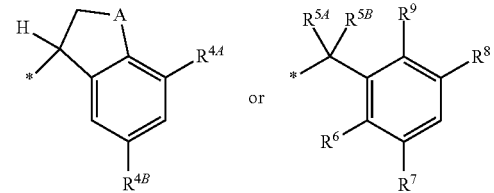

where
* is the attachment site to the uracil nitrogen atom,
A is —$CH_2$— or oxygen,
$R^{4A}$ is hydrogen, fluorine, chlorine, trifluoromethyl or methyl,
$R^{4B}$ is hydrogen, fluorine, chlorine, trifluoromethyl or methyl,
with the proviso that at least one of the $R^{4A}$ and $R^{4B}$ radicals is not hydrogen,
$R^{5A}$ is hydrogen,
$R^{5B}$ is hydrogen,
$R^6$ is hydrogen,
$R^7$ is hydrogen,
$R^8$ is fluorine, chlorine, difluoromethyl, trifluoromethyl or methyl,
$R^9$ is fluorine, chlorine, difluoromethyl, trifluoromethyl or methyl,
$R^3$ is a group of the formula

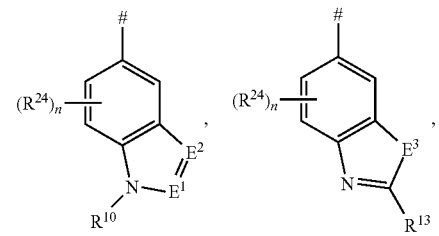

-continued

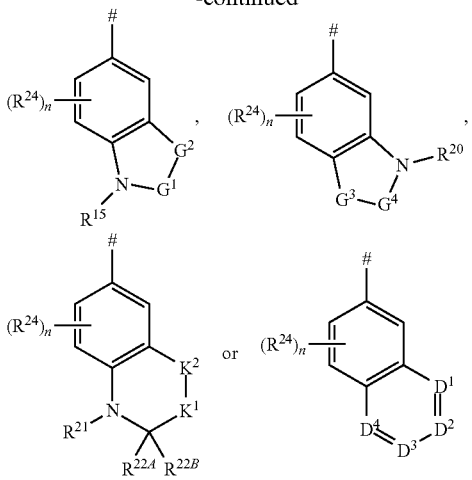

where
# is the attachment site to the uracil nitrogen atom,
$E^1$ is $CR^{11}$ or N,
in which
$R^{11}$ is hydrogen, $(C_1-C_4)$-alkyl, $(C_3-C_7)$-cycloalkyl or aminocarbonyl,
$E^2$ is $CR^{12}$ or N,
in which
$R^{12}$ is hydrogen, $(C_1-C_4)$-alkyl or $(C_3-C_7)$-cycloalkyl,
$E^3$ is $NR^{14}$ or S,
in which
$R^{14}$ is hydrogen, $(C_1-C_4)$-alkyl or $(C_3-C_7)$-cycloalkyl,
$G^1$ is C=O or $SO_2$,
$G^2$ is $CR^{16A}R^{16B}$, $NR^{17}$, O or S,
in which
$R^{16A}$ is hydrogen, fluorine, $(C_1-C_4)$-alkyl or hydroxyl,
$R^{16B}$ is hydrogen, fluorine, chlorine, $(C_1-C_4)$-alkyl or trifluoromethyl,
or
$R^{16A}$ and $R^{16B}$ together with the carbon atom to which they are bonded form a 3- to 6-membered carbocycle,
$R^{17}$ is hydrogen, $(C_1-C_6)$-alkyl, $(C_3-C_7)$-cycloalkyl or $(C_1-C_4)$-alkoxycarbonyl, in which $(C_1-C_6)$-alkyl may be substituted by 1 to 3 substituents independently selected from the group of fluorine, trifluoromethyl, cyano, $(C_3-C_7)$-cycloalkyl, hydroxyl, trifluoromethoxy, $(C_1-C_4)$-alkoxy, azetidinyl, oxetanyl, tetrahydrofuranyl and pyrrolidinyl,
$G^3$ is $CR^{18A}R^{18B}$, $NR^{19}$, O or S,
in which
$R^{18A}$ is hydrogen, fluorine, $(C_1-C_4)$-alkyl or hydroxyl,
$R^{18B}$ is hydrogen, fluorine, chlorine, $(C_1-C_4)$-alkyl or trifluoromethyl,
or
$R^{18A}$ and $R^{18B}$ together with the carbon atom to which they are bonded form a 3- to 6-membered carbocycle,
$R^{19}$ is hydrogen, $(C_1-C_6)$-alkyl, $(C_3-C_7)$-cycloalkyl or $(C_1-C_4)$-alkoxycarbonyl, in which $(C_1-C_6)$-alkyl may be substituted by 1 to 3 substituents independently selected from the group of fluorine, trifluoromethyl, cyano, $(C_3-C_7)$-cycloalkyl, hydroxyl, trifluoromethoxy, $(C_1-C_4)$-alkoxy, azetidinyl, oxetanyl, tetrahydrofuranyl and pyrrolidinyl, $G^4$ is $CH_2$, C=O or $SO_2$,
$K^1$ is $CH_2$ or O,
$K^2$ is $CH_2$ or O,
with the proviso that only one of the $K^1$ and $K^2$ groups is O,
$D^1$, $D^2$, $D^3$ and $D^4$ are each independently $CR^{23}$ or N,
in which
$R^{23}$ is hydrogen, halogen, $(C_1-C_6)$-alkyl or $(C_3-C_7)$-cycloalkyl, with the proviso that not more than 2 of the $D^1$, $D^2$, $D^3$ and $D^4$ groups are N,
$R^{24}$ is fluorine or methyl,
n is a number 0 or 1,
$R^{10}$ to is $(C_1-C_4)$-alkyl or $(C_3-C_7)$-cycloalkyl,
in which $(C_1-C_4)$-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl,
$R^{13}$ is hydrogen, $(C_1-C_4)$-alkyl or $(C_3-C_7)$-cycloalkyl,
$R^{15}$ is hydrogen, $(C_1-C_6)$-alkyl or $(C_3-C_7)$-cycloalkyl,
in which $(C_1-C_6)$-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl,
$R^{20}$ is hydrogen, $(C_1-C_6)$-alkyl, $(C_3-C_7)$-cycloalkyl or $(C_1-C_4)$-alkylcarbonyl, in which $(C_1-C_6)$-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl,
$R^{21}$ is hydrogen, $(C_1-C_6)$-alkyl, $(C_3-C_7)$-cycloalkyl or $(C_1-C_4)$-alkylsulphonyl,
$R^{22A}$ is hydrogen or $(C_1-C_4)$-alkyl,
$R^{22B}$ is hydrogen or $(C_1-C_4)$-alkyl,
or
$R^{22A}$ and $R^{22B}$ together with the carbon atom to which they are bonded form a carbonyl group,
and the salts, solvates and solvates of the salts thereof.
Preference is given in the context of the present invention to compounds of the formula (I) in which
$R^1$ is hydrogen, methyl or ethyl,
$R^2$ is a group of the formula

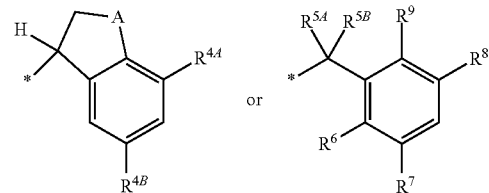

where
* is the attachment site to the uracil nitrogen atom,
A is —$CH_2$—, —$CH_2$—$CH_2$—, —O—$CH_2$-## or oxygen,
in which
## is the attachment site to the phenyl ring,
$R^{4A}$ is hydrogen, fluorine, chlorine, trifluoromethyl or methyl,
$R^{4B}$ is hydrogen, fluorine, chlorine, trifluoromethyl or methyl,
with the proviso that at least one of the $R^{4A}$ and $R^{4B}$ radicals is not hydrogen, $R^{5A}$ is hydrogen,
$R^{5B}$ is hydrogen,
$R^6$ is hydrogen,
$R^7$ is hydrogen,
$R^8$ is fluorine, chlorine, difluoromethyl, trifluoromethyl or methyl,
$R^9$ is fluorine, chlorine, difluoromethyl, trifluoromethyl or methyl,
$R^3$ is a group of the formula

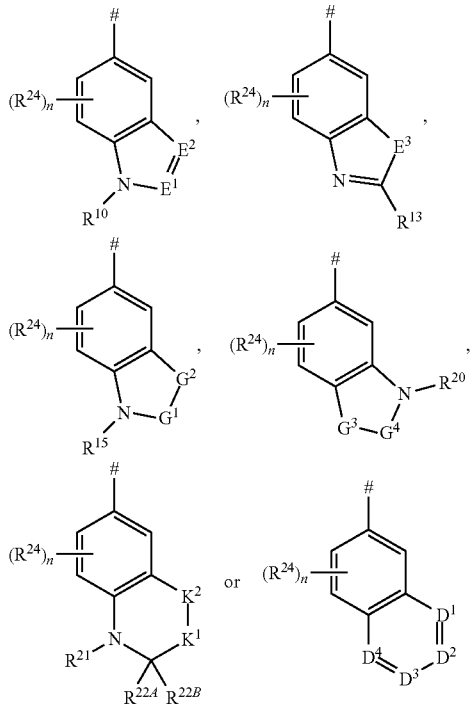

where
# is the attachment site to the uracil nitrogen atom,
$E^1$ is $CR^{11}$ or N,
  in which
    $R^{11}$ is hydrogen, $(C_1-C_4)$-alkyl, $(C_3-C_7)$-cycloalkyl or aminocarbonyl,
$E^2$ is $CR^{12}$ or N,
  in which
    $R^{12}$ is hydrogen, $(C_1-C_4)$-alkyl or $(C_3-C_7)$-cycloalkyl,
$E^3$ is $NR^{14}$ or S,
  in which
    $R^{14}$ is hydrogen, $(C_1-C_4)$-alkyl or $(C_3-C_7)$-cycloalkyl,
$G^1$ is C=O or $SO_2$,
$G^2$ is $CR^{16A}R^{16B}$, $NR^{17}$, O or S.
  in which
    $R^{16A}$ is hydrogen, fluorine, $(C_1-C_4)$-alkyl or hydroxyl,
    $R^{16B}$ is hydrogen, fluorine, chlorine, $(C_1-C_4)$-alkyl or trifluoromethyl,
    or
    $R^{16A}$ and $R^{16B}$ together with the carbon atom to which they are bonded form a 3- to 6-membered carbocycle,
    $R^{17}$ is hydrogen, $(C_1-C_6)$-alkyl, $(C_3-C_7)$-cycloalkyl or $(C_1-C_4)$-alkoxycarbonyl, in which $(C_1-C_6)$-alkyl may be substituted by 1 to 3 substituents independently selected from the group of fluorine, trifluoromethyl, cyano, $(C_3-C_7)$-cycloalkyl, hydroxyl, trifluoromethoxy, $(C_1-C_4)$-alkoxy, azetidinyl, oxetanyl, tetrahydrofuranyl and pyrrolidinyl,
$G^3$ is $CR^{18A}R^{18B}$, $NR^{19}$, O or S,
  in which
    $R^{18A}$ is hydrogen, fluorine, $(C_1-C_4)$-alkyl or hydroxyl,
    $R^{18B}$ is hydrogen, fluorine, chlorine, $(C_1-C_4)$-alkyl or trifluoromethyl,
    or
    $R^{18A}$ and $R^{18B}$ together with the carbon atom to which they are bonded form a 3- to 6-membered carbocycle,
    $R^{19}$ is hydrogen, $(C_1-C_6)$-alkyl, $(C_3-C_7)$-cycloalkyl or $(C_1-C_4)$-alkoxycarbonyl, in which $(C_1-C_6)$-alkyl may be substituted by 1 to 3 substituents independently selected from the group of fluorine, trifluoromethyl, cyano, $(C_3-C_7)$-cycloalkyl, hydroxyl, trifluoromethoxy, $(C_1-C_4)$-alkoxy, azetidinyl, oxetanyl, tetrahydrofuranyl and pyrrolidinyl,
$G^4$ is $CH_2$, C=O or $SO_2$,
$K^1$ is $CH_2$ or O,
$K^2$ is $CH_2$ or O,
with the proviso that only one of the $K^1$ and $K^2$ groups is O,
$D^1$, $D^2$, $D^3$ and $D^4$ are each independently $CR^{23}$ or N,
  in which
    $R^{23}$ is hydrogen, halogen, $(C_1-C_6)$-alkyl or $(C_3-C_7)$-cycloalkyl,
with the proviso that not more than 2 of the $D^1$, $D^2$, $D^3$ and $D^4$ groups are N,
$R^{24}$ is fluorine or methyl,
n is a number 0 or 1,
$R^{10}$ is $(C_1-C_4)$-alkyl or $(C_3-C_7)$-cycloalkyl,
  in which $(C_1-C_4)$-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl,
$R^{13}$ is hydrogen, $(C_1-C_4)$-alkyl or $(C_3-C_7)$-cycloalkyl,
$R^{15}$ is hydrogen, $(C_1-C_6)$-alkyl or $(C_3-C_7)$-cycloalkyl,
  in which $(C_1-C_6)$-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl,
$R^{20}$ is hydrogen, $(C_1-C_6)$-alkyl, $(C_3-C_7)$-cycloalkyl or $(C_1-C_4)$-alkylcarbonyl,
  in which $(C_1-C_6)$-alkyl may be substituted by 1 or 2 substituents independently selected from the group of fluorine, trifluoromethyl, cyclopropyl, cyclobutyl, hydroxyl, methoxy, ethoxy, azetidinyl, oxetanyl, tetrahydrofuranyl and pyrrolidinyl,
$R^{21}$ is hydrogen, $(C_1-C_6)$-alkyl, $(C_3-C_7)$-cycloalkyl or $(C_1-C_4)$-alkylsulphonyl,
$R^{22A}$ is hydrogen or $(C_1-C_4)$-alkyl,
$R^{22B}$ is hydrogen or $(C_1-C_4)$-alkyl,
or
$R^{22A}$ and $R^{22B}$ together with the carbon atom to which they are bonded form a carbonyl group,
and the salts, solvates and solvates of the salts thereof.

Particular preference is given in the context of the present invention to compounds of the formula (I) in which
$R^1$ is hydrogen,
$R^2$ is a group of the formula

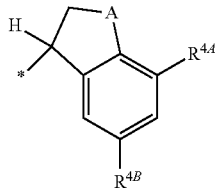

where
* is the attachment site to the uracil nitrogen atom,
A is —CH$_2$—,
$R^{4A}$ is chlorine or trifluoromethyl,
$R^{4B}$ is hydrogen,
$R^3$ is a group of the formula

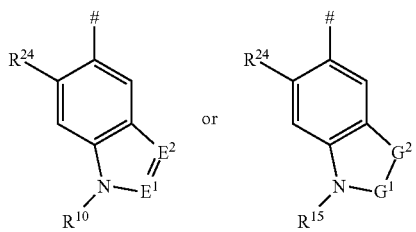

where
# is the attachment site to the uracil nitrogen atom,
$E^1$ is $CR^{11}$
  in which
  $R^{11}$ is hydrogen,
$E^2$ is N,
$G^1$ is C=O,
$G^2$ is $CR^{16A}R^{16B}$, $NR^{17}$, O or S,
  in which
  $R^{16A}$ is hydrogen, fluorine, methyl or hydroxyl,
  $R^{16B}$ is hydrogen, fluorine, methyl or trifluoromethyl,
  or
  $R^{16A}$ and $R^{16B}$ together with the carbon atom to which they are bonded form a cyclopropyl ring,
  $R^{17}$ is hydrogen, $(C_1-C_4)$-alkyl or $(C_3-C_5)$-cycloalkyl,
    in which $(C_1-C_4)$-alkyl may be substituted by 1 to 3 substituents independently selected from the group of fluorine, trifluoromethyl, cyano, cyclopropyl, cyclobutyl, hydroxyl, trifluoromethoxy, methoxy, ethoxy, azetidinyl, oxetanyl, tetrahydrofuranyl and pyrrolidinyl,
$R^{24}$ is hydrogen or fluorine,
$R^{10}$ is $(C_1-C_4)$-alkyl,
$R^{15}$ is hydrogen, methyl or ethyl,
  in which methyl and ethyl may be substituted by 1 substituent selected from the group of fluorine, trifluoromethyl and cyclopropyl,
and the salts, solvates and solvates of the salts thereof.

Preference is also given in the context of the present invention to compounds of the formula (I) in which
$R^1$ is hydrogen,
$R^2$ is a group of the formula

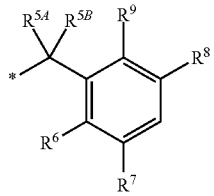

where
* is the attachment site to the uracil nitrogen atom,
$R^{5A}$ is hydrogen,
$R^{5B}$ is hydrogen,
$R^6$ is hydrogen,
$R^7$ is hydrogen,
$R^8$ is fluorine, chlorine or trifluoromethyl,
$R^9$ is fluorine, chlorine, trifluoromethyl or methyl,
$R^3$ is a group of the formula

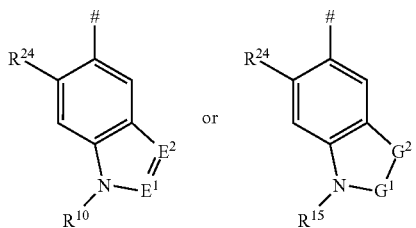

where
# is the attachment site to the uracil nitrogen atom,
$E^1$ is $CR^{11}$
  in which
  $R^{11}$ is hydrogen,
$E^2$ is N,
$G^1$ is C=O,
$G^2$ is $CR^{16A}R^{16B}$, $NR^{17}$, O or S,
  in which
  $R^{16A}$ is hydrogen, fluorine, methyl or hydroxyl,
  $R^{16B}$ is hydrogen, fluorine, methyl or trifluoromethyl,
  or
  $R^{16A}$ and $R^{16B}$ together with the carbon atom to which they are bonded form a cyclopropyl ring,
  $R^{17}$ is hydrogen, $(C_1-C_4)$-alkyl or $(C_3-C_5)$-cycloalkyl,
    in which $(C_1-C_4)$-alkyl may be substituted by 1 to 3 substituents independently selected from the group of fluorine, trifluoromethyl, cyano, cyclopropyl, cyclobutyl, hydroxyl, trifluoromethoxy, methoxy, ethoxy, azetidinyl, oxetanyl, tetrahydrofuranyl and pyrrolidinyl,
$R^{24}$ is hydrogen or fluorine,
$R^{10}$ is $(C_1-C_4)$-alkyl,
$R^{15}$ is hydrogen, methyl or ethyl,
  in which methyl and ethyl may be substituted by 1 substituent selected from the group of fluorine, trifluoromethyl and cyclopropyl,
and the salts, solvates and solvates of the salts thereof.

Preference is also given in the context of the present invention to compounds of the formula (I) in which
$R^1$ is hydrogen, methyl or ethyl,
$R^2$ is a group of the formula

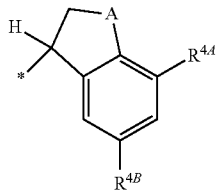

where
* is the attachment site to the uracil nitrogen atom,
A is —CH$_2$—,
$R^{4A}$ is chlorine or trifluoromethyl,
$R^{4B}$ is hydrogen,
and the salts, solvates and solvates of the salts thereof.

Preference is also given in the context of the present invention to compounds of the formula (I) in which
$R^3$ is a group of the formula

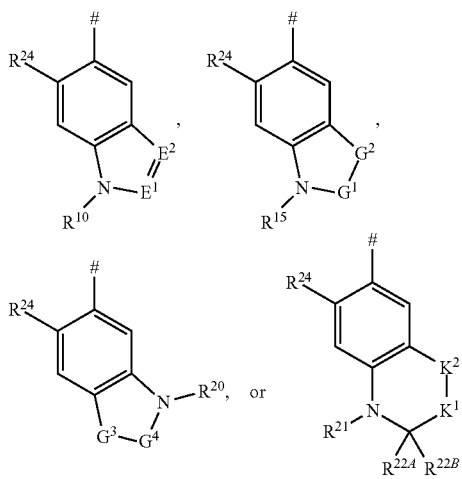

where
# is the attachment site to the uracil nitrogen atom,
$E^1$ is $CR^{11}$ or N,
in which
$R^{11}$ is hydrogen, methyl, ethyl or aminocarbonyl,
$E^2$ is $CR^{12}$ or N,
in which
$R^{12}$ is hydrogen,
$G^1$ is C=O or SO$_2$,
$G^2$ is $CR^{16A}R^{16B}$, $NR^{17}$, O or S,
in which
$R^{16A}$ is hydrogen, fluorine, methyl or hydroxyl,
$R^{16B}$ is hydrogen, fluorine, chlorine, methyl or trifluoromethyl,
or
$R^{16A}$ and $R^{16B}$ together with the carbon atom to which they are bonded form a cyclopropyl ring,
$R^{17}$ is hydrogen, (C$_1$-C$_4$)-alkyl, cyclopropyl or cyclobutyl,
in which (C$_1$-C$_4$)-alkyl may be substituted by 1 or 2 substituents independently selected from the group of fluorine, trifluoromethyl, cyclopropyl, cyclobutyl, hydroxyl, azetidinyl and oxetanyl,
$G^3$ is $CR^{18A}R^{18B}$
in which
$R^{18A}$ is hydrogen, fluorine, methyl or hydroxyl,
$R^{18B}$ is hydrogen, fluorine, methyl or trifluoromethyl,
$G^4$ is C=O,
$K^1$ is CH$_2$ or O,
$K^2$ is CH$_2$,
$R^{24}$ is hydrogen, fluorine or methyl,
$R^{10}$ is methyl or ethyl,
$R^{15}$ is methyl or ethyl,
$R^{20}$ is hydrogen, methyl, ethyl or methylcarbonyl,
$R^{21}$ is methyl or ethyl,
$R^{22A}$ and $R^{22B}$ together with the carbon atom to which they are bonded form a carbonyl group,
and the salts, solvates and solvates of the salts thereof.

Preference is also given in the context of the present invention to compounds of the formula (I) in which
$R^2$ is a group of the formula

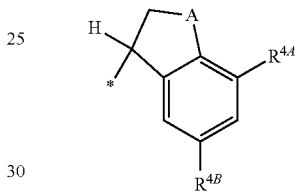

where
* is the attachment site to the uracil nitrogen atom,
A is —CH$_2$—,
$R^{4A}$ is chlorine or trifluoromethyl,
$R^{4B}$ is hydrogen,
and the carbon atom bonded to the uracil nitrogen atom has R configuration,
and the salts, solvates and solvates of the salts thereof.

Preference is also given in the context of the present invention to compounds of the formula (I) in which
$R^2$ is a group of the formula

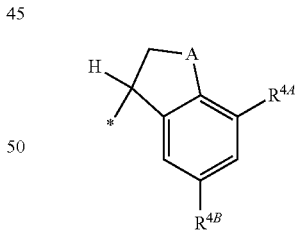

where
* is the attachment site to the uracil nitrogen atom,
A is —CH$_2$—,
$R^{4A}$ is hydrogen, fluorine, chlorine, trifluoromethyl or methyl,
$R^{4B}$ is hydrogen, fluorine, chlorine, trifluoromethyl or methyl,
with the proviso that at least one of the $R^{4A}$ and $R^{4B}$ radicals is not hydrogen,
and the carbon atom bonded to the uracil nitrogen atom has R configuration,
and the salts, solvates and solvates of the salts thereof.

The individual radical definitions specified in the particular combinations or preferred combinations of radicals are, independently of the particular combinations of the radicals specified, also replaced as desired by radical definitions of other combinations.

Very particular preference is given to combinations of two or more of the preferred ranges mentioned above.

The invention further provides a process for preparing inventive compounds of the formula (I), characterized in that

[A] a compound of the formula (II)

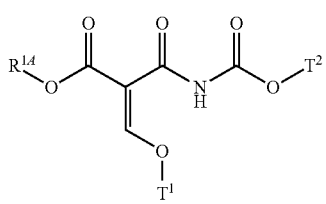

in which
$R^{1A}$ is $(C_1-C_4)$-alkyl,
$T^1$ is $(C_1-C_4)$-alkyl
$T^2$ is $(C_1-C_4)$-alkyl
is reacted in an inert solvent, optionally in the presence of a suitable base, with a compound of the formula (III)

in which $R^3$ is as defined above
to give a compound of the formula (IV)

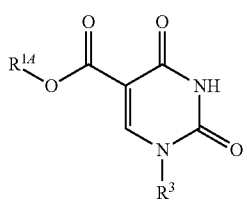

in which $R^{1A}$ and $R^3$ are each as defined above,
this is then reacted in an inert solvent, in the presence of a suitable base, with a compound of the formula (V)

in which $R^2$ is as defined above
and
$X^1$ is hydroxyl or a suitable leaving group, especially chlorine, bromine or iodine
to give a compound of the formula (I-1)

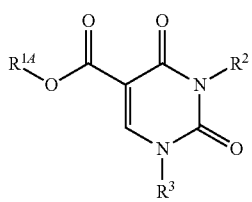

in which $R^{1A}$, $R^2$ and $R^3$ are each as defined above,
or

[B] a compound of the formula (VI)

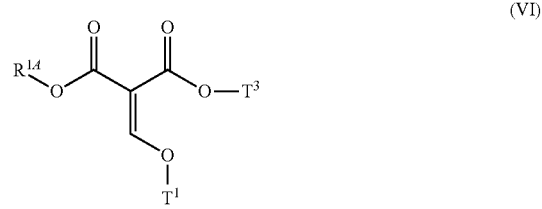

in which $R^{1A}$ and $T^1$ are each as defined above and
$T^3$ is $(C_1-C_4)$-alkyl
is converted in an inert solvent or else without solvent with a compound of the formula (III) to a compound of the formula (VII)

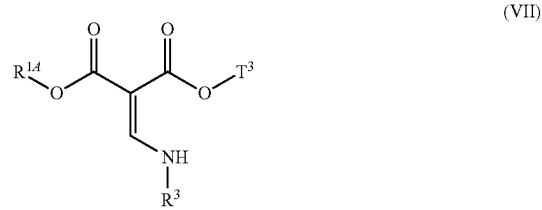

in which $R^{1A}$, $R^3$ and $T^3$ are each as defined above,
this is subsequently reacted in an inert solvent with chlorosulphonyl isocyanate to give a compound of the formula (IV) and this is subsequently converted analogously to process [A] to a compound of the formula (I-1), or

[C] a compound of the formula (VIII)

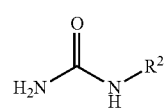

in which $R^2$ is as defined above
is reacted in an inert solvent with a compound of the formula (IX)

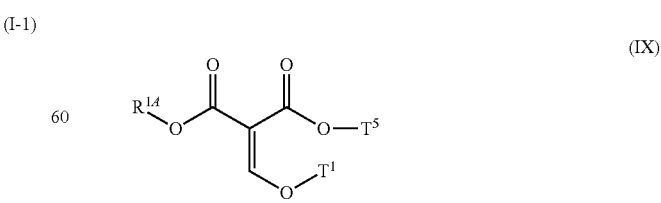

in which $R^{1A}$ and $T^1$ are each as defined above and
$T^5$ is $(C_1-C_4)$-alkyl and cyclized in the presence of a suitable base to give a compound of the formula (X)

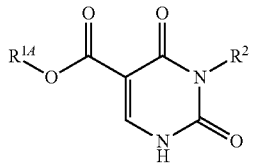
(X)

in which $R^{1A}$ and $R^2$ are each as defined above,
and this is then reacted in an inert solvent, in the presence of a suitable catalyst and a suitable base, with a compound of the formula (XI)

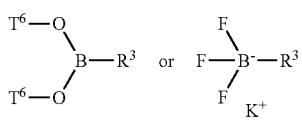
(XI)

in which $R^3$ is as defined above, and
$T^6$ is hydrogen, $(C_1-C_4)$-alkyl, or the two $T^6$ radicals together form a —$C(CH_3)_2$—$C(CH_3)_2$ bridge
to give a compound of the formula (I-1),
or
[D] a compound of the formula (I-1) is hydrolysed in an inert solvent in the presence of a suitable acid or base to give a compound of the formula (I-2)

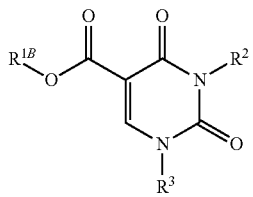
(I-2)

in which $R^2$ and $R^3$ are each as defined above, and
$R^{1B}$ is hydrogen,
any protecting groups are detached and/or the compounds of the formulae (I-1) and (I-2) are, where appropriate, converted with the appropriate (i) solvents and/or (ii) bases or acids to the solvates, salts and/or solvates of the salts thereof.

The compounds of the formulae (I-1) and (I-2) together form the group of inventive compounds of the formula (I).

Inert solvents for the process steps (II)+(III)→(IV), (VI)+(III)→(VII) and (VIII)+(IX)→(X) are, for example, ethers such as diethyl ether, dioxane, tetrahydrothran, glycol dimethyl ether or diethylene glycol dimethyl ether, hydrocarbons such as benzene, toluene, xylene, hexane, cyclohexane or mineral oil fractions, halohydrocarbons such as dichloromethane, 1,2-dichloroethane, trichloroethylene or chlorobenzene, alcohols such as methanol, ethanol, n-propanol, isopropanol or n-butanol, or other solvents such as dimethylformamide, dimethyl sulphoxide, N,N'-dimethylpropyleneurea (DMPU), N-methylpyrrolidinone (NMP), pyridine, acetone, 2-butanone or acetonitrile. It is likewise possible to use mixtures of the solvents mentioned. Preference is given to using ethanol.

Suitable bases for the process steps (II)+(III)→(IV) and (VIII)+(IX)→(X) are alkali metal alkoxides such as sodium or potassium methoxide, sodium or potassium ethoxide or sodium or potassium tert-butoxide, alkali metal hydrides such as sodium or potassium hydride, amides such as sodium amide, lithium or potassium bis(trimethylsilyl)amide or lithium diisopropylamide, or organic bases such as triethylamine, diisopropylethylamine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®) or phosphazene bases, for example 1-[N-tert-butyl-P,P-di(pyrrolidin-1-yl)-phosphorimidoyl]pyrrolidine or N''-tert-butyl-N,N,N',N'-tetramethyl-N''-[tris(dimethylamino)-lambda$^5$-phosphanylidene]phosphoramide imide. Preference is given to sodium ethoxide and potassium tert-butoxide.

The base is generally used here in an amount of 1 to 5 mol, preferably in an amount of 1.2 to 3 mol, based on 1 mol of the compound of the formula (II) or (IX).

The conversions (II)+(III)→(IV), (VI)+(III)→(VH) and (VIII)+(IX)→(X) are effected generally within a temperature range from 0° C. to +150° C., preferably at +20° C. to +120° C., optionally in a microwave. The reaction can be performed at standard, elevated or reduced pressure (for example from 0.5 to 5 bar). In general, standard pressure is employed.

If $X^1$=OH, the conversion (IV)+(V)→(I-1) is effected under Mitsunobu conditions [see: a) Hughes, D. L. "The Mitsunobu Reaction" *Organic Reactions*; John Wiley & Sons, Ltd, 1992, vol. 42, p. 335. b) Hughes, D. L. *Org. Prep. Proceed. Int.* 1996, 28, 127]. The Mitsunobu reaction is effected using triphenylphosphine, or tri-n-butylphosphine, 1,2-bis(diphenylphosphino)ethane (DPPE), diphenyl(2-pyridyl)phosphine (Ph2P-Py), (p-dimethylaminophenyl)diphenylphosphine (DAP-DP), tris(4-dimethylaminophenyl)phosphine (tris-DAP), and a suitable dialkyl azodicarboxylate, tor example diethyl azodicarboxylate (DEAD), diisopropyl azodicarboxylate (DIAD), di-tert-butyl azodicarboxylate, N,N,N'N'-tetramethylazodicarboxamide (TMAD), 1,1'-(azodicarbonyl)dipiperidine (ADDP) or 4,7-dimethyl-3,5,7-hexahydro-1,2,4,7-tetrazocin-3,8-dione (DHTD). Preference is given to using triphenylphosphine and diisopropyl azodicarboxylate (DIAD).

Inert solvents for the Mitsunobu reaction (IV)+(V)→(I-1) are, for example, ethers such as tetrahydrofuran, diethyl ether, hydrocarbons such as benzene, toluene, xylene, halohydrocarbons such as dichloromethane, dichloroethane or other solvents such as acetonitrile or dimethylformamide (DMF). It is likewise possible to use mixtures of the solvents mentioned. Preference is given to using THF or a mixture of THF and DMF.

The Mitsunobu reaction (IV)+(V)→(I-1) is effected generally within a temperature range from −78° C. to +180° C., preferably at 0° C. to +50° C., optionally in a microwave. The conversions can be performed at standard, elevated or reduced pressure (for example from 0.5 to 5 bar).

If $X^1$ is a suitable leaving group, the conversion (IV)+(V)→(I-1) is effected under conditions for a nucleophilic substitution. In that case, inert solvents for the process step (IV)+(V)→(I-1) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, 1,2-dichloroethane, trichloroethylene or chlorobenzene, or other solvents such as dimethylformamide, dimethyl sulphoxide, N,N'-dimethylpropyleneurea (DMPU), N-methylpyrrolidinone (NMP), pyridine, acetone, 2-butanone or acetonitrile. It is likewise possible to use mixtures of the solvents mentioned. Preference is given to using acetonitrile, DMF or acetonitrile in a mixture with dimethylformamide.

Suitable bases for the process step (IV)+(V)→(I-1) are customary inorganic bases. These include especially alkali metal or alkaline earth metal carbonates such as lithium, sodium, potassium, calcium or caesium carbonate, optionally with addition of an alkali metal iodide, for example potassium iodide, alkali metal alkoxides such as sodium or potassium methoxide, sodium or potassium ethoxide or sodium or potassium tert-butoxide, alkali metal hydrides such as sodium or potassium hydride, amides such as sodium amide, lithium or potassium bis(trimethylsilyl)amide or lithium diisopropylamide. Preference is given to using potassium carbonate with potassium iodide or sodium hydride.

The base is generally used here in an amount of 1 to 5 mol, preferably in an amount of 1.2 to 3 mol, based on 1 mol of the compound of the formula (IV).

The conversion (IV)+(V)→(I-1) is effected generally within a temperature range from 0° C., to +100° C., preferably at +20° C. to +80° C., optionally in a microwave. The reaction can be performed at standard, elevated or reduced pressure (for example from 0.5 to 5 bar). In general, standard pressure is employed.

Inert solvents for the process step (VII)→(IV) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, or other solvents such as chlorobenzene, dimethylformamide, dimethyl sulphoxide, N,N'-dimethylpropyleneurea (DMPU), N-methylpyrrolidinone (NMP), pyridine, acetone, 2-butanone or acetonitrile. It is likewise possible to use mixtures of the solvents mentioned. Preference is given to using toluene.

The conversion (VII)→(IV) is effected generally within a temperature range from 0° C. to +150° C., preferably at +20° C. to +120° C., optionally in a microwave. The reaction can be performed at standard, elevated or reduced pressure (for example from 0.5 to 5 bar). In general, standard pressure is employed.

The process step (X)+(XI)→(I-1) is similar to a conversion called the Chan-Lam coupling in the literature. Inert solvents for the process step (X)+(XI)→(I-1) are ethers such as 1,4-dioxane or tetrahydrofuran, halohydrocarbons such as dichloromethane, trichloromethane, 1,2-dichloroethane, or other solvents such as dimethylformamide (DMF), N-methylpyrrolidone (NMP), acetonitrile or dimethyl sulphoxide (DMSO). It is likewise possible to use mixtures of the solvents mentioned. Preference is given to a mixture of acetonitrile and DMSO when (XI) is a boronic ester or a trifluoroborate salt, or dichloromethane when (XI) is a boronic acid. In some cases, the addition of molecular sieve is advantageous.

Suitable bases for the process step (X)+(XI)→(I-1) are pyridine, pyridine derivatives, for example DMAP or organic tertiary amines, for example diisopropylethylamine or triethylamine. Preference is given to triethylamine when (XI) is a boronic ester or a trifluoroborate salt, or pyridine when (XI) is a boronic acid.

Suitable catalysts for the process step (X)+(XI)→(I-1) are copper (II) salts, for example copper(II) acetate or copper(II) triflate, preference being given to copper(II) acetate.

The process step (X)+(XI)→(I-1) is performed under air or under an oxygenous atmosphere.

The reaction (X)+(XI)→(I-1) is generally performed within a temperature range from 0° C. to +150° C., preferably at +20° C. to +80° C.

The hydrolysis of the ester group $R^{1.4}$ of the compound (I-1) to compounds of the formula (I-2) is effected by treating the esters in inert solvents with acids or bases, in which latter case the salts formed at first are converted to the free carboxylic acids by treating with acid. In general, the ester hydrolysis is preferably effected with acids.

Suitable inert solvents for these reactions are water, diethyl ether, tetrahydrofuran, dioxane or glycol dimethyl ether, or other solvents such as acetonitrile, acetic acid, dimethylformamide or dimethyl sulphoxide. It is likewise possible to use mixtures of the solvents mentioned. In the case of a basic ester hydrolysis, preference is given to using mixtures of water with dioxane, tetrahydrofuran or acetonitrile. For the hydrolysis of tert-butyl esters, the solvent used in the case of reaction with trifluoroacetic acid is preferably dichloromethane, and in the case of reaction with hydrogen chloride preferably tetrahydrofuran, diethyl ether or dioxane. For the hydrolysis of other esters under acidic conditions, preference is given to acetic acid or a mixture of acetic acid and water.

Suitable bases are the alkali metal or alkaline earth metal hydrogencarbonates such as sodium or potassium hydrogencarbonate. Preference is given to sodium hydrogencarbonate.

Suitable acids for the ester hydrolysis are generally sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid or mixtures thereof, optionally with addition of water. Preference is given to hydrogen chloride or trifluoroacetic acid in the case of the tert-butyl esters, and to hydrochloric acid in a mixture with acetic acid, and to sulphuric acid in a mixture with acetic acid and water in the case of the methyl esters and ethyl esters.

The ester hydrolysis is effected generally within a temperature range from 0° C. to 180° C., preferably at +20° C. to 120° C.

These conversions can be performed at standard, elevated or reduced pressure (for example from 0.5 to 5 bar). In general, standard pressure is employed in each case.

The preparation of the inventive compounds can be illustrated by way of example by the following synthesis schemes (Schemes 1 to 3):

Scheme 1:

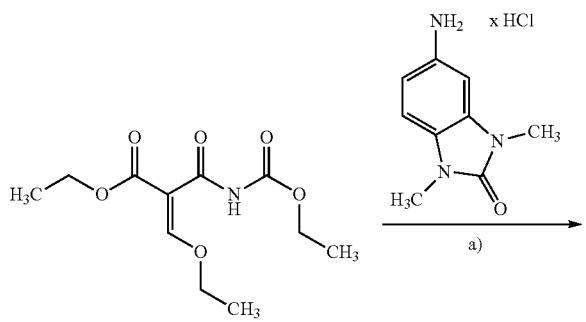

23
-continued
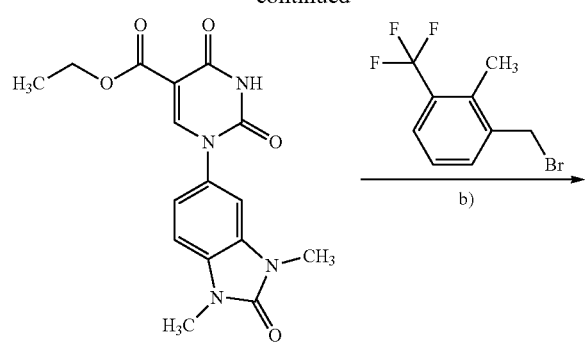
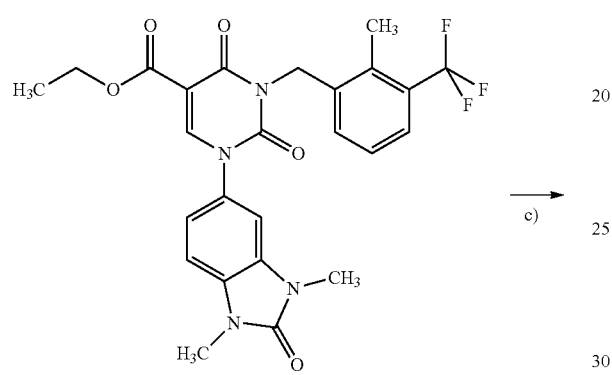
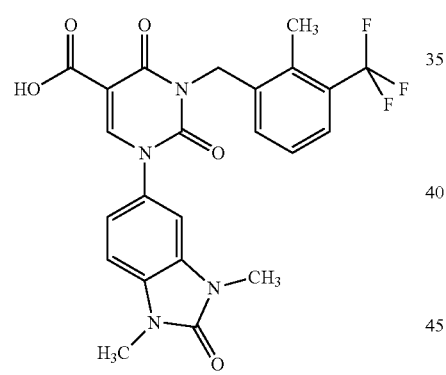
[a]: 1. triethylamine, ethanol, 80° C.; 2. potassium tert-butoxide, 0° C.-80° C.; b): K₂CO₃, KI, DMF; c): acetic acid/hydrochloric acid (2:1), 120° C.].
Scheme 2:
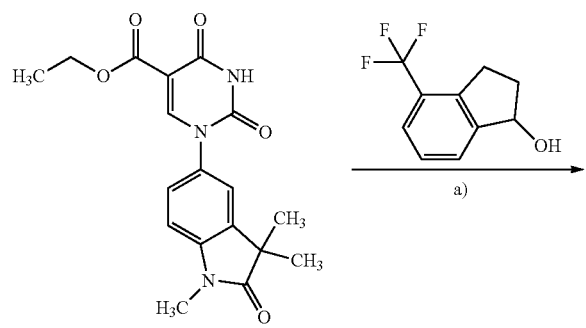
24
-continued
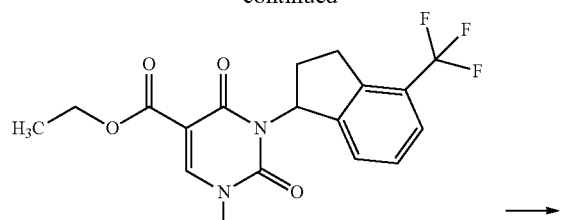
[a]: triphenylphosphine, DIAD, THF/DMF 1:1, 0° C.-RT; b): acetic acid/hydrochloric acid (2:1), 120° C.].
Scheme 3:
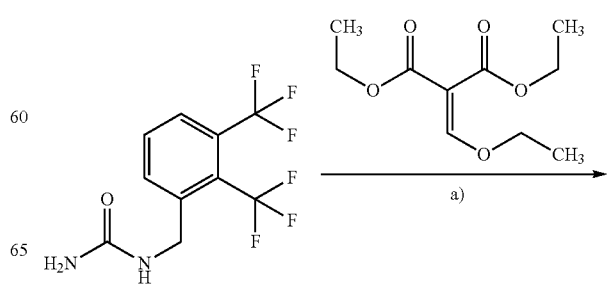

-continued

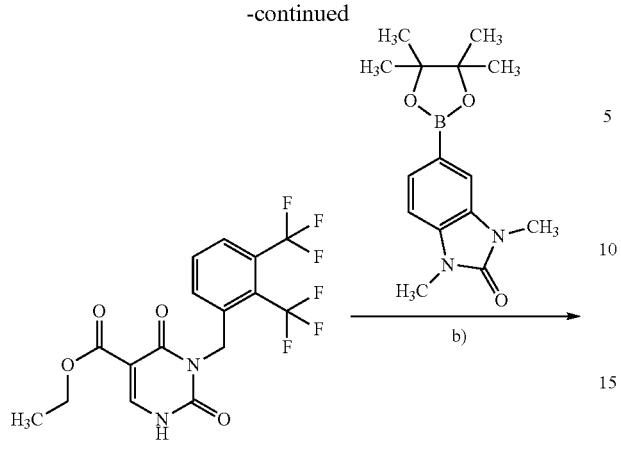

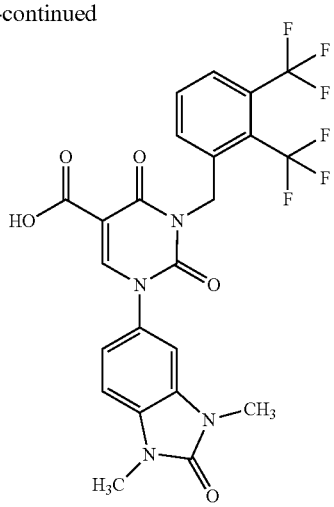

[a): i) 140° C., ii) sodium ethoxide, ethanol, 80° C.; b): Cu(OAc)₂, NEt₃, CH₃CN, DMSO. molecular sieve, 80° C.; c): acetic acid/hydrochloric acid (2:1), 120° C.].

The compounds of the formulae (II), (III), (V), (VI), (VIII), (IX) and (XI) are commercially available or known from the literature, or can be prepared in analogy to processes known from the literature.

Further inventive compounds can optionally also be prepared by conversions of functional groups of individual substituents, especially those listed for $R^3$, proceeding from compounds of the formula (I) obtained by above processes. These conversions are performed as described in the present experimental section, by customary methods known to those skilled in the art and include, for example, reactions such as nucleophilic and electrophilic substitutions, oxidations, reductions, hydrogenations, transition metal-catalysed coupling reactions, eliminations, alkylation, amination, esterification, ester hydrolysis, etherification, ether cleavage, formation of carbonamides, and introduction and removal of temporary protecting groups, The conversion of functional groups can be illustrated by way of example by the following synthesis scheme (Scheme 4):

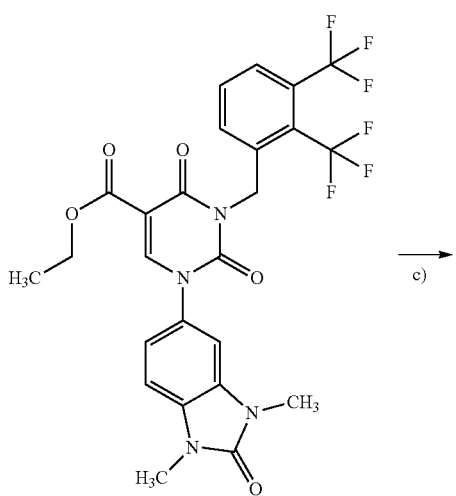

Scheme 4:

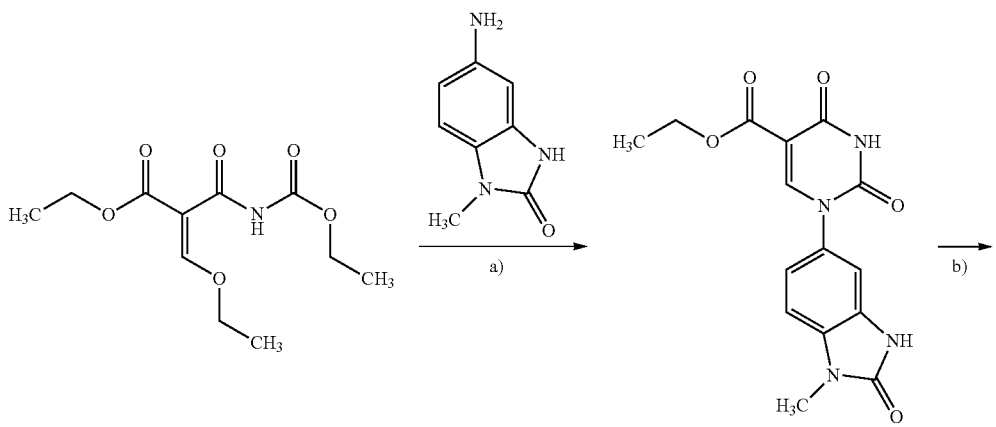

-continued

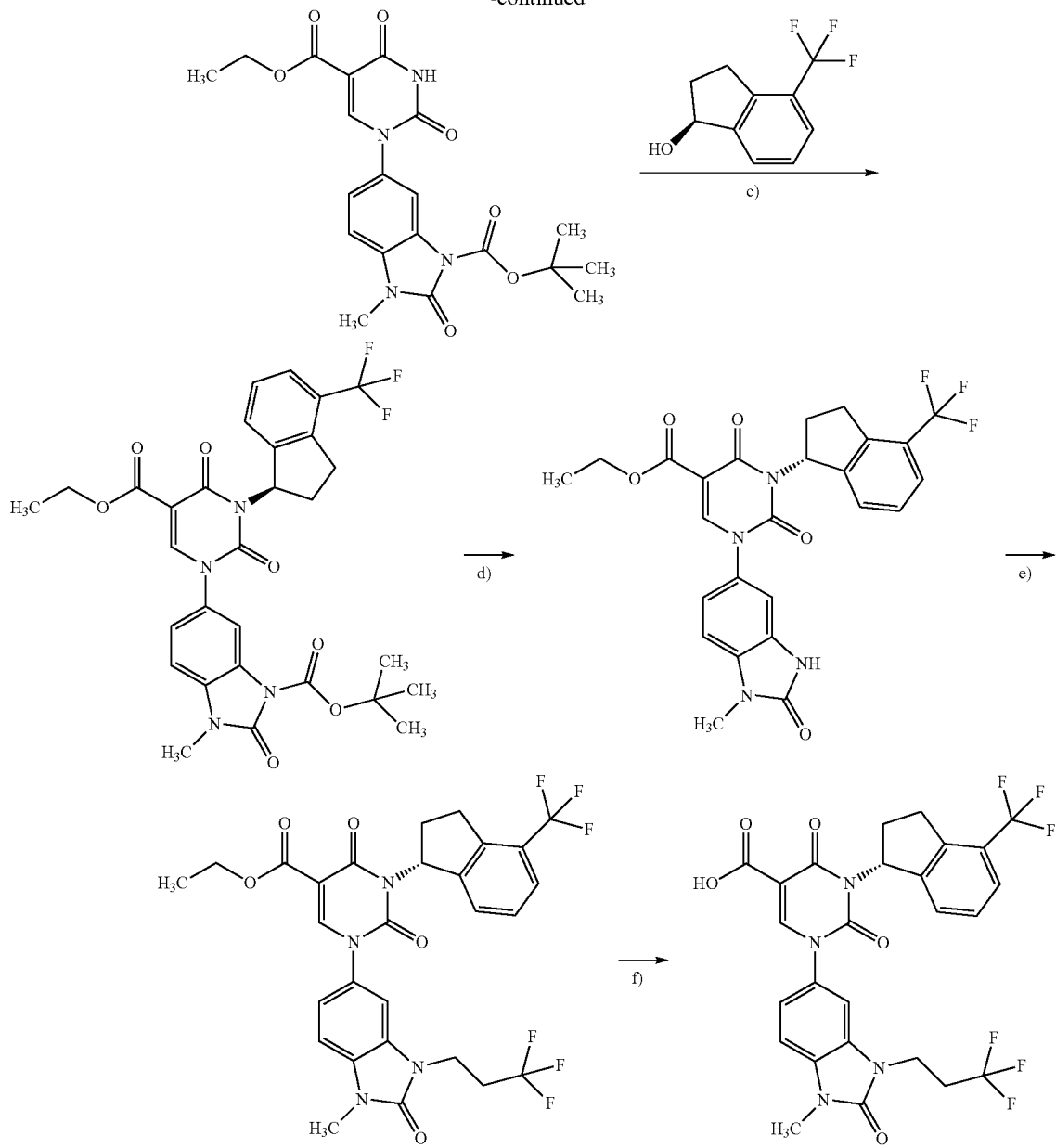

[a): 1. ethanol, 80° C. 2. potassium tert-butoxide 80° C.; b): (ᵗBuOCO)₂O, DMAP, DMF/CH₂Cl₂, RT; c) tri-phenylphosphine, DIAD, THF/DMF 1:1, 0° C.-RT; d) CF₃COOH, CH₂Cl₂, RT; e) CF₃CH₂CH₂Br, Cs₂CO₃, KI, DMF, 60° C.; f): acetic acid/hydrochloric acid (2:1), 120° C.].

The inventive compounds have valuable pharmacological properties and can be used for treatment and/or prophylaxis of diseases in humans and animals.

The inventive compounds are chymase inhibitors and are therefore suitable for treatment and/or prophylaxis of cardiovascular, inflammatory, allergic and/or fibrotic disorders.

In the context of the present invention, disorders of the cardiovascular system or cardiovascular disorders are understood to mean, for example, the following disorders: acute and chronic heart failure, arterial hypertension, coronary heart disease, stable and unstable angina pectoris, myocardial ischaemia, myocardial infarction, shock, atherosclerosis, cardiac hypertrophy, cardiac fibrosis, atrial and ventricular arrhythmias, transitory and ischaemic attacks, stroke, pre-eclampsia, inflammatory cardiovascular disorders, peripheral and cardiac vascular disorders, peripheral perfusion disorders, arterial pulmonary hypertension, spasms of the coronary arteries and peripheral arteries, thromboses, thromboembolic disorders, oedema development, for example pulmonary oedema, cerebral oedema, renal oedema or heart failure-related oedema, and restenoses such as after thrombolysis treatments, percutaneous transluminal angioplasty (PTA), transluminal coronary angioplasty (PTCA), heart transplants and bypass operations, and micro- and macrovascular damage (vasculitis), reperfusion damage, arterial and venous thromboses, microalbuminuria, myocardial insufficiency, endothelial dysfunction, elevated levels of fibrinogen and of low-density LDL elevated concentrations of plasminogen activator/inhibitor 1 (PAI-1).

In the context of the present invention, the term "heart failure" also includes more specific or related types of disease, such as acutely decompensated heart failure, right heart failure, left heart failure, global failure, ischaemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

The inventive compounds are further suitable for the prophylaxis and/or treatment of polycystic kidney disease (PCKD) and of syndrome of inappropriate ADH secretion (SIADH).

Furthermore, the inventive compounds are suitable for treatment and/or prophylaxis of renal disorders, especially of acute and chronic renal insufficiency, and of acute and chronic kidney failure.

In the context of the present invention, the term acute renal insufficiency encompasses acute manifestations of kidney disease, of kidney failure and/or renal insufficiency with and without the need for dialysis, and also underlying or related renal disorders such as renal hypoperfusion, intradialytic hypotension, volume deficiency (e.g. dehydration, blood loss), shock, acute glomerulonephritis, haemolytic-uraemic syndrome (HUS), vascular catastrophe (arterial or venous thrombosis or embolism), cholesterol embolism, acute Bence-Jones kidney in the event of plasmacytoma, acute supravesicular or subvesicular efflux obstructions, immunological renal disorders such as kidney transplant rejection, immune complex-induced renal disorders, tubular dilatation, hyperphosphataemia and/or acute renal disorders characterized by the need for dialysis, including in the case of partial resections of the kidney, dehydration through forced diuresis, uncontrolled blood pressure rise with malignant hypertension, urinary tract obstruction and infection and amyloidosis, and systemic disorders with glomerular factors, such as rheumatological-immunological systemic disorders, for example lupus erythematodes, renal artery thrombosis, renal vein thrombosis, analgesic nephropathy and renal tubular acidosis, and x-ray contrast agent- and medicament-induced acute interstitial renal disorders.

In the context of the present invention, the term chronic renal insufficiency encompasses chronic manifestations of kidney disease, of kidney failure and/or renal insufficiency with and without the need for dialysis, and also underlying or related renal disorders such as renal hypoperfusion, intradialytic hypotension, obstructive uropathy, glomerulopathy, glomerular and tubular proteinuria, renal oedema, haematuria, primary, secondary and chronic glomerulonephritis, membranous and membranoprolithrative glomerulonephritis, Alport syndrome, glomerulosclerosis, tubulointerstitial disorders, nephropathic disorders such as primary and congenital kidney disease, renal inflammation, immunological renal disorders such as kidney transplant rejection, immune complex-induced renal disorders, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, glomerular and arteriolar lesions, tubular dilatation, hyperphosphataemia and/or the need for dialysis, and in the event of renal cell carcinoma, after partial resections of the kidney, dehydration through forced diuresis, uncontrolled blood pressure rise with malignant hypertension, urinary tract obstruction and infection and amyloidosis, and systemic disorders with glomerular factors, such as rheumatological-immunological systemic disorders, for example lupus erythematodes, and also renal artery stenosis, renal artery thrombosis, renal vein thrombosis, analgesic nephropathy and renal tubular acidosis. In addition, x-ray contrast agent- and medicament-induced chronic interstitial renal disorders, metabolic syndrome and dyslipidaemia. The present invention also encompasses the use of the inventive compounds for treatment and/or prophylaxis of sequalae of renal insufficiency, for example pulmonary oedema, heart failure, uraemia, anaemia, electrolyte disturbances (for example hypercalaemia, hyponatraemia) and disturbances in bone and carbohydrate metabolism.

In addition, the inventive compounds are also suitable for treatment and/or prophylaxis of pulmonary arterial hypertension (PAH) and other forms of pulmonary hypertension (PH), of chronic obstructive pulmonary disease (COPD), of acute respiratory distress syndrome (ARDS), of acute lung injury (ALI), of alpha-1-antitrypsin deficiency (AATD), of pulmonary fibrosis, of pulmonary emphysema (for example pulmonary emphysema caused by cigarette smoke), of cystic fibrosis (CF), of acute coronary syndrome (ACS), heart muscle inflammation (myocarditis) and other autoimmune cardiac disorders (pericarditis, endocarditis, valvolitis, aortitis, cardiomyopathy), cardiogenic shock, aneurysms, sepsis (SIRS), multiple organ failure (MODS, MOF), inflammation disorders of the kidney, chronic intestinal disorders (IBD, Crohn's Disease, UC), pancreatitis, peritonitis, rheumatoid disorders, inflammatory skin disorders and inflammatory eye disorders.

The inventive compounds can additionally be used for treatment and/or prophylaxis of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of Bronchiolitis obliterans, bronchiectasis, pneumonia, idiopathic interstitial pneumonia, farmer's lung and related disorders, coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

In addition, the inventive compounds are suitable for treatment and/or prophylaxis of fibrotic disorders of the internal organs, for example of the lung, the heart, the kidney, the bone marrow and in particular the liver, and also of dermatological fibroses and fibrotic eye disorders. In the context of the present invention, the term "fibrotic disorders" encompasses particularly the following terms: hepatic fibrosis, cirrhosis of the liver, pulmonary fibrosis, endomyocardial fibrosis, cardiomyopathy, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy and proliferative vitroretinopathy.

In addition, the inventive compounds are suitable for control of postoperative scarring, for example resulting from glaucoma operations.

In addition, the inventive compounds can likewise be used cosmetically in the event of ageing and hornifying skin.

In addition, the inventive compounds can also be used for treatment and/or prophylaxis of dyslipidaemias (hypercholesterolaemia, hypeitiiglyceridaemia, elevated concentrations of the postprandial plasma triglycerides, hypoalphalipoproteinaemia, combined hyperlipidaemias), nephropathy and neuropathy), cancers (skin cancer, brain tumours, breast cancer, bone marrow tumours, leukaemias, liposarcomas, carcinoma of the gastrointestinal tract, of the liver, pancreas, lung, kidney, urinary tract, prostate and genital tract, and also malignant tumours in the lymphoproliferative system, for example Hodgkin's and non-Hodgkin's lymphoma), of disorders of the gastrointestinal tract and of the abdomen (glossitis, gingivitis, periodontitis, oesophagitis, eosinophilic gastroenteritis, mastocytosis, Crohn's disease, colitis, proctitis, pruritus ani, diarrhoea, coeliac disease, hepatitis, chronic hepatitis, hepatic fibrosis, cirrhosis of the liver, pancreatitis and cholecystitis), skin disorders (allergic skin disorders, psoriasis, acne, eczema, neurodermitis, various forms of dermatitis, and also keratitis, bullosis, vasculitis, cellulitis, panniculitis, lupus erythematodes, erythema, lymphoma, skin cancer, Sweet's syndrome, Weber-Christian syndrome, scarring, warts, chillblains), of disorders of the skeletal bone and of the joints, and also of the skeletal muscle (various forms of arthritis, various forms of arthropathies, scleroderma and of further disorders with an inflammatory or immunological component, for example paraneoplastic syndrome, in the event of rejection reactions after organ transplants and for wound healing and angiogenesis, especially in the case of chronic wounds.

The inventive compounds of the formula (I) are additionally suitable for treatment and/or prophylaxis of ophthalmologic disorders, for example glaucoma, normotensive glaucoma, high intraocular pressure and combinations thereof, of age-related macular degeneration (AMD), of dry or nonexudative AMD, moist or exudative or neovascular AMD, choroidal neovascularization (CNV), detached retina, diabetic retinopathy, atrophic lesions to the retinal pigment epithelium (RPE), hypertrophic lesions to the retinal pigment epithelium (RPE), diabetic macular oedema, retinal vein occlusion, choroidal retinal vein occlusion, macular oedema, macular oedema due to retinal vein occlusion, angiogenesis at the front of the eye, for example corneal angiogenesis, for example following keratitis, cornea transplant or keratoplasty, corneal angiogenesis due to hypoxia (extensive wearing of contact lenses), pterygium conjunctiva, subretinal oedema and intraretinal oedema.

In addition, the inventive compounds of the formula (I) for treatment and/or prophylaxis of elevated and high intraocular pressure resulting from traumatic hyphaema, periorbital oedema, postoperative viscoelastic retention, intraocular inflammation, use of corticosteroids, pupillary block or idiopathic causes, and of elevated intraocular pressure following trabeculectomy and due to pre-operative conditions.

The present invention further provides tor the use of the inventive compounds tor treatment and/or prophylaxis of disorders, especially of the aforementioned disorders.

The present invention further provides for the use of the inventive compounds for production of a medicament for treatment and/or prophylaxis of disorders, especially of the aforementioned disorders.

The present invention further provides the inventive compounds for use in a method for treatment and/or prophylaxis of heart failure, pulmonary hypertension, chronic obstructive pulmonary disease, asthma, kidney failure, nephropathy, fibrotic disorders of the internal organs and dermatological fibroses.

The inventive compounds can be employed alone or, if required, in combination with other active ingredients. The present invention therefore further provides medicaments comprising at least one of the inventive compounds and one or more further active ingredients, especially for treatment and/or prophylaxis of the aforementioned disorders. Preferred examples of suitable active ingredient combinations include:

compounds which inhibit the signal transduction cascade, by way of example and with preference from the group of the kinase inhibitors, especially from the group of the tyrosine kinase and/or serine/threonine kinase inhibitors;

compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);

compounds which block the binding of serotonin to its receptors, by way of example and with preference antagonists of the $5-HT_{2b}$ receptor;

organic nitrates and NO donors, for example sodium nitroprusside, nitroglycerin, isosorbide mononitrate, isosorbide dinitrate, molsidomine or SIN-1, and inhaled NO;

NO-independent but haem-dependent stimulators of soluble guanylate cyclase, such as especially the compounds described in WO 00/06568, WO 00/06569, WO 02/42301 and WO 03/095451;

NO- and haem-independent activators of soluble guanylate cyclase, such as especially the compounds described in WO 01/19355, WO 01/19776, WO 01/19778, WO 01/19780, WO 02/070462 and WO 02/070510;

prostacyclin analogues, by way of example and with preference iloprost, beraprost, treprostinil or epoprostenol; compounds which inhibit soluble epoxide hydrolase (sEH), for example N,N'-dicyclohexylurea, 12-(3-adamantan-1-yl-ureido)dodecanoic acid or 1-adamantan-1-yl-3-{5-[2-(2-ethoxyethoxy)ethoxy]pentyl}urea;

compounds which influence the energy metabolism of the heart, by way of example and with preference etomoxir, dichloroacetate, ranolazine or trimetazidine;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil and tadalafil;

antithrombotic agents, by way of example and with preference from the group of the platelet aggregation inhibitors, the anticoagulants or the profibrinolytic substances;

hypotensive active ingredients, for example and with preference from the group of calcium antagonists, angiotensin AII antagonists, ACE inhibitors, vasopeptidase inhibitors, endothelin antagonists, refill inhibitors, alpha-receptor blockers, beta-receptor blockers, mineralocorticoid receptor antagonists, and rho kinase inhibitors and the diuretics;

vasopressin receptor antagonists, for example and with preference conivaptan, tolvaptan, lixivaptan, mozavaptan, satavaptan, SR-121463, RWJ 676070 or BAY 86-8050;

bronchodilatory agents, by way of example and with preference from the group of the beta-adrenergic receptor agonists, such as especially albuterol, isoproterenol, metaproterenol, terbutalin, formoterol or salmeterol, or from the group of the anticholinergics, such as especially ipratropium bromide;

anti-inflammatory agents, by way of example and with preference from the group of the glucocorticoids, such as especially prednisone, prednisolone, methylprednisolone, triamcinolone, dexamethasone, beclomethasone, betamethasone, flunisolide, budesonide or fluticasone; and/or active ingredients Which modify lipid metabolism, by way of example and with preference from the group of thyroid receptor agonists, cholesterol synthesis inhibitors such as, by way of example and with preference, HMG-CoA reductase inhibitors or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

In a preferred embodiment of the invention, the inventive compounds are used in combination with a kinase inhibitor, by way of example and with preference bortezomib, canertinib, erlotinib, getitinib, imatinib, lapatinib, lestaurtinib, lonafamib, pegaptinib, pelitinib, semaxanib, sorafenib, regorafenib, sunitinib, tandutinib, tipifamib, vatalanib, fasudil, lonidamine, letlunomide, BMS-3354825 or Y-27632.

In a preferred embodiment of the invention, the inventive compounds are used in combination with a serotonin receptor antagonist, by way of example and with preference PRIX-08066.

Antithrombotic agents are preferably understood to mean compounds from the group of the platelet aggregation inhibitors, the anticoagulants or the profibrinolytic substances.

In a preferred embodiment of the invention, the inventive compounds are administered in combination with a platelet aggregation inhibitor, by way of example and with preference aspirin, clopidogrel, ticlopidin or dipyridamol.

In a preferred embodiment of the invention, the inventive compounds are administered in combination with a thrombin inhibitor, by way of example and with preference ximelagatran, melagatran, bivalirudin or clexane.

In a preferred embodiment of the invention, the inventive compounds are administered in combination with a GPIIb/IIIa antagonist, by way of example and with preference tirofiban or abciximab.

In a preferred embodiment of the invention, the inventive compounds are administered in combination with a factor Xa inhibitor, by way of example and with preference rivaroxaban, DU-176b, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the inventive compounds are administered in combination with heparin or a low molecular weight (LMW) heparin derivative.

In a preferred embodiment of the invention, the inventive compounds are administered in combination with a vitamin K antagonist, by way of example and with preference coumarin.

Hypotensive agents are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, rho kinase inhibitors, and the diuretics.

In a preferred embodiment of the invention, the inventive compounds are administered in combination with a calcium antagonist, by way of example and with preference nifedipine, amlodipine, verapamil or diltiazem.

In a preferred embodiment of the invention, the inventive compounds are administered in combination with an alpha-1 receptor blocker, by way of example and with preference prazosin.

In a preferred embodiment of the invention, the inventive compounds are administered in combination with a beta receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the inventive compounds are administered in combination with an angiotensin AII antagonist, by way of example and with preference losartan, candesartan, valsartan, telmisartan or embursatan.

In a preferred embodiment of the invention, the inventive compounds are administered in combination with an ACE inhibitor, by way of example and with preference enalapril, captopril, lisinopril, ramipril, delapril, fosinopril, quinopril, perindopril or trandopril.

In a preferred embodiment of the invention, the inventive compounds are administered in combination with an endothelin antagonist, by way of example and with preference bosentan, darusentan, ambrisentan or sitaxsentan.

In a preferred embodiment of the invention, the inventive compounds are administered in combination with a renin inhibitor, by way of example and with preference aliskiren, SPP-600 or SPP-800.

In a preferred embodiment of the invention, the inventive compounds are administered in combination with a mineralocorticoid receptor antagonist, by way of example and with preference spironolactone or eplerenone.

In a preferred embodiment of the invention, the inventive compounds are administered in combination with a rho kinase inhibitor, by way of example and with preference fasudil, Y-27632, SLx-2119, BF-66851, BF-66852, BF-66853, KI-23095, SB-772077, GSK-269962A or BA-1049.

In a preferred embodiment of the invention, the compounds according to the invention are administered in combination with a diuretic, by way of example and with preference furosemide.

Agents which modify lipid metabolism are preferably understood to mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein (a) antagonists.

In a preferred embodiment of the invention, the inventive compounds are administered in combination with a CETP inhibitor, by way of example and with preference torcetrapib (CP-529 414), JJT-705 or CETP vaccine (Avant).

In a preferred embodiment of the invention, the inventive compounds are administered in combination with a thyroid receptor agonist, by way of example and with preference D-thyroxin, 3,5,3'-triiodothyronin (T3), CGS 23425 or axitirome (CGS 26214).

In a preferred embodiment of the invention, the inventive compounds are administered in combination with a HMG-CoA reductase inhibitor from the class of the statins, by way of example and with preference lovastatin, simvastatin, pravastatin, fluvastatin, atorvastatin, rosuvastatin or pitavastatin.

In a preferred embodiment of the invention, the inventive compounds are administered in combination with a squalene synthesis inhibitor, by way of example and with preference BMS-188494 or TAK-475.

In a preferred embodiment of the invention, the inventive compounds are administered in combination with an ACAT inhibitor, by way of example and with preference avasimibe, melinamide, pactirnibe, eflucimibe or SMP-797.

In a preferred embodiment of the invention, the inventive compounds are administered in combination with an MTP inhibitor, by way of example and with preference implitapide, BMS-201038, R-103757 or JTT-130.

In a preferred embodiment of the invention, the inventive compounds are administered in combination with a PPAR-gamma agonist, by way of example and with preference pioglitazone or rosiglitazone.

In a preferred embodiment of the invention, the inventive compounds are administered in combination with a PPAR-delta agonist, by way of example and with preference GW 501516 or BAY 685042.

In a preferred embodiment of the invention, the inventive compounds are administered in combination with a cholesterol absorption inhibitor, by way of example and with preference ezetimibe, tiqueside or pamaqueside.

In a preferred embodiment of the invention, the inventive compounds are administered in combination with a lipase inhibitor, by way of example and with preference orlistat.

In a preferred embodiment of the invention, the inventive compounds are administered in combination with a polymeric bile acid adsorbent, by way of example and with preference cholestyramine, colestipol, colesolvam, Cholestagel or colestimide.

In a preferred embodiment of the invention, the inventive compounds are administered in combination with a bile acid reabsorption inhibitor, by way of example and with preference ASBT (=IBAT) inhibitors, for example AZD-7806, S-8921, AK-105, BART-1741, SC-435 or SC-635

In a preferred embodiment of the invention, the inventive compounds are administered in combination with a lipoprotein (a) antagonist, by way of example and with preference gemcabene calcium (CI-1027) or nicotinic acid.

The present invention further provides medicaments which comprise at least one inventive compound, typically together with one or more inert, nontoxic, pharmaceutically suitable excipients, and the use thereof for the aforementioned purposes.

The inventive compounds may act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The inventive compounds can be administered in administration forms suitable for these administration routes.

Suitable administration forms for oral administration are those which work according to the prior art and release the inventive compounds rapidly and/or in a modified manner and which contain the inventive compounds in crystalline and/or amorphized and/or dissolved form, for example tablets (uncoated or coated tablets, for example with gastric juice-resistant or retarded-dissolution or insoluble coatings which control the release of the inventive compound), tablets or films/oblates which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. inhalatively, intramuscularly, subcutaneously, intracutaneously, percutaneously or intraperitoneally). Suitable administration forms for parenteral administration include injection and infusion formulations in the form of solutions, suspensions, emulsions, lyophilizates or sterile powders.

For the other administration routes, suitable examples are inhalation medicaments (including powder inhalers, nebulizers, aerosols), nasal drops, solutions or sprays; tablets for lingual, sublingual or buccal administration, films/oblates or capsules, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral and parenteral administration are preferred, especially oral, intravenous and inhalative administration.

The inventive compounds can be converted to the administration forms listed. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

In general, it has been found lobe advantageous in the case of parenteral administration to administer amounts of about 0.001 to 1 mg/kg, preferably about 0.01 to 0.5 mg/kg, of body weight to achieve effective results. In the case of oral administration, the dosage is about 0.01 to 100 mg/kg, preferably about 0.01 to 20 mg/kg and most preferably 0.1 to 10 mg/kg of body weight.

In spite of this, it may be necessary to deviate from the amounts specified, specifically depending on body weight, administration route, individual behaviour towards the active ingredient, type of formulation, and time or interval of administration. For instance, less than the aforementioned minimum amount may be sufficient in some cases, while the upper limit mentioned has to be exceeded in other cases. In the case of administration of greater amounts, it may be advisable to divide them into several individual doses over the day.

The working examples which follow illustrate the invention. The invention is not limited to the examples.

The percentages in the tests and examples which follow are, unless indicated otherwise, percentages by weight; parts are parts by weight. Solvent ratios, dilution ratios and concentration data for liquid/liquid solutions, unless indicated otherwise, are based in each case on volume.

A. EXAMPLES

Abbreviations

Ac acetyl
aq. aqueous, aqueous solution
br.d broad doublet (NMR)
br.m broad multiplet (NMR)
br.s broad singlet (NMR)

br.t broad triplet (NMR)
c concentration
cat. catalytic
TLC thin layer chromatography
DCI direct chemical ionization (in MS)
dist. distilled
DIAD diisopropyl azodicarboxylate
DIEA N,N-diisopropylethylamine
DMAP 4-N, N-dimethylaminopyridine
DMF dimethylformamide
DMSO dimethyl sulphoxide
DSC differential scanning thermography
EDC N'-(3-dimethylaminopropyl)-N-ethylcarbodiimide hydrochloride
ee enantiomeric excess
ent enantiomerically pure, enantiomer
eq. equivalent(s)
ESI electrospray ionization (in MS)
Et ethyl
GC-MS gas chromatography-coupled mass spectrometry
h hour(s)
HATU O-(7-azabenzotriazol-1-yl)-N,N,N',N'-tetramethyluronium hexafluorophosphate
HOBt 1-hydroxy-1H-benzotriazole hydrate
HPLC high-pressure high-performance liquid chromatography
conc. concentrated
LC-MS liquid chromatography-coupled mass spectrometry
Me methyl
min minute(s)
MPLC medium-pressure liquid chromatography
MS mass spectrometry
MTBE methyl tert-butyl ether
NMR nuclear magnetic resonance spectrometry
Pd/C palladium on activated carbon
Ph phenyl
PyBOP benzotriazol-1-yloxytris(pyrrolidino)phosphonium hexafluorophosphate
quant. quantitative (in the case of yield)
rac racemic, racemate
RT room temperature
$R_t$ retention time (in HPLC)
m.p. melting point
tBu tert-butyl
tert tertiary
TFA trifluoroacetic acid
TFAA trifluoroacetic anhydride
THF tetrahydrofuran
TPPO triphenylphosphine oxide
UV ultraviolet spectrometry
cf. see
v/v volume to volume ratio (of a solution)

HPLC, GC-MS and LC-MS Methods:

Method 1: instrument: Waters ACQUITY SQD UPLC System; column: Waters Acquity UPLC HSS T3 1.8 μm 50×1 mm; eluent A: 1 l water+0.25 ml 99% formic acid, eluent B: 1 l acetonitrile+0.25 ml 99% formic acid; gradient: 0.0 mm 90% A→1.2 min 5% A→2.0 min 5% A; oven: 50° C.; flow rate: 0.40 ml/min; UV detection: 210 400 nm.

Method 2: MS instrument type: Waters (Micromass) Quattro Micro; HPLC instrument type: Agilent 1100 Series; column: Thermo Hypersil GOLD 3 μ20×4 mm; eluent A: 1 l water+0.5 ml 50% formic acid, eluent B: 1 l acetonitrile+ 0.5 ml 50% formic acid; gradient: 0.0 min 100% A→3.0 min 10% A→4.0 min 10% A→4.01 mm 100% A (flow 2.5 ml)→5.00 min 100% A; oven: 50° C.; flow rate: 2 ml/min; UV detection: 210 nm.

Method 3: instrument: Micromass Quattro Premier with Waters UPLC Acquity; column: Thermo Hypersil GOLD 1.9 μm 50×1 mm; eluent A: 1 l water+0.5 ml 50% formic acid, eluent B: 1 l acetonitrile+0.5 ml 50% formic acid; gradient: 0.0 mm 90% A→0.1 mm 90% A→1.5 min 10% A→2.2 min 10% A oven: 50° C.; flow rate: 0.33 ml/min; UV detection: 210 nm.

Method 4: instrument: Micromass Quattro Premier with Waters UPLC Acquity; column: Thermo Hypersil GOLD 1.9 μm 50×1 mm; eluent A: 1 l water+0.5 ml 50% formic acid, eluent B: 1 l acetonitrile+0.5 ml 50% formic acid; gradient: 0.0 mm 97% A→0.5 mm 97% A→3.2 mm 5% A→4.0 mm 5% A oven: 50° C.; flow rate: 0.3 ml/min; UV detection: 210 nm.

Method 5 (LC-MS): instrument: Waters ACQUITY SQD UPLC System; column: Waters Acquity UPLC HSS T3 1.8 μm 30×2 mm; eluent A: 1 l water+0.25 ml 99% formic acid, eluent B: 1 l acetonitrile+0.25 ml 99% formic acid; gradient: 0.0 mm 90% A→1.2 mm 5% A→2.0 mm 5% A oven: 50° C.; flow rate: 0.60 ml/min; UV detection: 208-400 nm.

Method 6 (GC-MS): instrument: Micromass GCT, GC6890; column: Restek RTX-35, 15 m×200 μm×0.33 μm; constant flow rate of helium: 0.88 ml/min; oven: 70° C.; inlet: 250° C.; gradient: 70° C., 30° C./min→310° C. (hold for 3 min).

Method 7 (preparative HPLC): column: Reprosil C18, 10 μm, 250 mm×30 min. eluent A: formic acid 0.1% in water, eluent B: acetonitrile; flow rate: 50 ml/min; program: 0 to 6 min: 90% A/10% B; 6 min to 27 min: gradient to 95% B; 27 min to 38 min 95% B; 38 min to 39 min gradient to 10% B; 39 min to 43 min (end): 60% A/40% B. Slight variations in the gradient are possible.

Method 8 (preparative HPLC): column: Reprosil C18, 10 μm, 250 mm×30 mm. eluent A: formic acid 0.1% in water, eluent B: methanol; flow rate: 50 ml/min; program: 0 to 4.25 min: 60% A/40% B; 4.25 to 4.50 min: gradient to 60% B; 4.50 min to 17 min gradient to 100% B; 17 min to 19.50 min 100% B; 19.50 min to 19.75 min gradient to 40% B; 19.75 to 22 min (end): 60% A/40% B. Slight variations in the gradient are possible.

Method 9 (preparative HPLC): column: Sunfire C18, 5 μm, 250 mm×20 mm. eluent methanol/TFA 1% in water 50/50; flow rate: 25 ml/min; detection 210 nm, temperature 40° C.

Method 10 (preparative HPLC): column: Sunfire C18, 5 μm, 250 mm×20 mm. eluent acetonitrile/TFA 1% in water 55/45; flow rate: 25 ml/min; detection 210 nm, temperature 40° C.

Method 11: (preparative HPLC): column: Reprosil C18, 10 μm, 250 mm×40 mm. eluent A: formic acid 0.1% in water, eluent B: acetonitrile; flow rate: 50 ml/min. program: 0-6 min: 90% A/10% B; 6-40 min: gradient to 95% B; 40-53 min: 5% A/95% B; 53.01-54 min: gradient to 10% B; 54.01-57 min: 90% A/10% B.

Method 12 (chiral preparative HPLC): Daicel Chiralpak AD-H 250 mm×20 mm column; flow rate: 20 ml/min; eluent: iso-propanol/ethanol/iso-hexane 15:15:70 (v/v/v); detector 230 nm.

Method 13 (chiral analytical HPLC): Daicel Chiralpak AD-H 5 μm column, 250 mm×4.6 mm; temperature 30° C.; flow rate: 1 ml/min; eluent: iso-propanol/ethanol/iso-hexane 15:15:70 (v/v/v); detector 220 nm.

Method 14 (chiral analytical HPLC): Daicel Chiralpak AS-H 5 μm column, 250 mm×4.6 mm; temperature 30° C.; flow rate: 1 ml/min; eluent: ethanol/iso-hexane 50:50 with addition of 1% water and 0.2% trifluoroacetic acid; detector 220 nm.

Method 15 (preparative HPLC): as Method 7 but with Chromatorex C18 250 mm×30 mm column.

Method 16 (chiral preparative HPLC): Daicel Chiralpak AZ-H 250 mm×20 mm column; flow rate: 20 ml/min; eluent: ethanol/iso-hexane 50:50 (v/v) with addition of 1% water and 0.2% trifluoroacetic acid; detector 230 nm.

Method 17 (chiral analytical HPLC): Daicel Chiralpak AZ-H 5 μm column, 250 mm×4.6 mm; temperature 40° C.; flow rate: 1 ml/min; eluent: ethanol/iso-hexane 50:50 (v/v) with addition of 1% water and 0.2% trifluoroacetic acid; detector 220 nm.

Method 18 (chiral preparative HPLC): Daicel Chiralpak AD-H 250 mm×20 mm column; flow rate: 20 ml/min; eluent: iso-propanol/iso-hexane 50:50 (v/v) with addition of 1% water and 0.2% trifluoroacetic acid; detector 230 nm.

Method 19 (chiral analytical HPLC): Daicel Chiralpak AD-H 5 μm column, 250 mm×4.6 mm; temperature 30° C.; flow rate: 1 ml/min; eluent: iso-propanol/iso-hexane 50:50 (v/v) with addition of 1% water and 0.2% trifluoroacetic acid; detector 220 nm.

Method 20 (chiral preparative HPLC): Daicel Chiralpak AD-H 250 mm×20 mm column; flow rate: 20 ml/min; eluent: ethanol/iso-hexane 70:30 (v/v) with addition of 1% water and 0.2% trifluoroacetic acid; detector 230 nm.

Method 21 (chiral analytical HPLC): Daicel Chiralpak AD-H 5 μm column, 250 mm×4.6 mm; temperature 40° C.; flow rate: 1 nil/min; eluent: ethanol/iso-hexane 70:30 (v/v) with addition of 1% water and 0.2% trifluoroacetic acid; detector 220 nm.

Method 22 (preparative HPLC): column: Sunfire C18, 5 nm, 250 mm×20 mm. eluent acetonitrile/water 60:40; flow rate: 25 nil/min; detection 210 nm, temperature 40° C.

Method 24 (preparative HPLC): column: Sunfire C18, 5 μm, 75 mm×30 mm. eluent acetonitrile/0.05% TFA in water 1:99 to 2.25 min, then acetonitrile/1% TFA in water 95:5; flow rate: 60 ml/min; detection 210 nm, temperature 40° C.

Method 25 (chiral analytical HPLC): Daicel Chiralpak AD-H 5 μm column, 250 mm×4.6 mm; temperature 30° C.; flow rate: 1 ml/min; eluent: iso-propanol/iso-hexane 5:95 (v/v); detector 220 nm.

Method 26: MS, instrument: Thermo Fisher-Scientific DSQ; chemical ionization; reactant gas $NH_3$; source temperature: 200° C.; ionization energy 70 eV.

Method 27 (chiral analytical HPLC): Daicel Chiralpak AD-H 5 μm column, 250 mm×4.6 mm; temperature 30° C.; flow rate: 1 ml/min; eluent: iso-propanol/ethanol/iso-hexane 25:25:50 (v/v/v); detector 220 nm.

Method 28 (LC-MS): MCW SQ-HSST3 long instrument: Waters ACQUITY SQD UPLC System; column: Waters Acquity UPLC HSS T3 1.8 μm 50×1 mm; eluent A: 11 water+0.25 ml 99% formic acid, eluent B: 11 acetonitrile+0.25 ml 99% formic acid; gradient: 0.0 min 95% A→6.0 min 5% A→7.5 min 5% A; oven: 50° C.; flow rate: 0.35 ml/min; UV detection: 210-400 nm.

Method 29 (chiral preparative HPLC): Daicel Chiralpak IC 5 μm column, 250 mm×20 mm; flow rate: 20 ml/min; temperature 25° C.; detector: 220 nm; eluent: acetonitrile/MTBE 50:50 (v/v).

Method 30 (chiral analytical HPLC): Daicel Chiralpak IC 5 μm column, 250 mm×4.6 mm; flow rate: 1 ml/min; temperature 30° C.; detector: 220 nm; eluent: acetonitrile/MTBE 50:50 (v/v).

Method 31 (chiral preparative HPLC): Daicel Chiralpak IA 5 μm column, 250 mm×20 mm; flow rate: 20 ml/min; temperature 30° C.; detector: 285 nm; eluent: acetonitrile/MTBE 50:50 (v/v).

Method 32 (chiral analytical HPLC): Daicel Chiralpak IA 5 μm column, 250 mm×4.6 mm; flow rate: 1 ml/min; temperature 30° C.; detector: 285 nm; eluent: acetonitrile/MTBE 50:50 (v/v).

Method 33 (chiral preparative HPLC): Daicel Chiralpak IA 5 nm column, 250 mm×20 prim; flow rate: 20 ml/min; temperature 30° C.; detector: 285 nm; eluent: acetonitrile/MTBE 20:80 (v/v).

Method 34 (chiral analytical HPLC): Daicel Chiralpak IA 5 μm column, 250 mm×4.6 mm; flow rate: 1 ml/min; temperature 30° C.; detector: 285 nm; eluent: acetonitrile/MTBE 50:50 (v/v).

STARTING COMPOUNDS AND INTERMEDIATES

Example 1A 5-amino-1,3-dimethyl-1,3-dihydro-2H-benzimidazol-2-one hydrochloride

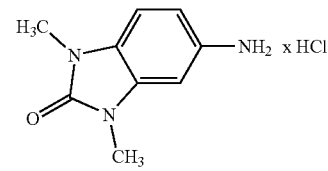

33.2 g (160 mmol) of 1,3-dimethyl-5-nitro-1,3-dihydro-2H-benzimidazol-2-one (preparation: see WO 2007/120339, Example 2, page 33) in 1790 ml of ethanol (only partly dissolved) were hydrogenated in the presence of 8.8 g of palladium catalyst (10% on activated carbon, moistened with 50% water) at RT and hydrogen pressure 1 atm. The starting material dissolved in the course of the reaction. After completion of conversion (6 h), the catalyst was removed by filtration through kieselguhr. The filtrate was admixed with 45 ml of a hydrogen chloride solution (4N in dioxane), then concentrated to dryness on a rotary evaporator. The residue was then dried further under HV. This gave 31.8 g (91% of theory) of the title compound.

LC-MS (Method 1): $R_t$=0.18 min; m/z=178 $(M+H)^+$.

$^1$H NMR (400 MHz, DMSO-$d_6$): δ [ppm]=3.33 (s, 3H), 3.34 (s, 3H), 7.06-7.15 (m, 2H), 7.23 (d, 1H), 10.29 (br.s, 3H).

Example 2A ethyl 1-(1,3-dimethyl-2-oxo-2,3-dihydro-1H-benzimidazol-5-yl)-2,4-dioxo-1,2,3,4-tetrahydropyrimidine-5-carboxylate

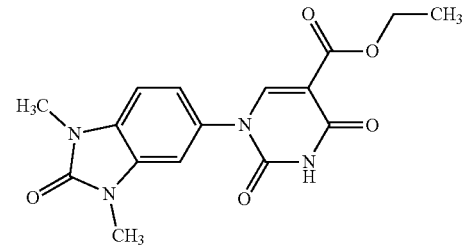 [SMILES: CCOC(=O)c1cn(-c2ccc3c(c2)n(C)c(=O)n3C)c(=O)[nH]c1=O]

52.80 g (247.1 mmol) of the compound from Example 1A and 64.07 g (247.1 mmol) ethyl 3-ethoxy-2-[(ethoxycarbonyl)carbamoyl]acrylate (for preparation see: Senda, Shigeo; Hirota, Kosaku; Notani, Jiyoji, Chemical & Pharmaceutical Bulletin (1972), 20(7), 1380-8) were initially charged in 2 l of ethanol, and 51.7 ml (370.7 mmol) of triethylamine were added. The thick suspension formed was heated to reflux temperature for 1.5 h, forming a clear solution. After cooling slightly (about 60° C.), 27.73 g (247.1 mmol) of potassium tell-butoxide were added. The reaction mixture was heated again to reflux temperature and stirred at this temperature for a further 7 h. After cooling to RT, about half the solvent was removed on a rotary evaporator. The concentrated reaction mixture was poured into 7.5 l of 1 N hydrochloric acid. The precipitated solid was filtered off, washed with 800 ml of water and dried under HV. This gave 71.7 g (85% of theory) of the title compound.

LC-MS (Method 1): $R_t$=0.63 min; m/z=345 $(M+H)^+$.

$^1$H NMR (400 MHz, DMSO-$d_6$): δ [ppm]=1.22 (t, 2H), 3.30 (s, 3H), 3.37 (s, 3H), 4.17 (q, 2H), 7.19 (dd, 1H), 7.25 (d, 1H), 7.37 (d, 1H), 8.26 (s, 1H).

Example 3A 1,3-dimethyl-5-(4,4,5,5-tetramethyl-1,3,2-dioxaborolan-2-yl)-1,3-dihydro-2H-benzimidazol-2-one

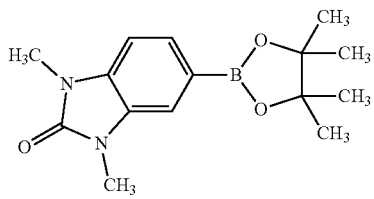 [SMILES: Cn1c(=O)n(C)c2cc(B3OC(C)(C)C(C)(C)O3)ccc21]

3.16 g of 4,4,4',4',5,5,5',5'-octamethyl-2,2'-bi-1,3,2-dioxaborolane (12.44 mmol) and 43 mg (70% purity, 0.124 mmol) of dibenzoyl peroxide were initially charged in 12 ml of acetonitrile at RT, and 1.47 g (8.3 mmol) of 5-amino-1,3-dimethyl-1,3-dihydro-2H-benzimidazol-2-one (prepared as described in Example 1A, except without treatment with hydrogen chloride) and 1.48 ml (12.44 mmol) of tert-butyl nitrite. The reaction mixture was stirred at RT overnight. The solvent was removed on a rotary evaporator. The residue was dissolved in a little dichloromethane, diatomaceous earth was added to the solution and the solution was concentrated again to dryness on a rotary evaporator. The residue was purified using a silica gel cartridge (eluent: cyclohexane/ethyl acetate 2:1 to 1:1). The product-containing fractions were concentrated on a rotary evaporator. The residue was stirred with 10 ml of pentane, and the precipitated solid was filtered off, washed with pentane and dried under HV. This gave 860 mg of the title compound (94% purity). Another silica gel chromatography operation with the mother liquor gave an additional 230 mg of the title compound (overall yield 43% of theory).

LC-MS (Method 1): $R_t$=0.95 mm; m/z=289 $(M+H)^+$.

$^1$H NMR (400 MHz, DMSO-$d_6$): δ [ppm]=1.30 (s, 12H), 3.33 (s, partly under the water signal), 3.35 (s, 3H), 7.16 (d, 1H), 7.35 (s, 1H), 7.44 (d, 1H).

Example 4A 1-(2-chloro-3,6-difluorobenzyl)urea

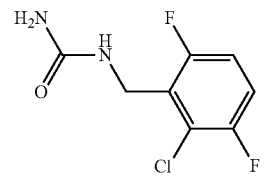 [SMILES: NC(=O)NCc1c(F)ccc(F)c1Cl]

1.50 g (8.44 mmol) of 2-chloro-3,6-difluorobenzylamine and 2.03 g (33.8 mmol) of urea were initially charged in 4 ml of water. After addition of 90 μl (approx. 1 mmol) of conc. hydrochloric acid, the reaction mixture was heated to reflux for 3.5 h. After cooling to RT, 100 ml of water were added and the mixture was stirred for 30 min. The precipitated crystals were filtered off, washed twice with a little water, then with a little MTBE, and dried under HV. This gave 1.16 g (62% of theory) of the title compound.

LC-MS (Method 1): $R_t$=0.79 min; m/z=221 $(M+H)^+$.

$^1$H NMR (400 MHz, DMSO-$d_6$): δ [ppm]=4.34 (dd, 2H), 5.51 (s, 2H), 6.36 (t, 1H), 7.26-7.34 (m, 1H), 7.39-7.48 (m, 1H).

Example 5A ethyl 3-(2-chloro-3,6-difluorobenzyl)-2,4-dioxo-1,2,3,4-tetrahydropyrimidine-5-carboxylate

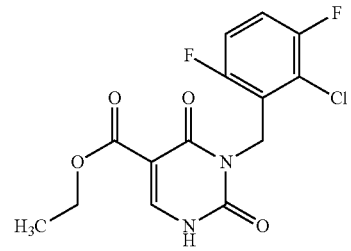 [SMILES: CCOC(=O)c1c[nH]c(=O)n(Cc2c(F)ccc(F)c2Cl)c1=O]

A suspension of 1.16 g (5.25 mmol) 1-(2-chloro-3,6-difluorobenzyl)urea from Example 4A and 1.59 ml (7.86 mmol) of diethyl ethoxymethylenemalonate in 2 ml of ethanol is heated to 140° C. (bath temperature) and stirred at this temperature overnight. The reaction mixture cooled to RT was dissolved in about 6 ml of ethanol, 535 mg (7.9 mmol) of sodium ethoxide were added and the mixture was again heated to reflux. After 2 days, an additional 0.5 equivalent of base was added and the mixture was heated to reflux temperature for a further 3 days. After cooling to RT, the mixture was acidified with 1M hydrochloric acid and extracted twice with ethyl acetate. The combined organic phases were washed with a saturated sodium chloride solution, dried over magnesium sulphate and concentrated on a rotary evaporator. The residue was stirred with ethyl acetate/MTBE 1:1. The solid was filtered off, washed with MTBE and dried under HV. This gave 851 mg (45% of theory) of the title compound.

LC-MS (Method 1): $R_t$=0.79 min; m/z=345 (M+H)$^+$.

$^1$H NMR (400 MHz, DMSO-d$_6$): δ [ppm]=1.22 (t, 3H), 4.16 (q, 2H), 5.13 (s, 2H), 7.20-7.29 (m, 1H), 7.38-7.46 (m, 1H), 8.20 (s, 1H), 11.94-12.05 (m, 1H).

Example 6A 1-(3-chloro-2-methylbenzyl)urea

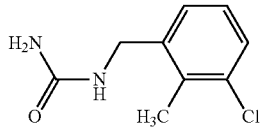

The preparation and purification of the title compound were analogous to Example 4A, with a reaction time of 6 h. Proceeding from 2.00 g (12.85 mmol) of 3-chloro-2-methylbenzylamine and 3.08 g (51.40 mmol) of urea, this gave 2.36 g (92% of theory) of the title compound.

LC-MS (Method 1): $R_t$=0.72 min; m/z=199 (M+H)$^+$.

$^1$H NMR (400 MHz, DMSO-d$_6$): δ [ppm]=2.29 (s, 3H), 4.19 (d, 2H), 5.53 (s, 2H), 6.36 (t, 1H), 7.14-7.22 (m, 2H), 7.28-7.35 (m, 1H).

Example 7A ethyl 3-(3-chloro-2-methylbenzyl)-2,4-dioxo-1,2,3,4-tetrahydropyrimidine-5-carboxylate

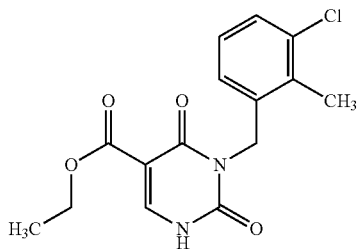 [SMILES: CCOC(=O)c1c[nH]c(=O)n(Cc2cccc(Cl)c2C)c1=O]

A suspension of 2.36 g (11.88 mmol) of 1-(3-chloro-2-methylbenzyl)urea from Example 6A and 3.60 ml (17.82 mmol) of diethyl ethoxymethylenemalonate in 3 ml of ethanol was heated to 140° C. (bath temperature) and the solution formed after about 3 h was stirred further at this temperature overnight. The mixture cooled to RT was dissolved in 20 ml of ethanol, 1.21 g (17.8 mmol) of sodium ethoxide were added and the mixture was again heated to reflux for 1.5 h. After cooling to RT, the reaction mixture was added dropwise to 100 ml of ice-cooled 0.5M hydrochloric acid. The precipitated solid was filtered off, washed with MTBE and dried under HV. This gave 2.20 g (57% of theory) of the title compound.

LC-MS (Method 1): $R_t$=0.90 min; m/z=323 (M+H)$^+$.

$^1$H NMR (400 MHz, DMSO-d$_6$): δ [ppm]=1.24 (t, 3H), 2.40 (s, 3H), 4.17 (q, 2H), 4.96 (s, 2H), 6.85 (d, 1H), 7.13 (t, 1H), 7.33 (d, 1H), 8.25 (s, 1H), 12.06 (br. s, 1H).

Example 8A

1-[2,3-bis(trifluoromethyl)phenyl]methanamine

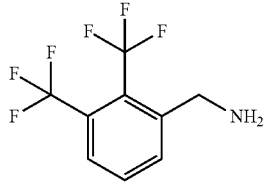 [SMILES: NCc1cccc(C(F)(F)F)c1C(F)(F)F]

Under argon, 69.38 ml (69.38 mmol) of borane-THF complex (1.0M) were initially charged and the reaction mixture was cooled to 0° C. Subsequently, a solution of 5.53 g (23.13 mmol) of 2,3-bis(trifluoromethyl)-benzonitrile (for preparation see: Zhurnal Organicheskoi Khimii 1973, 9(5), 1019-1024, 1046-1050) in 50 ml of THF and heated to reflux for 3 h. The reaction mixture was cooled to 0° C., acidified with 1N hydrochloric acid and concentrated under reduced pressure. The residue was diluted with water and the aqueous phase was washed three times with dichloromethane. Subsequently, 1N sodium hydroxide solution was used to adjust the pH to 14, the mixture was extracted three times with dichloromethane and the combined organic phases were dried over sodium sulphate, filtered and concentrated. This gave 4.07 g (70% of theory) of the title compound.

LC-MS (Method 1): $R_t$=0.49 min; MS (ESIpos): m/z=244 (M+H)$^+$.

$^1$H NMR (400 MHz, DMSO-d$_6$): δ [ppm]=1.99 (br.s, 2H), 3.90-3.97 (m, 2H), 7.83-7.92 (m, 2H), 8.17-8.23 (m, 1H).

Example 9A

1-[2,3-bis(trifluoromethyl)benzyl]urea

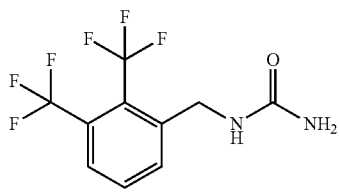 [SMILES: NC(=O)NCc1cccc(C(F)(F)F)c1C(F)(F)F]

780 mg (3.21 mmol) of 1-[2,3-bis(trifluoromethyl)phenyl]methanamine from Example 8A and 771 mg (12.83 mmol) of urea were initially charged in 1.3 ml of water, 34 µl (0.41 mmol) of conc. hydrochloric acid were added dropwise and the mixture was heated to reflux for 3 h. This was followed by dilution with water (100 ml) at RT and stirring for 30 min. The solid formed was filtered off, washed twice each with water and diethyl ether, and dried under high vacuum. This gave 541 mg (59% of theory) of the target compound.

LC-MS (Method 1): $R_t$=0.85 min; MS (ESIpos): m/z=287 (M+H)$^+$.

$^1$H NMR (400 MHz, DMSO-d$_6$): δ [ppm]=4.40-4.45 (m, 2H), 5.72 (s, 2H), 6.57-6.63 (m, 1H), 7.86-7.90 (m, 2H), 7.91-7.95 (m, 1H).

Example 10A ethyl 3-[2,3-bis(trifluoromethyl)benzyl]-2,4-dioxo-1,2,3,4-tetrahydropyrimidine-5-carboxylate

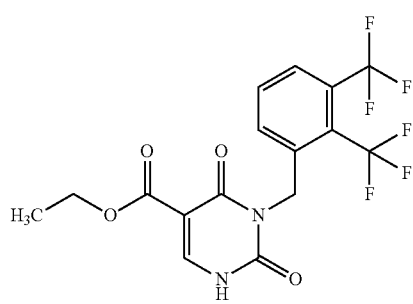 [SMILES: CCOC(=O)c1c[nH]c(=O)n(Cc2cccc(C(F)(F)F)c2C(F)(F)F)c1=O]

A mixture of 2.01 g (7.04 mmol) of 1-[2,3-bis(trifluoromethyl)benzyl]urea from Example 9A and 2.13 ml (10.60 mmol) of diethyl(ethoxymethylene)malonate was stirred in an opposing argon flow at 140° C. for 4 days. The reaction mixture was subsequently diluted with ethanol (20 ml), then 0.72 g (10.60 mmol) of sodium ethoxide was added and the mixture was heated to reflux for a further 2.5 h. The mixture brought to RT was added dropwise to ice-cooled hydrochloric acid (400 ml, 0.5M) and the solid formed was filtered off. The filter residue was stirred with MTBE, filtered off and dried under high vacuum. This gave 1.92 g (67% of theory) of the target compound.

LC-MS (Method 1): $R_t$=0.99 min; MS (ESIpos): m/z=411 (M+H)$^+$.

$^1$H NMR (400 MHz, DMSO-$d_6$): δ [ppm]=1.24 (t, 3H), 4.18 (q, 2H), 5.17 (br.s, 2H), 7.52 (d, 1H), 7.76-7.83 (m, 1H), 7.92-7.98 (m, 1H), 8.29 (s, 1H), 12.15 (br.s, 1H).

Example 11A

N-benzyl-4-(trifluoromethyl)indan-1-amine (Racemate)

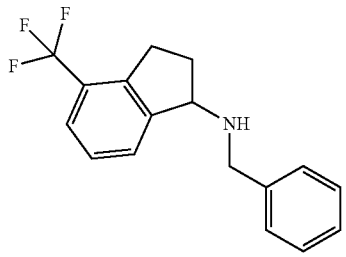 [SMILES: FC(F)(F)c1cccc2c1CCC2NCc1ccccc1]

To a mixture of 15.40 g (0.075 mol) of 4-(trifluoromethyl)-1-indanone and 9.78 ml (0.090 mol) of benzylamine in 462 ml of dichloromethane were added 33.0 ml (0.112 mol) of titanium(IV) isopropoxide and the mixture was stirred at RT for 1 h. Subsequently, at 0° C., 5.65 g (0.149 mol) of sodium borohydride were added in portions and the mixture was stirred at RT overnight. For workup, the mixture was subsequently added dropwise to water with vigorous evolution of gas. Thereafter, the mixture was diluted further with water and dichloro-methane (500 ml of each), the organic phase was dried over sodium sulphate and filtered, and the filtrate was concentrated. The crude product thus obtained was chromatographed on silica gel (petroleum ether/ethyl acetate, 10:1). This gave 12.80 g (58% of theory) of the target compound.

LC-MS (Method 1): $R_t$=0.80 min; MS (ESIpos): m/z=292 (M+H)$^+$.

$^1$H NMR (400 MHz, DMSO-$d_6$): δ [ppm]=1.81-1.93 (m, 1H), 2.31-2.42 (m, 1H), 2.57-2.65 (m, 1H), 2.81-2.93 (m, 1H), 3.04-3.15 (m, 1H), 3.72-3.85 (m, 2H), 4.14-4.22 (m, 1H), 7.19-7.25 (m, 1H), 7.32 (t, 2H), 7.37-7.44 (m, 3H), 7.53 (d, 1H), 7.68 (d, 1H).

Example 12A 4-(trifluoromethyl)indan-1-amine (Racemate)

9.70 g (0.032 mol) of N-benzyl-4-(trifluoromethyl)indan-1-amine from Example 11A were initially charged in 230 ml of THF, then 5.00 g of palladium (10% on activated carbon) were added and the mixture at RT was hydrogenated at RT under standard hydrogen pressure overnight. Subsequently, the mixture was filtered through kieselguhr and the filtrate was concentrated. This gave 6.40 g (98% of theory) of crude product, which was converted with out further purification.

LC-MS (Method 1): $R_t$=0.56 min; MS (ESIpos): m/z=202 (M+H)$^+$.

Example 13A

1-[4-(trifluoromethyl)-2,3-dihydro-1H-inden-1-yl]urea (Racemate)

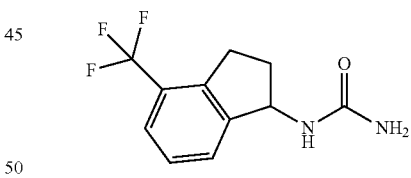

6.40 g (0.03 mol) of 4-(trifluoromethyl)indan-1-amine from Example 12A and 9.55 g (0.159 mol) of urea were initially charged in 25 ml of water, 0.34 ml (0.004 mol) of conc. hydrochloric acid were added dropwise and the mixture was heated to reflux for 3 h. The mixture was diluted with water (100 ml) at RT and stirred for 30 mm. The solid formed was filtered off, washed with water and dried under high vacuum. The crude product was recrystallized by stirring with diethyl ether (50 ml). This gave 4.60 g (59% of theory) of the target compound.

LC-MS (Method 1): $R_t$=0.83 min; MS (ESIpos): m/z=245 (M+H)$^+$.

$^1$H NMR (400 MHz, DMSO-$d_6$): δ [ppm]=1.71-1.82 (m, 1H), 2.39-2.49 (m, 1H), 2.84-2.96 (m, 1H), 3.00-3.11 (m, 1H), 5.12 (q, 1H), 5.53 (s, 2H), 6.42 (d, 1H), 7.39-7.45 (m, 1H), 7.53 (dd, 2H).

Example 14A (S)-4-trifluoromethylindan-1-ol

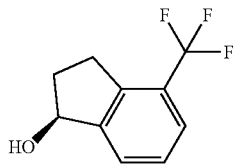

A solution of 55.7 g (278.3 mmol) of 4-trifluoromethyl-1-indanone, 194 ml (1.391 mol) of triethylamine and 1.60 g (2.50 mmol) of RuCl (p-cymene)[(S,S)-TsDPEN] (CAS No.: 192139-90-5; IUPAC name: (S,S)—N-(p-toluenesulphonyl)-1,2-diphenylethanediamino(chloro)[1-methyl-4-(propan-2-yl)benzene]ruthenium (II)) in 258 ml of dichloromethane was heated to 35° C. under argon and, at this temperature, 52.5 ml (1.391 mol) of formic acid were added gradually (addition time about 40 mm). In the course of this, the temperature of the reaction mixture rose to 42° C. On completion of addition, the mixture was stirred at 38° C. for a further 2 h. All volatile constituents were removed on a rotary evaporator and under HV. Subsequently, the residue was dissolved in a little dichloromethane and purified using 1 kg of silica gel (eluent: first 3 liters of cyclohexane/ethyl acetate 5:1, then 6 liters of cyclohexane/ethyl acetate 1:1). The suitable fractions were concentrated on a rotary evaporator and the product was dried under HV. This gave 51.2 g (90% of theory) of the title compound.

$^1$H NMR (400 MHz, DMSO-$d_6$): δ [ppm]=1.76-1.91 (m, 1H), 2.40 (ddt, 1H), 2.86 (dt, 1H), 3.01-3.13 (m, 1H), 5.09 (q, 1H), 5.45 (d, 1H), 7.38-7.48 (m, 1H), 7.55 (d, 1H), 7.62 (d, 1H).

Chiral analytical HPLC (Method 25): $R_t$=7.49 mm; 99% ee

Example 15A (R)-4-trifluoromethylindan-1-ol

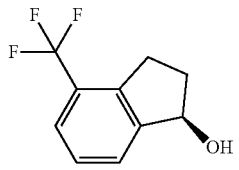 [SMILES: O[C@@H]1CCc2c1cccc2C(F)(F)F]

Analogously to Example 14A, 5 g (25.0 mmol) of 4-trifluoromethyl-1-indanone were reduced in the presence of 143 mg (0.225 mmol) of RuCl (p-cymene)[(R,R)-TsDPEN] (CAS No.: 192139-92-7; IUPAC name: (R,R)—N-(p-toluenesulphonyl)-1,2-diphenylethanediamino(chloro)[1-methyl-4-(propan-2-yl)benzene]ruthenium (II)). This gave 4.60 g (91% of theory) of the title compound.

GC-MS (Method 6): $R_t$=3.43 min; MS (CI-pos): m/z=202 (M)$^+$.

$^1$H NMR (400 MHz, CDCl$_3$): δ [ppm]=1.94 (br d, 1H), 1.96-2.05 (m, 1H), 2.55 (dddd, 1H), 2.91-3.04 (m, 1H), 3.19-3.30 (m, 1H), 5.27 (q, 1H), 7.32-7.38 (m, 1H), 7.53 (d, 1H), 7.60 (d, 1H).

Chiral analytical HPLC (Method 25): $R_t$=6.51 min; ee approx. 96%.

Example 16A 5-amino-1-methyl-1,3-dihydro-2H-benzimidazol-2-one

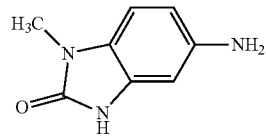

2.43 g (12.6 mmol) of 1-methyl-5-nitro-1,3-dihydro-2H-benzimidazol-2-one [synthesis described in U.S. Pat. No. 6,114,532] were initially charged in 78.0 ml of a THF/methanol mixture (1:2), then 134 mg (0.13 mmol) of palladium (10% on activated carbon) were added and the mixture was hydrogenated at standard hydrogen pressure overnight. Subsequently, the reaction mixture was filtered through kieselguhr, the residue was washed with THF and the filtrate was concentrated. This gave 1.89 g (92% of theory) of the target compound.

$^1$H NMR (400 MHz, DMSO-$d_6$): δ [ppm]=3.16 (s, 3H), 4.66-4.71 (m, 2H), 6.25 (dd, 1H), 6.28 (d, 1H), 6.71 (d, 1H), 10.39 (s, 1H).

Example 17A 5-fluoro-1,3-dimethyl-1,3-dihydro-2H-benzimidazol-2-one

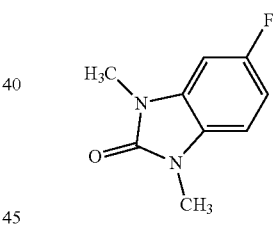

Under argon, 5.0 ml of DMF were initially charged at 0° C. and 318 mg (7.96 mmol) of sodium hydride (60% suspension in mineral oil) were added. Subsequently, a solution of 881 mg (5.30 mmol) of 5-fluoro-1-methyl-1,3-dihydro-2H-benzimidazol-2-one [synthesis described in US 2010/0305102, page 28, Example 26.3] in 5.0 ml of DMF was added dropwise and the reaction mixture was stirred for 30 min. Thereafter, 0.43 ml (6.90 mmol) of iodomethane was added dropwise and the mixture was stirred at RT overnight. Subsequently, sodium hydride (1.0 eq) was again added at 0° C., the mixture was stirred for a further 15 min and finally iodomethane (1.0 eq) was added dropwise. The reaction mixture was stirred at RT for 2 h, then water (100 ml) was added and the mixture was extracted with ethyl acetate (3×50 ml). The combined organic phases were washed with water and saturated sodium chloride solution, dried over magnesium sulphate and filtered, and the filtrate was concentrated. The crude product thus obtained was purified by means of flash silica gel chromatography (cyclohexane/ethyl acetate, gradient 7:1-4:1). This gave 672 mg (69% of theory) of the target compound.

LC-MS (Method 1): $R_t$=0.69 min; MS (ESIpos): m/z=181 (M+H)$^+$.

$^1$H NMR (400 MHz, DMSO-d$_6$): δ [ppm]=3.33 (s, 3H), 3.3 (s, concealed by water signal), 6.85-6.93 (m, 1H), 7.09-7.18 (m, 2H).

Example 18A 5-fluoro-1,3-dimethyl-6-nitro-1,3-dihydro-2H-benzimidazol-2-one

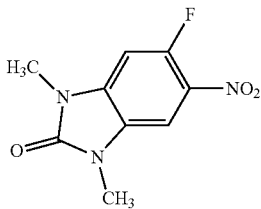 [SMILES: Cn1c(=O)n(C)c2cc([N+](=O)[O-])c(F)cc21]

670 mg (3.72 mmol) of 5-fluoro-1,3-dimethyl-1,3-dihydro-2H-benzimidazol-2-one from Example 17A were initially charged in 3.5 ml of THF under argon at 0° C. Thereafter, 0.24 ml (3.72 mmol) of nitric acid (65%) was added dropwise and the mixture was stirred at 0° C. for 1 h. Subsequently, the reaction mixture was added to ice-water (50 ml), and the solid formed was filtered off, washed with water (20 ml) and then dried at 40° C. under high vacuum. This gave 807 mg (92% of theory) of the target compound, which was converted without further purification.

LC-MS (Method 1): $R_t$=0.70 min; MS (ESIpos): m/z=226 (M+H)$^+$.

$^1$H NMR (400 MHz, DMSO-d$_6$): δ [ppm]=3.38 (s, 3H), 3.40 (s, 3H), 7.52 (d, 1H), 7.99 (d, 1H).

Example 19A 5-amino-6-fluoro-1,3-dimethyl-1,3-dihydro-2H-benzimidazol-2-one

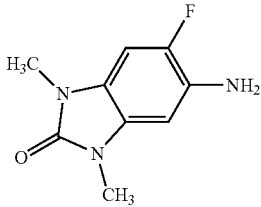

806 mg (3.58 mmol) of 5-fluoro-1,3-dimethyl-6-nitro-1,3-dihydro-2H-benzimidazol-2-one from Example 18A were initially charged in 22.2 ml of a THF/methanol mixture (1:2), then 38 mg (0.04 mmol) of palladium (10% on activated carbon) were added and the mixture was hydrogenated at standard hydrogen pressure overnight. Subsequently, the reaction mixture was filtered through kieselguhr, the residue was washed with methanol, and the filtrate was concentrated and dried under high vacuum. This gave 668 mg (85% purity, 81% of theory) of the target compound, which was converted without further purification.

LC-MS (Method 1): $R_t$=0.43 min; MS (ESIpos): m/z=196 (M+H)$^+$.

$^1$H NMR (400 MHz, DMSO-d$_6$): δ [ppm]=3.21 (s, 3H), 3.22 (s, 3H), 4.78 (br.s, 2H), 6.53 (d, 1H), 6.98 (d, 1H).

Example 20A 5-amino-3-hydroxy-1-methyl-3-(trifluoromethyl)-1,3-dihydro-2H-indol-2-one

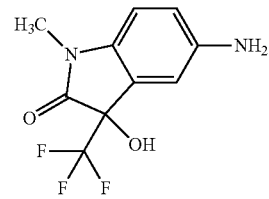 [SMILES: CN1C(=O)C(O)(C(F)(F)F)c2cc(N)ccc21]

2.45 g (8.87 mmol) of 3-hydroxy-1-methyl-5-nitro-3-(trifluoromethyl)-1,3-dihydro-2H-indol-2-one [for preparation see: Journal of Heterocyclic Chemistry, 2008, 45, 4, p. 969-973] were initially charged in 20.0 ml of ethanol, then 600 mg of palladium (10% on activated carbon) were added and the mixture was hydrogenated at standard hydrogen pressure for 4 h. Subsequently, the reaction mixture was filtered through kieselguhr, the residue was washed with methanol (30 ml) and the filtrate was concentrated. This gave 2.06 g (91% of theory) of the target compound.

LC-MS (Method 2): $R_t$=0.97 min; MS (ESIpos): m/z=247 (M+H)$^+$.

$^1$H NMR (400 MHz, DMSO-d$_6$): δ [ppm]=3.07 (s, 3H), 4.97-5.33 (m, 2H), 6.64 (dd, 1H), 6.77-6.81 (m, 2H), 7.51 (s, 1H).

Example 21A ethyl 2,4-dioxo-3-[4-(trifluoromethyl)-2,3-dihydro-1H-inden-1-yl]-1,2,3,4-tetrahydropyrimidine-5-carboxylate (Racemate)

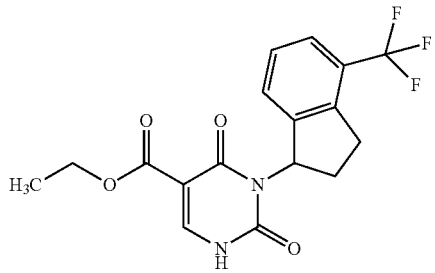 [SMILES: CCOC(=O)c1c[nH]c(=O)n(C2CCc3c2cccc3C(F)(F)F)c1=O]

A mixture of 5.2 g (20 mmol) of 1-[4-(trifluoromethyl)-2,3-dihydro-1H-inden-1-yl]urea from Example 13A and 8.26 ml (41 mmol) of diethyl(ethoxymethylene)malonate was heated to reflux at 140° C. for 24 h (barely stirrable at the start, then homogeneous and stirrable). After cooling to RT, 47.7 ml of ethanol and 2.78 g (41 mmol) of sodium ethoxide were added and the mixture was heated to reflux for a further 24 h. For workup, the reaction mixture was concentrated under reduced pressure, acidified with 1M hydrochloric acid (80 ml) and extracted three times with 80 ml each time of ethyl acetate. The combined organic phases were dried over sodium sulphate and filtered, and the filtrate was concentrated. The residue was chromatographed on silica gel (petroleum ether/ethyl acetate 3:1 to 1:3). This gave 4.20 g (56% of theory) of the title compound.

LC-MS (Method 1): $R_t$=0.94 min; MS (ESIpos): m/z=369 (M+H)+.

$^1$H NMR (400 MHz, DMSO-$d_6$): δ [ppm]=1.23 (t, 3H), 2.27-2.38 (m, 1H), 2.39-2.49 (m, 1H), 3.01-3.13 (m, 1H), 3.23-3.32 (m, 1H), 4.10-4.22 (m, 2H), 6.29-6.46 (m, 1H), 7.29-7.39 (m, 2H), 7.52 (d, 1H), 8.13-8.20 (m, 1H), 11.74-11.99 (m, 1H).

Example 22A ethyl 1-(1,3-diethyl-2-oxo-2,3-dihydro-1H-benzimidazol-5-yl)-2,4-dioxo-1,2,3,4-tetrahydropyrimidine-5-carboxylate

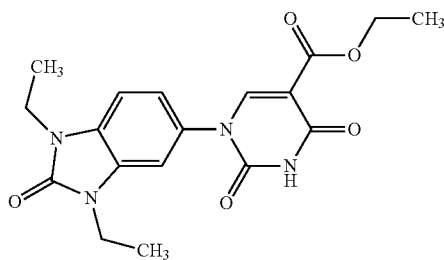 [SMILES: CCOC(=O)c1cn(-c2ccc3c(c2)n(CC)c(=O)n3CC)c(=O)[nH]c1=O]

1.00 g (4.13 mmol) of 5-amino-1,3-diethyl-1,3-dihydro-2H-benzimidazol-2-one hydrochloride, 0.63 ml (4.55 mmol) of triethylamine and 1.07 g (4.13 mmol) of ethyl 3-ethoxy-2-[(ethoxycarbonyl)carbamoyl]acrylate (for preparation see: Senda, Shigeo; Hirota, Kosaku; Notani, Jiyoji, Chemical & Pharmaceutical Bulletin (1972), 20(7), 1380-8) were initially charged in 31 ml of ethanol and the mixture was heated to reflux for 2 h. Subsequently, 464 mg (4.13 mmol) of potassium tert-butoxide were added at RT and the reaction mixture was stirred at RT overnight. Thereafter, the reaction mixture was heated to reflux for a further 3 h. For workup, water was added at RT and the mixture was acidified with 1N hydrochloric acid. The precipitated solid was filtered off with suction, washed once each with water and ethyl acetate, and dried under reduced pressure at 50° C. This gave 783 mg (51% of theory) of the target compound.

LC-MS (Method 3): $R_t$=0.84 min; MS (ESIpos): m/z=373 (M+H)+.

$^1$H NMR (400 MHz, DMSO-$d_6$): δ [ppm]=1.18-1.26 (m, 9H), 3.83-3.95 (m, 4H), 4.17 (q, 2H), 7.18 (dd, 1H), 7.31 (d, 1H), 7.44 (d, 1H), 8.30 (s, 1H), 11.68 (s, 1H).

Example 23A 1-methyl-5-nitro-3-(2,2,2-trifluoroethyl)-1,3-dihydro-2H-benzimidazol-2-one

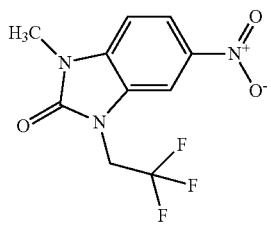 [SMILES: Cn1c(=O)n(CC(F)(F)F)c2cc([N+](=O)[O-])ccc21]

8.00 g (41.4 mmol) of 1-methyl-5-nitro-1,3-dihydro-2H-benzimidazol-2-one [synthesis described in U.S. Pat. No. 6,114,532] were initially charged together with 11.45 g (82.8 mmol) of potassium carbonate in 600 ml of acetonitrile/DMF 2:1 (v/v), and 7.48 ml (45.6 mmol) of 2,2,2-trifluoroethyl trichloromethanesulphonate were added. The reaction mixture was heated to reflux temperature and stirred at this temperature overnight. After cooling to RT, the mixture was poured into 1.8 l of 0.1N hydrochloric acid. The precipitated solid was filtered off and dried under HV. This gave 11.3 g (97% of theory) of the title compound.

$^1$H NMR (400 MHz, DMSO-$d_6$): δ [ppm]=3.44 (s, 3H), 4.97 (q, 2H), 7.44 (d, 1H), 8.14 (dd, 1H), 8.33 (d, 1H).

Example 24A 5-amino-1-methyl-3-(2,2,2-trifluoroethyl)-1,3-dihydro-2H-benzimidazol-2-one

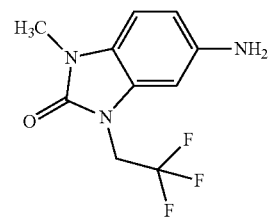 [SMILES: Cn1c(=O)n(CC(F)(F)F)c2cc(N)ccc21]

11.3 g (41.06 mmol) of the compound from Example 23A were initially charged in 623 ml of methanol/tetrahydrofuran 2:1 (v/v). 1.66 g of palladium on carbon (10% on carbon) and 25.9 g (410.6 mmol) of ammonium formate were added and the reaction mixture was stirred at 70° C. for 4 h. After cooling to RT, the catalyst was filtered off and the filtrate was freed of the solvents on a rotary evaporator. The residue was admixed with 100 ml of a saturated sodium hydrogencarbonate solution and 400 ml of water. The solid formed was filtered off, washed with 50 ml of water and dried under HV. This gave 8.90 g (86% of theory) of the title compound.

LC-MS (Method 5): $R_t$=0.41 min; m/z=246 (M+H)+.

$^1$H NMR (400 MHz, DMSO-$d_6$): δ [ppm]=3.25 (s, 3H), 4.63 (q, 2H), 4.89 (br. s, 2H), 6.37 (dd, 1H), 6.48 (s, 1H), 6.85 (d, 1H).

Example 25A ethyl 1-[1-methyl-2-oxo-3-(2,2,2-trifluoroethyl)-2,3-dihydro-1H-benzimidazol-5-yl]-2,4-dioxo-1,2,3,4-tetrahydropyrimidine-5-carboxylate

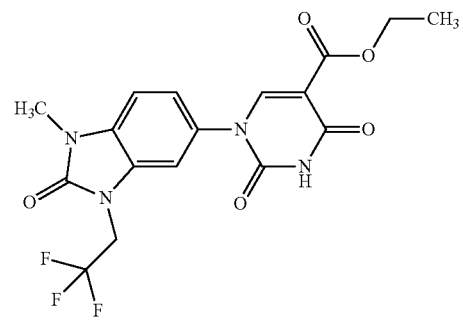 [SMILES: CCOC(=O)c1cn(-c2ccc3c(c2)n(CC(F)(F)F)c(=O)n3C)c(=O)[nH]c1=O]

8.90 g (36.3 mmol) of the compound from Example 24A and 9.41 g (36.3 mmol) of ethyl 3-ethoxy-2-[(ethoxycarbonyl)carbamoyl]acrylate (for preparation see: Senda, Shigeo; Hirota, Kosalcu; Notani, Jiyoji, Chemical & Pharmaceutical Bulletin (1972), 20(7), 1380-8) were heated to reflux temperature in 784 ml of ethanol for 1.5 h. After cooling slightly (about 60° C.), 4.07 g (36.3 mmol) of potassium tert-butoxide were added. The reaction mixture was heated again to reflux temperature for 30 min. After cooling to RT, the reaction mixture was poured into 5 l of ice-cooled 1N hydrochloric acid. The precipitated solid was filtered off, washed with 800 ml of water and dried under HV. This gave 12.7 g (83% of theory) of the title compound.

LC-MS (Method 1): $R_t$=0.70 min; m/z=413 (M+H)$^+$.

$^1$H NMR (400 MHz, DMSO-d$_6$): δ [ppm]=1.22 (t, 3H), 3.40 (s, 3H), 4.17 (q, 2H), 4.78 (q, 2H), 7.25-7.30 (m, 1H), 7.31-7.36 (m, 1H), 7.52 (s, 1H), 8.26 (s, 1H), 11.71 (s, 1H).

Example 26A ethyl 2,4-dioxo-1-(2-oxo-2,3-dihydro-1H-benzimidazol-5-yl)-1,2,3,4-tetrahydropyrimidine-5-carboxylate

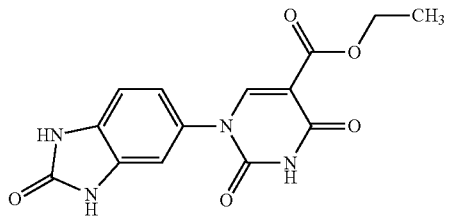 [SMILES: CCOC(=O)c1cn(-c2ccc3[nH]c(=O)[nH]c3c2)c(=O)[nH]c1=O]

The target compound was prepared analogously to Example 25A using 1.00 g (6.71 mmol) of 5-amino-1,3-dihydro-2H-benzimidazol-2-one and 1.74 g (6.71 mmol) of ethyl 3-ethoxy-2-[(ethoxycarbonyl)carbamoyl]acrylate. This gave 1.60 g (75% of theory) of the target compound.

LC-MS (Method 1): $R_t$=0.46 min; MS (ESIpos): m/z=317 (M+H)$^+$.

$^1$H NMR (400 MHz, DMSO-d$_6$): δ [ppm]=1.22 (t, 3H), 4.16 (q, 2H), 6.97-7.04 (m, 2H), 7.07-7.10 (m, 1H), 8.23 (s, 1H), 10.84-10.90 (m, 2H), 11.61 (s, 1H).

Example 27A ethyl 1-(6-methyl-2-oxo-2,3-dihydro-1H-benzimidazol-5-yl)-2,4-dioxo-1,2,3,4-tetrahydropyrimidine-5-carboxylate

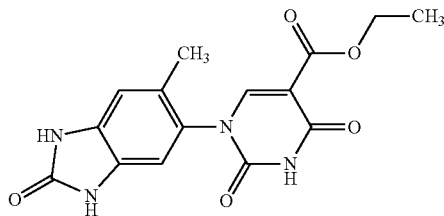 [SMILES: CCOC(=O)c1cn(-c2cc3[nH]c(=O)[nH]c3cc2C)c(=O)[nH]c1=O]

1.59 g (6.13 mmol) of ethyl 3-ethoxy-2-[(ethoxycarbonyl)carbamoyl]acrylate (for preparation see: Senda, Shigeo; Hirota, Kosaku; Notani, Jiyoji, Chemical & Pharmaceutical Bulletin (1972), 20(7), 1380-8) and 1.00 g (6.13 mmol) of 5-amino-6-methyl-1,3-dihydro-2H-benzimidazol-2-one were heated to reflux in 46 ml of ethanol for 2 h. Thereafter, 0.69 g (6.13 mmol) of potassium tert-butoxide were added at RT and the reaction mixture was stirred at RT overnight and at reflux for 1 h. For workup, the reaction mixture was admixed with water and acidified with 1N hydrochloric acid. The solid formed was filtered off, washed with water and ethyl acetate, and then dried under reduced pressure at 50° C. This gave 1.46 g (72% of theory) of the target compound.

LC-MS (Method 1): $R_t$=0.52 min; MS (ESIpos): m/z=331 (M+H)$^+$.

$^1$H NMR (400 MHz, DMSO-d$_6$): δ [ppm]=1.22 (t, 3H), 2.08 (s, 3H), 4.16 (q, 2H), 6.89 (s, 1H), 7.03 (s, 1H), 8.19 (s, 1H), 10.77 (s, 1H), 10.78 (s, 1H), 11.65 (s, 1H).

Example 28A ethyl 1-(3-methyl-2-oxo-2,3-dihydro-1,3-benzoxazol-6-yl)-2,4-dioxo-1,2,3,4-tetrahydropyrimidine-5-carboxylate

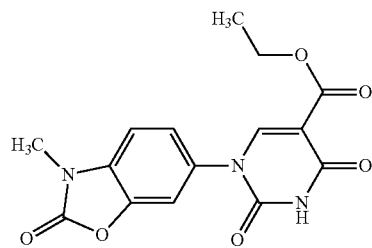 [SMILES: CCOC(=O)c1cn(-c2ccc3c(c2)oc(=O)n3C)c(=O)[nH]c1=O]

40.0 g (243.7 mmol) of 6-amino-3-methyl-1,3-benzoxazol-2(3H)-one were initially charged in 2.5 l of ethanol, and 63.2 g (243.7 mmol) ethyl 3-ethoxy-2-[(ethoxycarbonyl)carbamoyl]acrylate (for preparation see: Senda, Shigeo; Hirota, Kosaku; Notani, Jiyoji, Chemical & Pharmaceutical Bulletin (1972), 20(7), 1380-8) were added. After a few minutes, a thick suspension formed. This mixture was heated to reflux temperature for 1.5 ft After cooling slightly (about 60° C.), 27.3 g (243.7 mmol) of potassium tert-butoxide were added and the reaction mixture was stirred further at reflux temperature for 4.5 h. For workup, the reaction suspension was cooled slightly (about 60° C.), then stirred into about 10 liters of cold 1N hydrochloric acid. The solid was filtered off with suction, washed with water and dried in a vacuum drying cabinet at 70° C. overnight. This gave 64.0 g (79% of theory) of the title compound.

LC-MS (Method 1): $R_t$=0.59 min; MS (ESIpos): m/z=332 (M+H)$^+$.

$^1$H NMR (400 MHz, DMSO-d$_6$): δ [ppm]=1.22 (t, 3H), 3.38 (s, 3H), 4.17 (q, 2H), 7.38 (s, 2H), 7.59 (s, 1H), 8.26 (s, 1H), 11.69 (s, 1H).

Example 29A 6-amino-3-ethyl-1,3-benzoxazol-2 (3H)-one

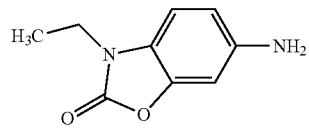

1.00 g (4.80 mmol) of 3-ethyl-6-nitro-1,3-benzoxazol-2 (3H)-one [for preparation see: WO 2007/120339 A1, 37-38]

was initially charged in 32.5 ml of ethanol, then 51 mg (0.05 mmol) of palladium (10% on activated carbon) were added and the mixture was hydrogenated at standard hydrogen pressure overnight. Subsequently, the reaction mixture was filtered through kieselguhr and the filtrate was concentrated. The residue was taken up in 50.0 ml of an ethanol/THF mixture (1:1), 50 mg (0.05 mmol) of palladium (10% on activated carbon) were added and the mixture was hydrogenated further at standard hydrogen pressure overnight. The reaction mixture was filtered again through kieselguhr, the filtercake was washed with ethanol and the filtrate was concentrated. The residue was subjected to extractive stirring in ethanol, and the solid was filtered off and washed with ethanol. After drying under high vacuum, this gave 747 mg of the target compound (83% of theory).

LC-MS (Method 3): $R_t$=0.29 min; MS (ESIpos): m/z=179 (M+H)$^+$.

$^1$H NMR (400 MHz, DMSO-d$_6$): δ [ppm]=1.21 (t, 3H), 3.74 (q, 2H), 4.99-5.05 (m, 2H), 6.42 (dd, 1H), 6.55 (d, 1H), 6.94 (d, 1H).

Example 30A ethyl 1-(3-ethyl-2-oxo-2,3-dihydro-1,3-benzoxazol-6-yl)-2,4-dioxo-1,2,3,4-tetrahydropyrimidine-5-carboxylate

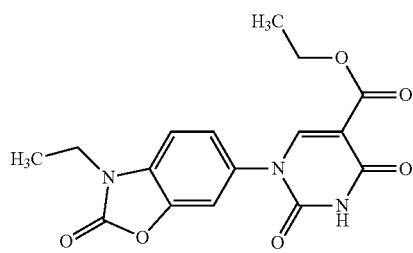 [SMILES: CCOC(=O)c1cn(-c2ccc3c(c2)oc(=O)n3CC)c(=O)[nH]c1=O]

746 mg (4.19 mmol) of 6-amino-3-ethyl-1,3-benzoxazol-2(3H)-one from Example 29A and 1.09 g (4.19 mmol) of ethyl 3-ethoxy-2-[(ethoxycarbonyl)carbamoyl]acrylate were initially charged in 32 ml of ethanol and the mixture was heated to reflux for 2 h. After cooling to RT, 470 mg (4.19 mmol) of potassium tert-butoxide were added and the reaction mixture was stirred further at RT overnight. Subsequently, the mixture was heated to reflux for 1 h. For workup, the reaction mixture was admixed with water at RT and acidified with 1M hydrochloric acid. The solid formed was filtered off, washed with water and ethyl acetate/MTBE (1:1) and dried at 50° C. under reduced pressure overnight. This gave 951 mg (66% of theory) of the target compound.

LC-MS (Method 1): $R_t$=0.71 min; MS (ESIpos): m/z=346 (M+H)$^+$.

$^1$H NMR (400 MHz, DMSO-d$_6$): δ [ppm]=1.22 (t, 3H), 1.28 (t, 3H), 3.90 (q, 2H), 4.17 (q, 2H), 7.36-7.41 (m, 1H), 7.43-7.47 (m, 1H), 7.59-7.62 (m, 1H), 8.28 (s, 1H), 11.70 (s, 1H).

Example 31A ethyl 1-(3-methyl-2-oxo-2,3-dihydro-1,3-benzothiazol-6-yl)-2,4-dioxo-1,2,3,4-tetrahydropyrimidine-5-carboxylate

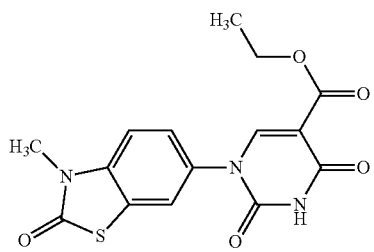 [SMILES: CCOC(=O)c1cn(-c2ccc3c(c2)sc(=O)n3C)c(=O)[nH]c1=O]

450 mg (2.50 mmol) of 6-amino-3-methyl-1,3-benzothiazol-2(3H)-one (J. Het. Chem. 1992, 29 (5), 1069-1076, Example 8b) and 647 mg (2.50 mmol) of ethyl 3-ethoxy-2-[(ethoxycarbonyl)carbamoyl]acrylate were initially charged in 19 ml of ethanol and the mixture was heated to reflux for 2 h. After cooling to RT, 280 mg (2.50 mmol) of potassium tert-butoxide were added and the reaction mixture was stirred further at RT overnight. For workup, the reaction mixture was diluted with water and acidified with 1M hydrochloric acid, and the solid formed was filtered off. The solid was washed with water and ethyl acetate, and dried under reduced pressure at 50° C. overnight. This gave 736 mg (85% of theory) of the target compound.

LC-MS (Method 1): $R_t$=0.70 min; MS (ESIpos): m/z=348 (M+H)$^+$.

$^1$H NMR (400 MHz, DMSO-d$_6$): δ [ppm]=1.22 (t, 3H), 3.45 (s, 3H), 4.17 (q, 2H), 7.42-7.47 (m, 1H), 7.51-7.55 (m, 1H), 7.83-7.86 (m, 1H), 8.32 (s, 1H), 11.71 (s, 1H).

Example 32A 1-methyl-6-nitro-1,3-dihydro-2H-benzimidazol-2-one

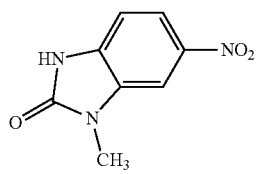

500 mg (2.99 mmol) of N$^2$-methyl-4-nitrobenzene-1,2-diamine [synthesis described in WO 2008/128009, page 49] were initially charged in DMF (9 ml), then 4.17 ml (0.73 mmol) of triethylamine and 2.42 g (15.0 mmol) of N,N'-carbonyldiimidazole were added and the mixture was stirred at 100° C. for 5 h. Subsequently, the reaction mixture was admixed with water and adjusted to pH 3 with 1M hydrochloric acid. The solid formed was filtered off, washed with water and dried at 50° C. under reduced pressure overnight. This gave 482 mg (91% purity, 76% of theory) of the target compound. The crude product was converted without further purification.

LC-MS (Method 3): $R_t$=0.71 min; MS (ESIpos): m/z=194 (M+H)$^+$.

$^1$H NMR (400 MHz, DMSO-d$_6$): δ [ppm]=3.37 (s, 3H), 7.15 (d, 1H), 7.97-8.01 (m, 1H), 8.02-8.03 (m, 1H), 11.64 (s, 1H).

Example 33A 6-amino-1-methyl-1,3-dihydro-2H-benzimidazol-2-one

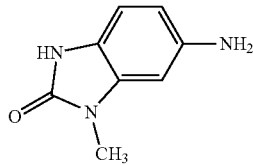

480 mg (2.49 mmol) of the nitro compound from Example 32A were initially charged in 31 ml of ethanol, then 132 mg (0.12 mmol) of palladium (10% on activated carbon) were added and the mixture was hydrogenated at standard hydrogen pressure for 2 h. Subsequently, the reaction mixture was filtered through kieselguhr, the residue was washed with methanol and the filtrate was concentrated. This gave 418 mg (90% purity, 93% of theory) of the target compound. The crude product was converted without further purification.

LC-MS (Method 2): R$_t$=0.27 min; MS (ESIpos): m/z=164 (M+H)$^+$.

$^1$H NMR (400 MHz, DMSO-d$_6$): δ [ppm]=3.16 (s, 3H), 4.72 (s, 2H), 6.23 (dd, 1H), 6.28-6.31 (m, 1H), 6.63 (d, 1H), 10.28 (s, 1H).

Example 34A ethyl 1-(3-methyl-2-oxo-2,3-dihydro-1H-benzimidazol-5-yl)-2,4-dioxo-1,2,3,4-tetrahydropyrimidine-5-carboxylate

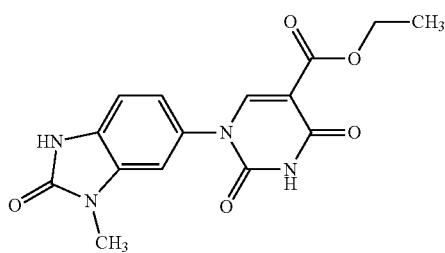 [SMILES: CCOC(=O)c1cn(-c2ccc3[nH]c(=O)n(C)c3c2)c(=O)[nH]c1=O]

410 mg (2.51 mmol) of 6-amino-1-methyl-1,3-dihydro-2H-benzimidazol-2-on e from Example 33A and 651 mg (2.51 mmol) of ethyl (2E)-3-ethoxy-2-[(ethoxycarbonyl)carbamoyl]acrylate [for preparation see: Senda, Shigeo; Hirota, Kosaku; Notani, Jiyoji, Chemical & Pharmaceutical Bulletin (1972), 20(7), 1380-1388] were initially charged in 19 ml of ethanol and the mixture was heated to reflux for 2 h. Subsequently, 282 mg (2.51 mmol) of potassium tert-butoxide were added at RT and the mixture was heated to reflux for a further 3 h. For workup, the reaction mixture was admixed with water and acidified to pH 3 with 1N hydrochloric acid. The solid formed was filtered off with suction, washed with ethyl acetate and dried under reduced pressure at 50° C. This gave 251 mg (73% purity, 22% of theory) of the target compound, which were converted without further purification. The remaining filtrate was extracted three times with ethyl acetate, and the combined organic phases were dried over magnesium sulphate, filtered and concentrated. The residue was subjected to extractive stirring in ethyl acetate/MTBE mixture, and the solid was filtered off and dried under high vacuum. This gave a further 443 mg (53% of theory) of the target compound.

LC-MS (Method 1): R$_t$=0.51 min; MS (ESIpos): m/z=331 (M+H)$^+$.

Example 35A 5-amino-1-methyl-1,3-dihydro-2H-benzimidazol-2-one

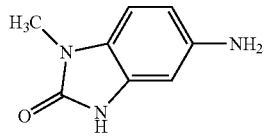

29.5 g (150 mmol) of 1-methyl-5-nitro-1,3-dihydro-2H-benzimidazol-2-one [synthesis described in U.S. Pat. No. 6,114,532] were initially charged in 630 ml of methanol and 315 ml of THF, 1.62 g of palladium (10% on activated carbon) were added and the mixture was hydrogenated under standard hydrogen pressure at RT. At the end of the reaction, the reaction mixture was filtered through kieselguhr and the filtrate was concentrated on a rotary evaporator. The residue was stirred with diethyl ether, filtered off with suction and dried. This gave 24.5 g (96% of theory) of the title compound.

LC-MS (Method 1): R$_t$=0.16 min; MS (ESIpos): m/z=164 (M+H)$^+$.

Example 36A ethyl 1-(1-methyl-2-oxo-2,3-dihydro-1H-benzimidazol-5-yl)-2,4-dioxo-1,2,3,4-tetrahydropyrimidine-5-carboxylate

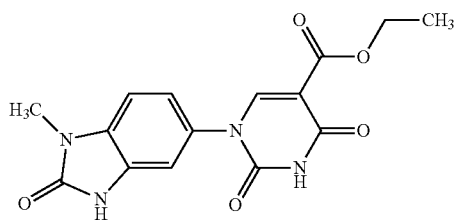 [SMILES: CCOC(=O)c1cn(-c2ccc3c(c2)[nH]c(=O)n3C)c(=O)[nH]c1=O]

5.00 g (29.3 mmol) of 5-amino-1-methyl-1,3-dihydro-2H-benzimidazol-2-one from Example 35A and 7.60 g (29.3 mmol) of ethyl 3-ethoxy-2-[(ethoxycarbonyl)carbamoyl]acrylate were heated to reflux in 250 ml of ethanol for 2 h. After cooling to RT, 3.29 g (29.3 mmol) of potassium tert-butoxide were added and the reaction mixture was heated to reflux for a further 2.5 h. For workup, the reaction mixture was acidified at RT with 4M hydrochloric acid and diluted with water. The mixture was partly concentrated under reduced pressure and the remaining suspension was filtered. The filter residue was washed with water and ethyl acetate, and dried under reduced pressure at 30° C. This gave 7.56 g (78% of theory) of the target compound.

LC-MS (Method 5): $R_t$=0.52 min; MS (ESIpos): m/z=331 (M+H)$^+$.

$^1$H NMR (400 MHz, DMSO-d$_6$): δ [ppm]=1.22 (t, 3H), 3.31 (s, 3H), 4.16 (q, 2H), 7.10-7.21 (m, 3H), 8.23 (s, 1H), 11.12 (s, 1H), 11.63 (s, 1H).

Example 37A

N-[4-(cyclobutylamino)-3-nitrophenyl]acetamide

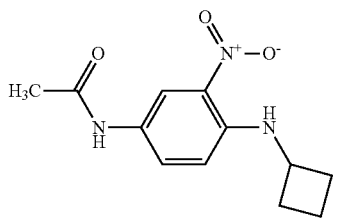 [SMILES: CC(=O)Nc1ccc(NC2CCC2)c([N+](=O)[O-])c1]

1.00 g (5.04 mmol) N-(4-fluoro-3-nitrophenyl)acetamide (for preparation see: WO2005/72741 page 26, Example 117A) and 0.86 ml (10.09 mmol) of cyclobutylamine were initially charged in 40 ml of ethanol, then 1.40 ml (10.09 mmol) of triethylamine were added and the reaction mixture was stirred in a microwave at 140° C. for 1.5 h. For workup, the mixture was concentrated under reduced pressure, the residue was stirred with MTBE, and the solid formed was filtered off and dried under high vacuum. This gave 185 mg (69% purity, 10% of theory) of the target compound. The remaining filtrate was concentrated, and the residue was taken up in ethyl acetate, washed once each with water and saturated sodium chloride solution, dried over magnesium sulphate, filtered and concentrated. After drying under high vacuum, this gave a further 1.01 g (78% of theory) of the target compound.

LC-MS (Method 3): $R_t$=1.31 min; MS (ESIpos): m/z=250 (M+H)$^+$.

$^1$H NMR (400 MHz, DMSO-d$_6$): δ [ppm]=1.70-1.85 (m, 2H), 1.93-2.04 (m, 5H), 2.39-2.47 (m, 2H), 4.12 (sxt, 1H), 6.92 (d, 1H), 7.65 (dd, 1H), 7.93 (d, 1H), 8.46 (d, 1H), 9.97 (s, 1H).

Example 38A

N-[3-amino-4-(cyclobutylamino)phenyl]acetamide

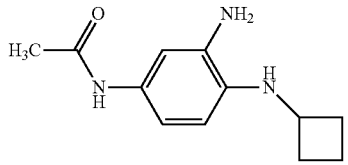 [SMILES: CC(=O)Nc1ccc(NC2CCC2)c(N)c1]

1.02 g (4.07 mmol) N-[4-(cyclobutylamino)-3-nitrophenyl]acetamide from Example 37A were initially charged in 96 ml of ethyl acetate, then 216 mg (0.20 mmol) of palladium (10% on activated carbon) were added and the mixture was hydrogenated at standard hydrogen pressure for 2 h. Subsequently, the reaction mixture was filtered through kieselguhr, the residue was washed with methanol and the filtrate was concentrated. This gave 870 mg (90% purity, 87% of theory) of the title compound. The crude product was converted without further purification.

LC-MS (Method 2): $R_t$=1.01 min; MS (ESIpos): m/z=220 (M+H)$^+$.

$^1$H NMR (400 MHz, DMSO-d$_6$): δ [ppm]=1.64-1.87 (m, 4H), 1.93 (s, 3H), 2.28-2.38 (m, 2H), 3.76 (sxt, 1H), 4.42 (d, 1H), 4.51-4.60 (m, 2H), 6.20 (d, 1H), 6.61 (dd, 1H), 6.82 (d, 1H), 9.34 (s, 1H).

Example 39A

N-(1-cyclobutyl-1H-benzimidazol-5-yl)acetamide

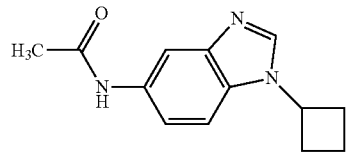 [SMILES: CC(=O)Nc1ccc2c(c1)ncn2C1CCC1]

870 mg (3.96 mmol) of N-[3-amino-4-(cyclobutylamino)phenyl]acetamide from Example 38A were initially charged in 25 ml of (diethoxymethoxy)ethane, then 0.43 ml (5.17 mmol) of conc. hydrochloric acid were added dropwise and the reaction mixture was stirred at RT overnight. The precipitated solid was filtered off with suction, washed with ethyl acetate and dried under high vacuum. This gave 930 mg (100% of theory) of the title compound.

LC-MS (Method 1): $R_t$=0.43 min; MS (ESIpos): m/z=230 (M+H)$^+$.

$^1$H NMR (400 MHz, DMSO-d$_6$): δ [ppm]=1.89-2.00 (m, 2H), 2.11 (s, 3H), 2.57-2.64 (m, 4H), 5.15 (quin, 1H), 7.59-7.64 (m, 1H), 7.86 (d, 1H), 8.38 (d, 1H), 9.66 (s, 1H), 10.53 (s, 1H).

Example 40A 1-cyclobutyl-1H-benzimidazol-5-amine

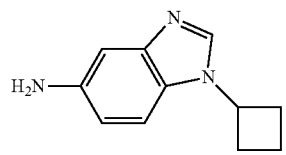 [SMILES: Nc1ccc2c(c1)ncn2C1CCC1]

920 mg (4.01 mmol) of N-(1-cyclobutyl-1H-benzimidazol-5-yl)acetamide from Example 39A were initially charged in 20 ml of a 1:1 mixture of 1M hydrochloric acid and ethanol, and the reaction mixture was stirred at 120° C. for 1 h. The reaction mixture cooled to RT was concentrated, taken up in ethyl acetate, washed once each with 1N sodium hydroxide solution and saturated sodium chloride solution, and the organic phase was dried over magnesium sulphate, filtered and concentrated under reduced pressure. This gave 593 mg (75% of theory) of the title compound.

LC-MS (Method 2): $R_t$=0.89 min; MS (ESIpos): m/z=189 (M+H)$^+$.

$^1$H NMR (400 MHz, DMSO-d$_6$): δ [ppm]=1.80-1.92 (m, 2H), 2.43-2.48 (m, partly concealed by DMSO signal), 4.66-4.76 (m, 2H), 4.82 (quin, 1H), 6.59 (dd, 1H), 6.76 (d, 1H), 7.24 (d, 1H), 8.07 (s, 1H).

Example 41A ethyl 1-(1-cyclobutyl-1H-benzimidazol-5-yl)-2,4-dioxo-1,2,3,4-tetrahydropyrimidine-5-carboxylate

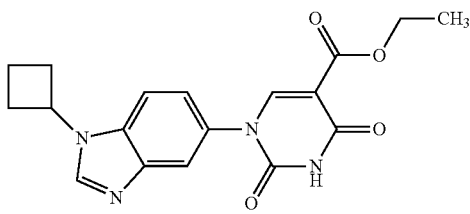 [SMILES: CCOC(=O)c1cn(-c2ccc3c(c2)ncn3C2CCC2)c(=O)[nH]c1=O]

The preparation and purification of the target compound were analogous to Example 27A, with a reaction time of 3 h under reflux. Proceeding from 590 mg (3.15 mmol) of 1-cyclobutyl-1H-benzimidazol-5-amine from Example 40A and 817 mg (3.15 mmol) of ethyl 3-ethoxy-2-[(ethoxycarbonyl)carbamoyl]acrylate, 832 mg (67% of theory) of the title compound were obtained.

LC-MS (Method 1): $R_t$=0.62 min; MS (ESIpos): m/z=355 (M+H)$^+$.

$^1$H NMR (400 MHz, DMSO-d$_6$): δ [ppm]=1.18 (t, 3H), 1.86-1.97 (m, 2H), 2.55-2.58 (m, partly concealed by DMSO signal), 3.40-3.48 (m, 1H), 4.06 (q, 2H), 5.01 (quin, 1H), 7.16 (dd, 1H), 7.54 (d, 1H), 7.62 (d, 1H), 7.96 (s, 1H), 8.45 (s, 1H).

Example 42A

N-ethyl-2,4-dinitroaniline

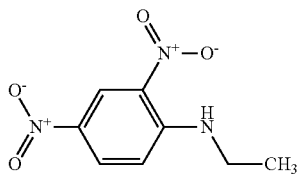

2.00 g (9.87 mmol) of 1-chloro-2,4-dinitrobenzene were initially charged in 20 ml of THF, then, at 0° C., 5.92 ml (11.84 mmol) of a 2M solution of ethylamine in THF were added dropwise and the reaction mixture was stirred at RT overnight. Thereafter, at 0° C., another 9.86 ml (19.73 mmol) of a 2M solution of ethylamine in THF were added and the reaction was stirred at RT for a further 5 h. Subsequently, at 0° C., a further 4.93 ml (9.86 mmol) of a 2M solution of ethylamine in THF were added and stirring was continued overnight. For workup, the reaction mixture was admixed with saturated sodium hydrogencarbonate solution and extracted three times with ethyl acetate. The combined organic phases were dried over magnesium sulphate, filtered and concentrated. The resulting residue was subjected to extractive stirring in MTBE and the precipitated solid was filtered off with suction. The filtrate was concentrated to obtain an overall yield of 2.29 g (100% of theory) of the title compound.

LC-MS (Method 1): $R_t$=0.97 min; MS (ESIpos): m/z=212 (M+H)±.

$^1$H NMR (400 MHz, DMSO-d$_6$): δ [ppm]=1.23 (t, 3H), 3.49-3.58 (m, 2H), 7.23 (d, 1H), 8.26 (dd, 1H), 8.81-8.89 (m, 2H).

Example 43A

N'-ethyl-4-nitrobenzene-1,2-diamine

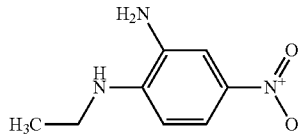

1.20 g (5.68 mmol) of N-ethyl-2,4-dinitroaniline from Example 42A were initially charged in 3 ml of acetonitrile under argon and 64 mg (0.06 mmol) of palladium (10% on activated carbon) and 3.40 ml (24.38 mmol) of triethylamine were added. The reaction mixture was cooled to −15° C., and a solution of 1.03 ml (27.44 mmol) of formic acid in 3 ml of acetonitrile was added. The reaction mixture was stirred at 40° C. for 1 h and at 60° C. for 2 h. For workup, the reaction mixture at RT was filtered through kieselguhr and washed with ethyl acetate/methanol (1:1), and the filtrate was concentrated. The residue was admixed with water, and the precipitated solid was filtered off with suction, washed with water and dried at 50° C. under reduced pressure. This gave 546 mg (47% of theory) of the title compound.

LC-MS (Method 1): $R_t$=0.79 min; MS (ESIpos): m/z=182 (M+H)$^+$.

$^1$H NMR (400 MHz, DMSO-d$_6$): δ [ppm]=1.23 (t, 3H), 3.18-3.26 (m, 2H), 5.09-5.20 (m, 2H), 5.87 (t, 1H), 6.46 (d, 1H), 7.39 (d, 2H), 7.52 (dd, 1H).

Example 44A 1-ethyl-5-nitro-1H-benzimidazole

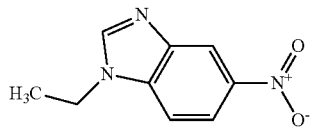

540 mg (2.98 mmol) of N$^1$-ethyl-4-nitrobenzene-1,2-diamine from Example 43A were initially charged in 19 ml of (diethoxymethoxy)ethane, then 0.32 ml (3.89 mmol) of conc. hydrochloric acid were added dropwise and the reaction mixture was stirred at RT for 2 h. Subsequently, the mixture was concentrated under reduced pressure, and the residue was subjected to extractive stirring in MTBE, filtered off, washed with MTBE and dried. This gave 486 mg (54% of theory) of the title compound.

LC-MS (Method 1): $R_t$=0.65 min; MS (ESIpos): m/z=192 (M+H)$^+$.

$^1$H NMR (400 MHz, DMSO-d$_6$): δ [ppm]=1.46 (t, 3H), 4.42 (q, 2H), 7.97 (d, 1H), 8.26 (d, 1H), 8.60 (d, 1H), 8.83-8.90 (m, 1H).

Example 45A 1-ethyl-1H-benzimidazol-5-amine

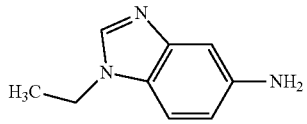

The preparation and purification of the target compound were analogous to Example 33A, and the reaction took place overnight. Proceeding from 485 mg (2.53 mmol) of 1-ethyl-5-nitro-1H-benzimidazole from Example 44A, 417 mg (101% of theory) of the title compound were obtained.

LC-MS (Method 2): $R_t$=0.23 min; MS (ESIpos): m/z=162 (M+H)$^+$.

$^1$H NMR (400 MHz, DMSO-d$_6$): δ [ppm]=1.47 (t, 3H), 4.36 (q, 2H), 6.85-6.96 (m, 2H), 7.64 (d, 1H), 9.16 (s, 1H).

Example 46A ethyl 1-(1-ethyl-1H-benzimidazol-5-yl)-2,4-dioxo-1,2,3,4-tetrahydropyrimidine-5-carboxylate

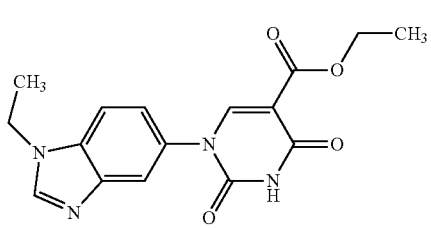 [SMILES: CCOC(=O)c1cn(-c2ccc3c(c2)ncn3CC)c(=O)[nH]c1=O]

659 mg (2.54 mmol) of ethyl 3-ethoxy-2-[(ethoxycarbonyl)carbamoyl]acrylate and 410 mg (2.54 mmol) of 1-ethyl-1H-benzimidazol-5-amine from Example 45A were initially charged in 19 ml of ethanol and the mixture was stirred at reflux for 2 h. Thereafter, at RT, 285 mg (2.54 mmol) of potassium tert-butoxide were added and the reaction mixture was heated to reflux for 3 h. For workup, the reaction mixture was admixed with water and the mixture was concentrated under reduced pressure. The residue was stirred with dichloromethane/methanol and filtered, and the filtrate was concentrated. The residue thus obtained was stirred in MTBE/ethyl acetate, and the solid was filtered off, washed with ethyl acetate and then dried at 50° C. under reduced pressure. This gave 491 mg (59% of theory) of the title compound.

LC-MS (Method 3): $R_t$=0.60 min; MS (ESIpos): m/z=329 (M+H)$^+$.

$^1$H NMR (400 MHz, DMSO-d$_6$): δ [ppm]=1.17-1.23 (m, 3H), 1.42 (t, 3H), 4.08-4.16 (m, 2H), 4.28-4.36 (m, 2H), 7.26 (d, 1H), 7.63-7.71 (m, 2H), 8.15 (s, 1H), 8.35 (s, 1H).

Example 47A

N-isopropyl-2,4-dinitroaniline

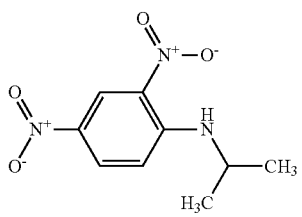 [SMILES: CC(C)Nc1ccc([N+](=O)[O-])cc1[N+](=O)[O-]]

1.00 g (4.93 mmol) of 1-chloro-2,4-dinitrobenzene were initially charged in 10 ml of THF, then 0.84 ml (9.87 mmol) of isopropylamine was added dropwise and the reaction mixture was stirred at RT for 16 h. For workup, the mixture was admixed with saturated sodium hydrogencarbonate solution and washed three times with ethyl acetate, and the combined organic phases were dried over magnesium sulphate, filtered and concentrated. This gave 1.13 g (99% of theory) of the title compound.

LC-MS (Method 3): $R_t$=1.30 min; MS (ESIpos): m/z=226 (M+H)$^+$.

$^1$H NMR (400 MHz, DMSO-d$_6$): δ [ppm]=1.31 (d, 6H), 4.02-4.15 (m, 1H), 7.27 (d, 1H), 8.27 (dd, 1H), 8.42 (d, 1H), 8.86 (d, 1H).

Example 48A

N$^1$-isopropyl-4-nitrobenzene-1,2-diamine

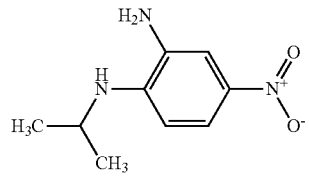

The preparation and purification of the target compound were analogous to Example 43A, with a reaction time of 7 h. Proceeding from 1.13 g (5.01 mmol) of N-isopropyl-2,4-dinitroaniline from Example 47A, 708 mg (72% of theory) of the title compound were obtained.

LC-MS (Method 1): $R_t$=0.88 min; MS (ESIpos): m/z=196 (M+H)$^+$.

$^1$H NMR (400 MHz, DMSO-d$_6$): δ [ppm]=1.21 (d, 6H), 3.69-3.81 (m, 1H), 5.11-5.24 (m, 2H), 5.62 (d, 1H), 6.49 (d, 1H), 7.39 (d, 1H), 7.51 (dd, 1H).

Example 49A 1-isopropyl-5-nitro-1H-benzimidazole

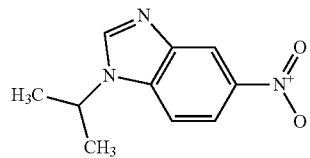

The preparation of the target compound was analogous to Example 39A, using 700 mg (3.58 mmol) of N$^1$-isopropyl-4-nitrobenzene-1,2-diamine from Example 48A and 23 ml (137.49 mmol) of (diethoxymethoxy)ethane. For workup, the mixture was concentrated, and the residue was stirred with MTBE, filtered off and dried under high vacuum. This gave 760 mg of the title compound. The crude product was converted without further purification.

LC-MS (Method 3): $R_t$=0.98 min; MS (ESIpos): m/z=206 (M+H)$^+$.

$^1$H NMR (400 MHz, DMSO-d$_6$): δ [ppm]=1.58 (d, 6H), 4.88-4.99 (m, 1H), 8.01 (d, 1H), 8.24 (dd, 1H), 8.60 (d, 1H), 8.94-9.01 (m, 1H).

Example 50A 1-isopropyl-1H-benzimidazol-5-amine

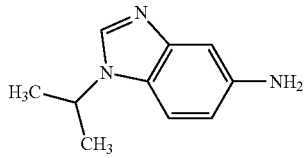

The preparation and purification of the target compound were analogous to Example 33A, with a reaction time of 16 h. Proceeding from 750 mg (3.65 mmol) of 1-isopropyl-5-nitro-1H-benzimidazole from Example 49A, 612 mg (95% of theory) of the title compound were obtained.

LC-MS (Method 1): $R_t$=0.23 min; MS (ESIpos): m/z=176 (M+H)$^+$.

$^1$H NMR (400 MHz, DMSO-d$_6$): δ [ppm]=1.56 (d, 6H), 3.34 (s, concealed by water signal), 4.77-4.90 (m 1H), 6.87-6.95 (m, 2H), 7.67 (d, 1H), 9.22 (s, 1H).

Example 51A ethyl 1-(1-isopropyl-1H-benzimidazol-5-yl)-2,4-dioxo-1,2,3,4-tetrahydropyrimidine-5-carboxylate

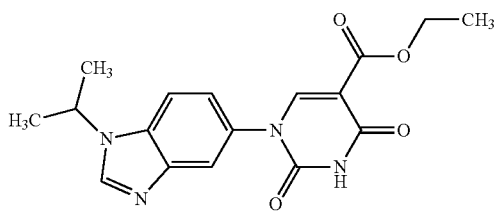 [SMILES: CCOC(=O)c1cn(-c2ccc3c(c2)ncn3C(C)C)c(=O)[nH]c1=O]

The preparation and purification of the target compound were analogous to Example 27A. Proceeding from 612 mg (3.49 mmol) of 1-isopropyl-1H-benzimidazol-5-amine from Example 50A and 905 nag (3.49 mmol) of ethyl 3-ethoxy-2-[(ethoxycarbonyl)carbamoyl]acrylate, 684 mg (57% of theory) of the title compound were obtained.

LC-MS (Method 1): $R_t$=0.56 min; MS (ESIpos): m/z=343 (M+H)$^+$.

$^1$H NMR (400 MHz, DMSO-d$_6$): δ [ppm]=1.21 (t, 3H), 1.56 (d, 6H), 4.15 (q, 2H), 4.81 (spt, 1H), 7.32 (d, 1H), 7.71-7.79 (m, 2H), 8.26 (s, 1H), 8.47 (s, 1H), 11.66 (br.s, 1H).

Example 52A

N-{4-[(cyclopropylmethyl)amino]-3-nitrophenyl}acetamide

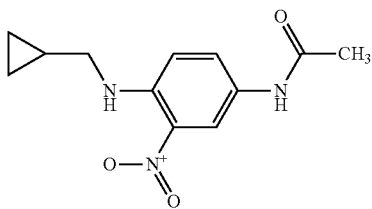

The preparation and purification of the target compound were analogous to Example 37A. Proceeding from 1.00 g (5.04 mmol) of N-(4-fluoro-3-nitrophenyl)acetamide and 1.04 ml (10.09 mmol) of cyclopropylmethylamine, 1.34 g of the title compound were obtained. The crude product was converted without further purification.

LC-MS (Method 3): $R_t$=1.10 min; MS (ESIpos): m/z=250 (M+H)$^+$.

$^1$H NMR (400 MHz, DMSO-d$_6$): δ [ppm]=0.27-0.33 (m, 2H), 0.49-0.55 (m, 2H), 1.10-1.22 (m, 1H), 2.02 (s, 3H), 3.21 (t, 2H), 7.07 (d, 1H), 7.65 (dd, 1H), 8.09 (t, 1H), 8.46 (d, 1H), 9.96 (s, 1H).

Example 53A

N-{3-amino-4-[(cyclopropylmethyl)amino]phenyl}acetamide

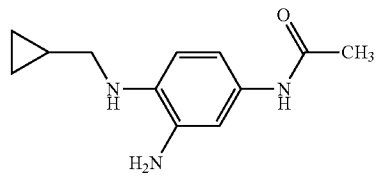

The preparation and purification of the target compound were analogous to Example 38A. Proceeding from 1.10 g (4.41 mmol) of N-{4-[(cyclopropylmethyl)amino]-3-nitrophenyl}acetamide from Example 52A, 952 mg (98% of theory) of the title compound were obtained.

LC-MS (Method 2): $R_t$=0.92 min; MS (ESIpos): m/z=220 (M+H)$^+$.

$^1$H NMR (400 MHz, DMSO-d$_6$): δ [ppm]=0.17-0.23 (m, 2H), 0.42-0.52 (m, 2H), 1.01-1.13 (m, 1H), 1.93 (s, 3H), 2.83 (t, 2H), 4.22 (t, 1H), 4.50-4.65 (m, 2H), 6.31 (d, 1H), 6.64 (dd, 1H), 6.84 (d, 1H), 9.36 (s, 1H).

Example 54A

N-[1-(cyclopropylmethyl)-1H-benzimidazol-5-yl]acetamide

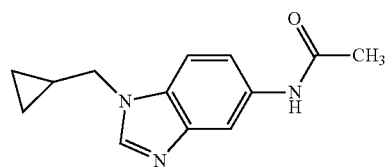 [SMILES: CC(=O)Nc1ccc2c(c1)ncn2CC1CC1]

The preparation and purification of the target compound were analogous to Example 39A. Proceeding from 951 mg (4.33 mmol) of N-{3-amino-4-[(cyclopropylmethyl)amino]phenyl}acetamide from Example 53A and 28 ml (166.29 mmol) of (diethoxymethoxy)ethane, 929 mg (84% of theory) of the title compound were obtained.

LC-MS (Method 3): $R_t$=0.39 min; MS (ESIpos): m/z=230 (M+H)$^+$.

$^1$H NMR (400 MHz, DMSO-d$_6$): δ [ppm]=0.47-0.53 (m, 2H), 0.58-0.64 (m, 2H), 1.32-1.43 (m, 1H), 2.10 (s, 3H), 4.25 (d, 2H), 7.55 (dd, 1H), 7.87 (d, 1H), 8.30 (d, 1H), 9.22 (s, 1H), 10.34 (s, 1H).

Example 55A 1-(cyclopropylmethyl)-1H-benzimidazol-5-amine

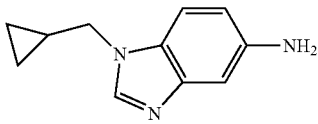 [SMILES: Nc1ccc2c(c1)ncn2CC1CC1]

The preparation and purification of the target compound were analogous to Example 40A. Proceeding from 828 mg (3.61 mmol) of N-[1-(cyclopropylmethyl)-1H-benzimidazol-5-yl]acetamide from Example 54A, 482 mg (70% of theory) of the title compound were obtained.

LC-MS (Method 2): $R_t$=0.87 min; MS (ESIpos): m/z=188 (M+H)$^+$.

$^1$H NMR (400 MHz, DMSO-d$_6$): δ [ppm]=0.34-0.40 (m, 2H), 0.48-0.55 (m, 2H), 1.19-1.30 (m, 1H), 3.96 (d, 2H), 4.71 (br.s, 2H), 6.59 (dd, 1H), 6.77 (d, 1H), 7.27 (d, 1H), 7.97 (s, 1H).

Example 56A ethyl 1-[1-(cyclopropylmethyl)-1H-benzimidazol-5-yl]-2,4-dioxo-1,2,3,4-tetrahydropyrimidine-5-carboxylate

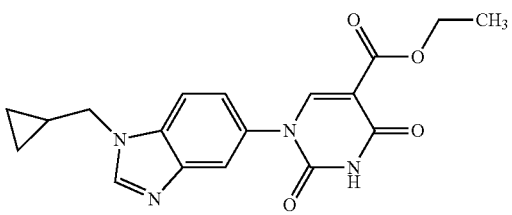 [SMILES: CCOC(=O)c1cn(-c2ccc3c(c2)ncn3CC2CC2)c(=O)[nH]c1=O]

The preparation of the target compound was analogous to Example 31A, with a reaction time of 5 h using 547 mg (2.92 mmol) of 1-(cyclopropylmethyl)-1H-benzimidazol-5-amine from Example 55A and 757 mg (2.92 mmol) of ethyl 3-ethoxy-2-[(ethoxycarbonyl)carbamoyl]acrylate. For workup, the reaction mixture was concentrated, the residue was subjected to extractive stirring in ethyl acetate/methanol, and the solid was filtered off with suction and dried under high vacuum. This gave 1.02 g (98% of theory) of the title compound.

LC-MS (Method 1): $R_t$=0.61 min; MS (ESIpos): m/z=355 (M+H)$^+$.

$^1$H NMR (400 MHz, DMSO-d$_6$): δ [ppm]=0.41-0.46 (m, 2H), 0.51-0.58 (m, 2H), 1.18 (t, 3H), 1.25-1.37 (m, 1H), 4.06 (q, 2H), 4.15 (d, 2H), 7.18 (dd, 1H), 7.53 (d, 1H), 7.67 (d, 1H), 7.97 (s, 1H), 8.33 (s, 1H).

Example 57A 1,3,3-trimethyl-5-nitro-1,3-dihydro-2H-indol-2-one

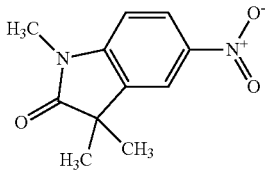

2.44 g (13.96 mmol) of 1,3,3-tri methyl-1,3-dihydro-2H-indol-2-one [for preparation see: Journal of Organic Chemistry, 2000, vol. 65, 24, p. 8317-8325] were initially charged in 12 ml of acetic acid, then 0.96 ml (13.96 mmol) of nitric acid (65%) was added dropwise at RT and the reaction mixture was stirred at RT for 2 weeks. The reaction mixture was added to ice-water, and the precipitated solid was filtered off with suction, washed with water and dried at 50° C. under reduced pressure. This gave 2.32 g (72% of theory) of the title compound.

LC-MS (Method 5): $R_t$=0.89 min; MS (ESIpos): m/z=221 (M+H)$^+$.

$^1$H NMR (400 MHz, DMSO-d$_6$): δ [ppm]=1.35 (s, 6H), 3.22 (s, 3H), 7.25 (d, 1H), 8.26 (dd, 1H), 8.33 (d, 1H).

Example 58A 5-amino-1,3,3-trimethyl-1,3-dihydro-2H-indol-2-one

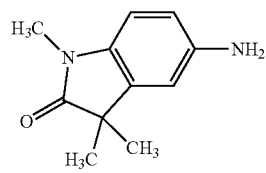

The preparation and purification of the target compound were analogous to Example 33A, with a reaction time of 2 days. Proceeding from 2.32 g (10.56 mmol) of 1,3,3-trimethyl-5-nitro-1,3-dihydro-2H-indol-2-one from Example 57A, 1.95 g (93% of theory) of the title compound were obtained.

LC-MS (Method 2): $R_t$=0.76 min; MS (ESIpos): m/z=191 (M+H)$^+$.

$^1$H NMR (400 MHz, DMSO-d$_6$): δ [ppm]=1.20 (s, 6H), 3.04 (s, 3H), 4.70-4.80 (m, 2H), 6.46 (dd, 1H), 6.58 (d, 1H), 6.67 (d, 1H).

Example 59A ethyl 2,4-dioxo-1-(1,3,3-trimethyl-2-oxo-2,3-dihydro-1H-indol-5-yl)-1,2,3,4-tetrahydropyrimidine-5-carboxylate

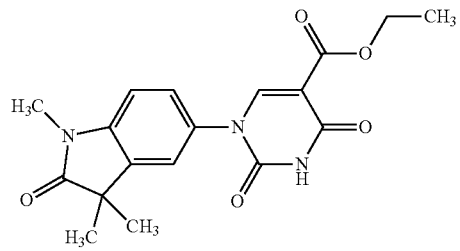 [SMILES: CCOC(=O)c1cn(-c2ccc3c(c2)C(C)(C)C(=O)N3C)c(=O)[nH]c1=O]

The preparation and purification of the target compound were analogous to Example 31A. Proceeding from 1.95 g (10.26 mmol) of 5-amino-1,3,3-trimethyl-1,3-dihydro-2H-indol-2-one from Example 58A and 2.66 g (10.26 mmol) of ethyl 3-ethoxy-2-[(ethoxycarbonyl)carbamoyl]acrylate, 2.84 g (77% of theory) of the title compound were obtained.

LC-MS (Method 2): $R_t$=1.62 min; MS (ESIpos): m/z=358 (M+H)$^+$.

$^1$H NMR (400 MHz, DMSO-d$_6$): δ [ppm]=1.22 (t, 3H), 1.29 (s, 6H), 3.17 (s, 3H), 4.17 (q, 2H), 7.13 (d, 1H), 7.40 (dd, 1H), 7.51 (d, 1H), 8.25 (s, 1H), 11.65-11.71 (m, 1H).

Example 60A

1'-methylspiro[cyclopropane-1,3'-indole]-2'(1'H)-one

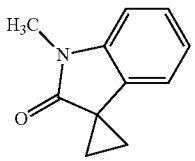

5.43 g (135.89 mmol) of sodium hydride (60% in mineral oil) were initially charged in 40 ml of DMF, then, at 0° C., a solution of 5.00 g (33.97 mmol) of 1-methyl-1,3-dihydro-2H-indol-2-one in 40 ml of DMF were added dropwise and the reaction mixture was stirred at RT for 30 min. Subsequently, 8.81 ml (101.91 mmol) of dibromoethane were added dropwise and the mixture was stirred at RT for 1 h. For workup, the reaction mixture was admixed with water and washed three times with ethyl acetate, and the combined organic phases were dried over magnesium sulphate, filtered and concentrated. This gave 3.78 g (64% of theory) of the title compound.

LC-MS (Method 1): R$_t$=0.76 min; MS (ESIpos): m/z=174 (M+H)±.

$^1$H NMR (400 MHz, DMSO-d$_6$): δ [ppm]=1.48-1.53 (m, 2H), 1.57-1.61 (m, 2H), 3.21 (s, 3H), 6.97-7.03 (m, 2H), 7.06 (d, 1H), 7.23-7.28 (m, 1H).

Example 61A

1'-methyl-5'-nitrospiro[cyclopropane-1,3'-indole]-2'(1'H)-one

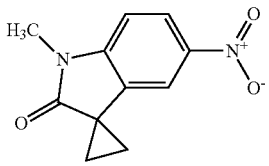

3.77 g (21.79 mmol) of 1'-methylspiro[cyclopropane-1,3'-indole]-2'(1'H)-one from Example 60A were initially charged in 40 ml of glacial acetic acid, then 0.90 ml (21.79 mmol) of conc. nitric acid were added dropwise, and the mixture was stirred at RT for 2 h. Thereafter, a further 0.45 ml (10.89 mmol) of conc. nitric acid was added dropwise and the mixture was stirred at RT for a further 1.5 h. For workup, the mixture was added to ice-water, and the precipitated solid was filtered off with suction, washed with water and dried at 30° C. under reduced pressure. This gave 4.01 g (84% of theory) of the title compound.

GC-MS (Method 6): R$_t$=7.21 min; MS (ESIpos): m/z=219 (M+H)$^+$.

$^1$H NMR (400 MHz, DMSO-d$_6$): δ [ppm]=1.54-1.72 (m, 2H), 1.80-1.99 (m, 2H), 3.3 (s, partly concealed by water signal), 7.17-7.38 (m, 1H), 7.91-8.09 (m, 1H), 8.14-8.31 (m, 1H).

Example 62A

5'-amino-1'-methylspiro[cyclopropane-1,3'-indole]-2' (1'H)-one

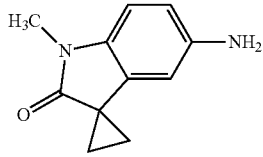

1.00 g (4.58 mmol) of 1'-methyl-5'-nitrospiro[cyclopropane-1,3'-indole]-2'(1'H)-one from Example 61A were initially charged in 11 ml of ethyl acetate, 4.13 g (18.33 mmol) of tin (II) chloride dihydrate were added and the mixture was heated to reflux for 2.5 h. The reaction mixture cooled to RT was diluted with ethyl acetate and extracted twice with 1 N hydrochloric acid. The aqueous phase was set to pH 10 with 1N sodium hydroxide solution and extracted four times with dichloromethane. The combined organic phases were washed with saturated sodium chloride solution, dried over magnesium sulphate, filtered and concentrated. This gave 375 mg (42% of theory) of the title compound.

LC-MS (Method 2): R$_t$=0.73 min; MS (ESIpos): m/z=189 (M+H)$^+$.

$^1$H NMR (400 MHz, DMSO-d$_6$): δ [ppm]=1.38-1.46 (m, 4H), 3.11 (s, 3H), 4.65-4.76 (m, 2H), 6.24 (d, 1H), 6.46 (dd, 1H), 6.73 (d, 1H).

Example 63A ethyl 1-(1'-methyl-2'-oxo-1',2'-dihydrospiro[cyclopropane-1,3'-indole]-5'-yl)-2,4-dioxo-1,2,3,4-tetrahydropyrimidine-5-carboxylate

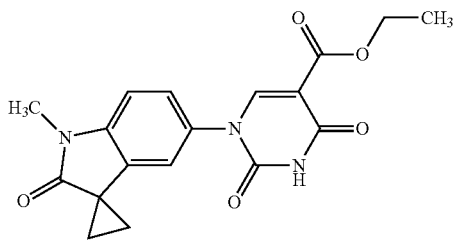 [SMILES: CCOC(=O)c1cn(-c2ccc3c(c2)C2(CC2)C(=O)N3C)c(=O)[nH]c1=O]

510 mg (1.97 mmol) of ethyl 3-ethoxy-2-[(ethoxycarbonyl)carbamoyl]acrylate and 370 mg (1.97 mmol) of 5'-amino-1'-methylspiro[cyclopropane-1,3'-indole]-2'(1'H)-one from Example 62A were heated to reflux in 10 ml of ethanol for 45 min. Thereafter, at RT, 221 trig (1.97 mmol) of potassium tert-butoxide were added and the mixture was stirred at RT for 1.5 h and to reflux for 1 h. For workup, the reaction mixture was admixed with water and acidified with 1N hydrochloric acid. The solid formed was filtered off, washed with water, and then dried under reduced pressure at 30° C. This gave 557 mg (78% of theory) of the title compound.

LC-MS (Method 1): R$_t$=0.69 min; MS (ESIpos): m/z=356 (M+H)$^+$.

¹H NMR (400 MHz, DMSO-d₆): δ [ppm]=1.22 (t, 3H), 1.54-1.59 (m, 2H), 1.62-1.68 (m, 2H), 3.25 (s, 3H), 4.17 (q, 2H), 7.15-7.20 (m, 2H), 7.35-7.41 (m, 1H), 8.25 (s, 1H), 11.68 (s, 1H).

Example 64A ethyl 2,4-dioxo-1-(1,3,3-trimethyl-2-oxo-2,3-dihydro-1H-indol-6-yl)-1,2,3,4-tetrahydropyrimidine-5-carboxylate

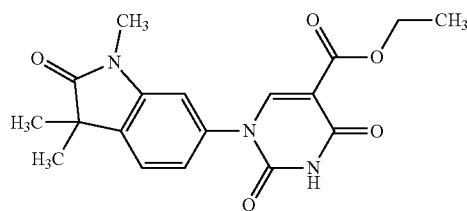 [SMILES: CCOC(=O)c1cn(-c2ccc3c(c2)N(C)C(=O)C3(C)C)c(=O)[nH]c1=O]

388 mg (1.49 mmol) of ethyl 3-ethoxy-2-[(ethoxycarbonyl)carbamoyl]acrylate and 285 mg (1.49 mmol) of 6-amino-1,3,3-trimethyl-1,3-dihydro-2H-indol-2-one [for preparation see: Journal of Medicinal Chemistry, 1989, Vol. 32, (7), 1481-1491] were initially charged in 10 ml of ethanol and the mixture was heated to reflux for 2 h. Thereafter, at RT, 167 mg (1.49 mmol) of potassium tert-butoxide were added and the mixture was stirred at RT for 1 h and at reflux for 15 min. For workup, the reaction mixture was admixed with water, acidified with 1N hydrochloric acid and extracted twice with ethyl acetate. The combined organic phases were dried over magnesium sulphate, filtered and concentrated. The residue was subjected to extractive stirring in MTBE/ethyl acetate, filtered off, washed with ethyl acetate and then dried at 50° C. under reduced pressure. The solid which precipitated in the filtrate was filtered off with suction and dried under reduced pressure. This gave a total of 388 mg (68% of theory) of the title compound.

LC-MS (Method 1): R$_t$=0.75 min; MS (ESIpos): m/z=358 (M+H)'.

¹H NMR (400 MHz, DMSO-d₆): δ [ppm]=1.22 (t, 3H), 1.30 (s, 6H), 3.14 (s, 3H), 4.17 (q, 2H), 7.16 (d, 1H), 7.23 (s, 1H), 7.48 (d, 1H), 8.30 (s, 1H), 11.73 (s, 3H).

Example 65A ethyl 1-(3,3-dimethyl-2-oxo-2,3-dihydro-1H-indol-6-yl)-2,4-dioxo-1,2,3,4-tetrahydropyrimidine-5-carboxylate

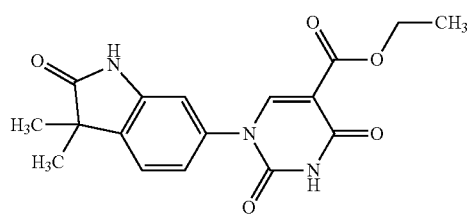 [SMILES: CCOC(=O)c1cn(-c2ccc3c(c2)NC(=O)C3(C)C)c(=O)[nH]c1=O]

570 mg (2.20 mmol) of ethyl 3-ethoxy-2-[(ethoxycarbonyl)carbamoyl]acrylate and 388 mg (2.20 mmol) of 6-amino-3,3-dimethyl-1,3-dihydro-2H-indol-2-one [for preparation see: US 2006/258689, page 35] were initially charged in 14 ml of ethanol and heated to reflux for 2 h. Subsequently, at RT, 247 mg (2.20 mmol) of potassium tert-butoxide were added and the mixture was stirred at RT for 1 h and at 60° C. for 1 h. For workup, the reaction mixture was admixed with water, acidified with 1N hydrochloric acid and extracted twice with ethyl acetate. The combined organic phases were dried over magnesium sulphate, filtered and concentrated. The residue was subjected to extractive stirring in MTBE/ethyl acetate, and the solid formed was filtered off, washed with ethyl acetate and then dried at 50° C. under reduced pressure. This gave 630 mg (79% of theory) of the title compound.

LC-MS (Method 1): R$_t$=0.65 min; MS (ESIpos): m/z=344 (M+H)⁺.

¹H NMR (400 MHz, DMSO-d₆): δ [ppm]=1.22 (t, 3H), 1.28 (s, 6H), 4.16 (q, 2H), 6.96-7.01 (m, 1H), 7.04-7.09 (m, 1H), 7.42 (d, 1H), 8.27 (s, 1H), 10.58 (s, 1H), 11.65 (s, 1H).

Example 66A ethyl 1-(1-acetyl-3,3-dimethyl-2,3-dihydro-1H-indol-6-yl)-2,4-dioxo-1,2,3,4-tetrahydropyrimidine-5-carboxylate

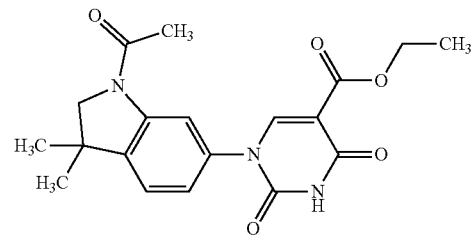 [SMILES: CCOC(=O)c1cn(-c2ccc3c(c2)N(C(C)=O)CC3(C)C)c(=O)[nH]c1=O]

The preparation and purification of the target compound were analogous to Example 31A. Proceeding from 0.81 g (3.96 mmol) of 1-(6-amino-3,3-dimethyl-2,3-dihydro-1H-indol-1-yl)ethanone [synthesis described in: WO 2006/12374 A1, 2006] and 1.06 g (3.96 mmol) of ethyl 3-ethoxy-2-[(ethoxycarbonyl)carbamoyl]acrylate, 626 mg (40% of theory) of the title compound were obtained.

LC-MS (Method 1): R$_t$=0.84 min; MS (ESIpos): m/z=372 (M+H)⁺.

¹H NMR (400 MHz, DMSO-d₆): δ [ppm]=1.22 (t, 3H), 1.34 (s, 6H), 2.18 (s, 3H), 3.93 (s, 2H), 4.16 (q, 2H), 7.13 (dd, 1H), 7.38 (d, 1H), 8.05 (d, 1H), 8.23 (s, 1H), 11.64 (br.s, 1H).

Example 67A 5-bromo-1,3,3-trimethyl-1,3-dihydro-2H-indol-2-one

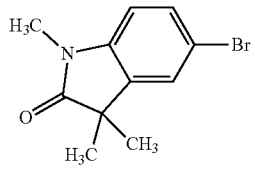

Under argon, 2.64 g (66 mmol) of sodium hydride (60% in mineral oil) were suspended in 25 ml of THF and cooled to 0° C. A solution of 4.00 g (18.86 mmol) of 5-bromo-1,3-dihydro-2H-indol-2-one in 25 ml of DMF was added dropwise and the mixture was stirred at 0° C. for 30 min. Subsequently, 4.11 ml (66 mmol) of methyl iodide were slowly added dropwise thereto, then the reaction mixture was warmed to RT and stirring continued at this temperature overnight. For workup, the mixture was poured onto 200 ml of 1M hydrochloric acid and extracted three times with ethyl acetate. The combined organic phases were washed with water, then a saturated sodium chloride solution, dried over sodium sulphate and concentrated on a rotary evaporator. The residue was dissolved in 200 ml of acetonitrile and the mineral oil was extracted with n-pentane. The acetonitrile phase removed was concentrated on a rotary evaporator and the remaining brownish solid was dried under HV. This gave 4.45 g (84% of theory) of the title compound in 91% purity.

LC-MS (Method 3): $R_t$=1.18 min; m/z=254, 256 (M+H)$^+$.

$^1$H NMR (400 MHz, DMSO-$d_6$): δ [ppm]=1.27 (s, 6H), 3.12 (s, 3H), 6.99 (d, 1H), 7.45 (dd, 1H), 7.60 (d, 1H).

Example 68A 1,3,3-trimethyl-5-(4,4,5,5-tetramethyl-1,3,2-dioxaborolan-2-yl)-1,3-dihydro-2H-indol-2-one

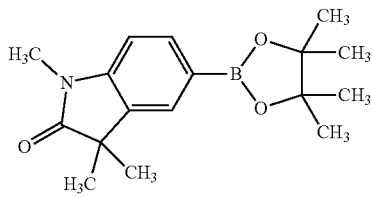 [SMILES: CN1C(=O)C(C)(C)c2cc(B3OC(C)(C)C(C)(C)O3)ccc21]

A solution of 3.45 g (approx. 12.35 mmol) of the compound from Example 67A, 4.71 g (18.5 mmol) of 4,4,4',4',5,5,5',5'-octamethyl-2,2'-bi-1,3,2-dioxaborolane (bispinacolatodiboron) and 2.18 g (22.2 mmol) of potassium acetate in 60 ml of dioxane was degassed and put under an argon atmosphere. 1.0 g (1.23 mmol) of 1,1'-bis(diphenylphosphino)ferrocenepalladium(II) dichloride dichloromethane complex was added and the mixture was heated to reflux overnight. After cooling to RT, the reaction mixture was filtered through Celite, Celite was washed with ethyl acetate and the overall filtrate was concentrated on a rotary evaporator. The residue was adsorbed on diatomaceous earth in dichloromethane and applied to a Biotage silica gel cartridge. The cartridge was eluted with cyclohexane/ethyl acetate. The product-containing fractions were concentrated on a rotary evaporator. The residue was stirred with 20 ml of diethyl ether. The solid was filtered off, washed with a little diethyl ether and dried under HV. This gave 1.82 g of the title compound. By concentrating the mother liquor, stirring the residue in pentane and filtering off the solid, an additional 1.13 g of product were obtainable. Overall yield: 79% of theory.

LC-MS (Method 1): $R_t$=1.09 min; m/z=302 (M+H)±.

$^1$H NMR (400 MHz, DMSO-$d_6$): δ [ppm]=1.27 (s, 6H), 1.29 (s, 12H), 3.14 (s, 3H), 7.03 (d, 1H), 7.58 (br.s, 1H), 7.62 (br d, 1H).

Example 69A ethyl 1-[3-hydroxy-1-methyl-2-oxo-3-(trifluoromethyl)-2,3-dihydro-1H-indol-5-yl]-2,4-dioxo-1,2,3,4-tetrahydropyrimidine-5-carboxylate (Racemate)

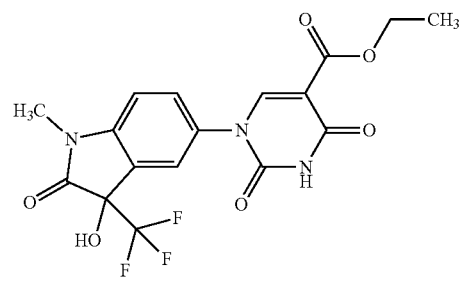 [SMILES: CCOC(=O)c1cn(-c2ccc3c(c2)C(O)(C(F)(F)F)C(=O)N3C)c(=O)[nH]c1=O]

1.00 g (4.06 mmol) of 5-amino-3-hydroxy-1-methyl-3-(trifluoromethyl)-1,3-dihydro-2H-indol-2-one from Example 20A and 1.05 g (4.06 mmol) of ethyl 3-ethoxy-2-[(ethoxycarbonyl)carbamoyl]acrylate were heated to reflux in 100 ml of ethanol for 1 h. After cooling to RT, 0.46 mg (4.06 mmol) of potassium tert-butoxide was added and the reaction mixture was stirred further at RT overnight and to reflux for 1 h. For workup, the reaction mixture was acidified with 1M hydrochloric acid, diluted with water and partly concentrated. The solid formed was filtered off, washed with water, and dried under reduced pressure at 40° C. overnight. This gave 1.47 g (88% of theory) of the target compound.

LC-MS (Method 1): $R_t$=0.72 min; MS (ESIpos): m/z=414 (M+H)$^+$.

$^1$H NMR (400 MHz, DMSO-$d_6$): δ [ppm]=1.24 (t, 3H), 3.21 (s, 3H), 4.18 (q, 2H), 7.27 (d, 1H), 7.60-7.68 (m, 2H), 7.90 (s, 1H), 8.23 (s, 1H), 11.68 (s, 1H).

Example 70A 3-hydroxy-1,3-dimethyl-5-nitro-1,3-dihydro-2H-indol-2-one (Racemate)

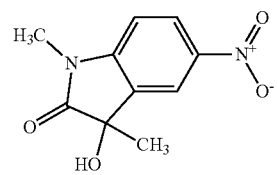 [SMILES: CN1C(=O)C(C)(O)c2cc([N+](=O)[O-])ccc21]

Under argon, 8.70 g (42.20 mmol) of 1-methyl-5-nitro-1H-indole-2,3-dione [for preparation see: Bioorganic & Medicinal Chemistry, 2006, 14(18), p. 6434-6443] were initially charged in 200 ml, then, at 0° C., 33 ml (46.42 mmol) of a 1.4M solution of magnesium bromide in toluene/THF were added dropwise within 10 min and the reaction mixture was stirred at RT for 16 h. For workup, the reaction mixture was admixed with cold water and extracted twice with dichloromethane. The combined organic phases were dried over magnesium sulphate, filtered and concentrated. The residue was separated by means of preparative HPLC (Method 7). This gave 1.41 g (12% of theory) of the title compound.

LC-MS (Method 5): $R_t$=0.63 min; MS (ESIpos): m/z=223 (M+H)$^+$.
$^1$H NMR (400 MHz, DMSO-d$_6$): δ [ppm]=1.46 (s, 3H), 3.19 (s, 3H), 3.22 (s, 1H), 7.24 (d, 1H), 8.19 (d, 1H), 8.30 (dd, 1H).

Example 71A 5-amino-3-hydroxy-1,3-dimethyl-1,3-dihydro-2H-indol-2-one (Racemate)

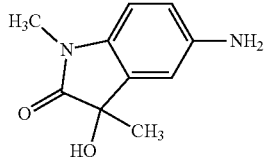

The preparation and purification of the target compound were analogous to Example 33A, with a reaction time of 4 h. Proceeding from 1.40 g (6.30 mmol) of 3-hydroxy-1,3-dimethyl-5-nitro-1,3-dihydro-2H-indol-2-one from Example 70A, after additional purification by means of preparative HPLC (Method 24), 1.15 g (95% of theory) of the title compound were obtained.

LC-MS (Method 2): $R_t$=0.48 min; MS (ESIpos): m/z=193 (M+H)$^+$.
$^1$H NMR (400 MHz, DMSO-d$_6$): δ [ppm]=1.39 (s, 3H), 3.11 (s, 3H), 7.08 (d, 1H), 7.25-7.32 (m, 2H).

Example 72A ethyl 1-(3-hydroxy-1,3-dimethyl-2-oxo-2,3-dihydro-1H-indol-5-yl)-2,4-dioxo-1,2,3,4-tetrahydropyrimidine-5-carboxylate (Racemate)

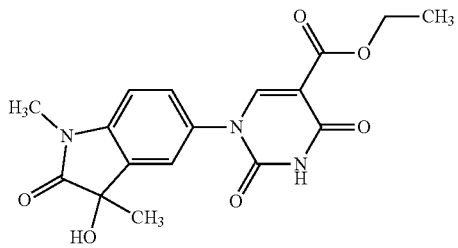 [SMILES: CCOC(=O)c1cn(-c2ccc3c(c2)C(C)(O)C(=O)N3C)c(=O)[nH]c1=O]

674 mg (2.60 mmol) of ethyl 3-ethoxy-2-[(ethoxycarbonyl)carbamoyl]acrylate and 500 mg (2.60 mmol) of 5-amino-3-hydroxy-1,3-dimethyl-1,3-dihydro-2H-indol-2-one from Example 71A were initially charged in 15 ml of ethanol and the mixture was heated to reflux for 1.5 h. Thereafter, at RT, 292 mg (2.60 mmol) of potassium tert-butoxide were added and the reaction mixture was heated to reflux for 10 h. For workup, the reaction mixture at RT was acidified with 1N hydrochloric acid and extracted twice with ethyl acetate. The combined organic phases were washed with saturated sodium chloride solution, dried over magnesium sulphate, filtered and concentrated. The residue was stirred in MTBE/ethyl acetate, and the solid formed was filtered off and then dried at 30° C. under reduced pressure. The solid which precipitated in the filtrate was filtered off, washed with water and dried under reduced pressure. This gave a total of 218 mg (22% of theory) of the title compound.

LC-MS (Method 5): $R_t$=0.53 min; MS (ESIpos): m/z=360 (M+H)$^+$.
$^1$H NMR (400 MHz, DMSO-d$_6$): δ [ppm]=1.23 (t, 3H), 1.41 (s, 3H), 3.14 (s, 3H), 4.18 (q, 2H), 6.10 (s, 1H), 7.11 (d, 1H), 7.43 (d, 1H), 7.52 (s, 1H), 8.20 (s, 1H), 11.67 (s, 1H).

Example 73A ethyl 1-[3-fluoro-1-methyl-2-oxo-3-(trifluoromethyl)-2,3-dihydro-1H-indol-5-yl]-2,4-dioxo-1,2,3,4-tetrahydropyrimidine-5-carboxylate (Racemate)

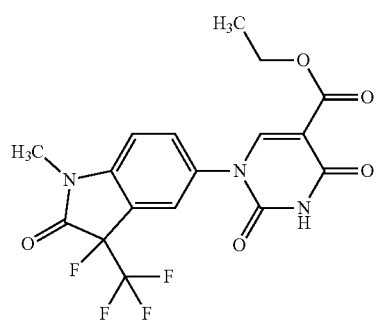 [SMILES: CCOC(=O)c1cn(-c2ccc3c(c2)C(F)(C(F)(F)F)C(=O)N3C)c(=O)[nH]c1=O]

Under argon, 200 mg (0.48 mmol) of ethyl 1-[3-hydroxy-1-methyl-2-oxo-3-(trifluoromethyl)-2,3-dihydro-1H-indol-5-yl]-2,4-dioxo-1,2,3,4-tetrahydropyrimidine-5-carboxylate from Example 69A were initially charged at −78° C. in 4.74 ml of dichloromethane. Subsequently, 128 μl (0.97 mmol) of diethylaminosulphur trifluoride were added dropwise, and the mixture was brought to RT and stirred further overnight. Thereafter, diethylaminosulphur trifluoride (0.5 eq.) was again added at −78° C. and the mixture was stirred at RT for 1 h. For workup, the mixture was diluted with dichloromethane, washed once each with saturated sodium hydrogencarbonate solution and saturated sodium chloride solution, dried over magnesium sulphate, filtered and concentrated. This gave 191 mg (91% of theory) of the title compound.

LC-MS (Method 5): $R_t$=0.83 min; MS (ESIpos): m/z=416 (M+H)$^+$.
$^1$H NMR (400 MHz, DMSO-d$_6$): δ [ppm]=1.23 (t, 3H), 3.26 (s, 3H), 4.18 (q, 2H), 7.40 (d, 1H), 7.77-7.83 (m, 1H), 7.91 (s, 1H), 8.34 (s, 1H), 11.72 (s, 1H).

Example 74A ethyl 1-(1-methyl-1H-benzotriazol-5-yl)-2,4-dioxo-1,2,3,4-tetrahydropyrimidine-5-carboxylate

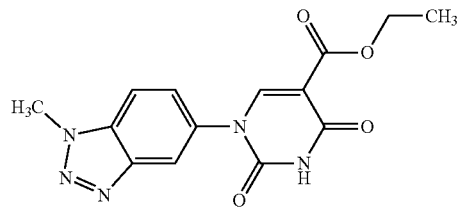

717 mg (2.77 mmol) of ethyl 3-ethoxy-2-[(ethoxycarbonyl)carbamoyl]acrylate and 410 mg (2.77 mmol) of 1-methyl-1H-benzotriazol-5-amine [for preparation see: WO 2005/092899, Ex. 142; Preparation 265] were heated to reflux in 21 ml of ethanol for 2 h. Thereafter, at RT, 311 mg (2.77 mmol) of potassium tert-butoxide were added and the reaction mixture was heated to reflux for a further 3 h. For workup, the reaction mixture was admixed with water and acidified with 1N hydrochloric acid. The solid formed was filtered off, washed with ethyl acetate and dried under reduced pressure at 50° C. This gave 659 mg (76% of theory) of the title compound.

LC-MS (Method 1): $R_t$=0.59 min; MS (ESIpos): m/z=316 (M+H)$^+$.

$^1$H NMR (400 MHz, DMSO-d$_6$): δ [ppm]=1.22 (t, 3H), 4.18 (q, 2H), 4.36 (s, 3H), 7.68 (dd, 1H), 7.97 (d, 1H), 8.25-8.29 (m, 1H), 8.40 (s, 1H), 11.75 (s, 1H).

Example 75A ethyl 1-(1-methyl-1H-indazol-5-yl)-2,4-dioxo-1,2,3,4-tetrahydropyrimidine-5-carboxylate

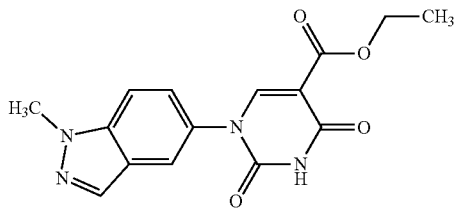 [SMILES: CCOC(=O)c1cn(-c2ccc3c(cnn3C)c2)c(=O)[nH]c1=O]

1.76 g (6.79 mmol) of ethyl 3-ethoxy-2-[(ethoxycarbonyl)carbamoyl]acrylate and 1.00 g (6.79 mmol) of 1-methyl-1H-indazol-5-amine in 51 ml of ethanol were heated to reflux for 2 h. Thereafter, at RT, 762 mg (6.79 mmol) of potassium tert-butoxide were added and the reaction mixture was heated to reflux for a further 3 h. For workup, the reaction mixture was admixed with water and acidified with 1N hydrochloric acid. The solid formed was filtered off, washed with ethyl acetate/MTBE (1:1) and dried under reduced pressure at 50° C. This gave 1.97 g (92% of theory) of the title compound.

LC-MS (Method 1): $R_t$=0.62 min; MS (ESIpos): m/z=315 (M+H)$^+$.

$^1$H NMR (400 MHz, DMSO-d$_6$): δ [ppm]=1.22 (t, 3H), 4.09 (s, 3H), 4.17 (q, 2H), 7.45-7.52 (m, 1H), 7.75 (d, 1H), 7.91 (s, 1H), 8.15 (s, 1H), 8.32 (s, 1H), 11.68 (s, 1H).

Example 76A ethyl 1-(1-methyl-1H-benzimidazol-5-yl)-2,4-dioxo-1,2,3,4-tetrahydropyrimidine-5-carboxylate

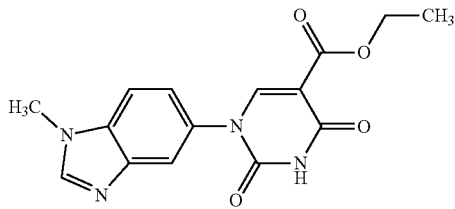 [SMILES: CCOC(=O)c1cn(-c2ccc3c(c2)ncn3C)c(=O)[nH]c1=O]

1.76 g (6.79 mmol) of ethyl 3-ethoxy-2-[(ethoxycarbonyl)carbamoyl]acrylate and 1.00 g (6.79 mmol) of 1-methyl-1H-benzimidazol-5-amine [for preparation see: US 2008/0090856, Ex. B23] in 51 ml of ethanol were heated to reflux for 2 h. Thereafter, at RT, 0.76 g (6.79 mmol) of potassium tert-butoxide were added and the reaction mixture was heated to reflux for a further 3 h. For workup, the reaction mixture was admixed with water and acidified with 1N hydrochloric acid. The aqueous phase was concentrated, dichloromethane/methanol (1:1) was added and the solid formed was filtered off. The filtrate was concentrated, MTBE/ethyl acetate (1:1) was added, and the solid formed was filtered off, washed with ethyl acetate and then dried at 50° C. under reduced pressure. This gave 1.55 g (73% of theory) of the title compound.

LC-MS (Method 2): $R_t$=1.00 min; MS (ESIpos): m/z=315 (M+H)$^+$.

$^1$H NMR (400 MHz, DMSO-d$_6$): δ [ppm]=1.22 (t, 3H), 4.03 (s, 3H), 4.18 (q, 2H), 7.62-7.68 (m, 1H), 7.94-8.00 (m, 1H), 8.00-8.03 (m, 1H), 8.35 (s, 1H), 9.24 (br.s, 1H), 11.73 (s, 1H).

Example 77A 1-methyl-5-nitro-2-(trichloromethyl)-1H-benzimidazole

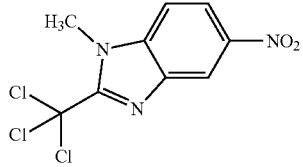 [SMILES: Cn1c(C(Cl)(Cl)Cl)nc2cc([N+](=O)[O-])ccc21]

To a suspension, cooled to 0° C., of 1.50 g (8.97 mmol) of N$^1$-methyl-4-nitrobenzene-1,2-diamine in 40.0 ml of glacial acetic acid were added dropwise 1.22 ml (9.87 mmol) of methyl 2,2,2-trichloroacetimidate and the mixture was stirred at RT for 3 h. For workup, the mixture was added to water, and the solid was filtered off and washed with water. The solid was dried at 50° C. under high vacuum. This gave 2.50 g (93% of theory) of the title compound.

LC-MS (Method 1): $R_t$=1.06 min; MS (ESIpos): m/z=296 (M+H)$^+$.

$^1$H NMR (400 MHz, DMSO-d$_6$): δ [ppm]=4.20 (s, 3H), 8.00 (d, 1H), 8.35 (dd, 1H), 8.75 (d, 1H).

Example 78A ethyl 1-methyl-5-nitro-1H-benzimidazole-2-carboxylate

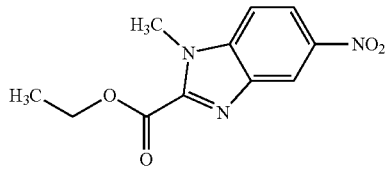 [SMILES: CCOC(=O)c1nc2cc([N+](=O)[O-])ccc2n1C]

2.50 g (8.48 mmol) of 1-methyl-5-nitro-2-(trichloromethyl)-1H-benzimidazole from Example 77A were initially charged in 24.0 ml of ethanol, then 4.75 g (27.98 mmol) of silver (I) nitrate were added and the mixture was heated to reflux overnight. For workup, the mixture was concentrated and the residue was admixed with 1M hydrochloric acid and ethyl acetate. Thereafter, the mixture was filtered through Celite and washed with ethyl acetate. The organic phase was dried over magnesium sulphate, filtered and concentrated. The resulting residue was stirred with MTBE, and the solid formed was filtered off and washed with MTBE. The solid was dried under high vacuum. This gave 0.32 g (15% of theory) of the title compound.

LC-MS (Method 5): $R_t$=0.86 min; MS (ESIpos): m/z=250 (M+H)$^+$.

$^1$H NMR (400 MHz, DMSO-d$_6$): δ [ppm]=1.39 (t, 3H), 4.15 (s, 3H), 4.44 (q, 2H), 7.99 (d, 1H), 8.28-8.35 (m, 1H), 8.69-8.74 (m, 1H).

Example 79A 1-methyl-5-nitro-1H-benzimidazole-2-carboxamide

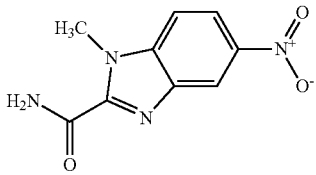 [SMILES: Cn1c(C(N)=O)nc2cc([N+](=O)[O-])ccc21]

745 mg (2.99 mmol) of ethyl 1-methyl-5-nitro-1H-benzimidazole-2-carboxylate from Example 78A were initially charged in 10.0 ml of THF, then 27.4 ml (54.90 mmol) of 25% aqueous ammonia solution were added and the mixture was stirred at RT for 2.5 h. For workup, the reaction mixture was admixed with water, and the solid formed was filtered off, washed with water and dried under high vacuum at 50° C. This gave 512 mg (88% purity, 68% of theory) of the title compound.

LC-MS (Method 5): $R_t$=0.64 min; MS (ESIpos): m/z=221 (M+H)$^+$.

$^1$H NMR (400 MHz, DMSO-d$_6$): δ [ppm]=4.18 (s, 3H), 7.94 (d, 1H), 8.04 (br.s, 1H), 8.28 (dd, 1H), 8.46 (br.s, 1H), 8.60 (d, 1H).

Example 80A 5-amino-1-methyl-1H-benzimidazole-2-carboxamide

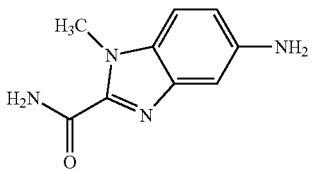

512 mg (2.33 mmol) of the nitro compound from Example 79A were initially charged in 16 ml of ethanol, then 74 mg (0.07 mmol) of palladium (10% on activated carbon) were added and the mixture was hydrogenated at standard hydrogen pressure overnight. Subsequently, the reaction mixture was filtered through kieselguhr, the residue was washed with ethanol and the filtrate was concentrated. This gave 440 mg (90% purity, 90% of theory) of the target compound.

LC-MS (Method 5): $R_t$=0.19 min; MS (ESIpos): m/z=191 (M+H)$^+$.

$^1$H NMR (400 MHz, DMSO-d$_6$): δ [ppm]=4.02 (s, 3H), 4.88-4.96 (m, 2H), 6.73-6.77 (m, 1H), 6.77-6.81 (m, 1H), 7.31 (d, 1H), 7.64 (br.s, 1H), 8.06 (br.s, 1H).

Example 81A ethyl 1-(2-carbamoyl-1-methyl-1H-benzimidazol-5-yl)-2,4-dioxo-1,2,3,4-tetrahydropyrimidine-5-carboxylate

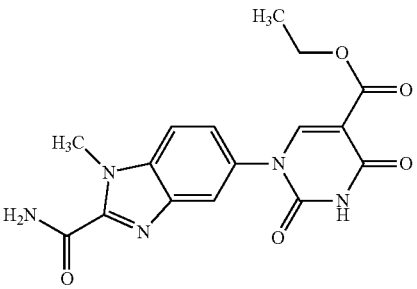 [SMILES: CCOC(=O)c1cn(-c2ccc3c(c2)nc(C(N)=O)n3C)c(=O)[nH]c1=O]

The preparation and purification of the target compound were analogous to Example 31A. Proceeding from 440 mg (2.31 mmol) of 5-amino-1-methyl-1H-benzimidazole-2-carboxamide from Example 80A and 600 mg (2.31 mmol) of ethyl 3-ethoxy-2-[(ethoxycarbonyl)carbamoyl]acrylate, 158 mg (87% purity, 17% of theory) of the title compound were obtained. The crude product was converted without further purification.

LC-MS (Method 1): $R_t$=0.55 min; MS (ESIpos): m/z=358 (M+H)$^+$.

$^1$H NMR (400 MHz, DMSO-d$_6$): δ [ppm]=1.22 (t, 3H), 4.13-4.21 (m, 5H), 7.46-7.53 (m, 1H), 7.80 (d, 1H), 7.89-7.93 (m, 2H), 8.31-8.37 (m, 2H), 11.69 (s, 1H).

Example 82A ethyl 1-(1-methyl-1H-benzimidazol-6-yl)-2,4-dioxo-1,2,3,4-tetrahydropyrimidine-5-carboxylate

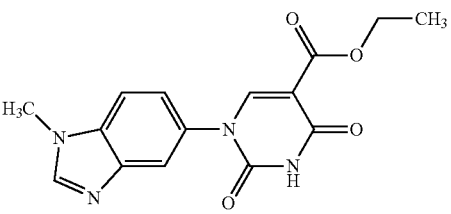 [SMILES: CCOC(=O)c1cn(-c2ccc3c(c2)ncn3C)c(=O)[nH]c1=O]

The preparation and purification of the target compound were analogous to Example 31A. Proceeding from 1.00 g (6.79 mmol) of 1-methyl-1H-benzimidazol-6-amine and 1.76 g (6.79 mmol) of ethyl 3-ethoxy-2-[(ethoxycarbonyl)carbamoyl]acrylate, 1.03 g (48% of theory) of the title compound were obtained.

LC-MS (Method 1): $R_t$=0.36 min; MS (ESIpos): m/z=315 (M+H)$^+$.

$^1$H NMR (400 MHz, DMSO-d$_6$): δ [ppm]=1.23 (t, 3H), 4.01 (s, 3H), 4.19 (q, 2H), 7.61-7.67 (m, 1H), 7.90-7.96 (m, 1H), 8.15 (s, 1H), 8.37 (s, 1H), 9.29-9.37 (m, 1H), 11.80 (s, 1H).

Example 83A 1,3-dihydro-2,1,3-benzothiadiazole 2,2-dioxide

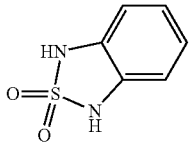 [SMILES: O=S1(=O)Nc2ccccc2N1]

1.00 g (9.25 mmol) of 1,2-phenylenediamine and 2.67 g (27.74 mmol) of sulphamide were initially charged in 14 ml of pyridine and the mixture was stirred at 130° C. overnight. For workup, the reaction mixture was concentrated under reduced pressure and the residue was separated by means of flash silica gel chromatography (cyclohexane/ethyl acetate gradient 7:1, 5:1). This gave 659 mg (42% of theory) of the title compound.

LC-MS (Method 5): $R_t$=0.51 min; MS (ESIpos): m/z=171 (M+H)$^+$.

$^1$H NMR (400 MHz, DMSO-d$_6$): δ [ppm]=6.76-6.83 (m, 2H), 6.85-6.91 (m, 2H), 10.95 (br.s, 2H).

Example 84A 1,3-dimethyl-1,3-dihydro-2,1,3-benzothiadiazole 2,2-dioxide

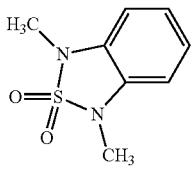

Under argon, 1.54 g (38.45 mmol) of sodium hydride (60% in mineral oil) in 41 ml of DMF were initially charged, then, at 0° C., a solution of 2.62 g (15.38 mmol) of 1,3-dihydro-2,1,3-benzothiadiazole 2,2-dioxide from Example 83A in 5 ml of DMF was added dropwise and the reaction mixture was stirred at 0° C. for 30 min. Thereafter, 2.39 ml (38.45 mmol) of iodomethane were added dropwise, and the reaction mixture was brought to RT and stirred for 1 h. For workup, water (200 ml) was added at 0° C. and the mixture was extracted three times with ethyl acetate. The combined organic phases were washed with water and saturated sodium chloride solution, dried over magnesium sulphate, filtered and concentrated. The residue was subjected to extractive stirring in MTBE, and the solid was filtered off, washed with MTBE and dried under high vacuum. This gave 1.89 g (62% of theory) of the title compound. The crude product was converted without further purification.

LC-MS (Method 1): $R_t$=0.78 min; MS (ESIpos): m/z=199 (M+H)$^+$.

$^1$H NMR (400 MHz, DMSO-d$_6$): δ [ppm]=3.23 (s, 6H), 6.98-7.05 (m, 4H).

Example 85A 1,3-dimethyl-5-nitro-1,3-dihydro-2,1,3-benzothiadiazole 2,2-dioxide

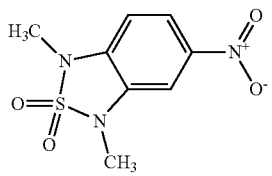 [SMILES: CN1c2ccc([N+](=O)[O-])cc2N(C)S1(=O)=O]

1.88 g (9.52 mmol) of 1,3-dimethyl-1,3-dihydro-2,1,3-benzothiadiazole 2,2-dioxide from Example 84A were initially charged in 8 ml of acetic acid, then 0.60 ml (9.52 mmol) of conc. nitric acid was added dropwise and the reaction mixture was stirred at RT for 1 h. For workup, the reaction mixture was added to ice-water, and the precipitated solid was filtered off with suction, washed with water and dried under reduced pressure at 50° C. This gave 2.17 g (93% of theory) of the title compound.

LC-MS (Method 1): $R_t$=0.81 mm; MS (ESIpos): m/z=244 (M+H)$^+$.

$^1$H NMR (400 MHz, DMSO-d$_6$): δ [ppm]=3.37-3.42 (m, 6H), 7.23 (d, 1H), 7.92 (d, 1H), 8.03 (dd, 1H).

Example 86A 1,3-dimethyl-1,3-dihydro-2,1,3-benzothiadiazol-5-amine 2,2-dioxide

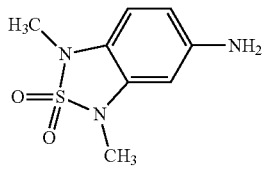

The preparation and purification of the target compound were analogous to Example 33A, with a reaction time of 16 h. Proceeding from 2.17 g (8.92 mmol) of 1,3-dimethyl-5-nitro-1,3-dihydro-2,1,3-benzothiadiazole 2,2-dioxide from Example 85A, 851 mg (44% of theory) of the title compound were obtained.

LC-MS (Method 1): $R_t$=0.31 min; MS (ESIpos): m/z=214 (M+H)±.

$^1$H NMR (400 MHz, DMSO-d$_6$): δ [ppm]=3.07 (s, 3H), 3.10 (s, 3H), 4.89-4.99 (m, 2H), 6.18-6.24 (m, 2H), 6.70 (d, 1H).

Example 87A ethyl 1-(1,3-dimethyl-2,2-dioxido-1,3-dihydro-2,1,3-benzothiadiazol-5-yl)-2,4-dioxo-1,2,3,4-tetrahydropyrimidine-5-carboxylate

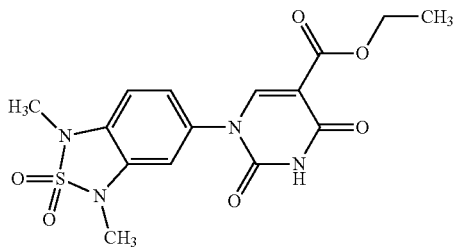 [SMILES: CCOC(=O)c1cn(-c2ccc3c(c2)N(C)S(=O)(=O)N3C)c(=O)[nH]c1=O]

1.03 g (3.99 mmol) of ethyl 3-ethoxy-2-[(ethoxycarbonyl)carbamoyl]acrylate and 851 nag (3.99 mmol) of 1,3-dimethyl-1,3-dihydro-2,1,3-benzothiadiazol-5-amine 2,2-dioxide from Example 86A were initially charged in 30 ml of ethanol and heated to reflux for 2 h. Subsequently, at RT, 448 mg (3.99 mmol) of potassium tert-butoxide were added and the mixture was stirred at RT for 16 h and at reflux for 5 h. For workup, the reaction mixture was acidified with 1N hydrochloric acid, and the solid formed was filtered off, washed with water and ethyl acetate and then dried under reduced pressure at 50° C. This gave 1.36 g (84% purity, 75% of theory) of the title compound.

LC-MS (Method 1): $R_t$=0.74 min; MS (ESIpos): m/z=381 (M+H)$^+$.

$^1$H NMR (400 MHz, DMSO-d$_6$): δ [ppm]=1.20-1.24 (m, 3H), 3.25 (s, 3H), 3.30 (s, 3H), 4.17 (q, 2H), 7.12-7.19 (m, 2H), 7.24-7.28 (m, 1H), 8.29 (s, 1H), 11.71 (br.s, 1H).

Example 88A ethyl 1-(1,3-benzothiazol-6-yl)-2,4-dioxo-1,2,3,4-tetrahydropyrimidine-5-carboxylate

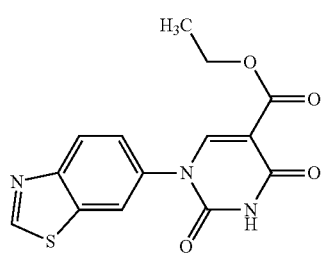 [SMILES: CCOC(=O)c1cn(-c2ccc3ncsc3c2)c(=O)[nH]c1=O]

The preparation of the target compound was analogous to Example 76A, using 1.00 g (6.65 mmol) of 1,3-benzothiazol-6-amine and 1.72 g (6.65 mmol) of ethyl 3-ethoxy-2-[(ethoxycarbonyl)carbamoyl]acrylate. For workup, the reaction mixture was admixed with water and 1N hydrochloric acid, and the precipitated solid was filtered off with suction, washed with ethyl acetate and dried at 50° C. under reduced pressure. This gave 1.85 g (87% of theory) of the title compound.

LC-MS (Method 1): $R_t$=0.61 min; MS (ESIpos): m/z=318 (M+H)$^+$.

$^1$H NMR (400 MHz, DMSO-d$_6$): δ [ppm]=1.22 (t, 3H), 4.18 (q, 2H), 7.67 (dd, 1H), 8.20 (d, 1H), 8.36 (d, 1H), 8.42 (s, 1H), 9.53 (s, 1H), 11.76 (s, 1H).

Example 89A 1-methyl-6-nitro-3,4-dihydroquinolin-2(1H)-one

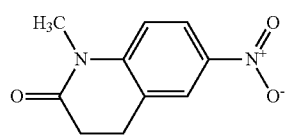

Under argon, 1.00 g (5.20 mmol) of 6-nitro-3,4-dihydroquinolin-2(1H)-one [for preparation see: WO 2006/71940, 416] was initially charged in 148 ml of THF, then 229 mg (5.72 mmol) of sodium hydride (60% in mineral oil) were added at 0° C. and the mixture was stirred for 30 min. Thereafter, 0.36 ml (5.72 mmol) of iodomethane was added dropwise and the reaction mixture was stirred at RT overnight. For workup, the reaction mixture was diluted with ethyl acetate, and the organic phase was washed twice with saturated sodium hydrogencarbonate solution, dried over magnesium sulphate, filtered and concentrated. The residue was stirred with ethanol, and the solid was filtered off, washed with ethanol and dried under high vacuum overnight. This gave 535 mg (50% of theory) of the title compound. The crude product was converted without further purification.

LC-MS (Method 3): $R_t$=0.88 min; MS (ESIpos): m/z=207 (M+H)$^+$.

$^1$H NMR (400 MHz, DMSO-d$_6$): δ [ppm]=2.60-2.66 (m, 2H), 3.02 (t, 2H), 3.31 (s, 3H), 7.26-7.32 (m, 1H), 8.12-8.20 (m, 2H).

Example 90A 6-amino-1-methyl-3,4-dihydroquinolin-2(1H)-one

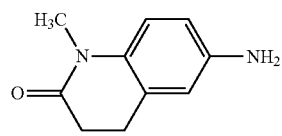

1.10 g (5.33 mmol) of the nitro compound from Example 89A were initially charged in 36 ml of ethanol, then 170 mg (0.16 mmol) of palladium (10% on activated carbon) were added and the mixture was hydrogenated at standard hydrogen pressure overnight. Subsequently, the reaction mixture was filtered through kieselguhr, the residue was washed with ethanol and the filtrate was concentrated. This gave 936 mg (99% of theory) of the target compound. The crude product was converted without further purification.

LC-MS (Method 2): $R_t$=0.73 min; MS (ESIpos): m/z=177 (M+H)$^+$.

$^1$H NMR (400 MHz, DMSO-d$_6$): δ [ppm]=2.43 (t, 2H), 2.69 (t, 2H), 3.16 (s, 3H), 4.79-4.90 (m, 2H), 6.41-6.47 (m, 2H), 6.77 (d, 1H).

Example 91A ethyl 1-(1-methyl-2-oxo-1,2,3,4-tetrahydroquinolin-6-yl)-2,4-dioxo-1,2,3,4-tetrahydropyrimidine-5-carboxylate

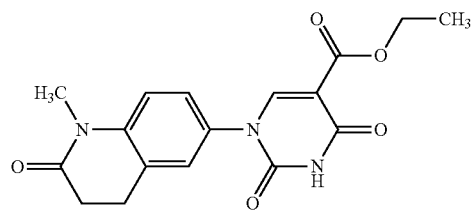 [SMILES: CCOC(=O)c1cn(-c2ccc3c(c2)CCC(=O)N3C)c(=O)[nH]c1=O]

The preparation and purification of the target compound were analogous to Example 31A. Proceeding from 935 mg (5.30 mmol) of 6-amino-1-methyl-3,4-dihydroquinolin-2 (1H)-one from Example 90A [synthesis described in: WO 2003/72553, page 150-151] and 1.37 g (5.30 mmol) of ethyl 3-ethoxy-2-[(ethoxycarbonyl)-carbamoyl]acrylate, 1.33 g (73% of theory) of the title compound were obtained.

LC-MS (Method 1): $R_t$=0.65 min; MS (ESIpos): m/z=344 (M+H)±.

$^1$H NMR (400 MHz, DMSO-d$_6$): δ [ppm]=1.22 (t, 3H), 2.56-2.61 (m, partly concealed by DMSO signal), 2.87-2.94 (m, 2H), 3.28 (s, 3H), 4.17 (q, 2H), 7.20 (d, 1H), 7.35-7.41 (m, 2H), 8.25 (s, 1H), 11.68 (s, 1H).

Example 92A ethyl 1-(1-methyl-2-oxo-1,4-dihydro-2H-3,1-benzoxazin-6-yl)-2,4-dioxo-1,2,3,4-tetrahydropyrimidine-5-carboxylate

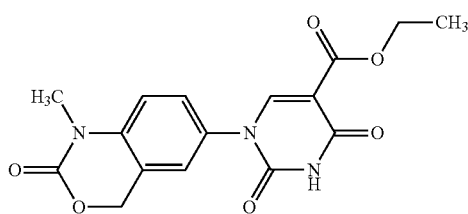 [SMILES: CCOC(=O)c1cn(-c2ccc3c(c2)COC(=O)N3C)c(=O)[nH]c1=O]

916 mg (3.53 mmol) of ethyl 3-ethoxy-2-[(ethoxycarbonyl)carbamoyl]acrylate and 630 mg (3.53 mmol) of 6-amino-1-methyl-1,4-dihydro-2H-3,1-benzoxazin-2-one [for preparation see: WO 2007/93904; p. 22, step 3] were initially charged in 20 ml of ethanol and heated to reflux for 1 h. Thereafter, at RT, 397 mg (3.53 mmol) of potassium tert-butoxide were added and the reaction mixture was stirred at RT for 16 h and at reflux for 3 h. For workup, the mixture was acidified with 1N hydrochloric acid at RT, and the solid formed was filtered off, washed with MTBE and then dried under reduced pressure at 50° C. This gave 1.11 g (90% of theory) of the title compound.

LC-MS (Method 1): $R_t$=0.58 min; MS (ESIpos): m/z=346 (M+H)$^+$.

$^1$H NMR (400 MHz, DMSO-d$_6$): δ [ppm]=1.22 (t, 3H), 3.3 (s, partly concealed by water signal), 4.17 (q, 2H), 5.29 (s, 2H), 7.21 (d, 1H), 7.40-7.44 (m, 1H), 7.48-7.54 (m, 1H), 8.27 (s, 1H), 11.70 (s, 1H).

Example 93A ethyl 1-(4-methylquinolin-7-yl)-2,4-dioxo-1,2,3,4-tetrahydropyrimidine-5-carboxylate

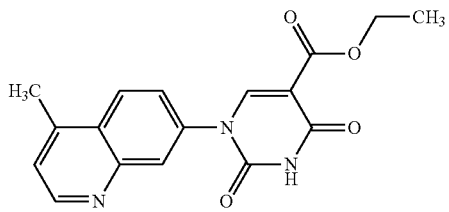 [SMILES: CCOC(=O)c1cn(-c2ccc3c(C)ccnc3c2)c(=O)[nH]c1=O]

The preparation and purification of the target compound were analogous to Example 31A. Proceeding from 987 mg (5.31 mmol) of 4-methylquinolin-7-amine [for preparation see: Nasr, M. et al., J. Med. Chem. 1988, vol. 31 (7), p. 1347-1351] and 1.37 g (5.31 mmol) of ethyl 3-ethoxy-2-[(ethoxycarbonyl)carbamoyl]acrylate, 745 mg (43% of theory) of the title compound were obtained.

LC-MS (Method 1): $R_t$=0.63 min; MS (ESIpos): m/z=326 (M+H)$^+$.

$^1$H NMR (400 MHz, DMSO-d$_6$): δ [ppm]=1.24 (t, 3H), 2.88 (s, 3H), 4.19 (q, 2H), 7.79 (d, 1H), 7.93 (dd, 1H), 8.32 (d, 1H), 8.41 (d, 1H), 8.50 (s, 1H), 9.06 (d, 1H), 11.82 (s, 1H).

Example 94A ethyl 1-(imidazo[1,2-a]pyridin-7-yl)-2,4-dioxo-1,2,3,4-tetrahydropyrimidine-5-carboxylate

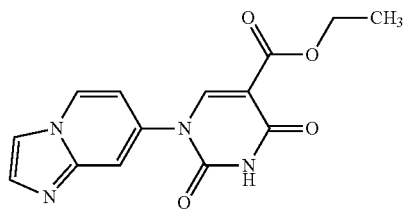 [SMILES: CCOC(=O)c1cn(-c2ccn3ccnc3c2)c(=O)[nH]c1=O]

The preparation and purification of the target compound were analogous to Example 31A. Proceeding from 500 mg (3.75 mmol) of imidazo[1,2-a]pyridin-7-amine [for preparation see: Tetrahedron, 2002, vol. 58 (2), p. 295-308] and 973 mg (3.75 mmol) of ethyl 3-ethoxy-2-[(ethoxycarbonyl)carbamoyl]acrylate, 1.11 g (94% of theory) of the title compound were obtained.

LC-MS (Method 1): $R_t$=0.19 min; MS (ESIpos): m/z=301 (M+H)$^+$.

$^1$H NMR (400 MHz, DMSO-d$_6$): δ [ppm]=1.24 (t, 3H), 4.21 (q, 2H), 7.60 (d, 1H), 8.21 (d, 2H), 8.39 (s, 1H), 8.48 (s, 1H), 8.96 (d, 1H), 11.91 (s, 1H).

Example 95A ethyl 1-(6-fluoro-1,3-dimethyl-2-oxo-2,3-dihydro-1H-benzimidazol-5-yl)-2,4-dioxo-1,2,3,4-tetrahydropyrimidine-5-carboxylate

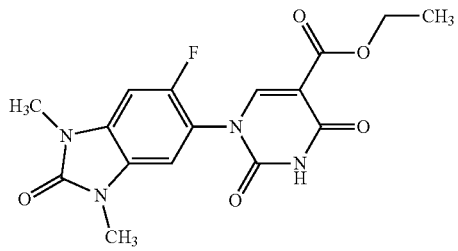 [SMILES: CCOC(=O)c1cn(-c2cc3c(cc2F)n(C)c(=O)n3C)c(=O)[nH]c1=O]

The preparation of the target compound was analogous to Example 31A, using 660 mg (3.38 mmol) of 5-amino-6-fluoro-1,3-dimethyl-1,3-dihydro-2H-benzimidazol-2-one from Example 19A and 877 mg (3.38 mmol) of ethyl 3-ethoxy-2-[(ethoxycarbonyl)carbamoyl]acrylate. The resulting crude product was purified by means of flash silica gel chromatography (dichloromethane/methanol gradient 54:1 20:1) to obtain 437 mg (36% of theory) of the title compound.

LC-MS (Method 1): $R_t$=0.62 min; MS (ESIpos): m/z=363 (M+H)⁺.

¹H NMR (400 MHz, DMSO-$d_6$): δ [ppm]=1.23 (t, 3H), 3.32 (s, 3H), 3.36 (s, 3H), 4.18 (q, 2H), 7.40 (d, 1H), 7.48 (d, 1H), 8.40 (s, 1H), 11.85 (s, 1H).

Example 96A (3-chloro-4-methyl-2-thienyl)methanol

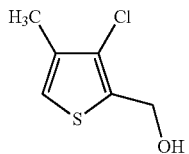

To a solution of borane-tetrahydrofuran complex (1M in THF, 3.40 ml, 3.40 mmol) were added, at RT under argon, 200 mg (1.13 mmol) of 3-chloro-4-methylthiophene-2-carboxylic acid in portions and the reaction mixture was stirred at RT for 1 h. Subsequently, the reaction mixture was cautiously added to 1N hydrochloric acid until the evolution of gas had ended. The whole mixture was separated by preparative HPLC (Method 8). This gave 115 mg (62% of theory) of the title compound.

GC-MS (Method 6): $R_t$=4.00 min; EI⁺: m/z=162 (M)⁺

¹H NMR (400 MHz, DMSO-$d_6$): δ [ppm]=2.12 (s, 3H), 4.58 (d, 2H), 5.57 (t, 1H), 7.25 (s, 1H).

Example 97A 4,6-difluoroindan-1-ol (Racemate)

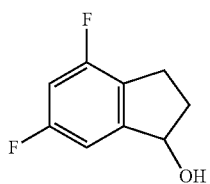 [SMILES: OC1CCc2c(F)cc(F)cc21]

146.3 mg (3.87 mmol) of sodium borohydride were added to a solution of 1.00 g (5.95 mmol) of 4,6-difluoro-2,3-dihydro-1H-inden-1-one in 15 ml of ethanol at RT and the reaction mixture was stirred at RT overnight. The mixture was admixed with ethyl acetate and water and shaken vigorously. The organic phase was removed, washed with a saturated ammonium chloride solution and a saturated sodium chloride solution, dried over magnesium sulphate and freed of the solvent on a rotary evaporator. The residue was dried briefly under HV. This gave 950 mg (94% of theory) of the title compound.

GC-MS (Method 6): $R_t$=3.35 min; MS (CI-pos): m/z=170 (M)⁺.

¹H NMR (400 MHz, DMSO-$d_6$): δ [ppm]=1.78-1.88 (m, 1H), 2.35-2.44 (m, 1H), 2.67 (dt, 1H), 2.90 (ddd, 1H), 5.05 (q, 1H), 5.49 (d, 1H), 6.99 (dd, 1H), 7.04 (td, 1H).

Example 98A 6-fluoro-4-(trifluoromethyl)indan-1-ol (Racemate)

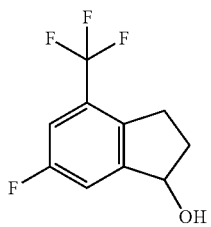

23.3 mg (0.62 mmol) of sodium borohydride were added to a solution of 207 mg (0.95 mmol) of 6-fluoro-4-(trifluoromethyl)-2,3-dihydro-1H-inden-1-one (preparation: see US2011/53974, Page 77, Example 61C) in 6 ml of ethanol at RT and the reaction mixture was stirred at RT overnight. The mixture was admixed with ethyl acetate and 1N hydrochloric acid and shaken vigorously. The organic phase was removed, washed with 1N hydrochloric acid and then with a saturated sodium chloride solution, dried over sodium sulphate and freed completely of the solvent on a rotary evaporator. This gave 203 mg (97% of theory) of the title compound.

GC-MS (Method 6): $R_t$=3.19 min; MS (CI-pos): m/z=220 (M)⁺.

¹H NMR (400 MHz, $CD_2Cl_2$): δ [ppm]=1.84-1.96 (m, 1H), 2.43-2.54 (m, 1H), 2.82 (dt, 1H), 3.02-3.14 (m, 1H), 5.14 (t, 1H), 7.17 (d, 1H), 7.21 (d, 1H).

Example 99A 7-(trifluoromethyl)-2,3-dihydro-1-benzofuran-3-ol (Racemate)

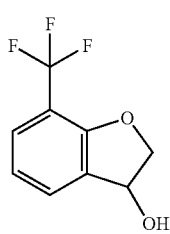

Analogously to Example 98A, 388 mg (1.92 mmol) of 7-(trifluoromethyl)-2,3-dihydro-1-benzofuran-3-one (preparation: see US 2011/53974, Page 56, Example 47E) were reduced with sodium borohydride. This gave 210 mg (51% of theory) of the title compound.

GC-MS (Method 6): $R_t$=3.80 min; MS (CI-pos): m/z=204 (M)⁺.

¹H NMR (400 MHz, DMSO-$d_6$): δ [ppm]=4.38 (dd, 1H), 4.66 (dd, 1H), 5.33 (dd, 1H), 5.72-5.91 (br. m, 1H), 7.07 (t, 1H), 7.52 (d, 1H), 7.66 (d, 1H).

Example 100A 6-methylindan-1-ol (Racemate)

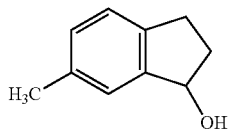

Analogously to Example 97A, 1.00 g (6.84 mmol) of 6-methyl-2,3-dihydro-1H-inden-1-one was reduced with sodium borohydride. This gave 950 mg (94% of theory) of the title compound.

GC-MS (Method 6): $R_t$=3.89 min; MS (CI-pos): m/z=148 (M)$^+$.

$^1$H NMR (400 MHz, DMSO-d$_6$): δ [ppm]=1.74 (dddd, 1H), 2.25-2.35 (m, 1H), 2.64 (dt, 1H), 2.84 (ddd, 1H), 4.99 (q, 1H), 5.14 (d, 1H), 6.99 (br. d, 1H), 7.08 (d, 1H), 7.12 (s, 1H).

Example 101A tert-butyl 6-[5-(ethoxycarbonyl)-2,4-dioxo-3,4-dihydropyrimidin-1(2H)-yl]-3-methyl-2-oxo-2,3-dihydro-1H-benzimidazole-1-carboxylate

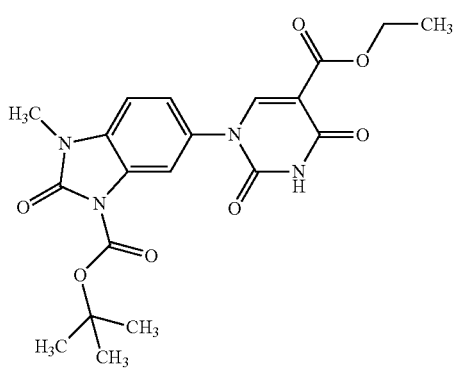 [SMILES: CCOC(=O)c1cn(-c2ccc3c(c2)n(C(=O)OC(C)(C)C)c(=O)n3C)c(=O)[nH]c1=O]

A suspension of 8.00 g (24.2 mmol) of the compound from Example 36A and 30 mg (0.24 mmol) of DMAP in 500 ml of DMF and 100 ml of dichloromethane was admixed at RT with 6.12 ml (26.6 mmol) of di-tert-butyl di-carbonate and stirred at RT overnight. For workup, 1.6 l of water were added and the mixture was extracted three times with ethyl acetate. The combined organic phases were washed twice with water, dried over sodium sulphate and concentrated on a rotary evaporator. The residue was stirred with diethyl ether, and the precipitated product was isolated by filtration and dried under HV. This gave 6.00 g (58% of theory) of the title compound.

LC-MS (Method 4): $R_t$=1.80 min; m/z=431 (M+H)$^+$.

$^1$H NMR (400 MHz, DMSO-d$_6$): δ [ppm]=1.22 (t, 3H), 1.58 (s, 9H), 4.17 (q, 2H), 7.28-7.40 (m, 2H), 7.84 (d, 1H), 8.25 (s, 1H), 11.65 (s, 1H) (methyl group probably under the DMSO signal).

Example 102A 5-methoxyindan-1-ol (Racemate)

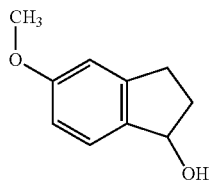

Analogously to Example 97A, 1.00 g (6.17 mmol) of 5-methoxy-2,3-dihydro-1H-inden-1-one was reduced with sodium borohydride. This gave 930 mg (80% purity, 73% of theory) of the title compound.

GC-MS (Method 6): $R_t$=4.70 min; MS (CI-pos): m/z=164 (M)'.

$^1$H NMR (400 MHz, DMSO-d$_6$): δ [ppm]=1.71-1.82 (m, 1H), 2.25-2.34 (m, 1H), 2.61-2.72 (m, 1H), 2.83-2.93 (m, 1H), 3.72 (s, 3H), 4.97 (q, 1H), 5.05 (d, 1H), 6.71-6.76 (m, 1H), 6.77 (br. s, 1H), 7.21 (d, 1H).

Example 103A 4-methoxyindan-1-ol (Racemate)

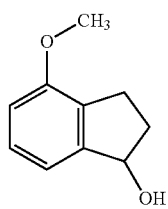

Analogously to Example 97A, 1.00 g (6.17 mmol) of 4-methoxy-2,3-dihydro-1H-inden-1-one was reduced with sodium borohydride. This gave 910 mg (90% of theory) of the title compound.

GC-MS (Method 6): $R_t$=4.65 min; MS (CI-pos): m/z=164 (M)$^+$.

$^1$H NMR (400 MHz, DMSO-d$_6$): δ [ppm]=1.68-1.80 (m, 1H), 2.25-2.35 (m, 1H), 2.54-2.62 (m, 1H), 2.83 (ddd, 1H), 3.76 (s, 3H), 5.02 (q, 1H), 5.18 (d, 1H), 6.80 (d, 1H), 6.93 (d, 1H), 7.17 (t, 1H).

Example 104A methyl (2E)-3-[4-chloro-2-(trifluoromethyl)phenyl] acrylate

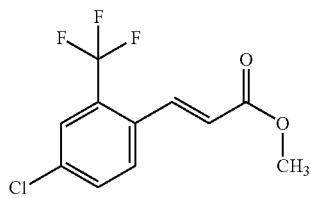 [SMILES: COC(=O)/C=C/c1ccc(Cl)cc1C(F)(F)F]

A mixture of 8.00 g (26.1 mmol) of 4-chloro-1-iodo-2-(trifluoromethyl)benzene, 3.76 ml (41.8 mmol) of me-acrylate, 7.47 g (26.9 mmol) of tetra-n-butylammonium chloride, 117 mg (0.52 mmol) of palladium(II) acetate and 7.22 g (52.2 mmol) of potassium carbonate in 80 ml of DMF was stirred at RT for 3 days. The mixture was diluted with 1 l of diethyl ether and washed three times with 200 ml each time of water. The organic phase was dried over sodium sulphate and concentrated on a rotary evaporator. The residue solidified after a while. This gave 6.65 g (92% of theory) of the title compound.

$^1$H NMR (400 MHz, DMSO-$d_6$): δ [ppm]=3.76 (s, 3H), 6.81 (d, 1H), 7.79 (dq, 1H), 7.84 (dd, 1H), 7.91 (d, 1H), 8.12 (d, 1H).

Example 105A methyl 3-[4-chloro-2-(trifluoromethyl)phenyl]propanoate

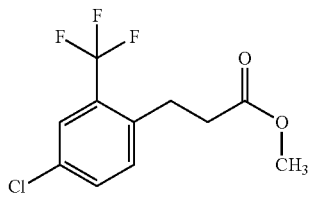 [SMILES: COC(=O)CCc1ccc(Cl)cc1C(F)(F)F]

6.65 g (25.1 mmol) of the compound from Example 104A were hydrogenated under standard hydrogen pressure in 250 ml of ethyl acetate in the presence of 2 g of palladium (10% on carbon) for 2 days. The catalyst was removed by filtration through kieselguhr and the filtrate was concentrated on a rotary evaporator. This gave 5.26 g of the title compound in about 75% purity (59% of theory).

$^1$H NMR (400 MHz, DMSO-$d_6$): δ [ppm]=2.62-2.68 (m, 2H), 3.01 (t, 2H), 3.61 (s, 3H), 7.56 (d, 1H), 7.69-7.76 (m, 2H).

Example 106A

3-[4-chloro-2-(trifluoromethyl)phenyl]propanoic acid

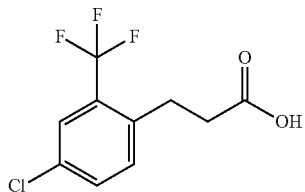 [SMILES: O=C(O)CCc1ccc(Cl)cc1C(F)(F)F]

A solution of 5.26 g (19.7 mmol) of the compound from Example 105A in 150 ml of methanol was admixed with 59.2 ml (59.2 mmol) of 1M sodium hydroxide solution and stirred at RT for 2 h. The methanol was removed on a rotary evaporator. The remaining aqueous residue was diluted with 600 ml of water and filtered. The filtrate was acidified with 1M hydrochloric acid. The precipitated solid was filtered off with suction, washed with water and dried under HV. This gave 4.45 g of the title compound in about 90% purity (80% of theory).

LC-MS (Method 5): $R_t$=1.02 min; MS (ESIneg): m/z=251 (M−H)$^-$.

$^1$H NMR (400 MHz, DMSO-$d_6$): δ [ppm]=2.52-2.58 (m, 2H, partly hidden under the DMSO signal), 2.97 (t, 2H), 7.56 (d, 1H), 7.68-7.76 (m, 2H), 12.32 (br.s, 1H).

Example 107A 6-chloro-4-(trifluoromethyl)indan-1-one

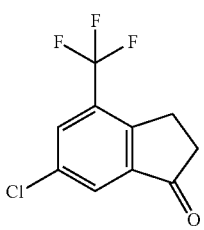 [SMILES: O=C1CCc2c1cc(Cl)cc2C(F)(F)F]

4.08 g (92% purity, 14.8 mmol) of the compound from Example 106A were admixed with 44 ml of chlorosulphonic acid while cooling with ice and then stirred at RT for 5 h. Subsequently, the reaction mixture was cautiously added dropwise to 600 g of crushed ice (very exothermic). The mixture was extracted three times with dichloromethane. The combined organic phases were washed twice with a 1M sodium carbonate solution, dried over sodium sulphate and concentrated on a rotary evaporator. The residue was dried only briefly under HV. This gave 2.38 g of the title compound in about 92% purity (63% of theory).

$^1$H NMR (400 MHz, DMSO-$d_6$): δ [ppm]=2.73-2.82 (m, 2H), 3.19-3.28 (m, 2H), 7.96 (s, 1H), 8.13 (s, 1H).

Example 108A 6-chloro-4-(trifluoromethyl)indan-1-ol (Racemate)

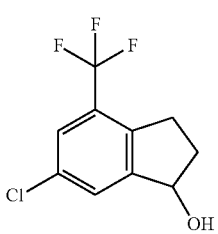

Analogously to Example 98A, 2.38 g (10.1 mmol) of 6-chloro-4-(trifluoromethyl)indan-1-one from Example 107A were reduced with sodium borohydride. This gave 1.97 g (82% of theory) of the title compound.

$^1$H NMR (400 MHz, DMSO-$d_6$): δ [ppm]=1.79-1.92 (m, 1H), 2.35-2.47 (m, 1H), 2.84 (dt, 1H), 2.98-3.10 (m, 1H), 5.09 (q, 1H), 5.58 (d, 1H), 7.64 (br. d, 2H).

Example 109A methyl (2E)-3-[4-bromo-2-(trifluoromethyl)phenyl]acrylate

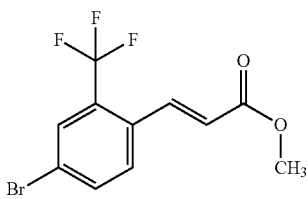

Analogously to Example 104A, 8.00 g (22.8 mmol) of 4-bromo-1-iodo-2-(trifluoromethyl)benzene were reacted with 3.29 ml (36.5 mmol) of methyl acrylate and the product was isolated. The crude product was purified by means of chromatography on silica gel (eluent: cyclohexane/ethyl acetate 10:1). This gave 5.70 g (81% of theory) of the title compound.

GC-MS (Method 6): $R_t$=4.75 min; MS (CI-pos): m/z=308/310 (M)$^+$.

$^1$H NMR (400 MHz, DMSO-d$_6$): δ [ppm]=3.76 (s, 3H), 6.82 (d, 1H), 7.77 (dq, 1H), 7.94-8.07 (m, 3H).

Example 110A methyl 3-[4-bromo-2-(trifluoromethyl)phenyl]propanoate

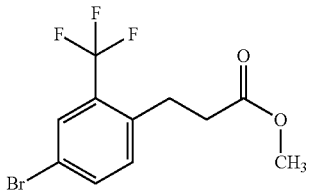

5.70 g (18.4 mmol) of the compound from Example 109A were first hydrogenated analogously to Example 105A with palladium (10% on carbon) under standard hydrogen pressure. Monitoring the reaction by means of LC-MS showed no reduction of the double bond, but about 25% debromination. The hydrogenation was stopped, the catalyst was filtered off and the solvent was removed on a rotary evaporator. The reactant thus recovered (5.0 g) was heated in 30 ml of toluene with 87 mg (0.16 mmol) of [Rh{(S,S)-Phebox-iPr}(OAc)$_2$].H$_2$O (preparation: see H. Nishiyama et al, Chem. Eur. J. 2006, 12 (1), 63-71, Example 3a) to 60° C. and admixed at this temperature with 3.89 ml (24.26 mmol) of methyldiethoxysilane. The mixture was stirred further at 60° C. for 4 h, then at reflux temperature overnight. After cooling to RT, the mixture was admixed with 50 ml of 1N hydrochloric acid and extracted with 150 ml of ethyl acetate. The organic phase was washed twice with water, twice with a saturated sodium hydrogencarbonate solution and once with a saturated sodium chloride solution, dried over sodium sulphate and concentrated on a rotary evaporator. The residue corresponded to the title compound in about 80% purity (5.84 g, 93% of theory) and was converted further without purification.

GC-MS (Method 6): $R_t$=4.42 min; MS (CI-pos): m/z=310/312 (M)$^+$.

$^1$H NMR (400 MHz, CD$_2$Cl$_2$): δ [ppm]=2.54-2.64 (m, 2H), 3.07 (t, 2H), 3.66 (s, 3H), 7.27 (d, 1H), 7.63 (d, 1H), 7.78 (d, 1H).

Example 111A

3-[4-bromo-2-(trifluoromethyl)phenyl]propanoic acid

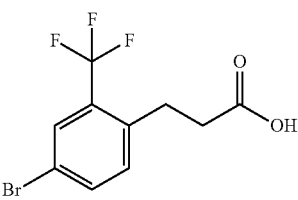

Analogously to Example 106A, 5.60 g (18 mmol) of the compound from Example 110A were converted and isolated. This gave 3.42 g (54% of theory) of the title compound in about 85% purity.

LC-MS (Method 4): $R_t$=2.25 min; MS (ESIpos): m/z=295/297 (M-H)$^-$.

$^1$H NMR (400 MHz, DMSO-d$_6$): δ [ppm]=2.52-2.58 (m, 2H, partly hidden under the DMSO signal), 2.95 (t, 2H), 7.49 (d, 1H), 7.81-7.88 (m, 2H), 12.37 (br.s, 1H).

Example 112A 6-bromo-4-(trifluoromethyl)indan-1-one

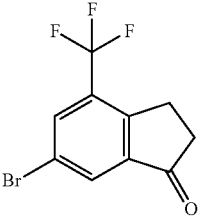

Analogously to Example 107A, 3.42 g (85% purity, 9.8 mmol) of the compound from Example 111A were converted and isolated. This gave 2.10 g (69% of theory) of the title compound in about 90% purity.

GC-MS (Method 6): $R_t$=4.34 min; MS (CI-pos): m/z=278/280 (M)$^+$.

$^1$H NMR (400 MHz, CDCl$_3$): δ [ppm]=2.75-2.82 (m, 2H), 3.23-3.31 (m, 2H), 7.96 (s, 1H), 8.05 (s, 1H).

Example 113A 6-bromo-4-(trifluoromethyl)indan-1-ol (Racemate)

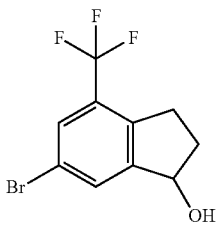 [SMILES: OC1CCc2c1cc(Cl)cc2C(F)(F)F]

A solution of 500 mg (1.79 mmol) of the compound from Example 112A in 3.9 ml of ethanol was admixed with 44.0 mg (1.16 mmol) of sodium borohydride and stirred at RT overnight. 3 ml of 1N hydrochloric acid were added, and the mixture was stirred for a few minutes, then separated completely by HPLC (Method 7).

The product-containing fractions were concentrated fully in vacuo and the residue was dried under HV. This gave 352 mg (92% of theory) of the title compound.

GC-MS (Method 6): $R_t$=4.58 min; MS (CI-pos): m/z=280/282 (M)$^+$.

$^1$H NMR (400 MHz, DMSO-d$_6$): δ [ppm]=1.79-1.90 (m, 1H), 2.35-2.46 (m, 1H), 2.82 (dt, 1H), 2.97-3.07 (m, 1H), 5.09 (q, 1H), 5.57 (dd, 1H), 7.74 (br.s, 1H), 7.77 (br.s, 1H).

Example 114A 4,6-dichloroindan-1-ol (Racemate)

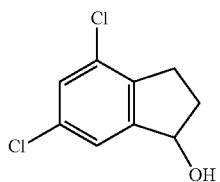 [SMILES: OC1CCc2c(Cl)cc(Cl)cc21]

Analogously to Example 98A, 1.25 g (6.22 mmol) of 4,6-dichloroindan-1-one was reduced with sodium borohydride and the product was isolated. This gave 1.20 g (95% of theory) of the title compound.

MS (Method 26 DCI/NH$_3$): m/z=202 (M$^+$)

$^1$H NMR (400 MHz, DMSO-d$_6$): δ [ppm]=1.75-1.90 (m, 1H), 2.30-2.44 (m, 1H), 2.64-2.78 (m, 1H), 2.85-2.98 (m, 1H), 5.09 (q, 1H), 5.53 (d, 1H), 7.32 (s, 1H), 7.44 (d, 1H).

Example 115A

1-[2-methyl-3-(trifluoromethyl)phenyl]ethanol

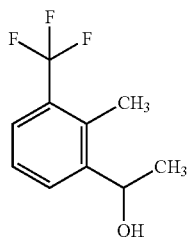

4.25 ml of a solution of methylmagnesium bromide (3M in diethyl ether, 12.75 mmol) were added dropwise to a solution of 2.00 g (10.6 mmol) of 2-methyl-3-(trifluoromethyl)benzaldehyde in 50 ml of diethyl ether, in the course of which the reaction mixture warmed up to reflux temperature. After addition had ended, the reaction mixture was heated to reflux for a further hour. After cooling to RT, small pieces of ice were added, then 6N hydrochloric acid was added dropwise until the precipitate which had formed dissolved again. The phases were separated. The aqueous phase was extracted once more with diethyl ether. The combined organic phases were dried over magnesium sulphate and concentrated on a rotary evaporator. This gave 2.40 g of the title compound (100% of theory, according to NMR still contains about 10% diethyl ether).

$^1$H NMR (500 MHz, CDCl$_3$): δ [ppm]=1.48 (d, 3H), 5.25 (q, 1H), 7.32 (t, 1H), 7.56 (d, 1H), 7.76 (d, 1H).

Example 116A

1-[2-chloro-3-(trifluoromethyl)phenyl]ethanol

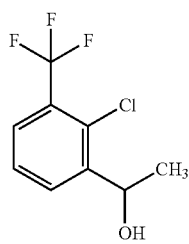

Analogously to Example 115A, 2.00 g (9.59 mmol) of 2-methyl-3-(trifluoromethyl)benzaldehyde were reacted with methylmagnesium bromide. This gave 2.40 g of the title compound (89% of theory, according to NMR still contains about 20% diethyl ether).

$^1$H NMR (500 MHz, CDCl$_3$): δ [ppm]=1.51 (d, 3H), 5.41 (q, 1H), 7.41 (t, 1H), 7.62 (d, 1H), 7.85 (d, 1H).

Example 117A ethyl 1-(1-ethyl-2-methyl-1H-benzimidazol-5-yl)-2,4-dioxo-1,2,3,4-tetrahydropyrimidine-5-carboxylate

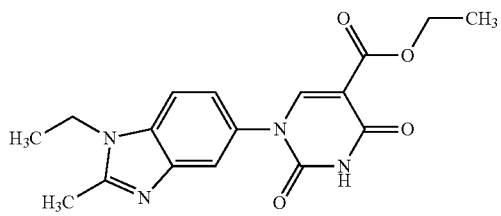 [SMILES: CCOC(=O)c1cn(-c2ccc3c(c2)nc(C)n3CC)c(=O)[nH]c1=O]

1.04 g (4.03 mmol) of ethyl 3-ethoxy-2-[(ethoxycarbonyl)carbamoyl]acrylate and 1.00 g (4.03 mmol) of 1-ethyl-2-methyl-1H-benzimidazol-5-amine dihydrochloride were initially charged in 30 ml of ethanol, then 1.24 ml (8.87 mmol) of triethylamine were added and the mixture was heated to reflux for 2 h. Thereafter, at RT, 452 mg (4.03 mmol) of potassium tert-butoxide were added and the reaction mixture was first stirred further at RT overnight, then heated to reflux and stirred at this temperature overnight. For workup, the reaction mixture was admixed with water and acidified with 1N hydrochloric acid. The mixture was concentrated to dryness, and the residue was stirred with dichloromethane/methanol (1:1) and filtered. The filtrate was concentrated again, the residue was stirred with MTBE/ethyl acetate and the solid formed was filtered off. After drying under HV, 1.07 g (87% pure, 68% of theory) of the target compound were obtained.

LC-MS (Method 2): $R_t$=1.06 min; MS (ESIpos): m/z=343 (M+H)$^+$.

$^1$H NMR (400 MHz, DMSO-d$_6$): δ [ppm]=1.23 (t, 3H), 1.41 (t, 3H), 2.84 (s, 3H), 4.18 (q, 2H), 4.47 (q, 2H), 7.64-7.70 (m, 1H), 7.99-8.02 (m, 1H), 8.06 (d, 1H), 8.35 (s, 1H), 11.75 (s, 1H).

Example 118A ethyl 1-(1-cyclohexyl-2-methyl-1H-benzimidazol-5-yl)-2,4-dioxo-1,2,3,4-tetrahydropyrimidine-5-carboxylate

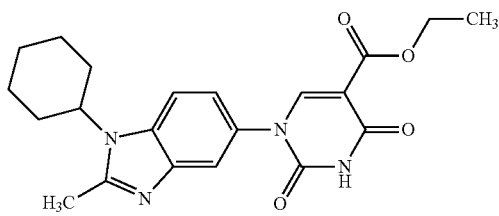 [SMILES: CCOC(=O)c1cn(-c2ccc3c(c2)nc(C)n3C2CCCCC2)c(=O)[nH]c1=O]

0.86 g (3.31 mmol) of ethyl 3-ethoxy-2-[(ethoxycarbonyl)carbamoyl]acrylate and 1.00 g (3.31 mmol) of 1-cyclohexyl-2-methyl-1H-benzimidazol-5-amine dihydrochloride were initially charged in 25 ml of ethanol and the mixture was heated to reflux for 2 h. Subsequently, at RT, 371 mg (3.31 mmol) of potassium tert-butoxide were added and the reaction mixture was stirred at RT overnight and at reflux for 5 days. For workup, the reaction mixture was admixed with water, acidified with 1N hydrochloric acid and then concentrated on a rotary evaporator. The residue was stirred in dichloromethane/methanol (1:1) and the insoluble residues were filtered off. The filtrate was concentrated and admixed with ethanol, and the solid formed was filtered off and dried. This gave 1.85 g of the title compound as a crude product, which was converted without further purification.

LC-MS (Method 1): R$_t$=0.72 min; MS (ESIpos): m/z=397 (M+H)$^+$.

Example 119A ethyl 1-(4-methyl-3-oxo-3,4-dihydro-2H-1,4-benzoxazin-7-yl)-2,4-dioxo-1,2,3,4-tetrahydropyrimidine-5-carboxylate

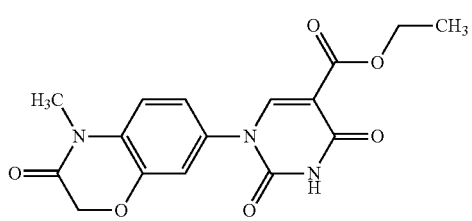 [SMILES: CCOC(=O)c1cn(-c2ccc3c(c2)OCC(=O)N3C)c(=O)[nH]c1=O]

2.00 g (11.2 mmol) of 7-amino-4-methyl-2H-1,4-benzoxazin-3(4H)-one and 2.65 g (10.2 mmol) of ethyl 3-ethoxy-2-[(ethoxycarbonyl)carbamoyl]acrylate were initially charged in 100 ml of ethanol and the mixture was heated to reflux for 2 h. After cooling to RT, 1.15 g (10.2 mmol) of potassium tert-butoxide were added and the reaction mixture was stirred further at RT for two days and then at reflux temperature for 1 h. For workup, the reaction mixture was diluted with water and acidified with 1M hydrochloric acid. The solid formed was filtered off, washed with water and dried under HV. This gave 2.79 mg (70% of theory) of the title compound.

LC-MS (Method 3): R$_t$=0.76 min; MS (ESIpos): m/z=346 (M+H)$^+$.

$^1$H NMR (400 MHz, DMSO-d$_6$): δ [ppm]=1.22 (t, 3H), 4.17 (q, 2H), 4.71 (s, 2H), 7.18-7.23 (m, 2H), 7.28 (d, 1H), 8.22 (s, 1H), 11.68 (s, 1H).

Example 120A 8-chloro-3,4-dihydro-1H-isochromen-4-ol

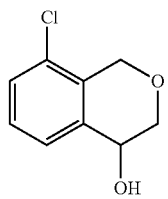 [SMILES: OC1COCc2c(Cl)cccc21]

To a solution of 270 mg (1.48 mmol) of 8-chloro-1H-isochromen-4(3H)-one (reactant prepared in house, not described in literature but available from ACD supplier with catalogue number and CAS No.) in 5 ml of methanol were added, at RT, 224 mg (5.91 mmol) of sodium borohydride, and the mixture was stirred at RT for 1 h. Subsequently, 5 ml of aqueous 1N hydrochloric acid were added, and the mixture was stirred for a further 10 mm and then separated by means of preparative HPLC (Method 15). The suitable fractions were freed of acetonitrile on a rotary evaporator at 130 mbar and the remaining aqueous phase was extracted three times with di-chloromethane. The combined organic phases were dried over sodium sulphate and concentrated on a rotary evaporator at 130 mbar. This gave 400 mg of the title compound, which according to NMR still contains acetonitrile and dichloromethane. It was used as such for the preparation of Example 302.

LC/MS (Method 4): R$_t$=1.69 mm; m/z=167 (M-OH)$^+$ $^1$H NMR (400 MHz, CDCl$_3$): δ [ppm]=2.57 (br. s, 1H), 3.85 (dd, 1H), 4.09 (dd, 1H), 4.56 (br. s., 1H), 4.62 (d, 1H), 4.89 (d, 1H), 7.22-7.35 (m, 2H), 7.39 (d, 1H).

WORKING EXAMPLES

Example 1 ethyl 1-(1,3-dimethyl-2-oxo-2,3-dihydro-1H-benzimidazol-5-yl)-3-[2-methyl-3-(trifluoromethyl)-benzyl]-2,4-dioxo-1,2,3,4-tetrahydropyrimidine-5-carboxylate

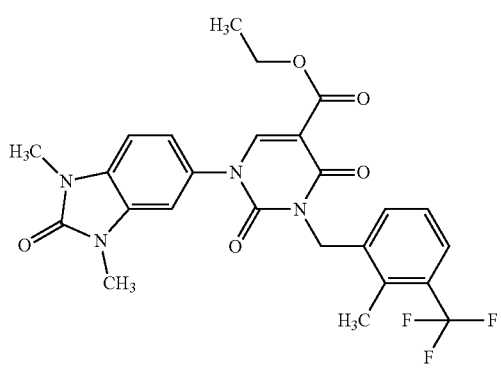

To a solution of 14.95 g (43.42 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate from Example 2A in DMF (200 ml) were added 12.00 g (86.84 mmol) of potassium carbonate, 12.09 g (47.76 mmol) of 2-methyl-3-(trifluoromethyl)benzyl bromide and 0.721 g (4.34 mmol) of potassium iodide, and the reaction mixture was left to stir at 80° C. for 3 h. Subsequently, the mixture was cooled to RT, water was added and the precipitate formed was filtered off. The solid was washed successively with water and MTBE, and dried under reduced pressure at 50° C. This gave 21.04 g (94% of theory) of the title compound.

LC-MS (Method 1): $R_t$=1.07 min; m/z=517 (M+H)$^+$.

$^1$H NMR (400 MHz, DMSO-d$_6$): δ [ppm]=1.23 (t, 3H), 2.46 (s, 3H), 3.34 (s, 3H), 3.37 (s, 3H), 4.20 (q, 2H), 5.09 (s, 2H), 7.23-7.30 (m, 2H), 7.32-7.43 (m, 3H), 7.58-7.62 (m, 1H), 8.42 (s, 1H).

In analogy to Example 1, the above-described 1,2,3,4-tetrahydropyrimidine-2,4-dione-5-carboxylic esters (uracil-5-carboxylic esters) were used to obtained, by reaction with the respective benzyl chlorides or benzyl bromides in the presence of potassium carbonate and potassium iodide, the benzyl-substituted uracil compounds which follow. A difference is that 1-3 equivalents of potassium carbonate and 0.1 to 2 equivalents of potassium iodide may also be used. Given compounds of sufficient solubility, acetonitrile was used as a solvent in some cases.

Example 2 ethyl 3-[2-chloro-3-(trifluoromethyl)benzyl]-1-(1,3-dimethyl-2-oxo-2,3-dihydro-1H-benzimidazol-5-yl)-2,4-dioxo-1,2,3,4-tetrahydropyrimidine-5-carboxylate

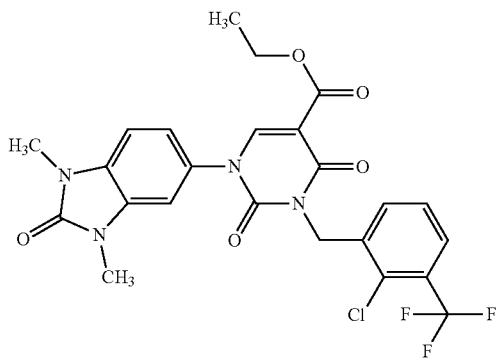 [SMILES: CCOC(=O)c1cn(-c2ccc3c(c2)n(C)c(=O)n3C)c(=O)n(Cc2cccc(C(F)(F)F)c2Cl)c1=O]

The preparation and purification of the title compound were analogous to Example 1. Proceeding from 200 mg (0.58 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate from Example 2A and 175 mg (0.64 mmol) of 2-chloro-3-(trifluoromethyl)benzyl bromide, 234 mg (73% of theory) of the title compound were obtained.

LC-MS (Method 1): $R_t$=1.08 min; m/z=537 (M+H)$^+$.

$^1$H NMR (400 MHz, DMSO-d$_6$): δ [ppm]=1.23 (t, 3H), 3.34 (s, 3H), 3.37 (s, 3H), 4.20 (d, 2H), 5.16 (s, 2H), 7.27 (s, 2H), 7.39-7.42 (m, 1H), 7.50-7.60 (m, 2H), 7.78-7.83 (m, 1H), 8.44 (s, 1H).

Example 3 ethyl 3-(2,3-dichlorobenzyl)-1-(1,3-dimethyl-2-oxo-2,3-dihydro-1H-benzimidazol-5-yl)-2,4-dioxo-1,2,3,4-tetrahydropyrimidine-5-carboxylate

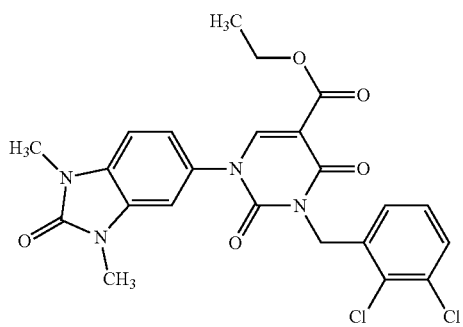 [SMILES: CCOC(=O)c1cn(-c2ccc3c(c2)n(C)c(=O)n3C)c(=O)n(Cc2cccc(Cl)c2Cl)c1=O]

The preparation and purification of the title compound were analogous to Example 1, using acetonitrile as a solvent. Proceeding from 200 mg (0.58 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate from Example 2A and 125 mg (0.64 mmol) of 2,3-dichlorobenzyl chloride, 241 mg (79% of theory) of the title compound were obtained.

LC-MS (Method 1): $R_t$=1.05 min; m/z=503 (M+H)$^+$.

$^1$H NMR (400 MHz, DMSO-d$_6$): δ [ppm]=1.23 (t, 3H), 3.34 (s, 3H), 3.37 (s, 3H), 4.20 (q, 2H), 5.11 (s, 2H), 7.20-7.29 (m, 3H), 7.31-7.36 (m, 1H), 7.39-7.41 (m, 1H), 7.56-7.60 (m, 1H), 8.43 (s, 1H).

Example 4 ethyl 1-(1,3-dimethyl-2-oxo-2,3-dihydro-1H-benzimidazol-5-yl)-3-[2-fluoro-3-(trifluoromethyl)benzyl]-2,4-dioxo-1,2,3,4-tetrahydropyrimidine-5-carboxylate

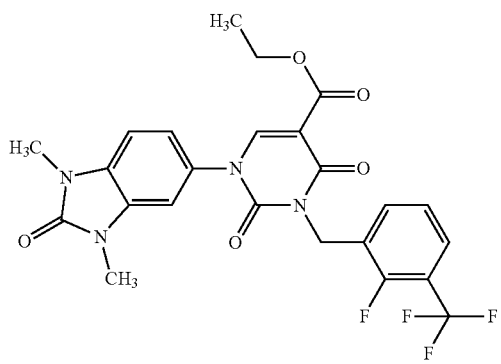 [SMILES: CCOC(=O)c1cn(-c2ccc3c(c2)n(C)c(=O)n3C)c(=O)n(Cc2cccc(C(F)(F)F)c2F)c1=O]

The preparation and purification of the title compound were analogous to Example 1. Proceeding from 200 mg (0.58 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate from Example 2A and 164 mg (0.64 mmol) of 2-fluoro-3-(trifluoromethyl)benzyl bromide, 162 mg (53% of theory) of the title compound were obtained.

LC-MS (Method 1): $R_t$=1.13 min; m/z=521 (M+H)$^+$.

¹H NMR (400 MHz, DMSO-d₆): δ=1.23 (t, 3H), 3.33 (s, 3H), 3.34 (s, 3H), 4.20 (d, 2H), 5.15 (s, 2H), 7.19-7.31 (m, 2H), 7.31-7.44 (m, 2H), 7.68 (d, 2H), 8.40 (s, 1H).

Example 5 ethyl 1-(1,3-dimethyl-2-oxo-2,3-dihydro-1H-benzimidazol-5-yl)-3-[3-fluoro-2-(trifluoromethyl)-benzyl]-2,4-dioxo-1,2,3,4-tetrahydropyrimidine-5-carboxylate

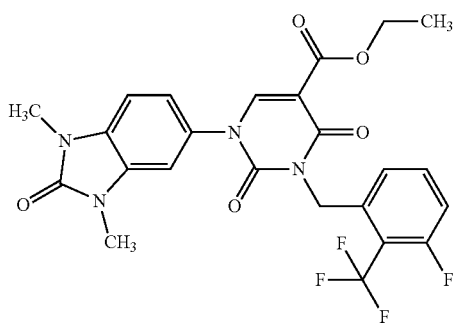 [SMILES: CCOC(=O)c1cn(-c2ccc3c(c2)n(C)c(=O)n3C)c(=O)n(Cc2cccc(F)c2C(F)(F)F)c1=O]

The preparation and purification of the title compound were analogous to Example 1. Proceeding from 179 mg (0.52 mmol) of ethyl 1-(4-methoxyphenyl)-2,4-dioxo-1,2,3,4-tetrahydropyrimidine-5-carboxylate from Example 2A and 147 mg (0.57 mmol) of 3-fluoro-2-trifluorobenzyl bromide, 207 mg (74% of theory) of the title compound were obtained.

LC-MS (Method 1): $R_t$=1.12 min; m/z=521 (M+H)⁺.

¹H NMR (400 MHz, DMSO-d₆): δ [ppm]=1.23 (t, 3H), 3.34 (s, 3H), 3.37 (s, 3H), 4.20 (q, 2H), 5.21 (s, 2H), 7.17-7.22 (m, 1H), 7.22-7.30 (m, 2H), 7.37-7.44 (m, 2H), 7.63-7.71 (m, 1H), 8.45 (s, 1H).

Example 6 ethyl 3-(2-chloro-3,6-difluorobenzyl)-1-(1,3-dimethyl-2-oxo-2,3-dihydro-1H-benzimidazol-5-yl)-2,4-dioxo-1,2,3,4-tetrahydropyrimidine-5-carboxylate

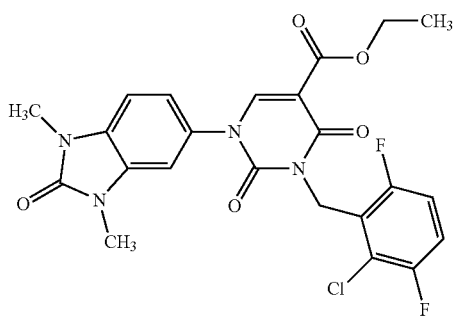 [SMILES: CCOC(=O)c1cn(-c2ccc3c(c2)n(C)c(=O)n3C)c(=O)n(Cc2c(F)ccc(F)c2Cl)c1=O]

150 mg (0.43 mmol) of the compound from Example 5A were initially charged in acetonitrile (2.06 ml), together with 417 mg of the boronic ester from Example 3A (60% purity, 0.87 mmol) and 0.18 ml (1.30 mmol) of triethylamine. Subsequently, molecular sieve (3 Å), 118 mg (0.65 mmol) of copper(II) acetate and 0.13 ml (1.83 mmol) of DMSO were added and the reaction mixture was stirred in a closed vessel at 80° C. for 3 days. For workup, the reaction mixture was admixed with ethyl acetate, then washed twice with hydrochloric acid (1M), once with saturated sodium hydrogencarbonate solution and once with saturated sodium chloride solution. The organic phase was then dried over magnesium sulphate, filtered and concentrated. The residue was stirred with methanol, and the solid was filtered off with suction, washed with methanol and dried at 50° C. under reduced pressure. This gave 114 mg (84% purity, 44% of theory) of the title compound.

LC-MS (Method 2): $R_t$=2.06 min; m/z=505 (M+H)₊.

¹H NMR (400 MHz, DMSO-d₆): δ [ppm]=1.22 (t, 3H), 4.16 (q, 2H), 5.21 (s, 2H), 7.16 (d, 1H), 7.22-7.31 (m, 2H), 7.34 (s, 1H), 7.38-7.48 (m, 1H), 8.36 (s, 1H).

Example 7 ethyl 3-(3-chloro-2-methylbenzyl)-1-(1,3-dimethyl-2-oxo-2,3-dihydro-1H-benzimidazol-5-yl)-2,4-dioxo-1,2,3,4-tetrahydropyrimidine-5-carboxylate

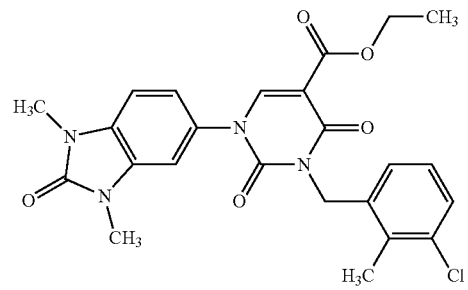 [SMILES: CCOC(=O)c1cn(-c2ccc3c(c2)n(C)c(=O)n3C)c(=O)n(Cc2cccc(Cl)c2C)c1=O]

150 mg (0.46 mmol) of the compound from Example 7A were initially charged in acetonitrile (4.00 ml), together with 267 mg of the boronic ester from Example 3A (0.93 mmol) and 0.19 ml (1.39 mmol) of triethylamine. Subsequently, molecular sieve (3 Å), 126 mg (0.69 mmol) of copper(II) acetate and 0.13 ml (1.83 mmol) of DMSO were added and the reaction mixture was stirred in a closed vessel at 80° C. for 1 day. For workup, the mixture was admixed with ethyl acetate, then washed twice with 1M hydrochloric acid, once with saturated sodium hydrogencarbonate solution and once with saturated sodium chloride solution. The organic phase was then dried over magnesium sulphate, filtered and concentrated. The residue was stirred with MTBE, and the solid was filtered off with suction and dried at 50° C. under reduced pressure. This solid was purified by means of preparative HPLC (Method 8). This gave 78 mg (35% of theory) of the title compound.

LC-MS (Method 3): $R_t$=1.34 min; m/z=483 (M+H)⁺.

¹H NMR (400 MHz, DMSO-d₆): δ [ppm]=1.23 (t, 3H), 2.41 (s, 3H), 3.34 (s, 3H), 3.37 (s, 3H), 4.19 (q, 2H), 5.05 (s, 2H), 7.05 (d, 1H), 7.17 (t, 1H), 7.22-7.30 (m, 2H), 7.35 (d, 1H), 7.41 (d, 1H), 8.40 (s, 1H).

Example 8 ethyl 3-[2,3-bis(trifluoromethyl)benzyl]-1-(1,3-dimethyl-2-oxo-2,3-dihydro-1H-benzimidazol-5-yl)-2,4-dioxo-1,2,3,4-tetrahydropyrimidine-5-carboxylate

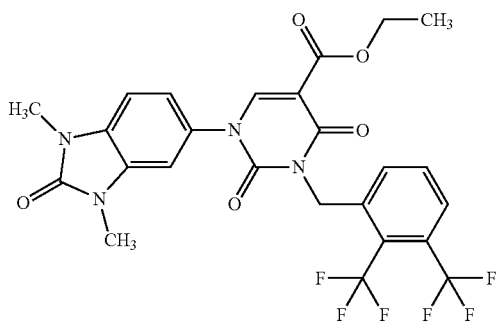 [SMILES: CCOC(=O)c1cn(-c2ccc3c(c2)n(C)c(=O)n3C)c(=O)n(Cc2cccc(C(F)(F)F)c2C(F)(F)F)c1=O]

150 mg (0.37 mmol) of the compound from Example 10A were initially charged in acetonitrile (4.00 ml), together with 248 mg of the boronic ester from Example 3A (85% purity, 0.73 mmol) and 0.15 ml (1.10 mmol) of triethylamine. Subsequently, molecular sieve (3 Å), 100 mg (0.54 mmol) of copper(II) acetate and 0.13 ml (1.83 mmol) of DMSO were added and the reaction mixture was agitated in a closed vessel at 80° C. for 3 days. For workup, the reaction mixture was diluted with ethyl acetate, then washed twice with 1M hydrochloric acid and once each with saturated sodium hydrogencarbonate solution and saturated sodium chloride solution. The organic phase was then dried over magnesium sulphate, filtered and concentrated. The residue was separated by means of preparative HPLC (Method 8). The product-containing fractions were partly concentrated on a rotary evaporator. The solid which precipitated out was filtered off, washed with water and dried under high vacuum. This gave 127 mg (61% of theory) of the title compound.

LC-MS (Method 1): $R_t$=1.05 min; m/z=571 (M+H)$^+$.

$^1$H NMR (400 MHz, DMSO-d$_6$): δ [ppm]=1.23 (t, 3H), 3.2-3.4 (2 s, partly concealed by water signal), 4.20 (q, 2H), 5.25 (br.s, 2H), 7.26 (q, 2H), 7.39 (s, 1H), 7.73 (d, 1H), 7.85 (t, 1H), 7.98 (d, 1H), 8.46 (s, 1H).

Example 9 ethyl 3-(3-chloro-5-fluorobenzyl)-1-(1,3-dimethyl-2-oxo-2,3-dihydro-1H-benzimidazol-5-yl)-2,4-dioxo-1,2,3,4-tetrahydropyrimidine-5-carboxylate

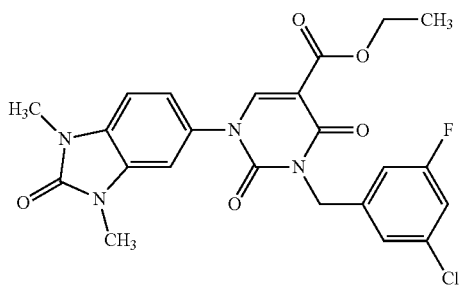 [SMILES: CCOC(=O)c1cn(-c2ccc3c(c2)n(C)c(=O)n3C)c(=O)n(Cc2cc(F)cc(Cl)c2)c1=O]

The preparation and purification of the title compound were analogous to Example 1. The reaction time was 1 h. Proceeding from 200 mg (0.58 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate from Example 2A and 142 mg (0.63 mmol) of 1-(bromomethyl)-3-chloro-5-fluorobenzene, 255 mg (90% of theory) of the title compound were obtained.

LC-MS (Method 1): $R_t$=0.97 min; m/z=487 (M+H)$^+$.

$^1$H NMR (400 MHz, DMSO-d$_6$): δ=1.23 (t, 3H), 3.34 (s, 3H), 3.37 (s, 3H), 4.19 (q, 2H), 5.03 (s, 2H), 7.19 (d, 1H), 7.22-7.25 (m, 1H), 7.27 (s, 1H), 7.28-7.31 (m, 1H), 7.32-7.37 (m, 1H), 7.40 (d, 1H), 8.36 (s, 1H).

Example 10 ethyl 1-(1,3-dimethyl-2-oxo-2,3-dihydro-1H-benzimidazol-5-yl)-3-[3-fluoro-5-(trifluoromethyl)benzyl]-2,4-dioxo-1,2,3,4-tetrahydropyrimidine-5-carboxylate

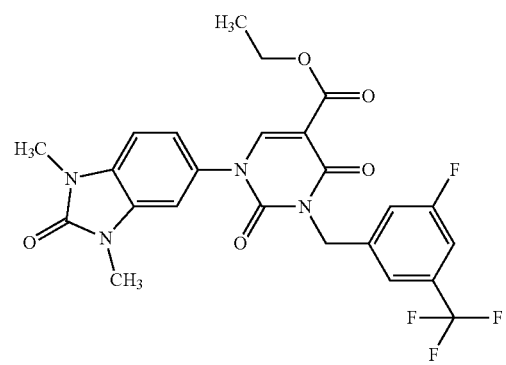 [SMILES: CCOC(=O)c1cn(-c2ccc3c(c2)n(C)c(=O)n3C)c(=O)n(Cc2cc(F)cc(C(F)(F)F)c2)c1=O]

The preparation and purification of the title compound were analogous to Example 1. The reaction time was 1 h. Proceeding from 200 mg (0.58 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate from Example 2A and 164 mg (0.63 mmol) of 1-(bromomethyl)-3-fluoro-5-(trifluoromethyl)benzene, 278 mg (91% of theory) of the title compound were obtained.

LC-MS (Method 1): $R_t$=1.01 min; m/z=521 (M+H)$^+$.

$^1$H NMR (400 MHz, DMSO-d$_6$): δ=1.23 (s, 3H), 3.31 (s, 3H), 3.37 (s, 3H), 4.20 (q, 2H), 5.12 (s, 2H), 7.23 (dd, 1H), 7.28 (d, 1H), 7.39 (d, 1H), 7.52 (d, 1H), 7.58-7.63 (m, 2H), 8.37 (s, 1H).

Example 11 ethyl 1-(1,3-dimethyl-2-oxo-2,3-dihydro-1H-benzimidazol-5-yl)-2,4-dioxo-3-[4-(trifluoromethyl)-2,3-dihydro-1H-inden-1-yl]-1,2,3,4-tetrahydropyrimidine-5-carboxylate (Racemate)

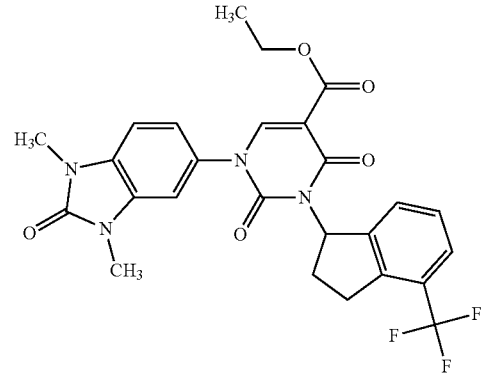 [SMILES: CCOC(=O)c1cn(-c2ccc3c(c2)n(C)c(=O)n3C)c(=O)n(C2CCc3c2cccc3C(F)(F)F)c1=O]

Method A:

The preparation and purification of the title compound were analogous to Example 8. The reaction time was 4 days. Proceeding from 300 mg (80% purity, 0.65 mmol) of ethyl 2,4-dioxo-3-[4-(trifluoromethyl)-2,3-dihydro-1H-inden-1-yl]-1,2,3,4-tetrahydropyrimidine-5-carboxylate from Example 21A and 375 mg (1.30 mmol) of 1,3-dimethyl-5-(4,4,5,5-tetramethyl-1,3,2-dioxaborolan-2-yl)-1,3-dihydro-2H-benzimidazol-2-one from Example 3A, after additional purification by means of flash chromatography (dichloromethane/methanol 98:2), 190 mg (52% of theory) of the title compound were obtained.

LC-MS (Method 5): $R_t$=1.08 min; m/z=529 (M+H)$^+$.

$^1$H NMR (400 MHz, DMSO-d$_6$): δ [ppm]=1.23 (t, 3H), 2.35-2.43 (m, 1H), 2.44-2.48 (m, 1H), 3.03-3.15 (m, 1H), 3.21-3.29 (m, 1H), 3.31 (s, 3H), 3.36 (s, 3H), 4.18 (q, 2H), 6.35-6.58 (m, 1H), 7.13-7.28 (m, 2H), 7.37 (t, 2H), 7.45-7.55 (m, 2H), 8.33 (s, 1H).

Method B:

In another experiment, in an analogous manner, 1.00 g of the compound from Example 21A were used. After purification by flash chromatography, however, the product (1.20 g) was only of 63% purity (corresponding to about 50% of theory). This was separated directly by preparative chiral HPLC (Method 12) into the enantiomers: 377 mg (24% of theory) of the enantiomer which elutes first (see Example 12) and 331 mg (21% of theory) of the enantiomer which elutes later (see Example 13) were obtained.

Example 12 ethyl 1-(1,3-dimethyl-2-oxo-2,3-dihydro-1H-benzimidazol-5-yl)-2,4-dioxo-3-[(1S)-4-(trifluoromethyl)-2,3-dihydro-1H-inden-1-yl]-1,2,3,4-tetrahydropyrimidine-5-carboxylate (S enantiomer)

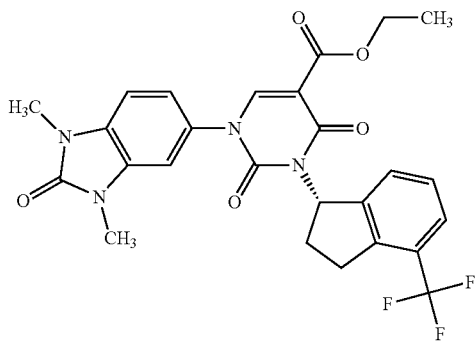 [SMILES: CCOC(=O)c1cn(-c2ccc3c(c2)n(C)c(=O)n3C)c(=O)n([C@H]2CCc3c2cccc3C(F)(F)F)c1=O]

Method A:

Enantiomer which elutes first (377 mg) from the separation of the compound from Example 11 (Method B) by preparative HPLC on a chiral phase (Method 12).

Chiral HPLC (Method 13): $R_t$=9.39 min, 100% ee.

Specific optical rotation: $α_D^{20}$=−117.1° (acetonitrile, c=0.05 g/100 ml).

Method B:

Under an argon atmosphere, 5.68 g (16.49 mmol) of the compound from Example 2A, 4.00 g (19.79 mmol) of (1R)-4-(trifluoromethyl)indan-1-ol from Example 15A and 7.78 g (29.68 mmol) of triphenylphosphine were initially charged in 200 ml of DMF and 100 ml of THF and cooled to 0° C. 5.19 ml (5.33 g, 26.4 mmol) of diisopropyl azodicarboxylate were added dropwise. The cooling bath was removed and the mixture was stirred at RT for 2 h. Subsequently, 25 ml of 1N hydrochloric acid were added and the mixture was stirred for 15 min. For workup, about 2 l of ethyl acetate and 1.33 l of dilute hydrochloric acid (about 2.5N) were added. After stirring, the organic phase was separated, washed twice with dilute hydrochloric acid, once with a 1N sodium carbonate solution and once with a saturated sodium chloride solution and dried over sodium sulphate. The solvents were removed on a rotary evaporator. The residue was purified by preparative HPLC (Method 11). This gave 5.15 g of the title compound (59% of theory).

LC-MS (Method 1): $R_t$=1.04 min; m/z=529 (M+H)$^+$.

$^1$H NMR (400 MHz, CD$_2$Cl$_2$): δ [ppm]=1.31 (t, 3H), 2.36-2.51 (m, 1H), 2.59 (ddt, 1H), 3.07-3.20 (m, 1H), 3.39 (s, 3H), 3.40 (s, 3H), 3.42-3.54 (m, 1H), 4.29 (q, 2H), 6.57-6.68 (br. m, 1H), 6.94 (br.s, 1H), 7.02 (s, 2H), 7.25-7.38 (m, 2H), 7.49 (d, 1H), 8.31 (s, 1H).

Chiral HPLC (Method 13): $R_t$=9.39 min, 92% ee.

Example 13 ethyl 1-(1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer)

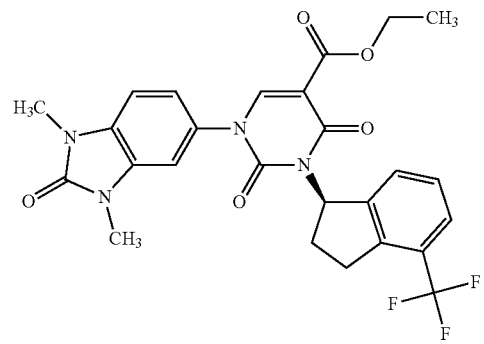 [SMILES: CCOC(=O)c1cn(-c2ccc3c(c2)n(C)c(=O)n3C)c(=O)n([C@@H]2CCc3c2cccc3C(F)(F)F)c1=O]

Method A:

Enantiomer which elutes last (331 mg) from the separation of the compound from Example 11 (Method B) by preparative HPLC on a chiral phase (Method 12).

Chiral HPLC (Method 13): $R_t$=11.12 min, 92% ee.

Method B:

3.05 g (8.86 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate from Example 2A, 2.15 g (10.63 mmol) of (1S)-4-(trifluoromethyl)indan-1-ol from Example 14A and 6.97 g (26.6 mmol) of triphenylphosphine were initially charged under argon in THF/DMF 1:1 (1.7 l) and cooled to −15° C. 3.48 ml (17.71 mmol) of diisopropyl azodicarboxylate were added gradually. Subsequently, the reaction mixture was stirred at RT for another 30 min. While cooling with ice, a further 0.8 equivalent (1.39 ml, 6.86 mmol) of diisopropyl azodicarboxylate was added dropwise and the reaction mixture was stirred at RT for 1 h. The reaction mixture was cooled to −40° C., admixed with 1M hydrochloric acid, diluted with ethyl acetate and stirred vigorously for a few minutes. The organic phase was separated, washed twice with 1M sodium carbonate solution and once with saturated sodium chloride solution, dried over sodium sulphate and concentrated on a rotary evaporator. The residue was admixed with MTBE and stirred at RT overnight, then stirred with ice bath cooling for 20 min. The precipitated solid was filtered off with suction and washed with cold MTBE. The whole filtrate was concentrated and purified by means of preparative HPLC (Method 7). This gave 2.90 g (62% of theory) of the title compound.

LC-MS (Method 1): $R_t$=1.05 min; m/z=529 (M+H)$^+$.

$^1$H NMR (400 MHz, CD$_2$Cl$_2$): δ=1.36 (t, 3H), 2.42-2.55 (m, 1H), 2.57-2.71 (m, 1H), 3.12-3.24 (m, 1H), 3.43 (s, 3H), 3.43-3.58 (m, 1H), 3.45 (s, 3H), 4.33 (q, 2H), 6.60-6.73 (m, 1H), 6.99 (s, 1H), 7.07 (s, 2H), 7.30-7.42 (m, 2H), 7.54 (d, 2H), 8.36 (s, 1H).

Example 14 ethyl 1-(1-methyl-2-oxo-2,3-dihydro-1H-benzimidazol-5-yl)-3-[2-methyl-3-(trifluoromethyl)-benzyl]-2,4-dioxo-1,2,3,4-tetrahydropyrimidine-5-carboxylate

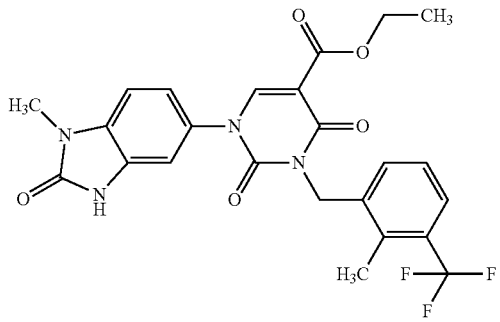 [SMILES: CCOC(=O)c1cn(-c2ccc3c(c2)[nH]c(=O)n3C)c(=O)n(Cc2cccc(C(F)(F)F)c2C)c1=O]

The preparation and purification of the title compound were analogous to Example 1. The reaction time was 1 h. Proceeding from 500 mg (1.51 mmol) of ethyl 1-(1-methyl-2-oxo-2,3-dihydro-1H-benzimidazol-5-yl)-2,4-dioxo-1,2,3,4-tetrahydropyrimidine-5-carboxylate from Example 36A and 421 mg (1.67 mmol) of 2-methyl-3-(trifluoromethyl)benzyl bromide, 606 mg (purity approx. 83%, 66% of theory) of the title compound were obtained.

LC-MS (Method 1): $R_t$=0.96 min; m/z=503 (M+H)$^+$.

$^1$H NMR (400 MHz, DMSO-d$_6$): δ [ppm]=1.23 (t, 3H), 2.46 (s, 3H), 3.30 (s, partly concealed by water signal), 4.19 (q, 2H), 5.07 (s, 2H), 7.18-7.23 (m, 3H), 7.31-7.42 (m, 2H), 7.57-7.62 (m, 1H), 8.39 (s, 1H), 11.13 (s, 1H).

Example 15 ethyl 3-(2,3-dichlorobenzyl)-1-(1-methyl-2-oxo-2,3-dihydro-1H-benzimidazol-5-yl)-2,4-dioxo-1,2,3,4-tetrahydropyrimidine-5-carboxylate

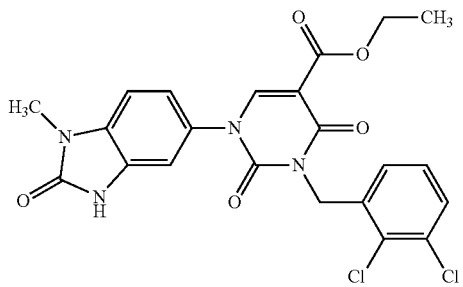 [SMILES: CCOC(=O)c1cn(-c2ccc3c(c2)[nH]c(=O)n3C)c(=O)n(Cc2cccc(Cl)c2Cl)c1=O]

The preparation and purification of the title compound were analogous to Example 1. The reaction time was 5 h. Proceeding from 200 mg (0.61 mmol) of ethyl 1-(1-methyl-2-oxo-2,3-dihydro-1H-benzimidazol-5-yl)-2,4-dioxo-1,2,3,4-tetrahydropyrimidine-5-carboxylate from Example 36A and 130 mg (0.67 mmol) of 2,3-dichlorobenzyl chloride, after additional purification by means of preparative HPLC (Method 8), 40 mg (13% of theory) of the title compound were obtained.

LC-MS (Method 1): $R_t$=0.94 min; m/z=489 (M+H)$^+$.

$^1$H NMR (400 MHz, DMSO-d$_6$): δ [ppm]=1.23 (t, 3H), 3.30 (s, partly concealed by water signal), 4.19 (q, 2H), 5.09 (s, 2H), 7.16-7.27 (m, 4H), 7.32 (t, 1H), 7.56-7.60 (m, 1H), 8.41 (s, 1H), 11.14 (s, 1H).

Example 16 ethyl 3-[2-chloro-3-(trifluoromethyl)benzyl]-1-(1-methyl-2-oxo-2,3-dihydro-1H-benzimidazol-5-yl)-2,4-dioxo-1,2,3,4-tetrahydropyrimidine-5-carboxylate

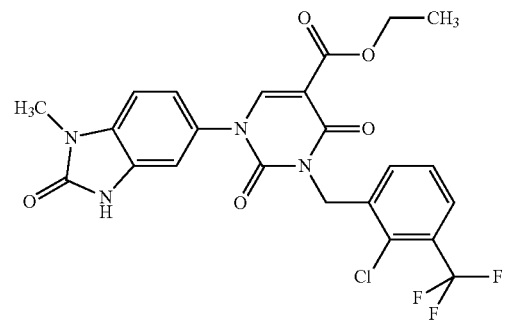 [SMILES: CCOC(=O)c1cn(-c2ccc3c(c2)[nH]c(=O)n3C)c(=O)n(Cc2cccc(C(F)(F)F)c2Cl)c1=O]

The preparation and purification of the title compound were analogous to Example 1. The reaction time was 5 h. Proceeding from 200 mg (0.61 mmol) of ethyl 1-(1-methyl-2-oxo-2,3-dihydro-1H-benzimidazol-5-yl)-2,4-dioxo-1,2,3,4-tetrahydropyrimidine-5-carboxylate from Example 36A and 182 mg (0.67 mmol) of 2-chloro-3-(trifluoromethyl)benzyl bromide, after purification by means of preparative HPLC (Method 8), 33 mg (10% of theory) of the title compound were obtained.

LC-MS (Method 1): $R_t$=0.97 min; m/z=523 (M+H)$^+$.

$^1$H NMR (400 MHz, DMSO-d$_6$): δ [ppm]=1.23 (t, 3H), 3.30 (s, partly concealed by water signal), 4.20 (q, 2H), 5.14 (s, 2H), 7.19-7.23 (m, 3H), 7.48-7.55 (m, 1H), 7.58-7.62 (m, 1H), 7.78-7.82 (m, 1H), 8.42 (s, 1H), 11.14 (s, 1H).

Example 17 ethyl 3-[3-chloro-2-(trifluoromethyl)benzyl]-1-(1-methyl-2-oxo-2,3-dihydro-1H-benzimidazol-5-yl)-2,4-dioxo-1,2,3,4-tetrahydropyrimidine-5-carboxylate

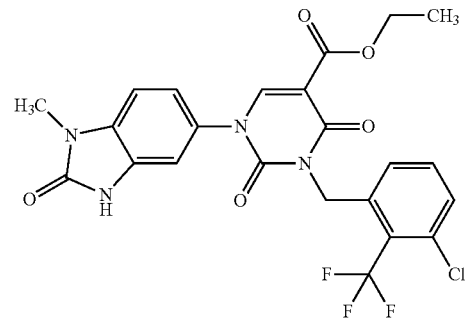 [SMILES: CCOC(=O)c1cn(-c2ccc3c(c2)[nH]c(=O)n3C)c(=O)n(Cc2cccc(Cl)c2C(F)(F)F)c1=O]

To a solution of 0.74 g (2.24 mmol) of ethyl 1-(1-methyl-2-oxo-2,3-dihydro-1H-benzimidazol-5-yl)-2,4-dioxo-1,2,3,4-tetrahydropyrimidine-5-carboxylate from Example 36A in 28 ml of DMF were added 1.04 g (65% purity, 2.46 mmol) of 1-(bromomethyl)-3-chloro-2-(trifluoromethyl)benzene (preparation: see WO 2004/52858, page 149, Example 176), 0.62 g (4.48 mmol) of potassium carbonate and 0.04 g (0.22 mmol) of potassium iodide, and the mixture was stirred at 60° C. for 5 h. For workup, the reaction mixture was admixed with water and extracted three times with ethyl acetate. The combined organic phases were washed with saturated sodium chloride solution, dried over magnesium sulphate, filtered and concentrated. The residue was purified by means of flash silica gel chromatography (dichloromethane/methanol, 50:1). This gave 0.36 g (29% of theory) of the title compound.

LC-MS (Method 1): $R_t$=0.96 min; MS (ESIpos): m/z=523 (M+H)$^+$.

$^1$H NMR (400 MHz, DMSO-d$_6$): δ [ppm]=1.23 (t, 3H), 3.3 (s, concealed by DMSO signal), 4.19 (q, 2H), 5.18-5.24 (m, 2H), 7.16-7.23 (m, 3H), 7.33-7.38 (m, 1H), 7.55-7.67 (m, 2H), 8.43 (s, 1H), 11.15 (s, 1H).

Example 18 ethyl 3-[3-chloro-2-(trifluoromethyl)benzyl]-1-(3-ethyl-1-methyl-2-oxo-2,3-dihydro-1H-benzimidazol-5-yl)-2,4-dioxo-1,2,3,4-tetrahydropyrimidine-5-carboxylate

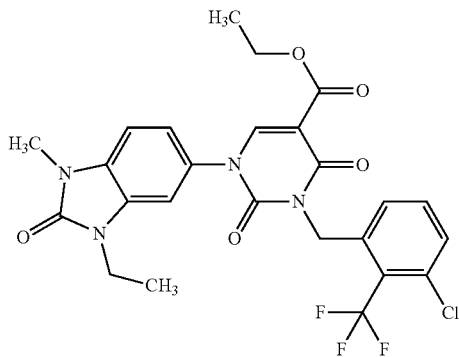 [SMILES: CCOC(=O)c1cn(-c2ccc3c(c2)n(CC)c(=O)n3C)c(=O)n(Cc2cccc(Cl)c2C(F)(F)F)c1=O]

120 mg (0.23 mmol) of ethyl 3-[3-chloro-2-(trifluoromethyl)benzyl]-1-(1-methyl-2-oxo-2,3-dihydro-1H-benzimidazol-5-yl)-2,4-dioxo-1,2,3,4-tetrahydropyrimidine-5-carboxylate from Example 17 were initially charged in DMF (3 ml), and 39 mg (0.25 mmol) of iodoethane, 63 mg (0.46 mmol) of potassium carbonate and 4 mg (0.02 mmol) of potassium iodide were added. The reaction mixture was left to stir at 60° C. for 5 h. The reaction mixture cooled to RT was admixed with water, and the precipitate was filtered off with suction, washed with water and MTBE, and dried under reduced pressure at 50° C. After additional purification by means of flash chromatography (dichloromethane/methanol 70:1), 73 mg (55% of theory) of the title compound were obtained.

LC-MS (Method 1): $R_t$=1.11 min; m/z=551 (M+H)$^+$.

$^1$H NMR (400 MHz, DMSO-d$_6$): δ [ppm]=1.19-1.26 (m, 6H), 3.37 (s, 3H), 3.87 (q, 2H), 4.20 (q, 2H), 5.20-5.25 (m, 2H), 7.22-7.30 (m, 2H), 7.31-7.35 (m, 1H), 7.44-7.46 (m, 1H), 7.57-7.67 (m, 2H), 8.47 (s, 1H).

Example 19 ethyl 3-[2-chloro-3-(trifluoromethyl)benzyl]-1-(3-ethyl-1-methyl-2-oxo-2,3-dihydro-1H-benzimidazol-5-yl)-2,4-dioxo-1,2,3,4-tetrahydropyrimidine-5-carboxylate

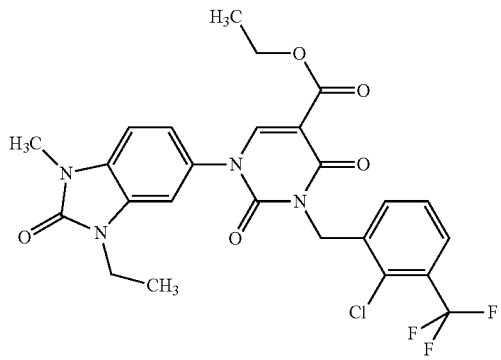 [SMILES: CCOC(=O)c1cn(-c2ccc3c(c2)n(CC)c(=O)n3C)c(=O)n(Cc2cccc(C(F)(F)F)c2Cl)c1=O]

The preparation and purification of the title compound were analogous to Example 18. Proceeding from 90 mg (0.17 mmol) of ethyl 3-[2-chloro-3-(trifluoromethyl)benzyl]-1-(1-methyl-2-oxo-2,3-dihydro-1H-benzimidazol-5-yl)-2,4-dioxo-1,2,3,4-tetrahydropyrimidine-5-carboxylate from Example 16 and 29 mg (0.19 mmol) of iodoethane, 75 mg (77% of theory) of the title compound were obtained.

LC-MS (Method 1): $R_t$=1.11 min; m/z=551 (M+H)$^+$.

$^1$H NMR (400 MHz, DMSO-d$_6$): δ [ppm]=1.19-1.27 (m, 6H), 3.37 (s, partly concealed by water signal), 3.88 (q, 2H), 4.20 (q, 2H), 5.16 (s, 2H), 7.22-7.31 (m, 2H), 7.44-7.48 (m, 1H), 7.50-7.60 (m, 2H), 7.78-7.82 (m, 1H), 8.47 (s, 1H).

Example 20 ethyl 1-(3-ethyl-1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate

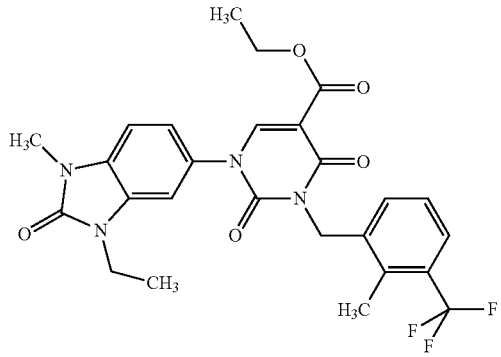 [SMILES: CCOC(=O)c1cn(-c2ccc3c(c2)n(CC)c(=O)n3C)c(=O)n(Cc2cccc(C(F)(F)F)c2C)c1=O]

The preparation and purification of the title compound were analogous to Example 18. Proceeding from 214 mg (0.42 mmol) of ethyl 1-(1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate from Example 14 and 73 mg (0.47 mmol) of iodoethane, 152 mg (65% of theory) of the title compound were obtained.

LC-MS (Method 1): R$_t$=1.06 min; m/z=531 (M+H)$^+$.

$^1$H NMR (400 MHz, DMSO-d$_6$): δ [ppm]=1.19-1.26 (m, 6H), 2.46 (s, partly concealed by DMSO signal), 3.37 (s, partly concealed by water signal), 3.87 (q, 2H), 4.20 (q, 2H), 5.09 (s, 2H), 7.23-7.30 (m, 2H), 7.33-7.39 (m, 2H), 7.47-7.49 (m, 1H), 7.59-7.62 (m, 1H), 8.44 (s, 1H).

Example 21 ethyl 3-[2-chloro-3-(trifluoromethyl)benzyl]-1-(1,3-diethyl-2-oxo-2,3-dihydro-1H-benzimidazol-5-yl)-2,4-dioxo-1,2,3,4-tetrahydropyrimidine-5-carboxylate

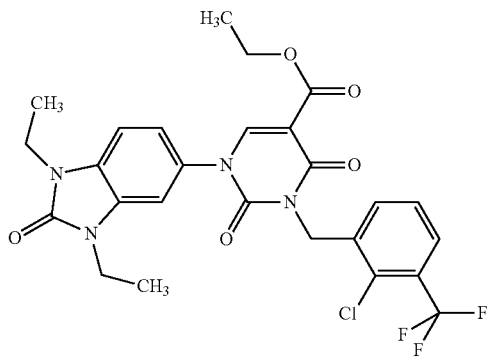 [SMILES: CCOC(=O)c1cn(-c2ccc3c(c2)n(CC)c(=O)n3CC)c(=O)n(Cc2cccc(C(F)(F)F)c2Cl)c1=O]

The preparation and purification of the title compound were analogous to Example 1. The reaction time was 5 h. Proceeding from 200 mg (0.54 mmol) of ethyl 1-(1,3-diethyl-2-oxo-2,3-dihydro-1H-benzimidazol-5-yl)-2,4-dioxo-1,2,3,4-tetrahydropyrimidine-5-carboxylate from Example 22A and 162 mg (0.59 mmol) of 2-chloro-3-(trifluoromethyl)benzyl bromide, 204 mg (66% of theory) of the title compound were obtained.

LC-MS (Method 1): R$_t$=1.17 min; m/z=565 (M+H)$^+$.

$^1$H NMR (400 MHz, DMSO-d$_6$): δ [ppm]=1.19-1.26 (m, 9H), 3.84-3.95 (m, 4H), 4.20 (q, 2H), 5.16 (s, 2H), 7.22-7.27 (m, 1H), 7.34 (d, 1H), 7.44-7.48 (m, 1H), 7.50-7.60 (m, 2H), 7.78-7.83 (m, 1H), 8.48 (s, 1H).

Example 22 ethyl 1-(1,3-diethyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate

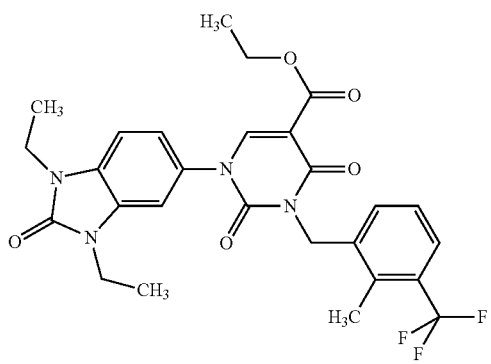 [SMILES: CCOC(=O)c1cn(-c2ccc3c(c2)n(CC)c(=O)n3CC)c(=O)n(Cc2cccc(C(F)(F)F)c2C)c1=O]

The preparation and purification of the title compound were analogous to Example 1. The reaction time was 5 h. Proceeding from 200 mg (0.54 mmol) of ethyl 1-(1,3-diethyl-2-oxo-2,3-dihydro-1H-benzimidazol-5-yl)-2,4-dioxo-1,2,3,4-tetrahydropyrimidine-5-carboxylate from Example 22A and 150 mg (0.59 mmol) of 2-methyl-3-(trifluoromethyl)benzyl bromide, 174 mg (59% of theory) of the title compound were obtained.

LC-MS (Method 1): R$_E$=1.16 min; m/z=545 (M+H)$^+$.

$^1$H NMR (400 MHz, DMSO-d$_6$): δ [ppm]=1.23 (d, 9H), 2.46 (s, 3H), 3.83-3.95 (m, 4H), 4.20 (q, 2H), 5.09 (s, 2H), 7.22-7.26 (m, 1H), 7.31-7.41 (m, 3H), 7.46-7.49 (m, 1H), 7.58-7.62 (m, 1H), 8.46 (s, 1H).

Example 23 ethyl 3-(2,3-dichlorobenzyl)-1-(1,3-diethyl-2-oxo-2,3-dihydro-1H-benzimidazol-5-yl)-2,4-dioxo-1,2,3,4-tetrahydropyrimidine-5-carboxylate

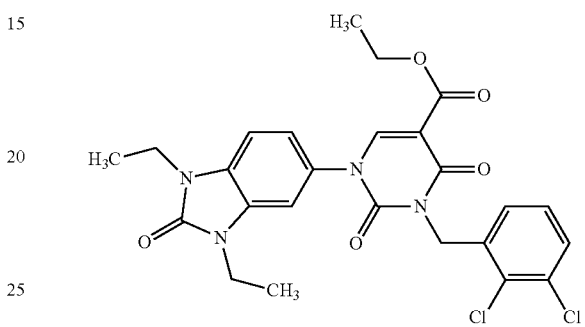

The preparation and purification of the title compound were analogous to Example 1. The reaction time was 5 h. Proceeding from 200 mg (0.53 mmol) of ethyl 1-(1,3-diethyl-2-oxo-2,3-dihydro-1H-benzimidazol-5-yl)-2,4-dioxo-1,2,3,4-tetrahydropyrimidine-5-carboxylate from Example 22A and 115 mg (0.59 mmol) of 2,3-dichlorobenzyl chloride, 244 mg (81% of theory) of the title compound were obtained.

LC-MS (Method 1): R$_t$=1.15 min; m/z=531 (M+H)$^+$.

$^1$H NMR (400 MHz, DMSO-d$_6$): δ [ppm]=1.18-1.27 (m, 9H), 3.82-3.97 (m, 4H), 4.20 (q, 2H), 5.11 (s, 2H), 7.19-7.27 (m, 2H), 7.30-7.38 (m, 2H), 7.46 (d, 1H), 7.59 (d, 1H), 8.47 (s, 1H).

Example 24 ethyl 1-(1,3-diethyl-2-oxo-2,3-dihydro-1H-benzimidazol-5-yl)-3-[3-fluoro-2-(trifluoromethyl)benzyl]-2,4-dioxo-1,2,3,4-tetrahydropyrimidine-5-carboxylate

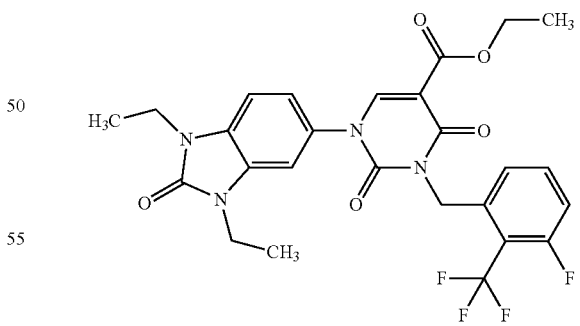

The preparation and purification of the title compound were analogous to Example 1. The reaction time was 5 h. Proceeding from 165 mg (0.44 mmol) of ethyl 1-(1,3-diethyl-2-oxo-2,3-dihydro-1H-benzimidazol-5-yl)-2,4-dioxo-1,2,3,4-tetrahydropyrimidine-5-carboxylate from Example 22A and 125 mg (0.48 mmol) of 1-(bromomethyl)-3-fluoro-2-(trifluoromethyl)benzene, 198 mg (82% of theory) of the title compound were obtained.

LC-MS (Method 3): R$_t$=1.28 min; m/z=549 (M+H)$^+$.

$^1$H NMR (400 MHz, DMSO-d$_6$): δ [ppm]=1.23 (td, 9H), 3.82-3.96 (m, 4H), 4.20 (q, 2H), 5.21 (s, 2H), 7.17-7.26 (m, 2H), 7.31-7.49 (m, 3H), 7.67 (q, 1H), 8.49 (s, 1H).

Example 25 ethyl 3-[3-chloro-2-(trifluoromethyl)benzyl]-1-[1-methyl-2-oxo-3-(2,2,2-trifluoroethyl)-2,3-dihydro-1H-benzimidazol-5-yl]-2,4-dioxo-1,2,3,4-tetrahydropyrimidine-5-carboxylate

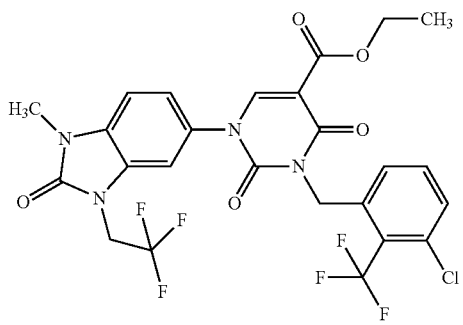 [SMILES: CCOC(=O)c1cn(-c2ccc3c(c2)n(CC(F)(F)F)c(=O)n3C)c(=O)n(Cc2cccc(Cl)c2C(F)(F)F)c1=O]

121 mg (0.23 mmol) of ethyl 3-[3-chloro-2-(trifluoromethyl)benzyl]-1-(1-methyl-2-oxo-2,3-dihydro-1H-benzimidazol-5-yl)-2,4-dioxo-1,2,3,4-tetrahydropyrimidine-5-carboxylate from Example 17 were initially charged in DMF (3 ml), and 76 µl (130 mg, 0.46 mmol) of 2,2,2-trifluoroethyl trichloromethanesulphonate, 64 mg (0.46 mmol) of potassium carbonate and 4 mg (0.02 mmol) of potassium iodide were added. The reaction mixture was left to stir at 60° C. for 5 h. The reaction mixture cooled to RT was admixed with water, and the precipitate was filtered off with suction, washed with water and MTBE, and dried under reduced pressure at 50° C. After additional purification by means of flash chromatography (dichloromethane/methanol 70:1), 91 mg (63% of theory) of the title compound were obtained.

LC-MS (Method 1): R$_t$=1.16 min; m/z=605 (M+H)$^+$.

$^1$H NMR (400 MHz, DMSO-d$_6$): δ [ppm]=1.23 (t, 3H), 3.41 (s, 3H), 4.20 (q, 2H), 4.80 (q, 2H), 5.22 (br.s, 2H), 7.31-7.39 (m, 3H), 7.53 (s, 1H), 7.57-7.67 (m, 2H), 8.44 (s, 1H).

Example 26 ethyl 3-[2-chloro-3-(trifluoromethyl)benzyl]-1-[1-methyl-2-oxo-3-(2,2,2-trifluoroethyl)-2,3-dihydro-1H-benzimidazol-5-yl]-2,4-dioxo-1,2,3,4-tetrahydropyrimidine-5-carboxylate

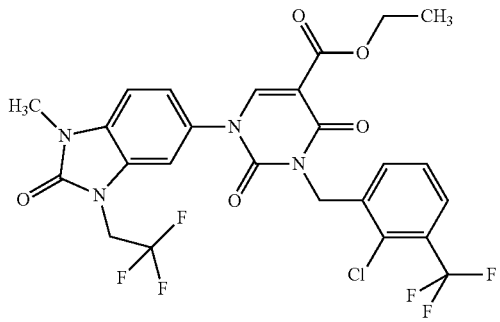 [SMILES: CCOC(=O)c1cn(-c2ccc3c(c2)n(CC(F)(F)F)c(=O)n3C)c(=O)n(Cc2cccc(C(F)(F)F)c2Cl)c1=O]

The preparation and purification of the title compound were analogous to Example 25. Proceeding from 89 mg (0.17 mmol) of ethyl 3-[2-chloro-3-(trifluoromethyl)benzyl]-1-(1-methyl-2-oxo-2,3-dihydro-1H-benzimidazol-5-yl)-2,4-dioxo-1,2,3,4-tetrahydropyrimidine-5-carboxylate from Example 16 and 96 mg (0.34 mmol) of 2,2,2-trifluoroethyl trichloromethanesulphonate, 80 mg (75% of theory) of the title compound were obtained.

LC-MS (Method 1): R$_t$=1.16 min; m/z=605 (M+H)$^+$.

$^1$H NMR (400 MHz, DMSO-d$_6$): δ [ppm]=1.23 (t, 3H), 3.41 (s, 3H), 4.21 (q, 2H), 4.80 (q, 2H), 5.15 (s, 2H), 7.31-7.39 (m, 2H), 7.50-7.56 (m, 2H), 7.57-7.61 (m, 1H), 7.78-7.82 (m, 1H), 8.43 (s, 1H).

Example 27 ethyl 1-[1-methyl-2-oxo-3-(2,2,2-trifluoroethyl)-2,3-dihydro-1H-benzimidazol-5-yl]-3-[2-methyl-3-(trifluoromethyl)benzyl]-2,4-dioxo-1,2,3,4-tetrahydropyrimidine-5-carboxylate

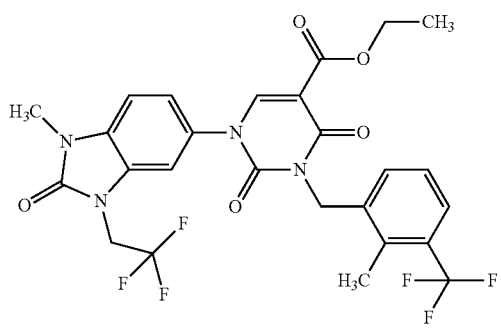 [SMILES: CCOC(=O)c1cn(-c2ccc3c(c2)n(CC(F)(F)F)c(=O)n3C)c(=O)n(Cc2cccc(C(F)(F)F)c2C)c1=O]

The preparation and purification of the title compound were analogous to Example 25. Proceeding from 133 mg (purity 75%, 0.19 mmol) of ethyl 1-(1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate from Example 14 and 111 mg (0.39 mmol) of 2,2,2-trifluoroethyl trichloromethanesulphonate, after purification by means of flash chromatography (dichloromethane/methanol 100:1), 41 mg (35% of theory) of the title compound were obtained.

LC-MS (Method 1): R$_t$=1.15 min; m/z=585 (M+H)$^+$.

$^1$H NMR (400 MHz, DMSO-d$_6$): δ [ppm]=1.23 (t, 3H), 2.46 (s, 3H), 3.41 (s, 3H), 4.20 (q, 2H), 4.79 (q, 2H), 5.08 (s, 2H), 7.32-7.41 (m, 4H), 7.54-7.57 (m, 1H), 7.58-7.63 (m, 1H), 8.41 (s, 1H).

Example 28 ethyl 1-[1-methyl-2-oxo-3-(2,2,2-trifluoroethyl)-2,3-dihydro-1H-benzimidazol-5-yl]-2,4-dioxo-3-[(1R)-4-(trifluoromethyl)-2,3-dihydro-1H-inden-1-yl]-1,2,3,4-tetrahydropyrimidine-5-carboxylate (R enantiomer)

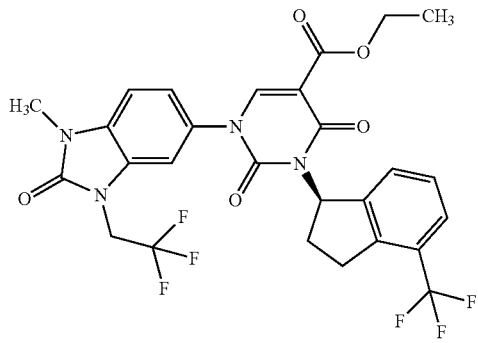 [SMILES: CCOC(=O)c1cn(-c2ccc3c(c2)n(CC(F)(F)F)c(=O)n3C)c(=O)n([C@@H]2CCc3c2cccc3C(F)(F)F)c1=O]

400 mg (0.97 mmol) of ethyl 1-[1-methyl-2-oxo-3-(2,2,2-trifluoroethyl)-2,3-dihydro-1H-benzimidazol-5-yl]-2,4- dioxo-1,2,3,4-tetrahydropyrimidine-5-carboxylate from Example 25A, 235 mg (1.16 mmol) of (1S)-4-(trifluoromethyl)indan-1-ol from Example 14A and 763 mg (2.91 mmol) of triphenylphosphine were initially charged under argon in DMF/THF 1:1 (19.6 ml), and the reaction mixture was cooled to −15° C. and admixed with 0.53 ml (2.71 mmol) of diisopropyl azodicarboxylate. The reaction mixture was left to stir at RT for 30 min, then, while cooling with ice, a further 0.2 equivalent (38 µl, 0.19 mmol) of diisopropyl azodicarboxylate was added dropwise and the mixture was stirred at RT for 1 h. The reaction mixture was cooled to 0° C., admixed with 1 N hydrochloric acid and stirred at RT for 15 mm. The solution formed was extracted with ethyl acetate. The organic phase was successively washed twice with 1 N hydrochloric acid, twice with saturated sodium carbonate solution and once with saturated sodium chloride solution, dried over magnesium sulphate and concentrated. The residue was purified by preparative HPLC (Method 7). This gave 370 mg (57% of theory) of the title compound.

LC-MS (Method 5) $R_t$=1.17 mm; m/z=597 (M+H)$^+$.

$^1$H NMR (400 MHz, CD$_2$Cl$_2$): δ [ppm]=1.23 (t, 3H), 2.29-2.42 (m, 1H), 2.43-2.57 (m, 1H), 3.00-3.12 (m, 1H), 3.31-3.44 (m, 4H), 4.20 (q, 2H), 4.41 (q, 2H), 6.47-6.60 (m, 1H), 6.94-7.07 (m, 3H), 7.17-7.28 (m, 2H), 7.41 (d, 1H), 8.22 (s, 1H).

Example 29 ethyl 3-[2-chloro-3-(trifluoromethyl)benzyl]-1-[3-(cyclopropylmethyl)-1-methyl-2-oxo-2,3-dihydro-1H-benzimidazol-5-yl]-2,4-dioxo-1,2,3,4-tetrahydropyrimidine-5-carboxylate

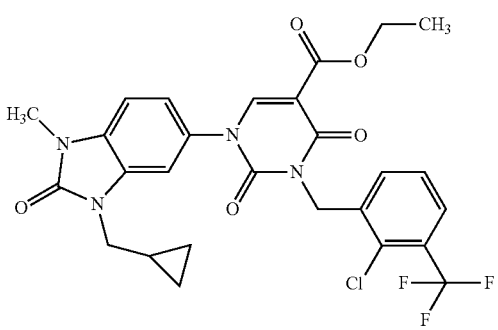 [SMILES: CCOC(=O)c1cn(-c2ccc3c(c2)n(CC2CC2)c(=O)n3C)c(=O)n(Cc2cccc(C(F)(F)F)c2Cl)c1=O]

To a solution of 90 mg (0.17 mmol) of ethyl 3-[2-chloro-3-(trifluoromethyl)benzyl]-1-(1-methyl-2-oxo-2,3-dihydro-1H-benzimidazol-5-yl)-2,4-dioxo-1,2,3,4-tetrahydropyrimidine-5-carboxylate from Example 16 in DMF (2 ml) were added 254 mg (0.18 mmol) of (bromomethyl)cyclopropane, 47 mg of potassium carbonate and 3 mg of potassium iodide. Subsequently, the reaction mixture was left to stir at 60° C. for 5 h. After cooling to RT, water was added and the precipitate formed was filtered off. The solid was washed successively with water and MTBE, and dried under reduced pressure at 50° C. The solid was dissolved in dichloromethane and purified by means of flash chromatography (dichloromethane/methanol 70/1). The resulting product was dried under high vacuum. This gave 67 mg (66% of theory) of the title compound.

LC-MS (Method 1): $R_t$=1.17 min; m/z=577 (M+H)$^+$.

$^1$H NMR (400 MHz, DMSO-d$_6$): δ=0.34-0.50 (m, 4H), 1.14-1.26 (m, 4H), 3.38 (s, 3H), 3.72 (d, 2H), 4.20 (q, 2H), 5.15 (s, 2H), 7.23-7.31 (m, 2H), 7.50-7.60 (m, 3H), 7.80 (d, 1H), 8.46 (s, 1H).

Example 30 ethyl 1-[3-(cyclopropylmethyl)-1-methyl-2-oxo-2,3-dihydro-1H-benzimidazol-5-yl]-3-[2-methyl-3-(trifluoromethyl)benzyl]-2,4-dioxo-1,2,3,4-tetrahydropyrimidine-5-carboxylate

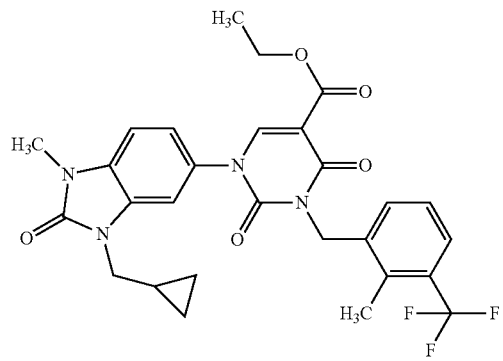 [SMILES: CCOC(=O)c1cn(-c2ccc3c(c2)n(CC2CC2)c(=O)n3C)c(=O)n(Cc2cccc(C(F)(F)F)c2C)c1=O]

The preparation and purification of the title compound were analogous to Example 29. Proceeding from 133 mg (75% purity, 0.19 mmol) of ethyl 1-(1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate from Example 14 and 29 mg (0.18 mmol) of (bromomethyl)cyclopropane, 69 mg (56% of theory) of the title compound were obtained.

LC-MS (Method 1): $R_t$=1.16 min; m/z=557 (M+H)$^+$.

$^1$H NMR (400 MHz, DMSO-d$_6$): δ [ppm]=0.35-0.41 (m, 2H), 0.42-0.49 (m, 2H), 1.16-1.26 (m, 4H), 2.46 (s, 3H), 3.38 (s, 3H), 3.72 (d, 2H), 4.20 (q, 2H), 5.09 (s, 2H), 7.23-7.30 (m, 2H), 7.33-7.40 (m, 2H), 7.52-7.54 (m, 1H), 7.59-7.62 (m, 1H), 8.44 (s, 1H).

Example 31 ethyl 3-[3-chloro-2-(trifluoromethyl)benzyl]-1-[3-(cyclopropylmethyl)-1-methyl-2-oxo-2,3-dihydro-1H-benzimidazol-5-yl]-2,4-dioxo-1,2,3,4-tetrahydropyrimidine-5-carboxylate

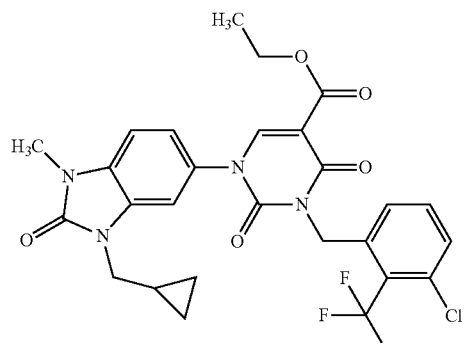

The preparation and purification of the title compound were analogous to Example 29. Proceeding from 120 mg (0.23 mmol) of ethyl 3-[3-chloro-2-(trifluoromethyl)benzyl]-1-(1-methyl-2-oxo-2,3-dihydro-1H-benzimidazol-5-yl)-2,4-dioxo-1,2,3,4-tetrahydropyrimidine-5-carboxylate from Example 17 and 34 mg (0.25 mmol) of (bromomethyl)cyclopropane, 89 mg (62% of theory) of the title compound were obtained.

LC-MS (Method 1): $R_t$=1.17 min; m/z=577 (M+H)$^+$.

$^1$H NMR (400 MHz, DMSO-d$_6$): δ [ppm]=0.35-0.41 (m, 2H), 0.41-0.49 (m, 2H), 1.14-1.27 (m, 4H), 3.38 (s, 3H), 3.72 (d, 2H), 4.20 (q, 2H), 5.22 (br.s, 2H), 7.22-7.30 (m, 2H), 7.31-7.36 (m, 1H), 7.49-7.52 (m, 1H), 7.57-7.67 (m, 2H), 8.47 (s, 1H).

Example 32 ethyl 3-[2-chloro-3-(trifluoromethyl)benzyl]-1-[1-methyl-3-(oxetan-2-ylmethyl)-2-oxo-2,3-dihydro-1H-benzimidazol-5-yl]-2,4-dioxo-1,2,3,4-tetrahydropyrimidine-5-carboxylate (Racemate)

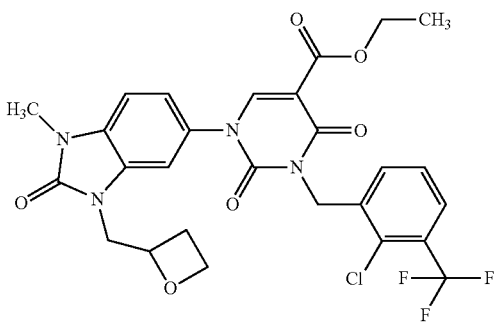 [SMILES: CCOC(=O)c1cn(-c2ccc3c(c2)n(CC2CCO2)c(=O)n3C)c(=O)n(Cc2cccc(C(F)(F)F)c2Cl)c1=O]

100 mg (0.23 mmol) of ethyl 3-[2-chloro-3-(trifluoromethyl)benzyl]-1-(1-methyl-2-oxo-2,3-dihydro-1H-benzimidazol-5-yl)-2,4-dioxo-1,2,3,4-tetrahydropyrimidine-5-carboxylate from Example 16 were initially charged in 2.4 ml of DMF, and 32 mg (0.21 mmol) of 2-(bromomethyl)oxetane, 53 mg (0.38 mmol) of potassium carbonate and 3 mg (0.02 mmol) of potassium iodide were added. The reaction mixture was stirred at 60° C. for 2 h. Subsequently, another 1 equivalent of 2-(bromomethyl)oxetane was added at RT and the reaction mixture was stirred at 80° C. for 2 h. For workup, the reaction mixture was admixed with water, and the precipitate was filtered off with suction, washed with water and dried under reduced pressure at 50° C. The solid was dissolved in dichloromethane and purified by means of flash silica gel chromatography (dichloro-methane/methanol 70:1). This gave 56 mg (50% of theory) of the title compound.

LC-MS (Method 1): $R_t$=1.09 min; m/z=593 (M+H)$^+$.

$^1$H NMR (400 MHz, DMSO-d$_6$): δ=1.23 (t, 3H), 2.10-2.22 (m, 1H), 2.25-2.38 (m, 1H), 3.36 (s, 3H), 3.39-3.48 (m, 1H), 3.73 (q, 1H), 3.85-3.92 (m, 1H), 3.92-3.98 (m, 1H), 4.11-4.17 (m, 1H), 4.21 (q, 2H), 5.15 (s, 2H), 7.25-7.33 (m, 2H), 7.45 (s, 1H), 7.53 (t, 1H), 7.60 (d, 1H), 7.80 (d, 1H), 8.46 (s, 1H).

Example 33 ethyl 1-(3-cyclobutyl-1-methyl-2-oxo-2,3-dihydro-1H-benzimidazol-5-yl)-3-[2-methyl-3-(trifluoromethyl)-benzyl]-2,4-dioxo-1,2,3,4-tetrahydropyrimidine-5-carboxylate

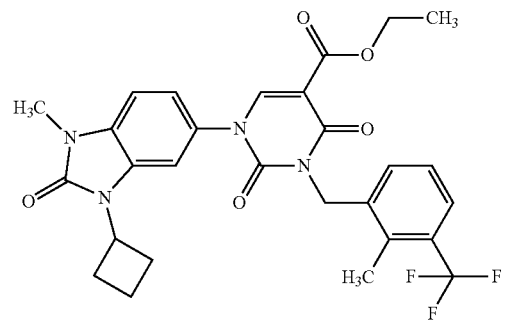 [SMILES: CCOC(=O)c1cn(-c2ccc3c(c2)n(C2CCC2)c(=O)n3C)c(=O)n(Cc2cccc(C(F)(F)F)c2C)c1=O]

39 µl (0.49 mmol) of cyclobutanol and 130 mg (0.49 mmol) of triphenylphosphine were initially charged under argon in THF (2.5 ml), 98 µl (0.49 mmol) of diisopropyl azodicarboxylate were slowly added dropwise and then 100 mg (0.19 mmol) of ethyl 1-(1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate from Example 14 were added.

The reaction mixture was stirred at RT for 16 h. The mixture was concentrated and purified by means of preparative HPLC (Method 8). This gave 46 mg (41% of theory) of the title compound.

LC-MS (Method 1): $R_t$=1.16 min; m/z=557 (M+H)$^+$.

$^1$H NMR (400 MHz, DMSO-d$_6$): δ [ppm]=1.23 (t, 3H), 1.72-1.91 (m, 2H), 2.20-2.30 (m, 2H), 2.47 (s, partly concealed by DMSO signal), 2.75-2.87 (m, 2H), 3.31 (s, partly concealed by water signal), 4.20 (q, 2H), 4.78-4.88 (m, 1H), 5.09 (s, 2H), 7.24-7.29 (m, 2H), 7.33-7.42 (m, 2H), 7.60 (d, 1H), 7.67 (s, 1H), 8.45 (s, 1H).

Example 34 ethyl 1-(3-isopropyl-1-methyl-2-oxo-2,3-dihydro-1H-benzimidazol-5-yl)-3-[2-methyl-3-(trifluoromethyl)-benzyl]-2,4-dioxo-1,2,3,4-tetrahydropyrimidine-5-carboxylate

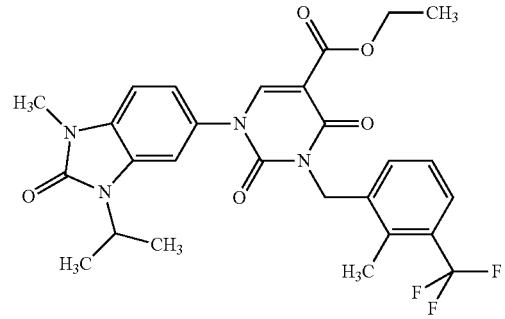 [SMILES: CCOC(=O)c1cn(-c2ccc3c(c2)n(C(C)C)c(=O)n3C)c(=O)n(Cc2cccc(C(F)(F)F)c2C)c1=O]

The preparation and purification of the title compound were analogous to Example 33. Proceeding from 100 mg (0.19 mmol) of ethyl 1-(1-methyl-2-oxo-2,3-dihydro-1H-benzimidazol-5-yl)-3-[2-methyl-3-(trifluoromethyl)-benzyl]-2,4-dioxo-1,2,3,4-tetrahydropyrimidine-5-carboxylate from Example 14 and 38 pa (0.49 mmol) of 2-propanol, after additional purification by means of preparative HPLC (Method 8), 38 mg (34% of theory) of the title compound were obtained.

LC-MS (Method 1): $R_t$=1.12 min; m/z=545 (M+H)$^+$.

$^1$H NMR (400 MHz, DMSO-d$_6$): δ [ppm]=1.23 (t, 3H), 1.45 (d, 6H), 2.46 (s, partly concealed by DMSO signal), 3.31 (s, partly concealed by water signal), 4.20 (q, 2H), 4.54-4.65 (m, 1H), 5.09 (s, 2H), 7.22-7.29 (m, 2H), 7.32-7.41 (m, 2H), 7.58-7.62 (m, 2H), 8.43 (s, 1H).

Example 35 ethyl 1-(3-cyclopropyl-1-methyl-2-oxo-2,3-dihydro-1H-benzimidazol-5-yl)-3-[2-methyl-3-(trifluoromethyl)-benzyl]-2,4-dioxo-1,2,3,4-tetrahydropyrimidine-5-carboxylate

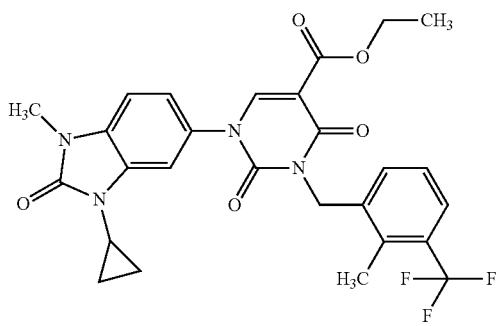 [SMILES: CCOC(=O)c1cn(-c2ccc3c(c2)n(C2CC2)c(=O)n3C)c(=O)n(Cc2cccc(C(F)(F)F)c2C)c1=O]

250 mg (0.49 mmol) of ethyl 1-(1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate from Example 14, 85 mg (0.99 mmol) of cyclopropylboronic acid and 0.41 ml (2.98 mmol) of triethylamine were initially charged in dichloro-methane (4 ml). Molecular sieve (3 Å) and 271 mg (1.49 mmol) of copper(II) acetate were added and the reaction mixture was stirred at RT for 3 days. The mixture was diluted with ethyl acetate, washed twice with 1M hydrochloric acid, once with saturated sodium hydrogencarbonate solution and once with saturated sodium chloride solution. The organic phase was dried over magnesium sulphate, filtered and concentrated. The residue was purified by means of preparative HPLC (Method 8). This gave 155 mg (56% of theory) of the title compound.

LC-MS (Method 1): $R_t$=1.06 min; m/z=543 (M+H)$^+$.

$^1$H NMR (400 MHz, DMSO-d$_6$): δ [ppm]=0.86-0.92 (m, 2H), 0.99-1.06 (m, 2H), 1.23 (t, 3H), 2.46 (s, partly concealed by DMSO signal), 2.87-2.95 (m, 1H), 3.31 (s, partly concealed by water signal), 4.20 (q, 2H), 5.08 (s, 2H), 7.22-7.28 (m, 2H), 7.32-7.43 (m, 2H), 7.47 (s, 1H), 7.60 (d, 1H), 8.41 (s, 1H).

Example 36 ethyl 1-(3-methyl-2-oxo-2,3-dihydro-1H-benzimidazol-5-yl)-3-[2-methyl-3-(trifluoromethyl)-benzyl]-2,4-dioxo-1,2,3,4-tetrahydropyrimidine-5-carboxylate

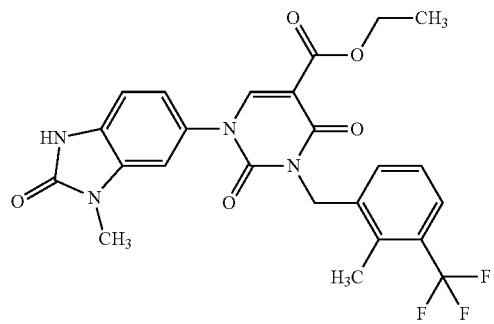 [SMILES: CCOC(=O)c1cn(-c2ccc3[nH]c(=O)n(C)c3c2)c(=O)n(Cc2cccc(C(F)(F)F)c2C)c1=O]

To a solution of 250 mg (0.76 mmol) of ethyl 1-(3-methyl-2-oxo-2,3-dihydro-1H-benzimidazol-5-yl)-2,4-dioxo-1,2,3,4-tetrahydropyrimidine-5-carboxylate from Example 34A in 10 ml of DMF were added 211 mg (0.83 mmol) of 1-(bromomethyl)-2-methyl-3-(trifluoromethyl) benzene, 209 mg (1.51 mmol) of potassium carbonate and 13 mg (0.08 mmol) of potassium iodide, and the mixture was stirred at 60° C. for 3 h. For workup, the reaction mixture was admixed with water, and the precipitate formed was filtered off with suction, washed with water and MTBE, and dried under high vacuum at 50° C. overnight. This gave 42 mg (11% of theory) of the target compound.

LC-MS (Method 3): $R_t$=1.19 min; MS (ESIpos): m/z=503 (M+H)$^+$.

$^1$H NMR (400 MHz, DMSO-d$_6$): δ [ppm]=1.22 (t, 3H), 3.41 (s, 3H), 4.17 (q, 2H), 5.20 (s, 2H), 7.07-7.16 (m, 3H), 7.29-7.36 (m, 1H), 7.46 (s, 1H), 7.62 (d, 1H), 8.28 (s, 1H), 11.70 (s, 1H).

Example 37 ethyl 3-[2-chloro-3-(trifluoromethyl)benzyl]-2,4-dioxo-1-(2-oxo-2,3-dihydro-1H-benzimidazol-5-yl)-1,2,3,4-tetrahydropyrimidine-5-carboxylate

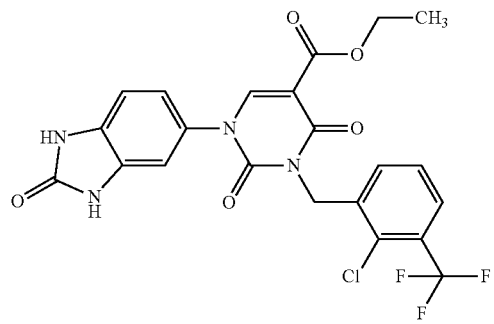 [SMILES: CCOC(=O)c1cn(-c2ccc3[nH]c(=O)[nH]c3c2)c(=O)n(Cc2cccc(C(F)(F)F)c2Cl)c1=O]

200 mg (0.63 mmol) of ethyl 2,4-dioxo-1-(2-oxo-2,3-dihydro-1H-benzimidazol-5-yl)-1,2,3,4-tetrahydropyrimidine-5-carboxylate from Example 26A were initially charged in 8 ml of DMF. 190 mg (0.70 mmol) of 1-(bromomethyl)-2-chloro-3-(trifluoromethyl)benzene, 175 mg (1.27 mmol) of potassium carbonate and 10.5 mg (63 mmol) of potassium iodide were added and the reaction mixture was stirred at 60° C. for 5 h. After cooling to RT, water was added to the mixture. The precipitate was filtered off, washed with a little water and MTBE, and dried in a drying cabinet at 50° C. The resulting product was dissolved in a little DMF and purified by means of preparative HPLC (Method 8). This gave 111 mg (35% of theory) of the title compound.

LC-MS (Method 3): $R_t$=1.13 min; m/z=509 (M+H)$^+$.

$^1$H NMR (400 MHz, DMSO-d$_6$): δ [ppm]=1.23 (t, 3H), 4.20 (q, 2H), 5.14 (s, 2H), 7.02 (d, 1H), 7.09 (dd, 1H), 7.15 (s, 1H), 7.51 (t, 1H), 7.59 (d, 1H), 7.79 (d, 1H), 8.41 (s, 1H), 10.88 (d, 2H).

Example 38 ethyl 1-[3-methyl-2-oxo-1-(2,2,2-trifluoroethyl)-2,3-dihydro-1H-benzimidazol-5-yl]-3-[2-methyl-3-(trifluoromethyl)benzyl]-2,4-dioxo-1,2,3,4-tetrahydropyrimidine-5-carboxylate

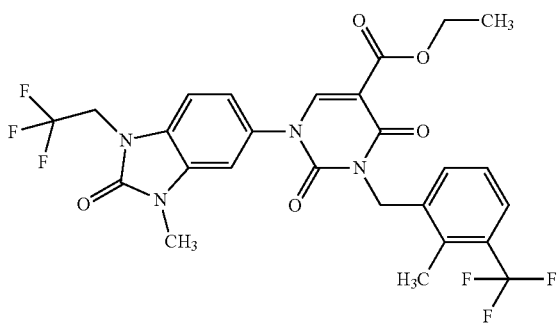 [SMILES: CCOC(=O)c1cn(-c2ccc3c(c2)n(C)c(=O)n3CC(F)(F)F)c(=O)n(Cc2cccc(C(F)(F)F)c2C)c1=O]

The preparation and purification of the title compound were analogous to Example 25. Proceeding from 91 mg (0.18 mmol) of ethyl 1-(3-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate from Example 36 and 101 mg (0.36 mmol) of 2,2,2-trifluoroethyl trichloromethanesulphonate, 57 mg (52% of theory) of the title compound were obtained.

LC-MS (Method 1): $R_t$=1.11 min; m/z=585 (M+H)$^+$.

$^1$H NMR (400 MHz, DMSO-d$_6$): δ [ppm]=1.23 (t, 3H), 2.46 (s, 3H), 3.38 (s, 3H), 4.19 (q, 2H), 4.86 (q, 2H), 5.09 (s, 2H), 7.28-7.41 (m, 3H), 7.44 (d, 1H), 7.50 (d, 1H), 7.61 (d, 1H), 8.47 (s, 1H).

Example 39 ethyl 1-[1-(cyclopropylmethyl)-3-methyl-2-oxo-2,3-dihydro-1H-benzimidazol-5-yl]-3-[2-methyl-3-(trifluoromethyl)benzyl]-2,4-dioxo-1,2,3,4-tetrahydropyrimidine-5-carboxylate

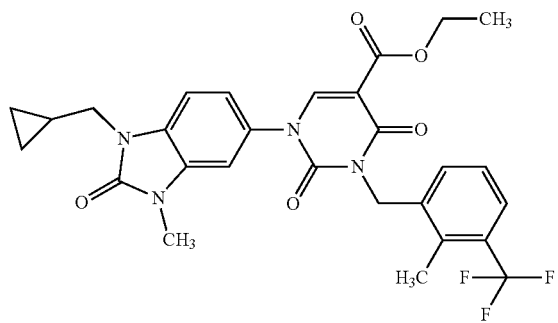 [SMILES: CCOC(=O)c1cn(-c2ccc3c(c2)n(C)c(=O)n3CC2CC2)c(=O)n(Cc2cccc(C(F)(F)F)c2C)c1=O]

91 mg (0.18 mmol) of ethyl 1-(3-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate from Example 36 were reacted analogously to Example 29 with 26 mg (0.19 mmol) of (bromomethyl)cyclopropane. After 2 h of reaction time, an additional 24 mg (0.17 mmol) of (bromomethyl)cyclopropane were added and the reaction mixture was stirred at 80° C. for another 1 h. The product was precipitated by addition of water and filtered off. After additional purification by means of flash chromatography (dichloromethane/methanol 70:1), 51 mg (51% of theory) of the title compound were obtained.

LC-MS (Method 1): $R_t$=1.13 min; m/z=557 (M+H)$^+$.

$^1$H NMR (400 MHz, DMSO-d$_6$): δ=0.36-0.42 (m, 2H), 0.42-0.50 (m, 2H), 1.14-1.20 (m, 1H), 1.23 (t, 3H), 2.46 (s, 3H), 3.35 (s, 3H), 3.77 (d, 2H), 4.19 (q, 2H), 5.09 (s, 2H), 7.24 (dd, 1H), 7.32-7.44 (m, 4H), 7.58-7.62 (m, 1H), 8.45 (s, 1H).

Example 40 ethyl 1-(3-methyl-2-oxo-2,3-dihydro-1,3-benzoxazol-6-yl)-3-[2-methyl-3-(trifluoromethyl)benzyl]-2,4-dioxo-1,2,3,4-tetrahydropyrimidine-5-carboxylate

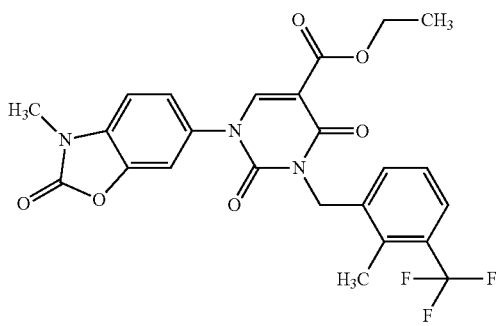 [SMILES: CCOC(=O)c1cn(-c2ccc3c(c2)oc(=O)n3C)c(=O)n(Cc2cccc(C(F)(F)F)c2C)c1=O]

The preparation and purification of the title compound were analogous to Example 1, with reaction time 2 h. Proceeding from 200 mg (0.60 mmol) of ethyl 1-(3-methyl-2-oxo-2,3-dihydro-1,3-benzoxazol-6-yl)-2,4-dioxo-1,2,3,4-tetrahydropyrimidine-5-carboxylate from Example 28A and 168 mg (0.66 mmol) of 1-(bromomethyl)-2-methyl-3-(trifluoromethyl)benzene, 288 mg (93% of theory) of the title compound were obtained.

LC-MS (Method 5): $R_t$=1.10 min; m/z=504 (M+H)$^+$.

$^1$H NMR (400 MHz, DMSO-d$_6$): δ [ppm]=1.23 (t, 3H), 2.46 (s, 3H), 3.38 (s, 3H), 4.20 (q, 2H), 5.07 (s, 2H), 7.31-7.42 (m, 3H), 7.43-7.48 (m, 1H), 7.58-7.62 (m, 1H), 7.63-7.66 (m, 1H), 8.44 (s, 1H).

Example 41 ethyl 3-[2-chloro-3-(trifluoromethyl)benzyl]-1-(3-methyl-2-oxo-2,3-dihydro-1,3-benzoxazol-6-yl)-2,4-dioxo-1,2,3,4-tetrahydropyrimidine-5-carboxylate

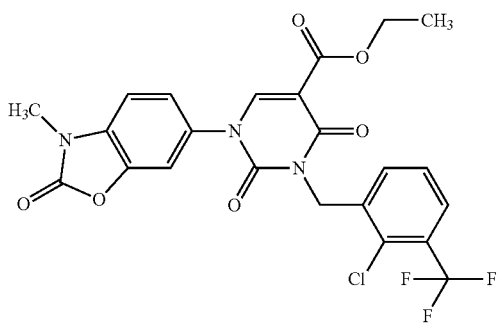 [SMILES: CCOC(=O)c1cn(-c2ccc3c(c2)oc(=O)n3C)c(=O)n(Cc2cccc(C(F)(F)F)c2Cl)c1=O]

The preparation and purification of the title compound were analogous to Example 1. The reaction time was 2 h. Proceeding from 200 mg (0.60 mmol) of ethyl 1-(3-methyl-2-oxo-2,3-dihydro-1,3-benzoxazol-6-yl)-2,4-dioxo-1,2,3,4-tetrahydropyrimidine-5-carboxylate from Example 28A and 181 mg (0.66 mmol) of 1-(bromomethyl)-2-chloro-3-(trifluoromethyl)benzene, 263 mg (79% of theory) of the title compound were obtained.

LC-MS (Method 5): $R_t$=1.11 min; m/z=523 (M+H)$^+$.

$^1$H NMR (400 MHz, DMSO-$d_6$): δ=1.23 (t, 3H), 3.38 (s, 3H), 4.20 (q, 2H), 5.14 (s, 2H), 7.38-7.48 (m, 2H), 7.53 (t, 1H), 7.59 (d, 1H), 7.64 (s, 1H), 7.80 (d, 1H), 8.47 (s, 1H).

Example 42 ethyl 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer)

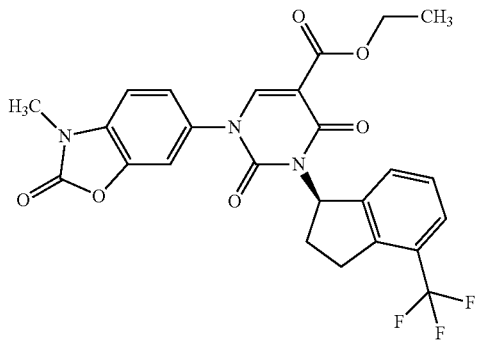 [SMILES: CCOC(=O)c1cn(-c2ccc3c(c2)oc(=O)n3C)c(=O)n([C@@H]2CCc3c2cccc3C(F)(F)F)c1=O]

Method A:

A solution of 200 mg (0.60 mmol) of ethyl 1-(3-methyl-2-oxo-2,3-dihydro-1,3-benzoxazol-6-yl)-2,4-dioxo-1,2,3,4-tetrahydropyrimidine-5-carboxylate from Example 28A and 475 mg (1.81 mmol) of triphenylphosphine in THF/DMF 1:1 (7.6 ml) under argon was cooled to −30° C. 238 μl (1.20 mmol) of diisopropyl azodicarboxylate were added dropwise and then a solution of 146 mg (0.69 mmol) of (1S)-4-(trifluoromethyl)indan-1-ol from Example 14A in about 1 ml of THF was added dropwise. The reaction mixture was warmed to RT and stirred at RT for 30 min. For workup, the mixture was cooled to 0° C., admixed with 5 ml of 1M hydrochloric acid, warmed to RT and stirred for 30 mm. The mixture was then extracted with ethyl acetate. The organic phase was washed twice with 1M hydrochloric acid and once with saturated sodium chloride solution, dried over magnesium sulphate and concentrated under reduced pressure. The residue was subjected to extractive stirring with ethanol, and the precipitated solid was filtered off with suction and discarded. The filtrate was concentrated, dissolved in a little dichloromethane and purified by means of flash chromatography (dichloromethane/methanol 120:1→20:1). This gave 135 mg (43% of theory) of the title compound in about 95% purity.

LC-MS (Method 1): $R_t$=1.13 min; m/z=516 (M+H)$^+$.

$^1$H NMR (400 MHz, DMSO-$d_6$): δ [ppm]=1.22 (t, 3H), 2.37-2.43 (m, 1H), 2.43-2.48 (m, 1H, partly concealed by DMSO signal), 3.03-3.14 (m, 1H), 3.22-3.30 (m, 1H, partly concealed by water signal), 3.38 (s, 3H), 4.18 (q, 2H), 6.34-6.56 (m, 1H), 7.32-7.43 (m, 3H), 7.45-7.50 (m, 1H), 7.53 (d, 1H), 7.55-7.64 (m, 1H), 8.35 (s, 1H).

In an analogous experiment, it was possible to isolate a fraction with 99% purity. For this batch, the specific optical rotation measured was:

Specific optical rotation: $α_D^{20}$=+132.9°, (chloroform, c=0.395 g/100 ml).

Method B:

A solution of 5.0 g (15.1 mmol) of ethyl 1-(3-methyl-2-oxo-2,3-dihydro-1,3-benzoxazol-6-yl)-2,4-dioxo-1,2,3,4-tetrahydropyrimidine-5-carboxylate from Example, 6.73 g (25.7 mmol) of triphenylphosphine and 3.66 g (18.1 mmol) of (1S)-4-(trifluoromethyl)indan-1-ol from Example 14A was initially charged under argon in 240 ml of DMF/THF 2:1 (v/v) and cooled to −15° C. 4.76 ml (24.15 mmol) of diisopropyl azodicarboxylate was slowly added dropwise at such a rate that the temperature of the reaction mixture did not rise above −10° C. At the end of the addition, the mixture was stirred at −10° C. for another 1 h, then warmed to RT and poured onto 1.3 l of water. The mixture was extracted twice with 300 ml each time of ethyl acetate. The combined organic phases were washed with a saturated sodium chloride solution, dried over magnesium sulphate and freed of the solvent on a rotary evaporator. The residue (18 g) was purified in two chromatography steps: first using a 200 g silica gel column with dichloromethane/acetone 97.5:2.5 as the eluent. The resulting product-containing fractions were concentrated and the residue was applied again to a 200 g silica gel column. 2.5 l of cyclohexane/ethyl acetate 1:1 as eluent were used to elute further impurities, then the desired product was eluted from the column with dichloromethane/methanol 95:5. This gave 3.40 g (44% of theory) of the title compound in 95% purity (NMR showed about 5% ethyl acetate). A further 920 mg were obtainable by a new purification of a mixed fraction. Overall yield: 4.32 g (56% of theory).

LC-MS (Method 1): $R_t$=1.15 min; m/z=516 (M+H)$^+$.

$^1$H NMR (400 MHz, $CD_2Cl_2$): δ [ppm]=1.31 (t, 3H), 2.37-2.49 (m, 1H), 2.59 (dtd, 1H), 3.14 (dt, 1H), 3.40 (s, 3H), 3.42-3.53 (m, 1H), 4.29 (q, 2H), 6.54-6.68 (m, 1H), 7.06 (d, 1H), 7.17 (d, 1H), 7.22 (s, 1H), 7.26-7.36 (m, 2H), 7.49 (d, 1H), 8.28 (s, 1H).

Example 43 ethyl 1-(3-methyl-2-oxo-2,3-dihydro-1,3-benzoxazol-6-yl)-2,4-dioxo-3-[(1S)-4-(trifluoromethyl)-2,3-dihydro-1H-inden-1-yl]-1,2,3,4-tetrahydropyrimidine-5-carboxylate (S enantiomer)

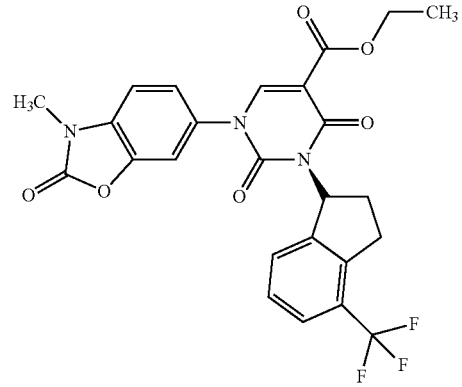

1.00 g (3.02 mmol) of the compound from Example 28A, 732 mg (3.62 mmol) of the compound from Example 15A and 1.35 g (5.13 mmol) of triphenylphosphine were initially charged in 9 ml of THF and 18 ml of DMF, and 951 μl (4.83 mmol) of diisopropyl azodicarboxylate were added dropwise at RT. The reaction mixture was stirred at RT for 1 h. For workup, 5 ml of 1N hydrochloric acid were added to the reaction mixture while cooling with ice and the mixture was stirred for 10 min. The mixture was then extracted with ethyl acetate. The combined organic phases were washed twice with 1N hydrochloric acid, twice with a 1M sodium carbonate solution and once with a saturated sodium chloride solution, dried over magnesium sulphate and concentrated on a rotary evaporator. The residue was purified by preparative HPLC (Method 15). This gave 590 mg (38% of theory) of the title compound.

LC-MS (Method 1): $R_t$=1.08 min; m/z=516 (M+H)$^+$.

$^1$H NMR (400 MHz, CD$_2$Cl$_2$): δ [ppm]=1.31 (t, 3H), 2.33-2.50 (m, 1H), 2.51-2.67 (m, 1H), 3.14 (dt, 1H), 3.39-3.52 (m, 1H), 3.40 (s, 3H), 4.29 (q, 2H), 6.55-6.68 (m, 1H), 7.06 (d, 1H), 7.18 (d, 1H), 7.22 (s, 1H), 7.26-7.35 (m, 2H), 7.49 (d, 1H), 8.28 (s, 1H).

Chiral analytical HPLC (Method 27): $R_t$=9.94 min; about 93% ee

Example 44 ethyl 1-(3-ethyl-2-oxo-2,3-dihydro-1,3-benzoxazol-6-yl)-3-[2-methyl-3-(trifluoromethyl)benzyl]-2,4-dioxo-1,2,3,4-tetrahydropyrimidine-5-carboxylate

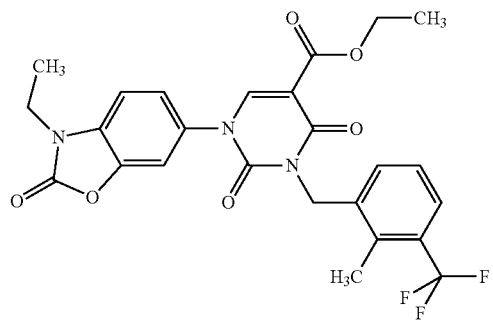 [SMILES: CCOC(=O)c1cn(-c2ccc3c(c2)oc(=O)n3CC)c(=O)n(Cc2cccc(C(F)(F)F)c2C)c1=O]

The preparation and purification of the title compound were analogous to Example 1. The reaction time was 5 h. Proceeding from 200 mg (0.58 mmol) of ethyl 1-(3-ethyl-2-oxo-2,3-dihydro-1,3-benzoxazol-6-yl)-2,4-dioxo-1,2,3,4-tetrahydropyrimidine-5-carboxylate from Example 30A and 161 mg (0.64 mmol) of 2-methyl-3-(trifluoromethyl)benzyl bromide, 192 mg (64% of theory) of the title compound were obtained.

LC-MS (Method 1): $R_t$=1.11 min; m/z=518 (M+H)$^+$.

$^1$H NMR (400 MHz, DMSO-d$_6$): δ [ppm]=1.23 (t, 3H), 1.28 (t, 3H), 2.46 (s, 3H), 3.90 (q, 2H), 4.20 (q, 2H), 5.08 (s, 2H), 7.31-7.42 (m, 2H), 7.43-7.50 (m, 2H), 7.58-7.62 (m, 1H), 7.64-7.67 (m, 1H), 8.45 (s, 1H).

Example 45 ethyl 3-(2,3-dichlorobenzyl)-1-(3-ethyl-2-oxo-2,3-dihydro-1,3-benzoxazol-6-yl)-2,4-dioxo-1,2,3,4-tetrahydropyrimidine-5-carboxylate

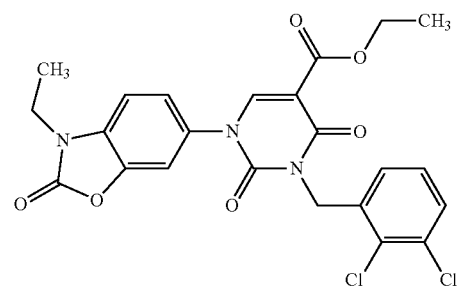 [SMILES: CCOC(=O)c1cn(-c2ccc3c(c2)oc(=O)n3CC)c(=O)n(Cc2cccc(Cl)c2Cl)c1=O]

The preparation and purification of the title compound were analogous to Example 1. The reaction time was 5 h. Proceeding from 200 mg (0.58 mmol) of ethyl 1-(3-ethyl-2-oxo-2,3-dihydro-1,3-benzoxazol-6-yl)-2,4-dioxo-1,2,3,4-tetrahydropyrimidine-5-carboxylate from Example 30A and 124 mg (0.64 mmol) of 1,2-dichloro-3-(chloromethyl)benzene, 220 mg (75% of theory) of the title compound were obtained.

LC-MS (Method 1): $R_t$=1.09 min; m/z=504 (M+H)$^+$.

$^1$H NMR (400 MHz, DMSO-d$_6$): δ [ppm]=1.23 (t, 3H), 1.28 (t, 3H), 3.90 (q, 2H), 4.20 (q, 2H), 5.10 (s, 2H), 7.21-7.25 (m, 1H), 7.30-7.36 (m, 1H), 7.41-7.50 (m, 2H), 7.56-7.60 (m, 1H), 7.63-7.66 (m, 1H), 8.47 (s, 1H).

Example 46 ethyl 3-[2-chloro-3-(trifluoromethyl)benzyl]-1-(3-ethyl-2-oxo-2,3-dihydro-1,3-benzoxazol-6-yl)-2,4-dioxo-1,2,3,4-tetrahydropyrimidine-5-carboxylate

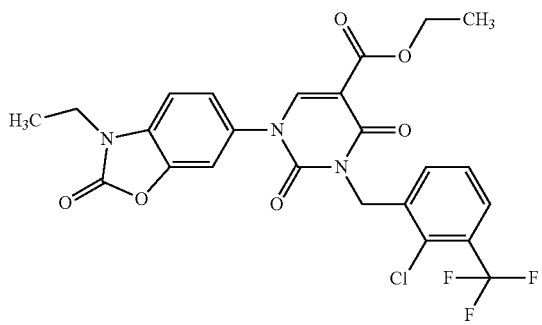 [SMILES: CCOC(=O)c1cn(-c2ccc3c(c2)oc(=O)n3CC)c(=O)n(Cc2cccc(C(F)(F)F)c2Cl)c1=O]

The preparation and purification of the title compound were analogous to Example 37. Proceeding from 200 mg (0.58 mmol) of ethyl 1-(3-ethyl-2-oxo-2,3-dihydro-1,3-benzoxazol-6-yl)-2,4-dioxo-1,2,3,4-tetrahydropyrimidine-5-carboxylate from Example 30A and 174 mg (0.63 mmol) of 1-(bromomethyl)-2-chloro-3-(trifluoromethyl)benzene, 209 mg (67% of theory) of the title compound were obtained.

LC-MS (Method 1): $R_t$=1.11 min; m/z=538 (M+H)$^+$.

$^1$H NMR (400 MHz, DMSO-d$_6$): δ [ppm]=1.23 (t, 3H), 1.28 (t, 3H), 3.90 (q, 2H), 4.20 (q, 2H), 5.14 (s, 2H), 7.42-7.56 (m, 3H), 7.59 (d, 1H), 7.65 (d, 1H), 7.81 (d, 1H), 8.48 (s, 1H).

Example 47 ethyl 1-(3-ethyl-2-oxo-2,3-dihydro-1,3-benzoxazol-6-yl)-3-[3-fluoro-2-(trifluoromethyl)benzyl]-2,4-dioxo-1,2,3,4-tetrahydropyrimidine-5-carboxylate

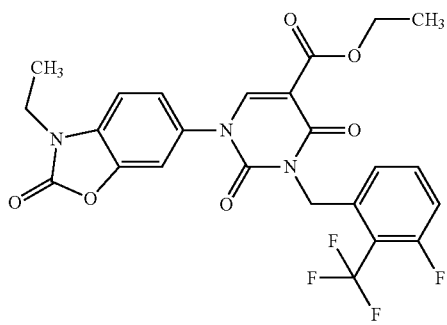 [SMILES: CCOC(=O)c1cn(-c2ccc3c(c2)oc(=O)n3CC)c(=O)n(Cc2cccc(F)c2C(F)(F)F)c1=O]

The preparation and purification of the title compound were analogous to Example 37. Proceeding from 200 mg (0.58 mmol) of ethyl 1-(3-ethyl-2-oxo-2,3-dihydro-1,3-benzoxazol-6-yl)-2,4-dioxo-1,2,3,4-tetrahydropyrimidine-5-carboxylate from Example 30A and 163 mg (0.63 mmol) of 1-(bromomethyl)-3-fluoro-2-(trifluoromethyl)benzene, 159 mg (52% of theory) of the title compound were obtained.

LC-MS (Method 1): $R_t$=1.06 min; m/z=522 (M+H)$^+$.

$^1$H NMR (400 MHz, DMSO-d$_6$): δ [ppm]=1.23 (t, 3H), 1.28 (t, 3H), 3.90 (q, 2H), 4.20 (q, 2H), 5.19 (s, 2H), 7.18-7.23 (m, 1H), 7.37-7.51 (m, 3H), 7.62-7.70 (m, 2H), 8.49 (s, 1H).

Example 48 ethyl 1-(3-methyl-2-oxo-2,3-dihydro-1,3-benzothiazol-6-yl)-3-[2-methyl-3-(trifluoromethyl)-benzyl]-2,4-dioxo-1,2,3,4-tetrahydropyrimidine-5-carboxylate

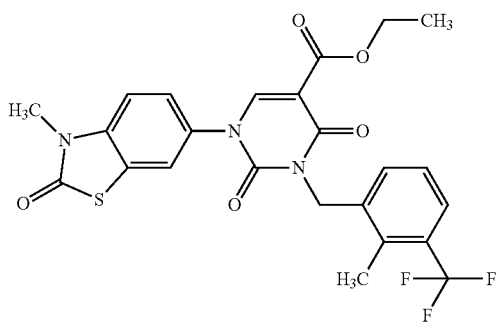 [SMILES: CCOC(=O)c1cn(-c2ccc3c(c2)sc(=O)n3C)c(=O)n(Cc2cccc(C(F)(F)F)c2C)c1=O]

The preparation and purification of the title compound were analogous to Example 37. Proceeding from 500 mg (1.44 mmol) of ethyl 1-(3-methyl-2-oxo-2,3-dihydro-1,3-benzothiazol-6-yl)-2,4-dioxo-1,2,3,4-tetrahydropyrimidine-5-carboxylate from Example 31A and 400 mg (1.58 mmol) of 1-(bromomethyl)-2-methyl-3-(trifluoromethyl)benzene, 392 mg (50% of theory) of the title compound were obtained.

LC-MS (Method 3): $R_t$=1.11 min; m/z=520 (M+H)±.

$^1$H NMR (400 MHz, DMSO-d$_6$): δ [ppm]=1.23 (t, 3H), 2.46 (s, partly concealed by DMSO signal), 3.45 (s, 3H), 4.20 (q, 2H), 5.08 (s, 2H), 7.31-7.42 (m, 2H), 7.46 (d, 1H), 7.56-7.63 (m, 2H), 7.88-7.91 (m, 1H), 8.48 (s, 1H).

Example 49 ethyl 3-[2-chloro-3-(trifluoromethyl)benzyl]-1-(3-methyl-2-oxo-2,3-dihydro-1,3-benzothiazol-6-yl)-2,4-dioxo-1,2,3,4-tetrahydropyrimidine-5-carboxylate

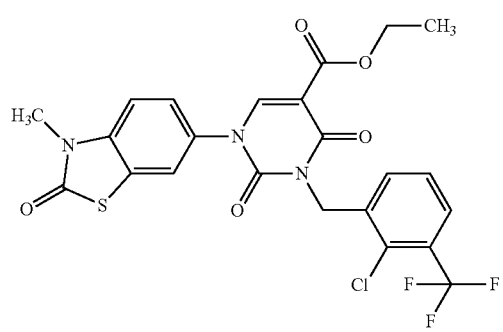 [SMILES: CCOC(=O)c1cn(-c2ccc3c(c2)sc(=O)n3C)c(=O)n(Cc2cccc(C(F)(F)F)c2Cl)c1=O]

The preparation and purification of the title compound were analogous to Example 37. Proceeding from 184 mg (0.53 mmol) of ethyl 1-(3-methyl-2-oxo-2,3-dihydro-1,3-benzothiazol-6-yl)-2,4-dioxo-1,2,3,4-tetrahydropyrimidine-5-carboxylate from Example 31A and 159 mg (0.58 mmol) of 1-(bromomethyl)-2-chloro-3-(trifluoromethyl)benzene, 216 mg (75% of theory) of the title compound were obtained.

LC-MS (Method 1): $R_t$=1.11 min; m/z=540 (M+H)$^+$.

$^1$H NMR (400 MHz, DMSO-d$_6$): δ [ppm]=1.24 (t, 3H), 3.45 (s, 3H), 4.20 (q, 2H), 5.15 (s, 2H), 7.46 (d, 1H), 7.49-7.55 (m, 1H), 7.56-7.61 (m, 2H), 7.78-7.82 (m, 1H), 7.88-7.90 (m, 1H), 8.51 (s, 1H).

Example 50 ethyl 3-[3-fluoro-2-(trifluoromethyl)benzyl]-1-(3-methyl-2-oxo-2,3-dihydro-1,3-benzothiazol-6-yl)-2,4-dioxo-1,2,3,4-tetrahydropyrimidine-5-carboxylate

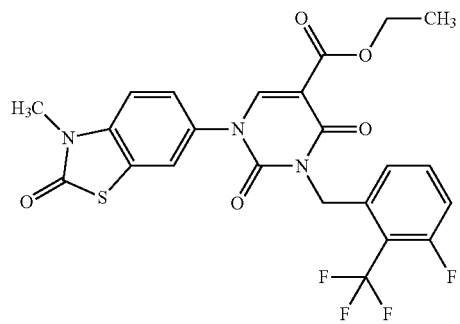 [SMILES: CCOC(=O)c1cn(-c2ccc3c(c2)sc(=O)n3C)c(=O)n(Cc2cccc(F)c2C(F)(F)F)c1=O]

The preparation and purification of the title compound were analogous to Example 37. Proceeding from 200 mg (0.53 mmol) of ethyl 1-(3-methyl-2-oxo-2,3-dihydro-1,3-benzothiazol-6-yl)-2,4-dioxo-1,2,3,4-tetrahydropyrimidine-5-carboxylate from Example 31A and 149 mg (0.58 mmol)

of 1-(bromomethyl)-3-fluoro-2-(trifluoromethyl)benzene, 241 mg (87% of theory) of the title compound were obtained.

LC-MS (Method 1): R$_t$=1.06 min; m/z=524 (M+H)$^+$.

$^1$H NMR (400 MHz, DMSO-d$_6$): δ [ppm]=1.23 (t, 3H), 3.45 (s, 3H), 4.20 (q, 2H), 5.19 (s, 2H), 7.21 (d, 1H), 7.41 (t, 1H), 7.47 (d, 1H), 7.57 (dd, 1H), 7.66 (q, 1H), 7.88 (d, 1H), 8.52 (s, 1H).

Example 51 ethyl 1-(3-methyl-2-oxo-2,3-dihydro-1,3-benzothiazol-6-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer)

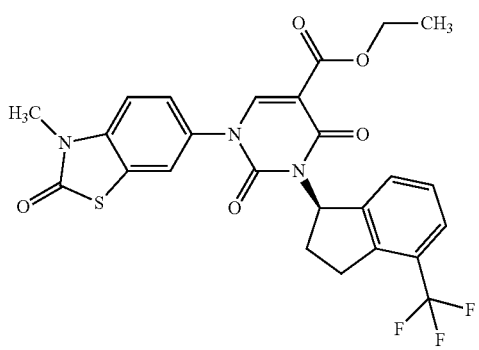 [SMILES: CCOC(=O)c1cn(-c2ccc3c(c2)sc(=O)n3C)c(=O)n([C@@H]2CCc3c2cccc3C(F)(F)F)c1=O]

8.00 g (23.03 mmol) of ethyl 1-(3-methyl-2-oxo-2,3-dihydro-1,3-benzothiazol-6-yl)-2,4-dioxo-1,2,3,4-tetrahydropyrimidine-5-carboxylate from Example 31A, 5.12 g (25.33 mmol) of (1S)-4-(trifluoromethyl)indan-1-ol from Example 14A and 10.27 g (39.15 mmol) of triphenylphosphine were initially charged in 317 ml of THF and 317 ml of DMF and cooled to 5° C. 7.25 ml (36.85 mmol) of diisopropyl azodicarboxylate were added in portions. The cooling bath was removed and the mixture was stirred at RT for 1 h. For workup, 200 ml of 1N hydrochloric acid were added and the mixture was stirred vigorously for 5 min. 400 ml of ethyl acetate were added. After stirring vigorously for 10 minutes, the organic phase was removed. The aqueous phase was extracted once more with 400 ml of ethyl acetate. The combined organic phases were washed twice with 100 ml each time of a saturated sodium carbonate solution, then with 100 ml of a saturated sodium chloride solution, then dried over sodium sulphate and concentrated on a rotary evaporator. The residue was admixed with 400 ml of MTBE and stirred while cooling with an ice bath for 30 min. The precipitated solid was filtered off with suction and washed twice with cold MTBE. The combined filtrates were concentrated and the residue was purified by means of flash chromatography (cyclohexane/ethyl acetate 1:2→1:4). The product thus obtained was recrystallized from acetonitrile and dried under high vacuum. This gave 6.3 g (50% of theory) of the title compound.

LC-MS (Method 1): R$_t$=1.18 min; m/z=532 (M+H)$^+$.

$^1$H NMR (400 MHz, CD$_2$Cl$_2$): δ [ppm]=1.31 (t, 3H), 2.37-2.49 (m, 1H), 2.53-2.65 (m, 1H), 3.08-3.20 (m, 1H), 3.40-3.52 (m, 1H), 3.45 (s, 3H), 4.29 (q, 2H), 6.56-6.68 (m, 1H), 7.09-7.18 (m, 1H), 7.25-7.36 (m, 3H), 7.44 (s, 1H), 7.47-7.54 (m, 1H), 8.29 (s, 1H).

Example 52 ethyl 3-[2-chloro-3-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylate

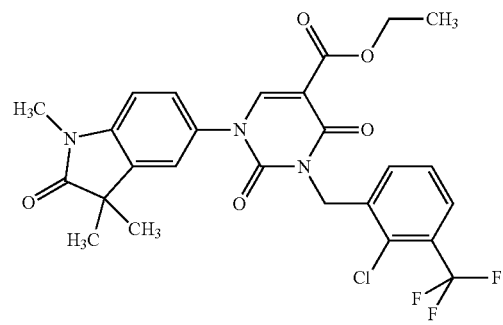 [SMILES: CCOC(=O)c1cn(-c2ccc3c(c2)C(C)(C)C(=O)N3C)c(=O)n(Cc2cccc(C(F)(F)F)c2Cl)c1=O]

The preparation and purification of the title compound were analogous to Example 37. Proceeding from 200 mg (0.56 mmol) of ethyl 2,4-dioxo-1-(1,3,3-trimethyl-2-oxo-2,3-dihydro-1H-indol-5-yl)-1,2,3,4-tetrahydropyrimidine-5-carboxylate from Example 59A and 168 mg (0.61 mmol) of 1-(bromomethyl)-2-chloro-3-(trifluoromethyl)benzene, 241 mg (77% of theory) of the title compound were obtained.

LC-MS (Method 1): R$_t$=1.11 min; in/z=550 (M+H)$^+$.

$^1$H NMR (400 MHz, DMSO-d$_6$): δ [ppm]=1.24 (t, 3H), 1.30 (s, 6H), 3.18 (s, 3H), 4.21 (q, 2H), 5.15 (s, 2H), 7.16 (d, 1H), 7.44-7.49 (m, 1H), 7.50-7.60 (m, 3H), 7.78-7.83 (m, 1H), 8.44 (s, 1H).

Example 53 ethyl 3-[2-methyl-3-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylate

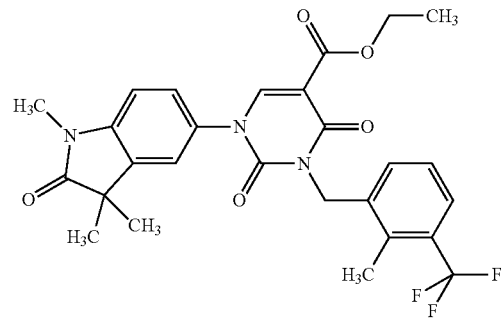 [SMILES: CCOC(=O)c1cn(-c2ccc3c(c2)C(C)(C)C(=O)N3C)c(=O)n(Cc2cccc(C(F)(F)F)c2C)c1=O]

The preparation and purification of the title compound were analogous to Example 37. Proceeding from 500 mg (1.39 mmol) of ethyl 2,4-dioxo-1-(1,3,3-trimethyl-2-oxo-2,3-dihydro-1H-indol-5-yl)-1,2,3,4-tetrahydropyrimidine-5-carboxylate from Example 59A and 389 mg (1.53 mmol) of 1-(bromomethyl)-2-methyl-3-(trifluoromethyl)benzene, 571 mg (77% of theory) of the title compound were obtained.

LC-MS (Method 1): R$_t$=1.11 min; in/z=530 (M+H)$^+$.

¹H NMR (400 MHz, DMSO-d₆): δ [ppm]=1.29 (s, 6H), 2.46 (s, 3H), 3.18 (s, 3H), 3.30 (s, 3H), 4.20 (q, 2H), 5.08 (s, 2H), 7.15 (d, 1H), 7.34-7.39 (m, 2H), 7.44-7.49 (m, 1H), 7.53-7.56 (m, 1H), 7.58-7.63 (m, 1H), 8.42 (s, 1H).

Example 54 ethyl 3-[3-chloro-2-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylate

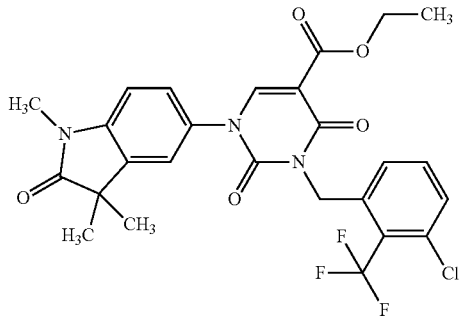 [SMILES: CCOC(=O)c1cn(-c2ccc3c(c2)C(C)(C)C(=O)N3C)c(=O)n(Cc2cccc(Cl)c2C(F)(F)F)c1=O]

153 mg (0.42 mmol) of ethyl 2,4-dioxo-1-(1,3,3-trimethyl-2-oxo-2,3-dihydro-1H-indol-5-yl)-1,2,3,4-tetrahydropyrimidine-5-carboxylate from Example 59A were reacted analogously to Example 37 with 198 mg (65% purity, 0.47 mmol) of 1-(bromomethyl)-3-chloro-2-(trifluoromethyl)benzene (preparation: see WO 2004/52858, page 149, Example 176). For workup, the reaction mixture cooled to RT was admixed with water and extracted twice with ethyl acetate. The combined organic phases were washed with saturated sodium chloride solution, dried over magnesium sulphate and concentrated. The residue was stirred with MTBE, and the precipitated solid was filtered off with suction, washed with MTBE and dried at the high-vacuum pump. This gave 109 mg (46% of theory) of the title compound.

LC-MS (Method 1): R$_t$=1.14 min; m/z=550 (M+H)⁺.

¹H NMR (400 MHz, DMSO-d₆): δ [ppm]=1.23 (t, 3H), 1.29 (s, 6H), 3.18 (s, 3H), 4.20 (q, 2H), 5.21 (br.s, 2H), 7.16 (d, 1H), 7.30-7.35 (m, 1H), 7.45 (dd, 1H), 7.53 (d, 1H), 7.57-7.66 (m, 2H), 8.45 (s, 1H).

Example 55 ethyl 3-[3-fluoro-2-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylate

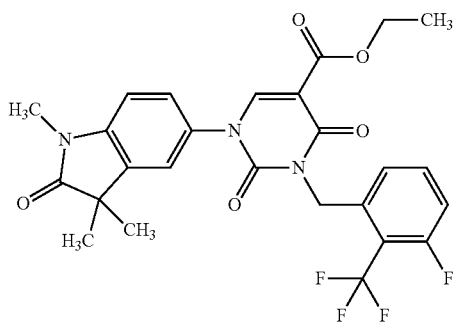 [SMILES: CCOC(=O)c1cn(-c2ccc3c(c2)C(C)(C)C(=O)N3C)c(=O)n(Cc2cccc(F)c2C(F)(F)F)c1=O]

The preparation and purification of the title compound were analogous to Example 37. Proceeding from 200 mg (0.56 mmol) of ethyl 2,4-dioxo-1-(1,3,3-trimethyl-2-oxo-2,3-dihydro-1H-indol-5-yl)-1,2,3,4-tetrahydropyrimidine-5-carboxylate from Example 59A and 158 mg (0.61 mmol) of 1-(bromomethyl)-3-fluoro-2-(trifluoromethyl)benzene, 247 mg (80% of theory) of the title compound were obtained.

LC-MS (Method 1): R$_t$=1.06 min; m/z=534 (M+H)⁺.

¹H NMR (400 MHz, DMSO-d₆): δ [ppm]=1.23 (t, 3H), 1.29 (s, 6H), 3.18 (s, 3H), 4.20 (q, 2H), 5.20 (s, 2H), 7.13-7.22 (m, 2H), 7.37-7.48 (m, 2H), 7.53 (d, 1H), 7.63-7.70 (m, 1H), 8.45 (s, 1H).

Example 56 ethyl 3-(2,3-dichlorobenzyl)-2,4-dioxo-1-(1,3,3-trimethyl-2-oxo-2,3-dihydro-1H-indol-5-yl)-1,2,3,4-tetrahydropyrimidine-5-carboxylate

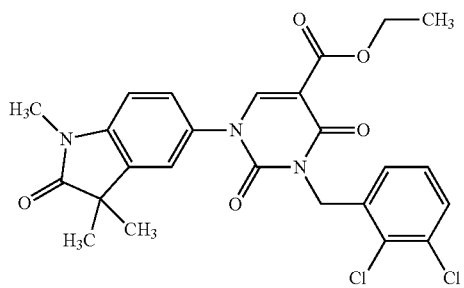 [SMILES: CCOC(=O)c1cn(-c2ccc3c(c2)C(C)(C)C(=O)N3C)c(=O)n(Cc2cccc(Cl)c2Cl)c1=O]

The preparation and purification of the title compound were analogous to Example 37. Proceeding from 200 mg (0.56 mmol) of ethyl 2,4-dioxo-1-(1,3,3-trimethyl-2-oxo-2,3-dihydro-1H-indol-5-yl)-1,2,3,4-tetrahydropyrimidine-5-carboxylate from Example 59A and 120 mg (0.61 mmol) of 1,2-dichloro-3-(chloromethyl)benzene, 230 mg (78% of theory) of the title compound were obtained.

LC-MS (Method 1): R$_t$=1.09 min; m/z=520 (M+H)⁺.

¹H NMR (400 MHz, DMSO-d₆): δ [ppm]=1.23 (t, 3H), 1.29 (s, 6H), 3.18 (s, 3H), 4.20 (q, 2H), 7.15 (d, 1H), 7.22 (d, 1H), 7.33 (t, 1H), 7.46 (dd, 1H), 7.54 (d, 1H), 7.58 (d, 1H), 8.43 (s, 1H).

Example 57 ethyl 2,4-dioxo-3-[4-(trifluoromethyl)-2,3-dihydro-1H-inden-1-yl]-1-(1,3,3-trimethyl-2-oxo-2,3-dihydro-1H-indol-5-yl)-1,2,3,4-tetrahydropyrimidine-5-carboxylate (Racemate)

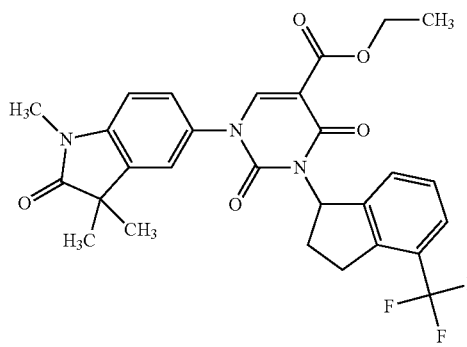

The preparation and purification of the title compound were analogous to Example 8, with a reaction time of 2 days. Proceeding from 190 mg (0.51 mmol) of ethyl 2,4-dioxo-3-[4-(trifluoromethyl)-2,3-dihydro-1H-inden-1-yl]-1,2,3,4-tetrahydropyrimidine-5-carboxylate from Example 21A and 310 mg (1.03 mmol) of 1,3,3-trimethyl-5-(4,4,5,5-tetramethyl-1,3,2-dioxaborolan-2-yl)-1,3-dihydro-2H-indol-2-one from Example 68A, after additional purification by means of flash chromatography (dichloromethane/methanol 98:2), a total of 169 mg (60% of theory) of the title compound were obtained.

LC-MS (Method 1): $R_t$=1.14 min; m/z=542 (M+H)$^+$.

$^1$H NMR (400 MHz, DMSO-d$_6$): δ [ppm]=1.20-1.25 (m, 3H), 1.29 (s, 6H), 2.38-2.43 (m, 1H), 2.44-2.48 (m, 1H, partly concealed by DMSO signal), 3.03-3.13 (m, 1H), 3.17 (s, 3H), 3.23-3.29 (m, 1H, partly concealed by water signal), 4.18 (q, 2H), 6.33-6.56 (m, 1H), 7.13 (d, 1H), 7.32-7.45 (m, 2H), 7.45-7.57 (m, 3H), 8.33 (s, 1H).

Example 58 ethyl 2,4-dioxo-3-[4-(trifluoromethyl)-2,3-dihydro-1H-inden-1-yl]-1-(1,3,3-trimethyl-2-oxo-2,3-dihydro-1H-indol-5-yl)-1,2,3,4-tetrahydropyrimidine-5-carboxylate (R enantiomer)

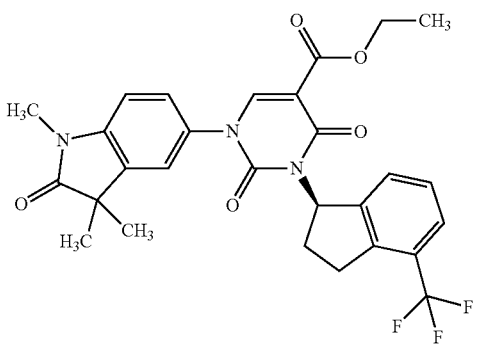 [SMILES: CCOC(=O)c1cn(-c2ccc3c(c2)C(C)(C)C(=O)N3C)c(=O)n([C@@H]2CCc3c2cccc3C(F)(F)F)c1=O]

700 mg (1.96 mmol) of the compound from Example 59A, 515 mg (2.55 mmol) of (S)-4-trifluoromethylindan-1-ol from Example 14A and 1.54 g (5.88 mmol) of triphenylphosphine were initially charged in 20 ml of THF and 20 ml of DMF at −15° C., and 1.12 ml (5.68 mmol) of diisopropyl azodicarboxylate were added dropwise. The reaction mixture was stirred at RT for 2 h. For workup, the mixture was cooled again to −15° C., admixed with 30 ml of 1N hydrochloric acid, stirred at RT for 10 min and then extracted with ethyl acetate. The organic phase was washed twice with 1N hydrochloric acid, once with a 1M sodium carbonate solution and once with a saturated sodium chloride solution, then dried over sodium sulphate and concentrated on a rotary evaporator. The residue was purified by preparative HPLC (Method 7). This gave 725 mg (68% of theory) of the title compound.

LC-MS (Method 5): $R_t$=1.18 min; m/z=542 (M+H)$^+$.

$^1$H NMR (400 MHz, CD$_2$Cl$_2$): δ [ppm]=1.31 (t, 3H), 1.35 (s., 3H), 1.36 (s., 3H), 2.37-2.50 (m, 1H), 2.58 (dtd, 1H), 3.08-3.18 (m, 1H), 3.20 (s, 3H), 3.47 (br.s, 1H), 4.29 (q, 2H), 6.54-6.68 (m, 1H), 6.92 (d, 1H), 7.16 (br.s, 1H), 7.21 (d, 1H), 7.26-7.36 (m, 2H), 7.49 (d, 1H), 8.29 (s, 1H).

Example 59 ethyl 3-[2-methyl-3-(trifluoromethyl)benzyl]-2,4-dioxo-1-(1,3,3-trimethyl-2-oxo-2,3-dihydro-1H-indol-6-yl)-1,2,3,4-tetrahydropyrimidine-5-carboxylate

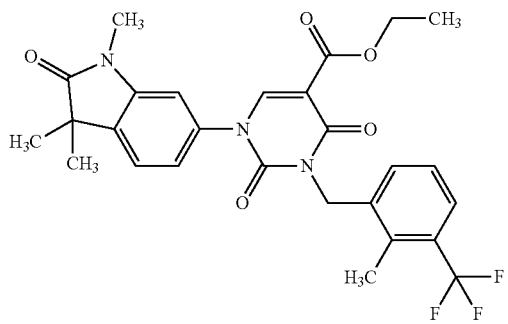 [SMILES: CCOC(=O)c1cn(-c2ccc3c(c2)N(C)C(=O)C3(C)C)c(=O)n(Cc2cccc(C(F)(F)F)c2C)c1=O]

125 mg (0.35 mmol) of ethyl 2,4-dioxo-1-(1,3,3-trimethyl-2-oxo-2,3-dihydro-1H-indol-6-yl)-1,2,3,4-tetrahydropyrimidine-5-carboxylate from Example 64A were initially charged in 3 ml of DMF. 97 mg (0.38 mmol) of 1-(bromomethyl)-2-methyl-3-(trifluoromethyl)benzene, 97 mg (0.70 mmol) of potassium carbonate and 6 mg (0.04 mmol) of potassium iodide were added and the reaction mixture was stirred at 60° C. for 2 h. After cooling to RT, water was added to the mixture. The precipitate was filtered off, washed with a little water and cyclohexane, and dried in a drying cabinet at 50° C. This gave 134 mg (90% purity, 65% of theory) of the title compound.

LC-MS (Method 1): $R_t$=1.16 min; m/z=530 (M+H)$^+$.

$^1$H NMR (400 MHz, DMSO-d$_6$): δ [ppm]=1.24 (t, 3H), 1.30 (s, 6H), 2.47 (s, 3H), 3.14 (s, 3H), 4.20 (q, 2H), 5.09 (s, 2H), 7.22 (dd, 1H), 7.27 (d, 1H), 7.31-7.41 (m, 2H), 7.51 (d, 1H), 7.60 (d, 1H), 8.47 (s, 1H).

Example 60 ethyl 3-[2-chloro-3-(trifluoromethyl)benzyl]-2,4-dioxo-1-(1,3,3-trimethyl-2-oxo-2,3-dihydro-1H-indol-6-yl)-1,2,3,4-tetrahydropyrimidine-5-carboxylate

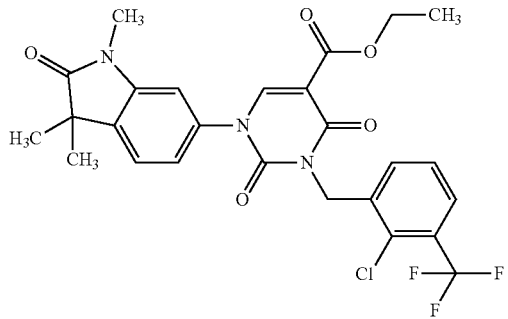 [SMILES: CCOC(=O)c1cn(-c2ccc3c(c2)N(C)C(=O)C3(C)C)c(=O)n(Cc2cccc(C(F)(F)F)c2Cl)c1=O]

The preparation and purification of the title compound were analogous to Example 59. Proceeding from 125 mg (0.35 mmol) of ethyl 2,4-dioxo-1-(1,3,3-trimethyl-2-oxo-2,3-dihydro-1H-indol-6-yl)-1,2,3,4-tetrahydropyrimidine-5-carboxylate from Example 64A and 105 mg (0.38 mmol) of 1-(bromomethyl)-2-chloro-3-(trifluoromethyl)benzene, 182 mg (85% of theory) of the title compound were obtained.

LC-MS (Method 1): $R_t$=1.16 min; m/z=550 (M+H)$^+$.

$^1$H NMR (400 MHz, DMSO-d$_6$): δ [ppm]=1.24 (t, 3H), 1.31 (s, 6H), 3.15 (s, 3H), 4.20 (q, 2H), 5.16 (s, 2H), 7.22 (dd, 1H), 7.26 (d, 1H), 7.50-7.55 (m, 2H), 7.58 (d, 1H), 7.80 (d, 1H), 8.49 (s, 1H).

Example 61 ethyl 3-[3-chloro-2-(trifluoromethyl)benzyl]-2,4-dioxo-1-(1,3,3-trimethyl-2-oxo-2,3-dihydro-1H-indol-6-yl)-1,2,3,4-tetrahydropyrimidine-5-carboxylate

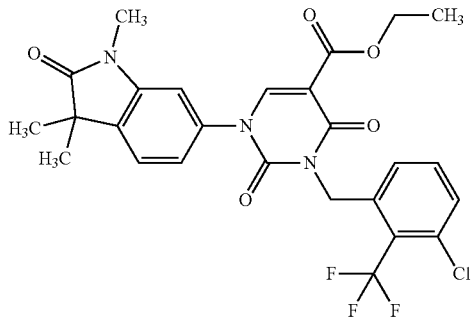 [SMILES: CCOC(=O)c1cn(-c2ccc3c(c2)N(C)C(=O)C3(C)C)c(=O)n(Cc2cccc(Cl)c2C(F)(F)F)c1=O]

125 mg (0.35 mmol) of ethyl 2,4-dioxo-1-(1,3,3-trimethyl-2-oxo-2,3-dihydro-1H-indol-6-yl)-1,2,3,4-tetrahydropyrimidine-5-carboxylate from Example 64A were initially charged in DMF (3 ml). 161 mg (65% purity, 0.38 mmol) of 1-(bromomethyl)-3-chloro-2-(trifluoromethyl)benzene, 96 mg (0.70 mmol) of potassium carbonate and 6 mg (0.03 mmol) of potassium iodide were added. Subsequently, the reaction mixture was left to stir at 60° C. for 2 h. The mixture cooled to RT was admixed with water and extracted twice with ethyl acetate. The combined organic phases were washed with a saturated sodium chloride solution, dried over magnesium sulphate and concentrated. The residue was stirred with cyclohexane/ethyl acetate, and the precipitated solid was filtered off with suction and dried under reduced pressure. This gave 133 mg (62% of theory) of the title compound.

LC-MS (Method 1): R$_t$=1.16 min; m/z=550 (M+H)$^+$.

$^1$H NMR (400 MHz, DMSO-d$_6$): δ [ppm]=1.24 (t, 3H), 1.30 (s, 6H), 3.15 (s, 3H), 4.20 (q, 2H), 5.22 (br.s, 2H), 7.21 (d, 1H), 7.25 (s, 1H), 7.33 (d, 1H), 7.51 (d, 1H), 7.56-7.68 (m, 2H), 8.50 (s, 1H).

Example 62 ethyl 3-[2-chloro-3-(trifluoromethyl)benzyl]-1-(3-hydroxy-1,3-dimethyl-2-oxo-2,3-dihydro-1H-indol-5-yl)-2,4-dioxo-1,2,3,4-tetrahydropyrimidine-5-carboxylate (Racemate)

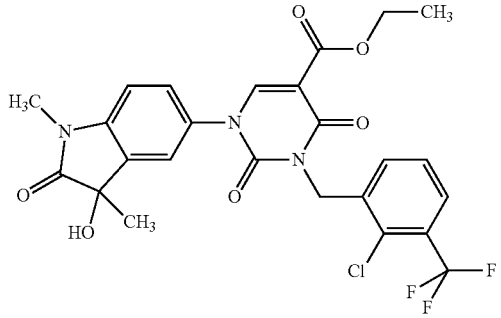 [SMILES: CCOC(=O)c1cn(-c2ccc3c(c2)C(C)(O)C(=O)N3C)c(=O)n(Cc2cccc(C(F)(F)F)c2Cl)c1=O]

The preparation and purification of the title compound were analogous to Example 1. The reaction time was 1 h. Proceeding from 105 mg (0.29 mmol) of ethyl 1-(3-hydroxy-1,3-dimethyl-2-oxo-2,3-dihydro-1H-indol-5-yl)-2,4-dioxo-1,2,3,4-tetrahydropyrimidine-5-carboxylate from Example 72A and 88 mg (0.32 mmol) of 1-(bromomethyl)-2-chloro-3-(trifluoromethyl)benzene, 133 mg (74% of theory) of the title compound were obtained.

LC-MS (Method 1): R$_t$=0.98 min; m/z=552 (M+H)$^+$.

$^1$H NMR (400 MHz, DMSO-d$_6$): δ [ppm]=1.23 (t, 3H), 1.41 (s, 3H), 3.14 (s, 3H), 4.21 (q, 2H), 5.14 (s, 2H), 6.13 (s, 1H), 7.14 (d, 1H), 7.47-7.57 (m, 3H), 7.58-7.62 (m, 1H), 7.78-7.82 (m, 1H), 8.40 (s, 1H).

Example 63 ethyl 1-[3-hydroxy-1-methyl-2-oxo-3-(trifluoromethyl)-2,3-dihydro-1H-indol-5-yl]-3-[2-methyl-3-(trifluoromethyl)benzyl]-2,4-dioxo-1,2,3,4-tetrahydropyrimidine-5-carboxylate (Racemate)

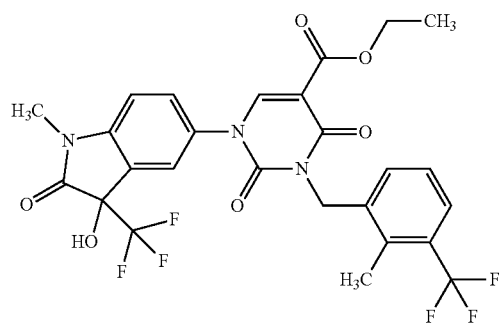 [SMILES: CCOC(=O)c1cn(-c2ccc3c(c2)C(O)(C(F)(F)F)C(=O)N3C)c(=O)n(Cc2cccc(C(F)(F)F)c2C)c1=O]

The preparation and purification of the title compound were analogous to Example 1. The reaction time was 45 min. Proceeding from 200 mg (0.48 mmol) of ethyl 1-[3-hydroxy-1-methyl-2-oxo-3-(trifluoromethyl)-2,3-dihydro-1H-indol-5-yl]-2,4-dioxo-1,2,3,4-tetrahydropyrimidine-5-carboxylate from Example 69A and 134 mg (0.53 mmol) of 1-(bromomethyl)-2-methyl-3-(trifluoromethyl)benzene, after additional purification by means of HPLC (Method 8), 76 mg (26% of theory) of the title compound were obtained.

LC-MS (Method 5): R$_t$=1.11 min; in/z=585 (M+H)$^+$.

$^1$H NMR (400 MHz, DMSO-d$_6$): δ [ppm]=1.24 (t, 3H), 2.46 (s, 3H), 3.22 (s, 3H), 4.21 (q, 2H), 5.07 (s, 2H), 7.30 (d, 1H), 7.35 (t, 1H), 7.41 (d, 1H), 7.60 (d, 1H), 7.67-7.71 (m, 1H), 7.73 (s, 1H), 7.92 (s, 1H), 8.40 (s, 1H).

Example 64 ethyl 1-[3-fluoro-1-methyl-2-oxo-3-(trifluoromethyl)-2,3-dihydro-1H-indol-5-yl]-3-[2-methyl-3-(trifluoromethyl)benzyl]-2,4-dioxo-1,2,3,4-tetrahydropyrimidine-5-carboxylate (Racemate)

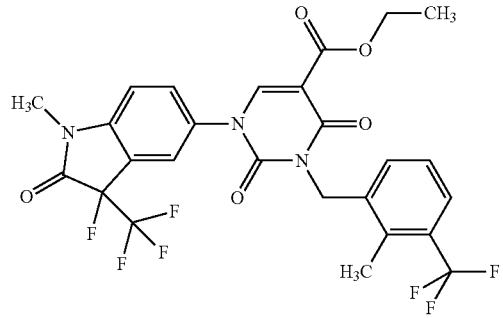 [SMILES: CCOC(=O)c1cn(-c2ccc3c(c2)C(F)(C(F)(F)F)C(=O)N3C)c(=O)n(Cc2cccc(C(F)(F)F)c2C)c1=O]

The preparation and purification of the title compound were analogous to Example 1. The reaction time was 45 min. Proceeding from 90 mg (0.21 mmol) of ethyl 1-[3-fluoro-1-methyl-2-oxo-3-(trifluoromethyl)-2,3-dihydro-1H-indol-5-yl]-2,4-dioxo-1,2,3,4-tetrahydropyrimidine-5-carboxylate from Example 73A and 60 mg (0.23 mmol) of 1-(bromomethyl)-2-methyl-3-(trifluoromethyl)benzene, after additional purification by means of HPLC (Method 8), 97 mg (72% of theory) of the title compound were obtained.

LC-MS (Method 5): $R_t$=1.24 min; m/z=588 (M+H)$^+$.

$^1$H NMR (400 MHz, DMSO-d$_6$): δ [ppm]=1.24 (t, 3H), 2.46 (s, 3H), 3.27 (s, 3H), 4.21 (q, 2H), 5.07 (s, 2H), 7.32-7.37 (m, 1H), 7.38-7.45 (m, 2H), 7.60 (d, 1H), 7.84-7.88 (m, 1H), 7.96 (s, 1H), 8.53 (s, 1H).

Example 65 ethyl 3-[2-chloro-3-(trifluoromethyl)benzyl]-1-(1'-methyl-2'-oxo-1',2'-dihydrospiro[cyclopropane-1,3'-indole]-5'-yl)-2,4-dioxo-1,2,3,4-tetrahydropyrimidine-5-carboxylate

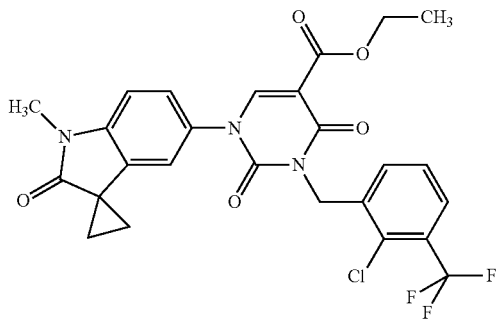 [SMILES: CCOC(=O)c1cn(-c2ccc3c(c2)C2(CC2)C(=O)N3C)c(=O)n(Cc2cccc(C(F)(F)F)c2Cl)c1=O]

The preparation and purification of the title compound were analogous to Example 1. The reaction time was 1 h. Proceeding from 120 mg (0.33 mmol) of ethyl 1-(1'-methyl-2'-oxo-1',2'-dihydrospiro[cyclopropane-1,3'-indole]-5'-yl)-2,4-dioxo-1,2,3,4-tetrahydropyrimidine-5-carboxylate from Example 63A and 101 mg (0.37 mmol) of 1-(bromomethyl)-2-chloro-3-(trifluoromethyl)benzene, 177 mg (90% of theory) of the title compound were obtained.

LC-MS (Method 1): $R_t$=1.12 min; m/z=548 (M+H)$^+$.

$^1$H NMR (400 MHz, DMSO-d$_6$): δ [ppm]=1.23 (t, 3H), 1.55-1.60 (m, 2H), 1.64-1.69 (m, 2H), 3.26 (s, 3H), 4.20 (q, 2H), 5.14 (s, 2H), 7.18-7.24 (m, 2H), 7.44 (dd, 1H), 7.49-7.58 (m, 2H), 7.78-7.82 (m, 1H), 8.44 (s, 1H).

Example 66 ethyl 1-(1'-methyl-2'-oxo-1',2'-dihydrospiro[cyclopropane-1,3'-indole]-5'-yl)-3-[2-methyl-3-(trifluoromethyl)-benzyl]-2,4-dioxo-1,2,3,4-tetrahydropyrimidine-5-carboxylate

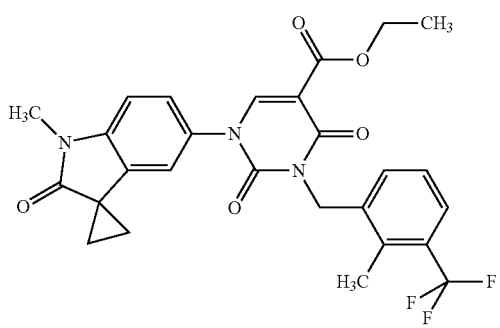 [SMILES: CCOC(=O)c1cn(-c2ccc3c(c2)C2(CC2)C(=O)N3C)c(=O)n(Cc2cccc(C(F)(F)F)c2C)c1=O]

The preparation and purification of the title compound were analogous to Example 1. The reaction time was 1.5 h. Proceeding from 120 mg (0.33 mmol) of ethyl 1-(1'-methyl-2'-oxo-1',2'-dihydrospiro[cyclopropane-1,3'-indole]-5'-yl)-2,4-dioxo-1,2,3,4-tetrahydropyrimidine-5-carboxylate from Example 63A and 94 mg (0.37 mmol) of 1-(bromomethyl)-2-methyl-3-(trifluoromethyl)benzene, 140 mg (77% of theory) of the title compound were obtained.

LC-MS (Method 1): $R_t$=1.12 min; m/z=528 (M+H)$^+$.

$^1$H NMR (400 MHz, DMSO-d$_6$): δ [ppm]=1.23 (t, 3H), 1.55-1.60 (m, 2H), 1.64-1.69 (m, 2H), 2.46 (s, partly concealed by DMSO signal), 3.26 (s, 3H), 4.19 (q, 2H), 5.07 (s, 2H), 7.17-7.25 (m, 2H), 7.32-7.37 (m, 2H), 7.44 (dd, 1H), 7.57-7.63 (m, 1H), 8.42 (s, 1H).

Example 67 ethyl 1-(1'-methyl-2'-oxo-1',2'-dihydrospiro[cyclopropane-1,3'-indole]-5'-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer)

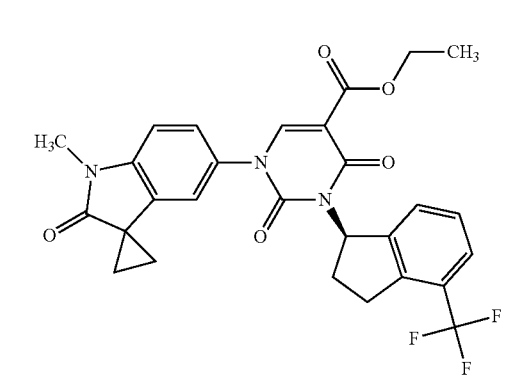 [SMILES: CCOC(=O)c1cn(-c2ccc3c(c2)C2(CC2)C(=O)N3C)c(=O)n([C@@H]2CCc3c2cccc3C(F)(F)F)c1=O]

8.00 g (22.5 mmol) of ethyl 1-(1'-methyl-2'-oxo-1',2'-dihydrospiro[cyclopropane-1,3'-indole]-5'-yl)-2,4-dioxo-1,2,3,4-tetrahydropyrimidine-5-carboxylate from Example 63A, 5.46 g (27.0 mmol) of (1S)-4-(trifluoromethyl)indan-1-ol (from Example 14A) and 10.0 g (38.26 mmol) of triphenylphosphine were initially charged at RT under argon in THF/DMF 1:1 (215 ml). To this mixture were added dropwise, while stirring, 7.09 ml (36.02 mmol) of diisopropyl azodicarboxylate. After 1 h, an additional 1.2 g (4.51 mmol) of triphenylphosphine and 0.89 ml (4.51 mmol) of diisopropyl azodicarboxylate were added. The reaction mixture was stirred at RT for a further 1.5 h. While cooling with ice, the mixture was admixed with 10 ml 1M hydrochloric acid, stirred for 15 min, then extracted with ethyl acetate. The combined organic phases were washed twice with 1M hydrochloric acid, then twice with a saturated sodium carbonate solution and once with a saturated sodium chloride solution, dried over sodium sulphate and concentrated on a rotary evaporator. The residue was stirred with 100 ml of MTBE and left to stand overnight. The solid formed was filtered off and discarded. The filtrate was concentrated on a rotary evaporator. The residue was taken up in a little dichloromethane and purified by means of flash chromatography (eluent: cyclohexane/ethyl acetate 1:2). This gave 7.81 g (59% of theory, 92% purity by NMR) of the title compound.

LC-MS (Method 4): $R_t$=2.49 min; m/z=540 (M+H)$^+$.

$^1$H NMR (400 MHz, CD$_2$Cl$_2$): δ [ppm]=1.31 (t, 3H), 1.54-1.61 (m, 2H), 1.69-1.81 (m, 2H), 2.35-2.49 (m, 1H), 2.51-2.66 (m, 1H), 3.05-3.21 (m, 1H), 3.28 (s, 3H), 3.39-3.54 (m, 1H), 4.28 (q, 2H), 6.54-6.67 (m, 1H), 6.80 (br.s, 1H), 6.97 (d, 1H), 7.19 (d, 1H), 7.24-7.36 (m, 2H), 7.49 (d, 1H), 8.26 (s, 1H).

Specific optical rotation: $\alpha_D^{20}$=+131.7°, (chloroform, c=0.405 g/100 ml).

Example 68 ethyl 3-[2-chloro-3-(trifluoromethyl)benzyl]-1-(3,3-dimethyl-2-oxo-2,3-dihydro-1H-indol-6-yl)-2,4-dioxo-1,2,3,4-tetrahydropyrimidine-5-carboxylate

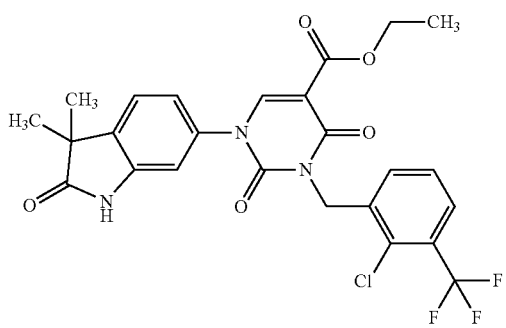 [SMILES: CCOC(=O)c1cn(-c2ccc3c(c2)NC(=O)C3(C)C)c(=O)n(Cc2cccc(C(F)(F)F)c2Cl)c1=O]

To a solution of 629 mg (1.83 mmol) of ethyl 1-(3,3-dimethyl-2-oxo-2,3-dihydro-1H-indol-5-yl)-2,4-dioxo-1,2,3,4-tetrahydropyrimidine-5-carboxylate from Example 65A in 10 ml of DMF were added 551 mg (2.02 mmol) of 1-(bromomethyl)-2-chloro-3-(trifluoromethyl)benzene, 506 mg (3.66 mmol) of potassium carbonate and 30 mg (0.18 mmol) of potassium iodide, and the mixture was stirred at 60° C. for 1.5 h. For workup, the reaction mixture was admixed with water, and the precipitate formed was filtered off with suction and washed with water. The crude product thus obtained was purified by means of flash silica gel chromatography (di-chloromethane/methanol, 98:2). This gave 371 mg (88% purity, 33% of theory) of the target compound.

LC-MS (Method 1): $R_t$=1.11 min; MS (ESIpos): m/z=536 (M+H)$^+$.

$^1$H NMR (400 MHz, DMSO-d$_6$): δ [ppm]=1.23 (s, 3H), 1.28 (s, 6H), 4.19 (q, 2H), 5.13 (s, 2H), 7.04-7.07 (m, 1H), 7.11-7.15 (m, 1H), 7.44-7.47 (m, 1H), 7.48-7.54 (m, 1H), 7.59-7.63 (m, 1H), 7.77-7.82 (m, 1H), 8.47 (s, 1H), 10.61 (s, 1H).

Example 69 ethyl 1-(1-acetyl-3,3-dimethyl-2,3-dihydro-1H-indol-6-yl)-3-[2-chloro-3-(trifluoromethyl)benzyl]-2,4-dioxo-1,2,3,4-tetrahydropyrimidine-5-carboxylate

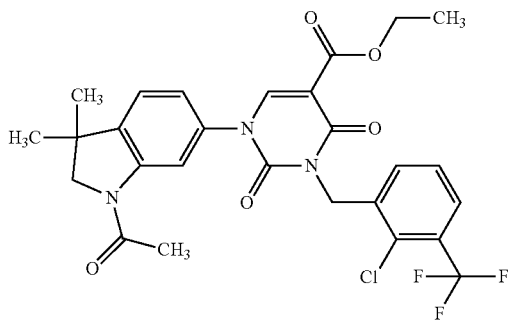 [SMILES: CCOC(=O)c1cn(-c2ccc3c(c2)N(C(C)=O)CC3(C)C)c(=O)n(Cc2cccc(C(F)(F)F)c2Cl)c1=O]

The preparation and purification of the title compound were analogous to Example 1. The reaction time was 2 h. Proceeding from 200 mg (0.53 mmol) of ethyl 1-(1-acetyl-3,3-dimethyl-2,3-dihydro-1H-indol-6-yl)-2,4-dioxo-1,2,3,4-tetrahydropyrimidine-5-carboxylate from Example 66A and 162 mg (0.59 mmol) of 1-(bromomethyl)-2-chloro-3-(trifluoromethyl)benzene, 228 mg (71% of theory) of the title compound were obtained.

LC-MS (Method 1): $R_t$=1.18 min; m/z=564 (M+H)$^+$.

$^1$H NMR (400 MHz, DMSO-d$_6$): δ [ppm]=1.23 (t, 3H), 1.34 (s, 6H), 2.18 (s, 3H), 3.94 (s, 2H), 4.19 (q, 2H), 5.12 (s, 2H), 7.19 (dd, 1H), 7.40 (d, 1H), 7.50 (t, 1H), 7.60 (d, 1H), 7.79 (d, 1H), 8.14 (s, 1H), 8.41 (s, 1H).

Example 70 ethyl 1-(1-acetyl-3,3-dimethyl-2,3-dihydro-1H-indol-6-yl)-3-[2-methyl-3-(trifluoromethyl)benzyl]-2,4-dioxo-1,2,3,4-tetrahydropyrimidine-5-carboxylate

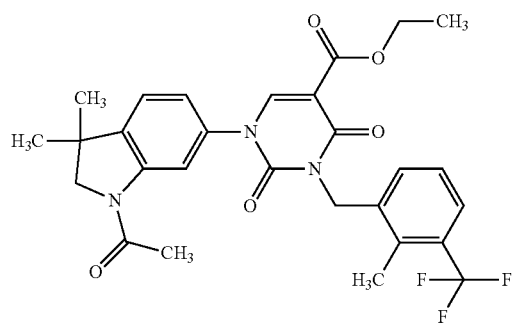 [SMILES: CCOC(=O)c1cn(-c2ccc3c(c2)N(C(C)=O)CC3(C)C)c(=O)n(Cc2cccc(C(F)(F)F)c2C)c1=O]

The preparation and purification of the title compound were analogous to Example 1. The reaction time was 2 h. Proceeding from 200 mg (0.53 mmol) of ethyl 1-(1-acetyl-3,3-dimethyl-2,3-dihydro-1H-indol-6-yl)-2,4-dioxo-1,2,3,4-tetrahydropyrimidine-5-carboxylate from Example 66A and 149 mg (0.59 mmol) of 1-(bromomethyl)-2-methyl-3-(trifluoromethyl)benzene, 253 mg (84% of theory) of the title compound were obtained.

LC-MS (Method 1): $R_t$=1.22 min; m/z=544 (M+H)$^+$.

$^1$H NMR (400 MHz, DMSO-d$_6$): δ [ppm]=1.23 (t, 3H), 1.34 (s, 6H), 2.18 (s, 3H), 2.45 (s, 3H), 3.93 (s, 2H), 4.19 (q, 2H), 5.06 (s, 2H), 7.19 (dd, 1H), 7.33 (t, 1H), 7.40 (d, 2H), 7.59 (d, 1H), 8.13 (d, 1H), 8.39 (s, 1H).

Example 71 ethyl 3-[2-chloro-3-(trifluoromethyl)benzyl]-1-(1-methyl-1H-benzotriazol-5-yl)-2,4-dioxo-1,2,3,4-tetrahydropyrimidine-5-carboxylate

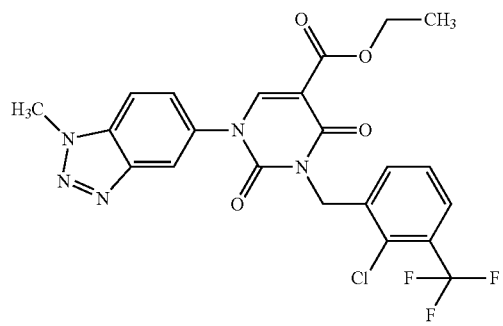 [SMILES: CCOC(=O)c1cn(-c2ccc3c(c2)nnn3C)c(=O)n(Cc2cccc(C(F)(F)F)c2Cl)c1=O]

162 mg (0.51 mmol) of ethyl 1-(1-methyl-1H-benzotriazol-5-yl)-2,4-dioxo-1,2,3,4-tetrahydropyrimidine-5-carboxylate from Example 74A were initially charged in 6.5 ml of DMF. 155 mg (0.56 mmol) of 1-(bromomethyl)-2-chloro-3-(trifluoromethyl)benzene, 142 mg (1.03 mmol) of potassium carbonate and 9 mg (52 µmol) of potassium iodide were added and the reaction mixture was stirred at 60° C. for 5 h. After cooling to RT, water was added to the mixture. The precipitate was filtered off, washed with a little water and MTBE, and dried in a drying cabinet at 50° C. This gave 149 mg (95% purity, 54% of theory) of the title compound.

LC-MS (Method 1): $R_t$=1.03 min; m/z=508 (M+H)$^+$.

$^1$H NMR (400 MHz, DMSO-$d_6$): δ [ppm]=1.23 (t, 3H), 4.21 (q, 2H), 4.37 (s, 3H), 5.17 (s, 2H), 7.51-7.57 (m, 1H), 7.61-7.65 (m, 1H), 7.71-7.75 (m, 1H), 7.79-7.83 (m, 1H), 7.99-8.02 (m, 1H), 8.31-8.33 (m, 1H), 8.61 (s, 1H).

Example 72 ethyl 1-(1-methyl-1H-benzotriazol-5-yl)-3-[2-methyl-3-(trifluoromethyl)benzyl]-2,4-dioxo-1,2,3,4-tetrahydropyrimidine-5-carboxylate

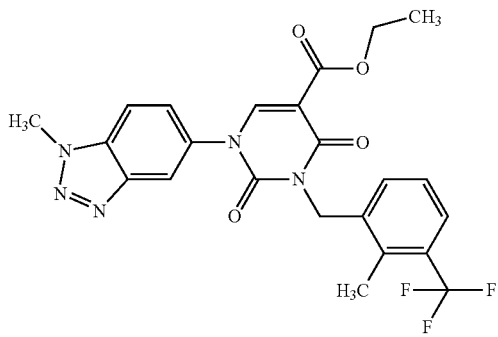 [SMILES: CCOC(=O)c1cn(-c2ccc3c(c2)nnn3C)c(=O)n(Cc2cccc(C(F)(F)F)c2C)c1=O]

The preparation and purification of the title compound were analogous to Example 71. Proceeding from 162 mg (0.51 mmol) of ethyl 1-(1-methyl-1H-benzotriazol-5-yl)-2,4-dioxo-1,2,3,4-tetrahydropyrimidine-5-carboxylate from Example 74A and 143 mg (0.56 mmol) of 1-(bromomethyl)-2-methyl-3-(trifluoromethyl)benzene, 152 mg (59% of theory) of the title compound were obtained.

LC-MS (Method 1): $R_t$=1.02 min; m/z=488 (M+H)$^+$.

$^1$H NMR (400 MHz, DMSO-$d_6$): δ [ppm]=1.23 (t, 3H), 2.47 (s, partly concealed by DMSO signal), 4.20 (q, 2H), 4.37 (s, 3H), 5.10 (s, 2H), 7.33-7.39 (m, 1H), 7.40-7.45 (m, 1H), 7.58-7.64 (m, 1H), 7.73 (dd, 1H), 8.00 (d, 1H), 8.32-8.34 (m, 1H), 8.58 (s, 1H).

Example 73 ethyl 3-(2,3-dichlorobenzyl)-1-(1-methyl-1H-benzotriazol-5-yl)-2,4-dioxo-1,2,3,4-tetrahydropyrimidine-5-carboxylate

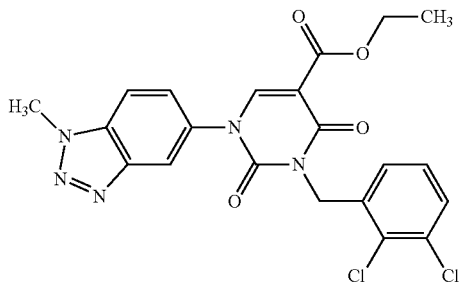 [SMILES: CCOC(=O)c1cn(-c2ccc3c(c2)nnn3C)c(=O)n(Cc2cccc(Cl)c2Cl)c1=O]

The preparation and purification of the title compound were analogous to Example 71. Proceeding from 162 mg (0.51 mmol) of ethyl 1-(1-methyl-1H-benzotriazol-5-yl)-2,4-dioxo-1,2,3,4-tetrahydropyrimidine-5-carboxylate from Example 74A and 136 mg (0.56 mmol) of 2,3-dichlorobenzyl bromide, 188 mg (74% of theory) of the title compound were obtained.

LC-MS (Method 1): $R_t$=0.99 min; m/z=474 (M+H)$^+$.

$^1$H NMR (400 MHz, DMSO-$d_6$): δ [ppm]=1.23 (t, 3H), 4.20 (q, 2H), 4.37 (s, 3H), 5.12 (s, 2H), 7.27 (d, 1H), 7.35 (t, 1H), 7.59 (d, 1H), 7.72 (d, 1H), 8.00 (d, 1H), 8.32 (s, 1H), 8.59 (s, 1H).

Example 74 ethyl 3-[3-chloro-2-(trifluoromethyl)benzyl]-1-(1-methyl-1H-benzotriazol-5-yl)-2,4-dioxo-1,2,3,4-tetrahydropyrimidine-5-carboxylate

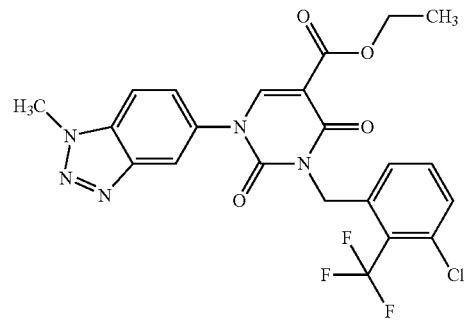 [SMILES: CCOC(=O)c1cn(-c2ccc3c(c2)nnn3C)c(=O)n(Cc2cccc(Cl)c2C(F)(F)F)c1=O]

162 mg (0.51 mmol) of ethyl 1-(1-methyl-1H-benzotriazol-5-yl)-2,4-dioxo-1,2,3,4-tetrahydropyrimidine-5-carboxylate from Example 74A were initially charged in DMF (6 ml), and 238 mg (65% purity, 0.56 mmol) of 1-(bromomethyl)-3-chloro-2-(trifluoromethyl)benzene, 142 mg (1.03 mmol) of potassium carbonate and 8 mg (0.05 mmol) of potassium iodide were added. Subsequently, the reaction mixture was left to stir at 60° C. for 5 h. The mixture cooled to RT was admixed with water and extracted twice with ethyl acetate. The combined organic phases were washed with a saturated sodium chloride solution, dried over magnesium sulphate, filtered off and concentrated. The residue was stirred with cyclohexane/ethyl acetate, and the precipitated solid was filtered off with suction and dried under reduced pressure. This gave 115 mg (43% of theory) of the title compound.

LC-MS (Method 1): $R_t$=1.02 min; m/z=508 (M+H)$^+$.

$^1$H NMR (400 MHz, DMSO-$d_6$): δ [ppm]=1.23 (t, 3H), 4.21 (q, 2H), 4.37 (s, 3H), 5.23 (br.s, 2H), 7.36-7.41 (m, 1H), 7.58-7.67 (m, 2H), 7.70-7.75 (m, 1H), 8.00 (d, 1H), 8.30-8.33 (m, 1H), 8.62 (s, 1H).

Example 75 ethyl 1-(1-methyl-1H-indazol-5-yl)-3-[2-methyl-3-(trifluoromethyl)benzyl]-2,4-dioxo-1,2,3,4-tetrahydropyrimidine-5-carboxylate

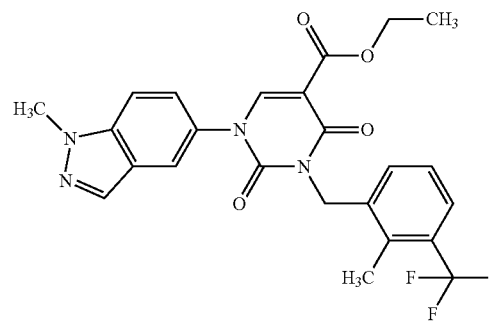

The preparation and purification of the title compound were analogous to Example 1. The reaction time was 2 h. Proceeding from 200 mg (0.63 mmol) of ethyl 1-(1-methyl-1H-indazol-5-yl)-2,4-dioxo-1,2,3,4-tetrahydropyrimidine-5-carboxylate from Example 75A and 177 mg (0.70 mmol) of 1-(bromomethyl)-2-methyl-3-(trifluoromethyl)benzene, 254 mg (80% of theory) of the title compound were obtained.

LC-MS (Method 1): $R_t$=1.11 min; m/z=487 (M+H)$^+$.

$^1$H NMR (400 MHz, DMSO-d$_6$): δ [ppm]=1.22 (t, 3H), 2.46 (s, 3H), 4.10 (s, 3H), 4.19 (q, 2H), 5.09 (s, 2H), 7.32-7.44 (m, 2H), 7.54 (d, 1H), 7.60 (d, 1H), 7.78 (d, 1H), 7.98 (s, 1H), 8.18 (s, 1H), 8.49 (s, 1H).

Example 76 ethyl 1-(1-methyl-1H-indazol-5-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer)

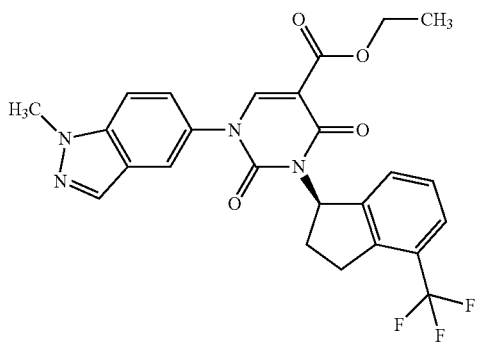 [SMILES: CCOC(=O)c1cn(-c2ccc3c(cnn3C)c2)c(=O)n([C@@H]2CCc3c2cccc3C(F)(F)F)c1=O]

200 mg (0.63 mmol) of ethyl 1-(1-methyl-1H-indazol-5-yl)-2,4-dioxo-1,2,3,4-tetrahydropyrimidine-5-carboxylate from Example 75A and 500 mg (1.90 mmol) of triphenylphosphine were initially charged in THF/DMF 1:1 (8.4 ml) under argon and cooled to −30° C. 257 mg (1.27 mmol) of diisopropyl azodicarboxylate and a solution of 154 mg (0.76 mmol) of (1S)-4-(trifluoromethyl)indan-1-ol from Example 14A in 1 ml of THF were added dropwise. The reaction mixture was stirred at RT for 16 h. For workup, the reaction mixture was cooled to −40° C., admixed with 1M hydrochloric acid, warmed to RT and extracted with ethyl acetate. The organic phase was successively washed twice with 1M hydrochloric acid and once with saturated sodium chloride solution, dried over magnesium sulphate and concentrated. The residue was purified by means of HPLC (Method 8). This gave 142 mg (43% of theory) of the title compound.

LC-MS (Method 1): $R_t$=1.11 min; m/z=499 (M+H)±.

$^1$H NMR (400 MHz, CDCl$_3$): δ [ppm]=1.36 (t, 3H), 2.40-2.52 (m, 1H), 2.53-2.61 (m, 1H, partly concealed by DMSO signal), 3.08-3.19 (m, 1H), 3.45-3.58 (m, 1H), 4.11 (s, 3H), 4.35 (q, 2H), 6.61-6.77 (m, 1H), 7.23-7.33 (m, 3H, partly concealed by CDCl$_3$ signal), 7.44-7.53 (m, 2H), 7.69 (s, 1H), 8.04 (s, 1H), 8.37 (s, 1H).

Specific optical rotation: $\alpha_D^{20}$=+146.6°, (chloroform, c=0.405 g/100 ml).

Example 77 ethyl 1-(1-methyl-1H-benzimidazol-5-yl)-3-[2-methyl-3-(trifluoromethyl)benzyl]-2,4-dioxo-1,2,3,4-tetrahydropyrimidine-5-carboxylate

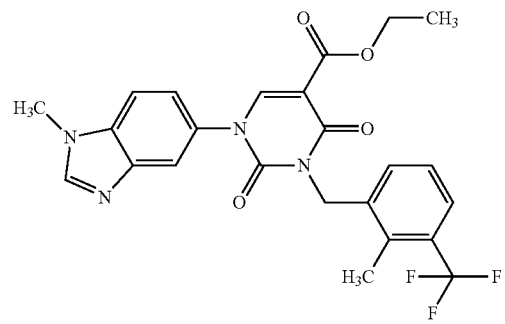 [SMILES: CCOC(=O)c1cn(-c2ccc3c(c2)ncn3C)c(=O)n(Cc2cccc(C(F)(F)F)c2C)c1=O]

1.00 g (3.18 mmol) of ethyl 1-(1-methyl-1H-benzimidazol-5-yl)-2,4-dioxo-1,2,3,4-tetrahydropyrimidine-5-carboxylate from Example 76A were initially charged in DMF (8 ml), and 886 mg (3.50 mmol) of 1-(bromomethyl)-2-methyl-3-(trifluoromethyl)benzene, 879 mg (6.36 mmol) of potassium carbonate and 53 mg (0.32 mmol) of potassium iodide were added. Subsequently, the reaction mixture was left to stir at 60° C. for 5 h. The mixture cooled to RT was admixed with water, and the precipitate was filtered off with suction, washed with water and ethanol/MTBE, and dried under reduced pressure at 50° C. This gave 1.06 g (68% of theory) of the title compound.

LC-MS (Method 1): $R_t$=0.93 min; m/z=487 (M+H)$^+$.

$^1$H NMR (400 MHz, DMSO-d$_6$): δ [ppm]=1.23 (t, 3H), 2.46 (s, 3H), 3.89 (s, 3H), 4.19 (q, 2H), 5.09 (s, 2H), 7.32-7.46 (m, 3H), 7.60 (d, 1H), 7.71 (d, 1H), 7.89 (d, 1H), 8.33 (s, 1H), 8.46 (s, 1H).

Example 78 ethyl 3-[3-chloro-2-(trifluoromethyl)benzyl]-1-(1-methyl-1H-benzimidazol-5-yl)-2,4-dioxo-1,2,3,4-tetrahydropyrimidine-5-carboxylate

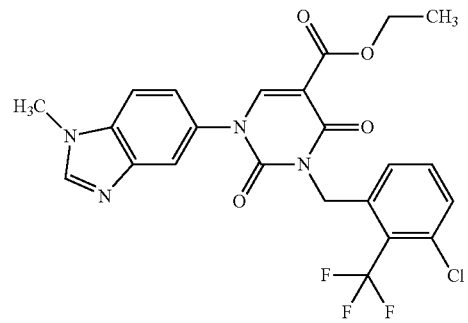 [SMILES: CCOC(=O)c1cn(-c2ccc3c(c2)ncn3C)c(=O)n(Cc2cccc(Cl)c2C(F)(F)F)c1=O]

The preparation and purification of the title compound were analogous to Example 77. Proceeding from 200 mg (0.63 mmol) of ethyl 1-(1-methyl-1H-benzimidazol-5-yl)-2,4-dioxo-1,2,3,4-tetrahydropyrimidine-5-carboxylate from Example 76A and 295 mg (65% purity, 0.70 mmol) of 1-(bromomethyl)-3-chloro-2-(trifluoromethyl)benzene, 82 mg (26% of theory) of the title compound were obtained.

LC-MS (Method 1): $R_t$=0.97 min; m/z=507 (M+H)$^+$.

$^1$H NMR (400 MHz, DMSO-d$_6$): δ [ppm]=1.23 (t, 3H), 3.89 (s, 3H), 4.20 (q, 2H), 5.23 (s, 2H), 7.36 (d, 1H), 7.41-7.46 (m, 1H), 7.57-7.67 (m, 2H), 7.70 (d, 1H), 7.87 (d, 1H), 8.32 (s, 1H), 8.49 (s, 1H).

Example 79 ethyl 3-[2-chloro-3-(trifluoromethyl)benzyl]-1-(1-methyl-1H-benzimidazol-5-yl)-2,4-dioxo-1,2,3,4-tetrahydropyrimidine-5-carboxylate

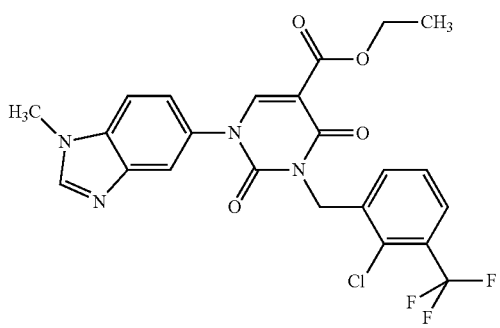 [SMILES: CCOC(=O)c1cn(-c2ccc3c(c2)ncn3C)c(=O)n(Cc2cccc(C(F)(F)F)c2Cl)c1=O]

The preparation of the title compound was analogous to Example 77. Proceeding from 200 mg (0.63 mmol) of ethyl 1-(1-methyl-1H-benzimidazol-5-yl)-2,4-dioxo-1,2,3,4-tetrahydropyrimidine-5-carboxylate from Example 76A and 191 mg (0.70 mmol) of 1-(bromomethyl)-2-chloro-3-(trifluoromethyl)benzene, after additional purification by means of preparative HPLC (Method 8), 153 g (47% of theory) of the title compound were obtained.

LC-MS (Method 1): $R_t$=0.97 min; m/z=507 (M+H)$^+$.

$^1$H NMR (400 MHz, DMSO-d$_6$): δ [ppm]=1.23 (t, 3H), 3.89 (s, 3H), 4.20 (q, 2H), 5.16 (s, 2H), 7.44 (dd, 1H), 7.50-7.56 (m, 1H), 7.59-7.63 (m, 1H), 7.71 (d, 1H), 7.78-7.83 (m, 1H), 7.88 (d, 1H), 8.33 (s, 1H), 8.49 (s, 1H).

Example 80 ethyl 1-(1-ethyl-1H-benzimidazol-5-yl)-3-[2-methyl-3-(trifluoromethyl)benzyl]-2,4-dioxo-1,2,3,4-tetrahydropyrimidine-5-carboxylate

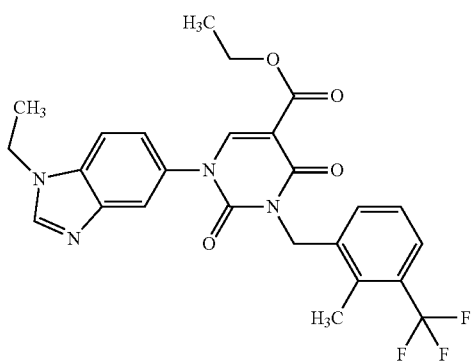 [SMILES: CCOC(=O)c1cn(-c2ccc3c(c2)ncn3CC)c(=O)n(Cc2cccc(C(F)(F)F)c2C)c1=O]

122.5 mg (0.37 mmol) of ethyl 1-(1-ethyl-1H-benzimidazol-5-yl)-2,4-dioxo-1,2,3,4-tetrahydropyrimidine-5-carboxylate from Example 46A and 103 mg (0.41 mmol) of 1-(bromomethyl)-2-methyl-3-(trifluoromethyl)benzene were initially charged in DMF (4 ml), and 103 mg (0.74 mmol) of potassium carbonate and 6 mg (0.04 mmol) of potassium iodide were added. The reaction mixture was stirred at 60° C. for 5 h, then brought to RT and admixed with water. The precipitate was filtered off with suction, washed with water and MTBE, and dried under reduced pressure at 50° C. overnight. This gave 38 mg (19% of theory) of the title compound.

LC-MS (Method 1): $R_t$=0.97 min; m/z=501 (M+H)$^+$.

$^1$H NMR (400 MHz, DMSO-d$_6$): δ [ppm]=1.23 (t, 3H), 1.43 (t, 3H), 2.46 (s, 3H), 4.19 (q, 2H), 4.33 (q, 2H), 5.09 (s, 2H), 7.31-7.46 (m, 3H), 7.60 (d, 1H), 7.76 (d, 1H), 7.89 (d, 1H), 8.40 (s, 1H), 8.48 (s, 1H), 8.48 (s, 1H).

Example 81 ethyl 1-(2-carbamoyl-1-methyl-1H-benzimidazol-5-yl)-3-[2-methyl-3-(trifluoromethyl)benzyl]-2,4-dioxo-1,2,3,4-tetrahydropyrimidine-5-carboxylate

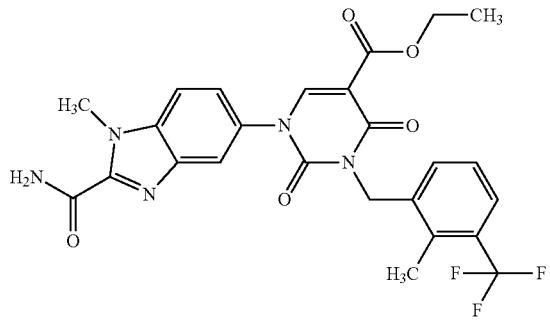 [SMILES: CCOC(=O)c1cn(-c2ccc3c(c2)nc(C(N)=O)n3C)c(=O)n(Cc2cccc(C(F)(F)F)c2C)c1=O]

158 mg (0.44 mmol) of ethyl 1-(2-carbamoyl-1-methyl-1H-benzimidazol-5-yl)-2,4-dioxo-1,2,3,4-tetrahydropyrimidine-5-carboxylate from Example 81A were initially charged in DMF (3 ml), and 123 mg (0.48 mmol) of 1-(bromomethyl)-2-methyl-3-(trifluoromethyl)benzene, 122 mg (0.88 mmol) of potassium carbonate and 7 mg (0.04 mmol) of potassium iodide were added. The reaction mixture was left to stir at 80° C. for 1 h. The cooled mixture was admixed with water, and the precipitated solid was filtered off and washed with water. The filtrate was extracted twice with dichloromethane, and the combined organic phases were dried over magnesium sulphate, filtered off and concentrated. The residue was combined with the previously isolated solid and purified by means of preparative HPLC (Method 8). This gave 131 mg (54% of theory) of the title compound.

LC-MS (Method 1): $R_t$=0.98 min; m/z=530 (M+H)$^+$.

$^1$H NMR (400 MHz, DMSO-d$_6$): δ [ppm]=1.23 (t, 3H), 2.47 (s, partly concealed by DMSO signal), 4.16 (s, 3H), 4.20 (q, 2H), 5.10 (s, 2H), 7.33-7.39 (m, 1H), 7.39-7.44 (m, 1H), 7.53-7.63 (m, 2H), 7.82 (d, 1H), 7.92 (br.s, 1H), 7.96-8.00 (m, 1H), 8.32 (br. s, 1H), 8.50 (s, 1H).

Example 82 ethyl 3-[2-chloro-3-(trifluoromethyl)benzyl]-1-(1-methyl-1H-benzimidazol-6-yl)-2,4-dioxo-1,2,3,4-tetrahydropyrimidine-5-carboxylate

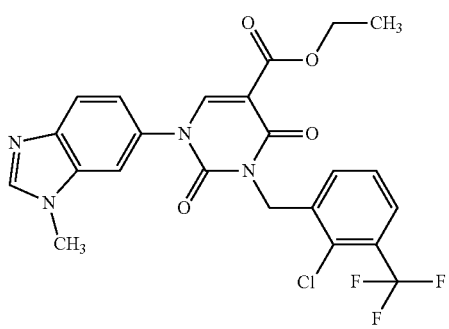 [SMILES: CCOC(=O)c1cn(-c2ccc3ncn(C)c3c2)c(=O)n(Cc2cccc(C(F)(F)F)c2Cl)c1=O]

The preparation and purification of the title compound were analogous to Example 80. The reaction time was 1 h. Proceeding from 150 mg (0.47 mmol) of ethyl 1-(1-methyl-1H-benzimidazol-6-yl)-2,4-dioxo-1,2,3,4-tetrahydropyrimidine-5-carboxylate from Example 82A and 143 mg (0.52 mmol) of 1-(bromomethyl)-2-chloro-3-(trifluoromethyl)benzene, after additional purification by means of flash chromatography (dichloro-methane/methanol 98:2), 110 mg (44% of theory) of the title compound were obtained.

LC-MS (Method 1): $R_t$=0.92 min; m/z=507 (M+H)$^+$.
$^1$H NMR (400 MHz, DMSO-d$_6$): δ [ppm]=1.23 (t, 3H), 3.87 (s, 3H), 4.20 (q, 2H), 5.17 (s, 2H), 7.37 (dd, 1H), 7.54 (t, 1H), 7.61 (d, 1H), 7.77 (d, 1H), 7.81 (d, 1H), 7.84 (d, 1H), 8.34 (s, 1H), 8.52 (s, 1H).

Example 83 ethyl 1-(1-ethyl-2-methyl-1H-benzimidazol-5-yl)-3-[3-fluoro-2-(trifluoromethyl)benzyl]-2,4-dioxo-1,2,3,4-tetrahydropyrimidine-5-carboxylate

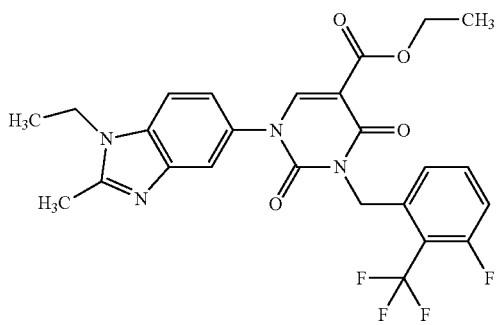 [SMILES: CCOC(=O)c1cn(-c2ccc3c(c2)nc(C)n3CC)c(=O)n(Cc2cccc(F)c2C(F)(F)F)c1=O]

200 mg (0.58 mmol) of ethyl 1-(1-ethyl-2-methyl-1H-benzimidazol-5-yl)-2,4-dioxo-1,2,3,4-tetrahydropyrimidine-5-carboxylate from Example 117A were initially charged in DMF (7 ml) and admixed with 165 mg (0.64 mmol) of 1-(bromomethyl)-3-fluoro-2-(trifluoromethyl)benzene, 161 mg (1.17 mmol) of potassium carbonate and 10 mg (0.06 mmol) of potassium iodide. The reaction mixture was left to stir at 60° C. for 5 h. The cooled mixture was admixed with water, and the precipitated solid was filtered off and washed with water. The solid was dissolved in dichloromethane and purified by means of flash silica gel chromatography (dichloromethane/methanol, 30:1). This gave 153 mg (50% of theory) of the title compound.

LC-MS (Method 1): $R_t$=0.85 min; m/z=519 (M+H)$^+$.
$^1$H NMR (400 MHz, DMSO-d$_6$): δ [ppm]=1.22 (t, 3H), 1.32 (t, 3H), 2.58 (s, 3H), 4.19 (q, 2H), 4.28 (q, 2H), 5.21 (s, 2H), 7.22 (d, 1H), 7.33 (d, 1H), 7.41 (t, 1H), 7.61-7.70 (m, 2H), 7.70-7.75 (m, 1H), 8.44-8.50 (m, 1H).

Example 84 ethyl 3-[2-chloro-3-(trifluoromethyl)benzyl]-1-(1-ethyl-2-methyl-1H-benzimidazol-5-yl)-2,4-dioxo-1,2,3,4-tetrahydropyrimidine-5-carboxylate

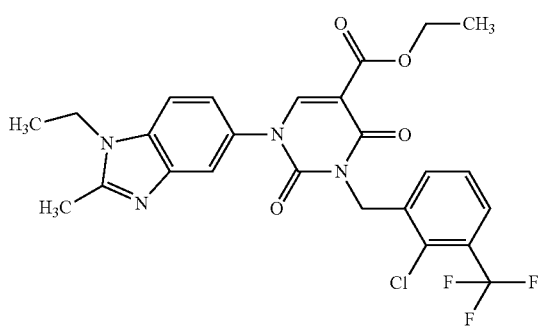 [SMILES: CCOC(=O)c1cn(-c2ccc3c(c2)nc(C)n3CC)c(=O)n(Cc2cccc(C(F)(F)F)c2Cl)c1=O]

The preparation and purification of the title compound were analogous to Example 83. Proceeding from 200 mg (0.58 mmol) of ethyl 1-(1-ethyl-2-methyl-1H-benzimidazol-5-yl)-2,4-dioxo-1,2,3,4-tetrahydropyrimidine-5-carboxylate from Example 117A and 175 mg (0.63 mmol) of 1-(bromomethyl)-2-chloro-3-(trifluoromethyl)benzene, 114 mg (36% of theory) of the title compound were obtained.

LC-MS (Method 1): $R_t$=0.89 min; m/z=535 (M+H)$^+$.
$^1$H NMR (400 MHz, DMSO-d$_6$): δ [ppm]=1.23 (t, 3H), 1.31 (t, 3H), 2.58 (s, 3H), 4.19 (q, 2H), 4.27 (q, 2H), 5.16 (s, 2H), 7.35 (dd, 1H), 7.53 (t, 1H), 7.60 (d, 1H), 7.65 (d, 1H), 7.73 (d, 1H), 7.80 (d, 1H), 8.47 (s, 1H).

Example 85 ethyl 1-(1-cyclohexyl-2-methyl-1H-benzimidazol-5-yl)-3-[3-fluoro-2-(trifluoromethyl)benzyl]-2,4-dioxo-1,2,3,4-tetrahydropyrimidine-5-carboxylate

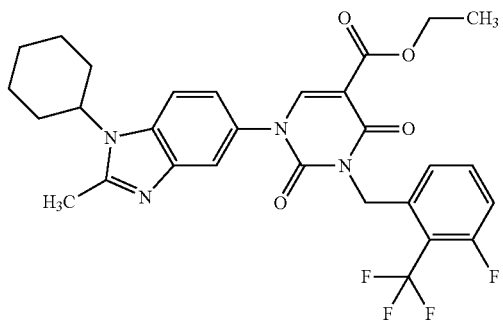 [SMILES: CCOC(=O)c1cn(-c2ccc3c(c2)nc(C)n3C2CCCCC2)c(=O)n(Cc2cccc(F)c2C(F)(F)F)c1=O]

The preparation and purification of the title compound were analogous to Example 83. Proceeding from 200 mg (0.50 mmol) of ethyl 1-(1-cyclohexyl-2-methyl-1H-benzimidazol-5-yl)-2,4-dioxo-1,2,3,4-tetrahydropyrimidine-5-carboxylate from Example 118A and 142 mg (0.55 mmol) of 1-(bromomethyl)-3-fluoro-2-(trifluoromethyl)benzene, 90 mg (30% of theory) of the title compound were obtained.

LC-MS (Method 1): $R_t$=1.05 min; m/z=573 (M+H)$^+$.

$^1$H NMR (400 MHz, DMSO-d$_6$): δ [ppm]=1.23 (t, 3H), 1.34-1.57 (m, 3H), 1.67-1.75 (m, 1H), 1.82-1.92 (m, 4H), 2.10-2.23 (m, 2H), 2.60 (s, 3H), 4.19 (q, 2H), 4.26-4.37 (m, 1H), 5.20 (s, 2H), 7.22 (d, 1H), 7.29 (dd, 1H), 7.36-7.45 (m, 1H), 7.62-7.70 (m, 1H), 7.71 (d, 1H), 7.83 (d, 1H), 8.47 (s, 1H).

Example 86 ethyl 3-[2-chloro-3-(trifluoromethyl)benzyl]-1-(1-isopropyl-1H-benzimidazol-5-yl)-2,4-dioxo-1,2,3,4-tetrahydropyrimidine-5-carboxylate

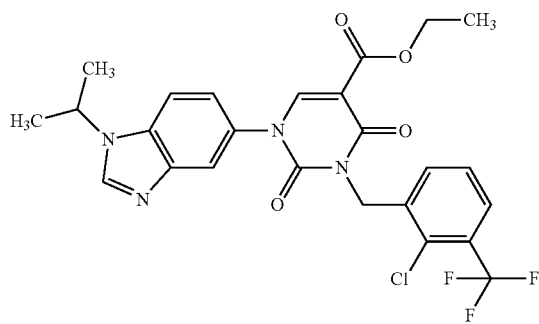 [SMILES: CCOC(=O)c1cn(-c2ccc3c(c2)ncn3C(C)C)c(=O)n(Cc2cccc(C(F)(F)F)c2Cl)c1=O]

The preparation of the title compound was analogous to Example 83. Proceeding from 200 mg (0.58 mmol) of ethyl 1-(1-isopropyl-1H-benzimidazol-5-yl)-2,4-dioxo-1,2,3,4-tetrahydropyrimidine-5-carboxylate from Example 51A and 175 mg (0.64 mmol) of 1-(bromomethyl)-2-chloro-3-(trifluoromethyl)benzene, after purification by means of flash chromatography (dichloromethane/methanol 50:0, 64 mg (19% of theory) of the title compound were obtained.

LC-MS (Method 1): $R_t$=1.05 min; m/z=535 (M+H)$^+$.

$^1$H NMR (400 MHz, DMSO-d$_6$): δ [ppm]=1.23 (t, 3H), 1.56 (d, 6H), 4.19 (q, 2H), 4.82 (spt, 1H), 5.16 (s, 2H), 7.42 (dd, 1H), 7.54 (t, 1H), 7.61 (d, 1H), 7.80 (d, 2H), 7.88 (d, 1H), 8.49 (s, 1H), 8.51 (s, 1H).

Example 87 ethyl 3-(2,3-dichlorobenzyl)-1-(1-isopropyl-1H-benzimidazol-5-yl)-2,4-dioxo-1,2,3,4-tetrahydropyrimidine-5-carboxylate

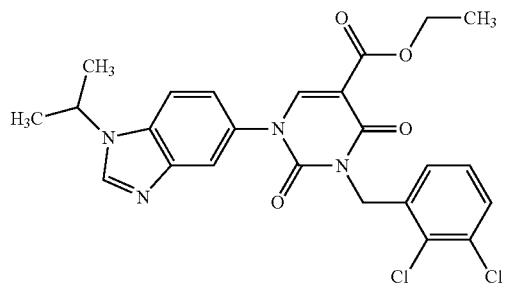 [SMILES: CCOC(=O)c1cn(-c2ccc3c(c2)ncn3C(C)C)c(=O)n(Cc2cccc(Cl)c2Cl)c1=O]

The preparation of the title compound was analogous to Example 83. Proceeding from 200 mg (0.58 mmol) of ethyl 1-(1-isopropyl-1H-benzimidazol-5-yl)-2,4-dioxo-1,2,3,4-tetrahydropyrimidine-5-carboxylate from Example 51A and 154 mg (0.64 mmol) of 1-(bromomethyl)-2,3-dichlorobenzene, after purification by means of flash chromatography (dichloromethane/methanol 50:1), 83 mg (28% of theory) of the title compound were obtained.

LC-MS (Method 1): $R_t$=1.02 min; m/z=501 (M+H)$^+$.

$^1$H NMR (400 MHz, DMSO-d$_6$): δ [ppm]=1.23 (t, 3H), 1.56 (d, 6H), 4.19 (q, 2H), 4.82 (spt, 1H), 5.11 (s, 2H), 7.26 (d, 1H), 7.34 (t, 1H), 7.42 (dd, 1H), 7.58 (d, 1H), 7.79 (d, 1H), 7.88 (d, 1H), 8.49 (s, 2H).

Example 88 ethyl 3-[2-chloro-3-(trifluoromethyl)benzyl]-1-(1-cyclobutyl-1H-benzimidazol-5-yl)-2,4-dioxo-1,2,3,4-tetrahydropyrimidine-5-carboxylate

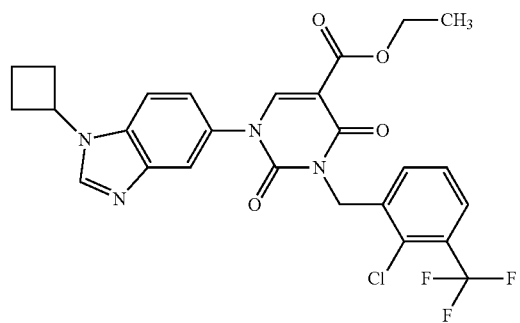 [SMILES: CCOC(=O)c1cn(-c2ccc3c(c2)ncn3C2CCC2)c(=O)n(Cc2cccc(C(F)(F)F)c2Cl)c1=O]

Preparation of the title compound was analogous to Example 83, using 200 mg (0.56 mmol) of ethyl 1-(1-cyclobutyl-1H-benzimidazol-5-yl)-2,4-dioxo-1,2,3,4-tetrahydropyrimidine-5-carboxylate from Example 41A and 169 mg (0.62 mmol) of 1-(bromomethyl)-2-chloro-3-(trifluoromethyl)benzene. For workup, the reaction mixture was admixed with water, and the precipitate was filtered off with suction, washed with water and MTBE, and dried under reduced pressure at 50° C. overnight. The solid was purified by means of flash chromatography (dichloromethane/methanol 70:1). The product-containing fractions were concentrated, and the residue was subjected to extractive stirring in ethanol, filtered off, washed with ethanol and dried under high vacuum. This gave 141 mg (42% of theory) of the title compound.

LC-MS (Method 1): $R_t$=1.06 min; m/z=547 (M+H)$^+$.

$^1$H NMR (400 MHz, DMSO-d$_6$): δ [ppm]=1.23 (t, 3H), 1.86-1.96 (m, 2H), 2.56 (s, 4H, partly concealed by DMSO signal), 4.20 (q, 2H), 5.04 (quin, 1H), 5.16 (s, 2H), 7.42 (dd, 1H), 7.53 (t, 1H), 7.62 (d, 1H), 7.74 (d, 1H), 7.81 (d, 1H), 7.89 (d, 1H), 8.50 (s, 1H), 8.55 (s, 1H).

Example 89 ethyl 3-[2-chloro-3-(trifluoromethyl)benzyl]-1-(1-methyl-1H-indazol-5-yl)-2,4-dioxo-1,2,3,4-tetrahydropyrimidine-5-carboxylate

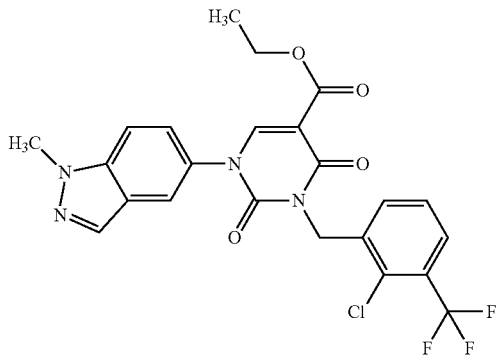 [SMILES: CCOC(=O)c1cn(-c2ccc3c(cnn3C)c2)c(=O)n(Cc2cccc(C(F)(F)F)c2Cl)c1=O]

The preparation and purification of the title compound were analogous to Example 80. Proceeding from 200 mg (0.63 mmol) of ethyl 1-(1-methyl-1H-indazol-5-yl)-2,4-dioxo-1,2,3,4-tetrahydropyrimidine-5-carboxylate from Example 75A and 191 mg (0.70 mmol) of 1-(bromomethyl)-2-chloro-3-(trifluoromethyl)benzene, 228 mg (67% of theory) of the title compound were obtained.

LC-MS (Method 1): $R_t$=1.11 min; m/z=507 (M+H)$^+$.

$^1$H NMR (400 MHz, DMSO-d$_6$): δ [ppm]=1.24 (t, 3H), 4.10 (s, 3H), 4.20 (q, 2H), 5.16 (s, 2H), 7.49-7.57 (m, 2H), 7.62 (d, 1H), 7.74-7.84 (m, 2H), 7.98 (d, 1H), 8.18 (s, 1H), 8.52 (s, 1H).

Example 90 ethyl 1-(1-ethyl-1H-benzimidazol-5-yl)-3-[3-fluoro-2-(trifluoromethyl)benzyl]-2,4-dioxo-1,2,3,4-tetrahydropyrimidine-5-carboxylate

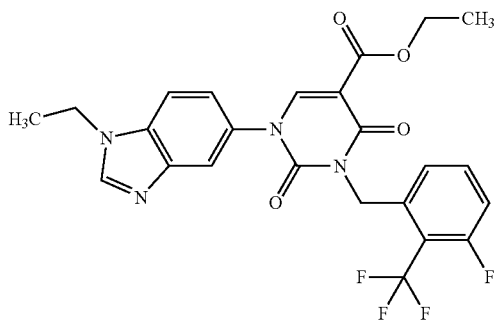 [SMILES: CCOC(=O)c1cn(-c2ccc3c(c2)ncn3CC)c(=O)n(Cc2cccc(F)c2C(F)(F)F)c1=O]

The preparation and purification of the title compound were analogous to Example 1. Proceeding from 122.5 mg (0.37 mmol) of ethyl 1-(1-ethyl-1H-benzimidazol-5-yl)-2,4-dioxo-1,2,3,4-tetrahydropyrimidine-5-carboxylate from Example 46A and 105 mg (0.41 mmol) of 1-(bromomethyl)-3-fluoro-2-(trifluoromethyl)-benzene, 73 mg (35% of theory) of the title compound were obtained.

LC-MS (Method 1): $R_t$=0.92 min; m/z=505 (M+H)$^+$.

$^1$H NMR (400 MHz, DMSO-d$_6$): δ [ppm]=1.23 (t, 3H), 1.43 (t, 3H), 4.20 (q, 2H), 4.33 (q, 2H), 5.21 (br. s, 2H), 7.22 (d, 1H), 7.36-7.46 (m, 2H), 7.67 (q, 1H), 7.76 (d, 1H), 7.84-7.90 (m, 1H), 8.40 (s, 1H), 8.51 (s, 1H).

Example 91 ethyl 3-[2-chloro-3-(trifluoromethyl)benzyl]-1-(1-ethyl-1H-benzimidazol-5-yl)-2,4-dioxo-1,2,3,4-tetrahydropyrimidine-5-carboxylate

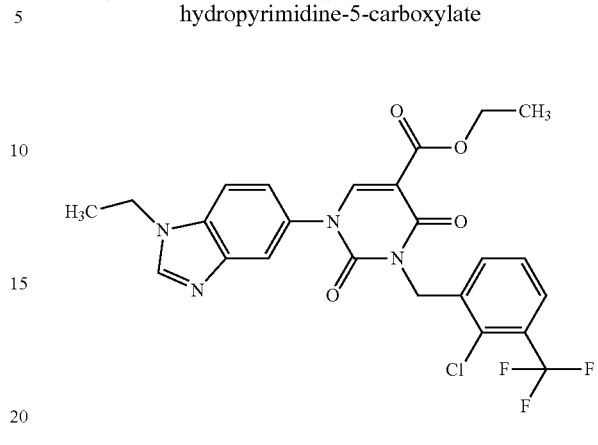

The preparation of the title compound was analogous to Example 80. Proceeding from 122.5 mg (0.37 mmol) of ethyl 1-(1-ethyl-1H-benzimidazol-5-yl)-2,4-dioxo-1,2,3,4-tetrahydropyrimidine-5-carboxylate from Example 46A and 112 mg (0.41 mmol) of 1-(bromomethyl)-2-chloro-3-(trifluoromethyl)benzene, after additional purification by means of flash chromatography (dichloromethane/methanol 30:1), 52 mg (27% of theory) of the title compound were obtained.

LC-MS (Method 1): $R_t$=1.01 min; m/z=521 (M+H)$^+$.

$^1$H NMR (400 MHz, DMSO-d$_6$): δ [ppm]=1.23 (t, 3H), 1.43 (t, 3H), 4.20 (q, 2H), 4.34 (q, 2H), 5.16 (s, 2H), 7.43 (dd, 1H), 7.53 (t, 1H), 7.61 (d, 1H), 7.76 (d, 1H), 7.81 (d, 1H), 7.88 (d, 1H), 8.40 (s, 1H), 8.50 (s, 1H).

Example 92 ethyl 3-[3-chloro-2-(trifluoromethyl)benzyl]-1-[1-(cyclopropylmethyl)-1H-benzimidazol-5-yl]-2,4-dioxo-1,2,3,4-tetrahydropyrimidine-5-carboxylate

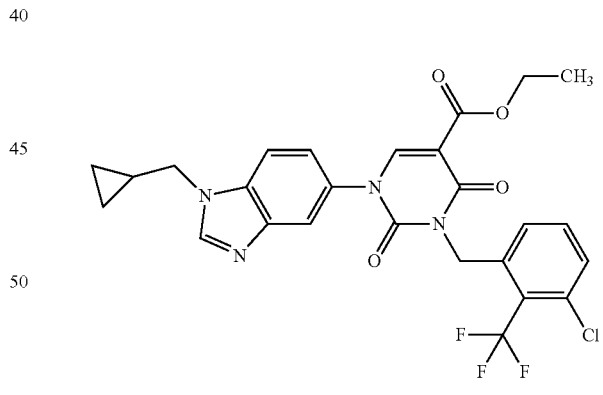

200 mg (0.56 mmol) of ethyl 1-[1-(cyclopropylmethyl)-1H-benzimidazol-5-yl]-2,4-dioxo-1,2,3,4-tetrahydropyrimidine-5-carboxylate from Example 56A were initially charged in 7.1 ml of DMF. 156 mg (1.13 mmol) of potassium carbonate, 9 mg (0.05 mmol) of potassium iodide and 261 mg (65% purity, 0.62 mmol) of 1-(bromomethyl)-3-chloro-2-(trifluoromethyl)benzene were added and the mixture was heated to 60° C. for 5 h.

The cooled reaction mixture was admixed with water, extracted twice with ethyl acetate, and the combined organic phases were washed with saturated sodium chloride solution, dried over magnesium sulphate and concentrated. The residue was stirred in ethanol, and the precipitated solid was filtered off with suction and dried at the high-vacuum pump. This gave 137 mg (44% of theory) of the title compound. The filtrate was concentrated and the residue was purified by means of flash chromatography (dichloromethane/methanol 50:1). It was thus possible to isolate an additional 56 mg of the title compound (overall yield 61% of theory).

LC-MS (Method 3): $R_t$=1.29 min; m/z=547 (M+H)$^+$.

$^1$H NMR (400 MHz, DMSO-d$_6$): δ [ppm]=0.40-0.48 (m, 2H), 0.51-0.58 (m, 2H), 1.23 (t, 3H), 1.27-1.37 (m, 1H), 4.14-4.24 (m, 4H), 5.23 (s, 2H), 7.36 (d, 1H), 7.42 (dd, 1H), 7.56-7.68 (m, 2H), 7.81 (d, 1H), 7.87 (d, 1H), 8.43 (s, 1H), 8.53 (s, 1H).

Example 93 ethyl 1-(1-isopropyl-1H-benzimidazol-5-yl)-3-[2-methyl-3-(trifluoromethyl)benzyl]-2,4-dioxo-1,2,3,4-tetrahydropyrimidine-5-carboxylate

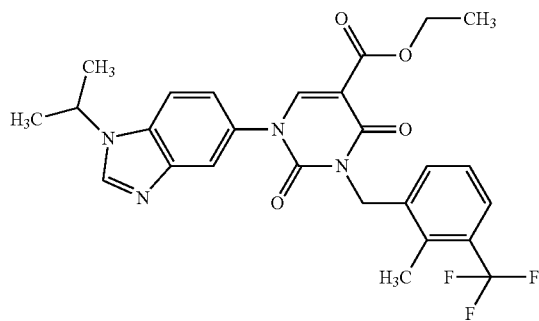 [SMILES: CCOC(=O)c1cn(-c2ccc3c(c2)ncn3C(C)C)c(=O)n(Cc2cccc(C(F)(F)F)c2C)c1=O]

The preparation of the title compound was analogous to Example 80. Proceeding from 200 mg (0.58 mmol) of ethyl 1-(1-isopropyl-1H-benzimidazol-5-yl)-2,4-dioxo-1,2,3,4-tetrahydropyrimidine-5-carboxylate from Example 51A and 162 mg (0.64 mmol) of 1-(bromomethyl)-2-methyl-3-(trifluoromethyl)benzene, after additional purification by means of flash chromatography (dichloromethane/methanol 50:1), 90 mg (29% of theory) of the title compound were obtained.

LC-MS (Method 1): $R_t$=1.04 min; m/z=515 (M+H)$^+$.

$^1$H NMR (400 MHz, DMSO-d$_6$): δ [ppm]=1.22 (t, 3H), 1.56 (d, 6H), 2.46 (s, 3H), 4.19 (q, 2H), 4.82 (spt, 1H), 5.09 (s, 2H), 7.32-7.46 (m, 3H), 7.60 (d, 1H), 7.80 (d, 1H), 7.89 (d, 1H), 8.48 (d, 2H).

Example 94 ethyl 1-(1,3-dimethyl-2,2-dioxido-1,3-dihydro-2,1,3-benzothiadiazol-5-yl)-3-[2-methyl-3-(trifluoromethyl)-benzyl]-2,4-dioxo-1,2,3,4-tetrahydropyrimidine-5-carboxylate

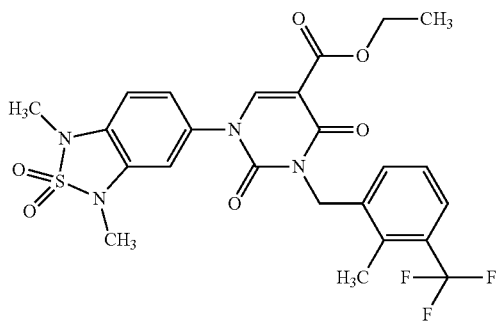 [SMILES: CCOC(=O)c1cn(-c2ccc3c(c2)N(C)S(=O)(=O)N3C)c(=O)n(Cc2cccc(C(F)(F)F)c2C)c1=O]

The preparation and purification of the title compound were analogous to Example 1. The reaction time was 2 h. Proceeding from 160 mg (0.42 mmol) of ethyl 1-(1,3-dimethyl-2,2-dioxido-1,3-dihydro-2,1,3-benzothiadiazol-5-yl)-2,4-dioxo-1,2,3,4-tetrahydropyrimidine-5-carboxylate from Example 87A and 117 mg (0.46 mmol) of 1-(bromomethyl)-2-methyl-3-(trifluoromethyl)benzene, 195 mg (84% of theory) of the title compound were obtained.

LC-MS (Method 1): $R_E$=1.10 min; m/z=553 (M+H)$^+$.

$^1$H NMR (400 MHz, DMSO-d$_6$): δ [ppm]=1.23 (t, 3H), 2.46 (s, 3H), 3.26 (s, 3H), 3.30 (s, 3H), 4.20 (q, 2H), 5.08 (s, 2H), 7.15 (d, 1H), 7.23 (dd, 1H), 7.29 (d, 1H), 7.31-7.39 (m, 2H), 7.58-7.63 (m, 1H), 8.45 (s, 1H).

Example 95 ethyl 3-[3-chloro-2-(trifluoromethyl)benzyl]-1-(1,3-dimethyl-2,2-dioxido-1,3-dihydro-2,1,3-benzothiadiazol-5-yl)-2,4-dioxo-1,2,3,4-tetrahydropyrimidine-5-carboxylate

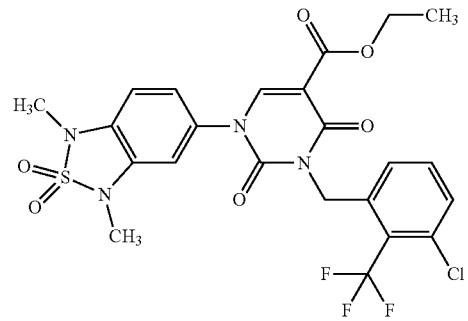 [SMILES: CCOC(=O)c1cn(-c2ccc3c(c2)N(C)S(=O)(=O)N3C)c(=O)n(Cc2cccc(Cl)c2C(F)(F)F)c1=O]

The preparation and purification of the title compound were analogous to Example 1. The reaction time was 2 h. Proceeding from 160 mg (0.42 mmol) of ethyl 1-(1,3-dimethyl-2,2-dioxido-1,3-dihydro-2,1,3-benzothiadiazol-5-yl)-2,4-dioxo-1,2,3,4-tetrahydropyrimidine-5-carboxylate from Example 87A and 194 mg (65% purity, 0.46 mmol) of 1-(bromomethyl)-3-chloro-2-(trifluoromethyl)benzene (preparation: see WO 2004/52858, page 149, Example 176), after additional purification by means of flash chromatography (di-chloromethane/methanol 250:1), 120 mg (50% of theory) of the title compound were obtained.

LC-MS (Method 1): $R_t$=1.11 min; m/z=573 (M+H)$^+$.

$^1$H NMR (400 MHz, DMSO-d$_6$): δ [ppm]=1.23 (t, 3H), 3.27 (s, 3H), 3.30 (s, 3H), 4.20 (q, 2H), 5.21 (br.s, 2H), 7.17 (d, 1H), 7.21 (dd, 1H), 7.26 (d, 1H), 7.32 (d, 1H), 7.56-7.67 (m, 2H), 8.49 (s, 1H).

Example 96 ethyl 3-[2-chloro-3-(trifluoromethyl)benzyl]-1-(1,3-dimethyl-2,2-dioxido-1,3-dihydro-2,1,3-benzothiadiazol-5-yl)-2,4-dioxo-1,2,3,4-tetrahydropyrimidine-5-carboxylate

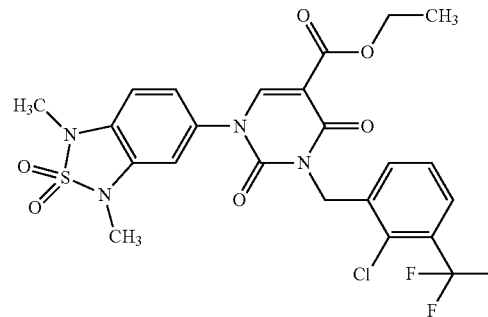

The preparation and purification of the title compound were analogous to Example 1. Proceeding from 160 mg (0.42 mmol) of ethyl 1-(1,3-dimethyl-2,2-dioxido-1,3-dihydro-2,1,3-benzothiadiazol-5-yl)-2,4-dioxo-1,2,3,4-tetrahydropyrimidine-5-carboxylate from Example 87A and 126 mg (0.46 mmol) of 1-(bromomethyl)-2-chloro-3-(trifluoromethyl)benzene, 167 mg (69% of theory) of the title compound were obtained.

LC-MS (Method 1): $R_t$=1.11 min; m/z=573 (M+H)$^+$.

$^1$H NMR (400 MHz, DMSO-d$_6$): δ [ppm]=1.23 (t, 3H), 3.27 (s, 3H), 3.31 (s, 3H), 4.20 (q, 2H), 5.15 (s, 2H), 7.16 (d, 1H), 7.22 (dd, 1H), 7.27 (d, 1H), 7.49-7.60 (m, 2H), 7.80 (d, 1H), 8.48 (s, 1H).

Example 97 ethyl 1-(1,3-dimethyl-2,2-dioxido-1,3-dihydro-2,1,3-benzothiadiazol-5-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer)

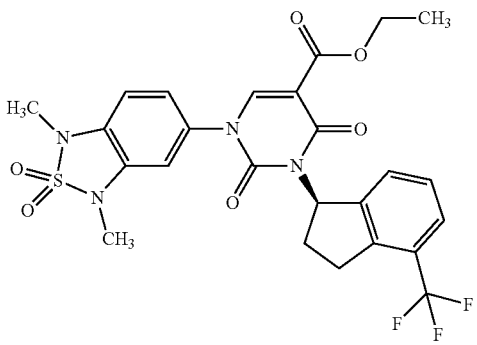 [SMILES: CCOC(=O)c1cn(-c2ccc3c(c2)N(C)S(=O)(=O)N3C)c(=O)n([C@@H]2CCc3c2cccc3C(F)(F)F)c1=O]

The preparation and purification of the title compound were analogous to Example 42 (Method A). Proceeding from 200 mg (0.52 mmol) of ethyl 1-(1,3-dimethyl-2,2-dioxido-1,3-dihydro-2,1,3-benzothiadiazol-5-yl)-2,4-dioxo-1,2,3,4-tetrahydropyrimidine-5-carboxylate from Example 87A and 127 mg (0.63 mmol) of (1 S)-4-(trifluoromethyl)indan-1-ol from Example 14A, 149 mg (50% of theory) of the title compound were obtained.

LC-MS (Method 1): $R_t$=1.15 min; m/z=565 (M+H)$^+$.

$^1$H NMR (400 MHz, DMSO-d$_6$): δ [ppm]=1.22 (t, 3H), 2.35-2.43 (m, 1H), 2.43-2.48 (m, 1H, partly concealed by DMSO signal), 3.03-3.15 (m, 1H), 3.22-3.27 (m, 4H), 3.29 (s, 3H), 4.17 (q, 2H), 6.31-6.59 (m, 1H), 7.09-7.31 (m, 3H), 7.36 (t, 1H), 7.47 (d, 1H), 7.53 (d, 1H), 8.37 (s, 1H).

Example 98 ethyl 1-(1,3-benzothiazol-6-yl)-3-[2-methyl-3-(trifluoromethyl)benzyl]-2,4-dioxo-1,2,3,4-tetrahydropyrimidine-5-carboxylate

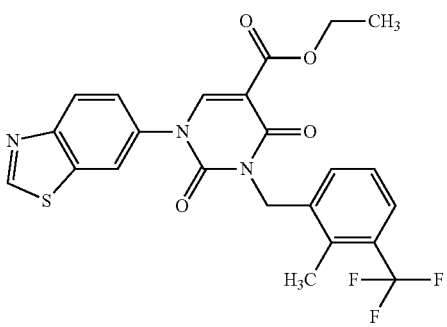 [SMILES: CCOC(=O)c1cn(-c2ccc3ncsc3c2)c(=O)n(Cc2cccc(C(F)(F)F)c2C)c1=O]

The preparation and purification of the title compound were analogous to Example 80. Proceeding from 200 mg (0.63 mmol) of ethyl 1-(1,3-benzothiazol-6-yl)-2,4-dioxo-1,2,3,4-tetrahydropyrimidine-5-carboxylate from Example 88A and 175 mg (0.69 mmol) of 1-(bromomethyl)-2-methyl-3-(trifluoromethyl)benzene, 204 mg (65% of theory) of the title compound were obtained.

LC-MS (Method 1): $R_t$=1.08 min; m/z=490 (M+H)$^+$.

$^1$H NMR (400 MHz, DMSO-d$_6$): δ [ppm]=1.23 (t, 3H), 2.46 (s, 3H), 4.20 (q, 2H), 5.10 (s, 2H), 7.36 (t, 1H), 7.42 (d, 1H), 7.60 (d, 1H), 7.73 (dd, 1H), 8.22 (d, 1H), 8.41 (d, 1H), 8.59 (s, 1H), 9.54 (s, 1H).

Example 99 ethyl 1-(4-methylquinolin-7-yl)-3-[2-methyl-3-(trifluoromethyl)benzyl]-2,4-dioxo-1,2,3,4-tetrahydropyrimidine-5-carboxylate

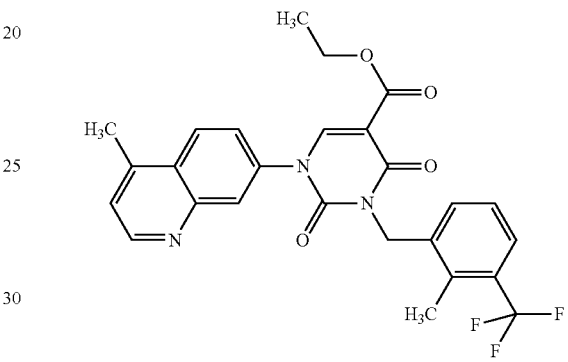

The preparation and purification of the title compound were analogous to Example 80. Proceeding from 200 mg (0.61 mmol) of ethyl 1-(4-methylquinolin-7-yl)-2,4-dioxo-1,2,3,4-tetrahydropyrimidine-5-carboxylate from Example 93A and 171 mg (0.67 mmol) of 1-(bromomethyl)-2-methyl-3-(trifluoromethyl)benzene, 230 mg (75% of theory) of the title compound were obtained.

LC-MS (Method 1): $R_t$=1.13 min; m/z=498 (M+H)$^+$.

$^1$H NMR (400 MHz, DMSO-d$_6$): δ [ppm]=1.24 (t, 3H), 2.47 (s, 3H), 2.74 (s, 3H), 4.21 (q, 2H), 5.11 (s, 2H), 7.33-7.39 (m, 1H), 7.43-7.47 (m, 1H), 7.48-7.51 (m, 1H), 7.59-7.63 (m, 1H), 7.77-7.81 (m, 1H), 8.22-8.27 (m, 2H), 8.62 (s, 1H), 8.85 (d, 1H).

Example 100 ethyl 1-(1-methyl-2-oxo-1,4-dihydro-2H-3,1-benzoxazin-6-yl)-3-[2-methyl-3-(trifluoromethyl)benzyl]-2,4-dioxo-1,2,3,4-tetrahydropyrimidine-5-carboxylate

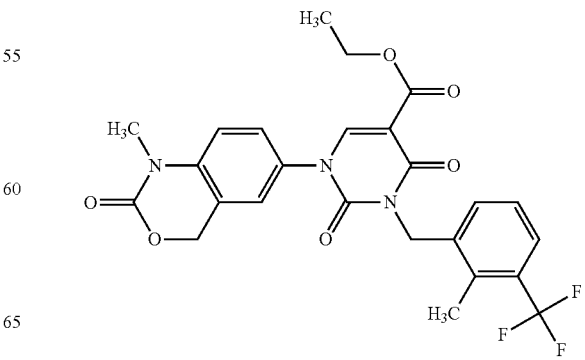

The preparation and purification of the title compound were analogous to Example 1. The reaction time was about 16 h. Proceeding from 200 mg (0.57 mmol) of ethyl 1-(1-methyl-2-oxo-1,4-dihydro-2H-3,1-benzoxazin-6-yl)-2,4-dioxo-1,2,3,4-tetrahydropyrimidine-5-carboxylate from Example 92A and 161 mg (0.63 mmol) of 1-(bromomethyl)-2-methyl-3-(trifluoromethyl)benzene, 255 mg (85% of theory) of the title compound were obtained.

LC-MS (Method 1): $R_t$=1.07 min; m/z=518 (M+H)$^+$.

$^1$H NMR (400 MHz, DMSO-d$_6$): δ [ppm]=1.23 (t, 3H), 2.46 (s, 3H), 3.30 (s, partly concealed by water signal), 4.20 (q, 2H), 5.07 (s, 2H), 5.30 (s, 2H), 7.24 (d, 1H), 7.30-7.41 (m, 2H), 7.47 (d, 1H), 7.54-7.62 (m, 2H), 8.44 (s, 1H).

Example 101 ethyl 1-(1-methyl-2-oxo-1,4-dihydro-2H-3,1-benzoxazin-6-yl)-2,4-dioxo-3-[(1R)-4-(trifluoromethyl)-2,3-dihydro-1H-inden-1-yl]-1,2,3,4-tetrahydropyrimidine-5-carboxylate

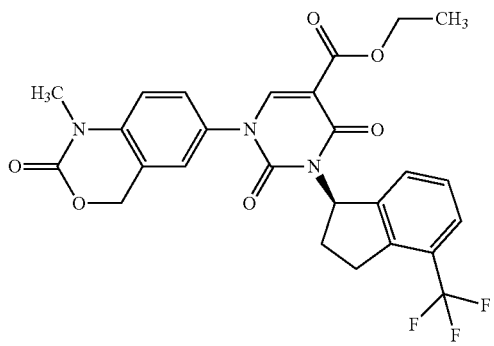 [SMILES: CCOC(=O)c1cn(-c2ccc3c(c2)COC(=O)N3C)c(=O)n([C@@H]2CCc3c2cccc3C(F)(F)F)c1=O]

The preparation and purification of the title compound were analogous to Example 67. Proceeding from 200 mg (0.56 mmol) of ethyl 1-(1-methyl-2-oxo-1,4-dihydro-2H-3,1-benzoxazin-6-yl)-2,4-dioxo-1,2,3,4-tetrahydropyrimidine-5-carboxylate from Example 92A and 140 mg (0.69 mmol) of (1S)-4-(trifluoromethyl)indan-1-ol from Example 14A, after purification by means of HPLC (Method 8), 160 mg (51% of theory) of the title compound were obtained.

LC-MS (Method 1): $R_t$=1.07 min; m/z=530 (M+H)$^+$.

$^1$H NMR (400 MHz, CDCl$_3$): δ [ppm]=1.36 (t, 3H), 2.37-2.48 (m, 1H), 2.53-2.60 (m, 1H), 3.08-3.19 (m, 1H), 3.39 (s, 3H), 3.45-3.58 (m, 1H), 4.36 (q, 2H), 5.21 (s, 2H), 6.61-6.73 (m, 1H), 7.03 (d, 1H), 7.13 (s, 1H), 7.26 (d, 3H, partly concealed by CHCl$_3$ signal), 7.47 (d, 1H), 8.26-8.30 (m, 1H).

Specific optical rotation: $α_D^{20}$=±124.4°, (chloroform, c=0.360 g/100 ml).

Example 102 ethyl 3-[2-chloro-3-(trifluoromethyl)benzyl]-1-(1-methyl-2-oxo-1,2,3,4-tetrahydroquinolin-6-yl)-2,4-dioxo-1,2,3,4-tetrahydropyrimidine-5-carboxylate

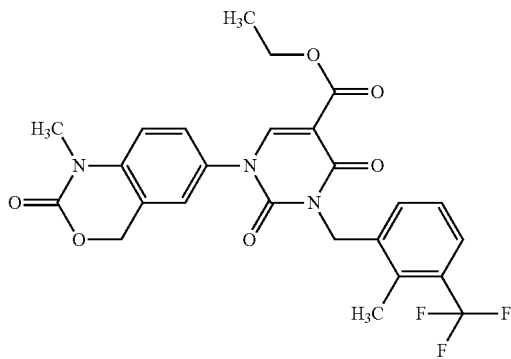 [SMILES: CCOC(=O)c1cn(-c2ccc3c(c2)COC(=O)N3C)c(=O)n(Cc2cccc(C(F)(F)F)c2C)c1=O]

The preparation and purification of the title compound were analogous to Example 80. Proceeding from 200 mg (0.58 mmol) of ethyl 1-(1-methyl-2-oxo-1,2,3,4-tetrahydroquinolin-6-yl)-2,4-dioxo-1,2,3,4-tetrahydropyrimidine-5-carboxylate from Example 91A and 162 mg (0.64 mmol) of 1-(bromomethyl)-2-methyl-3-(trifluoromethyl)benzene, 267 mg (89% of theory) of the title compound were obtained.

LC-MS (Method 1): $R_t$=1.06 min; m/z=516 (M+H)$^+$.

$^1$H NMR (400 MHz, DMSO-d$_6$): δ [ppm]=1.23 (t, 3H), 2.46 (s, 3H), 2.58 (t, 2H), 2.92 (t, 2H), 3.28 (s, 3H), 4.19 (q, 2H), 5.08 (s, 2H), 7.22 (d, 1H), 7.31-7.39 (m, 2H), 7.40-7.46 (m, 2H), 7.60 (d, 1H), 8.41 (s, 1H).

Example 103 ethyl 1-(1-methyl-2-oxo-1,2,3,4-tetrahydroquinolin-6-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer)

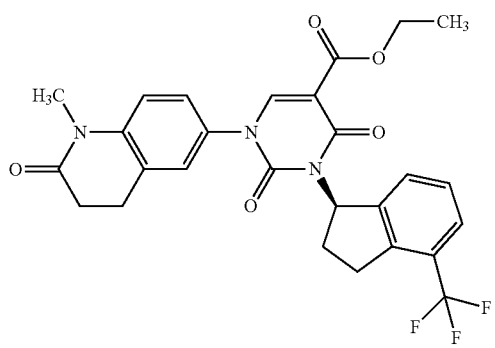 [SMILES: CCOC(=O)c1cn(-c2ccc3c(c2)CCC(=O)N3C)c(=O)n([C@@H]2CCc3c2cccc3C(F)(F)F)c1=O]

200 mg (0.58 mmol) of ethyl 1-(1-methyl-2-oxo-1,2,3,4-tetrahydroquinolin-6-yl)-2,4-dioxo-1,2,3,4-tetrahydropyrimidine-5-carboxylate from Example 91A and 475 mg (1.81 mmol) of triphenylphosphine were initially charged in THF/DMF 1:1 (7.6 ml) under argon. 235 mg (1.16 mmol) of diisopropyl azodicarboxylate were added dropwise and then 141 mg (0.69 mmol) of (1S)-4-(trifluoromethyl)indan-1-ol from Example 14A were added. The reaction mixture was stirred at RT for 16 h. For workup, the mixture was admixed with 1M hydrochloric acid and diluted with ethyl acetate, and phases were separated. The organic phase was successively washed twice with 1M hydrochloric acid and once with saturated sodium chloride solution, dried over magnesium sulphate, filtered and concentrated. The residue was purified by means of preparative HPLC (Method 8). This gave 125 mg (40% of theory) of the title compound.

LC-MS (Method 1): $R_t$=1.09 min; m/z=528 (M+H)$^+$.

$^1$H NMR (400 MHz, CDCl$_3$): δ [ppm]=1.36 (t, 3H), 2.38-2.50 (m, 1H), 2.53-2.61 (m, 1H, partly concealed by DMSO signal), 2.67 (t, 2H), 2.94 (t, 2H), 3.08-3.19 (m, 1H), 3.36 (s, 3H), 3.46-3.58 (m, 1H), 4.36 (q, 2H), 6.62-6.74 (m, 1H), 7.05 (d, 1H), 7.13 (s, 1H), 7.18-7.23 (m, 1H), 7.24-7.30 (m, 2H), 7.47 (d, 1H), 8.29 (s, 1H).

Specific optical rotation: $α_D^{20}$=+128.5°, (chloroform, c=0.415 g/100 ml).

Example 104 ethyl 1-(6-fluoro-1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer)

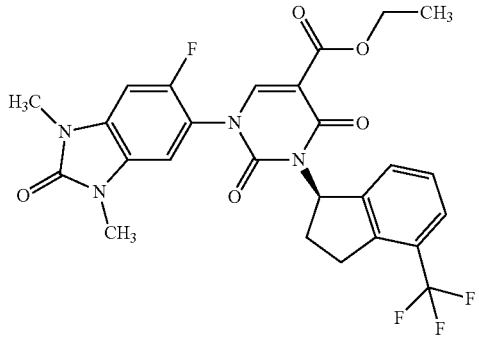 [SMILES: CCOC(=O)c1cn(-c2cc3c(cc2F)n(C)c(=O)n3C)c(=O)n([C@@H]2CCc3c2cccc3C(F)(F)F)c1=O]

200 mg (0.55 mmol) of ethyl 1-(6-fluoro-1,3-dimethyl-2-oxo-2,3-dihydro-1H-benzimidazol-5-yl)-2,4-dioxo-1,2,3,4-tetrahydropyrimidine-5-carboxylate from Example 95A and 434 mg (1.66 mmol) of triphenylphosphine were initially charged in THF/DMF 1:1 (7.3 ml) under argon and cooled to −30° C. 218 µl (1.10 mmol) of diisopropyl azodicarboxylate, then a solution of 134 mg (0.66 mmol) of (1S)-4-(trifluoromethyl)indan-1-ol from Example 14A in 3 ml of THF, were added dropwise. The reaction mixture was warmed to RT and stirred at RT for 30 min. For workup, the reaction mixture was cooled to 0° C., admixed with 5 ml of 1M hydrochloric acid, then extracted at RT with ethyl acetate. The organic phase was successively washed twice with 1M hydrochloric acid and once with saturated sodium chloride solution, dried over magnesium sulphate and concentrated. The residue was subjected to extractive stirring with ethanol, and the precipitated solid was filtered off with suction and discarded. The filtrate was concentrated on a rotary evaporator, dissolved in a little dichloromethane and purified by means of flash chromatography (eluent: dichloromethane/methanol 120:1→20:1). The resulting product was dried under HV, then stirred in 10 ml of cyclohexane/ethyl acetate 1:1. The solid was filtered off and dried under HV. This gave 146 mg (47% of theory) of the title compound.

LC-MS (Method 1): $R_t$=1.10 min; m/z=547 (M+H)$^+$.
$^1$H NMR (400 MHz, DMSO-$d_6$): δ [ppm]=1.22 (t, 3H), 2.30-2.42 (m, 1H), 2.52-2.53 (m, 1H, partly concealed by DMSO signal), 3.04-3.15 (m, 1H), 3.22-3.30 (m, 1H), 3.32 (s, 3H), 3.35 (s, 3H), 4.19 (q, 2H), 6.37-6.57 (m, 1H), 7.33-7.50 (m, 4H), 7.54 (d, 1H), 8.48 (s, 1H).

Example 105 ethyl 3-[(3-chloro-4-methyl-2-thienyl)methyl]-1-(1,3-dimethyl-2-oxo-2,3-dihydro-1H-benzimidazol-5-yl)-2,4-dioxo-1,2,3,4-tetrahydropyrimidine-5-carboxylate

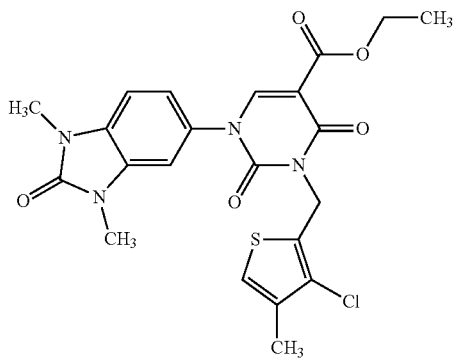 [SMILES: CCOC(=O)c1cn(-c2ccc3c(c2)n(C)c(=O)n3C)c(=O)n(Cc2scc(C)c2Cl)c1=O]

45 µl (0.23 mmol) of diisopropyl azodicarboxylate were added dropwise to a solution, initially charged under argon, of 33 mg (0.20 mmol) of (3-chloro-4-methyl-2-thienyl)methanol from Example 96A and 74 mg (0.28 mmol) in 2 ml of anhydrous THF at RT. After 5 min, 65 mg (0.18 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate from Example 2A were added and the reaction mixture was stirred at RT overnight. For workup, 3 drops of 1N hydrochloric acid were added and the entire reaction mixture was separated by means of preparative HPLC (Method 8). The product-containing fractions were concentrated on a rotary evaporator and the residue was stirred in diethyl ether. The solid was filtered off with suction and dried under high vacuum. This gave 26 mg (26% of theory) of the title compound.

LC-MS (Method 1): $R_t$=1.00 min; m/z=489 (M+H)$^+$.
$^1$H NMR (400 MHz, DMSO-$d_6$): δ [ppm]=1.23 (t, 3H), 2.12 (s., 3H), 3.30 (s., 3H, partly concealed by water signal), 3.37 (s, 3H), 4.19 (q, 2H), 5.19 (s., 2H), 7.14-7.23 (m, 1H), 7.24-7.32 (m, 2H), 7.38 (s, 1H), 8.36 (s, 1H).

Example 106 ethyl 3-(4,6-difluoro-2,3-dihydro-1H-inden-1-yl)-1-(1,3-dimethyl-2-oxo-2,3-dihydro-1H-benzimidazol-5-yl)-2,4-dioxo-1,2,3,4-tetrahydropyrimidine-5-carboxylate (Racemate)

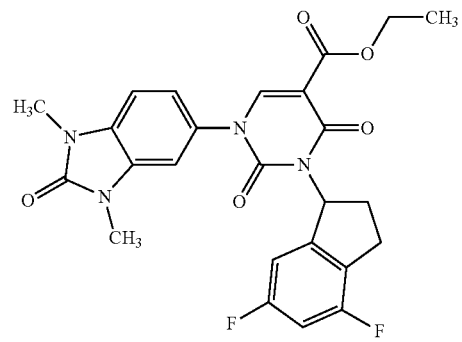 [SMILES: CCOC(=O)c1cn(-c2ccc3c(c2)n(C)c(=O)n3C)c(=O)n(C2CCc3c(F)cc(F)cc32)c1=O]

229 µl (1.16 mmol) of diisopropyl azodicarboxylate were added dropwise to a solution, initially charged under argon at −40° C., of 200 mg (0.58 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate from Example 2A and 457 mg (1.74 mmol) of triphenylphosphine in 16 ml of THF/DMF 1:1. 128 mg (1.16 mmol) of 4,6-difluoroindan-1-ol from Example 97A were added. The reaction mixture was warmed to RT and stirred further overnight. For workup, while cooling with ice, 5 ml of 1N hydrochloric acid were added, and the mixture was stirred further for 15 min, then extracted with ethyl acetate. The organic phase was washed twice with 1N hydrochloric acid, twice with a saturated sodium hydrogencarbonate solution, then with a saturated sodium chloride solution, then dried over sodium sulphate and concentrated on a rotary evaporator. The residue was purified by means of preparative HPLC (Method 8). This gave 178 mg (61% of theory) of the title compound.

LC-MS (Method 1): $R_t$=1.01 min; m/z=497 (M+H)$^+$.
$^1$H NMR (400 MHz, DMSO-$d_6$): δ [ppm]=1.22 (t, 3H), 2.35-2.48 (m, 2H), 2.84-2.96 (m, 1H), 3.02-3.16 (m, 1H), 3.31 (s, 3H), 3.37 (s, 3H), 4.18 (q, 2H), 6.25-6.55 (m, 1H), 6.93-7.08 (m, 1H), 7.13-7.30 (m, 2H), 7.31-7.45 (m, 1H), 8.33 (s, 1H).

Example 107 ethyl 1-(1,3-dimethyl-2-oxo-2,3-dihydro-1H-benz-imidazol-5-yl)-3-(6-methyl-2,3-dihydro-1H-inden-1-yl)-2,4-dioxo-1,2,3,4-tetrahydropyrimidine-5-carboxylate (Racemate)

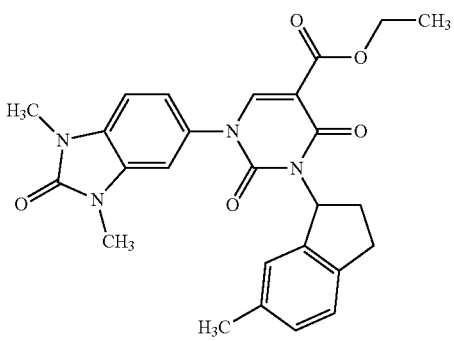 [SMILES: CCOC(=O)c1cn(-c2ccc3c(c2)n(C)c(=O)n3C)c(=O)n(C2CCc3ccc(C)cc32)c1=O]

The preparation and purification of the title compound were analogous to Example 106. Proceeding from 200 mg (0.58 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate from Example 2A and 112 mg (0.75 mmol) of 6-methylindan-1-ol from Example 100A, 130 mg (47% of theory) of the title compound were obtained.

LC-MS (Method 1): $R_t$=1.02 min; m/z=475 (M+H)±.
$^1$H NMR (400 MHz, DMSO-d$_6$): δ [ppm]=1.21 (t, 3H), 2.25 (s, 3H), 2.31-2.43 (m, 2H), 2.79-2.91 (m, 1H), 3.04-3.18 (m, 1H), 3.31 (s, 3H), 3.37 (s, 3H), 4.17 (q, 2H), 6.24-6.51 (m, 1H), 6.93-7.01 (m, 2H), 7.09 (d, 1H), 7.14-7.29 (m, 2H), 7.31-7.47 (m, 1H), 8.31 (s, 1H).

Example 108 ethyl 3-(4,6-difluoro-2,3-dihydro-1H-inden-1-yl)-1-(3-methyl-2-oxo-2,3-dihydro-1,3-benzothiazol-6-yl)-2,4-dioxo-1,2,3,4-tetrahydropyrimidine-5-carboxylate (Racemate)

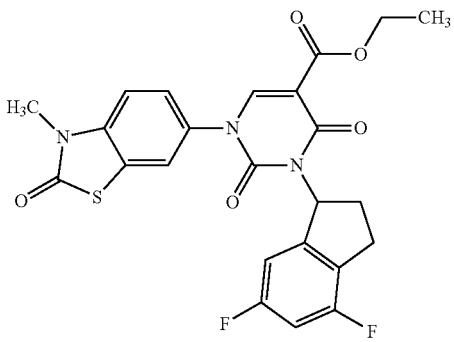 [SMILES: CCOC(=O)c1cn(-c2ccc3c(c2)sc(=O)n3C)c(=O)n(C2CCc3c(F)cc(F)cc32)c1=O]

Preparation of the title compound was analogous to Example 103, but with a reaction time of 1 h, proceeding from 200 mg (0.57 mmol) of ethyl 1-(3-methyl-2-oxo-2,3-dihydro-1,3-benzothiazol-6-yl)-2,4-dioxo-1,2,3,4-tetrahydropyrimidine-5-carboxylate from Example 31A and 127 mg (0.74 mmol) of 4,6-difluoroindan-1-ol from Example 97A. The product was purified by preparative HPLC (Method 7). This gave 173 mg (57% of theory) of the title compound.

LC-MS (Method 1): $R_t$=1.10 min; m/z=500 (M+H)$^+$.
$^1$H NMR (400 MHz, DMSO-d$_6$): δ [ppm]=1.23 (t, 3H), 2.35-2.48 (m, 2H), 2.84-2.96 (m, 1H), 3.00-3.15 (m, 1H), 3.44 (s, 3H), 4.18 (q, 2H), 6.27-6.52 (m, 1H), 6.93-7.07 (m, 2H), 7.39-7.65 (m, 2H), 7.76-7.92 (m, 1H), 8.40 (s, 1H).

Example 109 ethyl 3-(6-methyl-2,3-dihydro-1H-inden-1-yl)-1-(3-methyl-2-oxo-2,3-dihydro-1,3-benzothiazol-6-yl)-2,4-dioxo-1,2,3,4-tetrahydropyrimidine-5-carboxylate (Racemate)

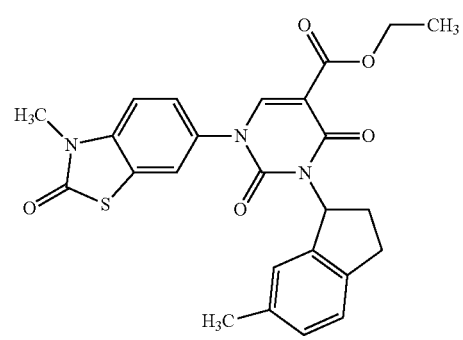 [SMILES: CCOC(=O)c1cn(-c2ccc3c(c2)sc(=O)n3C)c(=O)n(C2CCc3ccc(C)cc32)c1=O]

The preparation and purification of the title compound were analogous to Example 108. Proceeding from 200 mg (0.57 mmol) of ethyl 1-(3-methyl-2-oxo-2,3-dihydro-1,3-benzothiazol-6-yl)-2,4-dioxo-1,2,3,4-tetrahydropyrimidine-5-carboxylate from Example 31A and 111 mg (0.74 mmol) of 6-methylindan-1-ol from Example 100A, 131 mg (47% of theory) of the title compound were obtained.

LC-MS (Method 1): $R_t$=1.11 min; m/z=478 (M+H)$^+$.
$^1$H NMR (400 MHz, DMSO-d$_6$): δ [ppm]=1.22 (t, 3H), 2.24 (s, 3H), 2.31-2.43 (m, 2H), 2.79-2.91 (m, 1H), 3.01-3.17 (m, 1H), 3.44 (s, 3H), 4.17 (q, 2H), 6.21-6.51 (m, 1H), 6.91-7.02 (m, 2H), 7.09 (d, 1H), 7.42 (d, 1H), 7.48-7.63 (m, 1H), 7.77-7.92 (m, 1H), 8.38 (s, 1H).

Example 110 ethyl 1-(1,3-dimethyl-2-oxo-2,3-dihydro-1H-benz-imidazol-5-yl)-3-[6-fluoro-4-(trifluoromethyl)-2,3-dihydro-1H-inden-1-yl]-2,4-dioxo-1,2,3,4-tetrahydropyrimidine-5-carboxylate (Racemate)

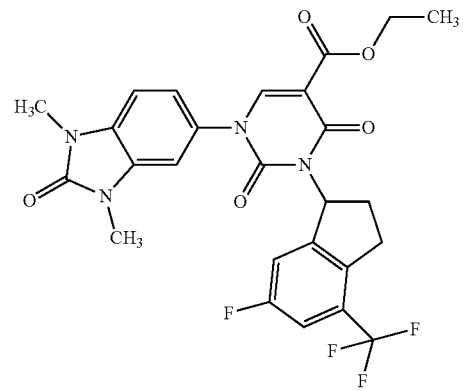

The preparation and purification of the title compound were analogous to Example 108. Proceeding from 60 mg (0.17 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate from Example 2A and 50 mg (0.22 mmol) of 6-fluoro-4-(trifluoromethyl)indan-1-ol from Example 98A, 68 mg (71% of theory) of the title compound were obtained.

LC-MS (Method 4): $R_t$=2.38 min; m/z=547 (M+H)$^+$.

$^1$H NMR (400 MHz, CD$_2$Cl$_2$): δ [ppm]=1.23 (t, 3H), 2.33-2.46 (m, 1H), 2.48-2.60 (m, 1H), 2.95-3.07 (m, 1H), 3.26-3.40 (m, 7H), 4.21 (q, 2H), 6.47-6.57 (m, 1H), 6.86 (s, 1H), 6.92-7.01 (m, 3H), 7.08-7.17 (m, 1H), 8.24 (s, 1H).

Example 111 tert-butyl 6-[5-(ethoxycarbonyl)-2,4-dioxo-3-[(1R)-4-(trifluoromethyl)-2,3-dihydro-1H-inden-1-yl]-3,4-dihydropyrimidin-1(2H)-yl]-3-methyl-2-oxo-2,3-dihydro-1H-benzimidazole-1-carboxylate (R enantiomer)

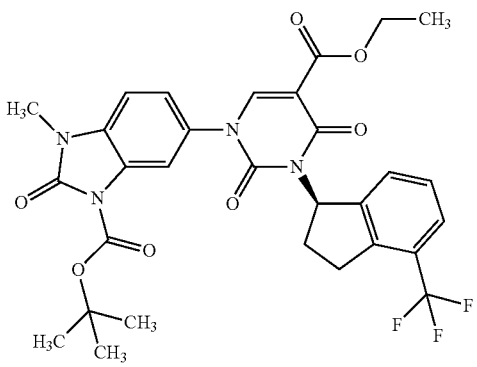 [SMILES: CCOC(=O)c1cn(-c2ccc3c(c2)n(C(=O)OC(C)(C)C)c(=O)n3C)c(=O)n([C@@H]2CCc3c2cccc3C(F)(F)F)c1=O]

The preparation and purification of the title compound were analogous to Example 108, with initial ice bath cooling. Proceeding from 2.50 g (5.80 mmol) of tert-butyl 6-[5-(ethoxycarbonyl)-2,4-dioxo-3,4-dihydropyrimidin-1(2H)-yl]-3-methyl-2-oxo-2,3-dihydro-1H-benzimidazole-1-carboxylate from Example 101A and 1.29 g (6.39 mmol) of 4-(trifluoromethyl)indan-1-ol (S enantiomer) from Example 14A, 2.29 g (61% of theory) of the title compound were obtained.

LC-MS (Method 1): $R_t$=1.24 min; m/z=615 (M+H)$^+$.

$^1$H NMR (400 MHz, DMSO-d$_6$): δ [ppm]=1.21 (t, 3H), 1.56 (s, 9H), 2.35-2.43 (m, 1H), 2.43-2.48 (m, 1H), 3.02-3.14 (m, 1H), 3.21-3.30 (m, 1H), 3.32 (br.s, 3H), 4.18 (q, 2H), 6.33-6.59 (m, 1H), 7.26-7.45 (m, 3H), 7.46-7.58 (m, 2H), 7.77-7.96 (m, 1H), 8.32 (s, 1H).

Example 112 ethyl 1-(1-methyl-2-oxo-2,3-dihydro-1H-benzimidazol-5-yl)-2,4-dioxo-3-[4-(trifluoromethyl)-2,3-dihydro-1H-inden-1-yl]-1,2,3,4-tetrahydropyrimidine-5-carboxylate (R enantiomer)

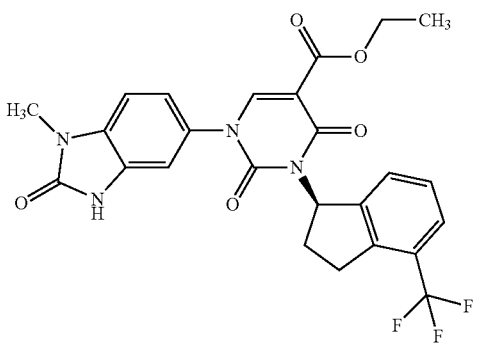 [SMILES: CCOC(=O)c1cn(-c2ccc3c(c2)[nH]c(=O)n3C)c(=O)n([C@@H]2CCc3c2cccc3C(F)(F)F)c1=O]

2.29 g (3.73 mmol) of the compound from Example 111 were stirred in 50 ml of dichloromethane and 50 ml of trifluoroacetic acid at RT for 1 h. The reaction mixture was concentrated to dryness on a rotary evaporator. The residue was admixed with ethyl acetate and a 1M sodium carbonate solution. The organic phase was separated, washed with a saturated sodium chloride solution, dried over sodium sulphate and concentrated on a rotary evaporator. The residue was dried under HV. This gave 1.66 g (84% of theory) of the title compound.

LC-MS (Method 1): $R_t$=1.03 min; m/z=515 (M+H)$^+$.

$^1$H NMR (400 MHz, DMSO-d$_6$): δ [ppm]=1.22 (t, 3H), 2.34-2.55 (m, 2H), 3.01-3.15 (m, 1H), 3.21-3.33 (m, 1H), 3.30 (s, 3H), 4.17 (q, 2H), 6.46 (br. m., 1H), 7.06-7.23 (m, 2H), 7.36 (t, 1H), 7.45-7.55 (m, 2H), 8.31 (s, 1H), 11.12 (br.s, 1H).

Example 113 ethyl 1-(3-ethyl-1-methyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer)

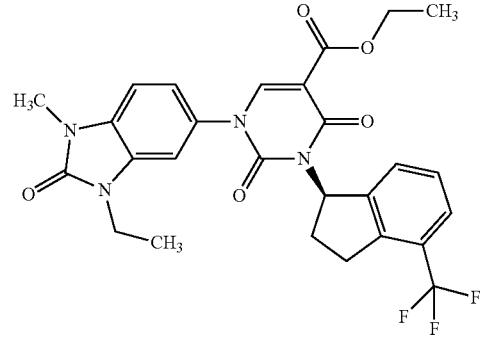 [SMILES: CCOC(=O)c1cn(-c2ccc3c(c2)n(CC)c(=O)n3C)c(=O)n([C@@H]2CCc3c2cccc3C(F)(F)F)c1=O]

100 mg (0.19 mmol) of ethyl 1-(1-methyl-2-oxo-2,3-dihydro-1H-benzimidazol-5-yl)-2,4-dioxo-3-[4-(trifluoromethyl)-2,3-dihydro-1H-inden-1-yl]-1,2,3,4-tetrahydropyrimidine-5-carboxylate (R enantiomer) from Example 112 were initially charged in DMF (3 ml). 36 mg (0.23 mmol) of iodoethane and 126 mg (0.38 mmol) of caesium carbonate were added. The reaction mixture was left to stir at 60° C. for 1 h. The reaction mixture cooled to RT was filtered and the filtrate was purified by preparative HPLC (Method 7). This gave 77 mg (72% of theory) of the title compound.

LC-MS (Method 4): $R_t$=2.40 min; m/z=543 (M+H)$^+$.

$^1$H NMR (400 MHz, CD$_2$Cl$_2$): δ [ppm]=1.22 (t, 6H), 2.31-2.45 (m, 1H), 2.45-2.56 (m, 1H), 2.99-3.12 (m, 1H), 3.32 (s, 3H), 3.35-3.43 (m, 1H), 3.82 (q, 2H), 4.20 (q, 2H), 6.48-6.59 (m, 1H), 6.88 (s, 1H), 6.91-6.98 (m, 2H), 7.17-7.29 (m, 2H), 7.41 (d, 1H), 8.24 (s, 1H).

Example 114 ethyl 1-(3-isopropyl-1-methyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer)

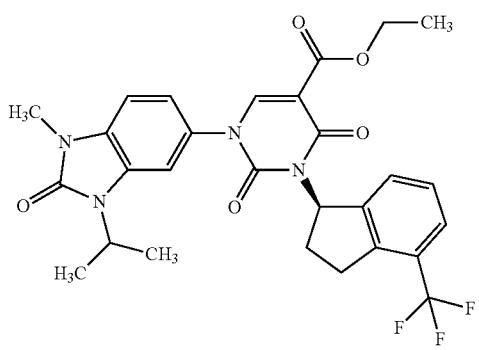 [SMILES: CCOC(=O)c1cn(-c2ccc3c(c2)n(C(C)C)c(=O)n3C)c(=O)n([C@@H]2CCc3c2cccc3C(F)(F)F)c1=O]

The preparation and purification of the title compound were analogous to Example 113. Proceeding from 200 mg (0.30 mmol) of ethyl 1-(1-methyl-2-oxo-2,3-dihydro-1H-benzimidazol-5-yl)-2,4-dioxo-3-[4-(trifluoromethyl)-2,3-dihydro-1H-inden-1-yl]-1,2,3,4-tetrahydropyrimidine-5-carboxylate (R enantiomer) from Example 112 and 79 mg (0.46 mmol) of 2-iodopropane, 125 mg (57% of theory) of the title compound were obtained.

LC-MS (Method 1): $R_t$=1.17 min; m/z=557 (M+H)$^+$.

$^1$H NMR (400 MHz, CD$_2$Cl$_2$): δ [ppm]=1.23 (t, 3H), 1.40-1.44 (m, 6H), 2.31-2.43 (m, 1H), 2.45-2.57 (m, 1H), 3.00-3.12 (m, 1H), 3.30 (s, 3H), 3.34-3.46 (m, 1H), 4.20 (q, 2H), 4.49-4.59 (m, 1H), 6.47-6.60 (m, 1H), 6.93 (s, 3H), 7.17-7.28 (m, 2H), 7.41 (d, 1H), 8.23 (s, 1H).

Example 115 ethyl 1-[1-methyl-2-oxo-3-(3,3,3-trifluoro-2-hydroxypropyl)-2,3-dihydro-1H-benzimidazol-5-yl]-2,4-dioxo-3-[(1R)-4-(trifluoromethyl)-2,3-dihydro-1H-inden-1-yl]-1,2,3,4-tetrahydropyrimidine-5-carboxylate (Diastereomer Mixture)

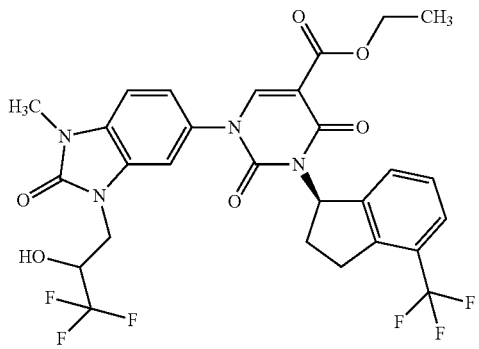 [SMILES: CCOC(=O)c1cn(-c2ccc3c(c2)n(CC(O)C(F)(F)F)c(=O)n3C)c(=O)n([C@@H]2CCc3c2cccc3C(F)(F)F)c1=O]

The preparation and purification of the title compound were analogous to Example 113, with a reaction time of 16 h. Proceeding from 250 mg (0.48 mmol) of ethyl 1-(1-methyl-2-oxo-2,3-dihydro-1H-benzimidazol-5-yl)-2,4-dioxo-3-[4-(trifluoromethyl)-2,3-dihydro-1H-inden-1-yl]-1,2,3,4-tetrahydropyrimidine-5-carboxylate (R enantiomer) from Example 112 and 112 mg (0.58 mmol) of 3-bromo-1,1,1-trifluoropropan-2-ol (Racemate), 186 mg (57% of theory) of the title compound were obtained.

LC-MS (Method 1): $R_t$=1.10 min; m/z=627 (M+H)$^+$.

$^1$H NMR (400 MHz, CD$_2$Cl$_2$): δ [ppm]=1.23 (t, 3H), 2.28-2.43 (m, 1H), 2.44-2.57 (m, 1H), 2.98-3.12 (m, 1H), 3.33-3.44 (m, 4H), 4.00-4.10 (m, 1H), 4.11-4.24 (m, 3H), 4.25-4.47 (m, 2H), 6.47-6.60 (m, 1H), 6.94-7.06 (m, 3H), 7.17-7.29 (m, 2H), 7.41 (d, 1H), 8.21 (s, 1H).

Example 116 ethyl 1-[1-methyl-2-oxo-3-(3,3,3-trifluoropropyl)-2,3-dihydro-1H-benzimidazol-5-yl]-2,4-dioxo-3-[(1R)-4-(trifluoromethyl)-2,3-dihydro-1H-inden-1-yl]1,2,3,4-tetrahydropyrimidine-5-carboxylate (R enantiomer)

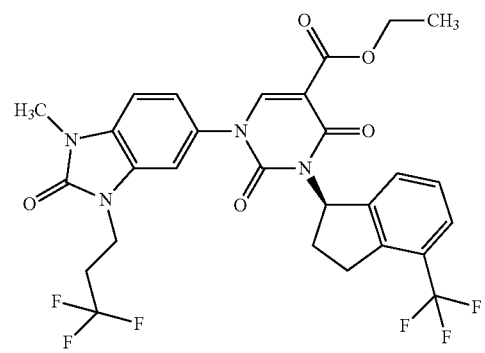 [SMILES: CCOC(=O)c1cn(-c2ccc3c(c2)n(CCC(F)(F)F)c(=O)n3C)c(=O)n([C@@H]2CCc3c2cccc3C(F)(F)F)c1=O]

250 mg (0.48 mmol) of ethyl 1-(1-methyl-2-oxo-2,3-dihydro-1H-benzimidazol-5-yl)-2,4-dioxo-3-[4-(trifluoromethyl)-2,3-dihydro-1H-inden-1-yl]-1,2,3,4-tetrahydropyrimidine-5-carboxylate (R enantiomer) from Example 112, 317 mg (0.97 mmol) of caesium carbonate, 2 mg (12 μmol) of potassium iodide and 103 mg (0.58 mmol) of 3-bromo-1,1,1-trifluoropropane in 7.5 ml of DMF were stirred at 60° C. Since conversion after 16 h was inadequate, an additional 1 eq. each of caesium carbonate and 3-bromo-1,1,1-trifluoropropane were added after 16 h and again after 40 h, and the mixture was stirred at 60° C. overnight. Subsequently, the reaction mixture cooled to RT was diluted with ethyl acetate and washed twice with 1 N hydrochloric acid. The organic phase was dried over sodium sulphate and the solvent was removed on a rotary evaporator. The residue was stirred in MTBE and the solid formed was filtered off with suction. The solid was unreacted reactant (88 mg). The filtrate was concentrated and the residue was purified by preparative HPLC (Method 7). This gave 106 mg (35% of theory) of the title compound.

LC-MS (Method 5): $R_t$=1.19 min; m/z=611 (M+H)$^+$.

$^1$H NMR (400 MHz, DMSO-d$_6$): δ [ppm]=1.22 (t, 3H), 2.36-2.44 (m, 1H), 2.44-2.48 (m, 1H), 2.69-2.82 (m, 2H), 3.03-3.15 (m, 1H), 3.23-3.30 (m, 1H), 3.37 (s, 3H), 4.10 (t, 2H), 4.18 (q, 2H), 6.36-6.55 (m, 1H), 7.17-7.32 (m, 2H), 7.37 (t, 1H), 7.45-7.51 (m, 2H), 7.51-7.56 (m, 1H), 8.35 (s, 1H).

Example 117 ethyl 1-(3-cyclopropyl-1-methyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer)

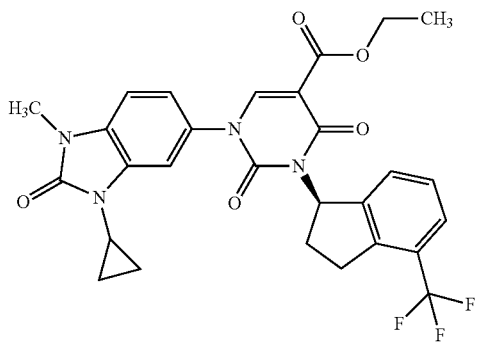 [SMILES: CCOC(=O)c1cn(-c2ccc3c(c2)n(C2CC2)c(=O)n3C)c(=O)n([C@@H]2CCc3c2cccc3C(F)(F)F)c1=O]

A mixture of 100 mg (0.19 mmol) of the compound from Example 112, 33.4 mg (0.39 mmol) of cyclopropylboronic acid, 24 mg (0.19 mmol) of copper (I) acetate, 41.2 mg (0.39 mmol) of sodium carbonate, 31 μl (0.39 mmol) of pyridine in 2 ml of toluene was stirred at 70° C. for 6 h. Subsequently, the reaction mixture cooled to RT was diluted with ethyl acetate and washed twice with 1 N hydrochloric acid. The organic phase was dried over sodium sulphate and the solvent was removed on a rotary evaporator. The residue was purified by preparative HPLC (Method 8). This gave 90 mg (84% of theory) of the title compound.

LC-MS (Method 1): $R_t$=1.09 min; m/z=555 (M+H)$^+$.

$^1$H NMR (400 MHz, CD$_2$Cl$_2$): δ [ppm]=0.92-1.01 (m, 2H), 1.04-1.11 (m, 2H), 1.31 (t, 3H), 2.39-2.51 (m, 1H), 2.53-2.65 (m, 1H), 2.86 (br. spt, 1H), 3.08-3.21 (m, 1H), 3.36 (s, 3H), 3.42-3.55 (m, 1H), 4.29 (q, 2H), 6.55-6.68 (m, 1H), 6.96-7.05 (m, 2H), 7.11-7.16 (m, 1H), 7.27-7.32 (m, 1H), 7.33 (d, 1H), 7.49 (d, 1H), 8.32 (s, 1H).

Example 118 ethyl 1-[3-(cyanomethyl)-1-methyl-2-oxo-2,3-dihydro-1H-benzimidazol-5-yl]-2,4-dioxo-3-[(1R)-4-(trifluoromethyl)-2,3-dihydro-1H-inden-1-yl]-1,2,3,4-tetrahydropyrimidine-5-carboxylate (R enantiomer)

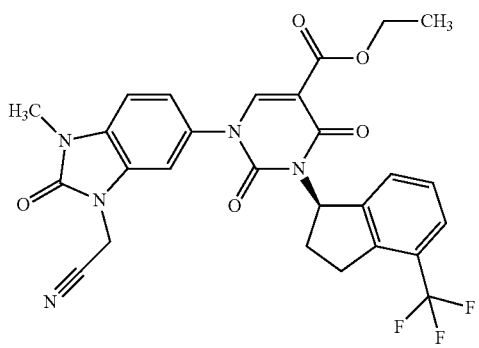 [SMILES: CCOC(=O)c1cn(-c2ccc3c(c2)n(CC#N)c(=O)n3C)c(=O)n([C@@H]2CCc3c2cccc3C(F)(F)F)c1=O]

200 mg (0.38 mmol) of ethyl 1-(1-methyl-2-oxo-2,3-dihydro-1H-benzimidazol-5-yl)-2,4-dioxo-3-[4-(trifluoromethyl)-2,3-dihydro-1H-inden-1-yl]-1,2,3,4-tetrahydropyrimidine-5-carboxylate (R enantiomer) from Example 112 were initially charged in acetonitrile (3.7 ml), and 93 mg (0.77 mmol) of bromoacetonitrile and 161 mg (1.16 mmol) of potassium carbonate were added. The reaction mixture was left to stir at 70° C. for 2 h. The reaction mixture cooled to RT was admixed with 3 ml of 1 N hydrochloric acid and stirred for 10 min. The whole mixture was separated directly by preparative HPLC (Method 7). This gave 180 mg (83% of theory) of the title compound.

LC-MS (Method 1): $R_t$=1.09 min; m/z=554 (M+H)$^+$.

$^1$H NMR (400 MHz, DMSO-d$_6$): δ [ppm]=1.22 (t, 3H), 2.38-2.47 (m, 2H), 3.03-3.15 (m, 1H), 3.23-3.28 (m, 1H), 3.40 (s, 3H), 4.17 (q, 2H), 5.13 (s, 2H), 6.35-6.56 (m, 1H), 7.26-7.40 (m, 3H), 7.46-7.61 (m, 3H), 8.36 (s, 1H).

Example 119 ethyl 1-(3-methyl-2-oxo-2,3-dihydro-1,3-benzothiazol-6-yl)-2,4-dioxo-3-[7-(trifluoromethyl)-2,3-dihydro-1-benzofur-3-yl]-1,2,3,4-tetrahydropyrimidine-5-carboxylate (Racemate)

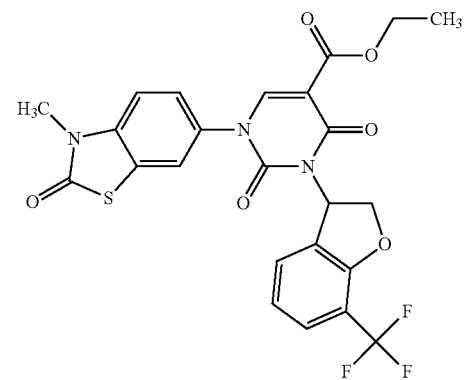 [SMILES: CCOC(=O)c1cn(-c2ccc3c(c2)sc(=O)n3C)c(=O)n(C2COc3c2cccc3C(F)(F)F)c1=O]

The preparation and purification of the title compound were analogous to Example 108. Proceeding from 71 mg (0.20 mmol) of ethyl 1-(3-methyl-2-oxo-2,3-dihydro-1,3-benzothiazol-6-yl)-2,4-dioxo-1,2,3,4-tetrahydropyrimidine-5-carboxylate from Example 31A and 50 mg (0.24 mmol) of 7-(trifluoromethyl)-2,3-dihydro-1-benzofuran-3-ol (Racemate) from Example 99A, 35 mg (31% of theory) of the title compound were obtained.

LC-MS (Method 4): $R_t$=2.35 min; m/z=534 (M+H)$^+$.

$^1$H NMR (400 MHz, CD$_2$Cl$_2$): δ [ppm]=1.24 (t, 3H), 3.37 (s, 3H), 4.22 (q, 2H), 4.69-4.75 (m, 1H), 4.79 (t, 1H), 6.75-6.82 (m, 1H), 6.87 (t, 1H), 7.05 (d, 1H), 7.22 (dd, 1H), 7.30 (d, 1H), 7.33-7.38 (m, 2H), 8.21 (s, 1H).

Example 120 ethyl 1-(1,3-dimethyl-2-oxo-2,3-dihydro-1H-benzimidazol-5-yl)-3-(5-methoxy-2,3-dihydro-1H-inden-1-yl)-2,4-dioxo-1,2,3,4-tetrahydropyrimidine-5-carboxylate (Racemate)

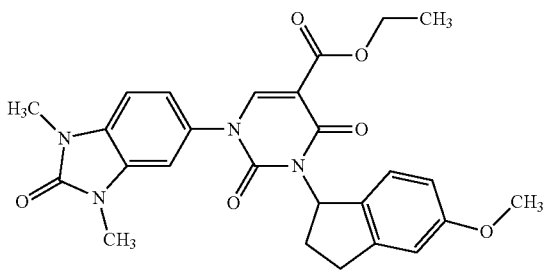 [SMILES: CCOC(=O)c1cn(-c2ccc3c(c2)n(C)c(=O)n3C)c(=O)n(C2CCc3cc(OC)ccc32)c1=O]

Under an argon atmosphere, 200 mg (0.58 mmol) of the compound from Example 2A and 457 mg (1.74 mmol) of triphenylphosphine were initially charged in 8 ml of DMF and 8 ml of THF and cooled to −40° C. 229 µl (1.16 mmol) of diisopropyl azodicarboxylate were added dropwise, then 155 mg (80% purity, 0.76 mmol) of the compound from Example 102A. The cooling bath was removed and the mixture was stirred at RT overnight. Subsequently, 25 ml of 1N hydrochloric acid were added and the mixture was stirred for a further 15 min. For workup, while cooling with ice, 5 ml of 1N hydrochloric acid were added to the reaction mixture, and the mixture was stirred further for 15 min, then extracted with ethyl acetate. The organic phase was washed twice with 1N hydrochloric acid, twice with a saturated sodium hydrogencarbonate solution, then with a saturated sodium chloride solution, then dried over sodium sulphate and concentrated on a rotary evaporator. The residue was purified by preparative HPLC (Method 7). This gave 89 mg (30% of theory) of the title compound.

LC-MS (Method 1): $R_t$=0.96 min; m/z=491 (M+H)$^+$.

$^1$H NMR (400 MHz, DMSO-$d_6$): δ [ppm]=1.22 (t, 3H), 2.24-2.48 (m, 2H), 2.80-2.96 (m, 1H), 3.09-3.21 (m, 1H), 3.31 (s, 3H), 3.36 (s, 3H), 3.72 (s, 3H), 4.17 (q, 2H), 6.25-6.48 (m, 1H), 6.69 (dd, 1H), 6.78 (s, 1H), 7.04 (d, 1H), 7.10-7.29 (m, 2H), 7.37 (br.s, 1H), 8.30 (s, 1H).

Example 121

1-(1,3-dimethyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylic acid

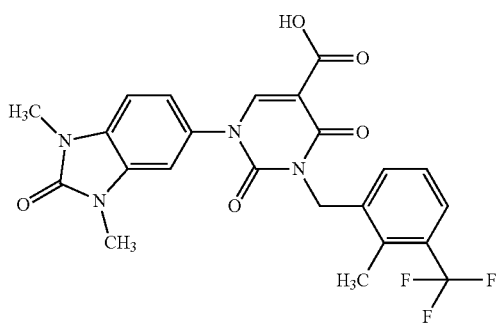

5.60 g (10.84 mmol) of ethyl 1-(1,3-dimethyl-2-oxo-2,3-dihydro-1H-benzimidazol-5-yl)-3-[2-methyl-3-(trifluoromethyl)-benzyl]-2,4-dioxo-1,2,3,4-tetrahydropyrimidine-5-carboxylate from Example 1 were initially charged in 78 ml of glacial acetic acid and 39 ml of conc. hydrochloric acid and stirred at 120° C. for 1 h. Subsequently, the mixture cooled to RT was admixed with water and the precipitate was filtered off with suction. The solid was washed successively with water and MTBE and then dried at 50° C. under reduced pressure. This gave 5.11 g (96% of theory) of the title compound.

LC-MS (Method 1): $R_t$=0.98 min; m/z=489 (M+H)$^+$.

$^1$H NMR (400 MHz, DMSO-$d_6$): δ [ppm]=2.47 (s, 3H), 3.31 (s, 3H), 3.37 (s, 3H), 5.11 (s, 2H), 7.22-7.30 (m, 2H), 7.33-7.43 (m, 3H), 7.59-7.63 (m, 1H), 8.45 (s, 1H), 12.73 (br.s, 1H).

Example 122

3-[2,3-bis(trifluoromethyl)benzyl]-1-(1,3-dimethyl-2-oxo-2,3-dihydro-1H-benzimidazol-5-yl)-2,4-dioxo-1,2,3,4-tetrahydropyrimidine-5-carboxylic acid

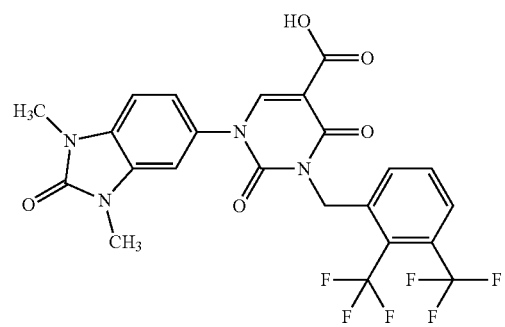 [SMILES: Cn1c(=O)n(C)c2cc(-n3cc(C(=O)O)c(=O)n(Cc4cccc(C(F)(F)F)c4C(F)(F)F)c3=O)ccc21]

The preparation and purification of the title compound were analogous to Example 121. Proceeding from 114 mg (0.20 mmol) of ethyl 3-[2,3-bis(trifluoromethyl)benzyl]-dimethyl-2-oxo-2,3-dihydro-1H-benzimidazol-5-yl)-2,4-dioxo-1,2,3,4-tetrahydropyrimidine-5-carboxylate from Example 8, 92 mg (85% of theory) of the title compound were obtained.

LC-MS (Method 1): $R_t$=1.01 min; m/z=543 (M+H)$^+$.

$^1$H NMR (400 MHz, DMSO-$d_6$): δ [ppm]=3.34 (s, 3H), 3.37 (s, 3H), 5.27 (m, 2H), 7.22-7.30 (m, 2H), 7.37-7.40 (m, 1H), 7.73-7.77 (m, 1H), 7.82-7.88 (m, 1H), 7.96-8.00 (m, 1H), 8.47 (s, 1H), 12.73 (br.s, 1H).

Example 123

3-[2-chloro-3-(trifluoromethyl)benzyl]-1-(1,3-dimethyl-2-oxo-2,3-dihydro-1H-benzimidazol-5-yl)-2,4-dioxo-1,2,3,4-tetrahydropyrimidine-5-carboxylic acid

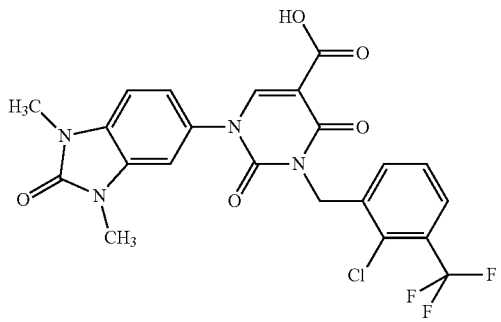 [SMILES: Cn1c(=O)n(C)c2cc(-n3cc(C(=O)O)c(=O)n(Cc4cccc(C(F)(F)F)c4Cl)c3=O)ccc21]

The preparation and purification of the title compound were analogous to Example 121. Proceeding from 200 mg (0.37 mmol) of ethyl 3-[2-chloro-3-(trifluoromethyl)benzyl]-1-(1,3-dimethyl-2-oxo-2,3-dihydro-1H-benzimidazol-5-yl)-2,4-dioxo-1,2,3,4-tetrahydropyrimidine-5-carboxylate from Example 2, 67 mg (88% of theory) of the title compound were obtained.

LC-MS (Method 3): $R_t$=1.21 min; m/z=509 (M+H)$^+$.

$^1$H NMR (400 MHz, DMSO-d$_6$): δ [ppm]=3.34 (s, 3H), 3.37 (s, 3H), 5.18 (s, 2H), 7.22-7.30 (m, 2H), 7.38-7.41 (m, 1H), 7.51-7.57 (m, 1H), 7.58-7.63 (m, 1H), 7.78-7.83 (m, 1H), 8.47 (s, 1H), 12.72 (br.s, 1H).

Example 124

3-(2,3-dichlorobenzyl)-1-(1,3-dimethyl-2-oxo-2,3-dihydro-1H-benzimidazol-5-yl)-2,4-dioxo-1,2,3,4-tetrahydropyrimidine-5-carboxylic acid

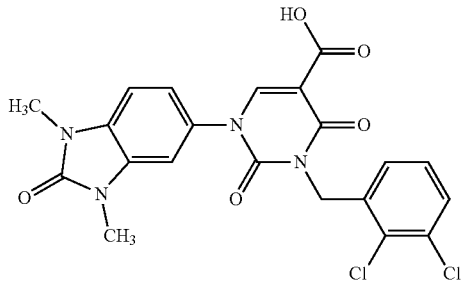 [SMILES: Cn1c(=O)n(C)c2cc(-n3cc(C(=O)O)c(=O)n(Cc4cccc(Cl)c4Cl)c3=O)ccc21]

The preparation and purification of the title compound were in analogy to Example 121. Proceeding from 200 mg (0.40 mmol) of ethyl 3-(2,3-dichlorobenzyl)-1-(1,3-dimethyl-2-oxo-2,3-dihydro-1H-benzimidazol-5-yl)-2,4-dioxo-1,2,3,4-tetrahydropyrimidine-5-carboxylate from Example 3, 147 mg (78% of theory) of the title compound were obtained.

LC-MS (Method 1): $R_t$=1.00 min; m/z=475 (M+H)±.

$^1$H NMR (400 MHz, DMSO-d$_6$): δ [ppm]=3.34 (s, 3H), 3.37 (s, 3H), 5.13 (s, 2H), 7.22-7.30 (m, 3H), 7.31-7.37 (m, 1H), 7.38-7.41 (m, 1H), 7.57-7.61 (m, 1H), 8.45 (s, 1H), 12.72 (br.s, 1H).

Example 125

1-(1,3-dimethyl-2-oxo-2,3-dihydro-1H-benzimidazol-5-yl)-3-[3-fluoro-2-(trifluoromethyl)benzyl]-2,4-dioxo-1,2,3,4-tetrahydropyrimidine-5-carboxylic acid

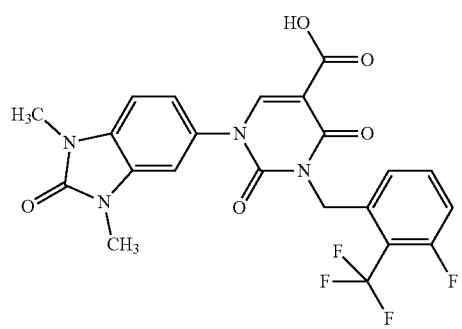 [SMILES: Cn1c(=O)n(C)c2cc(-n3cc(C(=O)O)c(=O)n(Cc4cccc(F)c4C(F)(F)F)c3=O)ccc21]

The preparation and purification of the title compound were in analogy to Example 121. Proceeding from 170 mg (0.33 mmol) of ethyl 1-(1,3-dimethyl-2-oxo-2,3-dihydro-1H-benzimidazol-5-yl)-3-[3-fluoro-2-(trifluoromethyl)benzyl]-2,4-dioxo-1,2,3,4-tetrahydropyrimidine-5-carboxylate from Example 5, 141 mg (87% of theory) of the title compound were obtained.

LC-MS (Method 1): $R_t$=0.98 min; m/z=493 (M+H)$^+$.

$^1$H NMR (400 MHz, DMSO-d$_6$): δ [ppm]=3.34 (s, 3H), 3.37 (s, 3H), 5.22 (s, 2H), 7.19-7.30 (m, 3H), 7.36-7.45 (m, 2H), 7.63-7.71 (m, 1H), 8.47 (s, 1H), 12.71 (br.s, 1H).

Example 126

1-(1,3-dimethyl-2-oxo-2,3-dihydro-1H-benzimidazol-5-yl)-3-[2-fluoro-3-(trifluoromethyl)benzyl]-2,4-dioxo-1,2,3,4-tetrahydropyrimidine-5-carboxylic acid

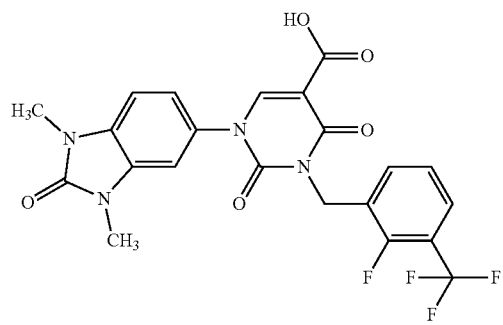

The preparation and purification of the title compound were in analogy to Example 121. Proceeding from 161 mg (0.31 mmol) of ethyl 1-(1,3-dimethyl-2-oxo-2,3-dihydro-1H-benzimidazol-5-yl)-3-[2-fluoro-3-(trifluoromethyl)benzyl]-2,4-dioxo-1,2,3,4-tetrahydropyrimidine-5-carboxylate from Example 4, 115 mg (76% of theory) of the title compound were obtained.

LC-MS (Method 1): $R_t$=0.98 min; m/z=493 (M+H)$^+$.

$^1$H NMR (400 MHz, DMSO-d$_6$): δ [ppm]=3.34 (s, 3H), 3.36-3.39 (m, 3H), 5.17 (s, 2H), 7.21-7.29 (m, 2H), 7.38 (s, 2H), 7.65-7.74 (m, 2H), 8.42 (s, 1H), 12.72 (br.s, 1H).

Example 127

3-(2-chloro-3,6-difluorobenzyl)-1-(1,3-dimethyl-2-oxo-2,3-dihydro-1H-benzimidazol-5-yl)-2,4-dioxo-1,2,3,4-tetrahydropyrimidine-5-carboxylic acid

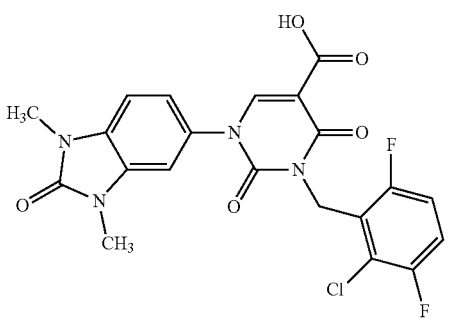 [SMILES: Cn1c(=O)n(C)c2cc(-n3cc(C(=O)O)c(=O)n(Cc4c(F)ccc(F)c4Cl)c3=O)ccc21]

The preparation and purification of the title compound were in analogy to Example 121, with reaction time 30 min. Proceeding from 110 mg (0.22 mmol) of ethyl 3-(2-chloro-3,6-difluorobenzyl)-1-(1,3-dimethyl-2-oxo-2,3-dihydro-1H-benzimidazol-5-yl)-2,4-dioxo-1,2,3,4-tetrahydropyrimidine-5-carboxylate from Example 6, 80 mg (76% of theory) of the title compound were obtained.

LC-MS (Method 1): R$_t$=0.93 min; m/z=477 (M+H)$^+$.

$^1$H NMR (400 MHz, DMSO-d$_6$): δ [ppm]=3.2-3.4 (2 s, concealed by water signal), 5.24 (s, 2H), 7.14-7.19 (m, 1H), 7.23-7.32 (m, 2H), 7.32-7.36 (m, 1H), 7.40-7.48 (m, 1H), 8.39 (s, 1H), 12.74 (br.s, 1H).

Example 128

3-(3-chloro-2-methylbenzyl)-1-(1,3-dimethyl-2-oxo-2,3-dihydro-1H-benzimidazol-5-yl)-2,4-dioxo-1,2,3,4-tetrahydropyrimidine-5-carboxylic acid

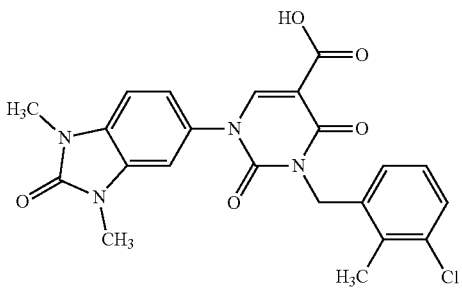 [SMILES: Cc1c(Cl)cccc1Cn1c(=O)c(C(=O)O)cn(-c2ccc3c(c2)n(C)c(=O)n3C)c1=O]

The preparation and purification of the title compound were in analogy to Example 121, with a reaction time of 30 min. Proceeding from 75 mg (0.16 mmol) of ethyl 3-(3-chloro-2-methylbenzyl)-1-(1,3-dimethyl-2-oxo-2,3-dihydro-1H-benzimidazol-5-yl)-2,4-dioxo-1,2,3,4-tetrahydropyrimidine-5-carboxylate from Example 7, 62 mg (87% of theory) of the title compound were obtained.

LC-MS (Method 1): R$_t$=0.96 min; m/z=455 (M+H)$^+$.

$^1$H NMR (400 MHz, DMSO-d$_6$): δ [ppm]=2.41 (s, 3H), 3.34 (s, 3H), 3.37 (s, 3H), 5.08 (s, 2H), 7.06-7.09 (m, 1H), 7.17 (t, 1H), 7.22-7.29 (m, 2H), 7.33-7.37 (m, 1H), 7.39-7.42 (m, 1H), 8.44 (s, 1H), 12.73 (br.s, 1H).

Example 129

3-(3-chloro-5-fluorobenzyl)-1-(1,3-dimethyl-2-oxo-2,3-dihydro-1H-benzimidazol-5-yl)-2,4-dioxo-1,2,3,4-tetrahydropyrimidine-5-carboxylic acid

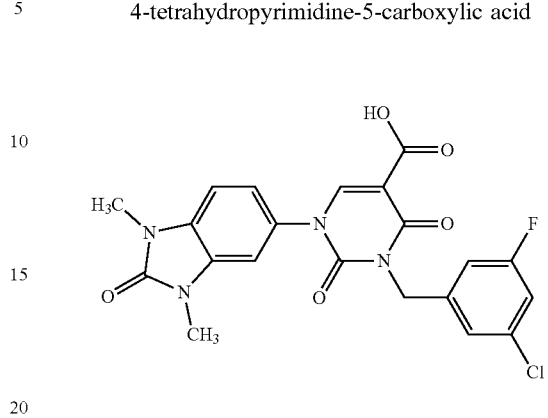

The preparation and purification of the title compound were analogous to Example 121. The reaction time was 45 min. Proceeding from 244 mg (0.50 mmol) of ethyl 3-(3-chloro-5-fluorobenzyl)-1-(1,3-dimethyl-2-oxo-2,3-dihydro-1H-benzimidazol-5-yl)-2,4-dioxo-1,2,3,4-tetrahydropyrimidine-5-carboxylate from Example 9, 198 mg (85% of theory) of the title compound were obtained.

LC-MS (Method 1): R$_t$=0.98 min; m/z=459 (M+H)$^+$.

$^1$H NMR (400 MHz, DMSO-d$_6$): δ [ppm]=3.31 (s, 3H), 3.37 (s, 3H), 5.02-5.09 (m, 2H), 7.19-7.33 (m, 4H), 7.33-7.38 (m, 1H), 7.39 (s, 1H), 8.39 (s, 1H), 12.73 (s, 1H).

Example 130

1-(1,3-dimethyl-2-oxo-2,3-dihydro-1H-benzimidazol-5-yl)-3-[3-fluoro-5-(trifluoromethyl)benzyl]-2,4-dioxo-1,2,3,4-tetrahydropyrimidine-5-carboxylic acid

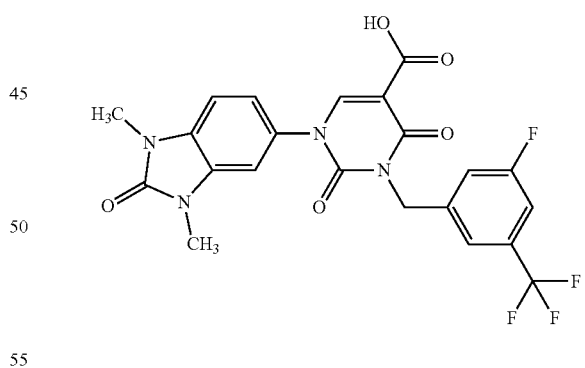

The preparation and purification of the title compound were analogous to Example 121. The reaction time was 45 min. Proceeding from 268 mg (0.51 mmol) of ethyl 1-(1,3-dimethyl-2-oxo-2,3-dihydro-1H-benzimidazol-5-yl)-3-[3-fluoro-5-(trifluoromethyl)benzyl]-2,4-dioxo-1,2,3,4-tetrahydropyrimidine-5-carboxylate from Example 10, 215 mg (84% of theory) of the title compound were obtained.

LC-MS (Method 1): R$_t$=1.00 min; m/z=493 (M+H)$^+$.

$^1$H NMR (400 MHz, DMSO-d$_6$): δ [ppm]=3.31 (s, 3H), 3.37 (s, 3H), 5.15 (s, 2H), 7.23 (dd, 1H), 7.28 (d, 1H), 7.38 (d, 1H), 7.54 (d, 1H), 7.58-7.65 (m, 2H), 8.40 (s, 1H), 12.73 (s, 1H).

Example 131

1-(1,3-dimethyl-2-oxo-2,3-dihydro-1H-benzimidazol-5-yl)-2,4-dioxo-3-[4-(trifluoromethyl)-2,3-dihydro-1H-inden-1-yl]-1,2,3,4-tetrahydropyrimidine-5-carboxylic acid (Racemate)

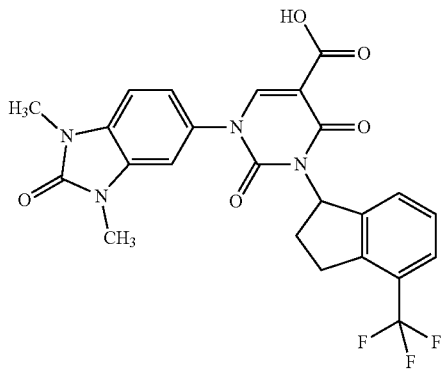 [SMILES: Cn1c(=O)n(C)c2cc(-n3cc(C(=O)O)c(=O)n(C4CCc5c4cccc5C(F)(F)F)c3=O)ccc21]

103 mg (0.19 mmol) of ethyl 1-(1,3-dimethyl-2-oxo-2,3-dihydro-1H-benzimidazol-5-yl)-2,4-dioxo-3-[4-(trifluoromethyl)-2,3-dihydro-1H-inden-1-yl]-1,2,3,4-tetrahydropyrimidine-5-carboxylate from Example 11 were initially charged in acetonitrile/water 1.5:1 (2.5 ml), 36 mg (0.43 mmol) of sodium hydrogencarbonate were added and the mixture was stirred at 80° C. for 4 h. The cooled reaction mixture was acidified with 1N hydrochloric acid and extracted twice with ethyl acetate, and the combined organic phases were dried over magnesium sulphate, filtered and concentrated. The residue was separated by means of HPLC (Method 7). The product fractions were almost completely concentrated on a rotary evaporator, and the precipitated solid was filtered off and dried at the high-vacuum pump. This gave 32 mg (33% of theory) of the title compound.

LC-MS (Method 1): $R_t$=1.01 min; m/z=501 (M+H)$^+$.

$^1$H NMR (400 MHz, DMSO-d$_6$): δ [ppm]=2.39-2.46 (m, 1H), 2.46-2.48 (m, 1H, partly concealed by DMSO signal), 3.04-3.16 (m, 1H), 3.23-3.29 (in, 1H, partly concealed by water signal), 3.31 (s, 3H), 3.35-3.38 (m, 3H), 6.36-6.60 (m, 1H), 7.13-7.29 (m, 2H), 7.31-7.42 (m, 2H), 7.49-7.57 (m, 2H), 8.38 (s, 1H), 12.70 (br.s, 1H).

Example 132

1-(1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

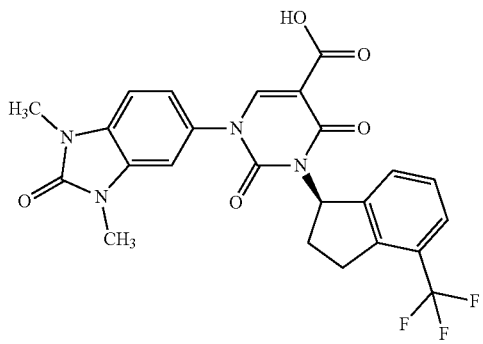 [SMILES: Cn1c(=O)n(C)c2cc(-n3cc(C(=O)O)c(=O)n([C@@H]4CCc5c4cccc5C(F)(F)F)c3=O)ccc21]

4.20 g (7.79 mmol) of ethyl 1-(1,3-dimethyl-2-oxo-2,3-dihydro-1H-benzimidazol-5-yl)-2,4-dioxo-3-[4-(trifluoromethyl)-2,3-dihydro-1H-inden-1-yl]-1,2,3,4-tetrahydropyrimidine-5-carboxylate from Example 13 were stirred with 40 ml of glacial acetic acid and 20 ml of conc. hydrochloric acid at reflux temperature for 1 h. The reaction mixture was cooled to RT, then diluted with 300 ml of water. The precipitated solid was filtered off with suction, washed with a little water and dried under HV. The solid thus obtained was stirred with 45 ml of toluene. At first it dissolved completely, but after a few minutes a crystalline solid formed. The mixture was cooled to 0° C. and stirred at this temperature for 30 min. Subsequently, the solid was filtered off, washed with 5 ml of toluene and dried under HV. This gave 3.17 g (81% of theory) of the title compound.

LC-MS (Method 1): $R_t$=1.06 min; m/z=501 (M+H)$^+$.

$^1$H NMR (400 MHz, DMSO-d$_6$): δ [ppm]=2.38-2.46 (m, 1H), 2.46-2.60 (m, 1H partly hidden under DMSO signal), 3.10 (dt, 1H), 3.23-3.35 (m, 1H partly hidden under DMSO signal), 3.31 (s, 4H), 3.36 (s, 3H), 6.36-6.60 (m, 1H), 7.12-7.30 (m, 2H), 7.31-7.43 (m, 2H), 7.48-7.58 (m, 2H), 8.38 (s, 1H), 12.71 (br.s, 1H).

$^1$H NMR (400 MHz, CD$_2$Cl$_2$): δ [ppm]=2.42-2.53 (m, 1H), 2.60-2.72 (m, 1H), 3.11-3.25 (m, 1H), 3.39 (s, 3H), 3.41 (s, 3H), 3.45-3.55 (m, 1H), 6.59-6.71 (m, 1H), 6.94 (br. s, 1H), 7.04 (s, 2H), 7.28-7.41 (m, 2H), 7.54 (d, 1H), 8.57 (s, 1H), 12.45 (br. s, 1H).

In an analogous experiment, it was possible to isolate a fraction with 99% purity. For this batch, the specific optical rotation measured was:

Specific optical rotation: $\alpha_D^{20}$=+110.6°, (methanol, c=0.405 g/100 ml).

An x-ray structure analysis in the complex with chymase confirmed the R configuration for this enantiomer.

Example 133

1-(1,3-dimethyl-2-oxo-2,3-dihydro-1H-benzimidazol-5-yl)-2,4-dioxo-3-[(1S)-4-(trifluoromethyl)-2,3-dihydro-1H-inden-1-yl]-1,2,3,4-tetrahydropyrimidine-5-carboxylic acid (S enantiomer)

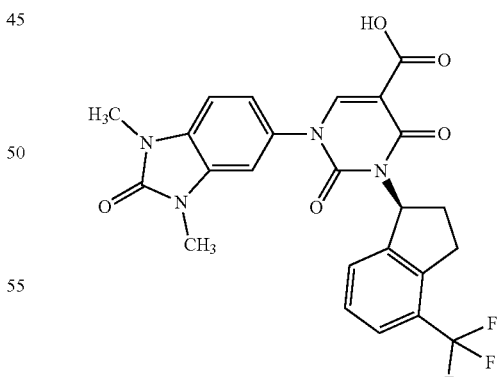

5.10 g (9.65 mmol) of the compound from Example 12 were stirred in 50 ml of glacial acetic acid and 25 ml of conc. hydrochloric acid at reflux temperature for 15 mm. After cooling to RT, the mixture was diluted with 5 ml of acetonitrile and separated in portions by preparative HPLC (Method 7). This gave 4.5 g (93% of theory) of the title compound.

LC-MS (Method 1): $R_t$=1.02 min; m/z=501 (M+H)$^+$.

$^1$H NMR (400 MHz, CD$_2$Cl$_2$): δ [ppm]=2.33-2.46 (m, 1H), 2.58 (dtd, 1H), 3.04-3.16 (m, 1H), 3.30 (s, 3H), 3.33 (s, 3H), 3.36-3.47 (m, 1H), 6.50-6.66 (m, 1H), 6.86 (br.s, 1H), 6.95 (br. s, 2H), 7.20-7.33 (m, 2H), 7.46 (d, 1H), 8.49 (s, 1H), 12.38 (br.s, 1H).

Example 134

1-(6-fluoro-1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

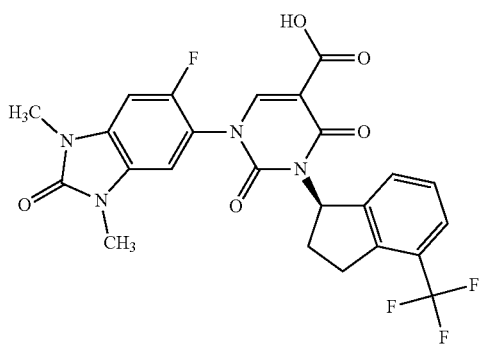 [SMILES: Cn1c(=O)n(C)c2cc(-n3cc(C(=O)O)c(=O)n([C@@H]4CCc5c4cccc5C(F)(F)F)c3=O)c(F)cc21]

The preparation and purification of the title compound were analogous to Example 121, with reaction time 45 min. Proceeding from 120 mg (0.22 mmol) of ethyl 1-(6-fluoro-1,3-dimethyl-2-oxo-2,3-dihydro-1H-benzimidazol-5-yl)-2,4-dioxo-3-[4-(trifluoromethyl)-2,3-dihydro-1H-inden-1-yl]-1,2,3,4-tetrahydropyrimidine-5-carboxylate from Example 104, after additional purification by means of HPLC (Method 8), 92 mg (80% of theory) of the title compound were obtained.

LC-MS (Method 5): R$_t$=1.09 min; m/z=519 (M+H)$^+$.

$^1$H NMR (400 MHz, CD$_2$Cl$_2$): δ [ppm]=2.31-2.43 (m, 1H), 2.51-2.62 (m, 1H), 3.03-3.14 (m, 1H), 3.28 (s, 3H), 3.29 (s, 3H), 3.34-3.47 (m, 1H), 6.50-6.58 (m, 1H), 6.76-6.84 (m, 2H), 7.21-7.27 (m, 2H), 7.41-7.47 (m, 1H), 8.41 (s, 1H), 12.31 (s, 1H).

Example 135

3-[2-chloro-3-(trifluoromethyl)benzyl]-1-(1,3-diethyl-2-oxo-2,3-dihydro-1H-benzimidazol-5-yl)-2,4-dioxo-1,2,3,4-tetrahydropyrimidine-5-carboxylic acid

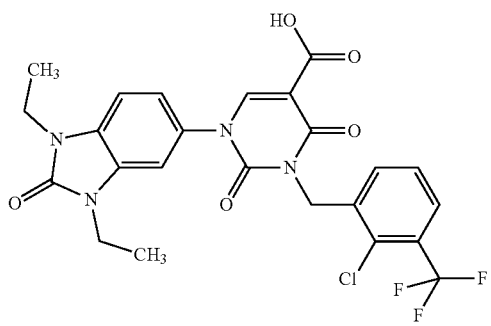 [SMILES: CCn1c(=O)n(CC)c2cc(-n3cc(C(=O)O)c(=O)n(Cc4cccc(C(F)(F)F)c4Cl)c3=O)ccc21]

The preparation and purification of the title compound were in analogy to Example 121. Proceeding from 170 mg (0.30 mmol) of ethyl 3-[2-chloro-3-(trifluoromethyl)benzyl]-1-(1,3-diethyl-2-oxo-2,3-dihydro-1H-benzimidazol-5-yl)-2,4-dioxo-1,2,3,4-tetrahydropyrimidine-5-carboxylate from Example 21, 133 mg (82% of theory) of the title compound were obtained.

LC-MS (Method 1): R$_t$=1.20 min; m/z=537 (M+H)$^+$.

$^1$H NMR (400 MHz, DMSO-d$_6$): δ [ppm]=1.22 (t, 6H), 3.82-3.96 (m, 4H), 5.18 (s, 2H), 7.21-7.27 (m, 1H), 7.34 (d, 1H), 7.43-7.48 (m, 1H), 7.50-7.63 (m, 2H), 7.77-7.84 (m, 1H), 8.50 (s, 1H), 12.71 (br.s, 1H).

Example 136

1-(1,3-diethyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylic acid

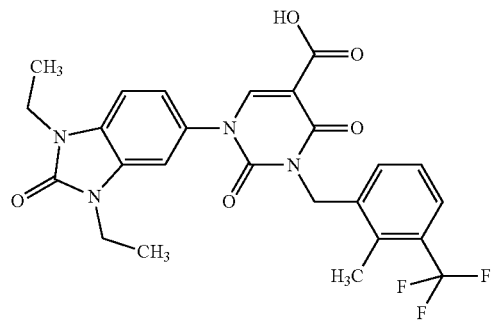 [SMILES: CCn1c(=O)n(CC)c2cc(-n3cc(C(=O)O)c(=O)n(Cc4cccc(C(F)(F)F)c4C)c3=O)ccc21]

The preparation and purification of the title compound were in analogy to Example 121. Proceeding from 170 mg (0.31 mmol) of ethyl 1-(1,3-diethyl-2-oxo-2,3-dihydro-1H-benzimidazol-5-yl)-3-[2-methyl-3-(trifluoromethyl)-benzyl]-2,4-dioxo-1,2,3,4-tetrahydropyrimidine-5-carboxylate from Example 22, 144 mg (89% of theory) of the title compound were obtained.

LC-MS (Method 1): R$_t$=1.10 min; m/z=517 (M+H)$^+$.

$^1$H NMR (400 MHz, DMSO-d$_6$): δ [ppm]=1.22 (t, 6H), 2.47 (s, 3H), 3.84-3.95 (m, 4H), 5.12 (s, 2H), 7.22-7.26 (m, 1H), 7.33 (s, 3H), 7.46-7.48 (m, 1H), 7.59-7.63 (m, 1H), 8.49 (s, 1H), 12.72 (br.s, 1H).

Example 137

3-(2,3-dichlorobenzyl)-1-(1,3-diethyl-2-oxo-2,3-dihydro-1H-benzimidazol-5-yl)-2,4-dioxo-1,2,3,4-tetrahydropyrimidine-5-carboxylic acid

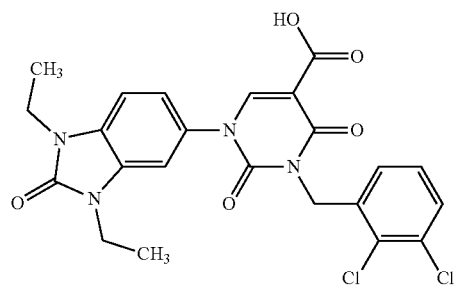 [SMILES: CCn1c(=O)n(CC)c2cc(-n3cc(C(=O)O)c(=O)n(Cc4cccc(Cl)c4Cl)c3=O)ccc21]

The preparation and purification of the title compound were in analogy to Example 121. Proceeding from 244 mg (0.46 mmol) of ethyl 3-(2,3-dichlorobenzyl)-1-(1,3-diethyl-2-oxo-2,3-dihydro-1H-benzimidazol-5-yl)-2,4-dioxo-1,2,3,4-tetrahydropyrimidine-5-carboxylate from Example 23, 188 mg (81% of theory) of the title compound were obtained.

LC-MS (Method 1): $R_t$=1.08 min; m/z=503 (M+H)±.
$^1$H NMR (400 MHz, DMSO-$d_6$): δ [ppm]=1.22 (t, 6H), 3.83-3.95 (m, 4H), 5.14 (s, 2H), 7.21-7.27 (m, 2H), 7.31-7.37 (m, 2H), 7.45-7.47 (m, 1H), 7.57-7.61 (m, 1H), 8.49 (s, 1H), 12.71 (br.s, 1H).

Example 138

1-(1,3-diethyl-2-oxo-2,3-dihydro-1H-benzimidazol-5-yl)-3-[3-fluoro-2-(trifluoromethyl)benzyl]-2,4-dioxo-1,2,3,4-tetrahydropyrimidine-5-carboxylic acid

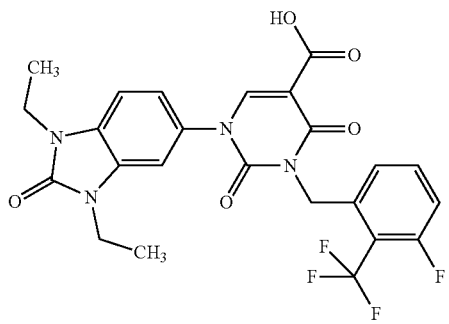 [SMILES: CCn1c(=O)n(CC)c2cc(-n3cc(C(=O)O)c(=O)n(Cc4cccc(F)c4C(F)(F)F)c3=O)ccc21]

The preparation and purification of the title compound were in analogy to Example 121. Proceeding from 167 mg (0.30 mmol) of ethyl 1-(1,3-diethyl-2-oxo-2,3-dihydro-1H-benzimidazol-5-yl)-3-[3-fluoro-2-(trifluoromethyl)benzyl]-2,4-dioxo-1,2,3,4-tetrahydropyrimidine-5-carboxylate from Example 24, 96 mg (61% of theory) of the title compound were obtained.

LC-MS (Method 3): $R_t$=1.24 min; m/z=521 (M+H)$^+$.
$^1$H NMR (400 MHz, DMSO-$d_6$): δ [ppm]=1.22 (t, 6H), 3.83-3.96 (m, 4H), 5.23 (s, 2H), 7.19-7.26 (m, 2H), 7.31-7.37 (m, 1H), 7.37-7.48 (m, 2H), 7.63-7.72 (m, 1H), 8.50 (s, 1H), 12.71 (br.s, 1H).

Example 139

3-[3-chloro-2-(trifluoromethyl)benzyl]-1-(3-ethyl-1-methyl-2-oxo-2,3-dihydro-1H-benzimidazol-5-yl)-2,4-dioxo-1,2,3,4-tetrahydropyrimidine-5-carboxylic acid

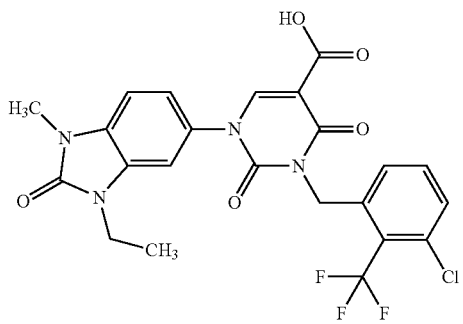 [SMILES: CCn1c(=O)n(C)c2ccc(-n3cc(C(=O)O)c(=O)n(Cc4cccc(Cl)c4C(F)(F)F)c3=O)cc21]

The preparation and purification of the title compound were in analogy to Example 121. Proceeding from 73 mg (0.13 mmol) of ethyl 3-[3-chloro-2-(trifluoromethyl)benzyl]-1-(3-ethyl-1-methyl-2-oxo-2,3-dihydro-1H-benzimidazol-5-yl)-2,4-dioxo-1,2,3,4-tetrahydropyrimidine-5-carboxylate from Example 18, 50 mg (69% of theory) of the title compound were obtained.

LC-MS (Method 1): $R_t$=1.08 min; m/z=523 (M+H)$^+$.
$^1$H NMR (400 MHz, DMSO-$d_6$): δ [ppm]=1.22 (t, 3H), 3.37 (s, 3H), 3.88 (q, 2H), 5.21-5.27 (m, 2H), 7.21-7.30 (m, 2H), 7.33-7.37 (m, 1H), 7.43-7.46 (m, 1H), 7.58-7.68 (m, 2H), 8.49 (s, 1H), 12.72 (br.s, 1H).

Example 140

3-[2-chloro-3-(trifluoromethyl)benzyl]-1-(3-ethyl-1-methyl-2-oxo-2,3-dihydro-1H-benzimidazol-5-yl)-2,4-dioxo-1,2,3,4-tetrahydropyrimidine-5-carboxylic acid

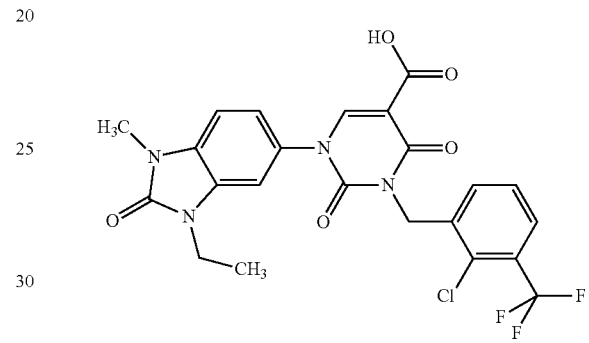

The preparation and purification of the title compound were in analogy to Example 121. Proceeding from 75 mg (0.14 mmol) of ethyl 3-[2-chloro-3-(trifluoromethyl)benzyl]-1-(3-ethyl-1-methyl-2-oxo-2,3-dihydro-1H-benzimidazol-5-yl)-2,4-dioxo-1,2,3,4-tetrahydropyrimidine-5-carboxylate from Example 19, 35 mg (49% of theory) of the title compound were obtained.

LC-MS (Method 1): $R_t$=1.02 min; m/z=523 (M+H)$^+$.
$^1$H NMR (400 MHz, DMSO-$d_6$): δ [ppm]=1.22 (t, 3H), 3.37 (s, 3H), 3.88 (q, 2H), 5.18 (s, 2H), 7.22-7.30 (m, 2H), 7.44-7.47 (m, 1H), 7.51-7.57 (m, 1H), 7.58-7.62 (m, 1H), 7.79-7.83 (m, 1H), 8.49 (s, 1H), 12.73 (br.s, 1H).

Example 141

1-(3-ethyl-1-methyl-2-oxo-2,3-dihydro-1H-benzimidazol-5-yl)-3-[2-methyl-3-(trifluoromethyl)-benzyl]-2,4-dioxo-1,2,3,4-tetrahydropyrimidine-5-carboxylic acid

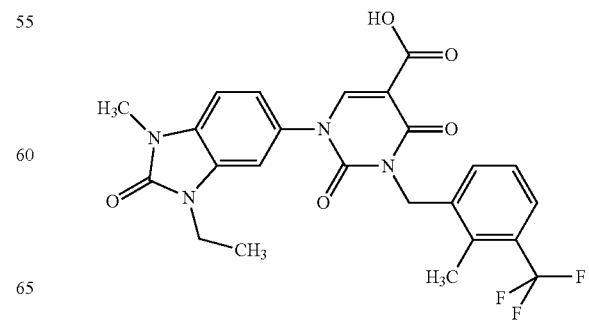

The preparation and purification of the title compound were in analogy to Example 121. Proceeding from 53 mg (0.10 mmol) of ethyl 1-(3-ethyl-1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate from Example 20, 23 mg (46% of theory) of the title compound were obtained.

LC-MS (Method 1): $R_t$=1.06 min; m/z=503 (M+H)$^+$.
$^1$H NMR (400 MHz, DMSO-d$_6$): δ [ppm]=1.22 (t, 3H), 2.47 (s, 3H), 3.37 (s, 3H), 3.87 (q, 2H), 5.11 (s, 2H), 7.22-7.30 (m, 2H), 7.33-7.43 (m, 2H), 7.46-7.49 (m, 1H), 7.59-7.64 (m, 1H), 8.48 (s, 1H), 12.74 (br.s, 1H).

Example 142

3-[3-chloro-2-(trifluoromethyl)benzyl]-1-[1-methyl-2-oxo-3-(2,2,2-trifluoroethyl)-2,3-dihydro-1H-benzimidazol-5-yl]-2,4-dioxo-1,2,3,4-tetrahydropyrimidine-5-carboxylic acid

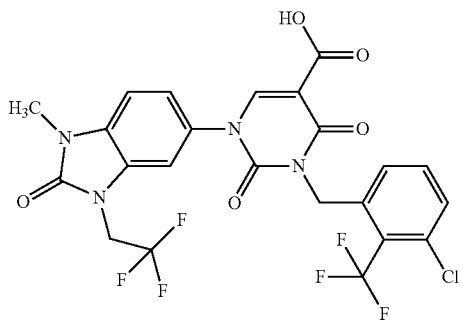 [SMILES: Cn1c(=O)n(CC(F)(F)F)c2cc(-n3cc(C(=O)O)c(=O)n(Cc4cccc(Cl)c4C(F)(F)F)c3=O)ccc21]

The preparation and purification of the title compound were in analogy to Example 121. Proceeding from 90 mg (0.15 mmol) of ethyl 3-[3-chloro-2-(trifluoromethyl)benzyl]-1-[1-methyl-2-oxo-3-(2,2,2-trifluoroethyl)-2,3-dihydro-1H-benzimidazol-5-yl]-2,4-dioxo-1,2,3,4-tetrahydropyrimidine-5-carboxylate from Example 25, 55 mg (61% of theory) of the title compound were obtained.

LC-MS (Method 1): $R_t$=1.12 min; m/z=577 (M+H)$^+$.
$^1$H NMR (400 MHz, DMSO-d$_6$): δ [ppm]=3.41 (s, 3H), 4.81 (q, 2H), 5.22-5.26 (m, 2H), 7.30-7.39 (m, 3H), 7.51-7.55 (m, 1H), 7.57-7.67 (m, 2H), 8.46 (s, 1H), 12.74 (br.s, 1H).

Example 143

3-[2-chloro-3-(trifluoromethyl)benzyl]-1-[1-methyl-2-oxo-3-(2,2,2-trifluoroethyl)-2,3-dihydro-1H-benzimidazol-5-yl]-2,4-dioxo-1,2,3,4-tetrahydropyrimidine-5-carboxylic acid

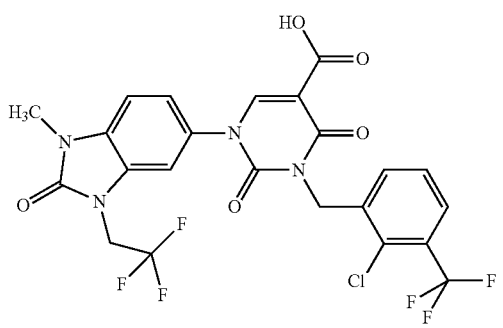 [SMILES: Cn1c(=O)n(CC(F)(F)F)c2cc(-n3cc(C(=O)O)c(=O)n(Cc4cccc(C(F)(F)F)c4Cl)c3=O)ccc21]

The preparation and purification of the title compound were in analogy to Example 121. Proceeding from 80 mg (0.13 mmol) of ethyl 3-[2-chloro-3-(trifluoromethyl)benzyl]-1-[1-methyl-2-oxo-3-(2,2,2-trifluoroethyl)-2,3-dihydro-1H-benzimidazol-5-yl]-2,4-dioxo-1,2,3,4-tetrahydropyrimidine-5-carboxylate from Example 26, 46 mg (57% of theory) of the title compound were obtained.

LC-MS (Method 1): $R_t$=1.12 min; m/z=577 (M+H)$^+$.
$^1$H NMR (400 MHz, DMSO-d$_6$): δ [ppm]=3.41 (s, 3H), 4.80 (q, 2H), 5.17 (s, 2H), 7.31-7.38 (m, 2H), 7.50-7.56 (m, 2H), 7.59-7.63 (m, 1H), 7.79-7.83 (m, 1H), 8.45 (s, 1H), 12.75 (br.s, 1H).

Example 144

1-[1-methyl-2-oxo-3-(2,2,2-trifluoroethyl)-2,3-dihydro-1H-benzimidazol-5-yl]-3-[2-methyl-3-(trifluoromethyl)benzyl]-2,4-dioxo-1,2,3,4-tetrahydropyrimidine-5-carboxylic acid

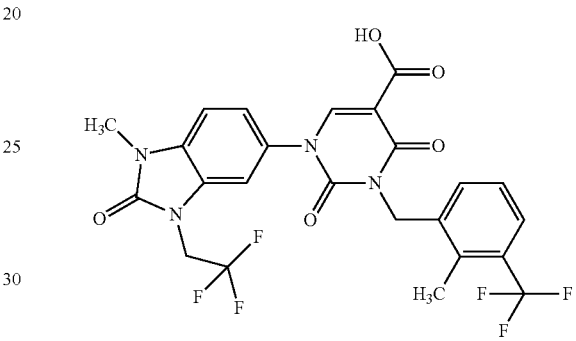

The preparation and purification of the title compound were in analogy to Example 121. Proceeding from 41 mg (0.07 mmol) of ethyl 1-[1-methyl-2-oxo-3-(2,2,2-trifluoroethyl)-2,3-dihydro-1H-benzimidazol-5-yl]-3-[2-methyl-3-(trifluoromethyl)benzyl]-2,4-dioxo-1,2,3,4-tetrahydropyrimidine-5-carboxylate from Example 27, 25 mg (63% of theory) of the title compound were obtained.

LC-MS (Method 3): $R_t$=1.33 min; m/z=557 (M+H)$^+$.
$^1$H NMR (400 MHz, DMSO-d$_6$): δ [ppm]=2.47 (s, 3H), 3.41 (s, 3H), 4.80 (q, 2H), 5.11 (s, 2H), 7.31-7.43 (m, 4H), 7.55 (s, 1H), 7.58-7.63 (m, 1H), 8.43 (s, 1H), 12.76 (br.s, 1H).

Example 145

3-[2-chloro-3-(trifluoromethyl)benzyl]-1-[3-(cyclopropylmethyl)-1-methyl-2-oxo-2,3-dihydro-1H-benzimidazol-5-yl]-2,4-dioxo-1,2,3,4-tetrahydropyrimidine-5-carboxylic acid

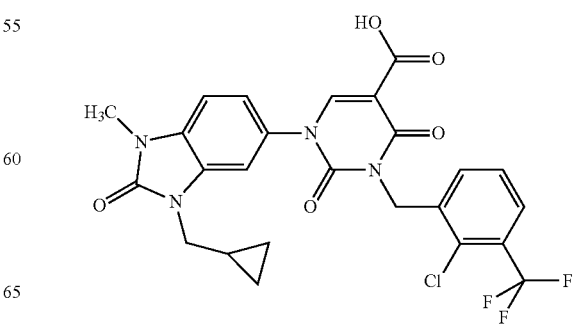

The preparation and purification of the title compound were in analogy to Example 121, proceeding from 65 mg (0.11 mmol) of ethyl 3-[2-chloro-3-(trifluoromethyl)benzyl]-1-[3-(cyclopropylmethyl)-1-methyl-2-oxo-2,3-dihydro-1H-benzimidazol-5-yl]-2,4-dioxo-1,2,3,4-tetrahydropyrimidine-5-carboxylate from Example 29. The resulting crude product was additionally purified by means of preparative HPLC (Method 22). This gave 23 mg (62% of theory) of the title compound.

LC-MS (Method 1): $R_t$=1.08 min; m/z=549 (M+H)$^+$.

$^1$H NMR (400 MHz, DMSO-d$_6$): δ [ppm]=0.35-0.49 (m, 4H), 1.14-1.26 (m, 1H), 2.5 (s, concealed by DMSO signal), 3.38 (s, 3H), 3.72 (d, 2H), 5.18 (s, 2H), 7.22-7.31 (m, 2H), 7.50-7.57 (m, 2H), 7.58-7.63 (m, 1H), 7.79-7.83 (m, 1H), 8.48 (s, 1H), 12.73 (br.s, 1H).

Example 146

1-[3-(cyclopropylmethyl)-1-methyl-2-oxo-2,3-dihydro-1H-benzimidazol-5-yl]-3-[2-methyl-3-(trifluoromethyl)benzyl]-2,4-dioxo-1,2,3,4-tetrahydropyrimidine-5-carboxylic acid

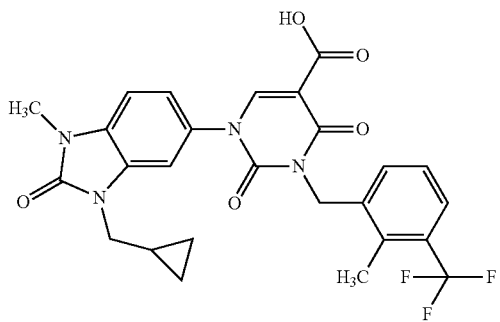 [SMILES: Cc1c(Cn2c(=O)c(C(=O)O)cn(-c3ccc4c(c3)n(CC3CC3)c(=O)n4C)c2=O)cccc1C(F)(F)F]

The preparation and purification of the title compound were analogous to Example 121. Proceeding from 69 mg (0.12 mmol) of ethyl 1-[3-(cyclopropylmethyl)-1-methyl-2-oxo-2,3-dihydro-1H-benzimidazol-5-yl]-3-[2-methyl-3-(trifluoromethyl)benzyl]-2,4-dioxo-1,2,3,4-tetrahydropyrimidine-5-carboxylate from Example 30, after additional purification by means of preparative HPLC (Method 10), 29 mg (90%, 40% of theory) of the title compound were obtained.

LC-MS (Method 1): $R_t$=1.08 min; m/z=529 (M+H)$^+$.

$^1$H NMR (400 MHz, DMSO-d$_6$): δ [ppm]=0.35-0.41 (m, 2H), 0.42-0.49 (m, 2H), 1.15-1.25 (m, 1H), 2.47 (s, 3H), 3.38 (s, concealed by DMSO signal), 3.72 (d, 2H), 5.12 (s, 2H), 7.23-7.30 (m, 2H), 7.33-7.43 (m, 2H), 7.51-7.54 (m, 1H), 7.59-7.63 (m, 1H), 8.47 (s, 1H), 12.73 (br.s, 1H).

Example 147

3-[3-chloro-2-(trifluoromethyl)benzyl]-1-[3-(cyclopropylmethyl)-1-methyl-2-oxo-2,3-dihydro-1H-benzimidazol-5-yl]-2,4-dioxo-1,2,3,4-tetrahydropyrimidine-5-carboxylic acid

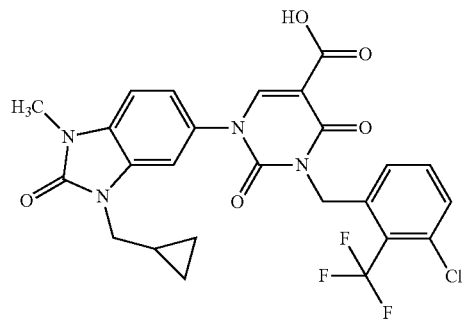 [SMILES: Cn1c(=O)n(CC2CC2)c2cc(-n3cc(C(=O)O)c(=O)n(Cc4cccc(Cl)c4C(F)(F)F)c3=O)ccc21]

The preparation and purification of the title compound were in analogy to Example 121. Proceeding from 115 mg (0.23 mmol) of ethyl 3-[3-chloro-2-(trifluoromethyl)benzyl]-1-[3-(cyclopropylmethyl)-1-methyl-2-oxo-2,3-dihydro-1H-benzimidazol-5-yl]-2,4-dioxo-1,2,3,4-tetrahydropyrimidine-5-carboxylate from Example 31, 92 mg (84% of theory) of the title compound were obtained.

LC-MS (Method 1): $R_t$=1.13 min; m/z=549 (M+H)$^+$.

$^1$H NMR (400 MHz, DMSO-d$_6$): δ [ppm]=0.35-0.41 (m, 2H), 0.41-0.49 (m, 2H), 1.15-1.25 (m, 1H), 3.4 (s, concealed by water signal), 3.72 (d, 2H), 5.25 (br.s, 2H), 7.22-7.31 (m, 2H), 7.32-7.38 (m, 1H), 7.49-7.52 (m, 1H), 7.57-7.68 (m, 2H), 8.48 (s, 1H), 12.73 (br.s, 1H).

Example 148

3-[2-chloro-3-(trifluoromethyl)benzyl]-1-[1-methyl-3-(oxetan-2-ylmethyl)-2-oxo-2,3-dihydro-1H-benzimidazol-5-yl]-2,4-dioxo-1,2,3,4-tetrahydropyrimidine-5-carboxylic acid (Racemate)

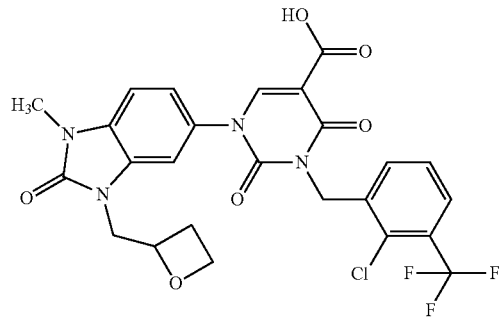 [SMILES: Cn1c(=O)n(CC2CCO2)c2cc(-n3cc(C(=O)O)c(=O)n(Cc4cccc(C(F)(F)F)c4Cl)c3=O)ccc21]

The preparation and purification of the title compound were in analogy to Example 121. Proceeding from 56 mg (0.09 mmol) of ethyl 3-[2-chloro-3-(trifluoromethyl)benzyl]-1-[1-methyl-3-(oxetan-2-ylmethyl)-2-oxo-2,3-dihydro-1H-benzimidazol-5-yl]-2,4-dioxo-1,2,3,4-tetrahydropyrimidine-5-carboxylate from Example 32, 10 mg (18% of theory) of the title compound were obtained.

LC-MS (Method 3): $R_t$=1.24 min; m/z=565 (M+H)$^+$.

¹H NMR (400 MHz, DMSO-d₆): δ [ppm]=2.11-2.21 (m, 1H), 2.26-2.36 (m, 1H), 3.36 (s, 3H), 3.72 (q, 1H), 3.84-3.91 (m, 1H), 3.93-3.99 (m, 1H), 4.11-4.18 (m, 1H), 5.09-5.20 (m, 3H), 7.25-7.32 (m, 2H), 7.43-7.46 (m, 1H), 7.50-7.57 (m, 1H), 7.60-7.65 (m, 1H), 7.78-7.84 (m, 1H), 8.48 (s, 1H), 12.74 (br.s, 1H).

Example 149

1-(3-cyclobutyl-1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylic acid

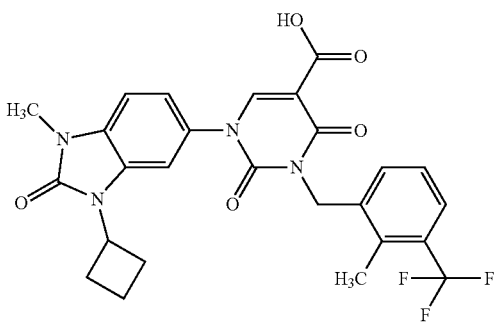 [SMILES: Cc1c(Cn2c(=O)c(C(=O)O)cn(-c3ccc4c(c3)n(C3CCC3)c(=O)n4C)c2=O)cccc1C(F)(F)F]

The preparation and purification of the title compound were in analogy to Example 121, with reaction time 5.5 h at 60° C. Proceeding from 33 mg (0.06 mmol) of ethyl 1-(3-cyclobutyl-1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate from Example 33, 18 mg (57% of theory) of the title compound were obtained.

LC-MS (Method 1): $R_t$=1.10 min; m/z=529 (M+H)⁺.

¹H NMR (400 MHz, DMSO-d₆): δ [ppm]=1.73-1.90 (m, 2H), 2.21-2.31 (m, 2H), 2.47 (s, partly concealed by DMSO signal), 2.75-2.87 (m, 2H), 3.34 (s, partly concealed by water signal), 4.78-4.89 (m, 1H), 5.12 (s, 2H), 7.24-7.29 (m, 2H), 7.34-7.39 (m, 1H), 7.40-7.44 (m, 1H), 7.59-7.63 (m, 1H), 7.64-7.67 (m, 1H), 8.49 (s, 1H), 12.73 (br.s, 1H).

Example 150

1-(3-cyclopropyl-1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylic acid

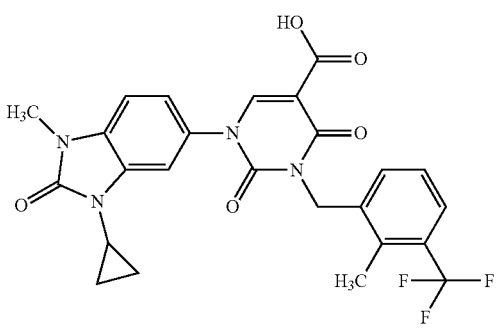 [SMILES: Cc1c(Cn2c(=O)c(C(=O)O)cn(-c3ccc4c(c3)n(C3CC3)c(=O)n4C)c2=O)cccc1C(F)(F)F]

The preparation and purification of the title compound were in analogy to Example 121, with reaction time 2 h at 60° C. Proceeding from 141 mg (0.26 mmol) of ethyl 1-(3-cyclopropyl-1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate from Example 35, 107 mg (80% of theory) of the title compound were obtained.

LC-MS (Method 5): $R_t$=1.07 min; m/z=515 (M+H)⁺.

¹H NMR (400 MHz, DMSO-d₆): δ [ppm]=0.86-0.92 (m, 2H), 0.99-1.05 (m, 2H), 2.47 (s, partly concealed by DMSO signal), 2.88-2.95 (m, 1H), 3.31 (s, partly concealed by water signal), 5.11 (s, 2H), 7.25 (s, 2H), 7.33-7.39 (m, 1H), 7.40-7.47 (m, 2H), 7.59-7.63 (m, 1H), 8.45 (s, 1H), 12.72 (br.s, 1H).

Example 151

1-(3-isopropyl-1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylic acid

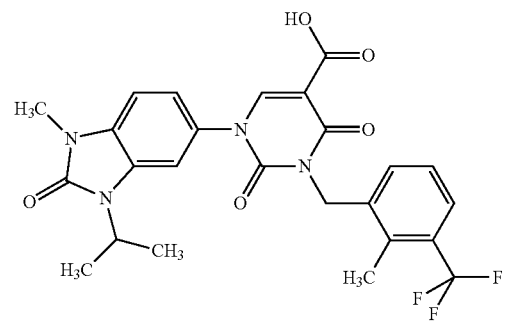 [SMILES: Cc1c(Cn2c(=O)c(C(=O)O)cn(-c3ccc4c(c3)n(C(C)C)c(=O)n4C)c2=O)cccc1C(F)(F)F]

The preparation and purification of the title compound were in analogy to Example 121, with reaction time 5.5 h at 60° C. Proceeding from 33 mg (0.06 mmol) of ethyl 1-(3-isopropyl-1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate from Example 34, 25 mg (76% of theory) of the title compound were obtained.

LC-MS (Method 1): $R_t$=1.06 min; m/z=517 (M+H)⁺.

¹H NMR (400 MHz, DMSO-d₆): δ [ppm]=1.44 (d, 6H), 2.47 (s, partly concealed by DMSO signal), 3.35 (s, partly concealed by water signal), 4.55-4.64 (m, 1H), 5.12 (s, 2H), 7.21-7.28 (m, 2H), 7.33-7.43 (m, 2H), 7.58-7.63 (m, 2H), 8.47 (s, 1H), 12.73 (br.s, 1H).

Example 152

1-[3-methyl-2-oxo-1-(2,2,2-trifluoroethyl)-2,3-di-hydro-1H-benzimidazol-5-yl]-3-[2-methyl-3-(trifluoromethyl)benzyl]-2,4-dioxo-1,2,3,4-tetrahydropyrimidine-5-carboxylic acid

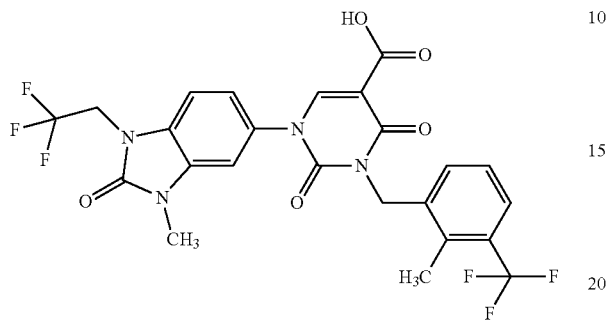

The preparation and purification of the title compound were in analogy to Example 121. Proceeding from 57 mg (0.09 mmol) of ethyl 1-[3-methyl-2-oxo-1-(2,2,2-trifluoroethyl)-2,3-dihydro-1H-benzimidazol-5-yl]-3-[2-methyl-3-(trifluoromethyl)benzyl]-2,4-dioxo-1,2,3,4-tetrahydropyrimidine-5-carboxylate from Example 38, 48 mg (83% of theory) of the title compound were obtained.

LC-MS (Method 1): $R_t$=1.08 min; m/z=557 (M+H)$^+$.

$^1$H NMR (400 MHz, DMSO-d$_6$): δ [ppm]=2.47 (s, 3H), 3.37 (s, 3H), 4.85 (q, 2H), 5.11 (s, 2H), 7.30 (dd, 1H), 7.33-7.45 (m, 3H), 7.47-7.50 (m, 1H), 7.59-7.63 (m, 1H), 8.49 (s, 1H), 12.73 (br.s, 1H).

Example 153

1-[1-(cyclopropylmethyl)-3-methyl-2-oxo-2,3-di-hydro-1H-benzimidazol-5-yl]-3-[2-methyl-3-(trifluoromethyl)benzyl]-2,4-dioxo-1,2,3,4-tetrahydropyrimidine-5-carboxylic acid

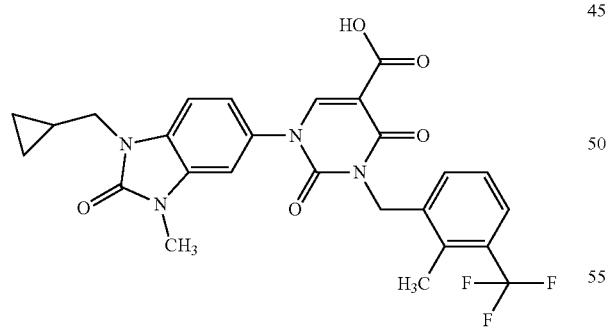

The preparation and purification of the title compound were analogous to Example 121. Proceeding from 52 mg (0.09 mmol) of ethyl 1-[1-(cyclopropylmethyl)-3-methyl-2-oxo-2,3-dihydro-1H-benzimidazol-5-yl]-3-[2-methyl-3-(trifluoromethyl)benzyl]-2,4-dioxo-1,2,3,4-tetrahydropyrimidine-5-carboxylate from Example 39, after purification by means of HPLC (Method 8) and additional fine purification of the compound by means of HPLC (Method 23), 19 mg (37% of theory) of the title compound were obtained.

LC-MS (Method 1): $R_t$=1.09 min; m/z=529 (M+H)$^+$.

$^1$H NMR (400 MHz, DMSO-d$_6$): δ [ppm]=0.36-0.42 (m, 2H), 0.44-0.50 (m, 2H), 1.15-1.25 (m, 1H), 2.47 (s, 3H), 3.35 (br.s, 3H, partly concealed by water signal), 3.77 (d, 2H), 5.11 (s, 2H), 7.24 (dd, 1H), 7.33-7.43 (m, 4H), 7.61 (d, 1H), 8.47 (s, 1H), 12.72 (s, 1H).

Example 154

3-[2-chloro-3-(trifluoromethyl)benzyl]-1-(1-methyl-1H-benzotriazol-5-yl)-2,4-dioxo-1,2,3,4-tetrahydropyrimidine-5-carboxylic acid

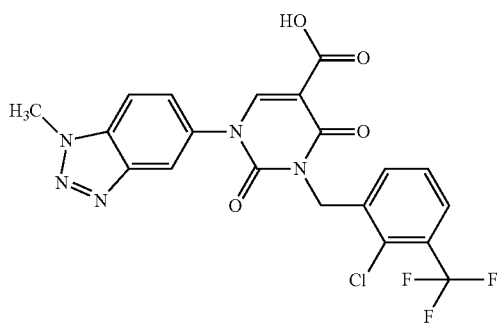 [SMILES: Cn1nnc2cc(-n3cc(C(=O)O)c(=O)n(Cc4cccc(C(F)(F)F)c4Cl)c3=O)ccc21]

The preparation and purification of the title compound were in analogy to Example 121. Proceeding from 149 mg (0.29 mmol) of ethyl 3-[2-chloro-3-(trifluoromethyl)benzyl]-1-(1-methyl-1H-benzotriazol-5-yl)-2,4-dioxo-1,2,3,4-tetrahydropyrimidine-5-carboxylate from Example 71, 115 mg (80% of theory) of the title compound were obtained.

LC-MS (Method 1): $R_t$=1.03 min; m/z=480 (M+H)$^+$.

$^1$H NMR (400 MHz, DMSO-d$_6$): δ [ppm]=4.37 (s, 3H), 5.19 (s, 2H), 7.51-7.58 (m, 1H), 7.62-7.67 (m, 1H), 7.73 (dd, 1H), 7.79-7.84 (m, 1H), 8.00 (d, 1H), 8.30-8.33 (m, 1H), 8.62 (s, 1H), 12.76 (br.s, 1H).

Example 155

1-(1-methyl-1H-benzotriazol-5-yl)-3-[2-methyl-3-(trifluoromethyl)benzyl]-2,4-dioxo-1,2,3,4-tetrahydropyrimidine-5-carboxylic acid

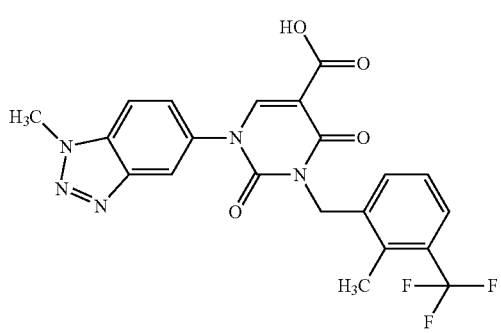 [SMILES: Cc1c(Cn2c(=O)c(C(=O)O)cn(-c3ccc4c(c3)nnn4C)c2=O)cccc1C(F)(F)F]

The preparation and purification of the title compound were in analogy to Example 121. Proceeding from 151 mg (0.31 mmol) of ethyl 1-(1-methyl-1H-benzotriazol-5-yl)-3-[2-methyl-3-(trifluoromethyl)benzyl]-2,4-dioxo-1,2,3,4-tetrahydropyrimidine-5-carboxylate from Example 72, 124 mg (86% of theory) of the title compound were obtained.

LC-MS (Method 1): $R_t$=1.02 min; m/z=460 (M+H)$^+$.

$^1$H NMR (400 MHz, DMSO-d$_6$): δ [ppm]=2.47 (s, 3H), 4.37 (s, 3H), 5.12 (s, 2H), 7.33-7.40 (m, 1H), 7.42-7.48 (m, 1H), 7.59-7.64 (m, 1H), 7.70-7.76 (m, 1H), 8.00 (d, 1H), 8.31-8.35 (m, 1H), 8.61 (s, 1H), 12.75 (br.s, 1H).

Example 156

3-(2,3-dichlorobenzyl)-1-(1-methyl-1H-benzotriazol-5-yl)-2,4-dioxo-1,2,3,4-tetrahydropyrimidine-5-carboxylic acid

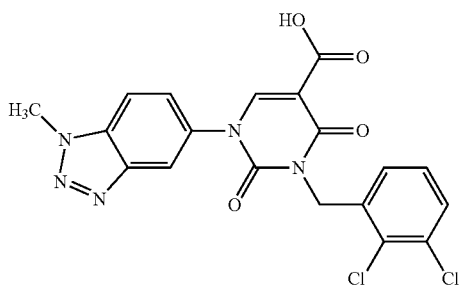 [SMILES: Cn1nnc2cc(-n3cc(C(=O)O)c(=O)n(Cc4cccc(Cl)c4Cl)c3=O)ccc21]

The preparation and purification of the title compound were in analogy to Example 121. Proceeding from 188 mg (0.40 mmol) of ethyl 3-(2,3-dichlorobenzyl)-1-(1-methyl-1H-benzotriazol-5-yl)-2,4-dioxo-1,2,3,4-tetrahydropyrimidine-5-carboxylate from Example 73, 143 mg (80% of theory) of the title compound were obtained.

LC-MS (Method 1): $R_t$=1.00 min; m/z=446 (M+H)$^+$.

$^1$H NMR (400 MHz, DMSO-d$_6$): δ [ppm]=4.37 (s, 3H), 5.14 (s, 2H), 7.27-7.31 (m, 1H), 7.32-7.38 (m, 1H), 7.56-7.62 (m, 1H), 7.70-7.74 (m, 1H), 8.00 (d, 1H), 8.30-8.33 (m, 1H), 8.61 (s, 1H), 12.75 (br.s, 1H).

Example 157

3-[3-chloro-2-(trifluoromethyl)benzyl]-1-(1-methyl-1H-benzotriazol-5-yl)-2,4-dioxo-1,2,3,4-tetrahydropyrimidine-5-carboxylic acid

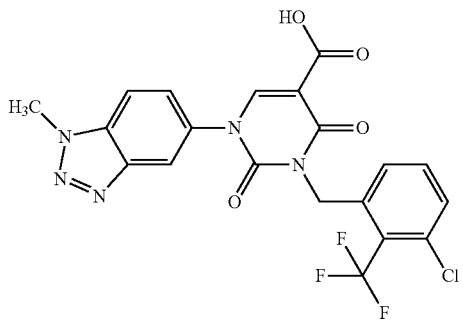 [SMILES: Cn1nnc2cc(-n3cc(C(=O)O)c(=O)n(Cc4cccc(Cl)c4C(F)(F)F)c3=O)ccc21]

The preparation and purification of the title compound were in analogy to Example 121. Proceeding from 115 mg (0.31 mmol) of ethyl 3-[3-chloro-2-(trifluoromethyl)benzyl]-1-(1-methyl-1H-benzotriazol-5-yl)-2,4-dioxo-1,2,3,4-tetrahydropyrimidine-5-carboxylate from Example 74, 92 mg (84% of theory) of the title compound were obtained.

LC-MS (Method 1): $R_t$=1.03 min; m/z=480 (M+H)$^+$.

$^1$H NMR (400 MHz, DMSO-d$_6$): δ [ppm]=4.37 (s, 3H), 5.22-5.28 (m, 2H), 7.37-7.42 (m, 1H), 7.58-7.68 (m, 2H), 7.69-7.74 (m, 1H), 8.00 (d, 1H), 8.29-8.33 (m, 1H), 8.63 (s, 1H), 12.75 (br.s, 1H).

Example 158

1-(1-methyl-1H-indazol-5-yl)-3-[2-methyl-3-(trifluoromethyl)benzyl]-2,4-dioxo-1,2,3,4-tetrahydropyrimidine-5-carboxylic acid

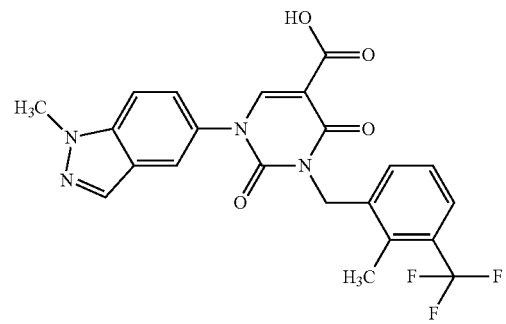 [SMILES: Cc1c(Cn2c(=O)c(C(=O)O)cn(-c3ccc4c(cnn4C)c3)c2=O)cccc1C(F)(F)F]

The preparation and purification of the title compound were in analogy to Example 121. Proceeding from 254 mg (0.52 mmol) of ethyl 1-(1-methyl-1H-indazol-5-yl)-3-[2-methyl-3-(trifluoromethyl)benzyl]-2,4-dioxo-1,2,3,4-tetrahydropyrimidine-5-carboxylate from Example 75, 212 mg (88% of theory) of the title compound were obtained.

LC-MS (Method 1): $R_t$=1.04 min; m/z=459 (M+H)$^+$.

$^1$H NMR (400 MHz, DMSO-d$_6$): δ [ppm]=2.47 (s, 3H), 4.10 (s, 3H), 5.12 (s, 2H), 7.33-7.39 (m, 1H), 7.41-7.46 (m, 1H), 7.52-7.56 (m, 1H), 7.59-7.63 (m, 1H), 7.76-7.80 (m, 1H), 7.97-7.99 (m, 1H), 8.16-8.19 (m, 1H), 8.52 (s, 1H), 12.72 (br.s, 1H).

Example 159

3-[2-chloro-3-(trifluoromethyl)benzyl]-1-(1-methyl-1H-benzimidazol-6-yl)-2,4-dioxo-1,2,3,4-tetrahydropyrimidine-5-carboxylic acid

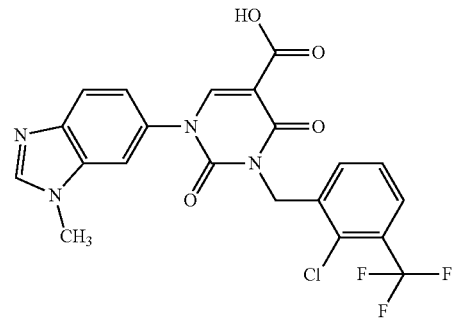 [SMILES: Cn1cnc2ccc(-n3cc(C(=O)O)c(=O)n(Cc4cccc(C(F)(F)F)c4Cl)c3=O)cc21]

94 mg (0.18 mmol) of ethyl 3-[2-chloro-3-(trifluoromethyl)benzyl]-1-(1-methyl-1H-benzimidazol-6-yl)-2,4-dioxo-1,2,3,4-tetrahydropyrimidine-5-carboxylate from Example 82 in 1.5 ml of glacial acetic acid/conc. hydrochloric acid 2:1 (v/v) were heated to 120° C. for 30 mm. The cooled reaction mixture was admixed with water and extracted twice with dichloromethane, and the combined organic phases were dried over magnesium sulphate and concentrated. The residue was stirred with ethyl acetate, and the precipitated solid was filtered off with suction and dried at 50° C. under reduced pressure. This gave 88 mg (98% of theory) of the title compound.

LC-MS (Method 3): $R_t$=1.12 min; m/z=479 (M+H)$^+$.

$^1$H NMR (400 MHz, DMSO-d$_6$): δ [ppm]=4.00 (s, 3H), 5.19 (s, 2H), 7.54 (t, 1H), 7.59-7.67 (m, 2H), 7.81 (d, 1H), 7.92 (d, 1H), 8.10 (s, 1H), 8.56 (s, 1H), 9.13 (s, 1H).

Example 160

1-(1-methyl-1H-benzimidazol-5-yl)-3-[2-methyl-3-(trifluoromethyl)benzyl]-2,4-dioxo-1,2,3,4-tetrahydropyrimidine-5-carboxylic acid

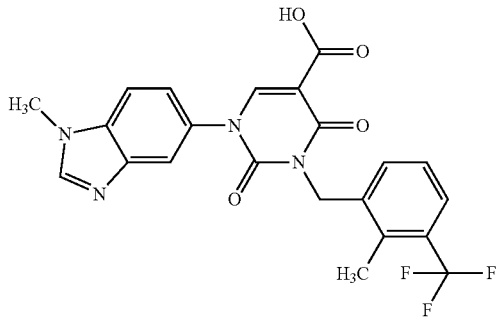 [SMILES: Cc1c(Cn2c(=O)c(C(=O)O)cn(-c3ccc4c(c3)ncn4C)c2=O)cccc1C(F)(F)F]

The preparation and purification of the title compound were in analogy to Example 121. Proceeding from 170 mg (0.35 mmol) of ethyl 1-(1-methyl-1H-benzimidazol-5-yl)-3-[2-methyl-3-(trifluoromethyl)benzyl]-2,4-dioxo-1,2,3,4-tetrahydropyrimidine-5-carboxylate from Example 77, 124 mg (77% of theory) of the title compound were obtained.

LC-MS (Method 1): $R_t$=0.90 min; m/z=459 (M+H)$^+$.

$^1$H NMR (400 MHz, DMSO-d$_6$): δ [ppm]=2.47 (s, 3H), 3.89 (s, 3H), 5.12 (s, 2H), 7.33-7.40 (m, 1H), 7.41-7.46 (m, 2H), 7.59-7.63 (m, 1H), 7.71 (d, 1H), 7.86-7.89 (m, 1H), 8.33 (s, 1H), 8.50 (s, 1H), 12.72 (br.s, 1H).

Example 161

3-[3-chloro-2-(trifluoromethyl)benzyl]-1-(1-methyl-1H-benzimidazol-5-yl)-2,4-dioxo-1,2,3,4-tetrahydropyrimidine-5-carboxylic acid

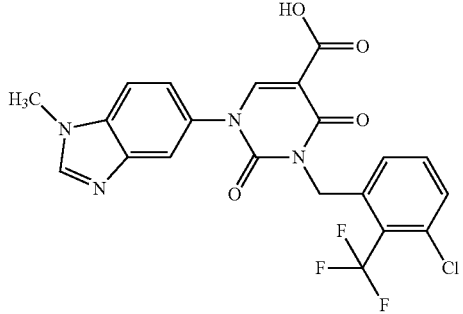 [SMILES: Cn1cnc2cc(-n3cc(C(=O)O)c(=O)n(Cc4cccc(Cl)c4C(F)(F)F)c3=O)ccc21]

The preparation and purification of the title compound were in analogy to Example 121. Proceeding from 82 mg (0.16 mmol) of ethyl 3-[3-chloro-2-(trifluoromethyl)benzyl]-1-(1-methyl-1H-benzimidazol-5-yl)-2,4-dioxo-1,2,3,4-tetrahydropyrimidine-5-carboxylate from Example 78, 52 mg (66% of theory) of the title compound were obtained.

LC-MS (Method 1): $R_t$=0.93 min; m/z=479 (M+H)$^+$.

$^1$H NMR (400 MHz, DMSO-d$_6$): δ [ppm]=3.89 (s, 3H), 5.25 (br.s, 2H), 7.35-7.46 (m, 2H), 7.58-7.68 (m, 2H), 7.71 (d, 1H), 7.84-7.88 (m, 1H), 8.33 (s, 1H), 8.51 (s, 1H), 12.70 (br.s, 1H).

Example 162

3-[2-chloro-3-(trifluoromethyl)benzyl]-1-(1-methyl-1H-benzimidazol-5-yl)-2,4-dioxo-1,2,3,4-tetrahydropyrimidine-5-carboxylic acid

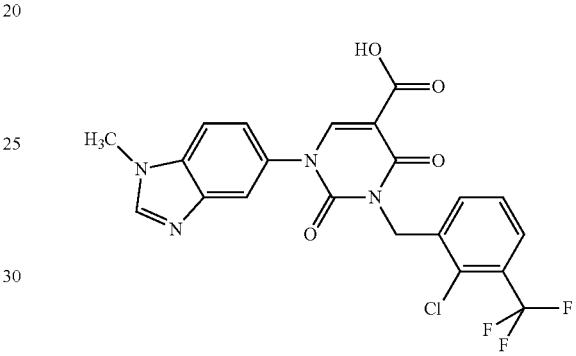

The preparation and purification of the title compound were in analogy to Example 121. Proceeding from 120 mg (0.16 mmol) of ethyl 3-[2-chloro-3-(trifluoromethyl)benzyl]-1-(1-methyl-1H-benzimidazol-5-yl)-2,4-dioxo-1,2,3,4-tetrahydropyrimidine-5-carboxylate from Example 79, 83 mg (74% of theory) of the title compound were obtained.

LC-MS (Method 1): $R_t$=0.89 min; m/z=479 (M+H)$^+$.

$^1$H NMR (400 MHz, DMSO-d$_6$): δ [ppm]=3.89 (s, 3H), 5.18 (s, 2H), 7.42-7.47 (m, 1H), 7.51-7.57 (m, 1H), 7.61-7.65 (m, 1H), 7.71 (d, 1H), 7.79-7.83 (m, 1H), 7.86-7.89 (m, 1H), 8.33 (s, 1H), 8.51 (s, 1H), 12.70 (br.s, 1H).

Example 163

1-(2-carbamoyl-1-methyl-1H-benzimidazol-5-yl)-3-[2-methyl-3-(trifluoromethyl)benzyl]-2,4-dioxo-1,2,3,4-tetrahydropyrimidine-5-carboxylic acid

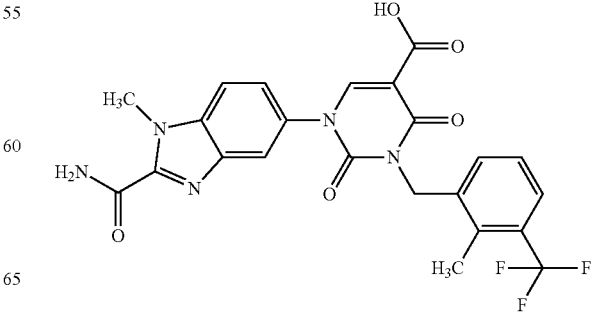

The preparation and purification of the title compound were in analogy to Example 121, with a reaction time of 3.5 h at 60° C. Proceeding from 116 mg (0.21 mmol) of ethyl 1-(2-carbamoyl-1-methyl-1H-benzimidazol-5-yl)-3-[2-methyl-3-(trifluoromethyl)benzyl]-2,4-dioxo-1,2,3,4-tetrahydropyrimidine-5-carboxylate from Example 81, after additional purification by means of preparative HPLC (Method 9), 40 mg (36% of theory) of the title compound were obtained.

LC-MS (Method 1): $R_t$=0.96 min; m/z=502 (M+H)$^+$.

$^1$H NMR (400 MHz, DMSO-d$_6$): δ [ppm]=2.47 (s, partly concealed by DMSO signal), 4.16 (s, 3H), 5.13 (s, 2H), 7.34-7.40 (m, 1H), 7.42-7.47 (m, 1H), 7.54-7.58 (m, 1H), 7.59-7.64 (m, 1H), 7.83 (d, 1H), 7.90-7.94 (m, 1H), 7.96-7.99 (m, 1H), 8.30-8.35 (m, 1H), 8.53 (s, 1H), 12.73 (br.s, 1H).

Example 164

1-(1-ethyl-2-methyl-1H-benzimidazol-5-yl)-3-[3-fluoro-2-(trifluoromethyl)benzyl]-2,4-dioxo-1,2,3,4-tetrahydropyrimidine-5-carboxylic acid

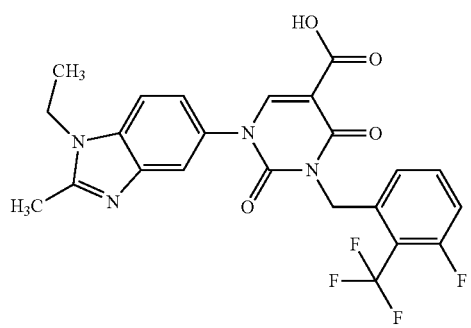 [SMILES: CCn1c(C)nc2cc(-n3cc(C(=O)O)c(=O)n(Cc4cccc(F)c4C(F)(F)F)c3=O)ccc21]

153 mg (0.30 mmol) of ethyl 1-(1-ethyl-2-methyl-1H-benzimidazol-5-yl)-3-[3-fluoro-2-(trifluoromethyl)-benzyl]-2,4-dioxo-1,2,3,4-tetrahydropyrimidine-5-carboxylate from Example 83 were initially charged in 2.1 ml of glacial acetic acid and 1.1 ml of conc. hydrochloric acid and stirred at 120° C. for 1 h. Subsequently, the mixture cooled to RT was admixed with water and extracted three times with dichloromethane. The combined organic phases were dried over magnesium sulphate, filtered and concentrated. In order to remove residues of acetic acid, the residue was stirred with methanol/dichloromethane, concentrated again and dried under reduced pressure. This gave 120 mg (81% of theory) of the title compound.

LC-MS (Method 3): $R_t$=1.02 min; m/z=491 (M+H)$^+$.

$^1$H NMR (400 MHz, DMSO-d$_6$): δ [ppm]=1.36 (t, 3H), 2.72 (s, 3H), 4.38 (q, 2H), 5.23 (s, 2H), 7.23-7.28 (m, 1H), 7.38-7.45 (m, 1H), 7.51-7.57 (m, 1H), 7.64-7.71 (m, 1H), 7.86-7.93 (m, 2H), 8.54 (s, 1H), 12.71 (br.s, 1H).

Example 165

1-(1-ethyl-1H-benzimidazol-5-yl)-3-[3-fluoro-2-(trifluoromethyl)benzyl]-2,4-dioxo-1,2,3,4-tetrahydropyrimidine-5-carboxylic acid

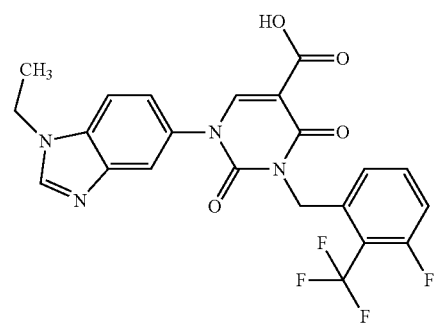 [SMILES: CCn1cnc2cc(-n3cc(C(=O)O)c(=O)n(Cc4cccc(F)c4C(F)(F)F)c3=O)ccc21]

The preparation and purification of the title compound were in analogy to Example 121. Proceeding from 73 mg (0.15 mmol) of ethyl 1-(1-ethyl-1H-benzimidazol-5-yl)-3-[3-fluoro-2-(trifluoromethyl)benzyl]-2,4-dioxo-1,2,3,4-tetrahydropyrimidine-5-carboxylate from Example 90, 16 mg (23% of theory) of the title compound were obtained.

LC-MS (Method 1): $R_t$=0.89 min; m/z=477 (M+H)$^+$.

$^1$H NMR (400 MHz, DMSO-d$_6$): δ [ppm]=1.43 (t, 3H), 4.33 (q, 2H), 5.23 (s, 2H), 7.21-7.27 (m, 1H), 7.37-7.45 (m, 2H), 7.63-7.71 (m, 1H), 7.76 (d, 1H), 7.84-7.88 (m, 1H), 8.40 (s, 1H), 8.49 (s, 1H), 12.70 (br.s, 1H).

Example 166

3-[2-chloro-3-(trifluoromethyl)benzyl]-1-(1-ethyl-1H-benzimidazol-5-yl)-2,4-dioxo-1,2,3,4-tetrahydropyrimidine-5-carboxylic acid

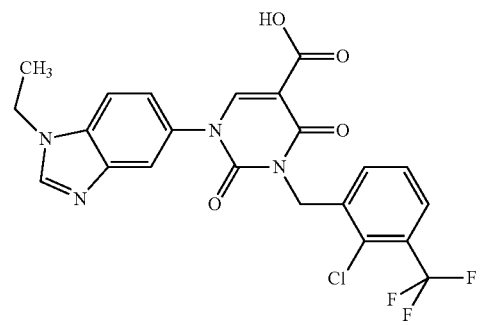 [SMILES: CCn1cnc2cc(-n3cc(C(=O)O)c(=O)n(Cc4cccc(C(F)(F)F)c4Cl)c3=O)ccc21]

53 mg (0.10 mmol) of ethyl 3-[2-chloro-3-(trifluoromethyl)benzyl]-1-(1-ethyl-1H-benzimidazol-5-yl)-2,4-dioxo-1,2,3,4-tetrahydropyrimidine-5-carboxylate from Example 91 were initially charged in 0.7 ml of glacial acetic acid and 0.4 ml of conc. hydrochloric acid and stirred at 120° C. for 1 h. Subsequently, the mixture cooled to RT was admixed with water and extracted three times with dichloromethane. The combined organic phases were dried over magnesium sulphate, filtered and concentrated. The residue was purified by means of preparative HPLC (Method 8). This gave 37 mg (75% of theory) of the title compound.

LC-MS (Method 1): $R_t$=0.94 min; m/z=493 (M+H)$^+$.

$^1$H NMR (400 MHz, DMSO-d$_6$): δ [ppm]=1.43 (t, 3H), 4.33 (q, 2H), 5.18 (s, 2H), 7.40-7.45 (m, 1H), 7.51-7.57 (m, 1H), 7.60-7.64 (m, 1H), 7.76 (d, 1H), 7.79-7.83 (m, 1H), 7.86-7.88 (m, 1H), 8.40 (s, 1H), 8.48 (s, 1H).

Example 167

1-(1-ethyl-1H-benzimidazol-5-yl)-3-[2-methyl-3-(trifluoromethyl)benzyl]-2,4-dioxo-1,2,3,4-tetrahydropyrimidine-5-carboxylic acid

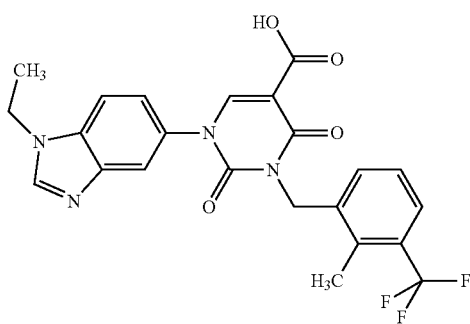 [SMILES: CCn1cnc2cc(-n3cc(C(=O)O)c(=O)n(Cc4cccc(C(F)(F)F)c4C)c3=O)ccc21]

The preparation and purification of the title compound were in analogy to Example 166. Proceeding from 38 mg (0.08 mmol) of ethyl 1-(1-ethyl-1H-benzimidazol-5-yl)-3-[2-methyl-3-(trifluoromethyl)benzyl]-2,4-dioxo-1,2,3,4-tetrahydropyrimidine-5-carboxylate from Example 80, 9 mg (25% of theory) of the title compound were obtained.

LC-MS (Method 1): R$_t$=0.94 min; m/z=473 (M+H)$^+$.
$^1$H NMR (400 MHz, DMSO-d$_6$): δ [ppm]=1.43 (t, 3H), 2.47 (s, 3H), 4.33 (q, 2H), 5.12 (s, 2H), 7.33-7.39 (m, 1H), 7.40-7.45 (m, 2H), 7.59-7.63 (m, 1H), 7.76 (d, 1H), 7.86-7.88 (m, 1H), 8.40 (s, 1H), 8.46 (s, 1H).

Example 168

3-[2-chloro-3-(trifluoromethyl)benzyl]-1-(1-ethyl-2-methyl-1H-benzimidazol-5-yl)-2,4-dioxo-1,2,3,4-tetrahydropyrimidine-5-carboxylic acid

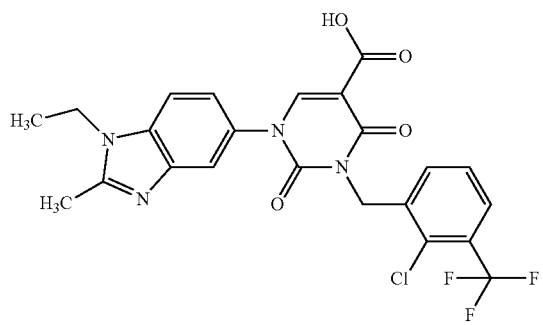 [SMILES: CCn1c(C)nc2cc(-n3cc(C(=O)O)c(=O)n(Cc4cccc(C(F)(F)F)c4Cl)c3=O)ccc21]

The preparation and purification of the title compound were in analogy to Example 166. Proceeding from 114 mg (0.21 mmol) of ethyl 3-[2-chloro-3-(trifluoromethyl)benzyl]-1-(1-ethyl-2-methyl-1H-benzimidazol-5-yl)-2,4-dioxo-1,2,3,4-tetrahydropyrimidine-5-carboxylate from Example 84, 93 mg (83% of theory) of the title compound were obtained.

LC-MS (Method 3): R$_t$=1.09 min; m/z=507 (M+H)$^+$.
$^1$H NMR (400 MHz, DMSO-d$_6$): δ [ppm]=1.34 (t, 3H), 2.66 (s, 3H), 4.33 (q, 2H), 5.18 (s, 2H), 7.43-7.49 (m, 1H), 7.51-7.57 (m, 1H), 7.61-7.65 (m, 1H), 7.76-7.85 (m, 3H), 8.51 (s, 1H), 12.70 (br.s, 1H).

Example 169

1-(1-cyclohexyl-2-methyl-1H-benzimidazol-5-yl)-3-[3-fluoro-2-(trifluoromethyl)benzyl]-2,4-dioxo-1,2,3,4-tetrahydropyrimidine-5-carboxylic acid

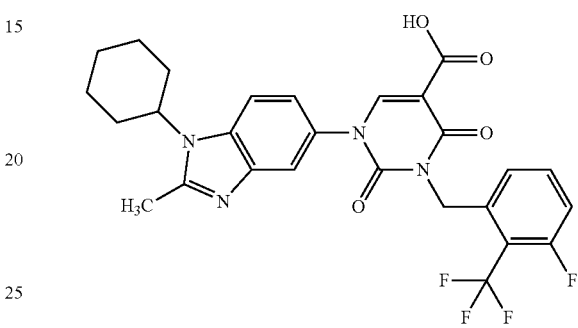

The preparation and purification of the title compound were in analogy to Example 166. Proceeding from 90 mg (0.15 mmol) of ethyl 1-(1-cyclohexyl-2-methyl-1H-benzimidazol-5-yl)-3-[3-fluoro-2-(trifluoromethyl)benzyl]-2,4-dioxo-1,2,3,4-tetrahydropyrimidine-5-carboxylate from Example 85, 74 mg (81% of theory) of the title compound were obtained.

LC-MS (Method 1): R$_t$=1.01 min; m/z=545 (M+H)$^+$.
$^1$H NMR (400 MHz, DMSO-d$_6$): δ [ppm]=1.38-1.57 (m, 3H), 1.67-1.74 (m, 1H), 1.84-1.94 (m, 4H), 2.12-2.25 (m, 2H), 2.68 (s, 3H), 4.33-4.43 (m, 1H), 5.23 (s, 2H), 7.25 (d, 1H), 7.36-7.46 (m, 2H), 7.64-7.71 (m, 1H), 7.77-7.82 (m, 1H), 7.92-8.01 (m, 1H), 8.51 (s, 1H), 12.70 (br.s, 1H).

Example 170

1-(1-isopropyl-1H-benzimidazol-5-yl)-3-[2-methyl-3-(trifluoromethyl)benzyl]-2,4-dioxo-1,2,3,4-tetrahydropyrimidine-5-carboxylic acid

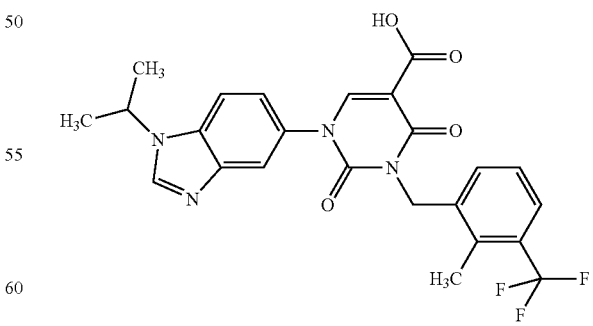

91 mg (0.18 mmol) of ethyl 1-(1-isopropyl-1H-benzimidazol-5-yl)-3-[2-methyl-3-(trifluoromethyl)benzyl]-2,4-dioxo-1,2,3,4-tetrahydropyrimidine-5-carboxylate from Example 93 were initially charged in 1.3 ml of glacial acetic acid and 0.6 ml of conc. hydrochloric acid and stirred at 120° C. for 1 h. Subsequently, the mixture cooled to RT was admixed with water and extracted three times with dichloromethane. The combined organic phases were dried over magnesium sulphate, filtered and concentrated. The residue was stirred with methanol, and the solid was filtered off and dried under reduced pressure. The filtrate was concentrated again and the residue was dried under reduced pressure. This gave a total of 61 mg (70% of theory) of the title compound.

LC-MS (Method 1): $R_t$=1.01 min; m/z=487 (M+H)$^+$.

$^1$H NMR (400 MHz, DMSO-d$_6$): δ [ppm]=1.56 (d, 6H), 2.47 (s, 3H), 4.78-4.87 (m, 1H), 5.12 (s, 2H), 7.33-7.39 (m, 1H), 7.40-7.46 (m, 2H), 7.59-7.63 (m, 1H), 7.80 (d, 1H), 7.87-7.90 (m, 1H), 8.48-8.52 (m, 2H), 12.71 (br.s, 1H).

Example 171

3-[2-chloro-3-(trifluoromethyl)benzyl]-1-(1-isopropyl-1H-benzimidazol-5-yl)-2,4-dioxo-1,2,3,4-tetrahydropyrimidine-5-carboxylic acid

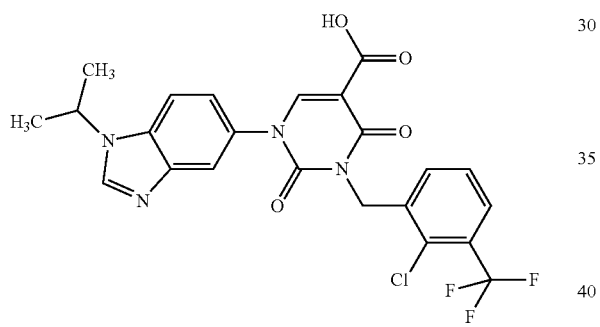

65 mg (0.12 mmol) of ethyl 3-[2-chloro-3-(trifluoromethyl)benzyl]-1-(1-isopropyl-1H-benzimidazol-5-yl)-2,4-dioxo-1,2,3,4-tetrahydropyrimidine-5-carboxylate from Example 86 were initially charged in 0.9 ml of glacial acetic acid and 0.4 ml of conc. hydrochloric acid and stirred at 120° C. for 1 h. Subsequently, the mixture cooled to RT was admixed with water and extracted three times with dichloromethane. The combined organic phases were dried over magnesium sulphate, filtered and concentrated. The residue was stirred with methanol, and the solid was filtered off, washed with methanol and dried under reduced pressure. The filtrate was concentrated and the residue was dried under reduced pressure. This gave a total of 44 mg (71% of theory) of the title compound.

LC-MS (Method 1): $R_t$=1.01 min; m/z=507 (M+H)$^+$.

$^1$H NMR (400 MHz, DMSO-d$_6$): δ [ppm]=1.55 (s, 3H), 1.57 (s, 3H), 4.78-4.87 (m, 1H), 5.18 (s, 2H), 7.39-7.45 (m, 1H), 7.51-7.57 (m, 1H), 7.61-7.66 (m, 1H), 7.78-7.83 (m, 2H), 7.86-7.89 (m, 1H), 8.50 (s, 1H), 8.52 (s, 1H), 12.70 (br.s, 1H).

Example 172

3-(2,3-dichlorobenzyl)-1-(1-isopropyl-1H-benzimidazol-5-yl)-2,4-dioxo-1,2,3,4-tetrahydropyrimidine-5-carboxylic acid

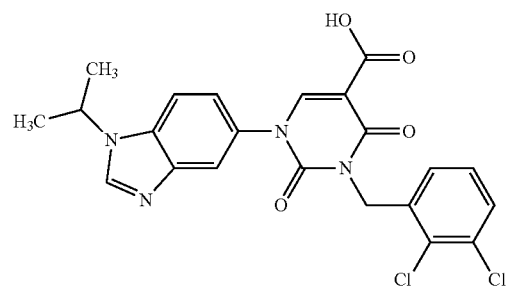 [SMILES: CC(C)n1cnc2cc(-n3cc(C(=O)O)c(=O)n(Cc4cccc(Cl)c4Cl)c3=O)ccc21]

The preparation and purification of the title compound were in analogy to Example 171. Proceeding from 83 mg (0.17 mmol) of ethyl 3-(2,3-dichlorobenzyl)-1-(1-isopropyl-1H-benzimidazol-5-yl)-2,4-dioxo-1,2,3,4-tetrahydropyrimidine-5-carboxylate from Example 87, 59 mg (72% of theory) of the title compound were obtained.

LC-MS (Method 1): $R_t$=0.99 min; m/z=473 (M+H)$^+$.

$^1$H NMR (400 MHz, DMSO-d$_6$): δ [ppm]=1.56 (d, 6H), 4.78-4.86 (m, 1H), 5.14 (s, 2H), 7.26-7.30 (m, 1H), 7.32-7.38 (m, 1H), 7.40-7.44 (m, 1H), 7.57-7.61 (m, 1H), 7.80 (d, 1H), 7.86-7.89 (m, 1H), 8.48-8.52 (m, 2H), 12.70 (br.s, 1H).

Example 173

3-[3-chloro-2-(trifluoromethyl)benzyl]-1-[1-(cyclopropylmethyl)-1H-benzimidazol-5-yl]-2,4-dioxo-1,2,3,4-tetrahydropyrimidine-5-carboxylic acid

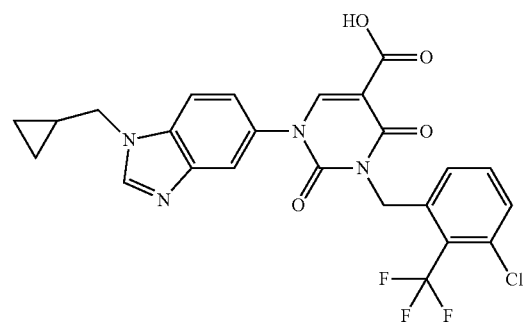 [SMILES: O=C(O)c1cn(-c2ccc3c(c2)ncn3CC2CC2)c(=O)n(Cc2cccc(Cl)c2C(F)(F)F)c1=O]

The preparation and purification of the title compound were in analogy to Example 171. Proceeding from 135 mg (0.24 mmol) of ethyl 3-[3-chloro-2-(trifluoromethyl)benzyl]-1-[1-(cyclopropylmethyl)-1H-benzimidazol-5-yl]-2,4-dioxo-1,2,3,4-tetrahydropyrimidine-5-carboxylate from Example 92, 59 mg (45% of theory) of the title compound were obtained.

LC-MS (Method 1): $R_t$=1.00 min; m/z=519 (M+H)$^+$.

$^1$H NMR (400 MHz, DMSO-d$_6$): δ [ppm]=0.41-0.48 (m, 2H), 0.52-0.58 (m, 2H), 1.27-1.36 (m, 1H), 4.17 (d, 2H), 5.25 (s, 2H), 7.36-7.44 (m, 2H), 7.58-7.68 (m, 2H), 7.81 (d, 1H), 7.85-7.89 (m, 1H), 8.43 (s, 1H), 8.53 (s, 1H), 12.70 (br.s, 1H).

Example 174

3-[2-chloro-3-(trifluoromethyl)benzyl]-1-(1-cyclobutyl-1H-benzimidazol-5-yl)-2,4-dioxo-1,2,3,4-tetrahydropyrimidine-5-carboxylic acid

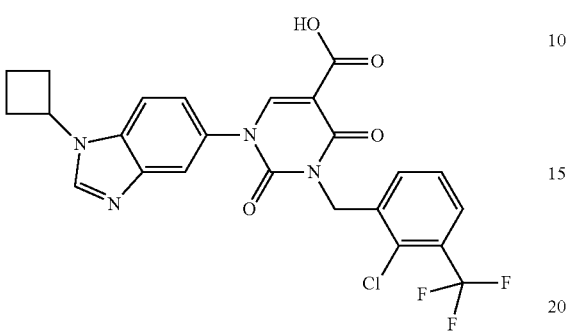

The preparation and purification of the title compound were in analogy to Example 171. Proceeding from 153 mg (0.25 mmol) of ethyl 3-[2-chloro-3-(trifluoromethyl)benzyl]-1-(1-cyclobutyl-1H-benzimidazol-5-yl)-2,4-dioxo-1,2,3,4-tetrahydropyrimidine-5-carboxylate from Example 88, 90 mg (68% of theory) of the title compound were obtained.

LC-MS (Method 1): $R_t$=1.02 min; m/z=519 (M+H)$^+$.

$^1$H NMR (400 MHz, DMSO-$d_6$): δ [ppm]=1.86-1.96 (m, 2H), 2.5-2.6 (m, partly concealed by DMSO signal), 4.99-5.09 (m, 1H), 5.18 (s, 2H), 7.40-7.45 (m, 1H), 7.50-7.57 (m, 1H), 7.60-7.66 (m, 1H), 7.75 (d, 1H), 7.79-7.83 (m, 1H), 7.87-7.90 (m, 1H), 8.51 (s, 1H), 8.55 (s, 1H), 12.71 (br.s, 1H).

Example 175

3-[2-chloro-3-(trifluoromethyl)benzyl]-1-(1-methyl-1H-indazol-5-yl)-2,4-dioxo-1,2,3,4-tetrahydropyrimidine-5-carboxylic acid

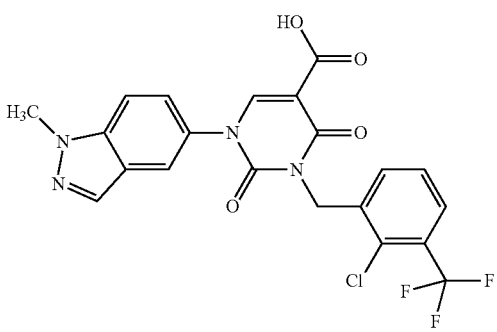 [SMILES: Cn1ncc2cc(-n3cc(C(=O)O)c(=O)n(Cc4cccc(C(F)(F)F)c4Cl)c3=O)ccc21]

The preparation and purification of the title compound were in analogy to Example 121. Proceeding from 228 mg (0.45 mmol) of ethyl 3-[2-chloro-3-(trifluoromethyl)benzyl]-1-(1-methyl-1H-indazol-5-yl)-2,4-dioxo-1,2,3,4-tetrahydropyrimidine-5-carboxylate from Example 89, 170 mg (77% of theory) of the title compound were obtained.

LC-MS (Method 1): $R_t$=1.04 min; m/z=479 (M+H)$^+$.

$^1$H NMR (400 MHz, DMSO-$d_6$): δ [ppm]=4.10 (s, 3H), 5.18 (s, 2H), 7.51-7.57 (m, 2H), 7.61-7.66 (m, 1H), 7.76-7.83 (m, 2H), 7.96-7.99 (m, 1H), 8.18 (s, 1H), 8.54 (s, 1H), 12.71 (br.s, 1H).

Example 176

1-(1-methyl-1H-indazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

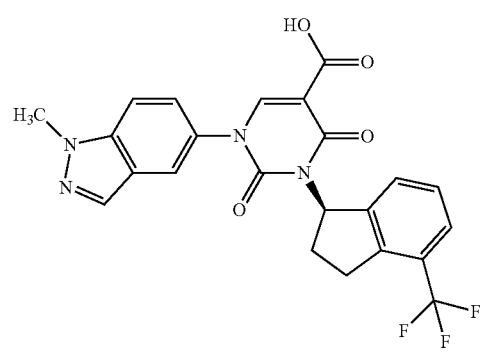 [SMILES: Cn1ncc2cc(-n3cc(C(=O)O)c(=O)n([C@@H]4CCc5c4cccc5C(F)(F)F)c3=O)ccc21]

The preparation and purification of the title compound were analogous to Example 121, with reaction time 45 mm. Proceeding from 119 mg (0.24 mmol) of ethyl 1-(1-methyl-1H-indazol-5-yl)-2,4-dioxo-3-[4-(trifluoromethyl)-2,3-dihydro-1H-inden-1-yl]-1,2,3,4-tetrahydropyrimidine-5-carboxylate from Example 76, 81 mg (71% of theory) of the title compound were obtained.

LC-MS (Method 1): $R_t$=1.08 min; m/z=471 (M+H)$^+$.

$^1$H NMR (400 MHz, CDCl$_3$): δ [ppm]=2.45-2.54 (m, 1H), 2.65-2.72 (m, 1H), 3.13-3.24 (m, 1H), 3.48-3.61 (m, 1H), 4.12 (s, 3H), 6.62-6.71 (m, 1H), 7.28-7.35 (m, 3H), 7.48-7.56 (m, 2H), 7.70 (s, 1H), 8.06 (s, 1H), 8.63 (s, 1H), 12.53 (s, 1H).

Example 177

1-(1,3-dimethyl-2,2-dioxido-1,3-dihydro-2,1,3-benzothiadiazol-5-yl)-3-[2-methyl-3-(trifluoromethyl)benzyl]-2,4-dioxo-1,2,3,4-tetrahydropyrimidine-5-carboxylic acid

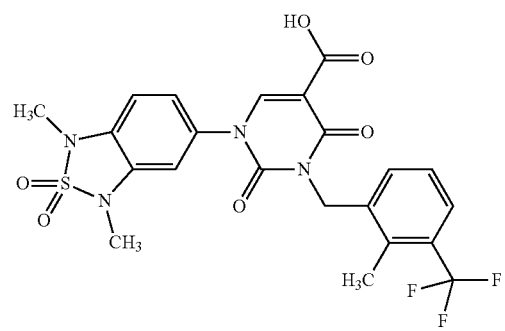 [SMILES: Cc1c(Cn2c(=O)c(C(=O)O)cn(-c3ccc4c(c3)N(C)S(=O)(=O)N4C)c2=O)cccc1C(F)(F)F]

The preparation and purification of the title compound were in analogy to Example 121. Proceeding from 195 mg (0.35 mmol) of ethyl 1-(1,3-dimethyl-2,2-dioxido-1,3-dihydro-2,1,3-benzothiadiazol-5-yl)-3-[2-methyl-3-(trifluoromethyl)benzyl]-2,4-dioxo-1,2,3,4-tetrahydropyrimidine-5-carboxylate from Example 94, 153 mg (79% of theory) of the title compound were obtained.

LC-MS (Method 1): $R_t$=1.11 min; m/z=525 (M+H)$^+$.

$^1$H NMR (400 MHz, DMSO-d$_6$): δ [ppm]=2.47 (s, 3H), 3.26 (s, 3H), 3.30 (s, partly concealed by water signal), 5.10 (s, 2H), 7.13-7.17 (m, 1H), 7.20-7.24 (m, 1H), 7.26-7.30 (m, 1H), 7.32-7.42 (m, 2H), 7.59-7.63 (m, 1H), 8.48 (s, 1H), 12.74 (br.s, 1H).

Example 178

3-[3-chloro-2-(trifluoromethyl)benzyl]-1-(1,3-dimethyl-2,2-dioxido-1,3-dihydro-2,1,3-benzothiadiazol-5-yl)-2,4-dioxo-1,2,3,4-tetrahydropyrimidine-5-carboxylic acid

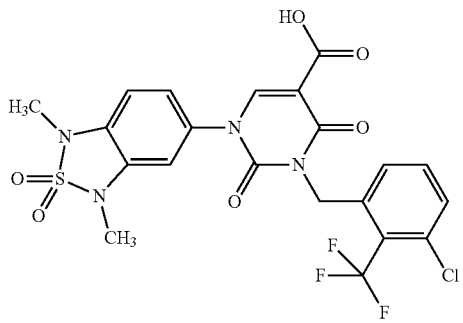 [SMILES: CN1c2ccc(-n3cc(C(=O)O)c(=O)n(Cc4cccc(Cl)c4C(F)(F)F)c3=O)cc2N(C)S1(=O)=O]

The preparation and purification of the title compound were in analogy to Example 121. Proceeding from 120 mg (0.21 mmol) of ethyl 3-[3-chloro-2-(trifluoromethyl)benzyl]-1-(1,3-dimethyl-2,2-dioxido-1,3-dihydro-2,1,3-benzothiadiazol-5-yl)-2,4-dioxo-1,2,3,4-tetrahydropyrimidine-5-carboxylate from Example 95, 98 mg (85% of theory) of the title compound were obtained.

LC-MS (Method 1): $R_t$=1.11 min; m/z=545 (M+H)$^+$.

$^1$H NMR (400 MHz, DMSO-d$_6$): δ [ppm]=3.27 (s, partly concealed by DMSO signal), 3.30 (s, 3H), 5.23 (s, 2H), 7.13-7.18 (m, 1H), 7.18-7.23 (m, 1H), 7.24-7.27 (m, 1H), 7.31-7.36 (m, 1H), 7.56-7.67 (m, 2H), 8.50 (s, 1H), 12.73 (br.s, 1H).

Example 179

3-[2-chloro-3-(trifluoromethyl)benzyl]-1-(1,3-dimethyl-2,2-dioxido-1,3-dihydro-2,1,3-benzothiadiazol-5-yl)-2,4-dioxo-1,2,3,4-tetrahydropyrimidine-5-carboxylic acid

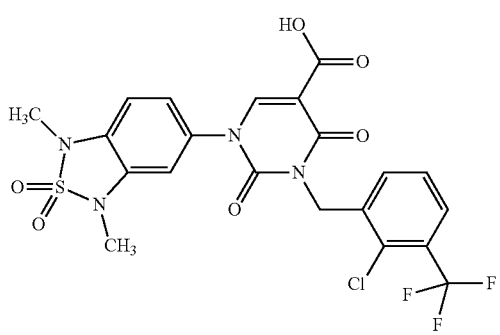 [SMILES: CN1c2ccc(-n3cc(C(=O)O)c(=O)n(Cc4cccc(C(F)(F)F)c4Cl)c3=O)cc2N(C)S1(=O)=O]

The preparation and purification of the title compound were in analogy to Example 121. Proceeding from 167 mg (0.29 mmol) of ethyl 3-[2-chloro-3-(trifluoromethyl)benzyl]-1-(1,3-dimethyl-2,2-dioxido-1,3-dihydro-2,1,3-benzothiadiazol-5-yl)-2,4-dioxo-1,2,3,4-tetrahydropyrimidine-5-carboxylate from Example 96, 129 mg (80% of theory) of the title compound were obtained.

LC-MS (Method 1): $R_t$=1.12 min; m/z=545 (M+H)$^+$.

$^1$H NMR (400 MHz, DMSO-d$_6$): δ [ppm]=3.27 (s, 3H), 3.30 (s, 3H), 5.17 (s, 2H), 7.13-7.18 (m, 1H), 7.20-7.24 (m, 1H), 7.25-7.28 (m, 1H), 7.50-7.56 (m, 1H), 7.56-7.61 (m, 1H), 7.79-7.83 (m, 1H), 8.49 (s, 1H), 12.74 (br.s, 1H).

Example 180

1-(1,3-dimethyl-2,2-dioxido-1,3-dihydro-2,1,3-benzothiadiazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

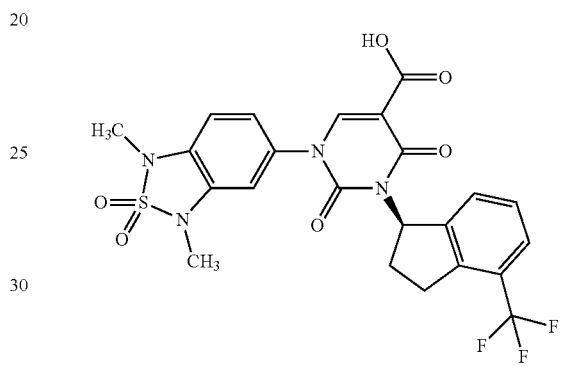

The preparation and purification of the title compound were analogous to Example 121. Proceeding from 130 mg (0.23 mmol) of ethyl 1-(1,3-dimethyl-2,2-dioxido-1,3-dihydro-2,1,3-benzothiadiazol-5-yl)-2,4-dioxo-3-[4-(trifluoromethyl)-2,3-dihydro-1H-inden-1-yl]-1,2,3,4-tetrahydropyrimidine-5-carboxylate from Example 97, after additional purification by means of preparative HPLC (Method 8), 50 mg (40% of theory) of the title compound were obtained.

LC-MS (Method 4): $R_t$=2.44 min; m/z=537 (M+H)$^+$.

$^1$H NMR (400 MHz, CD$_2$Cl$_2$): δ [ppm]=2.32-2.44 (m, 1H), 2.51-2.63 (m, 1H), 3.04-3.16 (m, 1H), 3.20 (s, 3H), 3.23 (s, 3H), 3.36-3.47 (m, 1H), 6.51-6.60 (m, 1H), 6.65 (s, 1H), 6.75 (d, 1H), 6.89 (d, 1H), 7.21-7.30 (m, 2H), 7.42-7.49 (m, 1H), 8.44 (s, 1H).

Example 181

3-[2-chloro-3-(trifluoromethyl)benzyl]-1-(1-methyl-2-oxo-2,3-dihydro-1H-benzimidazol-5-yl)-2,4-dioxo-1,2,3,4-tetrahydropyrimidine-5-carboxylic acid

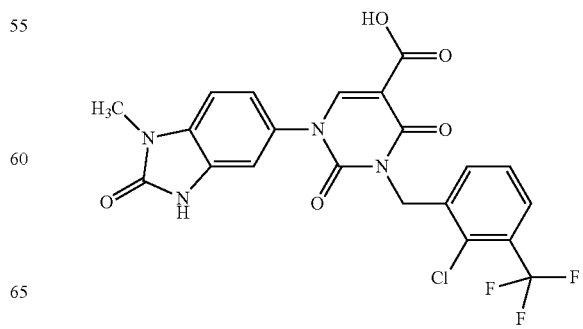

The preparation and purification of the title compound were in analogy to Example 121. Proceeding from 20 mg (0.04 mmol) of ethyl 3-[2-chloro-3-(trifluoromethyl)benzyl]-1-(1-methyl-2-oxo-2,3-dihydro-1H-benzimidazol-5-yl)-2,4-dioxo-1,2,3,4-tetrahydropyrimidine-5-carboxylate from Example 16, 14 mg (71% of theory) of the title compound were obtained.

LC-MS (Method 3): $R_t$=1.16 min; m/z=495 (M+H)$^+$.

$^1$H NMR (400 MHz, DMSO-d$_6$): δ [ppm]=3.30 (s, 3H), 5.16 (s, 2H), 7.17-7.23 (m, 3H), 7.49-7.55 (m, 1H), 7.60-7.64 (m, 1H), 7.78-7.83 (m, 1H), 8.44 (s, 1H), 11.14 (s, 1H), 12.69 (br.s, 1H).

Example 182

1-(1-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylic acid

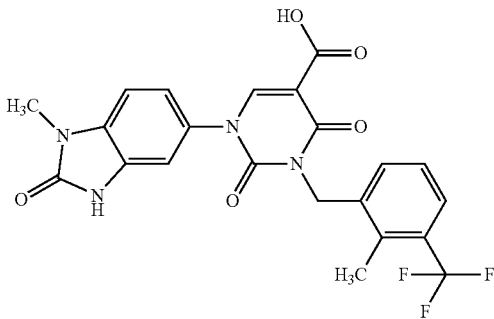 [SMILES: Cc1c(Cn2c(=O)c(C(=O)O)cn(-c3ccc4c(c3)[nH]c(=O)n4C)c2=O)cccc1C(F)(F)F]

The preparation and purification of the title compound were in analogy to Example 121. Proceeding from 129 mg (0.26 mmol) of ethyl 1-(1-methyl-2-oxo-2,3-dihydro-1H-benzimidazol-5-yl)-3-[2-methyl-3-(trifluoromethyl)-benzyl]-2,4-dioxo-1,2,3,4-tetrahydropyrimidine-5-carboxylate from Example 14, 113 mg (93% of theory) of the title compound were obtained.

LC-MS (Method 1): $R_t$=0.94 min; m/z=475 (M+H)$^+$.

$^1$H NMR (400 MHz, DMSO-d$_6$): δ [ppm]=2.46 (s, 3H), 3.32 (s, 3H), 5.10 (s, 2H), 7.17-7.23 (m, 3H), 7.32-7.38 (m, 1H), 7.40-7.45 (m, 1H), 7.58-7.63 (m, 1H), 8.43 (s, 1H), 11.14 (s, 1H), 12.70 (br.s, 1H).

Example 183

3-(2,3-dichlorobenzyl)-1-(1-methyl-2-oxo-2,3-dihydro-1H-benzimidazol-5-yl)-2,4-dioxo-1,2,3,4-tetrahydropyrimidine-5-carboxylic acid

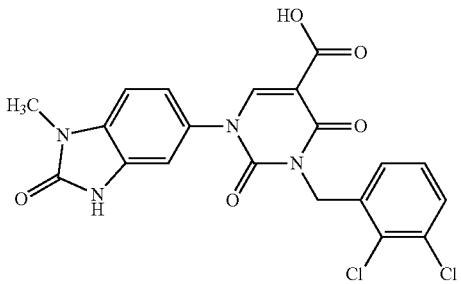 [SMILES: Cn1c(=O)[nH]c2cc(-n3cc(C(=O)O)c(=O)n(Cc4cccc(Cl)c4Cl)c3=O)ccc21]

The preparation and purification of the title compound were in analogy to Example 121. Proceeding from 30 mg (0.06 mmol) of ethyl 3-(2,3-dichlorobenzyl)-1-(1-methyl-2-oxo-2,3-dihydro-1H-benzimidazol-5-yl)-2,4-dioxo-1,2,3,4-tetrahydropyrimidine-5-carboxylate from Example 15, 22 mg (73% of theory) of the title corn-pound were obtained.

LC-MS (Method 1): $R_t$=0.91 min; m/z=461 (M+H)$^+$.

$^1$H NMR (400 MHz, DMSO-d$_6$): δ [ppm]=3.30 (s, partly concealed by water signal), 5.12 (s, 2H), 7.20 (s, 3H), 7.25-7.29 (m, 1H), 7.30-7.36 (m, 1H), 7.56-7.61 (m, 1H), 8.43 (s, 1H), 11.14 (s, 1H), 12.69 (br.s, 1H).

Example 184 ethyl 1-(6-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate

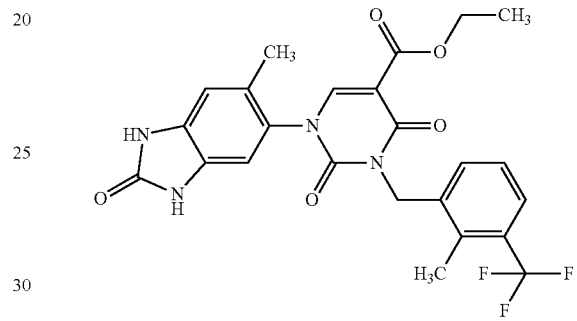

The preparation and purification of the title compound were analogous to Example 1. Proceeding from 200 mg (0.60 mmol) of ethyl 1-(6-methyl-2-oxo-2,3-dihydro-1H-benzimidazol-5-yl)-2,4-dioxo-1,2,3,4-tetrahydropyrimidine-5-carboxylate from Example 27A and 168 mg (0.66 mmol) of 1-(bromomethyl)-2-methyl-3-(trifluoromethyl)benzene, after additional recrystallization from ethanol, 207 mg (62% of theory) of the title compound were obtained.

LC-MS (Method 1): $R_t$=0.98 min; m/z=503 (M+H)$^+$.

$^1$H NMR (400 MHz, DMSO-d$_6$): δ [ppm]=1.22 (t, 3H), 2.09 (s, 3H), 2.45 (s, 3H), 4.18 (q, 2H), 5.08 (d, 2H), 6.89 (s, 1H), 7.12 (s, 1H), 7.30-7.36 (m, 2H), 7.57-7.62 (m, 1H), 8.37 (s, 1H), 10.80 (s, 1H).

Example 185 ethyl 3-[2-chloro-3-(trifluoromethyl)benzyl]-1-(6-methyl-2-oxo-2,3-dihydro-1H-benzimidazol-5-yl)-2,4-dioxo-1,2,3,4-tetrahydropyrimidine-5-carboxylate

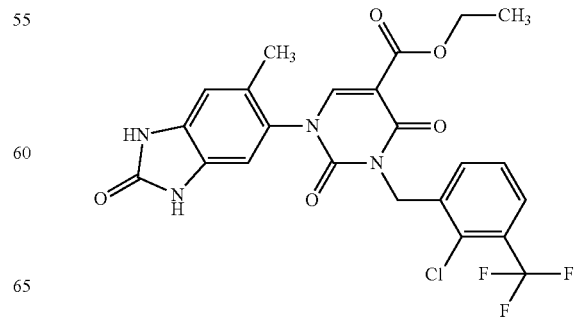

The preparation of the title compound was analogous to Example 37. Proceeding from 200 mg (0.60 mmol) of ethyl 1-(6-methyl-2-oxo-2,3-dihydro-1H-benzimidazol-5-yl)-2,4-dioxo-1,2,3,4-tetrahydropyrimidine-5-carboxylate from Example 27A and 182 mg (0.66 mmol) of 1-(bromomethyl)-2-chloro-3-(trifluoromethyl)-benzene, after purification by means of preparative HPLC (Method 8), 178 mg (56% of theory) of the title compound were obtained.

LC-MS (Method 1): $R_t$=1.01 min; m/z=523 (M+H)$^+$.
$^1$H NMR (400 MHz, DMSO-d$_6$): δ [ppm]=1.23 (t, 3H), 2.10 (s, 3H), 4.19 (q, 2H), 5.15 (s, 2H), 6.89 (s, 1H), 7.11 (s, 1H), 7.49-7.57 (m, 2H), 7.77-7.83 (m, 1H), 8.39 (s, 1H), 10.80 (s, 2H).

Example 186

3-[2-chloro-3-(trifluoromethyl)benzyl]-2,4-dioxo-1-(2-oxo-2,3-dihydro-1H-benzimidazol-5-yl)-1,2,3,4-tetrahydropyrimidine-5-carboxylic acid

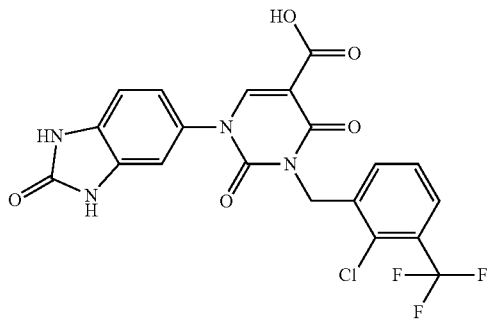 [SMILES: O=C(O)c1cn(-c2ccc3[nH]c(=O)[nH]c3c2)c(=O)n(Cc2cccc(C(F)(F)F)c2Cl)c1=O]

The preparation and purification of the title compound were analogous to Example 121, with a reaction time of 1 h. Proceeding from 99 mg (0.19 mmol) of ethyl 3-[2-chloro-3-(trifluoromethyl)benzyl]-2,4-dioxo-1-(2-oxo-2,3-dihydro-1H-benzimidazol-5-yl)-1,2,3,4-tetrahydropyrimidine-5-carboxylate from Example 37, 79 mg (85% of theory) of the title compound were obtained.

LC-MS (Method 1): $R_t$=0.89 min; m/z=481 (M+H)$^+$.
$^1$H NMR (400 MHz, DMSO-d$_6$): δ [ppm]=5.16 (s, 2H), 7.00-7.04 (m, 1H), 7.07-7.11 (m, 1H), 7.13-7.16 (m, 1H), 7.49-7.55 (m, 1H), 7.59-7.64 (m, 1H), 7.78-7.83 (m, 1H), 8.43 (s, 1H), 10.87-10.92 (m, 2H), 12.68 (br.s, 1H).

Example 187

1-(3-methyl-2-oxo-2,3-dihydro-1,3-benzoxazol-6-yl)-3-[2-methyl-3-(trifluoromethyl)benzyl]-2,4-dioxo-1,2,3,4-tetrahydropyrimidine-5-carboxylic acid

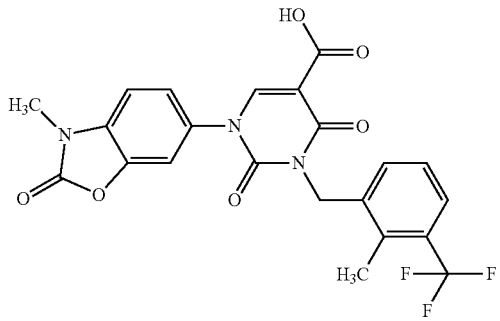 [SMILES: Cc1c(Cn2c(=O)c(C(=O)O)cn(-c3ccc4c(c3)oc(=O)n4C)c2=O)cccc1C(F)(F)F]

The preparation and purification of the title compound were analogous to Example 121, with a reaction time of 1 h. Proceeding from 280 mg (0.55 mmol) of ethyl 1-(3-methyl-2-oxo-2,3-dihydro-1,3-benzoxazol-6-yl)-3-[2-methyl-3-(trifluoromethyl)benzyl]-2,4-dioxo-1,2,3,4-tetrahydropyrimidine-5-carboxylate from Example 40, 186 mg (69% of theory) of the title compound were obtained.

LC-MS (Method 5): $R_t$=1.06 min; m/z=476 (M+H)$^+$.
$^1$H NMR (400 MHz, DMSO-d$_6$): δ [ppm]=2.47 (s, 3H), 3.38 (s, 3H), 5.10 (s, 2H), 7.32-7.47 (m, 4H), 7.58-7.66 (m, 2H), 8.47 (s, 1H), 12.74 (br.s, 1H).

Example 188

3-[2-chloro-3-(trifluoromethyl)benzyl]-1-(3-methyl-2-oxo-2,3-dihydro-1,3-benzoxazol-6-yl)-2,4-dioxo-1,2,3,4-tetrahydropyrimidine-5-carboxylic acid

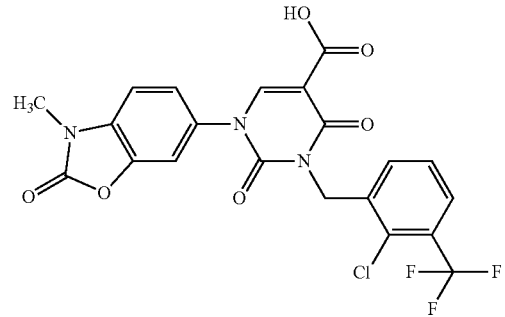 [SMILES: Cn1c(=O)oc2cc(-n3cc(C(=O)O)c(=O)n(Cc4cccc(C(F)(F)F)c4Cl)c3=O)ccc21]

The preparation and purification of the title compound were analogous to Example 121, with a reaction time of 1 h. Proceeding from 250 mg (0.47 mmol) of ethyl 3-[2-chloro-3-(trifluoromethyl)benzyl]-1-(3-methyl-2-oxo-2,3-dihydro-1,3-benzoxazol-6-yl)-2,4-dioxo-1,2,3,4-tetrahydropyrimidine-5-carboxylate from Example 41, 220 mg (91% of theory) of the title compound were obtained.

LC-MS (Method 5): $R_t$=1.07 min; m/z=496 (M+H)$^+$.
$^1$H NMR (400 MHz, DMSO-d$_6$): δ [ppm]=3.38 (s, 3H), 5.16 (s, 2H), 7.38-7.47 (m, 2H), 7.50-7.56 (m, 1H), 7.58-7.64 (m, 2H), 7.78-7.83 (m, 1H), 8.48 (s, 1H), 12.74 (br.s, 1H).

Example 189

1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

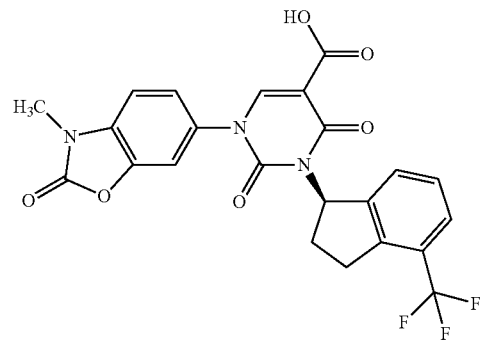 [SMILES: Cn1c(=O)oc2cc(-n3cc(C(=O)O)c(=O)n([C@@H]4CCc5c4cccc5C(F)(F)F)c3=O)ccc21]

3.40 g (6.60 mmol) of the compound from Example 42 in 44 ml of glacial acetic acid and 22 ml of concentrated hydrochloric acid were stirred at reflux temperature for 1 h. After cooling slightly (about 60° C.), the mixture was fully concentrated under reduced pressure. The amorphous residue was admixed with 50 ml of isopropanol and heated to reflux for 15 min, in the course of which a solid formed. The suspension was then cooled to 10° C. and then the solid was filtered off with suction. The solid was washed twice with 15 ml each time of isopropanol, filtered off with suction and dried under HV. This gave 2.53 g (79% of theory) of the title compound.

LC-MS (Method 1): $R_t$=1.12 min; m/z=488 (M+H)$^+$.

Chiral analytical HPLC (Method 14): $R_t$=13.3 min; about 99% ee $^1$H NMR (400 MHz, CD$_2$Cl$_2$): δ [ppm]=2.40-2.52 (m, 1H), 2.59-2.72 (m, 1H), 3.12-3.25 (m, 1H), 3.41 (s, 3H), 3.44-3.56 (m, 1H), 6.58-6.69 (m, 1H), 7.04-7.11 (m, 1H), 7.15-7.21 (m, 1H), 7.24 (br.s, 1H), 7.29-7.38 (m, 2H), 7.53 (s, 1H), 8.54 (s, 1H), 12.39 (br. s, 1H).

Specific rotation $α_D^{20}$=+135.3° (methanol, c=0.43).

In an analogous experiment, the specific rotation of the product was measured in chloroform: $α_D^{20}$=+159.5° (chloroform, c=0.395).

An x-ray structure analysis in the complex with chymase confirmed the R configuration for this enantiomer.

Example 190

1-(3-methyl-2-oxo-2,3-dihydro-1,3-benzoxazol-6-yl)-2,4-dioxo-3-[(1 S)-4-(trifluoromethyl)-2,3-dihydro-1H-inden-1-yl]-1,2,3,4-tetrahydropyrimidine-5-carboxylic acid (S enantiomer)

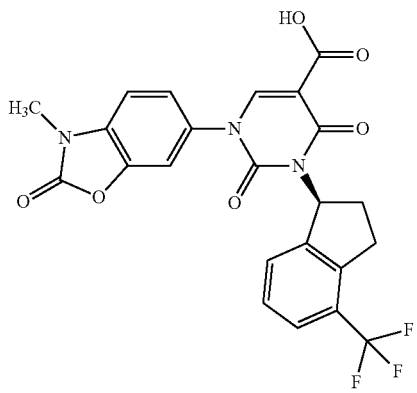 [SMILES: Cn1c(=O)oc2cc(-n3cc(C(=O)O)c(=O)n([C@H]4CCc5c4cccc5C(F)(F)F)c3=O)ccc21]

420 mg (0.80 mmol) of the compound from Example 43 in 7.7 ml of glacial acetic acid/conc. hydrochloric acid 2:1 (v/v) were heated to reflux for 1 h. Subsequently, the reaction mixture was concentrated on a rotary evaporator and the residue was dried under HV. This gave 390 mg (96% of theory) of the title compound.

LC-MS (Method 1): $R_t$=1.09 min; m/z=488 (M+H)$^+$.

$^1$H NMR (400 MHz, CD$_2$Cl$_2$): δ [ppm]=2.37-2.53 (m, 1H), 2.66 (dtd, 1H), 3.10-3.26 (m, 1H), 3.41 (s, 3H), 3.44-3.55 (m, 1H), 6.58-6.71 (m, 1H), 7.08 (d, 1H), 7.19 (br. d, 1H), 7.24 (br. s, 1H), 7.30-7.38 (m, 2H), 7.50-7.59 (m, 1H), 8.55 (s, 1H).

Chiral analytical HPLC (Method 14): $R_t$=9.97 min; about 95% ee.

Specific rotation: $α_D^{20}$=−122.5° (c=0.5, methanol).

Example 191

3-(2,3-dichlorobenzyl)-1-(3-ethyl-2-oxo-2,3-dihydro-1,3-benzoxazol-6-yl)-2,4-dioxo-1,2,3,4-tetrahydropyrimidine-5-carboxylic acid

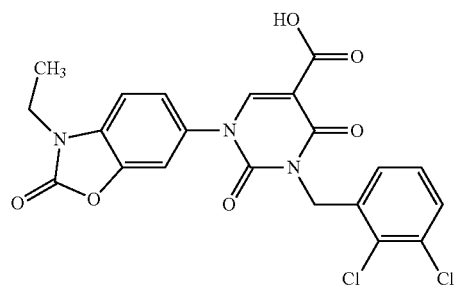 [SMILES: CCn1c(=O)oc2cc(-n3cc(C(=O)O)c(=O)n(Cc4cccc(Cl)c4Cl)c3=O)ccc21]

The preparation and purification of the title compound were in analogy to Example 121. Proceeding from 210 mg (0.42 mmol) of ethyl 3-(2,3-dichlorobenzyl)-1-(3-ethyl-2-oxo-2,3-dihydro-1,3-benzoxazol-6-yl)-2,4-dioxo-1,2,3,4-tetrahydropyrimidine-5-carboxylate from Example 45, 180 mg (89% of theory) of the title compound were obtained.

LC-MS (Method 1): $R_t$=1.08 min; m/z=476 (M+H)$^+$.

$^1$H NMR (400 MHz, DMSO-d$_6$): δ [ppm]=1.28 (t, 3H), 3.90 (q, 2H), 5.12 (s, 2H), 7.23-7.28 (m, 1H), 7.31-7.36 (m, 1H), 7.47 (s, 2H), 7.57-7.61 (m, 1H), 7.62-7.65 (m, 1H), 8.48 (s, 1H), 12.70 (br.s, 1H).

Example 192

1-(3-ethyl-2-oxo-2,3-dihydro-1,3-benzoxazol-6-yl)-3-[2-methyl-3-(trifluoromethyl)benzyl]-2,4-dioxo-1,2,3,4-tetrahydropyrimidine-5-carboxylic acid

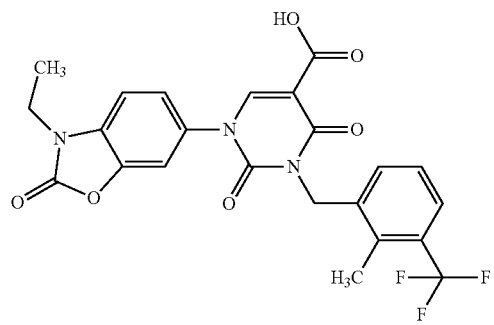 [SMILES: CCn1c(=O)oc2cc(-n3cc(C(=O)O)c(=O)n(Cc4cccc(C(F)(F)F)c4C)c3=O)ccc21]

The preparation and purification of the title compound were in analogy to Example 121. Proceeding from 185 mg (0.36 mmol) of ethyl 1-(3-ethyl-2-oxo-2,3-dihydro-1,3-benzoxazol-6-yl)-3-[2-methyl-3-(trifluoromethyl)benzyl]-2,4-dioxo-1,2,3,4-tetrahydropyrimidine-5-carboxylate from Example 44, 159 mg (90% of theory) of the title compound were obtained.

LC-MS (Method 1): $R_t$=1.10 min; m/z=490 (M+H)$^+$.

$^1$H NMR (400 MHz, DMSO-d$_6$): δ [ppm]=1.28 (t, 3H), 2.47 (s, 3H), 3.90 (q, 2H), 5.10 (s, 2H), 7.32-7.38 (m, 1H), 7.39-7.50 (m, 3H), 7.59-7.63 (m, 1H), 7.64-7.66 (m, 1H), 8.48 (s, 1H), 12.72 (br.s, 1H).

Example 193

3-[2-chloro-3-(trifluoromethyl)benzyl]-1-(3-ethyl-2-oxo-2,3-dihydro-1,3-benzoxazol-6-yl)-2,4-dioxo-1,2,3,4-tetrahydropyrimidine-5-carboxylic acid

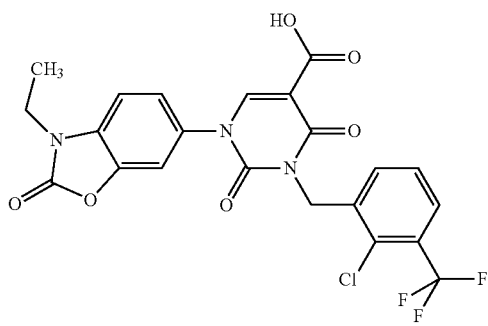 [SMILES: CCn1c(=O)oc2cc(-n3cc(C(=O)O)c(=O)n(Cc4cccc(C(F)(F)F)c4Cl)c3=O)ccc21]

The preparation and purification of the title compound were in analogy to Example 121. Proceeding from 200 mg (0.37 mmol) of ethyl 3-[2-chloro-3-(trifluoromethyl)benzyl]-1-(3-ethyl-2-oxo-2,3-dihydro-1,3-benzoxazol-6-yl)-2,4-dioxo-1,2,3,4-tetrahydropyrimidine-5-carboxylate from Example 46, 165 mg (85% of theory) of the title compound were obtained.

LC-MS (Method 1): $R_E$=1.10 min; m/z=510 (M+H)$^+$.
$^1$H NMR (400 MHz, DMSO-d$_6$): δ [ppm]=1.28 (d, 3H), 3.90 (q, 2H), 5.17 (s, 2H), 7.42-7.56 (m, 3H), 7.58-7.65 (m, 2H), 7.78-7.83 (m, 1H), 8.49 (s, 1H), 12.73 (br.s, 1H).

Example 194

1-(3-ethyl-2-oxo-2,3-dihydro-1,3-benzoxazol-6-yl)-3-[3-fluoro-2-(trifluoromethyl)benzyl]-2,4-dioxo-1,2,3,4-tetrahydropyrimidine-5-carboxylic acid

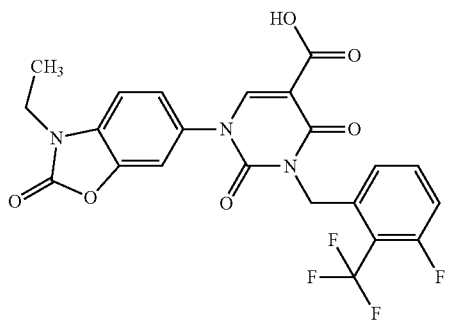 [SMILES: CCn1c(=O)oc2cc(-n3cc(C(=O)O)c(=O)n(Cc4cccc(F)c4C(F)(F)F)c3=O)ccc21]

The preparation and purification of the title compound were in analogy to Example 121. Proceeding from 150 mg (0.29 mmol) of ethyl 1-(3-ethyl-2-oxo-2,3-dihydro-1,3-benzoxazol-6-yl)-3-[3-fluoro-2-(trifluoromethyl)-benzyl]-2,4-dioxo-1,2,3,4-tetrahydropyrimidine-5-carboxylate from Example 47, 105 mg (73% of theory) of the title compound were obtained.

LC-MS (Method 1): $R_f$=1.05 min; m/z=494 (M+H)$^+$.
$^1$H NMR (400 MHz, DMSO-d$_6$): δ [ppm]=1.28 (t, 3H), 3.90 (q, 2H), 5.21 (s, 2H), 7.19-7.25 (m, 1H), 7.38-7.51 (m, 3H), 7.61-7.70 (m, 2H), 8.50 (s, 1H), 12.72 (br.s, 1H).

Example 195

1-(3-methyl-2-oxo-2,3-dihydro-1,3-benzothiazol-6-yl)-3-[2-methyl-3-(trifluoromethyl)benzyl]-2,4-dioxo-1,2,3,4-tetrahydropyrimidine-5-carboxylic acid

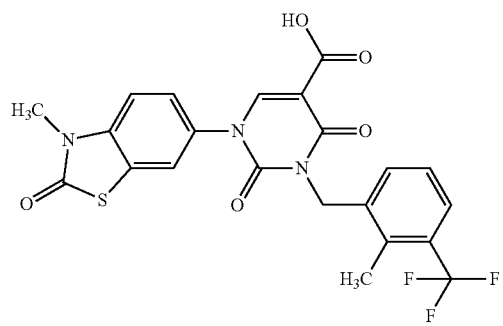 [SMILES: Cc1c(Cn2c(=O)c(C(=O)O)cn(-c3ccc4c(c3)sc(=O)n4C)c2=O)cccc1C(F)(F)F]

The preparation and purification of the title compound were in analogy to Example 121. Proceeding from 390 mg (0.75 mmol) of ethyl 1-(3-methyl-2-oxo-2,3-dihydro-1,3-benzothiazol-6-yl)-3-[2-methyl-3-(trifluoromethyl)-benzyl]-2,4-dioxo-1,2,3,4-tetrahydropyrimidine-5-carboxylate from Example 48, 314 mg (81% of theory) of the title compound were obtained.

LC-MS (Method 3): $R_t$=1.33 min; m/z=492 (M+H)$^+$.
$^1$H NMR (400 MHz, DMSO-d$_6$): δ [ppm]=2.47 (s, 3H), 3.45 (s, 3H), 5.10 (s, 2H), 7.32-7.38 (m, 1H), 7.39-7.43 (m, 1H), 7.46 (d, 1H), 7.60 (s, 2H), 7.89 (d, 1H), 8.52 (s, 1H), 12.73 (br.s, 1H).

Example 196

3-[2-chloro-3-(trifluoromethyl)benzyl]-1-(3-methyl-2-oxo-2,3-dihydro-1,3-benzothiazol-6-yl)-2,4-dioxo-1,2,3,4-tetrahydropyrimidine-5-carboxylic acid

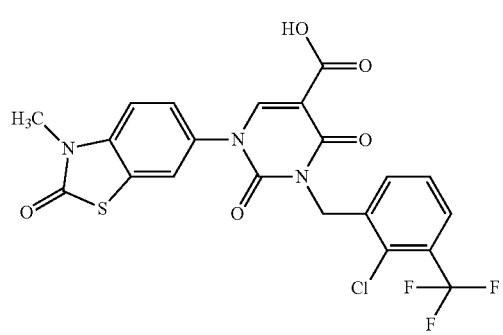 [SMILES: Cn1c(=O)sc2cc(-n3cc(C(=O)O)c(=O)n(Cc4cccc(C(F)(F)F)c4Cl)c3=O)ccc21]

The preparation and purification of the title compound were in analogy to Example 121. Proceeding from 216 mg (0.40 mmol) of ethyl 3-[2-chloro-3-(trifluoromethyl)benzyl]-1-(3-methyl-2-oxo-2,3-dihydro-1,3-benzothiazol-6-yl)-2,4-dioxo-1,2,3,4-tetrahydropyrimidine-5-carboxylate from Example 49, 155 mg (72% of theory) of the title compound were obtained.

LC-MS (Method 3): $R_t$=1.33 min; m/z=512 (M+H)$^+$.
$^1$H NMR (400 MHz, DMSO-d$_6$): δ [ppm]=3.45 (s, 3H), 5.17 (s, 2H), 7.46 (d, 1H), 7.49-7.64 (m, 3H), 7.78-7.84 (m, 1H), 7.89 (d, 1H), 8.53 (s, 1H), 12.73 (br.s, 1H).

Example 197

3-[3-fluoro-2-(trifluoromethyl)benzyl]-1-(3-methyl-2-oxo-2,3-dihydro-1,3-benzothiazol-6-yl)-2,4-dioxo-1,2,3,4-tetrahydropyrimidine-5-carboxylic acid

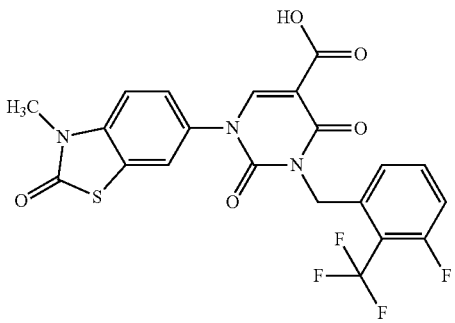 [SMILES: Cn1c(=O)sc2cc(-n3cc(C(=O)O)c(=O)n(Cc4cccc(F)c4C(F)(F)F)c3=O)ccc21]

The preparation and purification of the title compound were in analogy to Example 121. Proceeding from 241 mg (0.46 mmol) of ethyl 3-[3-fluoro-2-(trifluoromethyl)benzyl]-1-(3-methyl-2-oxo-2,3-dihydro-1,3-benzothiazol-6-yl)-2,4-dioxo-1,2,3,4-tetrahydropyrimidine-5-carboxylate from Example 50, 180 mg (73% of theory) of the title compound were obtained.

LC-MS (Method 3): $R_t$=1.27 min; m/z=496 (M+H)$^+$.

$^1$H NMR (400 MHz, DMSO-d$_6$): δ [ppm]=3.45 (s, 3H), 5.21 (s, 2H), 7.19-7.25 (m, 1H), 7.37-7.49 (m, 2H), 7.55-7.60 (m, 1H), 7.62-7.70 (m, 1H), 7.86-7.90 (m, 1H), 8.53 (s, 1H), 12.73 (br.s, 1H).

Example 198

1-(1,3-benzothiazol-6-yl)-3-[2-methyl-3-(trifluoromethyl)benzyl]-2,4-dioxo-1,2,3,4-tetrahydropyrimidine-5-carboxylic acid

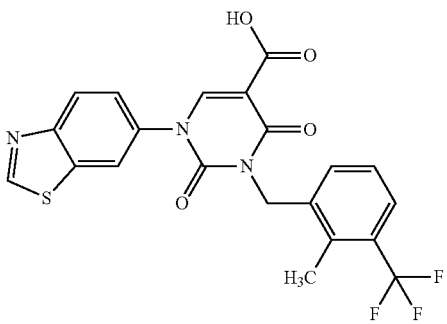 [SMILES: Cc1c(Cn2c(=O)c(C(=O)O)cn(-c3ccc4ncsc4c3)c2=O)cccc1C(F)(F)F]

The preparation and purification of the title compound were in analogy to Example 121. Proceeding from 204 mg (0.41 mmol) of ethyl 1-(1,3-benzothiazol-6-yl)-3-[2-methyl-3-(trifluoromethyl)benzyl]-2,4-dioxo-1,2,3,4-tetrahydropyrimidine-5-carboxylate from Example 98, 160 mg (82% of theory) of the title compound were obtained.

LC-MS (Method 1): $R_t$=1.07 min; m/z=462 (M+H)$^+$.

$^1$H NMR (400 MHz, DMSO-d$_6$): δ [ppm]=2.47 (partly concealed by DMSO signal), 5.12 (s, 2H), 7.33-7.39 (m, 1H), 7.42-7.47 (m, 1H), 7.58-7.64 (m, 1H), 7.70-7.75 (m, 1H), 8.22 (d, 1H), 8.39-8.43 (m, 1H), 8.61 (s, 1H), 9.54 (s, 1H), 12.75 (br.s, 1H).

Example 199

1-[3-hydroxy-1-methyl-2-oxo-3-(trifluoromethyl)-2,3-dihydro-1H-indol-5-yl]-3-[2-methyl-3-(trifluoromethyl)benzyl]-2,4-dioxo-1,2,3,4-tetrahydropyrimidine-5-carboxylic acid (Racemate)

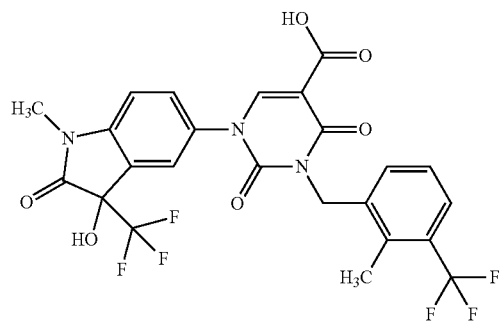 [SMILES: Cc1c(Cn2c(=O)c(C(=O)O)cn(-c3ccc4c(c3)C(O)(C(F)(F)F)C(=O)N4C)c2=O)cccc1C(F)(F)F]

The preparation and purification of the title compound were in analogy to Example 121, with a reaction time of 20 min. Proceeding from 74 mg (0.12 mmol) of ethyl 1-[3-hydroxy-1-methyl-2-oxo-3-(trifluoromethyl)-2,3-dihydro-1H-indol-5-yl]-3-[2-methyl-3-(trifluoromethyl)benzyl]-2,4-dioxo-1,2,3,4-tetrahydropyrimidine-5-carboxylate from Example 63, 37 mg (53% of theory) of the title compound were obtained.

LC-MS (Method 5): $R_t$=1.09 min; m/z=558 (M+H)$^+$.

$^1$H NMR (400 MHz, DMSO-d$_6$): δ [ppm]=2.46 (s, 3H), 3.22 (s, 3H), 5.10 (s, 2H), 7.29 (d, 1H), 7.32-7.38 (m, 1H), 7.41-7.45 (m, 1H), 7.58-7.63 (m, 1H), 7.66-7.73 (m, 2H), 7.92 (s, 1H), 8.44 (s, 1H), 12.74 (hr. s, 1H).

Example 200

1-[3-fluoro-1-methyl-2-oxo-3-(trifluoromethyl)-2,3-dihydro-1H-indol-5-yl]-3-[2-methyl-3-(trifluoromethyl)benzyl]-2,4-dioxo-1,2,3,4-tetrahydropyrimidine-5-carboxylic acid (Racemate)

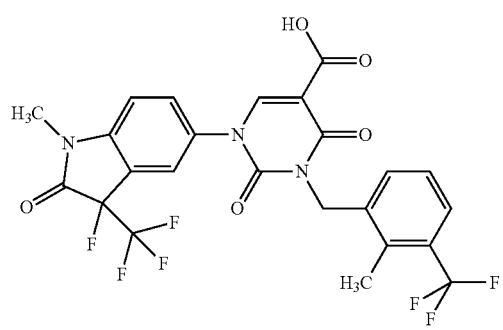 [SMILES: Cc1c(Cn2c(=O)c(C(=O)O)cn(-c3ccc4c(c3)C(F)(C(F)(F)F)C(=O)N4C)c2=O)cccc1C(F)(F)F]

The preparation and purification of the title compound were in analogy to Example 121. Proceeding from 85 mg (0.14 mmol) of ethyl 1-[3-fluoro-1-methyl-2-oxo-3-(trifluoromethyl)-2,3-dihydro-1H-indol-5-yl]-3-[2-methyl-3-(trifluoromethyl)benzyl]-2,4-dioxo-1,2,3,4-tetrahydropyrimidine-5-carboxylate from Example 64, 66 mg (82% of theory) of the title compound were obtained.

LC-MS (Method 1): $R_t$=1.18 min; m/z=560 (M+H)⁺.

¹H NMR (400 MHz, DMSO-$d_6$): δ [ppm]=2.46 (s, partly concealed by DMSO signal), 3.26 (s, partly concealed by water signal), 5.10 (s, 2H), 7.31-7.38 (m, 1H), 7.39-7.45 (m, 2H), 7.60 (d, 1H), 7.82-7.88 (m, 1H), 7.95 (s, 1H), 8.57 (s, 1H), 12.75 (br.s, 1H).

Example 201

3-[2-chloro-3-(trifluoromethyl)benzyl]-1-(3-hydroxy-1,3-dimethyl-2-oxo-2,3-dihydro-1H-indol-5-yl)-2,4-dioxo-1,2,3,4-tetrahydropyrimidine-5-carboxylic acid (Racemate)

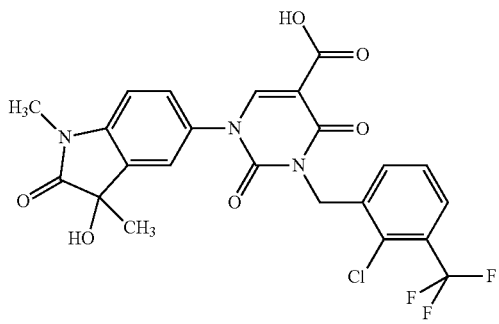 [SMILES: CN1C(=O)C(C)(O)c2cc(-n3cc(C(=O)O)c(=O)n(Cc4cccc(C(F)(F)F)c4Cl)c3=O)ccc21]

The preparation and purification of the title compound were in analogy to Example 121, with a reaction time of 45 min. Proceeding from 124 mg (0.22 mmol) of ethyl 3-[2-chloro-3-(trifluoromethyl)benzyl]-1-(3-hydroxy-1,3-dimethyl-2-oxo-2,3-dihydro-1H-indol-5-yl)-2,4-dioxo-1,2,3,4-tetrahydropyrimidine-5-carboxylate from Example 62, 54 mg (50% of theory) of the title compound were obtained, as were 24 mg (22% of theory) of Example 202. Analytical data for the title compound:

LC-MS (Method 1): $R_t$=0.95 min; m/z=524 (M+H)⁺.

¹H NMR (400 MHz, DMSO-$d_6$): δ [ppm]=1.41 (s, 3H), 3.14 (s, 3H), 5.16 (s, 2H), 6.12 (s, 1H), 7.14 (d, 1H), 7.47-7.57 (m, 3H), 7.59-7.64 (m, 1H), 7.78-7.83 (m, 1H), 8.42 (s, 1H), 12.73 (br. s, 1H).

Example 202

1-(3-chloro-1,3-dimethyl-2-oxo-2,3-dihydro-1H-indol-5-yl)-3-[2-chloro-3-(trifluoromethyl)benzyl]-2,4-dioxo-1,2,3,4-tetrahydropyrimidine-5-carboxylic acid

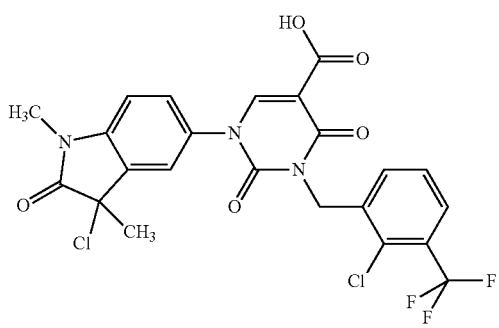 [SMILES: CN1C(=O)C(C)(Cl)c2cc(-n3cc(C(=O)O)c(=O)n(Cc4cccc(C(F)(F)F)c4Cl)c3=O)ccc21]

The title compound (24 mg) was isolated in the synthesis of Example 201.

LC-MS (Method 1): $R_t$=1.09 min; m/z=542 (M+H)⁺.

¹H NMR (400 MHz, DMSO-$d_6$): δ [ppm]=1.87 (s, 3H), 3.22 (s, 3H), 5.17 (s, 2H), 7.26 (d, 1H), 7.51-7.56 (m, 1H), 7.57-7.64 (m, 2H), 7.77-7.84 (m, 2H), 8.48 (s, 1H), 12.75 (br. s, 1H).

Example 203

3-[2-methyl-3-(trifluoromethyl)benzyl]-2,4-dioxo-1-(2-oxo-2,3-dihydro-1H-benzimidazol-5-yl)-1,2,3,4-tetrahydropyrimidine-5-carboxylic acid

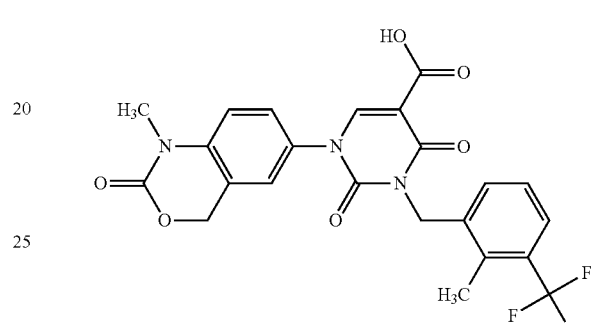

The preparation and purification of the title compound were analogous to Example 121, with a reaction time of 15 min. Proceeding from 265 mg (0.51 mmol) of ethyl 1-(1-methyl-2-oxo-1,4-dihydro-2H-3,1-benzoxazin-6-yl)-3-[2-methyl-3-(trifluoromethyl)benzyl]-2,4-dioxo-1,2,3,4-tetrahydropyrimidine-5-carboxylate from Example 100, after purification by means of preparative HPLC (Method 8), 121 mg (46% of theory) of the title compound were obtained.

LC-MS (Method 1): $R_t$=1.03 min; m/z=490 (M+H)⁺.

¹H NMR (400 MHz, DMSO-$d_6$): δ [ppm]=2.47 (s, 3H), 3.3 (concealed by water signal), 5.10 (s, 2H), 5.30 (s, 2H), 7.21-7.26 (m, 1H), 7.31-7.43 (m, 2H), 7.45-7.48 (m, 1H), 7.53-7.62 (m, 2H), 8.46 (s, 1H), 12.72 (br.s, 1H).

Example 204

1-(1-methyl-2-oxo-1,4-dihydro-2H-3,1-benzoxazin-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

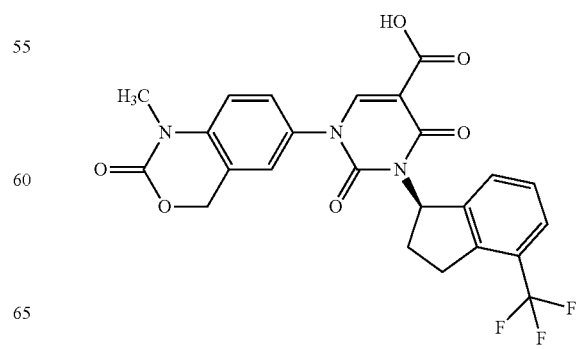

The preparation and purification of the title compound were analogous to Example 121, with reaction time 45 min. Proceeding from 135 mg (0.25 mmol) of ethyl 1-(1-methyl-2-oxo-1,4-dihydro-2H-3,1-benzoxazin-6-yl)-2,4-dioxo-3-[4-(trifluoromethyl)-2,3-dihydro-1H-inden-1-yl]-1,2,3,4-tetrahydropyrimidine-5-carboxylate from Example 101, 81 mg (59% of theory) of the title compound were obtained.

LC-MS (Method 1): $R_t$=1.04 min; m/z=502 (M+H)$^+$.

$^1$H NMR (400 MHz, CDCl$_3$): δ [ppm]=2.39-2.52 (m, 1H), 2.64-2.71 (m, 1H), 3.12-3.25 (m, 1H), 3.41 (s, 3H), 3.47-3.61 (m, 1H), 5.22 (s, 2H), 6.60-6.70 (m, 1H), 7.05 (d, 1H), 7.15 (s, 1H), 7.28-7.36 (m, 3H), 7.50-7.57 (m, 1H), 8.53 (s, 1H), 12.18-12.70 (m, 2H).

Example 205

3-[2-methyl-3-(trifluoromethyl)benzyl]-2,4-dioxo-1-(1,3,3-trimethyl-2-oxo-2,3-dihydro-1H-indol-6-yl)-1,2,3,4-tetrahydropyrimidine-5-carboxylic acid

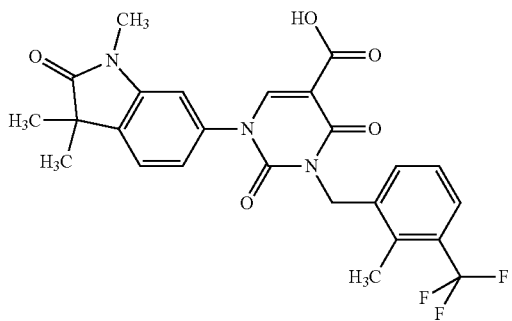 [SMILES: Cc1c(Cn2c(=O)c(C(=O)O)cn(-c3ccc4c(c3)N(C)C(=O)C4(C)C)c2=O)cccc1C(F)(F)F]

The preparation and purification of the title compound were in analogy to Example 121, with a reaction time of 45 min. Proceeding from 127 mg (0.24 mmol) of ethyl 3-[2-methyl-3-(trifluoromethyl)benzyl]-2,4-dioxo-1-(1,3,3-trimethyl-2-oxo-2,3-dihydro-1H-indol-6-yl)-1,2,3,4-tetrahydropyrimidine-5-carboxylate from Example 59, after additional purification by means of preparative HPLC (Method 8), 76 mg (63% of theory) of the title compound were obtained.

LC-MS (Method 1): $R_t$=1.08 min; m/z=502 (M+H)$^+$.

$^1$H NMR (400 MHz, DMSO-d$_6$): δ [ppm]=1.30 (s, 6H), 2.47 (s, 3H), 3.14 (s, 3H), 5.11 (s, 2H), 7.19-7.24 (m, 1H), 7.25-7.28 (m, 1H), 7.32-7.43 (m, 2H), 7.51 (d, 1H), 7.61 (d, 1H), 8.48 (s, 1H), 12.74 (br.s, 1H).

Example 206

3-[2-chloro-3-(trifluoromethyl)benzyl]-2,4-dioxo-1-(1,3,3-trimethyl-2-oxo-2,3-dihydro-1H-indol-6-yl)-1,2,3,4-tetrahydropyrimidine-5-carboxylic acid

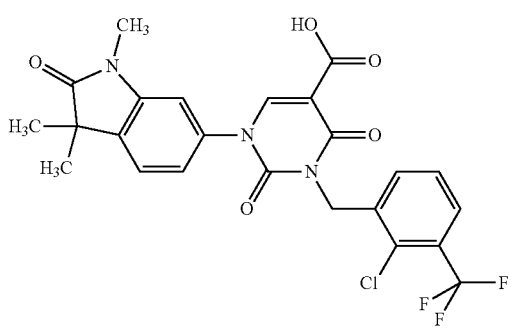 [SMILES: CN1C(=O)C(C)(C)c2ccc(-n3cc(C(=O)O)c(=O)n(Cc4cccc(C(F)(F)F)c4Cl)c3=O)cc21]

The preparation and purification of the title compound were in analogy to Example 121, with a reaction time of 2 h, except that MTBE was replaced by cyclohexane for the workup. Proceeding from 125 mg (0.35 mmol) of ethyl 3-[2-chloro-3-(trifluoromethyl)benzyl]-2,4-dioxo-1-(1,3,3-trimethyl-2-oxo-2,3-dihydro-1H-indol-6-yl)-1,2,3,4-tetrahydropyrimidine-5-carboxylate from Example 60, 134 mg (65% of theory) of the title compound were obtained.

LC-MS (Method 1): $R_t$=1.08 min; m/z=522 (M+H)$^+$.

$^1$H NMR (400 MHz, DMSO-d$_6$): δ [ppm]=1.30 (s, 6H), 3.15 (s, 3H), 5.17 (s, 2H), 7.19-7.24 (m, 1H), 7.24-7.27 (m, 1H), 7.48-7.56 (m, 2H), 7.58-7.62 (m, 1H), 7.78-7.83 (m, 1H), 8.49 (s, 1H), 12.74 (br.s, 1H).

Example 207

3-[3-chloro-2-(trifluoromethyl)benzyl]-2,4-dioxo-1-(1,3,3-trimethyl-2-oxo-2,3-dihydro-1H-indol-6-yl)-1,2,3,4-tetrahydropyrimidine-5-carboxylic acid

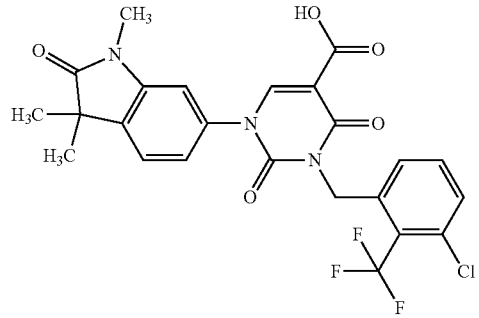 [SMILES: CN1C(=O)C(C)(C)c2ccc(-n3cc(C(=O)O)c(=O)n(Cc4cccc(Cl)c4C(F)(F)F)c3=O)cc21]

The preparation and purification of the title compound were in analogy to Example 121, with a reaction time of 45 min. Proceeding from 122 mg (0.22 mmol) of ethyl 3-[3-chloro-2-(trifluoromethyl)benzyl]-2,4-dioxo-1-(1,3,3-trimethyl-2-oxo-2,3-dihydro-1H-indol-6-yl)-1,2,3,4-tetrahydropyrimidine-5-carboxylate from Example 61, 87 mg (71% of theory) of the title compound were obtained.

LC-MS (Method 1): $R_t$=1.12 min; in/z=522 (M+H)$^+$.

$^1$H NMR (400 MHz, DMSO-d$_6$): δ [ppm]=1.30 (s, 6H), 3.15 (s, 3H), 5.24 (br.s, 2H), 7.19-7.23 (m, 1H), 7.23-7.26 (m, 1H), 7.33-7.37 (m, 1H), 7.51 (d, 1H), 7.57-7.67 (m, 2H), 8.50 (s, 1H), 12.73 (br.s, 1H).

Example 208 ethyl-3-[2-chloro-3-(trifluoromethyl)benzyl]-1-(1-ethyl-3,3-dimethyl-2-oxo-2,3-dihydro-1H-indol-6-yl)-2,4-dioxo-1,2,3,4-tetrahydropyrimidine-5-carboxylate

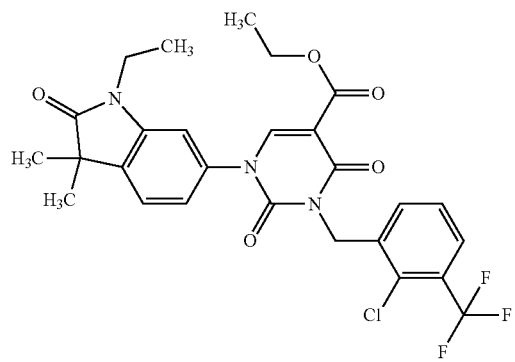 [SMILES: CCOC(=O)c1cn(-c2ccc3c(c2)N(CC)C(=O)C3(C)C)c(=O)n(Cc2cccc(C(F)(F)F)c2Cl)c1=O]

371 mg (0.69 mmol) of ethyl 3-[2-chloro-3-(trifluoromethyl)benzyl]-1-(3,3-dimethyl-2-oxo-2,3-dihydro-1H-indol-6-yl)-2,4-dioxo-1,2,3,4-tetrahydropyrimidine-5-carboxylate from Example 68 in THF (5 ml) were initially charged at 0° C. under argon, and 29 mg (content 60%, 0.72 mmol) of sodium hydride were added. The mixture was stirred at RT for 30 mm and then cooled again to 0° C. A solution of 113 mg (0.72 mmol) of iodoethane in 1 ml of THF was added dropwise. The reaction mixture was left to stir at RT for 2 days. For workup, the mixture was admixed with water and extracted twice with ethyl acetate. The combined organic phases were dried over magnesium sulphate and concentrated. The residue was purified by means of preparative HPLC (Method 7). This gave 50 mg (12% of theory) of the title compound.

LC-MS (Method 1): $R_t$=1.37 min; m/z=564 (M+H)$^+$.

$^1$H NMR (400 MHz, DMSO-$d_6$): δ [ppm]=1.16 (t, 3H), 1.24 (t, 3H), 1.30 (s, 6H), 3.70 (q, 2H), 4.20 (q, 2H), 5.16 (s, 2H), 7.21 (dd, 1H), 7.31 (d, 1H), 7.49-7.60 (m, 3H), 7.78-7.82 (m, 1H), 8.52 (s, 1H).

Example 209

1-(4-methylquinolin-4-yl)-3-[2-methyl-3-(trifluoromethyl)benzyl]-2,4-dioxo-1,2,3,4-tetrahydropyrimidine-5-carboxylic acid hydrochloride

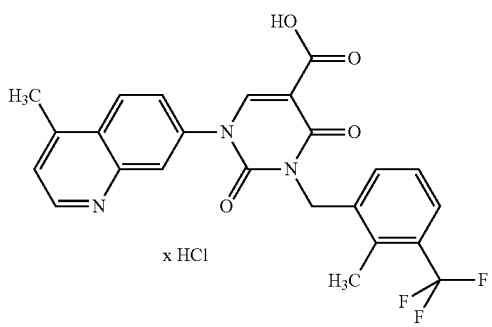 [SMILES: Cc1c(Cn2c(=O)c(C(=O)O)cn(-c3ccc4c(C)ccnc4c3)c2=O)cccc1C(F)(F)F]

The preparation and purification of the title compound were in analogy to Example 121. Proceeding from 200 mg (0.40 mmol) of ethyl 1-(4-methylquinolin-7-yl)-3-[2-methyl-3-(trifluoromethyl)benzyl]-2,4-dioxo-1,2,3,4-tetrahydropyrimidine-5-carboxylate from Example 99, 173 mg (91% of theory) of the title compound were obtained.

LC-MS (Method 3): $R_t$=1.25 min; m/z=470 (M+H)$^+$.

$^1$H NMR (400 MHz, DMSO-$d_6$): δ [ppm]=2.48 (s, 3H), 2.80 (s, 3H), 3.80 (br.s, 1H), 5.14 (s, 2H), 7.34-7.40 (m, 1H), 7.46-7.51 (m, 1H), 7.59-7.65 (m, 2H), 7.84-7.90 (m, 1H), 8.28-8.36 (m, 2H), 8.68 (s, 1H), 8.93-8.98 (m, 1H), 12.75 (br.s, 1H).

Example 210

3-[2-chloro-3-(trifluoromethyl)benzyl]-1-(3,3-dimethyl-2,3-dihydro-1H-indol-6-yl)-2,4-dioxo-1,2,3,4-tetrahydropyrimidine-5-carboxylic acid

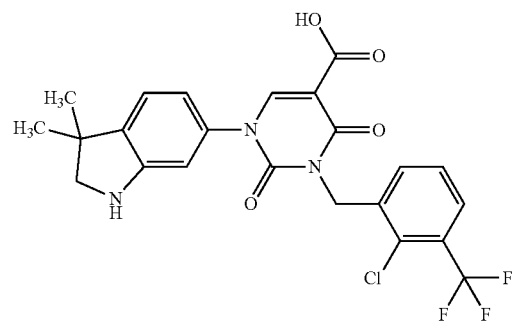 [SMILES: CC1(C)CNc2cc(-n3cc(C(=O)O)c(=O)n(Cc4cccc(C(F)(F)F)c4Cl)c3=O)ccc21]

228 mg (0.40 mmol) of the compound from Example 69 in 4.4 ml of glacial acetic acid/conc. hydrochloric acid 2:1 (v/v) were stirred at 120° C. (bath temperature) for 1 h. After cooling to RT, the mixture was admixed with water and extracted three times with dichloromethane. The combined organic phases were dried over magnesium sulphate and concentrated on a rotary evaporator. The residue was stirred in MTBE, and the solid formed was filtered off, washed with a little MTBE and dried under HV. This gave 160 mg (80% of theory) of the title compound.

LC-MS (Method 5): $R_t$=1.23 min; m/z=494 (M+H)$^+$.

$^1$H NMR (400 MHz, DMSO-$d_6$): δ [ppm]=1.25 (s, 6H), 3.25 (s, 2H), 5.15 (s, 2H), 5.88 (br.s, 1H), 6.59 (s, 1H), 6.65 (d, 1H), 7.09 (d, 1H), 7.47-7.55 (m, 1H), 7.56-7.61 (m, 1H), 7.80 (d, 1H), 8.36 (s, 1H), 12.67 (br.s, 1H).

Example 211

1-(1-acetyl-3,3-dimethyl-2,3-dihydro-1H-indol-6-yl)-3-[2-chloro-3-(trifluoromethyl)benzyl]-2,4-dioxo-1,2,3,4-tetrahydropyrimidine-5-carboxylic acid

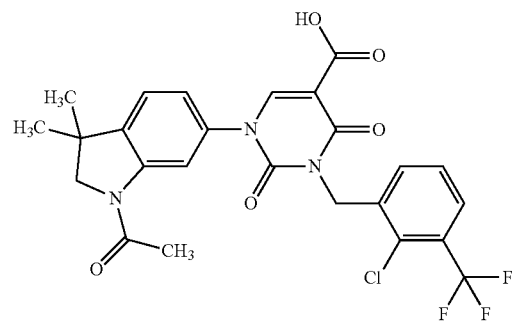 [SMILES: CC(=O)N1CC(C)(C)c2ccc(-n3cc(C(=O)O)c(=O)n(Cc4cccc(C(F)(F)F)c4Cl)c3=O)cc21]

160 mg (0.32 mmol) of the compound from Example 210 were initially charged in THF (1.4 ml), then 90 µl (0.65 mmol) of triethylamine and 34 µl (0.36 mmol) of acetic anhydride were added and the mixture was stirred at RT overnight. Thereafter, the reaction mixture was admixed with 1M hydrochloric acid and extracted three times with dichloromethane. The combined organic phases were dried over magnesium sulphate, filtered and concentrated. The residue was stirred with methanol, and the solid was filtered off and dried under reduced pressure. This gave 85 mg (47% of theory) of the title compound.

LC-MS (Method 1): $R_t$=1.13 min; m/z=536 (M+H)$^+$.

$^1$H NMR (400 MHz, DMSO-d$_6$): δ [ppm]=1.34 (s, 6H), 2.18 (s, 3H), 3.94 (s, 2H), 5.15 (s, 2H), 7.16-7.21 (m, 1H), 7.38-7.43 (m, 1H), 7.48-7.54 (m, 1H), 7.61-7.65 (m, 1H), 7.77-7.82 (m, 1H), 8.13-8.16 (m, 1H), 8.42 (s, 1H), 12.69 (br.s, 1H).

Example 212

1-(3,3-dimethyl-2,3-dihydro-1H-indol-6-yl)-3-[2-methyl-3-(trifluoromethyl)benzyl]-2,4-dioxo-1,2,3,4-tetrahydropyrimidine-5-carboxylic acid

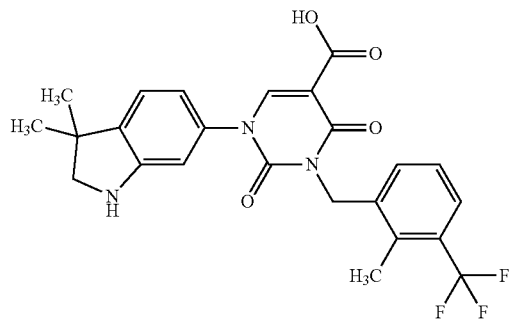 [SMILES: Cc1c(Cn2c(=O)c(C(=O)O)cn(-c3ccc4c(c3)NCC4(C)C)c2=O)cccc1C(F)(F)F]

Analogously to Example 210, 253 mg (0.47 mmol) of the compound from Example 70 were hydrolysed and the product was purified. This gave 174 mg (77% of theory) of the title compound.

LC-MS (Method 5): $R_t$=1.23 min; m/z=474 (M+H)$^+$.

$^1$H NMR (400 MHz, DMSO-d$_6$): δ [ppm]=1.24 (s, 6H), 2.46 (s, 3H), 3.24 (s, 2H), 5.09 (s, 2H), 5.86 (br.s, 1H), 6.58 (s, 1H), 6.64 (d, 1H), 7.08 (d, 1H), 7.26-7.45 (m, 2H), 7.60 (d, 1H), 8.35 (s, 1H), 12.68 (br.s, 1H).

Example 213

1-(1-acetyl-3,3-dimethyl-2,3-dihydro-1H-indol-6-yl)-3-[2-methyl-3-(trifluoromethyl)benzyl]-2,4-dioxo-1,2,3,4-tetrahydropyrimidine-5-carboxylic acid

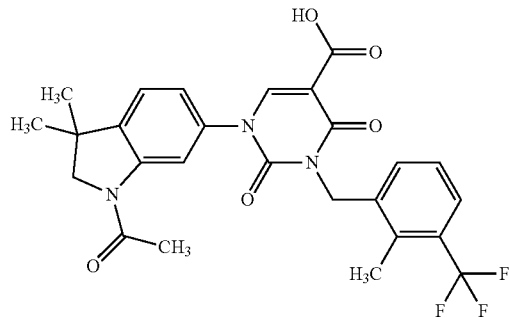 [SMILES: CC(=O)N1CC(C)(C)c2ccc(-n3cc(C(=O)O)c(=O)n(Cc4cccc(C(F)(F)F)c4C)c3=O)cc21]

The preparation and purification of the title compound were analogous to Example 211. Proceeding from 174 mg (0.36 mmol) of 1-(3,3-dimethyl-2,3-dihydro-1H-indol-6-yl)-3-[2-methyl-3-(trifluoromethyl)benzyl]-2,4-dioxo-1,2,3, 4-tetrahydropyrimidine-5-carboxylic acid from Example 212, 135 mg (70% of theory) of the title compound were obtained.

LC-MS (Method 5): $R_t$=1.18 min; m/z=516 (M+H)$^+$.

$^1$H NMR (400 MHz, DMSO-d$_6$): δ [ppm]=1.34 (s, 6H), 2.18 (s, 3H), 2.46 (s, 3H), 3.93 (s, 2H), 5.09 (s, 2H), 7.16-7.21 (m, 1H), 7.31-7.37 (m, 1H), 7.38-7.44 (m, 1H), 7.57-7.62 (m, 1H), 8.12-8.15 (m, 1H), 8.40 (s, 1H), 12.69 (br.s, 1H).

Example 214

1-(1-methyl-2-oxo-1,2,3,4-tetrahydroquinolin-6-yl)-3-[2-methyl-3-(trifluoromethyl)benzyl]-2,4-dioxo-1,2,3,4-tetrahydropyrimidine-5-carboxylic acid

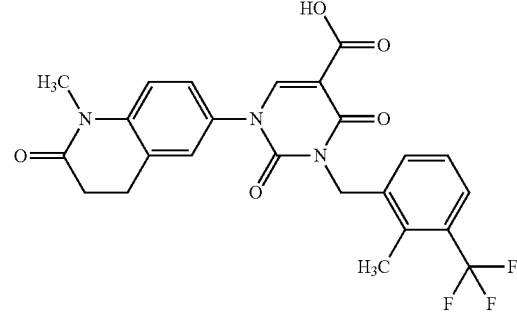 [SMILES: Cc1c(Cn2c(=O)c(C(=O)O)cn(-c3ccc4c(c3)CCC(=O)N4C)c2=O)cccc1C(F)(F)F]

The preparation and purification of the title compound were analogous to Example 121. Proceeding from 267 mg (0.51 mmol) of ethyl 1-(1-methyl-2-oxo-1,2,3,4-tetrahydroquinolin-6-yl)-3-[2-methyl-3-(trifluoromethyl)-benzyl]-2,4-dioxo-1,2,3,4-tetrahydropyrimidine-5-carboxylate from Example 102, 218 mg (83% of theory) of the title compound were obtained.

LC-MS (Method 3): $R_t$=1.28 min; m/z=488 (M+H)$^+$.

$^1$H NMR (400 MHz, DMSO-d$_6$): δ [ppm]=2.47 (s, 3H), 2.56-2.61 (m, 2H), 2.89-2.94 (m, 2H), 3.28 (s, 3H), 5.10 (s, 2H), 7.20-7.24 (m, 1H), 7.32-7.46 (m, 4H), 7.58-7.62 (m, 1H), 8.43 (s, 1H), 12.72 (br.s, 1H).

Example 215

1-(1-methyl-2-oxo-1,2,3,4-tetrahydroquinolin-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

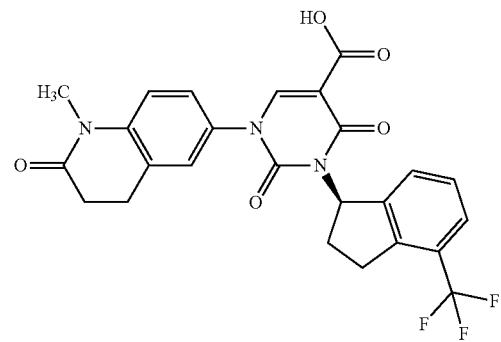 [SMILES: CN1C(=O)CCc2cc(-n3cc(C(=O)O)c(=O)n([C@@H]4CCc5c4cccc5C(F)(F)F)c3=O)ccc21]

The preparation and purification of the title compound were analogous to Example 121, with reaction time 45 min. Proceeding from 83 mg (0.15 mmol) of ethyl 1-(1-methyl-2-oxo-1,2,3,4-tetrahydroquinolin-6-yl)-2,4-dioxo-3-[4-(trifluoromethyl)-2,3-dihydro-1H-inden-1-yl]-1,2,3,4-tetrahydropyrimidine-5-carboxylate from Example 103, 39 mg (46% of theory) of the title compound were obtained.

LC-MS (Method 1): $R_t$=1.10 min; m/z=500 (M+H)$^+$.

$^1$H NMR (400 MHz, CDCl$_3$): δ [ppm]=2.42-2.52 (m, 1H), 2.63-2.66 (m, 1H, partly concealed by DMSO signal), 2.69 (t, 2H), 2.95 (t, 2H), 3.12-3.20 (m, 1H, 3.37 (s, 3H), 3.48-3.60 (m, 1H), 6.60-6.71 (m, 1H), 7.06 (d, 1H), 7.14 (s, 1H), 7.21 (d, 1H), 7.28-7.34 (m, 2H), 7.50-7.56 (m, 1H), 8.55 (s, 1H), 12.49 (s, 1H).

Example 216 ethyl 3-(2-methyl-3-nitrobenzyl)-1-(4-methyl-3-oxo-3,4-dihydro-2H-1,4-benzoxazin-7-yl)-2,4-dioxo-1,2,3,4-tetrahydropyrimidine-5-carboxylate

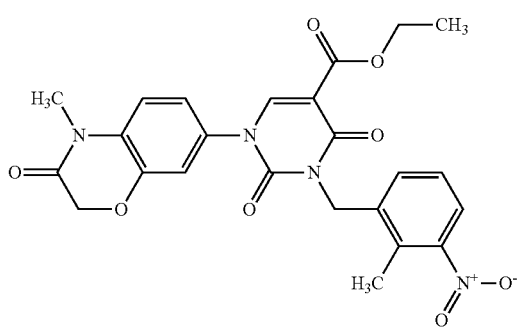 [SMILES: CCOC(=O)c1cn(-c2ccc3c(c2)OCC(=O)N3C)c(=O)n(Cc2cccc([N+](=O)[O-])c2C)c1=O]

200 mg (0.58 mmol) of ethyl 1-(4-methyl-3-oxo-3,4-dihydro-2H-1,4-benzoxazin-7-yl)-2,4-dioxo-1,2,3,4-tetrahydropyrimidine-5-carboxylate from Example 119A were initially charged in acetonitrile (7.5 ml). 108 mg (0.58 mmol) of 2-methyl-3-nitrobenzyl chloride, 160 mg (1.16 mmol) of potassium carbonate and 48 mg (0.29 mmol) of potassium iodide were added and the mixture was stirred at 60° C. for 41 h. The mixture cooled to RT was separated completely by preparative HPLC (Method 8) and the isolated product was dried under HV. This gave 218 mg (75% of theory) of the title compound.

LC-MS (Method 3): $R_t$=1.13 min; m/z=495 (M+H)$^+$.

$^1$H NMR (400 MHz, DMSO-d$_6$): δ [ppm]=1.22 (t, 3H), 2.41 (s, 3H), 4.21 (q, 2H), 3.30 (s, partly concealed by water signal, 3H), 4.71 (s, 2H), 5.06 (s, 2H), 7.22-7.32 (m, 3H), 7.36 (t, 1H), 7.41 (d, 1H), 7.72 (d, 1H), 8.38 (s, 1H).

Example 217

1-(3-isopropyl-1-methyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

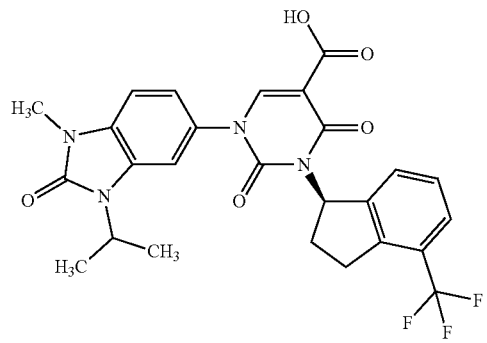 [SMILES: CC(C)n1c(=O)n(C)c2ccc(-n3cc(C(=O)O)c(=O)n([C@@H]4CCc5c4cccc5C(F)(F)F)c3=O)cc21]

122 mg (0.22 mmol) of the compound from Example 114 were heated in 3.8 ml of glacial acetic acid/conc. hydrochloric acid 2:1 (v/v) to 120° C. (bath temperature) for 1 h. After cooling to RT, 30 ml of water were added and the precipitated product was filtered off with suction. The solid was washed with water and dried under HV. This gave 107 mg (91% of theory) of the title compound.

LC-MS (Method 3): $R_t$=2.43 min; m/z=529 (M+H)$^+$.

$^1$H NMR (400 MHz, CD$_2$Cl$_2$): δ [ppm]=1.42 (d, 3H), 1.43 (d, 3H), 2.34-2.46 (m, 1H), 2.52-2.64 (m, 1H), 3.04-3.16 (m, 1H), 3.31 (s, 3H), 3.37-3.50 (m, 1H), 4.54 (sept, 1H), 6.51-6.62 (m, 1H), 6.88-7.01 (m, 3H), 7.21-7.31 (m, 2H), 7.46 (d, 1H), 8.49 (s, 1H), 12.29 (br. s, 1H).

Example 218

3-[2-chloro-3-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylic acid

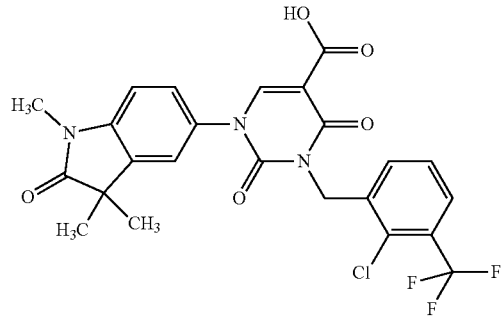 [SMILES: CN1C(=O)C(C)(C)c2cc(-n3cc(C(=O)O)c(=O)n(Cc4cccc(C(F)(F)F)c4Cl)c3=O)ccc21]

The preparation and purification of the title compound were in analogy to Example 121. Proceeding from 200 mg (0.36 mmol) of ethyl 3-[2-chloro-3-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylate from Example 52, 161 mg (83% of theory) of the title compound were obtained.

LC-MS (Method 3): $R_t$=1.29 min; m/z=522 (M+H)$^+$.

<sup>1</sup>H NMR (400 MHz, DMSO-d<sub>6</sub>): δ [ppm]=1.30 (s, 6H), 3.18 (s, 3H), 5.17 (s, 2H), 7.15 (d, 1H), 7.43-7.48 (m, 1H), 7.50-7.56 (m, 2H), 7.57-7.62 (m, 1H), 7.78-7.83 (m, 1H), 8.46 (s, 1H), 12.73 (br.s, 1H).

Example 219

3-[2-methyl-3-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylic acid

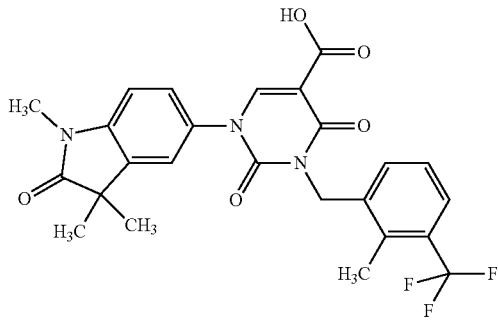 [SMILES: Cc1c(Cn2c(=O)c(C(=O)O)cn(-c3ccc4c(c3)C(C)(C)C(=O)N4C)c2=O)cccc1C(F)(F)F]

The preparation and purification of the title compound were in analogy to Example 121. Proceeding from 200 mg (0.38 mmol) of ethyl 3-[2-methyl-3-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylate from Example 53, 153 mg (80% of theory) of the title compound were obtained.

LC-MS (Method 1): $R_t$=1.07 min; m/z=502 (M+H)$^+$.
<sup>1</sup>H NMR (400 MHz, DMSO-d<sub>6</sub>): δ [ppm]=1.29 (s, 6H), 2.47 (s, 3H), 3.17 (s, 3H), 5.11 (s, 2H), 7.15 (d, 1H), 7.32-7.42 (m, 2H), 7.46 (dd, 1H), 7.54 (d, 1H), 7.58-7.64 (m, 1H), 8.45 (s, 1H), 12.73 (br.s, 1H).

Example 220

3-[3-chloro-2-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylic acid

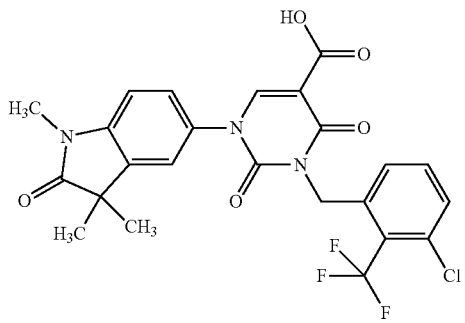 [SMILES: CN1C(=O)C(C)(C)c2cc(-n3cc(C(=O)O)c(=O)n(Cc4cccc(Cl)c4C(F)(F)F)c3=O)ccc21]

The preparation and purification of the title compound were in analogy to Example 121. Proceeding from 109 mg (0.20 mmol) of ethyl 3-[3-chloro-2-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylate from Example 54, 83 mg (79% of theory) of the title compound were obtained.

LC-MS (Method 1): $R_t$=1.10 min; m/z=522 (M+H)$^+$.
<sup>1</sup>H NMR (400 MHz, DMSO-d<sub>6</sub>): δ [ppm]=1.29 (s, 6H), 3.17 (s, 3H), 5.24 (br.s, 2H), 7.15 (d, 1H), 7.32-7.37 (m, 1H), 7.42-7.47 (m, 1H), 7.50-7.54 (m, 1H), 7.57-7.67 (m, 2H), 8.47 (s, 1H), 12.71 (br.s, 1H).

Example 221

3-[3-fluoro-2-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylic acid

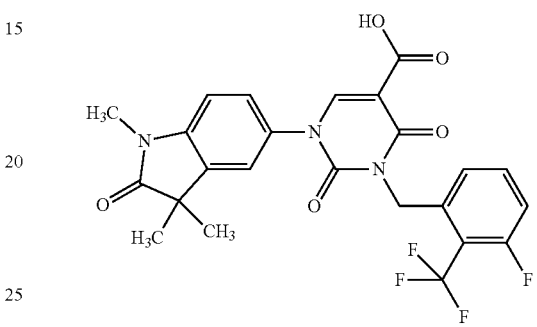

The preparation and purification of the title compound were in analogy to Example 121. Proceeding from 230 mg (0.43 mmol) of ethyl 3-[3-fluoro-2-(trifluoromethyl)benzyl]-2,4-dioxo-1-(1,3,3-trimethyl-2-oxo-2,3-dihydro-1H-indol-5-yl)-1,2,3,4-tetrahydropyrimidine-5-carboxylate from Example 55, 193 mg (85% of theory) of the title compound were obtained.

LC-MS (Method 1): $R_t$=1.02 min; m/z=506 (M+H)$^+$.
<sup>1</sup>H NMR (400 MHz, DMSO-d<sub>6</sub>): δ [ppm]=1.29 (s, 6H), 3.17 (s, 3H), 5.22 (s, 2H), 7.15 (d, 1H), 7.18-7.24 (m, 1H), 7.38-7.43 (m, 1H), 7.43-7.47 (m, 1H), 7.52-7.54 (m, 1H), 7.63-7.70 (m, 1H), 8.46 (s, 1H), 12.72 (br.s, 1H).

Example 222

3-(2,3-dichlorobenzyl)-2,4-dioxo-1-(1,3,3-trimethyl-2-oxo-2,3-dihydro-1H-indol-5-yl)-1,2,3,4-tetrahydropyrimidine-5-carboxylic acid

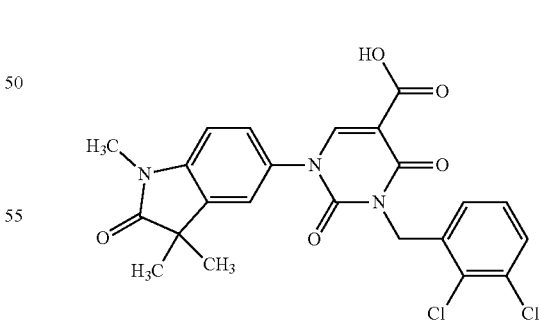

The preparation and purification of the title compound were in analogy to Example 121. Proceeding from 200 mg (0.39 mmol) of ethyl 3-(2,3-dichlorobenzyl)-2,4-dioxo-1-(1,3,3-trimethyl-2-oxo-2,3-dihydro-1H-indol-5-yl)-1,2,3,4-tetrahydropyrimidine-5-carboxylate from Example 56, 173 mg (90% of theory) of the title compound were obtained.

LC-MS (Method 1): $R_t$=1.05 min; m/z=488 (M+H)$^+$.

$^1$H NMR (400 MHz, DMSO-d$_6$): δ [ppm]=1.29 (s, 6H), 3.17 (s, 3H), 5.13 (s, 2H), 7.15 (d, 1H), 7.22-7.27 (m, 1H), 7.34 (t, 1H), 7.45 (dd, 1H), 7.54 (d, 1H), 7.57-7.61 (m, 1H), 8.45 (s, 1H), 12.72 (br.s, 1H).

Example 223

2,4-dioxo-3-[4-(trifluoromethyl)-2,3-dihydro-1H-inden-1-yl]-1-(1,3,3-trimethyl-2-oxo-2,3-dihydro-1H-indol-5-yl)-1,2,3,4-tetrahydropyrimidine-5-carboxylic acid (Racemate)

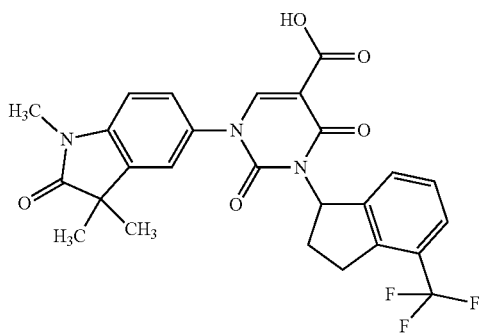 [SMILES: CN1C(=O)C(C)(C)c2cc(-n3cc(C(=O)O)c(=O)n(C4CCc5c4cccc5C(F)(F)F)c3=O)ccc21]

The preparation and purification of the title compound were analogous to Example 131. Proceeding from 507 mg (0.93 mmol) of ethyl 2,4-dioxo-3-[4-(trifluoromethyl)-2,3-dihydro-1H-inden-1-yl]-1-(1,3,3-trimethyl-2-oxo-2,3-dihydro-1H-indol-5-yl)-1,2,3,4-tetrahydropyrimidine-5-carboxylate from Example 57, after purification by means of HPLC (Method 8), 131 mg (26% of theory) of the title compound were obtained.

LC-MS (Method 5): R$_t$=1.15 min; m/z=514 (M+H)$^+$.

$^1$H NMR (400 MHz, DMSO-d$_6$): δ [ppm]=1.29 (br.s, 6H), 2.38-2.47 (m, 1H), 2.46-2.48 (m, 1H, concealed by DMSO signal), 3.03-3.14 (m, 1H), 3.17 (s, 3H), 3.20-3.27 (m, 1H, partly concealed by water signal), 6.34-6.60 (m, 1H), 7.08-7.18 (m, 1H), 7.33-7.46 (m, 2H), 7.47-7.58 (m, 3H), 8.38 (s, 1H), 12.69 (br. s, 1H).

Example 224

2,4-dioxo-3-[(1R)-4-(trifluoromethyl)-2,3-dihydro-1H-inden-1-yl]-1-(1,3,3-trimethyl-2-oxo-2,3-dihydro-1H-indol-5-yl)-1,2,3,4-tetrahydropyrimidine-5-carboxylic acid (R enantiomer)

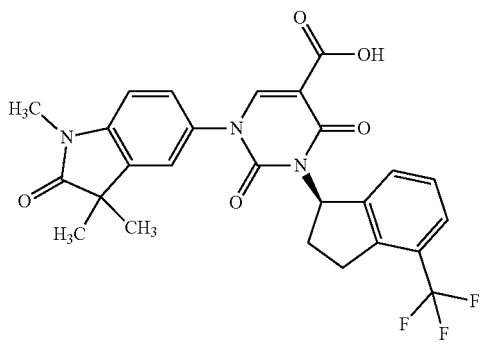 [SMILES: CN1C(=O)C(C)(C)c2cc(-n3cc(C(=O)O)c(=O)n([C@@H]4CCc5c4cccc5C(F)(F)F)c3=O)ccc21]

Analogously to Example 217, 147 mg (0.27 mmol) of the compound from Example 58 were hydrolysed and the product was isolated. This gave 120 mg (84% of theory) of the title compound.

LC-MS (Method 1): R$_t$=1.14 min; m/z=514 (M+H)$^+$.

$^1$H NMR (400 MHz, DMSO-d$_6$): δ [ppm]=1.29 (br.s, 6H), 2.39-2.46 (m, 1H), 2.46-2.60 (m, 1H, concealed by DMSO signal), 3.04-3.18 (m, 1H), 3.17 (s, 3H), 3.22-3.36 (m, 1H partly concealed by water signal), 6.34-6.61 (br. m, 1H), 7.13 (d, 1H), 7.33-7.46 (m, 2H), 7.47-7.57 (m, 3H), 8.38 (s, 1H), 12.69 (br. s, 1H). α$_D^{20}$ [chloroform, c=0.385]=+130.1°.

Example 225

3-[2-chloro-3-(trifluoromethyl)benzyl]-1-(1'-methyl-2'-oxo-1',2'-dihydrospiro[cyclopropane-1,3'-indole]-5'-yl)-2,4-dioxo-1,2,3,4-tetrahydropyrimidine-5-carboxylic acid

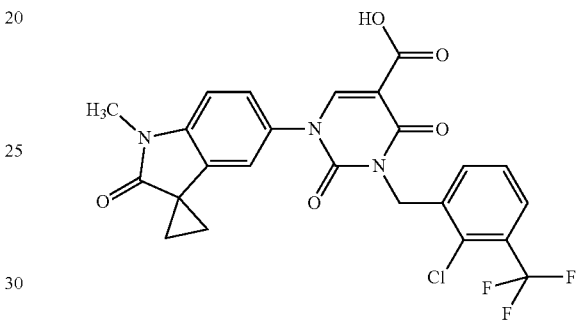

The preparation and purification of the title compound were analogous to Example 131. Proceeding from 147 mg (0.26 mmol) of ethyl 3-[2-chloro-3-(trifluoromethyl)benzyl]-1-(1'-methyl-2'-oxo-1',2'-dihydrospiro[cyclopropane-1,3'-indole]-5'-yl)-2,4-dioxo-1,2,3,4-tetrahydropyrimidine-5-carboxylate from Example 65, after purification by means of HPLC (Method 7), 30 mg (21% of theory) of the title compound were obtained.

LC-MS (Method 1): R$_t$=1.08 min; m/z=520 (M+H)$^+$.

$^1$H NMR (400 MHz, DMSO-d$_6$): δ [ppm]=1.55-1.60 (m, 2H), 1.65-1.70 (m, 2H), 3.26 (s, 3H), 5.16 (s, 2H), 7.20-7.23 (m, 2H), 7.41-7.46 (m, 1H), 7.50-7.55 (m, 1H), 7.56-7.60 (m, 1H), 7.78-7.83 (m, 1H), 8.46 (s, 1H), 12.73 (br.s, 1H).

Example 226

1-(1'-methyl-2'-oxo-1',2'-dihydrospiro[cyclopropane-1,3'-indole]-5'-yl)-3-[2-methyl-3-(trifluoromethyl)benzyl]-2,4-dioxo-1,2,3,4-tetrahydropyrimidine-5-carboxylic acid

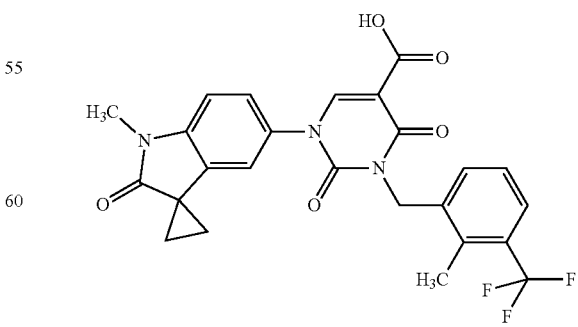

The preparation and purification of the time compound were analogous to Example 131. Proceeding from 130 mg (0.24 mmol) of ethyl 1-(1'-methyl-2'-oxo-1',2'-dihydrospiro[cyclopropane-1,3'-indole]-5'-yl)-3-[2-methyl-3-(trifluoromethyl)benzyl]-2,4-dioxo-1,2,3,4-tetrahydropyrimidine-5-carboxylate from Example 66, after purification by means of HPLC (Method 7), 27 mg (22% of theory) of the title compound were obtained.

LC-MS (Method 1): $R_t$=1.08 min; m/z=500 (M+H)$^+$.

$^1$H NMR (400 MHz, DMSO-d$_6$): δ [ppm]=1.55-1.60 (m, 2H), 1.65-1.69 (m, 2H), 2.46 (s, 3H), 3.26 (s, 3H), 5.10 (s, 2H), 7.18-7.24 (m, 2H), 7.32-7.40 (m, 2H), 7.42-7.46 (m, 1H), 7.59-7.63 (m, 1H), 8.45 (s, 1H), 12.73 (br.s, 1H).

Example 227

1-(1'-methyl-2'-oxo-1',2'-dihydrospiro[cyclopropane-1,3'-indole]-5'-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

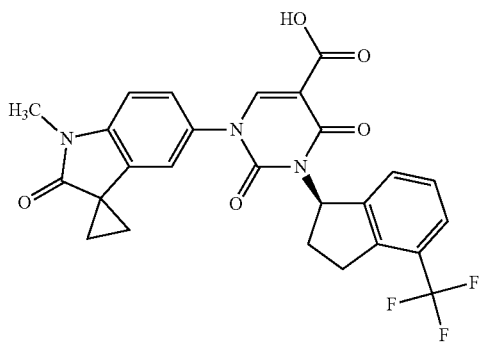 [SMILES: CN1C(=O)C2(CC2)c2cc(-n3cc(C(=O)O)c(=O)n([C@@H]4CCc5c4cccc5C(F)(F)F)c3=O)ccc21]

7.81 g (92% purity, 13.31 mmol) of ethyl 1-(1'-methyl-2'-oxo-1',2'-dihydrospiro[cyclopropane-1,3'-indole]-5'-yl)-2,4-dioxo-3-[4-(trifluoromethyl)-2,3-dihydro-1H-inden-1-yl]-1,2,3,4-tetrahydropyrimidine-5-carboxylate from Example 67 in 117 ml of a mixture of acetic acid/water/conc. sulphuric acid (12:8:1) were stirred at 120° C. for 2.5 h. The cooled reaction mixture was admixed with water, and the precipitated solid was filtered off with suction, washed with water and dried under high vacuum. The mother liquor was extracted twice with di-chloromethane. The combined organic phases were dried over sodium sulphate and concentrated. The residue was purified by means of HPLC (Method 7) together with the previously isolated solid. The isolated product (95% purity) was dissolved in boiling 2-propanol and the solution was cooled overnight. The solid formed was filtered off with suction, washed with 2-propanol and then dried under high vacuum. This gave 5.22 g (74% of theory) of the title compound.

LC-MS (Method 1): $R_t$=1.08 min; m/z=512 (M+H)$^+$.

$^1$H NMR (400 MHz, CD$_2$Cl$_2$): δ [ppm]=1.46-1.53 (m, 2H), 1.62-1.69 (m, 2H), 2.31-2.44 (m, 1H), 2.50-2.63 (m, 1H), 3.04-3.14 (m, 1H), 3.20 (s, 3H), 3.35-3.48 (m, 1H), 6.50-6.60 (m, 1H), 6.71 (br.s, 1H), 6.90 (d, 1H), 7.08-7.16 (m, 1H), 7.20-7.29 (m, 2H), 7.42-7.49 (m, 1H), 8.44 (s, 1H).

Example 228

3-[(3-chloro-4-methyl-2-thienyl)methyl]-1-(1,3-dimethyl-2-oxo-2,3-dihydro-1H-benzimidazol-5-yl)-2,4-dioxo-1,2,3,4-tetrahydropyrimidine-5-carboxylic acid

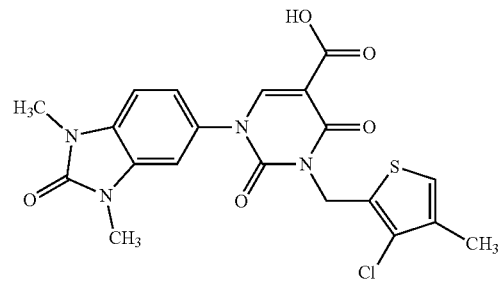 [SMILES: Cc1csc(Cn2c(=O)c(C(=O)O)cn(-c3ccc4c(c3)n(C)c(=O)n4C)c2=O)c1Cl]

22 mg (43 μmol) of the compound from Example 105 in 1 ml of glacial acetic acid/conc. hydrochloric acid 2:1 were heated to 120° C. (bath temperature) for 4 h. After cooling to RT, 10 ml of water were added and the precipitated product was filtered off with suction. The solid was stirred with diethyl ether, filtered off with suction again and dried under HV. This gave 15 mg (74% of theory) of the title compound.

LC-MS (Method 1): $R_t$=0.97 min; m/z=461 (M+H)$^+$.

$^1$H NMR (400 MHz, DMSO-d$_6$): δ [ppm]=2.12 (s, 3H), 3.33 (s, 3H), 3.37 (s, 3H), 5.21 (s, 2H), 7.20 (dd, 1H), 7.27 (d, 1H), 7.30 (s, 1H), 7.37 (d, 1H), 8.37 (s, 1H), 12.74 (br. s, 1H).

Example 229

1-(3-methyl-2-oxo-2,3-dihydro-1,3-benzothiazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

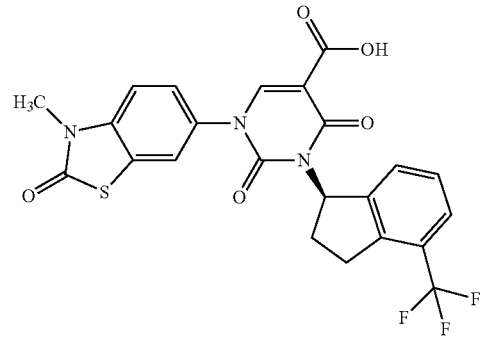 [SMILES: Cn1c(=O)sc2cc(-n3cc(C(=O)O)c(=O)n([C@@H]4CCc5c4cccc5C(F)(F)F)c3=O)ccc21]

6.20 g (11.3 mmol) of the compound from Example 51 in 150 ml of glacial acetic acid/conc, hydrochloric acid 2:1 were heated to 120° C. (bath temperature) for 1 h. After cooling to RT, the reaction mixture was poured into 1l of ice-water. The precipitated product was filtered off with suction. The solid was stirred with diethyl ether, filtered off with suction again and dried under HV. This gave 5.04 g (88% of theory) of the title compound.

LC-MS (Method 5): $R_t$=1.14 min; m/z=504 (M+H)$^+$.

¹H NMR (400 MHz, CD₂Cl₂): δ [ppm]=2.39-2.53 (m, 1H), 2.60-2.72 (m, 1H), 3.12-3.24 (m, 1H), 3.42-3.56 (m, 4H), 6.58-6.71 (m, 1H), 7.15 (d, 1H), 7.26-7.38 (m, 3H), 7.45 (s, 1H), 7.50-7.58 (m, 1H), 8.55 (s, 1H).

For further batches of the title compound, which have been prepared analogously, the following additional data have been collected:
α$_D$$^{20}$[chloroform, c=0.365]=+148.6°.

Example 230

1-(1,3-dimethyl-2-oxo-2,3-dihydro-1H-benzimidazol-5-yl)-3-(5-methoxy-2,3-dihydro-1H-inden-1-yl)-2,4-dioxo-1,2,3,4-tetrahydropyrimidine-5-carboxylic acid (Racemate)

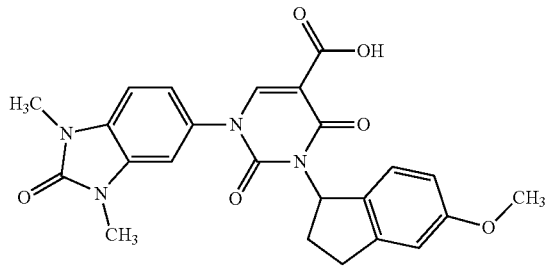 [SMILES: COc1ccc2c(c1)CCC2n1c(=O)c(C(=O)O)cn(-c2ccc3c(c2)n(C)c(=O)n3C)c1=O]

86 mg (0.18 mmol) of the compound from Example 120 and 49 mg (0.58 mmol) of sodium hydrogencarbonate in 2 ml of acetonitrile and 2 ml of water were heated to reflux for 6 h. After cooling to RT, the mixture was acidified by addition of 1N hydrochloric acid and separated directly by means of preparative HPLC (Method 7). This gave 24 mg (29% of theory) of the title compound.

LC-MS (Method 1): R$_t$=0.90 min; m/z=463 (M+H)⁺.
¹H NMR (400 MHz, DMSO-d₆): δ [ppm]=2.31-2.47 (m, 2H), 2.83-2.95 (m, 1H), 3.09-3.22 (m, 1H), 3.34 (s, 6H), 3.72 (s, 3H), 6.29-6.47 (m, 1H), 6.67-6.74 (m, 1H), 6.79 (s, 1H), 7.08 (d, 1H), 7.13-7.21 (m, 1H), 7.22-7.30 (m, 1H), 7.37 (s, 1H), 8.38 (s, 1H), 12.74 (hr. s, 1H).

Example 231

3-(4,6-difluoro-2,3-dihydro-1H-inden-1-yl)-1-(1,3-dimethyl-2-oxo-2,3-dihydro-1H-benzimidazol-5-yl)-2,4-dioxo-1,2,3,4-tetrahydropyrimidine-5-carboxylic acid (Racemate)

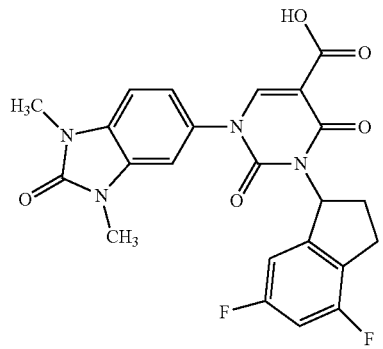 [SMILES: Cn1c(=O)n(C)c2cc(-n3cc(C(=O)O)c(=O)n(C4CCc5c(F)cc(F)cc54)c3=O)ccc21]

Analogously to Example 217, 173 mg (0.35 mmol) of the compound from Example 106 were hydrolysed. This gave 130 mg (80% of theory) of the title compound.

LC-MS (Method 5): R$_t$=0.99 min; m/z=469 (M+H)⁺.
¹H NMR (400 MHz, DMSO-d₆): δ [ppm]=2.38-2.48 (m, 2H, partly concealed by DMSO signal), 2.84-2.98 (m, 1H), 3.02-3.18 (m, 1H), 3.34 (br.s, 3H), 6.22-6.60 (m, 1H), 7.03 (t, 2H), 7.12-7.29 (m, 2H), 7.31-7.43 (m, 1H), 8.38 (s, 1H), 12.67 (hr. s, 1H).

Example 232

1-(1,3-dimethyl-2-oxo-2,3-dihydro-1H-benzimidazol-5-yl)-3-(6-methyl-2,3-dihydro-1H-inden-1-yl)-2,4-dioxo-1,2,3,4-tetrahydropyrimidine-5-carboxylic acid (Racemate)

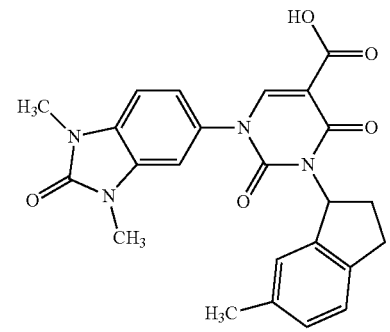 [SMILES: Cc1ccc2c(c1)C(n1c(=O)c(C(=O)O)cn(-c3ccc4c(c3)n(C)c(=O)n4C)c1=O)CC2]

127 mg (0.27 mmol) of the compound from Example 107 were initially charged in 2.5 ml of acetonitrile. 74 mg (0.88 mmol) of sodium hydrogencarbonate and 2.5 ml of water were added and the mixture was heated to reflux for 6 h. After cooling to RT, the mixture was acidified with 1N hydrochloric acid and separated completely by preparative HPLC (Method 7). This gave 78 mg (65% of theory) of the title compound.

LC-MS (Method 1): R$_t$=0.98 min; m/z=447 (M+H)⁺.
¹H NMR (400 MHz, DMSO-d₆): δ [ppm]=2.25 (s, 3H), 2.35-2.45 (m, 2H), 2.82-2.93 (m, 1H), 3.04-3.18 (m, 1H), 3.31 (s, 3H), 3.36 (s, 3H), 6.23-6.54 (m, 1H), 6.96-7.03 (m, 2H), 7.10 (d, 1H), 7.16-7.30 (m, 2H), 7.33-7.45 (m, 1H), 8.39 (s, 1H), 12.73 (br. s, 1H).

Example 233 ethyl 3-(4-methoxy-2,3-dihydro-1H-inden-1-yl)-1-(3-methyl-2-oxo-2,3-dihydro-1,3-benzothiazol-6-yl)-2,4-dioxo-1,2,3,4-tetrahydropyrimidine-5-carboxylate (Racemate)

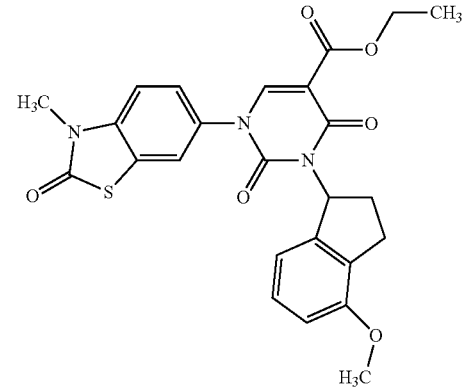 [SMILES: CCOC(=O)c1cn(-c2ccc3c(c2)sc(=O)n3C)c(=O)n(C2CCc3c(OC)cccc32)c1=O]

Under argon, a solution of 200 mg (0.58 mmol) of the compound from Example 31A and 453 mg (1.73 mmol) of triphenylphosphine in 15.8 ml of THF/DMF 1:1 (v/v) was admixed dropwise with 227 µl (1.15 mmol) of diisopropyl azodicarboxylate. Then 123 mg (0.75 mmol) of the compound from Example 103A were added and the mixture was stirred at RT for 1 h. While cooling with ice, 2 ml of 1N hydrochloric acid were added, and the mixture was stirred further for 15 min and then separated by preparative HPLC (Method 7). This gave 118 mg (41% of theory) of the title compound.

LC-MS (Method 1): $R_t$=1.05 min; m/z=494 (M+H)$^+$.

$^1$H NMR (400 MHz, DMSO-d$_6$): δ [ppm]=1.22 (t, 3H), 2.26-2.46 (m, 2H), 2.73-2.85 (m, 1H), 2.95-3.10 (m, 1H), 3.44 (s, 3H), 3.77 (s, 3H), 4.09-4.27 (m, 2H), 6.25-6.57 (m, 1H), 6.74 (d, 1H), 6.78 (d, 1H), 7.12 (t, 1H), 7.35-7.64 (m, 2H), 7.83 (br.s, 1H), 8.38 (s, 1H).

Example 234

3-(4-methoxy-2,3-dihydro-1H-inden-1-yl)-1-(3-methyl-2-oxo-2,3-dihydro-1,3-benzothiazol-6-yl)-2,4-dioxo-1,2,3,4-tetrahydropyrimidine-5-carboxylic acid (Racemate)

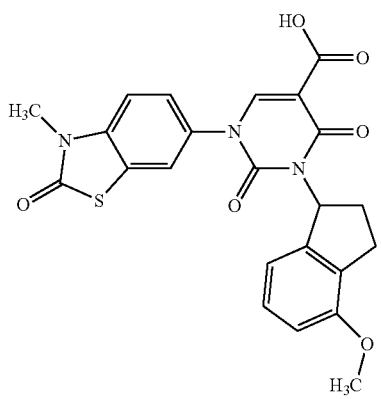 [SMILES: COc1cccc2c1CCC2n1c(=O)c(C(=O)O)cn(-c2ccc3c(c2)sc(=O)n3C)c1=O]

115 mg (0.23 mmol) of the compound from Example 233 in 7.2 ml of glacial acetic acid/conc. hydrochloric acid 2:1 (v/v) was heated to reflux for 1 h. After cooling to RT, the whole reaction mixture was separated by preparative HPLC (Method 7). This gave 42 mg (39% of theory) of the title compound.

LC-MS (Method 1): $R_t$=1.03 min; m/z=466 (M+H)$^+$.

$^1$H NMR (400 MHz, CD$_2$Cl$_2$): δ [ppm]=2.26-2.38 (m, 1H), 2.44-2.56 (m, 1H), 2.78-2.89 (m, 1H), 3.07-3.19 (m, 1H), 3.38 (s, 3H), 3.75 (s, 3H), 6.46-6.58 (m, 1H), 6.62-6.73 (m, 2H), 7.02-7.14 (m, 2H), 7.18-7.28 (m, 2H), 7.37 (br.s, 1H), 8.44 (s, 1H).

Example 235

3-(4,6-difluoro-2,3-dihydro-1H-inden-1-yl)-1-(3-methyl-2-oxo-2,3-dihydro-1,3-benzothiazol-6-yl)-2,4-dioxo-1,2,3,4-tetrahydropyrimidine-5-carboxylic acid (Racemate)

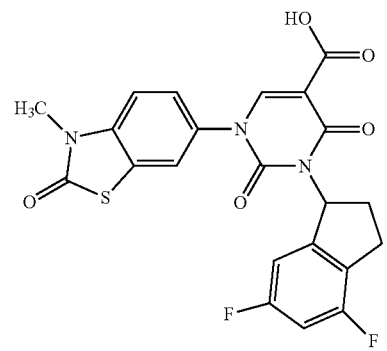 [SMILES: Cn1c(=O)sc2cc(-n3cc(C(=O)O)c(=O)n(C4CCc5c(F)cc(F)cc54)c3=O)ccc21]

170 mg (0.34 mmol) of the compound from Example 108 in 7 ml of glacial acetic acid and 3.5 ml of conc. hydrochloric acid was heated to reflux for 1 h. After cooling to RT, the reaction mixture was purified by preparative HPLC (Method 7). This gave 133 mg (83% of theory) of the title compound.

LC-MS (Method 1): $R_t$=1.07 min; m/z=472 (M+H)$^+$.

$^1$H NMR (400 MHz, CD$_2$Cl$_2$): δ [ppm]=2.32-2.45 (m, 1H), 2.52-2.64 (m, 1H), 2.84-2.97 (m, 1H), 3.14-3.26 (m, 1H), 3.38 (s, 3H), 6.44-6.56 (m, 1H), 6.58-6.70 (m, 2H), 7.07 (d, 1H), 7.23 (d, 2H), 7.37 (br.s, 1H), 8.46 (s, 1H).

Example 236

3-(6-methyl-2,3-dihydro-1H-inden-1-yl)-1-(3-methyl-2-oxo-2,3-dihydro-1,3-benzothiazol-6-yl)-2,4-dioxo-1,2,3,4-tetrahydropyrimidine-5-carboxylic acid (Racemate)

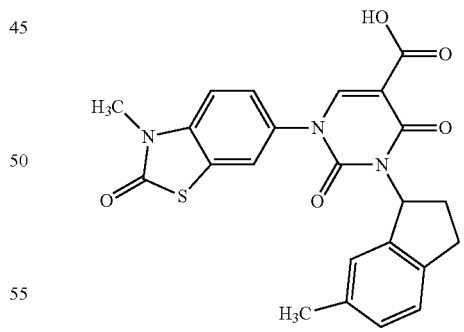

127 mg (0.27 mmol) of the compound from Example 109 were hydrolysed under alkaline conditions analogously to Example 232 and the product was purified. This gave 56 mg (47% of theory) of the title compound.

LC-MS (Method 1): $R_t$=1.10 min; m/z=450 (M+H)$^+$.

$^1$H NMR (400 MHz, CD$_2$Cl$_2$): δ [ppm]=2.22 (s, 3H), 2.28-2.39 (m, 1H), 2.43-2.55 (m, 1H), 2.82-2.94 (m, 1H), 3.12-3.24 (m, 1H), 3.38 (s, 3H), 6.44-6.55 (m, 1H), 6.86 (s, 1H), 6.98 (d, 1H), 7.02-7.12 (m, 2H), 7.24 (d, 1H), 7.38 (br.s, 1H), 8.45 (s, 1H).

Example 237 ethyl 3-[6-chloro-4-(trifluoromethyl)-2,3-dihydro-1H-inden-1-yl]-1-(1,3-dimethyl-2-oxo-2,3-dihydro-1H-benzimidazol-5-yl)-2,4-dioxo-1,2,3,4-tetrahydropyrimidine-5-carboxylate (Racemate)

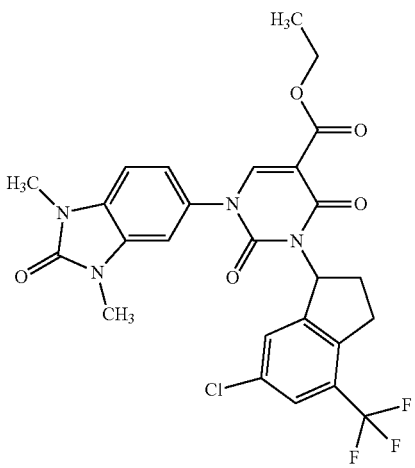 [SMILES: CCOC(=O)c1cn(-c2ccc3c(c2)n(C)c(=O)n3C)c(=O)n(C2CCc3c2cc(Cl)cc3C(F)(F)F)c1=O]

Analogously to Example 233, 200 mg (0.58 mmol) of the compound from Example 2A were reacted with 179 mg (0.76 mmol) of 6-chloro-4-(trifluoromethyl)indan-1-ol from Example 108A and the product was isolated. This gave 260 mg (69% of theory) of the title compound in 87% purity.

LC-MS (Method 1): $R_t$=1.14 min; m/z=563 (M+H)$^+$.

$^1$H NMR (400 MHz, DMSO-d$_6$): δ [ppm]=1.22 (br. t, 3H), 2.36-2.55 (m, 2H, partly concealed by DMSO signal), 3.00-3.14 (m, 1H), 3.14-3.29 (m, 1H), 3.31 (s, 3H), 3.37 (s, 3H), 4.13-4.25 (m, 2H), 6.29-6.54 (m, 1H), 7.18-7.31 (m, 2H), 7.39 (br.s, 1H), 7.59 (s, 1H), 7.68 (br.s, 1H), 8.34 (s, 1H).

Example 238

3-[6-chloro-4-(trifluoromethyl)-2,3-dihydro-1H-inden-1-yl]-1-(1,3-dimethyl-2-oxo-2,3-dihydro-1H-benzimidazol-5-yl)-2,4-dioxo-1,2,3,4-tetrahydropyrimidine-5-carboxylic acid (Racemate)

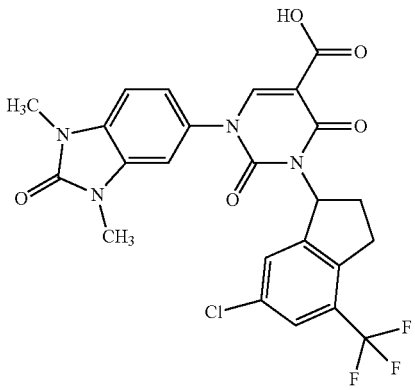 [SMILES: Cn1c(=O)n(C)c2cc(-n3cc(C(=O)O)c(=O)n(C4CCc5c4cc(Cl)cc5C(F)(F)F)c3=O)ccc21]

Analogously to Example 217, 260 mg (0.46 mmol) of the compound from Example 237 were hydrolysed and the product was isolated. This gave 200 mg (79% of theory) of the title compound.

LC-MS (Method 1): $R_t$=1.09 min; m/z=535 (M+H)$^+$.

$^1$H NMR (400 MHz, CD$_2$Cl$_2$): δ [ppm]=2.35-2.46 (m, 1H), 2.58 (s, 1H), 3.00-3.12 (m, 1H), 3.31 (s, 3H), 3.33 (s, 3H), 3.35-3.44 (m, 1H), 6.49-6.60 (m, 1H), 6.87 (s, 1H), 6.96 (s, 2H), 7.27 (s, 1H), 7.45 (s, 1H), 8.50 (s, 1H).

Example 239 ethyl 3-[6-bromo-4-(trifluoromethyl)-2,3-dihydro-1H-inden-1-yl]-1-(1,3-dimethyl-2-oxo-2,3-dihydro-1H-benzimidazol-5-yl)-2,4-dioxo-1,2,3,4-tetrahydropyrimidine-5-carboxylate (Racemate)

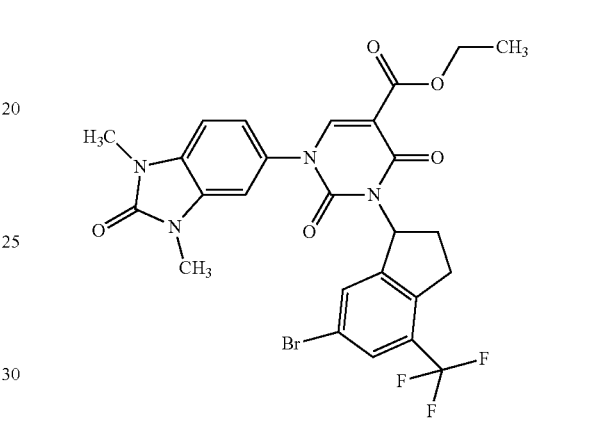

Analogously to Example 233, 226 mg (0.66 mmol) of the compound from Example 2A were reacted with 240 mg (0.85 mmol) of 6-bromo-4-(trifluoromethyl)indan-1-ol from Example 113A and the product was isolated. This gave 230 mg (58% of theory) of the title compound.

LC-MS (Method 1): $R_t$=1.17 min; m/z=607/609 (M+H)$^+$.

$^1$H NMR (400 MHz, CD$_2$Cl$_2$): δ [ppm]=1.23 (t, 2H), 2.28-2.43 (m, 1H), 2.52 (dtd, 1H), 3.00 (dt, 1H), 3.31 (s, 3H), 3.33 (s, 2H), 3.29-3.41 (m, 1H, partly concealed by the methyl signals), 4.21 (q, 2H), 6.42-6.65 (m, 1H), 6.88 (br.s, 1H), 6.96 (s, 2H), 7.40 (s, 1H), 7.54 (s, 1H), 8.24 (s, 1H).

Example 240

3-[6-bromo-4-(trifluoromethyl)-2,3-dihydro-1H-inden-1-yl]-1-(1,3-dimethyl-2-oxo-2,3-dihydro-1H-benzimidazol-5-yl)-2,4-dioxo-1,2,3,4-tetrahydropyrimidine-5-carboxylic acid (Racemate)

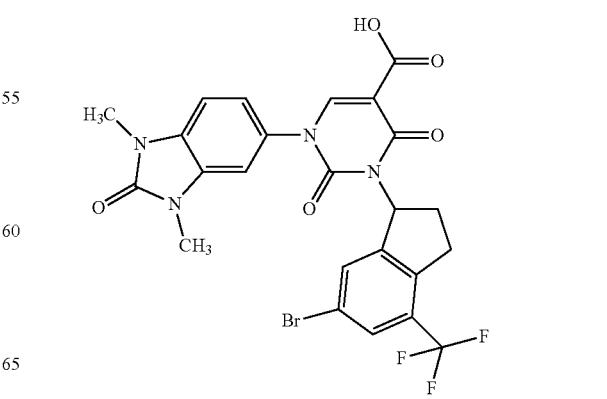

Analogously to Example 217, 52 mg (86 μmol) of the compound from Example 238 were hydrolysed and the product was isolated. This gave 23 mg (46% of theory) of the title compound.

LC-MS (Method 5): $R_t$=1.15 min; in/z=579 (M+H)$^+$.
$^1$H NMR (400 MHz, CD$_2$Cl$_2$): δ [ppm]=2.41-2.54 (m, 1H), 2.61-2.74 (m, 1H), 3.06-3.18 (m, 1H), 3.39 (s, 3H), 3.42 (s, 3H), 3.43-3.51 (m, 1H), 6.57-6.69 (m, 1H), 6.95 (s, 1H), 7.05 (s, 2H), 7.50 (s, 1H), 7.67 (s, 1H), 8.58 (s, 1H), Example 241

1-[1-methyl-2-oxo-3-(2,2,2-trifluoroethyl)-2,3-dihydro-1H-benzimidazol-5-yl]-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

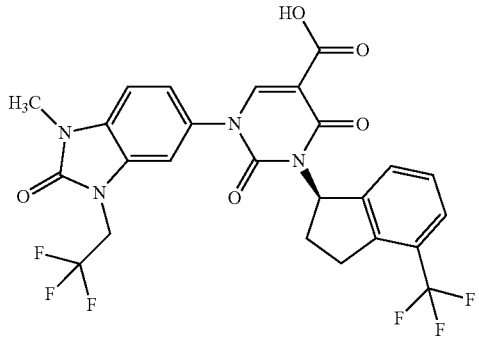 [SMILES: Cn1c(=O)n(CC(F)(F)F)c2cc(-n3cc(C(=O)O)c(=O)n([C@@H]4CCc5c4cccc5C(F)(F)F)c3=O)ccc21]

Analogously to Example 217, 370 mg (0.62 mmol) of the compound from Example 28 were hydrolysed and the product was isolated. This gave 314 mg (89% of theory) of the title compound.

LC-MS (Method 1): $R_t$=1.15 min; m/z=569 (M+H)$^+$.
$^1$H NMR (400 MHz, CD$_2$Cl$_2$): δ [ppm]=2.32-2.46 (m, 1H), 2.51-2.65 (m, 1H), 3.03-3.17 (m, 1H), 3.36 (s, 3H), 3.40-3.48 (m, 1H), 4.41 (q, 2H), 6.51-6.63 (m, 1H), 6.96 (s, 1H), 7.00-7.09 (m, 2H), 7.21-7.30 (m, 2H), 7.46 (d, 1H), 8.48 (s, 1H).

Example 242

1-(1,3-dimethyl-2-oxo-2,3-dihydro-1H-benzimidazol-5-yl)-3-[6-fluoro-4-(trifluoromethyl)-2,3-dihydro-1H-inden-1-yl]-2,4-dioxo-1,2,3,4-tetrahydropyrimidine-5-carboxylic acid (Racemate)

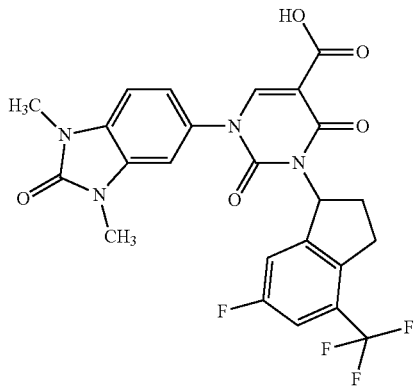 [SMILES: Cn1c(=O)n(C)c2cc(-n3cc(C(=O)O)c(=O)n(C4CCc5c4cc(F)cc5C(F)(F)F)c3=O)ccc21]

Analogously to Example 217, 63 mg (115 μmol) of the compound from Example 110 were hydrolysed and the product was isolated. This gave 47 mg (78% of theory) of the title compound.

LC-MS (Method 1): $R_t$=1.09 min; m/z=519 (M+H)$^+$.
$^1$H NMR (400 MHz, CD$_2$Cl$_2$): δ [ppm]=2.44-2.57 (m, 1H), 2.63-2.76 (m, 1H), 3.07-3.19 (m, 1H), 3.39 (s, 3H), 3.42 (s, 3H), 3.43-3.50 (m, 1H), 6.56-6.68 (m, 1H), 6.94 (s, 1H), 7.01-7.10 (m, 3H), 7.23-7.30 (m, 1H), 8.58 (s, 1H), 12.36 (br. s, 1H).

Example 243

1-(1-methyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

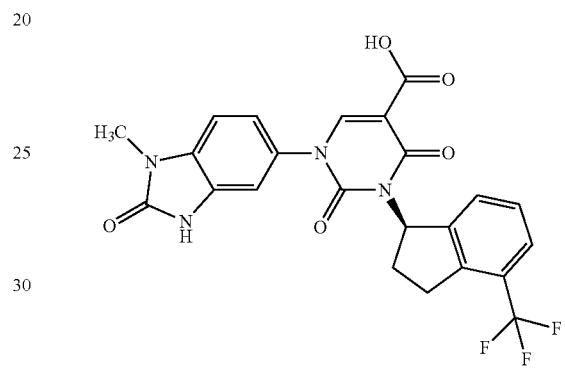

Analogously to Example 217, 600 mg (1.17 mmol) of the compound from Example 112 were hydrolysed (reaction time 4 h) and the product was isolated. This gave 540 mg (89% of theory) of the title compound.

LC-MS (Method 3): $R_t$=2.20 min; m/z=487 (M+H)$^+$.
$^1$H NMR (400 MHz, CD$_2$Cl$_2$): δ [ppm]=2.32-2.45 (m, 1H), 2.51-2.64 (m, 1H), 3.02-3.17 (m, 1H), 3.31 (s, 3H), 3.36-3.47 (m, 1H), 6.52-6.61 (m, 1H), 6.96 (s, 3H), 7.21-7.31 (m, 2H), 7.42-7.50 (m, 1H), 8.14 (s, 1H), 8.47 (s, 1H), 12.36 (br. s, 1H).

Example 244

1-(3-ethyl-1-methyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

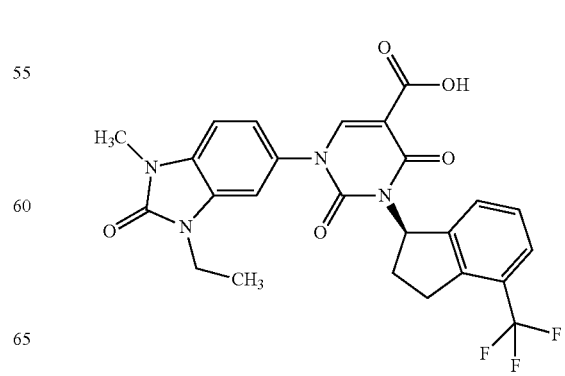

Analogously to Example 217, 73 mg (0.14 mmol) of the compound from Example 113 were hydrolysed and the product was isolated. This gave 58 mg (82% of theory) of the title compound.

LC-MS (Method 3): $R_t$=2.36 min; m/z=515 (M+H)$^+$.

$^1$H NMR (400 MHz, CD$_2$Cl$_2$): δ [ppm]=1.22 (t, 3H), 2.33-2.45 (m, 1H), 2.52-2.64 (m, 1H), 3.04-3.17 (m, 1H), 3.33 (s, 3H), 3.37-3.48 (m, 1H), 3.83 (q, 2H), 6.51-6.61 (m, 1H), 6.87 (s, 1H), 6.92-7.01 (m, 2H), 7.21-7.31 (m, 2H), 7.46 (d, 1H), 8.49 (s, 1H), 12.35 (br. s, 1H).

Example 245

1-(3-methyl-2-oxo-2,3-dihydro-1,3-benzothiazol-6-yl)-2,4-dioxo-3-[7-(trifluoromethyl)-2,3-dihydro-1-benzofur-3-yl]-1,2,3,4-tetrahydropyrimidine-5-carboxylic acid (Racemate)

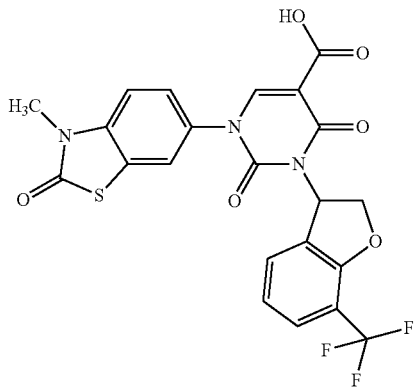 [SMILES: Cn1c(=O)sc2cc(-n3cc(C(=O)O)c(=O)n(C4COc5c4cccc5C(F)(F)F)c3=O)ccc21]

Analogously to Example 234, 32 mg (60 μmol) of the compound from Example 119 were hydrolysed and the product was isolated. This gave 19 mg (63% of theory) of the title compound.

LC-MS (Method 5): $R_t$=1.04 min; m/z=506 (M+H)$^+$.

$^1$H NMR (400 MHz, CD$_2$Cl$_2$): δ [ppm]=3.38 (s, 3H), 4.74-4.88 (m, 2H), 6.79 (dd, 1H), 6.91 (t, 1H), 7.07 (d, 1H), 7.21 (dd, 1H), 7.33 (d, 1H), 7.37 (d, 1H), 7.41 (d, 1H), 8.47 (s, 1H), 11.67-12.36 (br.s., 1H).

Example 246

1-[1-methyl-2-oxo-3-(3,3,3-trifluoro-2-hydroxypropyl)-2,3-dihydro-1H-benzimidazol-5-yl]-2,4-dioxo-3-[(1R)-4-(trifluoromethyl)-2,3-dihydro-1H-inden-1-yl]-1,2,3,4-tetrahydropyrimidine-5-carboxylic acid (Diastereomer Mixture)

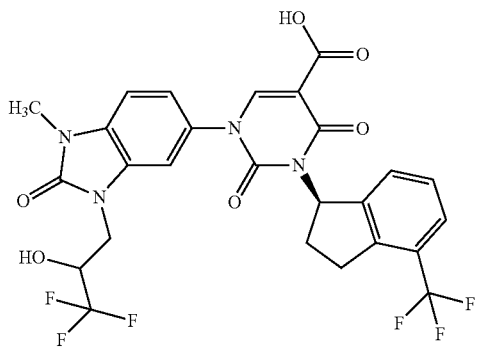 [SMILES: Cn1c(=O)n(CC(O)C(F)(F)F)c2cc(-n3cc(C(=O)O)c(=O)n([C@@H]4CCc5c4cccc5C(F)(F)F)c3=O)ccc21]

Analogously to Example 217, 180 mg (0.29 mmol) of the compound from Example 115 were hydrolysed and the product was isolated. This gave 152 mg (83% of theory) of the title compound.

LC-MS (Method 1): $R_t$=1.11 min; m/z=599 (M+H)$^+$.

$^1$H NMR (400 MHz, CD$_2$Cl$_2$): δ [ppm]=2.32-2.46 (m, 1H), 2.52-2.65 (m, 1H), 3.03-3.16 (m, 1H), 3.37 (s, 3H), 3.42-3.51 (m, 1H), 3.99-4.08 (m, 1H), 4.16 (d, 1H), 4.22-4.37 (m, 2H), 6.50-6.64 (m, 1H), 7.03 (d, 3H), 7.20-7.32 (m, 2H), 7.46 (d, 1H), 8.47 (s, 1H), 12.29 (br. s, 1H).

Example 247

1-[1-methyl-2-oxo-3-(3,3,3-trifluoropropyl)-2,3-dihydro-1H-benzimidazol-5-yl]-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

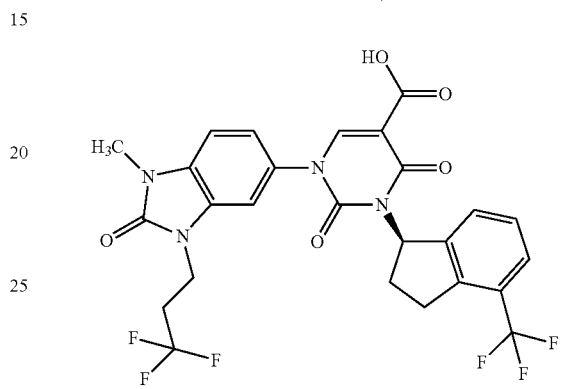

Analogously to Example 217, 160 mg (0.26 mmol) of the compound from Example 116 were hydrolysed and the product was isolated. This gave 140 mg (91% of theory) of the title compound.

LC-MS (Method 5): $R_t$=1.16 min; m/z=583 (M+H)$^+$.

$^1$H NMR (400 MHz, CD$_2$Cl$_2$): δ [ppm]=2.47-2.58 (m, 1H), 2.60-2.77 (m, 3H), 3.17-3.29 (m, 1H), 3.47 (s, 3H), 3.49-3.61 (m, 1H), 4.16 (t, 2H), 6.63-6.76 (m, 1H), 7.00 (s, 1H), 7.08-7.16 (m, 2H), 7.35-7.44 (m, 2H), 7.59 (d, 1H), 8.61 (s, 1H), 12.46 (br. s, 1H).

Example 248

1-(3-cyclopropyl-1-methyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer)

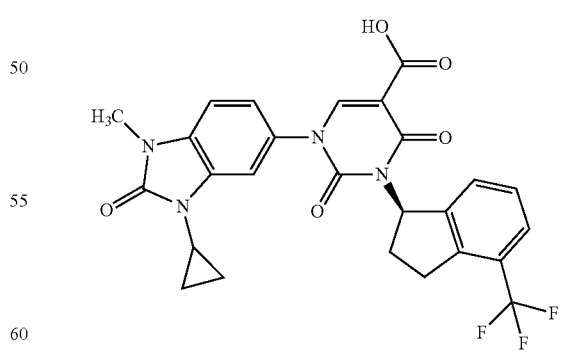

Analogously to Example 234, 160 mg (0.26 mmol) of the compound from Example 117 were hydrolysed. The reaction mixture was diluted with 5 ml of acetonitrile and purified by preparative HPLC (Method 7). This gave 140 mg (91% of theory) of the title compound.

LC-MS (Method 1): $R_t$=1.07 min; m/z=527 (M+H)$^+$.

¹H NMR (400 MHz, CD₂Cl₂): δ [ppm]=0.84-0.93 (m, 2H), 0.95-1.03 (m, 2H), 2.34-2.48 (m, 1H), 2.52-2.64 (m, 1H), 2.73-2.83 (m, 1H), 3.05-3.16 (m, 1H), 3.28 (s, 3H), 3.36-3.49 (m, 1H), 6.51-6.63 (m, 1H), 6.89-6.99 (m, 2H), 7.06 (s, 1H), 7.21-7.32 (m, 2H), 7.46 (d, 1H), 8.49 (s, 1H).

Example 249 ethyl 3-(4,6-dichloro-2,3-dihydro-1H-inden-1-yl)-1-(3-methyl-2-oxo-2,3-dihydro-1,3-benzothiazol-6-yl)-2,4-dioxo-1,2,3,4-tetrahydropyrimidine-5-carboxylate (Racemate)

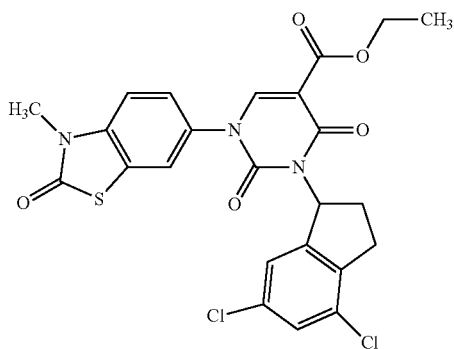 [SMILES: CCOC(=O)c1cn(-c2ccc3c(c2)sc(=O)n3C)c(=O)n(C2CCc3c(Cl)cc(Cl)cc32)c1=O]

Under argon, 101 mg (0.29 mmol) of the compound from Example 31A, 71 mg (0.35 mmol) of 4,6-dichloroindan-1-ol from Example 114A and 137 mg (0.52 mmol) of triphenylphosphine were initially charged in 8 ml of THF/DMF 1:1 (v/v), and 97 μl (0.49 mmol) of diisopropyl azodicarboxylate were added dropwise.

The mixture was stirred at RT for 1 h. While cooling with ice, 2 ml of 1N hydrochloric acid were added, and the mixture was stirred further for 15 min and then purified completely by means of preparative HPLC (Method 7). This gave 101 mg (65% of theory) of the title compound.

LC-MS (Method 1): R_t=1.20 min; m/z=532 (M+H)⁺.
¹H NMR (400 MHz, CD₂Cl₂): δ [ppm]=1.36 (t, 3H), 2.37-2.52 (m, 1H), 2.63 (dtd, 1H), 2.93-3.08 (m, 1H), 3.25-3.40 (m, 1H), 3.51 (s, 3H), 4.34 (q, 2H), 6.65 (br.s, 1H), 7.09 (s, 1H), 7.19 (d, 1H), 7.29 (s, 1H), 7.36 (d, 1H), 7.50 (br.s, 1H), 8.34 (s, 1H).

Example 250

3-(4,6-dichloro-2,3-dihydro-1H-inden-1-yl)-1-(3-methyl-2-oxo-2,3-dihydro-1,3-benzothiazol-6-yl)-2,4-dioxo-1,2,3,4-tetrahydropyrimidine-5-carboxylic acid (Racemate)

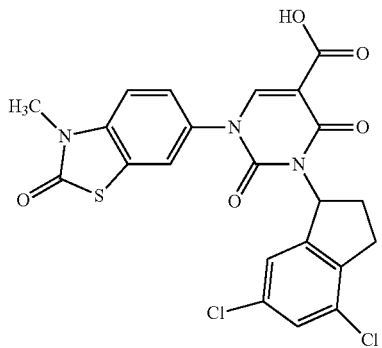 [SMILES: Cn1c(=O)sc2cc(-n3cc(C(=O)O)c(=O)n(C4CCc5c(Cl)cc(Cl)cc54)c3=O)ccc21]

Analogously to Example 217, 106 mg (0.20 mmol) of the compound from Example 249 were hydrolysed and the product was isolated. This gave 74 mg (73% of theory) of the title compound.

LC-MS (Method 1): R_t=1.17 min; m/z=505 (M+H)⁺.
¹H NMR (500 MHz, CD₂Cl₂): δ [ppm]=2.37-2.51 (m, 1H), 2.60-2.70 (m, 1H), 2.95-3.06 (m, 1H), 3.24-3.36 (m, 1H), 3.47 (s, 3H), 6.54-6.71 (m, 1H), 7.07 (s, 1H), 7.12-7.20 (m, 1H), 7.29 (s, 1H), 7.31-7.38 (m, 1H), 7.41-7.54 (m, 1H), 8.56 (s, 1H).

Example 251 ethyl 1-(1,3-dimethyl-2-oxo-2,3-dihydro-1H-benzimidazol-5-yl)-3-{1-[2-methyl-3-(trifluoromethyl)phenyl]-ethyl}-2,4-dioxo-1,2,3,4-tetrahydropyrimidine-5-carboxylate (Racemate)

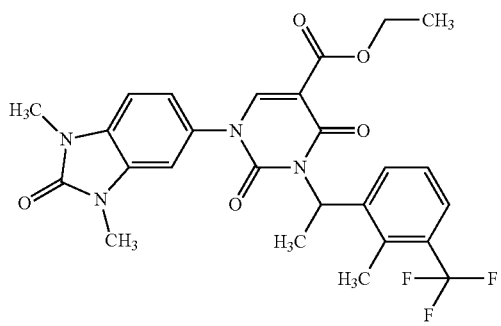 [SMILES: CCOC(=O)c1cn(-c2ccc3c(c2)n(C)c(=O)n3C)c(=O)n(C(C)c2cccc(C(F)(F)F)c2C)c1=O]

Under argon, 250 trig (0.73 mmol) of the compound from Example 2A, 198 mg (90% purity, 0.87 mmol) of 1-[2-methyl-3-(trifluoromethyl)phenyl]ethanol from Example 115A and 324 mg (1.23 mmol) of triphenylphosphine were initially charged in 6.5 ml of THF/DMF 1:2 (v/v), and 229 μl (1.16 mmol) of diisopropyl azodicarboxylate were added dropwise. The mixture was stirred at RT for 1 h. While cooling with ice, 1 ml of 1N hydrochloric acid was added, and the mixture was stirred further for 10 mm and then purified by preparative HPLC (Method 7). This gave 153 mg (40% of theory) of the title compound.

LC-MS (Method 1): R_t=1.05 min; m/z=531 (M+H)⁺.
¹H NMR (400 MHz, CD₂Cl₂): δ [ppm]=1.30 (t, 3H), 1.87 (d, 3H), 2.34 (s, 3H), 3.38 (s, 3H), 3.40 (s, 3H), 4.27 (q, 2H), 6.30 (q, 1H), 6.90 (d, 1H), 6.95-7.07 (m, 2H), 7.31 (t, 1H), 7.58 (d, 1H), 7.92 (d, 1H), 8.28 (s, 1H).

Example 252

1-(1,3-dimethyl-2-oxo-2,3-dihydro-1H-benzimidazol-5-yl)-3-{1-[2-methyl-3-(trifluoromethyl)phenyl]ethyl}-2,4-dioxo-1,2,3,4-tetrahydropyrimidine-5-carboxylic acid (Racemate)

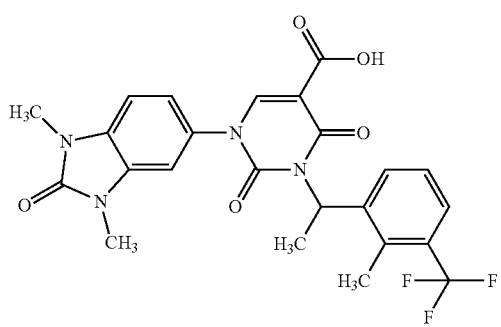 [SMILES: Cc1c(C(C)n2c(=O)c(C(=O)O)cn(-c3ccc4c(c3)n(C)c(=O)n4C)c2=O)cccc1C(F)(F)F]

Analogously to Example 217, 140 mg (0.26 mmol) of the compound from Example 251 were hydrolysed and the product was isolated. This gave 79 mg (58% of theory) of the title compound.

LC-MS (Method 1): $R_t$=1.08 min; m/z=503 (M+H)$^+$.

$^1$H NMR (400 MHz, CD$_2$Cl$_2$): δ [ppm]=1.92 (d, 3H), 2.35 (s, 3H), 3.38 (s, 3H), 3.41 (s, 3H), 6.35 (q, 1H), 6.90 (d, 1H), 6.97-7.05 (m, 2H), 7.34 (t, 1H), 7.62 (d, 1H), 7.93 (d, 1H), 8.53 (s, 1H), 12.5 (br.s, 1H). By preparative HPLC on a chiral phase (Method 16), the product was separated into its enantiomers: see Exam-pies 253 and 254.

Example 253

1-(1,3-dimethyl-2-oxo-2,3-dihydro-1H-benzimida-zol-5-yl)-3-{1-[2-methyl-3-(trifluoromethyl)phenyl]ethyl}-2,4-dioxo-1,2,3,4-tetrahydropyrimidine-5-carboxylic acid (enantiomer 1)

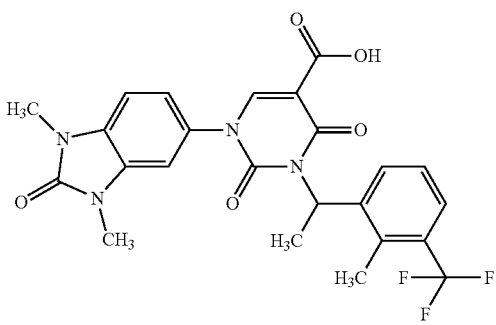 [SMILES: Cc1c(C(C)n2c(=O)c(C(=O)O)cn(-c3ccc4c(c3)n(C)c(=O)n4C)c2=O)cccc1C(F)(F)F]

Enantiomer eluting first from the preparative separation of 65 mg of the compound from Example 252 by Method 16. After drying under HV, 25 mg of the title compound were obtained.

Chiral analytical HPLC (Method 17): $R_t$=10.6 min

Example 254

1-(1,3-dimethyl-2-oxo-2,3-dihydro-1H-benzimida-zol-5-yl)-3-{1-[2-methyl-3-(trifluoromethyl)phenyl]ethyl}-2,4-dioxo-1,2,3,4-tetrahydropyrimidine-5-carboxylic acid (enantiomer 2)

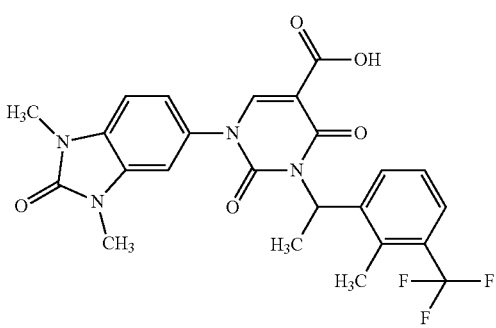 [SMILES: Cc1c(C(C)n2c(=O)c(C(=O)O)cn(-c3ccc4c(c3)n(C)c(=O)n4C)c2=O)cccc1C(F)(F)F]

Enantiomer eluting last from the preparative separation of 65 mg of the compound from Example 252 by Method 16. After drying under HV, 28 mg of the title compound were obtained.

Chiral analytical HPLC (Method 17): $R_t$=11.5 min

Example 255 ethyl 3-{1-[2-chloro-3-(trifluoromethyl)phenyl]ethyl}-1-(3-methyl-2-oxo-2,3-dihydro-1,3-benzoxazol-6-yl)-2,4-dioxo-1,2,3,4-tetrahydropyrimidine-5-carboxylate (Racemate)

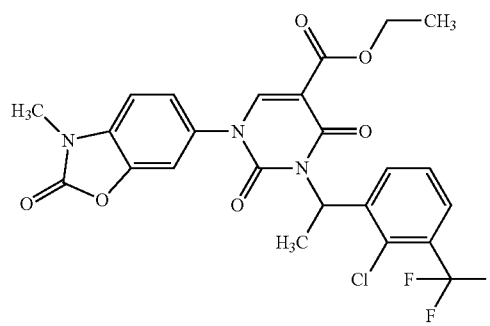

Analogously to Example 251, 500 mg (1.51 mmol) of the compound from Example 28A were reacted with 508 mg (80% purity, 1.81 mmol) of 1-[2-chloro-3-(trifluoromethyl)phenyl]ethanol from Example 116A and the product was purified. This gave 435 mg (54% of theory) of the title compound.

LC-MS (Method 4): $R_E$=2.38 min; m/z=538 (M+H)$^+$.

$^1$H NMR (500 MHz, CD$_2$Cl$_2$): δ [ppm]=1.22-1.35 (m, 3H), 1.87 (d, 3H), 3.40 (s, 3H), 4.26 (q, 2H), 6.30 (q, 1H), 7.05 (d, 1H), 7.11-7.17 (m, 1H), 7.20 (d, 1H), 7.42 (t, 1H), 7.67 (d, 1H), 7.97 (d, 1H), 8.23 (s, 1H).

Example 256

3-{1-[2-chloro-3-(trifluoromethyl)phenyl]ethyl}-1-(3-methyl-2-oxo-2,3-dihydro-1,3-benzoxazol-6-yl)-2,4-dioxo-1,2,3,4-tetrahydropyrimidine-5-carboxylic acid (Racemate)

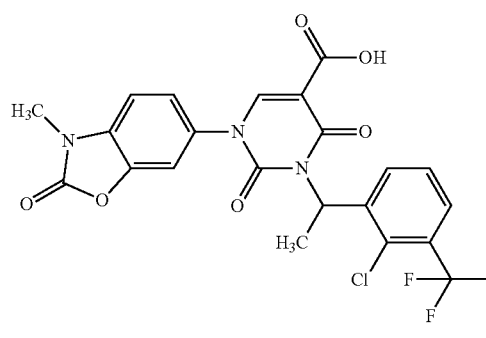

Analogously to Example 217, 400 mg (0.74 mmol) of the compound from Example 255 were hydrolysed and the product was isolated. This gave 320 mg (84% of theory) of the title compound.

LC-MS (Method 1): $R_t$=1.04 min; m/z=510 (M+H)$^+$.

¹H NMR (400 MHz, CD₂Cl₂): δ [ppm]=1.91 (d, 3H), 3.41 (s, 3H), 6.37 (q, 1H), 7.05-7.09 (m, 1H), 7.15 (dd, 1H), 7.21 (d, 1H), 7.45 (t, 1H), 7.71 (d, 1H), 7.97 (d, 1H), 8.50 (s, 1H), 12.37 (br. s, 1H). By preparative HPLC on a chiral phase (Method 18), the product was separated into its enantiomers: see Examples 257 and 258.

Example 257

3-{1-[2-chloro-3-(trifluoromethyl)phenyl]ethyl}-1-(3-methyl-2-oxo-2,3-dihydro-1,3-benzoxazol-6-yl)-2,4-dioxo-1,2,3,4-tetrahydropyrimidine-5-carboxylic acid (enantiomer 1)

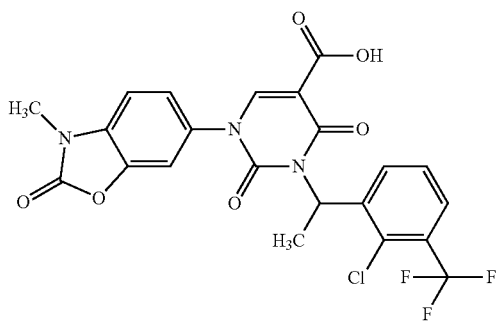 [SMILES: CC(c1cccc(C(F)(F)F)c1Cl)n1c(=O)c(C(=O)O)cn(-c2ccc3c(c2)oc(=O)n3C)c1=O]

Enantiomer eluting first from the preparative separation of 300 mg of the compound from Example 256 by Method 18. After drying under HV, 129 mg of the title compound were obtained.

Chiral analytical HPLC (Method 19): R$_t$=74 min

Example 258

3-{1-[2-chloro-3-(trifluoromethyl)phenyl]ethyl}-1-(3-methyl-2-oxo-2,3-dihydro-1,3-benzoxazol-6-yl)-2,4-dioxo-1,2,3,4-tetrahydropyrimidine-5-carboxylic acid (enantiomer 2)

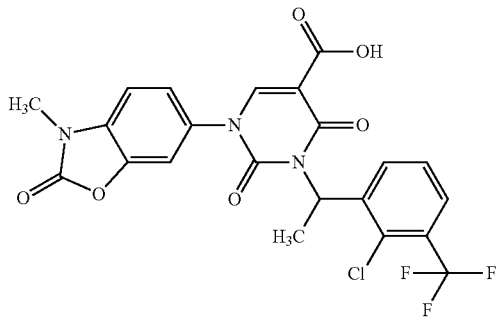 [SMILES: CC(c1cccc(C(F)(F)F)c1Cl)n1c(=O)c(C(=O)O)cn(-c2ccc3c(c2)oc(=O)n3C)c1=O]

Enantiomer eluting last from the preparative separation of 300 mg of the compound from Example 256 by Method 18. After drying under HV, 128 mg of the title compound were obtained.

Chiral analytical HPLC (Method 19): 16.6 min

Example 259 ethyl 1-(3-methyl-2-oxo-2,3-dihydro-1,3-benzoxazol-6-yl)-3-{1-[2-methyl-3-(trifluoromethyl)phenyl]ethyl}-2,4-dioxo-1,2,3,4-tetrahydropyrimidine-5-carboxylate (Racemate)

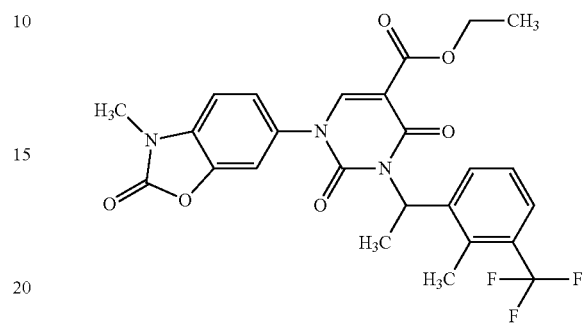

Analogously to Example 251, 500 mg (1.51 mmol) of the compound from Example 28A were reacted with 411 mg (90% purity, 1.81 mmol) of 1-[2-methyl-3-(trifluoromethyl)phenyl]ethanol from Example 115A and the product was purified. This gave 285 mg (36% of theory) of the title compound.

LC-MS (Method 1): R$_t$=1.09 min; m/z=518 (M+H)⁺.

¹H NMR (500 MHz, CD₂Cl₂): δ [ppm]=1.30 (t, 3H), 1.86 (d, 3H), 2.33 (s, 3H), 3.40 (s, 3H), 4.27 (q, 2H), 6.29 (q, 1H), 7.04 (d, 1H), 7.10-7.15 (m, 1H), 7.18 (d, 1H), 7.31 (t, 1H), 7.58 (d, 1H), 7.91 (d, 1H), 8.24 (s, 1H).

Example 260

1-(3-methyl-2-oxo-2,3-dihydro-1,3-benzoxazol-6-yl)-3-{1-[2-methyl-3-(trifluoromethyl)phenyl]ethyl}-2,4-dioxo-1,2,3,4-tetrahydropyrimidine-5-carboxylic acid (Racemate)

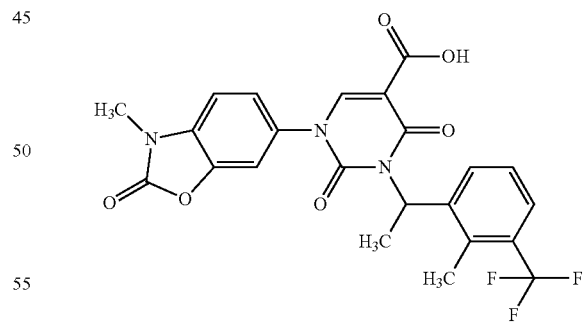

Analogously to Example 217, 260 mg (0.50 mmol) of the compound from Example 259 were hydrolysed and the product was isolated. This gave 200 mg (81% of theory) of the title compound.

LC-MS (Method 1): R$_t$=1.07 min; m/z=490 (M+H)⁺.

¹H NMR (400 MHz, CD₂Cl₂): δ [ppm]=1.91 (d, 3H), 2.34 (s, 3H), 3.41 (s, 3H), 6.35 (q, 1H), 7.07 (d, 1H), 7.14 (dd, 1H), 7.20 (d, 1H), 7.34 (t, 1H), 7.62 (d, 1H), 7.92 (d, 1H), 8.51 (s, 1H), 12.43 (br. s, 1H).

By preparative HPLC on a chiral phase (Method 20), it was possible to separate the product into its enantiomers: see Examples 261 and 262.

Example 261

1-(3-methyl-2-oxo-2,3-dihydro-1,3-benzoxazol-6-yl)-3-{1-[2-methyl-3-(trifluoromethyl)phenyl]ethyl}-2,4-dioxo-1,2,3,4-tetrahydropyrimidine-5-carboxylic acid (enantiomer 1)

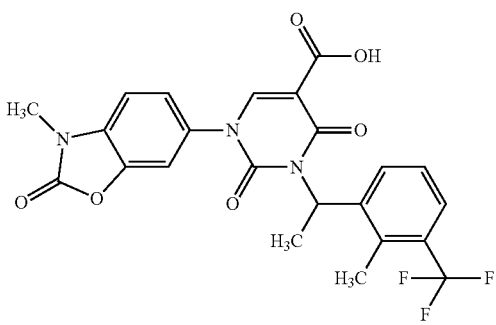 [SMILES: Cc1c(C(C)n2c(=O)c(C(=O)O)cn(-c3ccc4c(c3)oc(=O)n4C)c2=O)cccc1C(F)(F)F]

Enantiomer eluting first from the preparative separation of 190 mg of the compound from Example 256 by Method 20. After drying under HV, 80 mg of the title compound were obtained.

Chiral analytical HPLC (Method 21): $R_t$=6.61 min

Example 262

1-(3-methyl-2-oxo-2,3-dihydro-1,3-benzoxazol-6-yl)-3-{1-[2-methyl-3-(trifluoromethyl)phenyl]ethyl}-2,4-dioxo-1,2,3,4-tetrahydropyrimidine-5-carboxylic acid (enantiomer 2)

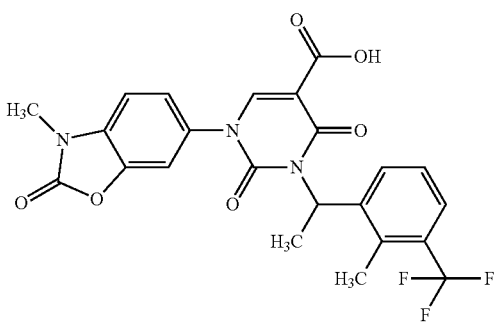 [SMILES: Cc1c(C(C)n2c(=O)c(C(=O)O)cn(-c3ccc4c(c3)oc(=O)n4C)c2=O)cccc1C(F)(F)F]

Enantiomer eluting last from the preparative separation of 190 mg of the compound from Example 256 by Method 20. After drying under HV, 82 mg of the title compound were obtained.

Chiral analytical HPLC (Method 21): $R_t$=10.6 min

Example 263

1-(6-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylic acid

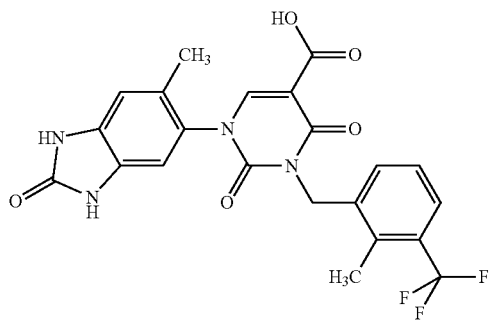 [SMILES: Cc1cc2[nH]c(=O)[nH]c2cc1-n1cc(C(=O)O)c(=O)n(Cc2cccc(C(F)(F)F)c2C)c1=O]

The preparation and purification of the title compound were in analogy to Example 121, proceeding from 130 mg (0.26 mmol) of ethyl 1-(6-methyl-2-oxo-2,3-dihydro-1H-benzimidazol-5-yl)-3-[2-methyl-3-(trifluoromethyl)benzyl]-2,4-dioxo-1,2,3,4-tetrahydropyrimidine-5-carboxylate from Example 184. The crude product obtained was purified by means of preparative HPLC (Method 8). The concentrated product fractions were stirred with dichloromethane, and the solid was filtered off and dried under reduced pressure. Thus, 67 mg (51% of theory) of the title compound were obtained.

LC-MS (Method 1): $R_t$=0.95 min; m/z=475 (M+H)$^+$.

$^1$H NMR (400 MHz, DMSO-d$_6$): δ [ppm]=2.09 (s, 3H), 2.46 (s, 3H), 5.04-5.17 (m, 2H), 6.88 (s, 1H), 7.10 (s, 1H), 7.36 (s, 2H), 7.58-7.62 (m, 1H), 8.37 (s, 1H), 10.77-10.83 (m, 2H), 12.72 (br.s, 1H).

Example 264

3-[2-chloro-3-(trifluoromethyl)benzyl]-1-(6-methyl-2-oxo-2,3-dihydro-1H-benzimidazol-5-yl)-2,4-dioxo-1,2,3,4-tetrahydropyrimidine-5-carboxylic acid

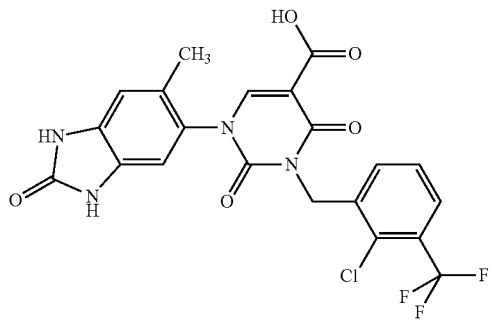 [SMILES: Cc1cc2[nH]c(=O)[nH]c2cc1-n1cc(C(=O)O)c(=O)n(Cc2cccc(C(F)(F)F)c2Cl)c1=O]

The preparation and purification of the title compound were in analogy to Example 121, with a reaction time of 1.5 h. Proceeding from 150 mg (0.29 mmol) of ethyl 3-[2-chloro-3-(trifluoromethyl)benzyl]-1-(6-methyl-2-oxo-2,3-dihydro-1H-benzimidazol-5-yl)-2,4-dioxo-1,2,3,4-tetrahydropyrimidine-5-carboxylate from Example 185, 126 mg (84% of theory) of the title compound were obtained.

LC-MS (Method 1): $R_t$=0.96 min; m/z=495 (M+H)$^+$.
$^1$H NMR (400 MHz, DMSO-d$_6$): δ [ppm]=2.10 (s, 3H), 5.17 (s, 2H), 6.88 (s, 1H), 7.10 (s, 1H), 7.50-7.60 (m, 2H), 7.78-7.83 (m, 1H), 8.39 (s, 1H), 10.80 (s, 2H), 12.69 (br.s, 1H).

Example 265

3-[2-chloro-3-(trifluoromethyl)benzyl]-1-(1-ethyl-3,3-dimethyl-2-oxo-2,3-dihydro-1H-indol-6-yl)-2,4-dioxo-1,2,3,4-tetrahydropyrimidine-5-carboxylic acid

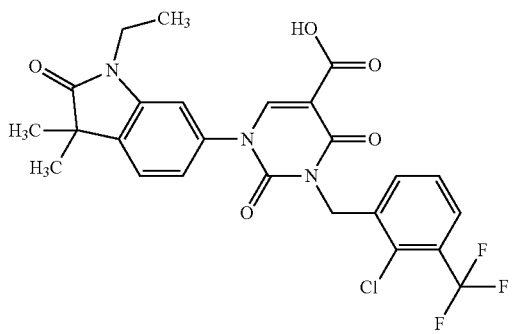 [SMILES: CCN1C(=O)C(C)(C)c2ccc(-n3cc(C(=O)O)c(=O)n(Cc4cccc(C(F)(F)F)c4Cl)c3=O)cc21]

The preparation and purification of the title compound were in analogy to Example 121, with a reaction time of 30 min. Proceeding from 50 mg (0.09 mmol) of ethyl 3-[2-chloro-3-(trifluoromethyl)benzyl]-1-(1-ethyl-3,3-dimethyl-2-oxo-2,3-dihydro-1H-indol-6-yl)-2,4-dioxo-1,2,3,4-tetrahydropyrimidine-5-carboxylate from Example 208, 26 mg (54% of theory) of the title compound were obtained.

LC-MS (Method 3): $R_t$=1.37 min; m/z=536 (M+H)$^+$.
$^1$H NMR (400 MHz, DMSO-d$_6$): δ [ppm]=1.11-1.19 (m, 3H), 1.30 (s, 6H), 3.65-3.75 (m, 2H), 5.18 (s, 2H), 7.17-7.23 (m, 1H), 7.31 (s, 1H), 7.48-7.57 (m, 2H), 7.57-7.63 (m, 1H), 7.77-7.85 (m, 1H), 8.52 (s, 1H), 12.73 (br.s, 1H).

Example 266 ethyl 1-(4-methyl-3-oxo-3,4-dihydro-2H-1,4-benzoxazin-7-yl)-3-[2-methyl-3-(trifluoromethyl)benzyl]-2,4-dioxo-1,2,3,4-tetrahydropyrimidine-5-carboxylate

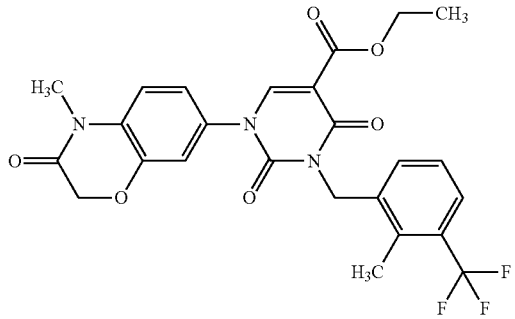 [SMILES: CCOC(=O)c1cn(-c2ccc3c(c2)OCC(=O)N3C)c(=O)n(Cc2cccc(C(F)(F)F)c2C)c1=O]

The preparation and purification were analogous to Example 216, proceeding from 200 mg (0.58 mmol) of ethyl 1-(4-methyl-3-oxo-3,4-dihydro-2H-1,4-benzoxazin-7-yl)-2,4-dioxo-1,2,3,4-tetrahydropyrimidine-5-carboxylate from Example 119A and 147 mg (0.58 mmol) of 2-methyl-3-(trifluoromethyl)benzyl bromide. This gave 168 mg (53% of theory) of the title compound.

LC-MS (Method 3): $R_t$=1.26 min; m/z=518 (M+H)$^+$.
$^1$H NMR (400 MHz, DMSO-d$_6$): δ [ppm]=1.22 (t, 3H), 2.46 (s, 3H), 3.30 (s, partly concealed by water signal, 3H), 4.20 (q, 2H), 4.71 (s, 2H), 5.06 (s, 2H), 7.22-7.32 (m, 3H), 7.32-7.41 (m, 2H), 7.59 (d, 1H), 8.39 (s, 1H).

Example 267

3-(2-methyl-3-nitrobenzyl)-1-(4-methyl-3-oxo-3,4-dihydro-2H-1,4-benzoxazin-7-yl)-2,4-dioxo-1,2,3,4-tetrahydropyrimidine-5-carboxylic acid

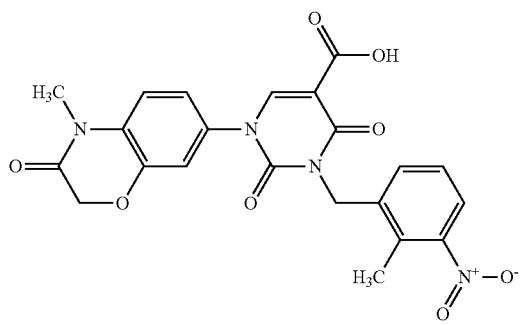 [SMILES: Cc1c(Cn2c(=O)c(C(=O)O)cn(-c3ccc4c(c3)OCC(=O)N4C)c2=O)cccc1[N+](=O)[O-]]

185 mg (0.58 mmol) of the compound from Example 216 were dissolved in 5 ml of glacial acetic acid and 2.5 ml of concentrated hydrochloric acid and stirred at 60° C. for 6 h. After cooling to RT, 75 ml of water were added. The precipitated solid was filtered off, washed with water and dried under HV. This gave 129 mg (70% of theory) of the title compound.

LC-MS (Method 1): $R_t$=0.96 min; m/z=467 (M+H)$^+$.
$^1$H NMR (400 MHz, DMSO-d$_6$): δ [ppm]=2.41 (s, 3H), 3.30 (s, partly concealed by water signal, 3H), 4.72 (s, 2H), 5.10 (s, 2H), 7.22-7.32 (m, 3H), 7.37 (t, 1H), 7.44 (d, 1H), 7.72 (d, 1H), 8.41 (s, 1H), 12.71 (br. s, 1H).

Example 268

1-(4-methyl-3-oxo-3,4-dihydro-2H-1,4-benzoxazin-7-yl)-3-[2-methyl-3-(trifluoromethyl)benzyl]-2,4-dioxo-1,2,3,4-tetrahydropyrimidine-5-carboxylic acid

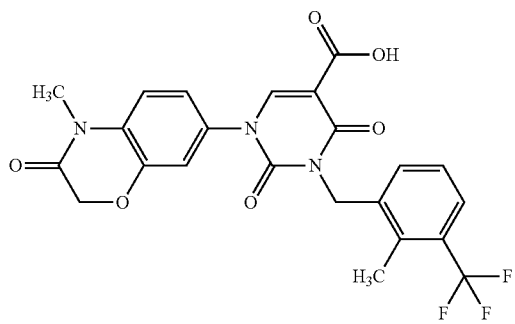 [SMILES: Cc1c(Cn2c(=O)c(C(=O)O)cn(-c3ccc4c(c3)OCC(=O)N4C)c2=O)cccc1C(F)(F)F]

130 mg (0.25 mmol) of the compound from Example 267 were dissolved in 5 ml of glacial acetic acid and 2.5 ml of concentrated hydrochloric acid and stirred at 60° C. for 6 h. After cooling to RT, 75 ml of water were added. The precipitated solid was filtered off, washed with water and dried under HV. This gave 109 mg (89% of theory) of the title compound.

LC-MS (Method 1): $R_t$=1.09 min; m/z=490 (M+H)$^+$.

$^1$H NMR (400 MHz, DMSO-d$_6$): δ [ppm]=2.48 (s, 3H), 3.30 (s, partly concealed by water signal, 3H), 4.72 (s, 2H), 5.10 (s, 2H), 7.22-7.42 (m, 5H), 7.60 (d, 1H), 8.42 (s, 1H), 12.70 (br. s, 1H).

Example 269 ethyl 3-(5-chloro-1,2,3,4-tetrahydronaphthalen-1-yl)-1-(1,3-dimethyl-2-oxo-2,3-dihydro-1H-benzimidazol-5-yl)-2,4-dioxo-1,2,3,4-tetrahydropyrimidine-5-carboxylate (Racemate)

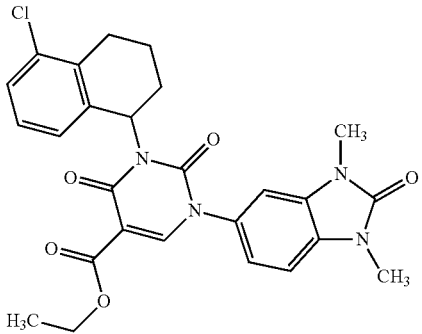 [SMILES: CCOC(=O)c1cn(-c2ccc3c(c2)n(C)c(=O)n3C)c(=O)n(C2CCCc3c(Cl)cccc32)c1=O]

400 mg (1.16 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate (Example 2A), 255 mg (1.39 mmol) of 5-chloro-1,2,3,4-tetrahydronaphthalen-1-ol and 518 mg (1.98 mmol) of triphenylphosphine were dissolved in 5 ml of THF and 10 ml of DMF. 376 mg (1.86 mmol) of DIAD were added and the mixture was stirred at RT for 2 h. The reaction mixture was admixed with a little 1 M aqueous hydrochloric acid and separated completely by means of preparative HPLC (Method 15). This gave 510 mg (86% of theory) of the title compound.

LC/MS (Method 1): $R_t$=1.09; m/z=509 (M+H)$^+$ $^1$H NMR (400 MHz, CD$_2$Cl$_2$): δ [ppm]=1.23 (t, 3H), 1.61-1.80 (m, 1H), 1.92-2.12 (m, 2H), 2.24-2.44 (m, 1H), 2.53-2.72 (m, 1H), 2.94 (br. d, 1H), 3.30 (s, 3H), 3.32 (s, 3H), 4.21 (br. q, 2H), 6.16 (br. s, 1H), 6.85 (d, 2H), 6.89-7.02 (m, 3H), 7.13 (d, 1H), 8.25 (s, 1H).

Example 270

3-(5-chloro-1,2,3,4-tetrahydronaphthalen-1-yl)-1-(1,3-dimethyl-2-oxo-2,3-dihydro-1H-benzimidazol-5-yl)-2,4-dioxo-1,2,3,4-tetrahydropyrimidine-5-carboxylic acid (Racemate)

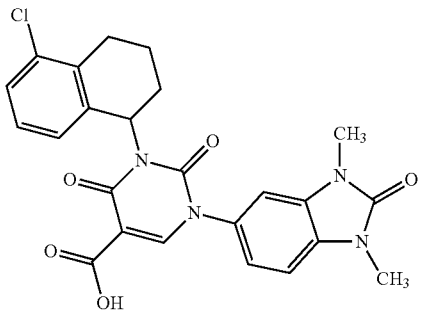 [SMILES: Cn1c(=O)n(C)c2cc(-n3cc(C(=O)O)c(=O)n(C4CCCc5c(Cl)cccc54)c3=O)ccc21]

490 mg (0.96 mmol) of ethyl 3-(5-chloro-1,2,3,4-tetrahydronaphthalen-1-yl)-1-(1,3-dimethyl-2-oxo-2,3-dihydro-1H-benzimidazol-5-yl)-2,4-dioxo-1,2,3,4-tetrahydropyrimidine-5-carboxylate from Example 269 were stirred in 3 ml of conc. hydrochloric acid and 7 ml of glacial acetic acid at reflux temperature. On completion of conversion, the reaction mixture was cooled and separated directly by means of preparative HPLC (Method 15). This gave 369 mg (80% of theory) of the title compound.

LC/MS (Method 1): $R_t$=1.10 min; m/z=481 (M+H)$^+$ $^1$H NMR (400 MHz, CD$_2$Cl$_2$): δ [ppm]=1.74-1.91 (m, 1H), 2.07-2.24 (m, 2H), 2.44 (q, 1H), 2.63-2.84 (m, 1H), 3.05 (d, 1H), 3.39 (s, 3H), 3.41 (s, 3H), 6.27 (br. s., 1H), 6.84-6.98 (m, 2H), 6.98-7.15 (m, 3H), 7.25 (d, 1H), 8.59 (s, 1H), 12.5 (br. s, 1H).

Example 271 methyl 3-(5-chloro-1,2,3,4-tetrahydronaphthalen-1-yl)-1-(1,3-dimethyl-2-oxo-2,3-dihydro-1H-benzimidazol-5-yl)-2,4-dioxo-1,2,3,4-tetrahydropyrimidine-5-carboxylate (Racemate)

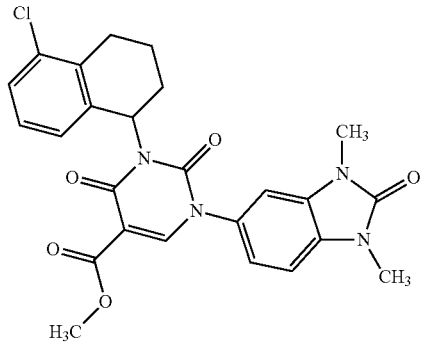 [SMILES: COC(=O)c1cn(-c2ccc3c(c2)n(C)c(=O)n3C)c(=O)n(C2CCCc3c(Cl)cccc32)c1=O]

To a solution of 300 mg (0.62 mmol) of 3-(5-chloro-1,2,3,4-tetrahydronaphthalen-1-yl)-1-(1,3-dimethyl-2-oxo-2,3-dihydro-1H-benzimidazol-5-yl)-2,4-dioxo-1,2,3,4-tetrahydropyrimidine-5-carboxylic acid from Example 270 in 5 ml of methanol were added 680 μl (9.36 mmol) of thionyl chloride. The mixture was stirred at reflux temperature for 7 hours, then concentrated on a rotary evaporator. The residue was dried under high vacuum. This gave 302 mg (94% of theory) of the title compound.

LC/MS (Method 28): $R_t$=3.10 min; m/z=495 (M+H)$^+$

Example 272 methyl 3-(5-chloro-1,2,3,4-tetrahydronaphthalen-1-yl)-1-(1,3-dimethyl-2-oxo-2,3-dihydro-1H-benzimidazol-5-yl)-2,4-dioxo-1,2,3,4-tetrahydropyrimidine-5-carboxylate (enantiomer 1)

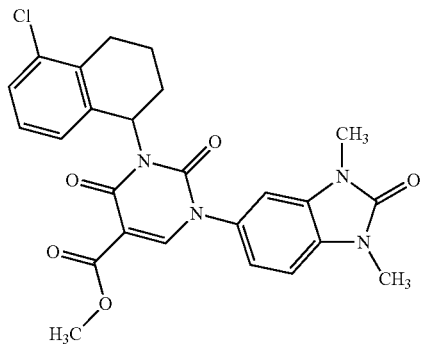 [SMILES: COC(=O)c1cn(-c2ccc3c(c2)n(C)c(=O)n3C)c(=O)n(C2CCCc3c(Cl)cccc32)c1=O]

Enantiomer which elutes first (56 mg) from the separation of 300 mg of the racemic substance from Example 271 by means of preparative HPLC on a chiral phase (Method 29).

Chiral analytical HPLC (Method 30): $R_t$=6.14 min, >99% ee.

In order to remove solvent impurities, the resulting product was purified by means of preparative HPLC (Method 15). This gave 49 mg of the title compound.

$^1$H NMR (400 MHz, CD$_2$Cl$_2$): δ [ppm]=1.72-1.87 (m, 1H), 2.01-2.20 (m, 2H), 2.33-2.50 (m, 1H), 2.62-2.79 (m, 1H), 3.03 (d, 1H), 3.38 (s, 3H), 3.41 (s, 3H), 3.82 (br. s., 3H), 6.23 (br. s., 1H), 6.85-7.13 (m, 5H), 7.21 (d, 1H), 8.36 (s, 1H).

Example 273 methyl 3-(5-chloro-1,2,3,4-tetrahydronaphthalen-1-yl)-1-(1,3-dimethyl-2-oxo-2,3-dihydro-1H-benzimidazol-5-yl)-2,4-dioxo-1,2,3,4-tetrahydropyrimidine-5-carboxylate (enantiomer 2)

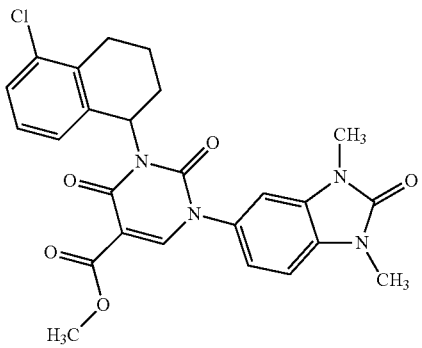

Enantiomer which elutes last (92 mg) from the separation of 300 mg of the racemic substance from Example 271 by means of preparative HPLC on a chiral phase (Method 29).

Chiral analytical HPLC (Method 30): $R_t$=7.29 min, 97% ee.

In order to remove solvent impurities, the resulting product was purified by means of preparative HPLC (Method 15). This gave 68 mg of the title compound.

$^1$H NMR (400 MHz, CD$_2$Cl$_2$): δ [ppm]=1.73-1.88 (μ, 1H), 2.01-2.21 (μ, 2H), 2.33-2.51 (μ, 1H), 2.62-2.80 (μ, 1H), 3.03 (δ, 1H), 3.38 (σ, 3H), 3.41 (σ, 3H), 3.82 (βρ. σ., 3H), 6.24 (βρ. σ., 1H), 6.84-7.11 (μ, 5H), 7.21 (δ, 1H), 8.36 (σ, 1H).

Example 274

3-(5-chloro-1,2,3,4-tetrahydronaphthalen-1-yl)-1-(1,3-dimethyl-2-oxo-2,3-dihydro-1H-benzimidazol-5-yl)-2,4-dioxo-1,2,3,4-tetrahydropyrimidine-5-carboxylic acid (enantiomer 1)

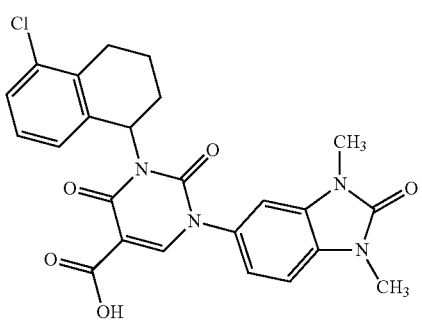 [SMILES: Cn1c(=O)n(C)c2cc(-n3cc(C(=O)O)c(=O)n(C4CCCc5c(Cl)cccc54)c3=O)ccc21]

47 mg (0.10 mmol) of methyl 3-(5-chloro-1,2,3,4-tetrahydronaphthalen-1-yl)-1-(1,3-dimethyl-2-oxo-2,3-dihydro-1H-benzimidazol-5-yl)-2,4-dioxo-1,2,3,4-tetrahydropyrimidine-5-carboxylate (enantiomer 1) from Example 272 were stirred in 2 ml of glacial acetic acid/conc. hydrochloric acid (2:1 v/v) at reflux temperature for 2 h. The reaction mixture was concentrated on a rotary evaporator and the residue was dissolved in acetonitrile/water and lyophilized. This gave 38 mg (76% of theory) of the title compound.

LC/MS (Method 1): $R_t$=1.08 min; m/z=481 (M+H)$^+$

Example 275

3-(5-chloro-1,2,3,4-tetrahydronaphthalen-1-yl)-1-(1,3-dimethyl-2-oxo-2,3-dihydro-1H-benzimidazol-5-yl)-2,4-dioxo-1,2,3,4-tetrahydropyrimidine-5-carboxylic acid (enantiomer 2)

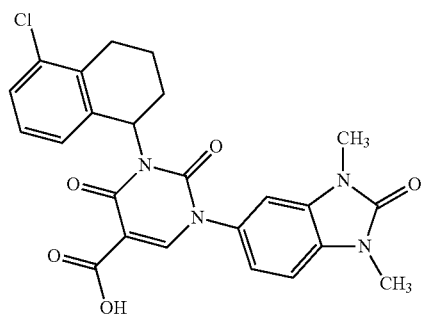 [SMILES: Cn1c(=O)n(C)c2cc(-n3cc(C(=O)O)c(=O)n(C4CCCc5c(Cl)cccc54)c3=O)ccc21]

66 mg (0.13 mmol) of methyl 3-(5-chloro-1,2,3,4-tetrahydronaphthalen-1-yl)-1-(1,3-dimethyl-2-oxo-2,3-dihydro-1H-benzimidazol-5-yl)-2,4-dioxo-1,2,3,4-tetrahydropyrimidine-5-carboxylate (enantiomer 2) from Example 273 were stirred in 2 ml of glacial acetic acid/conc. hydrochloric acid (2:1 v/v) at reflux temperature for 2 h. The reaction mixture was concentrated on a rotary evaporator and the residue was dissolved in acetonitrile/water and lyophilized. This gave 62 mg (87% of theory) of the title compound.

LC/MS (Method 1): $R_t$=1.08 min; m/z=481 (M+H)$^+$

Example 276 ethyl 1-(1,3-dimethyl-2-oxo-2,3-dihydro-1H-benzimidazol-5-yl)-2,4-dioxo-3-[5-(trifluoromethyl)-1,2,3,4-tetrahydronaphthalen-1-yl]-1,2,3,4-tetrahydropyrimidine-5-carboxylate (Racemate)

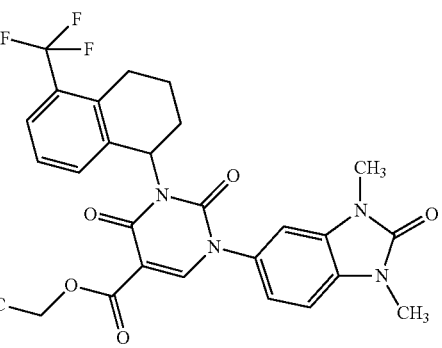

225 mg (0.66 mmol) of ethyl 1-(1,3-dimethyl-2-oxo-2,3-dihydro-1H-benzimidazol-5-yl)-2,4-dioxo-1,2,3,4-tetrahydropyrimidine-5-carboxylate (Example 2A), 170 mg (0.79 mmol) of 5-(trifluoromethyl)-1,2,3,4-tetrahydronaphthalen-1-ol and 292 mg (1.11 mmol) of triphenylphosphine in 3 ml of THF and 6 ml of DMF at RT were admixed with 212 mg (1.05 mmol) of DIAD. The mixture was stirred at RT for 2 h, then admixed with a little 1M aqueous hydrochloric acid, diluted with DMSO and purified by means of preparative HPLC (Method 15). This gave 136 mg (38% of theory) of the title compound.

LC/MS (Method 1): $R_t$=1.14 min; m/z=543 (M+H)$^+$ $^1$H NMR (400 MHz, CD$_2$Cl$_2$): δ [ppm]=1.23 (t, 3H), 1.65-1.80 (m, 1H), 1.99-2.11 (m, 2H), 2.25-2.41 (m, 1H), 2.74-2.92 (m, 1H), 2.99 (d, 1H), 3.30 (s, 3H), 3.32 (s, 3H), 4.21 (q, 2H), 6.20 (br. s., 1H), 6.78-7.00 (m, 3H), 7.09-7.18 (m, 2H), 7.40 (t, 1H), 8.25 (s, 1H).

Example 277

1-(1,3-dimethyl-2-oxo-2,3-dihydro-1H-benzimidazol-5-yl)-2,4-dioxo-3-[5-(trifluoromethyl)-1,2,3,4-tetrahydronaphthalen-1-yl]-1,2,3,4-tetrahydropyrimidine-5-carboxylic acid (Racemate)

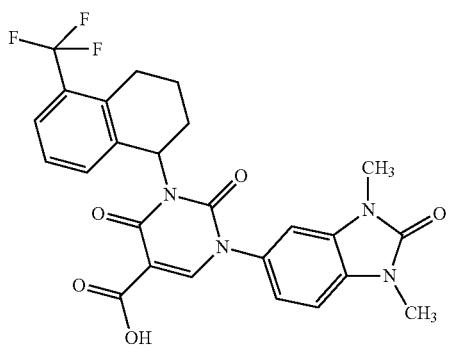 [SMILES: Cn1c(=O)n(C)c2cc(-n3cc(C(=O)O)c(=O)n(C4CCCc5c4cccc5C(F)(F)F)c3=O)ccc21]

120 mg (0.22 mmol) of ethyl 1-(1,3-dimethyl-2-oxo-2,3-dihydro-1H-benzimidazol-5-yl)-2,4-dioxo-3-[5-(trifluoromethyl)-1,2,3,4-tetrahydronaphthalen-1-yl]-1,2,3,4-tetrahydropyrimidine-5-carboxylate from Example 276 were stirred with 2 ml of conc. aqueous hydrochloric acid and 4 ml of glacial acetic acid at reflux temperature for 2 h. The reaction mixture was diluted with 5 ml of acetonitrile and purified by means of preparative HPLC (Method 15). This gave 54 mg (47% of theory) of the title compound.

LC/MS (Method 1): $R_t$=1.12 mm; m/z=515 (M+H)$^+$ $^1$H NMR (400 MHz, CD$_2$Cl$_2$): δ [ppm]=1.74-1.91 (m, 1H), 2.12-2.24 (m, 2H), 2.35-2.50 (m, 1H), 2.85-2.99 (m, 1H), 3.04-3.15 (m, 1H), 3.39 (s, 3H), 3.41 (s, 3H), 6.32 (br. s., 1H), 6.86-6.97 (m, 1H), 6.98-7.11 (m, 2H), 7.16-7.29 (m, 2H), 7.52 (d, 1H), 8.59 (s, 1H), 12.47 (hr. s, 1H).

Example 278 methyl 1-(1,3-dimethyl-2-oxo-2,3-dihydro-1H-benzimidazol-5-yl)-2,4-dioxo-3-[5-(trifluoromethyl)-1,2,3,4-tetrahydronaphthalen-1-yl]-1,2,3,4-tetrahydropyrimidine-5-carboxylate (Racemate)

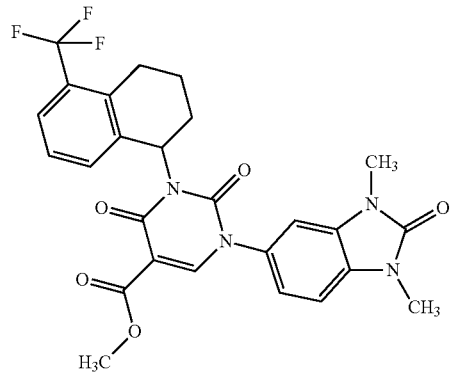 [SMILES: COC(=O)c1cn(-c2ccc3c(c2)n(C)c(=O)n3C)c(=O)n(C2CCCc3c2cccc3C(F)(F)F)c1=O]

45 mg (0.09 mmol) of 1-(1,3-dimethyl-2-oxo-2,3-dihydro-1H-benzimidazol-5-yl)-2,4-dioxo-3-[5-(trifluoromethyl)-1,2,3,4-tetrahydronaphthalen-1-yl]-1,2,3,4-tetrahydropyrimidine-5-carboxylic acid from Example 277 were dissolved in 5 ml of methanol, 100 μl (1.31 mmol) of thionyl chloride were added and the mixture was stirred at reflux temperature for 5 h. The reaction solution was concentrated under reduced pressure and the residue was dried under high vacuum. This gave 46 mg (92% of theory) of the title compound.

LC/MS (Method 28): R=3.25 min; m/z=529 (M+H)$^+$ $^1$H NMR (400 MHz, CD$_2$Cl$_2$): δ [ppm]=1.70-1.90 (m, 1H), 2.07-2.19 (m, 2H), 2.31-2.49 (m, 1H), 2.83-3.00 (m, 1H), 3.07 (d, 1H), 3.40 (s, 3H), 3.42 (s, 3H), 3.82 (s, 3H), 6.27 (hr. s., 1H), 6.91-6.99 (m, 1H), 7.00-7.11 (m, 2H), 7.21 (d, 2H), 7.48 (t, 1H), 8.37 (s, 1H).

Example 279 methyl 1-(1,3-dimethyl-2-oxo-2,3-dihydro-1H-benzimidazol-5-yl)-2,4-dioxo-3-[5-(trifluoromethyl)-1,2,3,4-tetrahydronaphthalen-1-yl]-1,2,3,4-tetrahydropyrimidine-5-carboxylate (enantiomer 1)

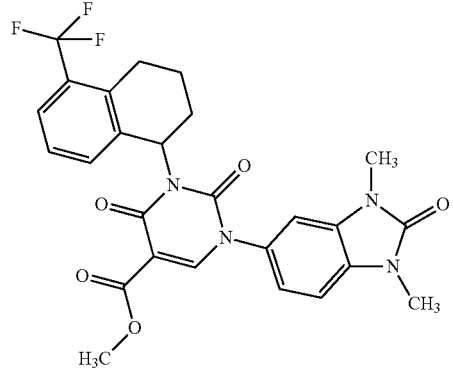 [SMILES: COC(=O)c1cn(-c2ccc3c(c2)n(C)c(=O)n3C)c(=O)n(C2CCCc3c2cccc3C(F)(F)F)c1=O]

Enantiomer which elutes first (17 mg) from the separation of 45 mg of the racemic substance from Example 278 by means of preparative HPLC on a chiral phase (Method 31).

Example 280 methyl 1-(1,3-dimethyl-2-oxo-2,3-dihydro-1H-benzimidazol-5-yl)-2,4-dioxo-3-[5-(trifluoromethyl)-1,2,3,4-tetrahydronaphthalen-1-yl]-1,2,3,4-tetrahydropyrimidine-5-carboxylate (enantiomer 2)

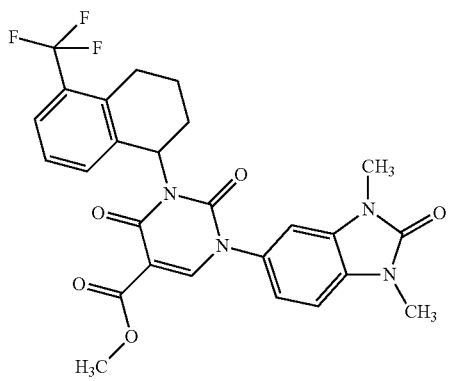 [SMILES: COC(=O)c1cn(-c2ccc3c(c2)n(C)c(=O)n3C)c(=O)n(C2CCCc3c2cccc3C(F)(F)F)c1=O]

Enantiomer which elutes last (19 mg) from the separation of 45 mg of the racemic substance from Example 278 by means of preparative HPLC on a chiral phase (Method 31).

Chiral analytical HPLC (Method 32): $R_t$=4.68 min, 98% ee.

LC/MS (Method 1): $R_t$=1.06 mm; m/z=529 (M+H)$^+$

Example 281

1-(1,3-dimethyl-2-oxo-2,3-dihydro-1H-benzimidazol-5-yl)-2,4-dioxo-3-[5-(trifluoromethyl)-1,2,3,4-tetrahydronaphthalen-1-yl]-1,2,3,4-tetrahydropyrimidine-5-carboxylic acid (enantiomer 1)

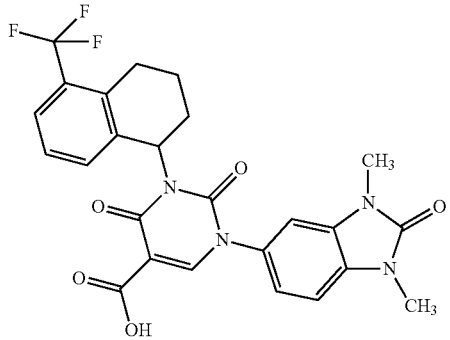 [SMILES: Cn1c(=O)n(C)c2cc(-n3cc(C(=O)O)c(=O)n(C4CCCc5c4cccc5C(F)(F)F)c3=O)ccc21]

14 mg (0.03 mmol) of the compound from Example 279 in 1.75 ml of glacial acetic acid/conc. hydrochloric acid 2:1 (v/v) were stirred at reflux temperature for 2 h. The reaction mixture was concentrated under reduced pressure, and the residue was dissolved in acetonitrile and water and lyophilized. This gave 7 mg (48% of theory) of the title compound.

LC/MS (Method 1): $R_t$: 1.10 min; m/z=515 (M+H)$^+$

Example 282

1-(1,3-dimethyl-2-oxo-2,3-dihydro-1H-benzimidazol-5-yl)-2,4-dioxo-3-[5-(trifluoromethyl)-1,2,3,4-tetrahydronaphthalen-1-yl]-1,2,3,4-tetrahydropyrimidine-5-carboxylic acid (enantiomer 2)

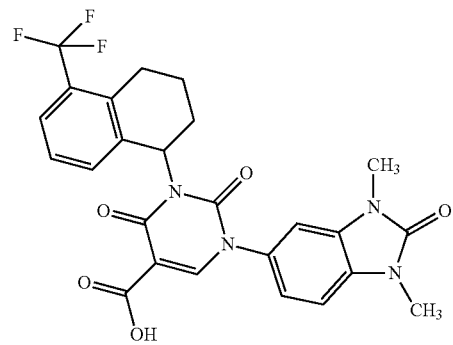 [SMILES: Cn1c(=O)n(C)c2cc(-n3cc(C(=O)O)c(=O)n(C4CCCc5c4cccc5C(F)(F)F)c3=O)ccc21]

16 mg (0.03 mmol) of the compound from Example 280 were stirred in 2 ml of a mixture of glacial acetic acid/conc. hydrochloric acid 2:1 (v/v) at reflux temperature for 2 h. The reaction mixture was concentrated under reduced pressure, and the residue was dissolved in acetonitrile and water and lyophilized. This gave 13 mg (76% of theory) of the title compound.

LC/MS (Method 1): $R_t$=1.10 min; m/z=515 (M+H)$^+$

Example 283 ethyl 3-(5-chloro-1,2,3,4-tetrahydronaphthalen-1-yl)-1-(3-methyl-2-oxo-2,3-benzoxazol-6-yl)-2,4-dioxo-1,2,3,4-tetrahydropyrimidine-5-carboxylate (Racemate)

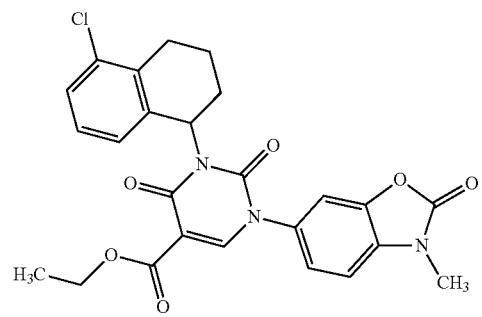 [SMILES: CCOC(=O)c1cn(-c2ccc3c(c2)oc(=O)n3C)c(=O)n(C2CCCc3c(Cl)cccc32)c1=O]

400 mg (1.21 mmol) of ethyl 1-(3-methyl-2-oxo-2,3-dihydro-1,3-benzoxazol-6-yl)-2,4-dioxo-1,2,3,4-tetrahydropyrimidine-5-carboxylate from Example 28A, 265 mg (1.45 mmol) of 5-chloro-1,2,3,4-tetrahydronaphthalen-1-ol and 538 mg (2.05 mmol) of triphenylphosphine were initially charged in 5 ml of THF and 10 ml of DMF at RT. 391 mg (1.93 mmol) of DIAD were added and the reaction mixture was stirred at RT for 2 h. After adding a little 1M aqueous hydrochloric acid, the mixture was dissolved in DMSO and purified by means of preparative HPLC (Method 11). This gave 300 mg (47% of theory) of the title compound.

LC/MS (Method 1): $R_t$=1.13 min; m/z=496 (M+H)$^+$

¹H NMR (400 MHz, CD₂Cl₂): δ [ppm]=1.24 (t, 3H), 1.64-1.81 (m, 1H), 1.93-2.11 (m, 2H), 2.21-2.42 (m, 1H), 2.51-2.71 (m, 1H), 2.94 (d, 1H), 3.32 (s, 3H), 4.21 (q, 2H), 6.14 (br. s., 1H), 6.83 (d, 1H), 6.97 (t, 2H), 7.13 (d, 3H), 8.22 (s, 1H).

Example 284

3-(5-chloro-1,2,3,4-tetrahydronaphthalen-1-yl)-1-(3-methyl-2-oxo-2,3-dihydro-1,3-benzoxazol-6-yl)-2,4-dioxo-1,2,3,4-tetrahydropyrimidine-5-carboxylic acid (Racemate)

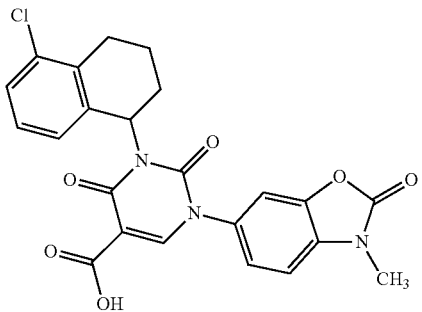 [SMILES: Cn1c(=O)oc2cc(-n3cc(C(=O)O)c(=O)n(C4CCCc5c(Cl)cccc54)c3=O)ccc21]

270 mg (0.54 mmol) of ethyl 3-(5-chloro-1,2,3,4-tetrahydronaphthalen-1-yl)-1-(3-methyl-2-oxo-2,3-dihydro-1,3-benzoxazol-6-yl)-2,4-dioxo-1,2,3,4-tetrahydropyrimidine-5-carboxylate from Example 283 were stirred in 2 ml of conc. hydrochloric acid and 4 ml of glacial acetic acid at reflux temperature. After cooling, the mixture was purified by means of preparative HPLC (Method 15). This gave 200 mg (79% of theory) of the title compound.

LC/MS (Method 1): $R_t$=1.14 min; m/z=468 (M+H)⁺

¹H NMR (400 MHz, CD₂Cl₂): δ [ppm]=1.73-1.90 (m, 1H), 2.03-2.23 (m, 2H), 2.31-2.51 (m, 1H), 2.63-2.80 (m, 1H), 3.05 (d, 1H), 3.41 (s, 3H), 6.27 (br. s., 1H), 6.89 (d, 1H), 7.08 (t, 2H), 7.14-7.29 (m, 3H), 8.56 (s, 1H), 12.40 (br. s., 1H).

Example 285 methyl 3-(5-chloro-1,2,3,4-tetrahydronaphthalen-1-yl)-1-(3-methyl-2-oxo-2,3-dihydro-1,3-benzoxazol-6-yl)-2,4-dioxo-1,2,3,4-tetrahydropyrimidine-5-carboxylate (Racemate)

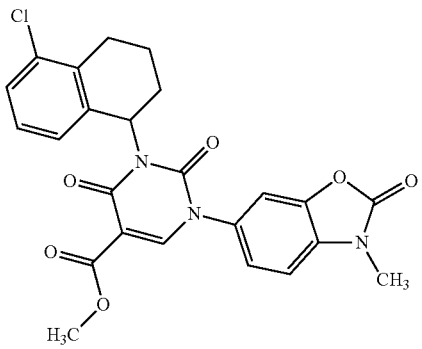 [SMILES: COC(=O)c1cn(-c2ccc3c(c2)oc(=O)n3C)c(=O)n(C2CCCc3c(Cl)cccc32)c1=O]

50 mg (0.11 mmol) of the compound from Example 284 were dissolved in 5 ml of methanol, and 117 μl (1.60 mmol) of thionyl chloride were added. The mixture was stirred at reflux temperature for 5 h, then concentrated on a rotary evaporator, and the residue was dried under high vacuum. This gave 51 mg (90% of theory) of the title compound.

LC/MS (Method 4): $R_t$=2.42 mm; m/z=482 (M+H)⁺

¹H NMR (400 MHz, CD₂Cl₂): δ [ppm]=1.80 (q, 1H), 2.01-2.21 (m, 2H), 2.30-2.50 (m, 1H), 2.63-2.79 (m, 1H), 3.03 (d, 1H), 3.41 (s, 3H), 3.83 (s, 3H), 6.06-6.41 (m, 1H), 6.91 (d, 1H), 7.03-7.11 (m, 2H), 7.14-7.26 (m, 3H), 8.33 (s, 1H).

Example 286 methyl 3-(5-chloro-1,2,3,4-tetrahydronaphthalen-1-yl)-1-(3-methyl-2-oxo-2,3-dihydro-1,3-benzoxazol-6-yl)-2,4-dioxo-1,2,3,4-tetrahydropyrimidine-5-carboxylate (enantiomer 1)

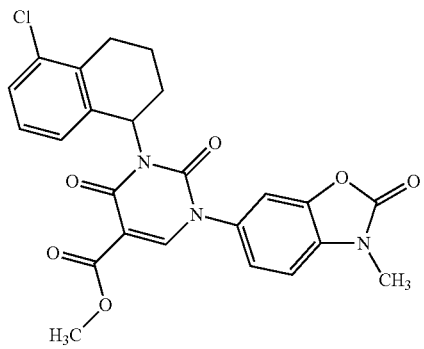 [SMILES: COC(=O)c1cn(-c2ccc3c(c2)oc(=O)n3C)c(=O)n(C2CCCc3c(Cl)cccc32)c1=O]

Enantiomer which elutes first from the separation of 152 mg of racemic methyl 3-(5-chloro-1,2,3,4-tetrahydronaphthalen-1-yl)-1-(3-methyl-2-oxo-2,3-dihydro-1,3-benzoxazol-6-yl)-2,4-dioxo-1,2,3,4-tetrahydropyrimidine-5-carboxylate (Example 285) by means of preparative HPLC on a chiral phase (Method 29).

Chiral analytical HPLC (Method 30): $R_t$=4.44 min, >99% ee.

In order to remove solvent impurities, the resulting product was purified by means of preparative HPLC (Method 15). This gave 34 mg of the title compound.

LC/MS (Method 1): $R_t$=1.08 min; m/z=482 (M+H)⁺

Example 287 methyl 3-(5-chloro-1,2,3,4-tetrahydronaphthalen-1-yl)-1-(3-methyl-2-oxo-2,3-dihydro-1,3-benzoxazol-6-yl)-2,4-dioxo-1,2,3,4-tetrahydropyrimidine-5-carboxylate (enantiomer 2)

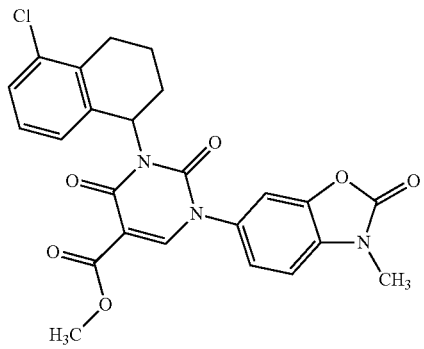 [SMILES: COC(=O)c1cn(-c2ccc3c(c2)oc(=O)n3C)c(=O)n(C2CCCc3c(Cl)cccc32)c1=O]

Enantiomer which elutes last from the separation of 152 mg of racemic methyl 3-(5-chloro-1,2,3,4-tetrahydronaphthalen-1-yl)-1-(3-methyl-2-oxo-2,3-dihydro-1,3-benzoxazol-6-yl)-2,4-dioxo-1,2,3,4-tetrahydropyrimidine-5-carboxylate (Example 285) by means of preparative HPLC on a chiral phase (Method 29).

Chiral analytical HPLC (Method 30): $R_t$=5.87 min, 99% ee.

In order to remove solvent impurities, the resulting product was purified by means of preparative HPLC (Method 15). This gave 27 mg of the title compound.

LC/MS (Method 1): $R_t$=1.08 min; m/z=482 (M+H)$^+$

Example 288

3-(5-chloro-1,2,3,4-tetrahydronaphthalen-1-yl)-1-(3-methyl-2-oxo-2,3-dihydro-1,3-benzoxazol-6-yl)-2,4-dioxo-1,2,3,4-tetrahydropyrimidine-5-carboxylic acid (enantiomer 1)

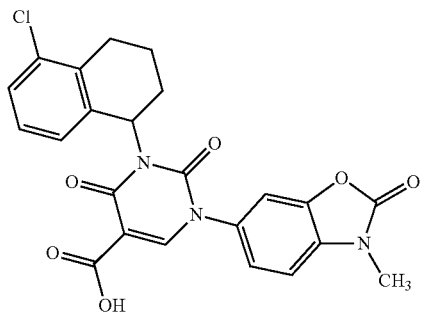 [SMILES: Cn1c(=O)oc2cc(-n3cc(C(=O)O)c(=O)n(C4CCCc5c(Cl)cccc54)c3=O)ccc21]

32 mg (66 µmol) of the compound from Example 286 in 2 ml of glacial acetic acid/conc. hydrochloric acid 2:1 (v/v) were stirred at reflux temperature for 2 h. The mixture was concentrated by rotary evaporation, dissolved in acetonitrile and water and lyophilized. This gave 33 mg (92% pure, 97% of theory) of the title compound.

LC/MS (Method 1): $R_t$=1.12 min; m/z=468 (M+H)$^+$

Example 289

3-(5-chloro-1,2,3,4-tetrahydronaphthalen-1-yl)-1-(3-methyl-2-oxo-2,3-dihydro-1,3-benzoxazol-6-yl)-2,4-dioxo-1,2,3,4-tetrahydropyrimidine-5-carboxylic acid (enantiomer 2)

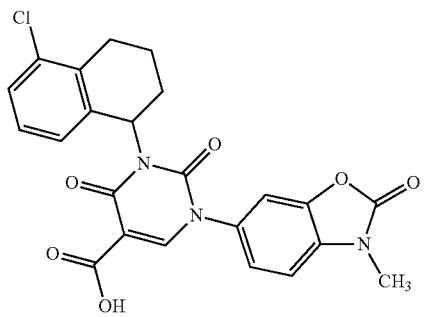 [SMILES: Cn1c(=O)oc2cc(-n3cc(C(=O)O)c(=O)n(C4CCCc5c(Cl)cccc54)c3=O)ccc21]

25 mg (0.052 mmol) of the compound from Example 287 in 1.6 ml of glacial acetic acid/conc. hydrochloric acid 2:1 (v/v) were stirred at reflux temperature for 2 h. The mixture was concentrated under reduced pressure, and the residue was dissolved in acetonitrile and water and lyophilized. This gave 24 mg (93% of theory) of the title compound.

LC/MS (Method 1): $R_t$=1.12 min; m/z=468 (M+H)$^+$

Example 290 ethyl 1-(3-methyl-2-oxo-2,3-dihydro-1,3-benzoxazol-6-yl)-2,4-dioxo-3 [5-(trifluoromethyl)-1,2,3,4-tetrahydronaphthalen-1-yl]-1,2,3,4-tetrahydropyrimidine-5-carboxylate (Racemate)

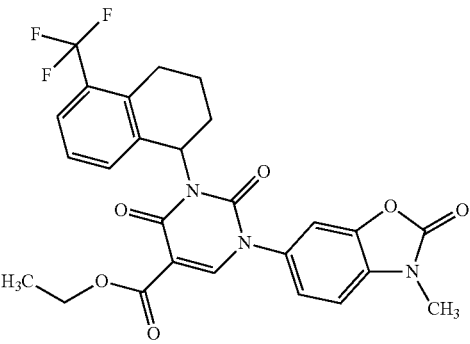 [SMILES: CCOC(=O)c1cn(-c2ccc3c(c2)oc(=O)n3C)c(=O)n(C2CCCc3c2cccc3C(F)(F)F)c1=O]

217 mg (0.66 mmol) of ethyl 1-(3-methyl-2-oxo-2,3-dihydro-1,3-benzoxazol-6-yl)-2,4-dioxo-1,2,3,4-tetrahydropyrimidine-5-carboxylate (Example 28A), 170 mg (0.79 mmol) of 5-(trifluoromethyl)-1,2,3,4-tetrahydronaphthalen-1-ol and 292 mg (1.11 mmol) of triphenylphosphine were initially charged in 3 ml of THF and 6 ml of DMF at RT. 212 mg (1.05 mmol) of DIAD were added and the mixture was stirred at RT for 2 h. After adding a little 1M aqueous hydrochloric acid, the mixture was dissolved in DMSO and purified by means of preparative HPLC (Method 15). This gave 114 mg (33% of theory) of the title compound.

LC/MS (Method 1): $R_t$=1.18 min; m/z=530 (M+H)$^+$ $^1$H NMR (400 MHz, CD$_2$Cl$_2$): δ [ppm]=1.24 (t, 3H), 1.65-1.80 (m, 1H), 1.98-2.11 (m, 2H), 2.21-2.39 (d, 1H), 2.73-2.91 (d, 1H), 2.93-3.04 (m, 1H), 3.32 (s, 3H), 4.22 (q, 2H), 6.19 (br. s., 1H), 6.97 (d, 1H), 7.03-7.20 (m, 4H), 7.37-7.44 (m, 1H), 8.22 (s, 1H).

Example 291

1-(3-methyl-2-oxo-2,3-dihydro-1,3-benzoxazol-6-yl)-2,4-dioxo-3-[5-(trifluoromethyl)-1,2,3,4-tetrahydronaphthalen-1-yl]-1,2,3,4-tetrahydropyrimidine-5-carboxylic acid (Racemate)

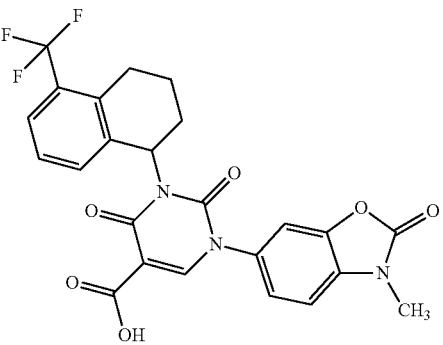 [SMILES: Cn1c(=O)oc2cc(-n3cc(C(=O)O)c(=O)n(C4CCCc5c4cccc5C(F)(F)F)c3=O)ccc21]

95 mg (0.18 mmol) of the compound from Example 290 were stirred with 2 ml of conc. hydrochloric acid and 4 ml of glacial acetic acid at reflux temperature for 2 h. After cooling, the mixture was diluted with 5 ml of acetonitrile and purified by means of preparative HPLC (Method 15). This gave 83 mg (92% of theory) of the title compound.

LC/MS (Method 1): $R_t$=1.15 min; m/z=502 (M+H)$^+$ $^1$H NMR (400 MHz, CD$_2$Cl$_2$): δ [ppm]=1.65-1.81 (m, 1H), 2.01-2.17 (m, 2H), 2.25-2.39 (m, 1H), 2.76-2.92 (m, 1H), 2.96-3.10 (m, 1H), 3.33 (s, 3H), 6.23 (br. s., 1H), 6.99 (d, 1H), 7.04-7.22 (m, 4H), 7.44 (d, 1H), 8.48 (s, 1H), 12.30 (br. s, 1H).

Example 292 methyl 1-(3-methyl-2-oxo-2,3-dihydro-1,3-benzoxazol-6-yl)-2,4-dioxo-3-[5-(trifluoromethyl)-1,2,3,4-tetrahydronaphthalen-1-yl]-1,2,3,4-tetrahydropyrimidine-5-carboxylate (Racemate)

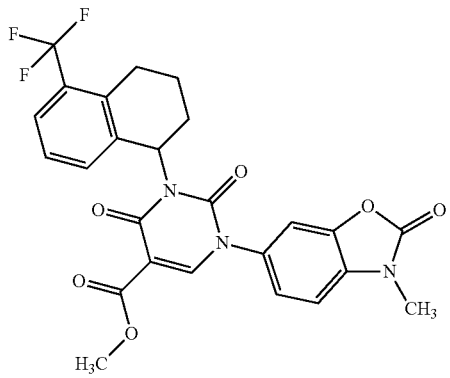 [SMILES: COC(=O)c1cn(-c2ccc3c(c2)oc(=O)n3C)c(=O)n(C2CCCc3c2cccc3C(F)(F)F)c1=O]

60 mg (0.12 mmol) of 1-(3-methyl-2-oxo-2,3-dihydro-1,3-benzoxazol-6-yl)-2,4-dioxo-3-[5-(trifluoromethyl)-1,2,3,4-tetrahydronaphthalen-1-yl]-1,2,3,4-tetrahydropyrimidine-5-carboxylic acid from Example 291 were dissolved in 5 ml of methanol, and 131 μl (1.80 mmol) of thionyl chloride were added. The mixture was stirred at reflux temperature for 7 h, then concentrated on a rotary evaporator, and the residue was dried under high vacuum. This gave 60 mg (77% of theory) of the title compound in 79% purity.

LC/MS (Method 28): $R_t$=3.40 min; m/z=516 (M+H)$^+$

Example 293 methyl 1-(3-methyl-2-oxo-2,3-dihydro-1,3-benzoxazol-6-yl)-2,4-dioxo-3-[5-(trifluoromethyl)-1,2,3,4-tetrahydronaphthalen-1-yl]-1,2,3,4-tetrahydropyrimidine-5-carboxylate (enantiomer 1)

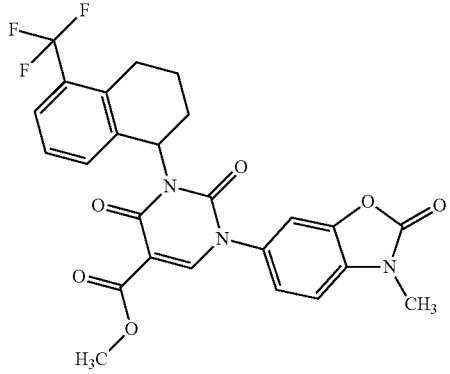 [SMILES: COC(=O)c1cn(-c2ccc3c(c2)oc(=O)n3C)c(=O)n(C2CCCc3c2cccc3C(F)(F)F)c1=O]

60 mg (0.12 mmol) of racemic methyl 1-(3-methyl-2-oxo-2,3-dihydro-1,3-benzoxazol-6-yl)-2,4-dioxo-3-[5-(trifluoromethyl)-1,2,3,4-tetrahydronaphthalen-1-yl]-1,2,3,4-tetrahydropyrimidine-5-carboxylate from Example 292 were dissolved in 3 ml of acetonitrile and 1 ml of ethanol and separated on a Daicel Chiralpak IC column with 40% acetonitrile and 60% MTBE. Partial transesterification to the ethyl ester took place. As the fraction which eluted first, 14.5 mg of the title compound were obtained.

Chiral analytical HPLC (Method 30): $R_t$=3.99 min, 99% ee.

LC/MS (Method 1): $R_t$=1.11 min; m/z=516 (M+H)$^+$ $^1$H NMR (400 MHz, CD$_2$Cl$_2$): δ [ppm]=1.64-1.80 (m, 1H), 1.99-2.10 (m, 2H), 2.23-2.36 (m, 1H), 2.75-2.90 (m, 1H), 2.94-3.04 (m, 1H), 3.32 (s, 3H), 3.75 (s, 3H), 6.18 (br. s., 1H), 6.97 (d, 1H), 7.03-7.22 (m, 4H), 7.37-7.45 (m, 1H), 8.25 (s, 1H).

As the fraction which eluted second, a mixture of the epimer of the title compound and the two enantiomers of the corresponding ethyl ester (43 mg) was obtained. This mixture was not purified any further.

Example 294

1-(3-methyl-2-oxo-2,3-dihydro-1,3-benzoxazol-6-yl)-2,4-dioxo-3-[5-(trifluoromethyl)-1,2,3,4-tetrahydronaphthalen-1-yl]-1,2,3,4-tetrahydropyrimidine-5-carboxylic acid (enantiomer 1)

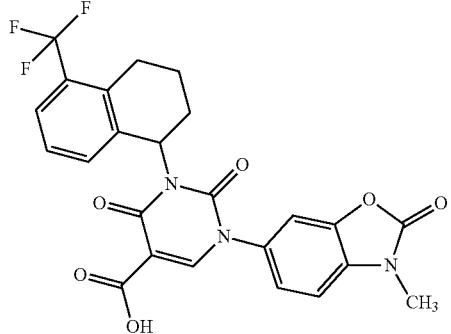 [SMILES: Cn1c(=O)oc2cc(-n3cc(C(=O)O)c(=O)n(C4CCCc5c4cccc5C(F)(F)F)c3=O)ccc21]

12 mg (0.02 mmol) of methyl 1-(3-methyl-2-oxo-2,3-dihydro-1,3-benzoxazol-6-yl)-2,4-dioxo-3-[5-(trifluoromethyl)-1,2,3,4-tetrahydronaphthalen-1-yl]-1,2,3,4-tetrahydropyrimidine-5-carboxylate from Example 293 were stirred with 0.4 ml of a mixture of glacial acetic acid and conc. hydrochloric acid in a ratio of 2:1 at reflux temperature for 2 h. The mixture was concentrated, and the residue was dissolved in acetonitrile/water and then lyophilized. This gave 11 mg (91% of theory) of the title compound.

LC/MS (Method 1): $R_t$=1.12 min; m/z=502 (M+H)$^+$

Example 295 ethyl 1-(3-methyl-2-oxo-2,3-dihydro-1,3-benzothiazol-6-yl)-2,4-dioxo-3-[5-(trifluoromethyl)-1,2,3,4-tetrahydronaphthalen-1-yl]-1,2,3,4-tetrahydropyrimidine-5-carboxylate (Racemate)

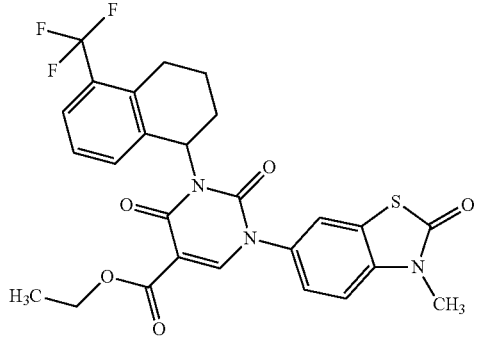 [SMILES: CCOC(=O)c1cn(-c2ccc3c(c2)sc(=O)n3C)c(=O)n(C2CCCc3c2cccc3C(F)(F)F)c1=O]

227 mg (0.66 mmol) of ethyl 1-(3-methyl-2-oxo-2,3-dihydro-1,3-benzothiazol-6-yl)-2,4-dioxo-1,2,3,4-tetrahydropyrimidine-5-carboxylate (Example 31A), 170 mg (0.79 mmol) of 5-(trifluoromethyl)-1,2,3,4-tetrahydronaphthalen-1-ol and 292.2 mg (1.11 mmol) of triphenylphosphine were initially charged in 3 ml of THF and 6 ml of DMF at RT. 206 µl (1.05 mmol) of DIAD were added and the reaction mixture was stirred at RT for 2 h. After adding a little 1M aqueous hydrochloric acid, the mixture was dissolved in DMSO and separated by means of preparative HPLC (Method 15). This gave 196 mg (52% of theory) of the title compound.

LC/MS (Method 1): $R_t$=1.23 min; m/z=546 (M+H)$^+$ $^1$H NMR (400 MHz, CD$_2$Cl$_2$): δ [ppm]=1.24 (t, 3H), 1.65-1.80 (m, 1H), 1.99-2.11 (m, 2H), 2.23-2.38 (m, 1H), 2.75-2.90 (m, 1H), 2.94-3.05 (m, 1H), 3.37 (s, 3H), 4.22 (q, 2H), 6.20 (br. s., 1H), 7.05 (d, 1H), 7.12 (d, 2H), 7.15-7.28 (m, 1H), 7.29-7.46 (m, 2H), 8.23 (s, 1H).

Example 296

1-(3-methyl-2-oxo-2,3-dihydro-1,3-benzothiazol-6-yl)-2,4-dioxo-3-[5-(trifluoromethyl)-1,2,3,4-tetrahydronaphthalen-1-yl]-1,2,3,4-tetrahydropyrimidine-5-carboxylic acid (Racemate)

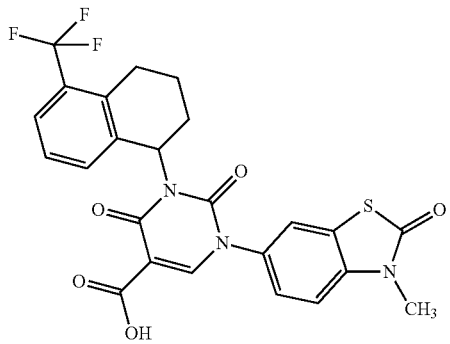 [SMILES: Cn1c(=O)sc2cc(-n3cc(C(=O)O)c(=O)n(C4CCCc5c4cccc5C(F)(F)F)c3=O)ccc21]

120 mg (0.21 mmol) of the compound from Example 295 in 2 ml of glacial acetic acid and 4 ml of conc. hydrochloric acid were stirred at reflux temperature for 2 h. The reaction mixture was cooled, diluted with 5 ml of acetonitrile and purified by means of preparative HPLC (Method 15). This gave 85 mg (78% of theory) of the title compound.

LC/MS (Method 1): R=1.18 min; m/z=518 (M+H)$^+$ $^1$H NMR (400 MHz, CD$_2$Cl$_2$): δ [ppm]=1.74-1.90 (m, 1H), 2.10-2.25 (m, 2H), 2.40 (q, 1H), 2.83-2.99 (m, 1H), 3.05-3.15 (m, 1H), 3.46 (s, 3H), 6.32 (br. s., 1H), 7.11-7.20 (m, 2H), 7.21-7.35 (m, 2H), 7.44 (br. s., 1H), 7.52 (d, 1H), 8.57 (s, 1H), 12.38 (br. s, 1H).

Example 297 methyl 1-(3-methyl-2-oxo-2,3-dihydro-1,3-benzothiazol-6-yl)-2,4-dioxo-3-[5-(trifluoromethyl)-1,2,3,4-tetrahydronaphthalen-1-yl]-1,2,3,4-tetrahydropyrimidine-5-carboxylate (Racemate)

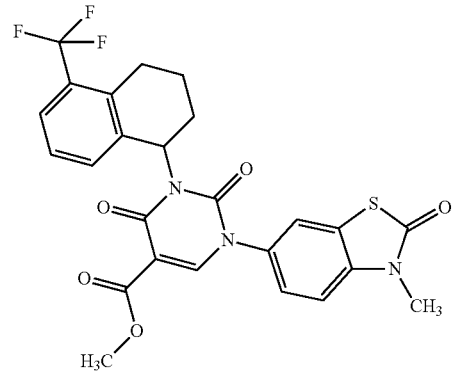 [SMILES: COC(=O)c1cn(-c2ccc3c(c2)sc(=O)n3C)c(=O)n(C2CCCc3c2cccc3C(F)(F)F)c1=O]

70 mg (0.14 mmol) of the compound from Example 296 were dissolved in 5 ml of methanol, and 148 µl (2.03 mmol) of thionyl chloride were added. The mixture was stirred at reflux temperature for 7 h, then concentrated on a rotary evaporator, and the residue was dried under high vacuum. This gave 70 mg of the title compound in 75% purity (72% of theory).

LC/MS (Method 28): R=3.59 min; m/z=532 (M+H)$^+$

Example 298 methyl 1-(3-methyl-2-oxo-2,3-dihydro-1,3-benzothiazol-6-yl)-2,4-dioxo-3-[5-(trifluoromethyl)-1,2,3,4-tetrahydronaphthalen-1-yl]-1,2,3,4-tetrahydropyrimidine-5-carboxylate (enantiomer 1)

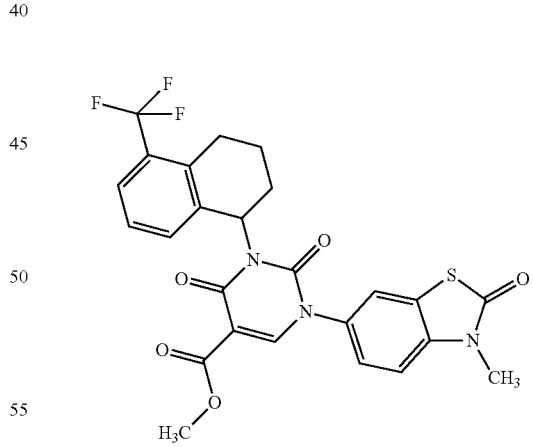

Enantiomer which elutes first (24 mg) from the separation of 70 mg of the racemic substance from Example 297 by means of preparative HPLC on a chiral phase (Method 33).

Chiral analytical HPLC (Method 34): 12, =6.03 mm, 99% ee.

LC/MS (Method 1): $R_t$=1.16 min; m/z=532 (M+H)$^+$ $^1$H NMR (400 MHz, CD$_2$Cl$_2$): δ [ppm]=1.72-1.88 (m, 1H), 2.05-2.20 (m, 2H), 2.30-2.47 (m, 1H), 2.83-2.98 (m, 1H), 3.01-3.14 (m, 1H), 3.45 (s, 3H), 3.83 (s, 3H), 6.18-6.37 (m, 1H), 7.05-7.37 (m, 4H), 7.48 (d, 2H), 8.34 (s, 1H).

Example 299 methyl 1-(3-methyl-2-oxo-2,3-dihydro-1,3-benzothiazol-6-yl)-2,4-dioxo-3-[5-(trifluoromethyl)-1,2,3,4-tetrahydronaphthalen-1-yl]-1,2,3,4-tetrahydropyrimidine-5-carboxylate (enantiomer 2)

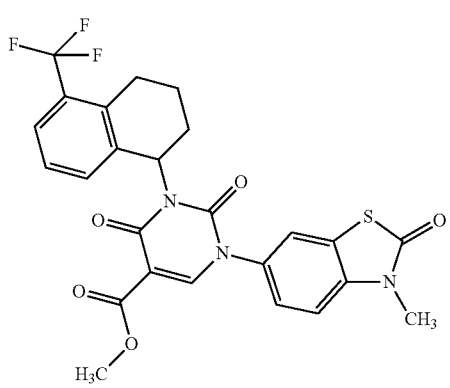 [SMILES: COC(=O)c1cn(-c2ccc3c(c2)sc(=O)n3C)c(=O)n(C2CCCc3c2cccc3C(F)(F)F)c1=O]

Enantiomer which elutes last (29 mg) from the separation of 70 mg of the racemic substance from Example 297 by means of preparative HPLC on a chiral phase (Method 33).

Chiral analytical HPLC (Method 34): $R_t$=7.37 mm 99% ee

LC/MS (Method 1): $R_t$=1.16 mm; m/z=532 (M+H)$^+$ $^1$H NMR (400 MHz, CD$_2$Cl$_2$): δ [ppm]=1.71-1.87 (m, 1H), 2.06-2.20 (m, 2H), 2.30-2.46 (m, 1H), 2.82-2.99 (m, 1H), 3.01-3.12 (m, 1H), 3.45 (s, 3H), 3.83 (s, 3H), 6.28 (br. s., 1H), 7.13 (d, 1H), 7.16-7.35 (m, 3H), 7.38-7.57 (m, 2H), 8.34 (s, 1H).

Example 300

1-(3-methyl-2-oxo-2,3-dihydro-1,3-benzothiazol-6-yl)-2,4-dioxo-3-[5-(trifluoromethyl)-1,2,3,4-tetrahydronaphthalen-1-yl]-1,2,3,4-tetrahydropyrimidine-5-carboxylic acid (enantiomer 1)

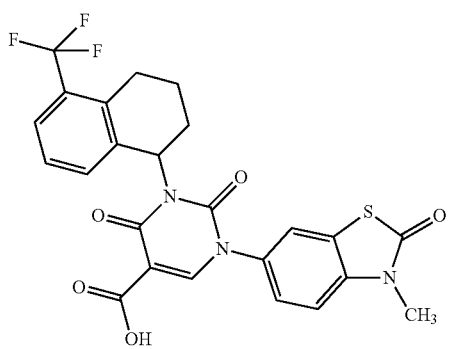 [SMILES: Cn1c(=O)sc2cc(-n3cc(C(=O)O)c(=O)n(C4CCCc5c4cccc5C(F)(F)F)c3=O)ccc21]

22 mg (0.04 mmol) of the compound from Example 298 were stirred with 2 ml of glacial acetic acid/conc. hydrochloric acid in a ratio of 2:1 (v/v) at reflux temperature for 2 h. The mixture was concentrated on a rotary evaporator, and the residue was dissolved in acetonitrile/water and then lyophilized. This gave 16 mg (75% of theory) of the title compound.

LC/MS (Method 1): $R_t$=1.16 min; m/z=518 (M+H)$^+$ $^1$H NMR (400 MHz, CD$_2$Cl$_2$): δ [ppm]=1.74-1.90 (m, 1H), 2.11-2.24 (m, 2H), 2.31-2.46 (m, 1H), 2.84-3.00 (m, 1H), 3.04-3.15 (m, 1H), 3.46 (s, 3H), 6.32 (br. s., 1H), 7.10-7.21 (m, 2H), 7.21-7.37 (m, 4H), 7.38-7.49 (m, 1H), 7.52 (d, 1H), 8.58 (s, 1H), 12.38 (br.s, 1H).

Example 301

1-(3-methyl-2-oxo-2,3-dihydro-1,3-benzothiazol-6-yl)-2,4-dioxo-3-[5-(trifluoromethyl)-1,2,3,4-tetrahydronaphthalen-1-yl]-1,2,3,4-tetrahydropyrimidine-5-carboxylic acid (enantiomer 2)

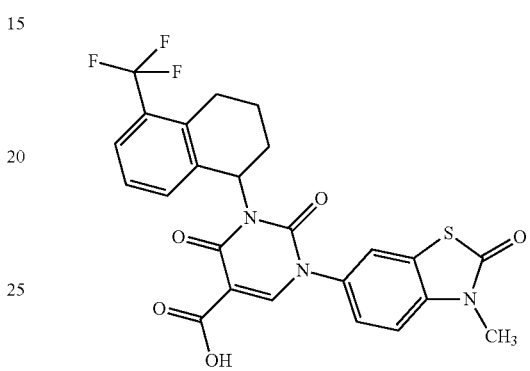

27 mg (0.05 mmol) of the compound from Example 299 in 2.5 ml of glacial acetic acid/conc. hydrochloric acid were stirred at reflux temperature for 2 h. The mixture was concentrated on a rotary evaporator and the residue was dissolved in acetonitrile/water and lyophilized. This gave 22 mg (81% of theory) of the title compound.

LC/MS (Method 1): $R_t$=1.19 mm; m/z=518 (M+H)$^+$

Example 302 ethyl 3-(8-chloro-3,4-dihydro-1H-iso chromen-4-yl)-1-(3-methyl-2-oxo-2,3-dihydro-1,3-benzoxazol-6-yl)-2,4-dioxo-1,2,3,4-tetrahydropyrimidine-5-carboxylate (Racemate)

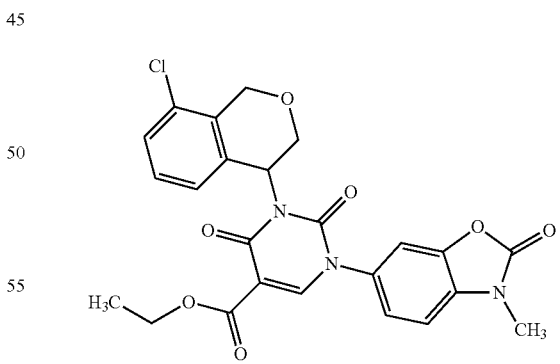

Under argon, 149.5 mg (0.45 mmol) of ethyl 1-(3-methyl-2-oxo-2,3-dihydro-1,3-benzoxazol-6-yl)-2,4-dioxo-1,2,3,4-tetrahydropyrimidine-5-carboxylate from Example 28A, 100.0 mg (0.54 mmol) of 8-chloro-3,4-dihydro-1H-isochromen-4-ol (Example 120A) and 201.3 mg (0.77 mmol) of triphenylphosphine were dissolved in 4.8 ml of DMF and 2.4 ml of THF. 146.0 mg (0.72 mmol) of DIAD were added dropwise and the reaction mixture was stirred at RT. After 2 h, 5 ml of aqueous 1M hydrochloric acid were added and the mixture was separated by means of preparative HPLC (Method 15). This gave 59.0 mg (26% of theory) of the title compound.

LC/MS (Method 1): $R_t$=1.02 min; m/z=498 (M+H)$^+$ $^1$H NMR (400 MHz, CD$_2$Cl$_2$): δ [ppm]=1.31 (t, 3H), 3.41 (s, 3H), 4.08-4.15 (m, 1H), 4.22-4.35 (m, 3H), 4.74 (d, 1H), 4.93 (d, 1H), 6.26-6.38 (m, 1H), 7.00 (d, 1H), 7.03-7.08 (m, 1H), 7.13-7.26 (m, 4H), 8.31 (s, 1H).

Example 303

3-(8-chloro-3,4-dihydro-1H-isochromen-4-yl)-1-(3-methyl-2-oxo-2,3-dihydro-1,3-benzoxazol-6-yl)-2,4-dioxo-1,2,3,4-tetrahydropyrimidine-5-carboxylic acid (Racemate)

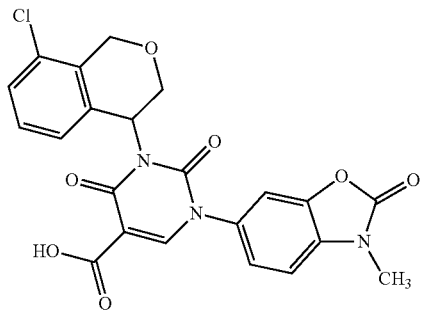 [SMILES: Cn1c(=O)oc2cc(-n3cc(C(=O)O)c(=O)n(C4COCc5c(Cl)cccc54)c3=O)ccc21]

50 mg (0.10 mmol) of the compound from Example 302 were heated to reflux temperature in 6.7 ml of a mixture of conc, hydrochloric acid/glacial acetic acid 1:2 for 50 min. After cooling to RT, the whole mixture was separated by means of preparative HPLC (Method 15). This gave 10 mg (21% of theory) of the title compound.

LC/MS (Method 1): $R_t$=0.98 min; m/z=470 (M+H)$^+$ $^1$H NMR (400 MHz, CD$_2$Cl$_2$): δ [ppm]=3.41 (s, 3H), 4.17 (dd, 1H), 4.22-4.30 (m, 1H), 4.76 (d, 1H), 4.94 (d, 1H), 6.28-6.40 (m, 1H), 6.99 (d, 1H), 7.08 (d, 1H), 7.19 (t, 2H), 7.28 (d, 1H), 8.57 (s, 1H).

B. ASSESSMENT OF PHARMACOLOGICAL EFFICACY

The pharmacological action of the inventive compounds can be shown in the assays described below:

Abbreviations

| | |
|---|---|
| Abz-HPFHL-Lys(Dnp)-NH$_2$ | 1-[N-(3-aminobenzoyl)histidylprolylphenylalanylhistidylleucyl-N$^6$-(2,4-dinitrophenyl)lysine |
| AMC | 7-amido-4-methylcoumarin |
| BNP | brain natriuretic peptide |
| BSA | bovine serum albumin |
| CHAPS | 3-[(3-cholamidopropyl)dimethylammonio]-1-propanesulphonate |
| HEPES | N-(2-Hydroxyethyl)piperazine-N'-2-ethanesulphonic acid |
| IC | inhibitory concentration |
| MeOSuc | methoxysuccinyl |
| NADP | nicotinamide adenine dinucleotide phosphate |
| PBS | phosphate-buffered saline solution |
| PEG | polyethylene glycol |
| v/v | volume to volume ratio (of a solution) |
| w/v | weight to volume ratio (of a solution) |

B-1. Enzymatic Chymase Assay

The enzyme source used is recombinant human chymase (expressed in HEK293 cells) or chymase purified from hamsters' tongues. The substrate used for chymase is Abz-HPFHL-Lys(Dnp)-NH$_2$. For the assay, 1 μl of a 50-fold concentrated solution of test substance in DMSO, 24 μl of enzyme solution (dilution 1:80 000 human or 1:4000 hamster) and 25 μl of substrate solution (final concentration 10 μM) in assay buffer (Tris 50 mM (pH 7.5), sodium chloride 150 mM, BSA 0.10%, Chaps 0.10%, glutathione 1 mM, EDTA 1 mM) were combined in a white 384-hole microtitre plate (Greiner Bio-One, Frickenhausen, Germany). The reaction is incubated at 32 degrees for 60 min and the fluorescence emission at 465 nm after excitation at 340 nm is measured in a fluorescence reader, for example Tecan Ultra (Tecan, Mannedorf, Switzerland).

One test compound is tested on the same microtitre plate in 10 different concentrations from 30 μM to 1 nM in a double determination. The data are normalized (enzyme reaction without inhibitor=0% inhibition, all assay components without enzyme=100% inhibition) and IC$_{50}$ values are calculated using in-house software. Corn-pounds in the context of the invention which were tested in this assay inhibited chymase activity with an IC$_{50}$ of less than 10 μM.

IC$_{50}$ values representative of the inventive compounds are shown in Tables 1 and 2 below:

TABLE 1

| Example No. | Hamster chymase IC 50 [nM] |
|---|---|
| 1 | 8 |
| 2 | 7 |
| 3 | 9 |
| 4 | 64 |
| 5 | 20 |
| 8 | 33 |
| 9 | 1500 |
| 10 | 1600 |
| 13 | 5 |
| 14 | 10 |
| 15 | 330 |
| 16 | 14 |
| 18 | 10 |
| 20 | 8 |
| 21 | 5 |
| 22 | 6 |
| 25 | 7 |
| 27 | 5 |
| 28 | 4 |
| 33 | 4 |
| 34 | 7 |
| 35 | 6 |
| 37 | 700 |
| 40 | 15 |
| 41 | 23 |
| 42 | 7 |
| 43 | 643 |
| 44 | 18 |
| 45 | 50 |
| 47 | 35 |
| 48 | 17 |
| 49 | 17 |
| 50 | 31 |
| 51 | 120 |
| 52 | 16 |
| 53 | 30 |
| 55 | 39 |
| 56 | 67 |
| 62 | 44 |
| 63 | 37 |
| 64 | 19 |
| 65 | 19 |
| 66 | 30 |

TABLE 1-continued

| Example No. | Hamster chymase IC 50 [nM] |
|---|---|
| 67 | 4 |
| 75 | 82 |
| 76 | 41 |
| 77 | 170 |
| 78 | 140 |
| 79 | 210 |
| 81 | 65 |
| 82 | |
| 83 | 220 |
| 86 | 140 |
| 89 | 84 |
| 94 | 62 |
| 95 | 100 |
| 96 | 80 |
| 97 | 33 |
| 99 | 64 |
| 101 | 24 |
| 103 | 27 |
| 104 | 2 |
| 105 | 64 |
| 106 | 56 |
| 107 | 29 |
| 108 | 76 |
| 109 | 24 |
| 110 | 150 |
| 111 | 20 |
| 112 | |
| 113 | 6 |
| 114 | 7 |
| 115 | 10 |
| 116 | 20 |
| 117 | 3 |
| 118 | 6 |
| 119 | 280 |
| 120 | 1025 |
| 121 | 3 |
| 122 | 2 |
| 123 | 4 |
| 124 | 7 |
| 125 | 6 |
| 126 | 10 |
| 127 | 34 |
| 128 | 7 |
| 129 | 450 |
| 130 | 350 |
| 131 | 4 |
| 132 | 2 |
| 133 | 465 |
| 134 | 2 |
| 135 | 4 |
| 136 | 2 |
| 137 | 4 |
| 138 | 4 |
| 139 | 2 |
| 140 | 1 |
| 141 | 2 |
| 142 | 1 |
| 143 | 2 |
| 144 | 2 |
| 145 | 2 |
| 146 | 1 |
| 147 | 2 |
| 148 | 4 |
| 149 | 2 |
| 150 | 5 |
| 151 | 2 |
| 152 | 19 |
| 153 | 4 |
| 154 | 4 |
| 155 | 5 |
| 156 | 12 |
| 157 | 6 |
| 158 | 10 |
| 159 | 92 |
| 160 | 32 |
| 161 | 53 |
| 162 | 58 |
| 163 | 28 |
| 164 | 34 |
| 165 | 40 |
| 166 | 62 |
| 167 | 91 |
| 168 | 49 |
| 169 | 370 |
| 170 | 20 |
| 171 | 17 |
| 172 | 27 |
| 173 | 110 |
| 174 | 44 |
| 175 | 8 |
| 176 | 29 |
| 177 | 30 |
| 178 | 16 |
| 179 | 10 |
| 180 | 7 |
| 181 | 4 |
| 182 | 4 |
| 183 | 10 |
| 184 | 170 |
| 185 | 140 |
| 186 | 23 |
| 187 | 4 |
| 188 | 4 |
| 189 | 3 |
| 190 | 140 |
| 191 | 16 |
| 192 | 5 |
| 193 | 8 |
| 194 | 13 |
| 195 | 4 |
| 196 | 6 |
| 197 | 10 |
| 198 | 54 |
| 199 | 8 |
| 200 | 4 |
| 201 | 7 |
| 202 | 4 |
| 203 | 20 |
| 204 | 39 |
| 205 | 3 |
| 206 | 3 |
| 207 | 4 |
| 209 | 13 |
| 211 | 20 |
| 213 | 18 |
| 214 | 20 |
| 215 | 26 |
| 216 | 183 |
| 217 | 1 |
| 218 | 4 |
| 219 | 5 |
| 220 | 6 |
| 221 | 10 |
| 222 | 12 |
| 223 | 3 |
| 224 | 2 |
| 225 | 4 |
| 226 | 3 |
| 227 | 2 |
| 228 | 14 |
| 229 | 4 |
| 230 | 170 |
| 231 | 21 |
| 232 | 6 |
| 233 | 470 |
| 234 | 270 |
| 235 | 9 |
| 236 | 5 |
| 238 | 45 |
| 239 | 490 |
| 240 | 67 |
| 241 | 2 |
| 242 | 40 |
| 243 | 6 |

TABLE 1-continued

| Example No. | Hamster chymase IC 50 [nM] |
|---|---|
| 244 | 2 |
| 245 | 67 |
| 246 | 1 |
| 247 | 1 |
| 248 | 2 |
| 249 | 200 |
| 250 | 37 |
| 251 | 420 |
| 252 | 190 |
| 253 | 1500 |
| 254 | 84 |
| 255 | 500 |
| 256 | 170 |
| 257 | 540 |
| 258 | 190 |
| 259 | 430 |
| 260 | 130 |
| 261 | 110 |
| 262 | 2100 |
| 263 | 38 |
| 264 | 31 |
| 265 | 2 |
| 266 | 59 |
| 267 | 16 |
| 268 | 18 |

TABLE 2

| Example No. | Hamster chymase IC 50 [nM] |
|---|---|
| 269 | 14 |
| 270 | 6 |
| 271 | 23 |
| 272 | 11 |
| 273 | 1100 |
| 274 | 2 |
| 275 | 2300 |
| 276 | 4 |
| 277 | 2 |
| 278 | 5 |
| 279 | 4 |
| 280 | 250 |
| 281 | 1 |
| 282 | 88 |
| 283 | 40 |
| 284 | 11 |
| 285 | 42 |
| 286 | 37 |
| 287 | 4500 |
| 288 | 14 |
| 289 | 970 |
| 290 | 8 |
| 291 | 4 |
| 292 | |
| 293 | 12 |
| 294 | 2 |
| 295 | 8 |
| 296 | 3 |
| 297 | |
| 298 | 6 |
| 299 | 120 |
| 300 | 2 |
| 301 | 33 |
| 302 | 19 |
| 303 | 9 |

B-2. Measurement of Contraction on Isolated Aorta Rings from Hamsters

Male Syrian hamsters (120-150 g) were euthanized with carbon dioxide. The aorta was prepared and placed into ice-cold Krebs-Henseleit buffer. (Composition in mmol/l: sodium chloride 112, potassium chloride 5.9, calcium chloride 2.0, magnesium chloride 1.2, sodium dihydrogenphosphate 1.2, sodium hydrogencarbonate 25, glucose 11.5). The aorta was cut into rings of length 2 mm, transferred to an organ bath filled with 5 ml of Krebs-Henseleit buffer and connected to a myograph (DMT, Denmark). The buffer was warmed to 37° C. and sparged with 95% oxygen, 5% carbon dioxide. In order to measure the isometric muscle contraction, the aorta rings were mounted between two hooks. One of the hooks was connected to a pressure transducer. The second hook was movable and allowed precise setting of the initial load by a protocol described by Mulvany and Halpern (Circulation Research 1977; 41:19-26).

Before each experiment, the responsiveness of the preparation was tested by adding potassium-containing Krebs-Henseleit solution (50 mmol/1 KCl). A synthetic peptide, angiotensin 1-18, was used to induce contraction of the aorta rings. The angiotensin 1-18 is converted to angiotensin II independently of ACE. Subsequently, the aorta rings were incubated with the test substance for 20 min and the contraction measurement was repeated. Chymase inhibition is shown as a reduction in the contraction induced by angiotensin 1-18.

B-3. Isoprenaline-Induced Cardiac Fibrosis Model in Hamsters

For the experiments, male Syrian hamsters having a body weight of 130-160 g were used. Cardiac hypertrophy and cardiac fibrosis were induced by a daily subcutaneous injection of 20 mg/kg isoprenaline over 7 days. The test substance was administered orally to the animals 2 hours before the injection of the isoprenaline. Control groups were treated subcutaneously and orally with solvents in a corresponding manner. At the end of the experiment, the hearts were removed, weighed and fixed. The fibrotic tissue on the histological sections from the hearts was marked with the aid of Sirius Red staining. Subsequently, the fibrotic area was determined by planimetry.

C. WORKING EXAMPLES OF PHARMACEUTICAL COMPOSITIONS

The inventive compounds can be converted to pharmaceutical formulations as follows:

Tablet:

Composition:

100 mg of the inventive compound, 50 mg of lactose (monohydrate), 50 mg of corn starch (native), 10 mg of polyvinylpyrrolidone (PVP 25) (BASF, Ludwigshafen, Germany) and 2 mg of magnesium stearate. Tablet weight 212 mg, diameter 8 mm, radius of curvature 12 mm.

Production:

The mixture of inventive compound, lactose and starch is granulated with a 5% solution (m/m) of the PVP in water. After drying, the granules are mixed with the magnesium stearate for 5 minutes. This mixture is pressed with a conventional tableting press (for tablet format see above). The guide value used for the pressing is a pressing force of 15 kN.

Suspension for Oral Administration:

Composition:

1000 mg of the inventive compound, 1000 mg of ethanol (96%), 400 mg of Rhodigel® (xanthan gum from FMC, Pennsylvania, USA) and 99 g of water.

A single dose of 100 mg of the inventive compound corresponds to 10 ml of oral suspension.

Production:

The Rhodigel is suspended in ethanol; the inventive compound is added to the suspension. The water is added while stirring. The mixture is stirred for approx. 6 h until swelling of the Rhodigel has ended.

Solution for Oral Administration:

Composition:

500 mg of the inventive compound, 2.5 g of polysorbate and 97 g of polyethylene glycol 400. A single dose of 100 mg of the inventive compound corresponds to 20 g of oral solution.

Production:

The inventive compound is suspended in the mixture of polyethylene glycol and polysorbate while stirring. The stirring operation is continued until dissolution of the inventive compound is complete.

i.v. Solution:

The inventive compound is dissolved in a concentration below the saturation solubility in a physiologically acceptable solvent (e.g. isotonic sodium chloride solution, glucose solution 5% and/or PEG 400 solution 30%). The solution is subjected to sterile filtration and dispensed into sterile and pyrogen-free injection vessels.

The invention claimed is:

1. A method for treatment of a renal disorder, comprising administering an effective amount of a compound of the formula (I)

or a salt, solvate, or a solvate of the salt thereof,
wherein
$R^1$ is hydrogen or $(C_1-C_4)$-alkyl,
$R^2$ is a group of the formula wherein
* is the attachment site to the uracil nitrogen atom,
A is —$CH_2$—, —$CH_2$—$CH_2$—, —O—$CH_2$-## or oxygen,
wherein
## is the attachment site to the phenyl ring,
m is a number 0, 1 or 2,
$R^4$ is halogen, difluoromethyl, trifluoromethyl, $(C_1-C_4)$-alkyl, difluoromethoxy, trifluoromethoxy or $(C_1-C_4)$-alkoxy,
$R^{5A}$ is hydrogen or deuterium,
$R^{5B}$ is hydrogen, deuterium or $(C_1-C_4)$-alkyl,
$R^6$ is hydrogen or fluorine,
$R^7$ is hydrogen or fluorine,
$R^8$ is halogen, difluoromethyl, trifluoromethyl, $(C_1-C_4)$-alkyl or nitro,
$R^9$ is hydrogen, halogen, difluoromethyl, trifluoromethyl, $(C_1-C_4)$-alkyl, nitro or $(C_1-C_4)$-alkylthio,
$R^3$ is a group of the formula wherein
# is the attachment site to the uracil nitrogen atom,
the ring Q is 5- to 7-membered heterocyclyl or 5- or 6-membered heteroaryl,
wherein 5- to 7-membered heterocyclyl and 5- or 6-membered heteroaryl may be substituted by 1 to 4 substituents independently selected from the group consisting of halogen, difluoromethyl, trifluoromethyl, trideuteromethyl, $(C_1-C_6)$-alkyl, $(C_3-C_7)$-cycloalkyl, oxo, hydroxyl, $(C_1-C_4)$-alkylcarbonyl, $(C_1-C_4)$-alkoxycarbonyl, aminocarbonyl and $(C_1-C_4)$-alkylsulphonyl,
wherein $(C_1-C_6)$-alkyl and $(C_3-C_7)$-cycloalkyl may in turn be substituted by 1 to 3 substituents independently selected from the group consisting of halogen, cyano, trifluoromethyl, $(C_3-C_7)$-cycloalkyl, hydroxyl, $(C_1-C_4)$-alkoxy and 4- to 7-membered heterocyclyl,
and
wherein two $(C_1-C_6)$-alkyl radicals bonded to a carbon atom of 5- to 7-membered heterocyclyl and 5- or 6-membered heteroaryl, together with the carbon atom to which they are bonded, may form a 3- to 6-membered carbocycle,
$R^{24}$ is halogen, $(C_1-C_4)$-alkyl or $(C_1-C_4)$-alkoxy,
n is a number 0, 1, 2 or 3.

2. The method according to claim 1, wherein
$R^1$ is hydrogen, methyl or ethyl,
$R^2$ is a group of the formula wherein
* is the attachment site to the uracil nitrogen atom,
A is —$CH_2$—, —$CH_2$—$CH_2$—, —O—$CH_2$-## or oxygen,
wherein
## is the attachment site to the phenyl ring,
$R^{4A}$ is hydrogen, fluorine, chlorine, trifluoromethyl or methyl, $R^{4B}$ is hydrogen, fluorine, chlorine, trifluoromethyl or methyl, with the proviso that at least one of the $R^{4A}$ and $R^{4B}$ radicals is not hydrogen, $R^{5A}$ is hydrogen, $R^{5B}$ is hydrogen, $R^6$ is hydrogen, $R^7$ is hydrogen, $R^8$ is fluorine, chlorine, difluoromethyl, trifluoromethyl or methyl, $R^9$ is fluorine, chlorine, difluoromethyl, trifluoromethyl or methyl, $R^3$ is a group of the formula

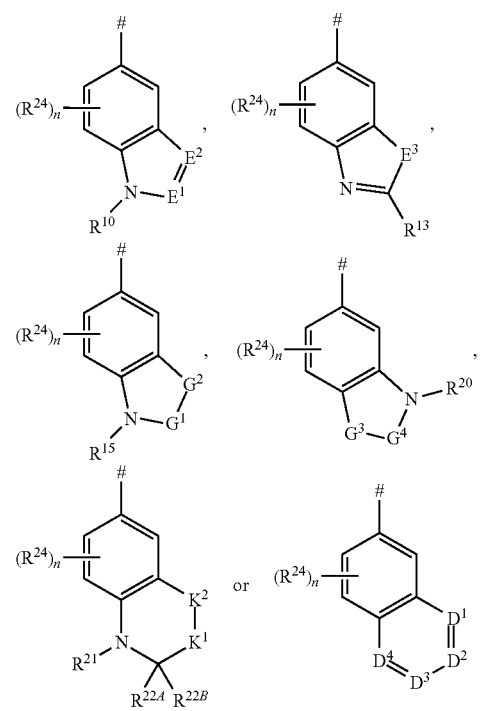

wherein # is the attachment site to the uracil nitrogen atom, $E^1$ is $CR^{11}$ or N,
  wherein
  $R^{11}$ is hydrogen, $(C_1-C_4)$-alkyl, $(C_3-C_7)$-cycloalkyl or aminocarbonyl, $E^2$ is $CR^{12}$ or N,
  wherein
  $R^{12}$ is hydrogen, $(C_1-C_4)$-alkyl or $(C_3-C_7)$-cycloalkyl, $E^3$ is $NR^{14}$ or S,
  wherein
  $R^{14}$ is hydrogen, $(C_1-C_4)$-alkyl or $(C_3-C_7)$-cycloalkyl, $G^1$ is C=O or $SO_2$, $G^2$ is $CR^{16A}R^{16B}$, $NR^{17}$, O or S,
  wherein
  $R^{16A}$ is hydrogen, fluorine, $(C_1-C_4)$-alkyl or hydroxyl,
  $R^{16B}$ is hydrogen, fluorine, chlorine, $(C_1-C_4)$-alkyl or trifluoromethyl,
  or
  $R^{16A}$ and $R^{16B}$ together with the carbon atom to which they are bonded form a 3- to 6-membered carbocycle, $R^{17}$ is hydrogen, $(C_1-C_6)$-alkyl, $(C_3-C_7)$-cycloalkyl or $(C_1-C_4)$-alkoxycarbonyl,
  wherein $(C_1-C_6)$-alkyl may be substituted by 1 to 3 substituents independently selected from the group consisting of fluorine, trifluoromethyl, cyano, $(C_3-C_7)$-cycloalkyl, hydroxyl, trifluoromethoxy, $(C_1-C_4)$-alkoxy, azetidinyl, oxetanyl, tetrahydrofuranyl and pyrrolidinyl, $G^3$ is $CR^{18A}R^{18B}$, $NR^{19}$, O or S,
  wherein
  $R^{18A}$ is hydrogen, fluorine, $(C_1-C_4)$-alkyl or hydroxyl,
  $R^{18B}$ is hydrogen, fluorine, chlorine, $(C_1-C_4)$-alkyl or trifluoromethyl, or
  $R^{18A}$ and $R^{18B}$ together with the carbon atom to which they are bonded form a 3- to 6-membered carbocycle, $R^{19}$ is hydrogen, $(C_1-C_6)$-alkyl, $(C_3-C_7)$-cycloalkyl or $(C_1-C_4)$-alkoxycarbonyl,
  wherein $(C_1-C_6)$-alkyl may be substituted by 1 to 3 substituents independently selected from the group consisting of fluorine, trifluoromethyl, cyano, $(C_3-C_7)$-cycloalkyl, hydroxyl, trifluoromethoxy, $(C_1-C_4)$-alkoxy, azetidinyl, oxetanyl, tetrahydrofuranyl and pyrrolidinyl, $G^4$ is $CH_2$, C=O or $SO_2$, $K^1$ is $CH_2$ or O, $K^2$ is $CH_2$ or O, with the proviso that only one of the $K^1$ and $K^2$ groups is O, $D^1$, $D^2$, $D^3$ and $D^4$ are each independently $CR^{23}$ or N,
  wherein
  $R^{23}$ is hydrogen, halogen, $(C_1-C_6)$-alkyl or $(C_3-C_7)$-cycloalkyl, with the proviso that not more than 2 of the $D^1$, $D^2$, $D^3$ and $D^4$ groups are N, $R^{24}$ is fluorine or methyl, n is a number 0 or 1, $R^{10}$ is $(C_1-C_4)$-alkyl or $(C_3-C_7)$-cycloalkyl,
  wherein $(C_1-C_4)$-alkyl may be substituted by 1 or 2 substituents independently selected from the group consisting of fluorine, trifluoromethyl, cyclopropyl, cyclobutyl, hydroxyl, methoxy, ethoxy, azetidinyl, oxetanyl, tetrahydrofuranyl and pyrrolidinyl, $R^{13}$ is hydrogen, $(C_1-C_4)$-alkyl or $(C_3-C_7)$-cycloalkyl, $R^{15}$ is hydrogen, $(C_1-C_6)$-alkyl or $(C_3-C_7)$-cycloalkyl,
  wherein $(C_1-C_6)$-alkyl may be substituted by 1 or 2 substituents independently selected from the group consisting of fluorine, trifluoromethyl, cyclopropyl, cyclobutyl, hydroxyl, methoxy, ethoxy, azetidinyl, oxetanyl, tetrahydrofuranyl and pyrrolidinyl, $R^{20}$ is hydrogen, $(C_1-C_6)$-alkyl, $(C_3-C_7)$-cycloalkyl or $(C_1-C_4)$-alkylcarbonyl,
  wherein $(C_1-C_6)$-alkyl may be substituted by 1 or 2 substituents independently selected from the group consisting of fluorine, trifluoromethyl, cyclopropyl, cyclobutyl, hydroxyl, methoxy, ethoxy, azetidinyl, oxetanyl, tetrahydrofuranyl and pyrrolidinyl, $R^{21}$ is hydrogen, $(C_1-C_6)$-alkyl, $(C_3-C_7)$-cycloalkyl or $(C_1-C_4)$-alkylsulphonyl, $R^{22A}$ is hydrogen or $(C_1-C_4)$-alkyl, $R^{22B}$ is hydrogen or $(C_1-C_4)$-alkyl, or $R^{22A}$ and $R^{22B}$ together with the carbon atom to which they are bonded form a carbonyl group.

3. The method according to claim 1, wherein
R$^1$ is hydrogen,
R$^2$ is a group of the formula

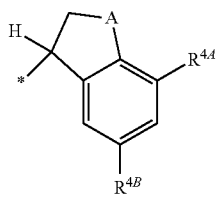

wherein
* is the attachment site to the uracil nitrogen atom,
A is —CH$_2$—,
R$^{4A}$ is chlorine or trifluoromethyl,
R$^{4B}$ is hydrogen,
R$^3$ is a group of the formula

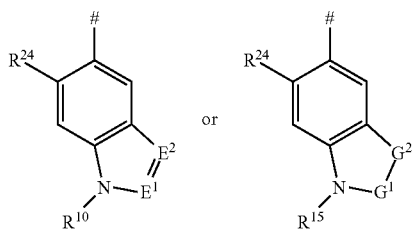

where
# is the attachment site to the uracil nitrogen atom,
E$^1$ is CR$^{11}$
  wherein
  R$^{11}$ is hydrogen,
E$^2$ is N,
G$^1$ is C=O,
G$^2$ is CR$^{16A}$R$^{16B}$, NR$^{17}$, O or S,
  wherein
  R$^{16A}$ is hydrogen, fluorine, methyl or hydroxyl,
  R$^{16B}$ is hydrogen, fluorine, methyl or trifluoromethyl,
  or
  R$^{16A}$ and R$^{16B}$ together with the carbon atom to which they are bonded form a cyclopropyl ring,
  R$^{17}$ is hydrogen, (C$_1$-C$_4$)-alkyl or (C$_3$-C$_5$)-cycloalkyl,
    wherein (C$_1$-C$_4$)-alkyl may be substituted by 1 to 3 substituents independently selected from the group consisting of fluorine, trifluoromethyl, cyano, cyclopropyl, cyclobutyl, hydroxyl, trifluoromethoxy, methoxy, ethoxy, azetidinyl, oxetanyl, tetrahydrofuranyl and pyrrolidinyl,
R$^{24}$ is hydrogen or fluorine,
R$^{10}$ is (C$_1$-C$_4$)-alkyl,
R$^{15}$ is hydrogen, methyl or ethyl,
  wherein methyl and ethyl may be substituted by 1 substituent selected from the group consisting of fluorine, trifluoromethyl and cyclopropyl.

4. The method according to claim 1, wherein
R$^1$ is hydrogen,
R$^2$ is a group of the formula

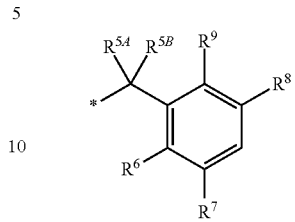

wherein
* is the attachment site to the uracil nitrogen atom,
R$^{5A}$ is hydrogen,
R$^{5B}$ is hydrogen,
R$^6$ is hydrogen,
R$^7$ is hydrogen,
R$^8$ is fluorine, chlorine or trifluoromethyl,
R$^9$ is fluorine, chlorine, trifluoromethyl or methyl,
R$^3$ is a group of the formula

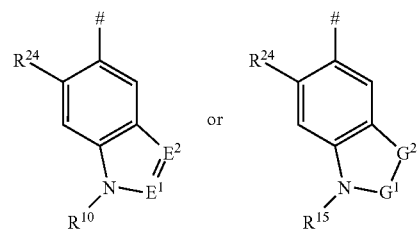

wherein
# is the attachment site to the uracil nitrogen atom,
E$^1$ is CR$^{11}$
  wherein
  R$^{11}$ is hydrogen,
E$^2$ is N,
G$^1$ is C=O,
G$^2$ is CR$^{16A}$R$^{16B}$, NR$^{17}$, O or S,
  wherein
  R$^{16A}$ is hydrogen, fluorine, methyl or hydroxyl,
  R$^{16B}$ is hydrogen, fluorine, methyl or trifluoromethyl,
  or
  R$^{16A}$ and R$^{16B}$ together with the carbon atom to which they are bonded form a cyclopropyl ring,
  R$^{17}$ is hydrogen, (C$_1$-C$_4$)-alkyl or (C$_3$-C$_5$)-cycloalkyl,
    wherein (C$_1$-C$_4$)-alkyl may be substituted by 1 to 3 substituents independently selected from the group consisting of fluorine, trifluoromethyl, cyano, cyclopropyl, cyclobutyl, hydroxyl, trifluoromethoxy, methoxy, ethoxy, azetidinyl, oxetanyl, tetrahydrofuranyl and pyrrolidinyl,
R$^{24}$ is hydrogen or fluorine,
R$^{10}$ is (C$_1$-C$_4$)-alkyl,
R$^{15}$ is hydrogen, methyl or ethyl,
  wherein methyl and ethyl may be substituted by 1 substituent selected from the group consisting of fluorine, trifluoromethyl and cyclopropyl.

5. The method according to claim 1, wherein the compound is 1-(1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

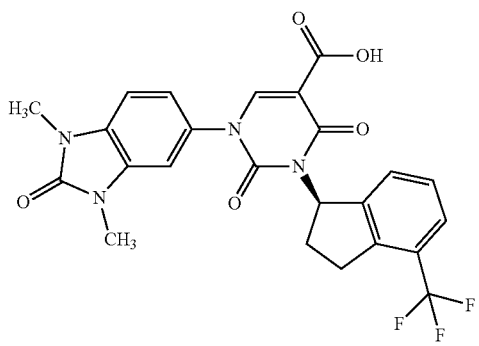 [SMILES: Cn1c(=O)n(C)c2cc(-n3cc(C(=O)O)c(=O)n([C@@H]4CCc5c4cccc5C(F)(F)F)c3=O)ccc21]

or a salt, solvate, or a solvate of the salt thereof.

6. The method according to claim 1, wherein the compound is 1-(6-fluoro-1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

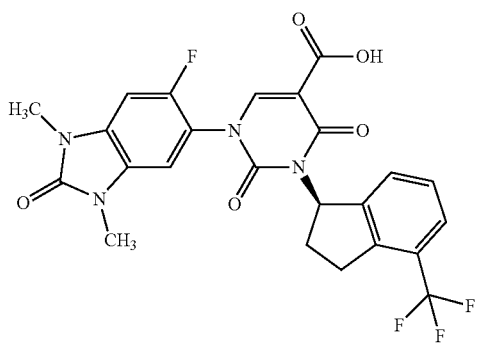 [SMILES: Cn1c(=O)n(C)c2cc(-n3cc(C(=O)O)c(=O)n([C@@H]4CCc5c4cccc5C(F)(F)F)c3=O)c(F)cc21]

or a salt, solvate, or a solvate of the salt thereof.

7. The method according to claim 1, wherein the compound is 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

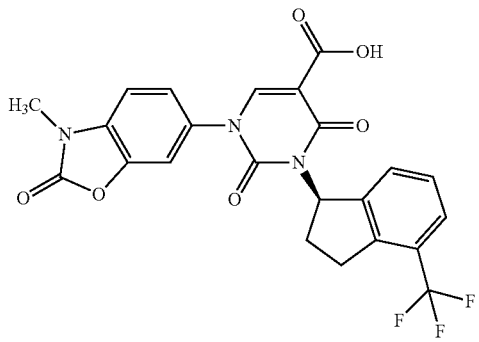 [SMILES: Cn1c(=O)oc2cc(-n3cc(C(=O)O)c(=O)n([C@@H]4CCc5c4cccc5C(F)(F)F)c3=O)ccc21]

or a salt, solvate, or a solvate of the salt thereof.

8. The method according to claim 1, wherein the compound is 2,4-dioxo-3-[(1R)-4-(trifluoromethyl)-2,3-dihydro-1H-inden-1-yl]-1-(1,3,3-trimethyl-2-oxo-2,3-dihydro-1H-indol-5-yl)-1,2,3,4-tetrahydropyrimidine-5-carboxylic acid (R enantiomer) of the formula

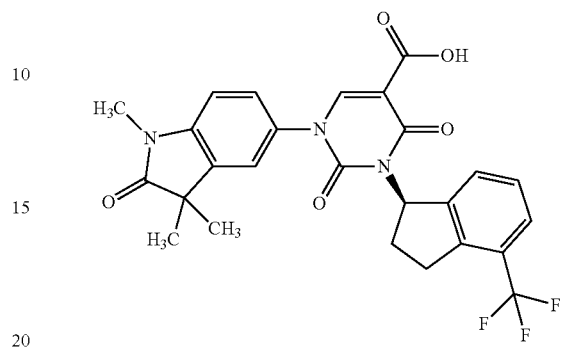

or a salt, solvate, or a solvate of the salt thereof.

9. The method according to claim 1, wherein the compound is 1-(1'-methyl-2'-oxo-1',2'-dihydrospiro[cyclopropane-1,3'-indole]-5'-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

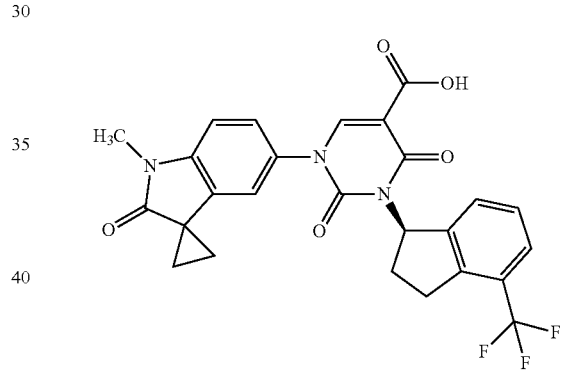

or a salt, solvate, or a solvate of the salt thereof.

10. The method according to claim 1, wherein the compound is 1-(3-methyl-2-oxo-2,3-dihydro-1,3-benzothiazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

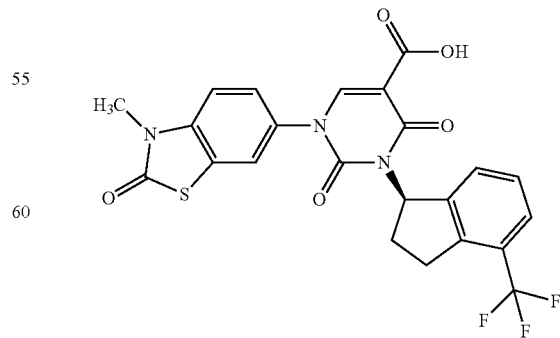

or a salt, solvate, or a solvate of the salt thereof.

11. The method according to claim 1, wherein the compound is ethyl 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer) of the formula

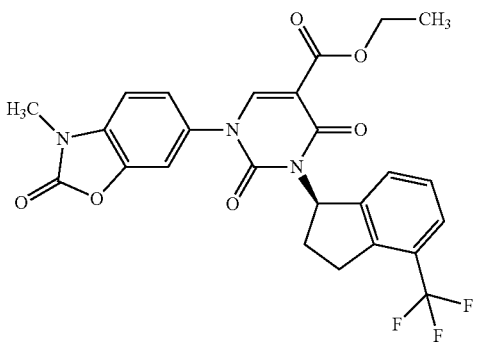 [SMILES: CCOC(=O)c1cn(-c2ccc3c(c2)oc(=O)n3C)c(=O)n([C@@H]2CCc3c2cccc3C(F)(F)F)c1=O]

or a salt, solvate, or a solvate of the salt thereof.

12. The method according to claim 1, wherein the compound is 1-(1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

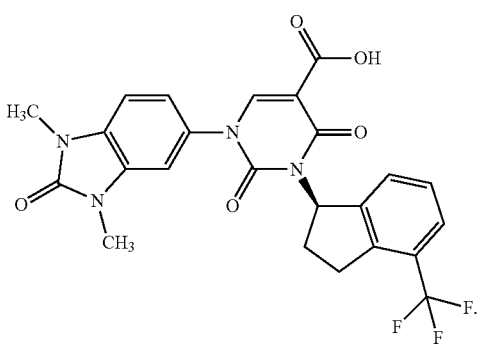 [SMILES: Cn1c(=O)n(C)c2cc(-n3cc(C(=O)O)c(=O)n([C@@H]4CCc5c4cccc5C(F)(F)F)c3=O)ccc21]

13. The method according to claim 1, wherein the compound is 1-(6-fluoro-1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

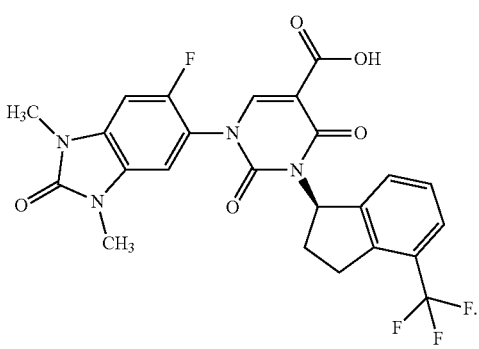 [SMILES: Cn1c(=O)n(C)c2cc(-n3cc(C(=O)O)c(=O)n([C@@H]4CCc5c4cccc5C(F)(F)F)c3=O)c(F)cc21]

14. The method according to claim 1, wherein the compound is 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

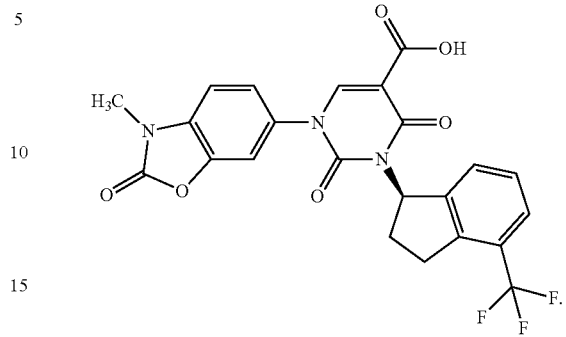

15. The method according to claim 1, wherein the compound is 2,4-dioxo-3-[(1R)-4-(trifluoromethyl)-2,3-dihydro-1H-inden-1-yl]-1-(1,3,3-trimethyl-2-oxo-2,3-dihydro-1H-indol-5-yl)-1,2,3,4-tetrahydropyrimidine-5-carboxylic acid (R enantiomer) of the formula

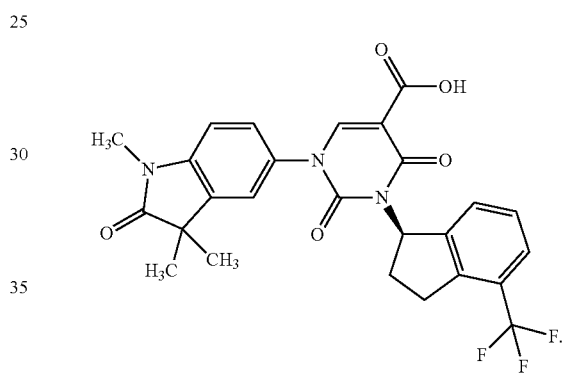

16. The method according to claim 1, wherein the compound is 1-(1'-methyl-2'-oxo-1',2'-dihydrospiro[cyclopropane-1,3'-indole]-5'-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

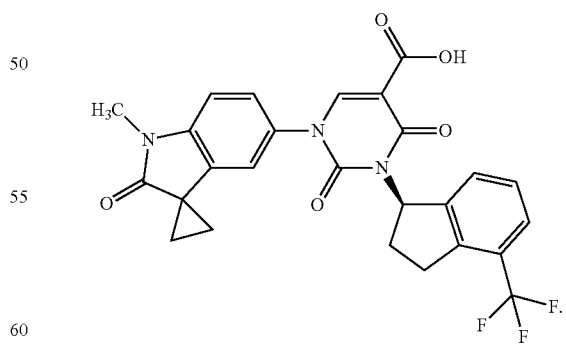

17. The method according to claim 1, wherein the compound is 1-(3-methyl-2-oxo-2,3-dihydro-1,3-benzothiazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

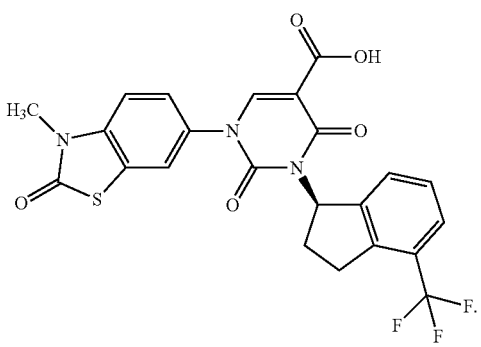 [SMILES: Cn1c(=O)sc2cc(-n3cc(C(=O)O)c(=O)n([C@@H]4CCc5c4cccc5C(F)(F)F)c3=O)ccc21]

18. The method according to claim 1, wherein the compound is ethyl 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer) of the formula

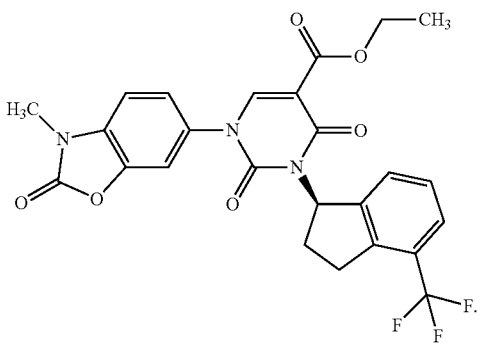 [SMILES: CCOC(=O)c1cn(-c2ccc3c(c2)oc(=O)n3C)c(=O)n([C@@H]2CCc3c2cccc3C(F)(F)F)c1=O]

19. The method according to claim 1, wherein the renal disorder is selected from the group consisting of acute renal insufficiency, chronic renal insufficiency, acute kidney failure and chronic kidney failure.

20. The method according to claim 1, wherein the renal disorder is selected from the group consisting of chronic renal insufficiency, kidney failure, renal hypoperfusion, non-diabetic nephropathy, glomerulonephritis, haemolytic-uraemic syndrome (HUS), fibrotic disorders of kidney, polycystic kidney disease (PCKD) and syndrome of inappropriate ADH secretion (SIADH).

21. The method according to claim 1, wherein the renal disorder is chronic renal insufficiency.

22. A method for treatment of a renal disorder comprising administering an effective amount of a pharmaceutical composition, wherein the pharmaceutical composition comprises the compound of the formula (I),

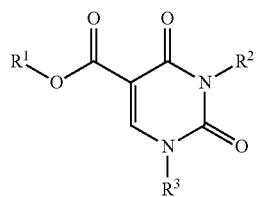

(I)

or a salt, solvate, or a solvate of the salt thereof, wherein
$R^1$ is hydrogen or $(C_1$-$C_4)$-alkyl,
$R^2$ is a group of the formula

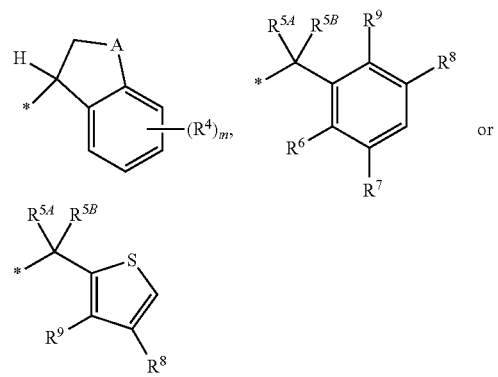

wherein
* is the attachment site to the uracil nitrogen atom,
A is —$CH_2$—, —$CH_2$—$CH_2$—, —O—$CH_2$-## or oxygen,
wherein
## is the attachment site to the phenyl ring,
m is a number 0, 1 or 2,
$R^4$ is halogen, difluoromethyl, trifluoromethyl, $(C_1$-$C_4)$-alkyl, difluoromethoxy, trifluoromethoxy or $(C_1$-$C_4)$-alkoxy,
$R^{5A}$ is hydrogen or deuterium,
$R^{5B}$ is hydrogen, deuterium or $(C_1$-$C_4)$-alkyl,
$R^6$ is hydrogen or fluorine,
$R^7$ is hydrogen or fluorine,
$R^8$ is halogen, difluoromethyl, trifluoromethyl, $(C_1$-$C_4)$-alkyl or nitro,
$R^9$ is hydrogen, halogen, difluoromethyl, trifluoromethyl, $(C_1$-$C_4)$-alkyl, nitro or $(C_1$-$C_4)$-alkylthio,
$R^3$ is a group of the formula

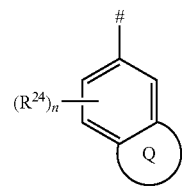

wherein
# is the attachment site to the uracil nitrogen atom,
the ring Q is 5- to 7-membered heterocyclyl or 5- or 6-membered heteroaryl,
wherein 5- to 7-membered heterocyclyl and 5- or 6-membered heteroaryl may be substituted by 1 to 4 substituents independently selected from the group consisting of halogen, difluoromethyl, trifluoromethyl, trideuteromethyl, $(C_1$-$C_6)$-alkyl, $(C_3$-$C_7)$-cycloalkyl, oxo, hydroxyl, $(C_1$-$C_4)$-alkylcarbonyl, $(C_1$-$C_4)$-alkoxycarbonyl, aminocarbonyl and $(C_1$-$C_4)$-alkylsulphonyl,
wherein $(C_1$-$C_6)$-alkyl and $(C_3$-$C_7)$-cycloalkyl may in turn be substituted by 1 to 3 substituents independently selected from the group consisting of halogen, cyano, trifluoromethyl, $(C_3$-$C_7)$- cycloalkyl, hydroxyl, $(C_1-C_4)$-alkoxy and 4- to 7-membered heterocyclyl,
and
wherein two $(C_1-C_6)$-alkyl radicals bonded to a carbon atom of 5- to 7-membered heterocyclyl and 5- or 6-membered heteroaryl, together with the carbon atom to which they are bonded, may form a 3- to 6-membered carbocycle, $R^{24}$ is halogen, $(C_1-C_4)$-alkyl or $(C_1-C_4)$-alkoxy,
n is a number 0, 1, 2 or 3,
in combination with one or more further active ingredients selected from the group consisting of calcium antagonists, angiotensin AII antagonists, ACE inhibitors, vasopeptidase inhibitors, endothelin antagonists, renin inhibitors, alpha-receptor blockers, beta-receptor blockers, mineralocorticoid receptor antagonists, rho-kinase inhibitors, diuretics, kinase inhibitors, matrix metalloprotease inhibitors, stimulators and activators of soluble guanylate cyclase and phosphodiesterase inhibitors.

23. The method according to claim 22, wherein
$R^1$ is hydrogen, methyl or ethyl,
$R^2$ is a group of the formula

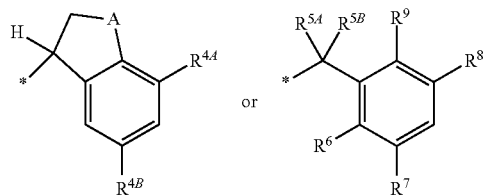

wherein
* is the attachment site to the uracil nitrogen atom,
A is —CH$_2$—, —CH$_2$—CH$_2$—, —O—CH$_2$-## or oxygen,
wherein
## is the attachment site to the phenyl ring,
$R^{4A}$ is hydrogen, fluorine, chlorine, trifluoromethyl or methyl,
$R^{4B}$ is hydrogen, fluorine, chlorine, trifluoromethyl or methyl,
with the proviso that at least one of the $R^{4A}$ and $R^{4B}$ radicals is not hydrogen,
$R^{5A}$ is hydrogen,
$R^{5B}$ is hydrogen,
$R^6$ is hydrogen,
$R^7$ is hydrogen,
$R^8$ is fluorine, chlorine, difluoromethyl, trifluoromethyl or methyl,
$R^9$ is fluorine, chlorine, difluoromethyl, trifluoromethyl or methyl,
$R^3$ is a group of the formula

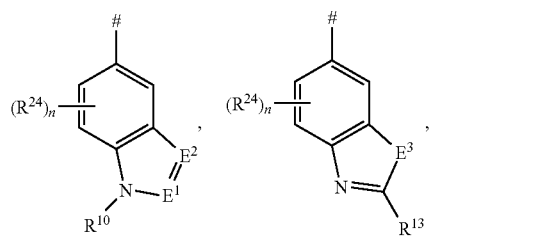

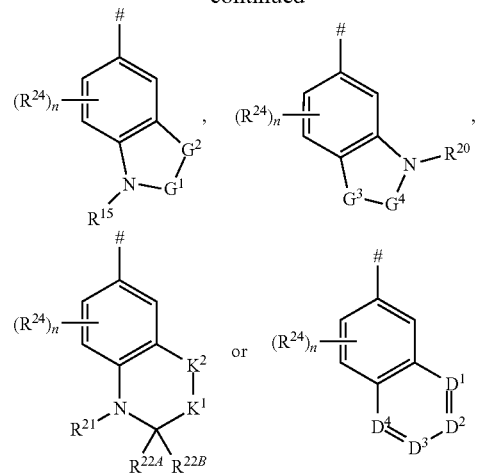

wherein
# is the attachment site to the uracil nitrogen atom,
$E^1$ is $CR^{11}$ or N,
wherein
$R^{11}$ is hydrogen, $(C_1-C_4)$-alkyl, $(C_3-C_7)$-cycloalkyl or aminocarbonyl,
$E^2$ is $CR^{12}$ or N,
wherein
$R^{12}$ is hydrogen, $(C_1-C_4)$-alkyl or $(C_3-C_7)$-cycloalkyl,
$E^3$ is $NR^{14}$ or S,
wherein
$R^{14}$ is hydrogen, $(C_1-C_4)$-alkyl or $(C_3-C_7)$-cycloalkyl,
$G^1$ is C=O or SO$_2$,
$G^2$ is $CR^{16A}R^{16B}$, $NR^{17}$, O or S,
wherein
$R^{16A}$ is hydrogen, fluorine, $(C_1-C_4)$-alkyl or hydroxyl,
$R^{16B}$ is hydrogen, fluorine, chlorine, $(C_1-C_4)$-alkyl or trifluoromethyl,
or
$R^{16A}$ and $R^{16B}$ together with the carbon atom to which they are bonded form a 3- to 6-membered carbocycle,
$R^{17}$ is hydrogen, $(C_1-C_6)$-alkyl, $(C_3-C_7)$-cycloalkyl or $(C_1-C_4)$-alkoxycarbonyl,
wherein $(C_1-C_6)$-alkyl may be substituted by 1 to 3 substituents independently selected from the group consisting of fluorine, trifluoromethyl, cyano, $(C_3-C_7)$-cycloalkyl, hydroxyl, trifluoromethoxy, $(C_1-C_4)$-alkoxy, azetidinyl, oxetanyl, tetrahydrofuranyl and pyrrolidinyl,
$G^3$ is $CR^{18A}R^{18B}$, $NR^{19}$, O or S,
wherein
$R^{18A}$ is hydrogen, fluorine, $(C_1-C_4)$-alkyl or hydroxyl,
$R^{18B}$ is hydrogen, fluorine, chlorine, $(C_1-C_4)$-alkyl or trifluoromethyl,
or
$R^{18A}$ and $R^{18B}$ together with the carbon atom to which they are bonded form a 3- to 6-membered carbocycle,
$R^{19}$ is hydrogen, $(C_1-C_6)$-alkyl, $(C_3-C_7)$-cycloalkyl or $(C_1-C_4)$-alkoxycarbonyl, wherein (C$_1$-C$_6$)-alkyl may be substituted by 1 to 3 substituents independently selected from the group consisting of fluorine, trifluoromethyl, cyano, (C$_3$-C$_7$)-cycloalkyl, hydroxyl, trifluoromethoxy, (C$_1$-C$_4$)-alkoxy, azetidinyl, oxetanyl, tetrahydrofuranyl and pyrrolidinyl, G$^4$ is CH$_2$, C=O or SO$_2$, K$^1$ is CH$_2$ or O, K$^2$ is CH$_2$ or O, with the proviso that only one of the K$^1$ and K$^2$ groups is O, D$^1$, D$^2$, D$^3$ and D$^4$ are each independently CR$^{23}$ or N, wherein R$^{23}$ is hydrogen, halogen, (C$_1$-C$_6$)-alkyl or (C$_3$-C$_7$)-cycloalkyl, with the proviso that not more than 2 of the D$^1$, D$^2$, D$^3$ and D$^4$ groups are N, R$^{24}$ is fluorine or methyl, n is a number 0 or 1, R$^{10}$ is (C$_1$-C$_4$)-alkyl or (C$_3$-C$_7$)-cycloalkyl,
    wherein (C$_1$-C$_4$)-alkyl may be substituted by 1 or 2 substituents independently selected from the group consisting of fluorine, trifluoromethyl, cyclopropyl, cyclobutyl, hydroxyl, methoxy, ethoxy, azetidinyl, oxetanyl, tetrahydrofuranyl and pyrrolidinyl, R$^{13}$ is hydrogen, (C$_1$-C$_4$)-alkyl or (C$_3$-C$_7$)-cycloalkyl, R$^{15}$ is hydrogen, (C$_1$-C$_6$)-alkyl or (C$_3$-C$_7$)-cycloalkyl,
    wherein (C$_1$-C$_6$)-alkyl may be substituted by 1 or 2 substituents independently selected from the group consisting of fluorine, trifluoromethyl, cyclopropyl, cyclobutyl, hydroxyl, methoxy, ethoxy, azetidinyl, oxetanyl, tetrahydrofuranyl and pyrrolidinyl, R$^{20}$ is hydrogen, (C$_1$-C$_6$)-alkyl, (C$_3$-C$_7$)-cycloalkyl or (C$_1$-C$_4$)-alkylcarbonyl,
    wherein (C$_1$-C$_6$)-alkyl may be substituted by 1 or 2 substituents independently selected from the group consisting of fluorine, trifluoromethyl, cyclopropyl, cyclobutyl, hydroxyl, methoxy, ethoxy, azetidinyl, oxetanyl, tetrahydrofuranyl and pyrrolidinyl, R$^{21}$ is hydrogen, (C$_1$-C$_6$)-alkyl, (C$_3$-C$_7$)-cycloalkyl or (C$_1$-C$_4$)-alkylsulphonyl, R$^{22A}$ is hydrogen or (C$_1$-C$_4$)-alkyl, R$^{22B}$ is hydrogen or (C$_1$-C$_4$)-alkyl, or R$^{22A}$ and R$^{22B}$ together with the carbon atom to which they are bonded form a carbonyl group.

24. The method according to claim 22, wherein

R$^1$ is hydrogen,

R$^2$ is a group of the formula

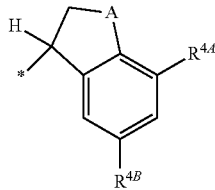

wherein

* is the attachment site to the uracil nitrogen atom,

A is —CH$_2$—,

R$^{4A}$ is chlorine or trifluoromethyl,

R$^{4B}$ is hydrogen,

R$^3$ is a group of the formula

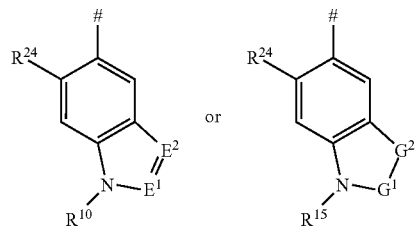

wherein # is the attachment site to the uracil nitrogen atom,

E$^1$ is CR$^{11}$
    wherein
    R$^{11}$ is hydrogen,

E$^2$ is N,

G$^1$ is C=O,

G$^2$ is CR$^{16A}$R$^{16B}$, NR$^{17}$, O or S,
    wherein
    R$^{16A}$ is hydrogen, fluorine, methyl or hydroxyl,
    R$^{16B}$ is hydrogen, fluorine, methyl or trifluoromethyl,
    or
    R$^{16A}$ and R$^{16B}$ together with the carbon atom to which they are bonded form a cyclopropyl ring,
    R$^{17}$ is hydrogen, (C$_1$-C$_4$)-alkyl or (C$_3$-C$_5$)-cycloalkyl,
        wherein (C$_1$-C$_4$)-alkyl may be substituted by 1 to 3 substituents independently selected from the group consisting of fluorine, trifluoromethyl, cyano, cyclopropyl, cyclobutyl, hydroxyl, trifluoromethoxy, methoxy, ethoxy, azetidinyl, oxetanyl, tetrahydrofuranyl and pyrrolidinyl, R$^{24}$ is hydrogen or fluorine, R$^{10}$ is (C$_1$-C$_4$)-alkyl, R$^{15}$ is hydrogen, methyl or ethyl,
    wherein methyl and ethyl may be substituted by 1 substituent selected from the group consisting of fluorine, trifluoromethyl and cyclopropyl.

25. The method according to claim 22, wherein

R$^1$ is hydrogen,

R$^2$ is a group of the formula

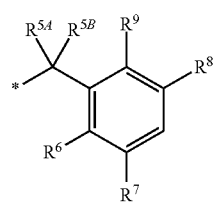

wherein

* is the attachment site to the uracil nitrogen atom,

R$^{5A}$ is hydrogen,

R$^{5B}$ is hydrogen,

R$^6$ is hydrogen,

R$^7$ is hydrogen,

R$^8$ is fluorine, chlorine or trifluoromethyl,

R$^9$ is fluorine, chlorine, trifluoromethyl or methyl,

R³ is a group of the formula

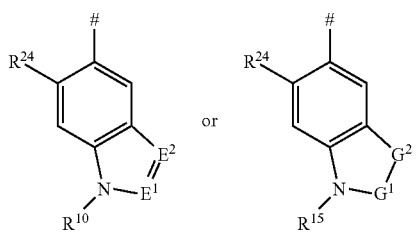

or wherein
# is the attachment site to the uracil nitrogen atom,
E¹ is CR¹¹
    wherein
    R¹¹ is hydrogen,
E² is N,
G¹ is C=O,
G² is CR¹⁶ᴬR¹⁶ᴮ, NR¹⁷, O or S,
    wherein
    R¹⁶ᴬ is hydrogen, fluorine, methyl or hydroxyl,
    R¹⁶ᴮ is hydrogen, fluorine, methyl or trifluoromethyl,
    or
    R¹⁶ᴬ and R¹⁶ᴮ together with the carbon atom to which they are bonded form a cyclopropyl ring,
    R¹⁷ is hydrogen, (C₁-C₄)-alkyl or (C₃-C₅)-cycloalkyl,
        wherein (C₁-C₄)-alkyl may be substituted by 1 to 3 substituents independently selected from the group consisting of fluorine, trifluoromethyl, cyano, cyclopropyl, cyclobutyl, hydroxyl, trifluoromethoxy, methoxy, ethoxy, azetidinyl, oxetanyl, tetrahydrofuranyl and pyrrolidinyl,
R²⁴ is hydrogen or fluorine,
R¹⁰ is (C₁-C₄)-alkyl,
R¹⁵ is hydrogen, methyl or ethyl,
    wherein methyl and ethyl may be substituted by 1 substituent selected from the group consisting of fluorine, trifluoromethyl and cyclopropyl.

26. The method according to claim 22, wherein the compound is 1-(1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

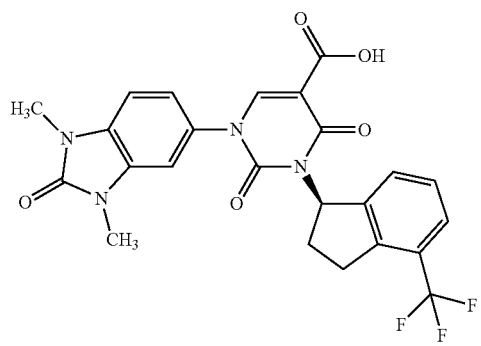 [SMILES: Cn1c(=O)n(C)c2cc(-n3cc(C(=O)O)c(=O)n([C@@H]4CCc5c4cccc5C(F)(F)F)c3=O)ccc21]

or a salt, solvate, or a solvate of the salt thereof.

27. The method according to claim 22, wherein the compound is 1-(6-fluoro-1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

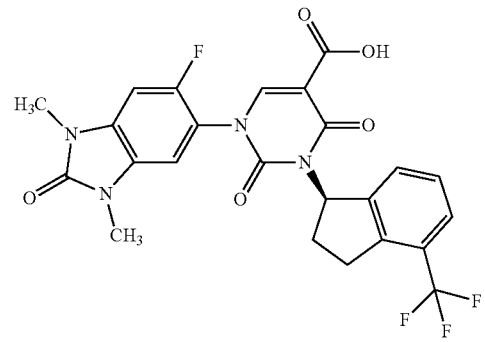 [SMILES: Cn1c(=O)n(C)c2cc(-n3cc(C(=O)O)c(=O)n([C@@H]4CCc5c4cccc5C(F)(F)F)c3=O)c(F)cc21]

or a salt, solvate, or a solvate of the salt thereof.

28. The method according to claim 22, wherein the compound is 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

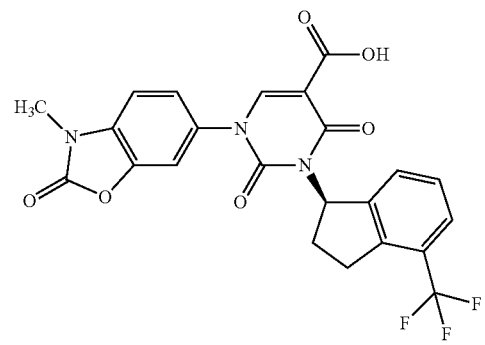 [SMILES: Cn1c(=O)oc2cc(-n3cc(C(=O)O)c(=O)n([C@@H]4CCc5c4cccc5C(F)(F)F)c3=O)ccc21]

or a salt, solvate, or a solvate of the salt thereof.

29. The method according to claim 22, wherein the compound is 2,4-dioxo-3-[(1R)-4-(trifluoromethyl)-2,3-dihydro-1H-inden-1-yl]-1-(1,3,3-trimethyl-2-oxo-2,3-dihydro-1H-indol-5-yl)-1,2,3,4-tetrahydropyrimidine-5-carboxylic acid (R enantiomer) of the formula

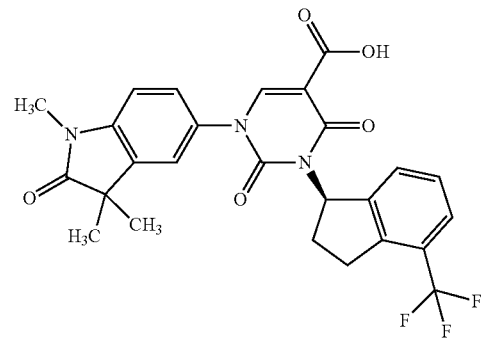 [SMILES: CN1C(=O)C(C)(C)c2cc(-n3cc(C(=O)O)c(=O)n([C@@H]4CCc5c4cccc5C(F)(F)F)c3=O)ccc21]

or a salt, solvate, or a solvate of the salt thereof.

30. The method according to claim 22, wherein the compound is 1-(1'-methyl-2'-oxo-1',2'-dihydrospiro[cyclopropane-1,3'-indole]-5'-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

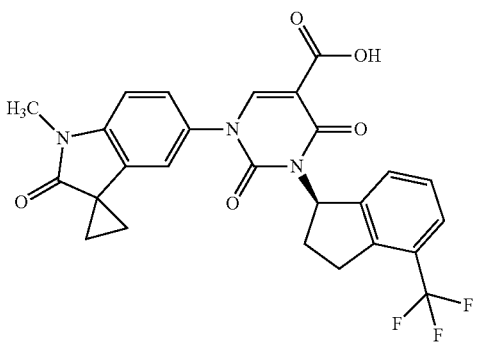 [SMILES: CN1C(=O)C2(CC2)c2cc(-n3cc(C(=O)O)c(=O)n([C@@H]4CCc5c4cccc5C(F)(F)F)c3=O)ccc21]

or a salt, solvate, or a solvate of the salt thereof.

31. The method according to claim 22, wherein the compound is 1-(3-methyl-2-oxo-2,3-dihydro-1,3-benzothiazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

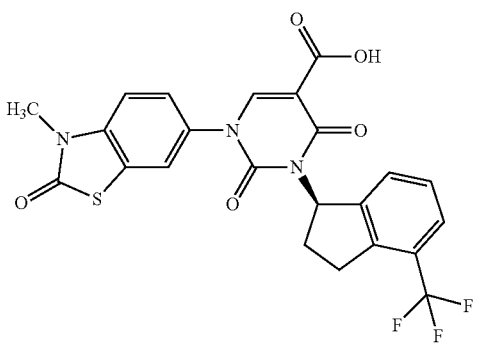

or a salt, solvate, or a solvate of the salt thereof.

32. The method according to claim 22, wherein the compound is ethyl 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer) of the formula

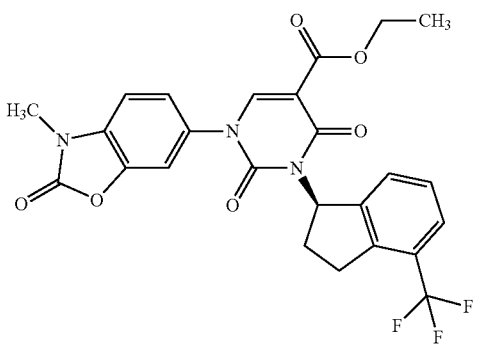 [SMILES: CCOC(=O)c1cn(-c2ccc3c(c2)oc(=O)n3C)c(=O)n([C@@H]2CCc3c2cccc3C(F)(F)F)c1=O]

33. The method according to claim 22, wherein the compound is 1-(1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

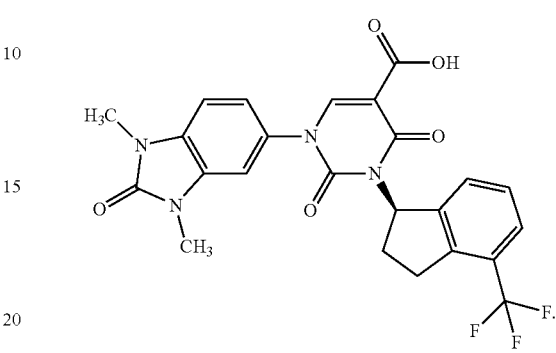

34. The method according to claim 22, wherein the compound is 1-(6-fluoro-1,3-dimethyl-2-oxo-2,3-dihydro-1H-benzimidazol-5-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

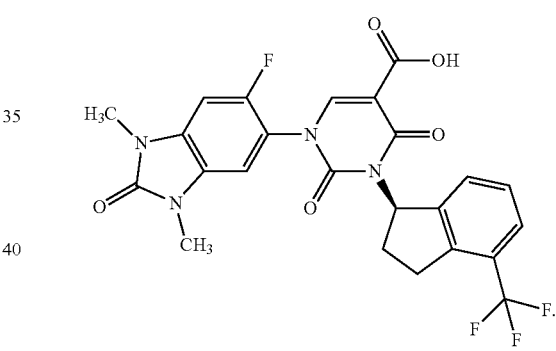

35. The method according to claim 22, wherein the compound is 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

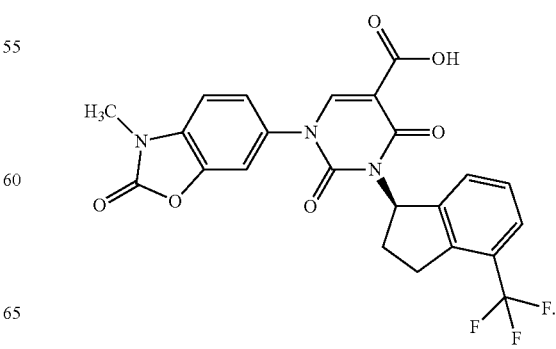

36. The method according to claim 22, wherein the compound is 2,4-dioxo-3-[(1R)-4-(trifluoromethyl)-2,3-dihydro-1H-inden-1-yl]-1-(1,3,3-trimethyl-2-oxo-2,3-dihydro-1H-indol-5-yl)-1,2,3,4-tetrahydropyrimidine-5-carboxylic acid (R enantiomer) of the formula

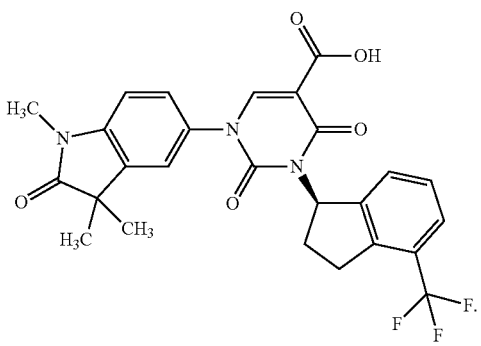 [SMILES: CN1C(=O)C(C)(C)c2cc(-n3cc(C(=O)O)c(=O)n([C@@H]4CCc5c4cccc5C(F)(F)F)c3=O)ccc21]

37. The method according to claim 22, wherein the compound is 1-(1'-methyl-2'-oxo-1',2'-dihydrospiro[cyclopropane-1,3'-indole]-5'-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

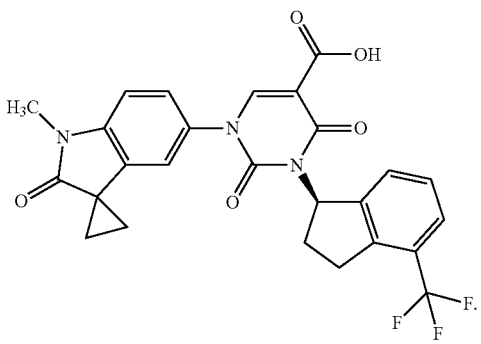 [SMILES: CN1C(=O)C2(CC2)c2cc(-n3cc(C(=O)O)c(=O)n([C@@H]4CCc5c4cccc5C(F)(F)F)c3=O)ccc21]

38. The method according to claim 22, wherein the compound is 1-(3-methyl-2-oxo-2,3-dihydro-1,3-benzothiazol-6-yl)-2,4-dioxo-3-[(1R)-4-(trifluoromethyl)-2,3-dihydro-1H-inden-1-yl]-1,2,3,4-tetrahydropyrimidine-5-carboxylic acid (R enantiomer) of the formula

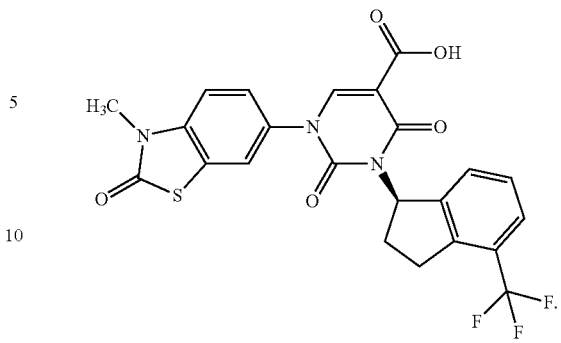

39. The method according to claim 22, wherein the compound is ethyl 1-(3-methyl-2-oxo-2,3-dihydro-1,3-benzoxazol-6-yl)-2,4-dioxo-3-[(1R)-4-(trifluoromethyl)-2,3-dihydro-1H-inden-1-yl]-1,2,3,4-tetrahydropyrimidine-5-carboxylate (R enantiomer) of the formula

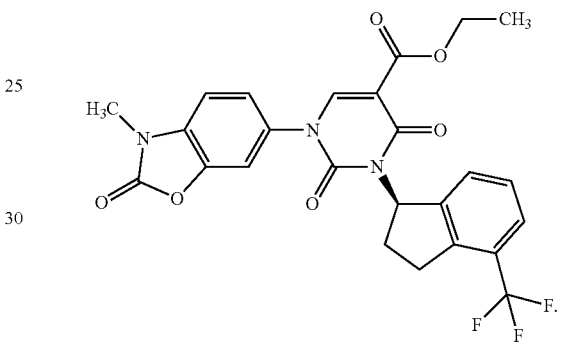

40. The method according to claim 22, wherein the renal disorder is selected from the group consisting of acute renal insufficiency, chronic renal insufficiency, acute kidney failure and chronic kidney failure.

41. The method according to claim 22, wherein the renal disorder is selected from the group consisting of chronic renal insufficiency, kidney failure, renal hypoperfusion, non-diabetic nephropathy, glomerulonephritis, haemolytic-uraemic syndrome (HUS), fibrotic disorders of kidney, polycystic kidney disease (PCKD) and syndrome of inappropriate ADH secretion (SIADH).

42. The method according to claim 22, wherein the renal disorder is chronic renal insufficiency.

* * * * *